(12) United States Patent
Regev et al.

(10) Patent No.: US 12,421,557 B2
(45) Date of Patent: Sep. 23, 2025

(54) METHODS FOR PREDICTING OUTCOMES AND TREATING COLORECTAL CANCER USING A CELL ATLAS

(71) Applicants: The Broad Institute, Inc., Cambridge, MA (US); Massachusetts Institute of Technology, Cambridge, MA (US); The Brigham and Women's Hospital, Inc., Boston, MA (US); The General Hospital Corporation, Boston, MA (US)

(72) Inventors: Aviv Regev, Cambridge, MA (US); Nir Hacohen, Boston, MA (US); Vijay K. Kuchroo, Boston, MA (US); Ana Carrizosa Anderson, Boston, MA (US); Orit Rozenblatt-Rosen, Cambridge, MA (US); Jonathan Chen, Boston, MA (US); Karin Pelka, Cambridge, MA (US); Matan Hofree, Cambridge, MA (US)

(73) Assignees: The Broad Institute, Inc., Cambridge, MA (US); Massachusetts Institute of Technology, Cambridge, MA (US); The Brigham and Women's Hospital, Inc., Boston, MA (US); The General Hospital Corporation, Boston, MA (US)

( * ) Notice: Subject to any disclaimer, the term of this patent is extended or adjusted under 35 U.S.C. 154(b) by 747 days.

(21) Appl. No.: 16/995,425

(22) Filed: Aug. 17, 2020

(65) Prior Publication Data

US 2021/0047694 A1  Feb. 18, 2021

Related U.S. Application Data

(60) Provisional application No. 62/888,347, filed on Aug. 16, 2019.

(51) Int. Cl.
| | |
|---|---|
| *A61K 40/11* | (2025.01) |
| *A61K 40/42* | (2025.01) |
| *A61K 45/06* | (2006.01) |
| *C12Q 1/6886* | (2018.01) |
| *G01N 33/50* | (2006.01) |
| *G01N 33/569* | (2006.01) |
| *G01N 33/574* | (2006.01) |

(52) U.S. Cl.
CPC ............ *C12Q 1/6886* (2013.01); *A61K 40/11* (2025.01); *A61K 40/421* (2025.01); *A61K 40/4236* (2025.01); *A61K 40/4242* (2025.01); *G01N 33/5011* (2013.01); *G01N 33/56972* (2013.01); *G01N 33/57419* (2013.01); *A61K 45/06* (2013.01); *A61K 2239/50* (2023.05); *C12Q 2600/112* (2013.01); *C12Q 2600/158* (2013.01); *G01N 2333/47* (2013.01); *G01N 2800/56* (2013.01); *G01N 2800/60* (2013.01)

(58) Field of Classification Search
CPC .. A61K 40/11; A61K 40/421; A61K 40/4236; A61K 45/06; A61K 2239/50; C12Q 1/6886; C12Q 2600/112; C12Q 2600/158; G01N 33/5011; G01N 33/505; G01N 33/56972; G01N 33/57419; G01N 2333/47; G01N 2800/56; G01N 2800/60; Y02A 50/30
See application file for complete search history.

(56) References Cited

U.S. PATENT DOCUMENTS

| | | | |
|---|---|---|---|
| 912,172 | A | 2/1909 | Rooney |
| 5,143,854 | A | 9/1992 | Fodor et al. |
| 5,288,644 | A | 2/1994 | Beavis et al. |
| 5,324,633 | A | 6/1994 | Fodor et al. |
| 5,432,049 | A | 7/1995 | Fischer et al. |
| 5,470,710 | A | 11/1995 | Weiss et al. |
| 5,492,806 | A | 2/1996 | Drmanac et al. |
| 5,503,980 | A | 4/1996 | Cantor |
| 5,510,270 | A | 4/1996 | Fodor et al. |
| 5,525,464 | A | 6/1996 | Drmanac et al. |
| 5,547,839 | A | 8/1996 | Dower et al. |
| 5,580,732 | A | 12/1996 | Grossman et al. |
| 5,580,737 | A | 12/1996 | Polisky et al. |
| 5,641,870 | A | 6/1997 | Rinderknecht et al. |

(Continued)

FOREIGN PATENT DOCUMENTS

| | | |
|---|---|---|
| EP | 0 785 280 A2 | 7/1997 |
| EP | 0 373 203 B2 | 2/2007 |

(Continued)

OTHER PUBLICATIONS

Zhou et al. (Oncoimmunology, 2018, vol. 7, No. 7, e1448332) (Year: 2018).*

(Continued)

*Primary Examiner* — Jeremy C Flinders
(74) *Attorney, Agent, or Firm* — Day Pitney LLP; Christopher R. Cowles; Richard B. Emmons

(57) ABSTRACT

The present invention is generally directed to a colorectal (CRC) cell atlas that provides methods of predicting outcomes of cancer patients and therapeutic targets for treating patients in need thereof. The atlas may be used to predict a response to immunotherapy, in particular checkpoint blockade therapy and adoptive cell transfer. Disclosed herein are previously unidentified gene programs in tumors that can be used to predict response and provide for therapeutic targets that can be used to shift a tumor to a responsive phenotype.

16 Claims, 108 Drawing Sheets
Specification includes a Sequence Listing.

(56) References Cited

U.S. PATENT DOCUMENTS

| | | | |
|---|---|---|---|
| 5,660,985 A | 8/1997 | Pieken et al. |
| 5,661,028 A | 8/1997 | Foote |
| 5,686,281 A | 11/1997 | Roberts |
| 5,800,992 A | 9/1998 | Fodor et al. |
| 5,811,097 A | 9/1998 | Allison et al. |
| 5,843,728 A | 12/1998 | Seed et al. |
| 5,851,828 A | 12/1998 | Seed et al. |
| 5,858,358 A | 1/1999 | June et al. |
| 5,883,223 A | 3/1999 | Gray |
| 5,906,936 A | 5/1999 | Eshhar et al. |
| 5,912,170 A | 6/1999 | Seed et al. |
| 6,004,811 A | 12/1999 | Seed et al. |
| 6,040,177 A | 3/2000 | Riddell et al. |
| 6,284,240 B1 | 9/2001 | Seed et al. |
| 6,352,694 B1 | 3/2002 | June et al. |
| 6,392,013 B1 | 5/2002 | Seed et al. |
| 6,410,014 B1 | 6/2002 | Seed et al. |
| 6,479,626 B1 | 11/2002 | Kim et al. |
| 6,489,458 B2 | 12/2002 | Hackett et al. |
| 6,534,055 B1 | 3/2003 | June et al. |
| 6,534,261 B1 | 3/2003 | Cox et al. |
| 6,607,882 B1 | 8/2003 | Cox et al. |
| 6,746,838 B1 | 6/2004 | Choo et al. |
| 6,753,162 B1 | 6/2004 | Seed et al. |
| 6,794,136 B1 | 9/2004 | Eisenberg et al. |
| 6,797,514 B2 | 9/2004 | Berenson et al. |
| 6,824,978 B1 | 11/2004 | Cox et al. |
| 6,866,997 B1 | 3/2005 | Choo et al. |
| 6,867,041 B2 | 3/2005 | Berenson et al. |
| 6,887,466 B2 | 5/2005 | June et al. |
| 6,903,185 B2 | 6/2005 | Kim et al. |
| 6,905,680 B2 | 6/2005 | June et al. |
| 6,905,681 B1 | 6/2005 | June et al. |
| 6,905,874 B2 | 6/2005 | Berenson et al. |
| 6,933,113 B2 | 8/2005 | Case |
| 6,979,539 B2 | 12/2005 | Cox et al. |
| 7,013,219 B2 | 3/2006 | Case et al. |
| 7,030,215 B2 | 4/2006 | Liu et al. |
| 7,144,575 B2 | 12/2006 | June et al. |
| 7,148,203 B2 | 12/2006 | Hackett et al. |
| 7,160,682 B2 | 1/2007 | Hackett et al. |
| 7,175,843 B2 | 2/2007 | June et al. |
| 7,220,719 B2 | 5/2007 | Case et al. |
| 7,232,566 B2 | 6/2007 | June et al. |
| 7,241,573 B2 | 7/2007 | Choo et al. |
| 7,241,574 B2 | 7/2007 | Choo et al. |
| 7,446,190 B2 | 11/2008 | Sadelain et al. |
| 7,572,631 B2 | 8/2009 | Berenson et al. |
| 7,585,849 B2 | 9/2009 | Liu et al. |
| 7,595,376 B2 | 9/2009 | Kim et al. |
| 7,741,465 B1 | 6/2010 | Eshhar et al. |
| 7,985,739 B2 | 7/2011 | Kay et al. |
| 8,021,867 B2 | 9/2011 | Smith et al. |
| 8,034,334 B2 | 10/2011 | Dudley et al. |
| 8,088,379 B2 | 1/2012 | Robbins et al. |
| 8,119,361 B2 | 2/2012 | Smith et al. |
| 8,119,381 B2 | 2/2012 | Smith et al. |
| 8,124,369 B2 | 2/2012 | Smith et al. |
| 8,129,134 B2 | 3/2012 | Smith et al. |
| 8,133,697 B2 | 3/2012 | Smith et al. |
| 8,163,514 B2 | 4/2012 | Smith et al. |
| 8,211,422 B2 | 7/2012 | Eshhar et al. |
| 8,227,432 B2 | 7/2012 | Hackett et al. |
| 8,399,645 B2 | 3/2013 | Campana et al. |
| 8,697,854 B2 | 4/2014 | Schendel et al. |
| 8,735,553 B1 | 5/2014 | Li et al. |
| 8,906,682 B2 | 12/2014 | June et al. |
| 8,911,993 B2 | 12/2014 | June et al. |
| 8,916,381 B1 | 12/2014 | June et al. |
| 8,975,071 B1 | 3/2015 | June et al. |
| 9,062,111 B2 | 6/2015 | Nichol et al. |
| 9,101,584 B2 | 8/2015 | June et al. |
| 9,102,760 B2 | 8/2015 | June et al. |
| 9,102,761 B2 | 8/2015 | June et al. |
| 9,132,281 B2 | 9/2015 | Zeng et al. |
| 9,233,125 B2 | 1/2016 | Davila et al. |
| 9,320,811 B2 | 4/2016 | Jure-kunkel |
| 9,327,014 B2 | 5/2016 | Gurney et al. |
| 2004/0224402 A1 | 11/2004 | Bonyhadi et al. |
| 2010/0104509 A1 | 4/2010 | King et al. |
| 2012/0244133 A1 | 9/2012 | Rosenberg et al. |
| 2013/0071414 A1 | 3/2013 | Dotti et al. |
| 2015/0368342 A1 | 12/2015 | Wu et al. |
| 2015/0368360 A1 | 12/2015 | Liang et al. |
| 2016/0046724 A1 | 2/2016 | Brogdon et al. |
| 2016/0060691 A1 | 3/2016 | Giresi et al. |
| 2016/0129109 A1 | 5/2016 | Davila et al. |
| 2016/0166613 A1 | 6/2016 | Spencer et al. |
| 2016/0175359 A1 | 6/2016 | Spencer et al. |
| 2016/0208323 A1 | 7/2016 | Bernstein et al. |
| 2017/0037125 A1 | 2/2017 | Leopold et al. |
| 2017/0283504 A1 | 10/2017 | Wiltzius et al. |
| 2018/0085444 A1 | 3/2018 | Morgan et al. |
| 2022/0282217 A1* | 9/2022 | Ang ................. C12N 5/0638 |

FOREIGN PATENT DOCUMENTS

| | | |
|---|---|---|
| WO | 92/15322 A1 | 9/1992 |
| WO | 95/21265 A1 | 8/1995 |
| WO | 96/31622 A1 | 10/1996 |
| WO | 96/40281 A2 | 12/1996 |
| WO | 97/10365 A1 | 3/1997 |
| WO | 97/27317 A1 | 7/1997 |
| WO | 03/020763 A2 | 3/2003 |
| WO | 03/057171 A2 | 7/2003 |
| WO | 2004/033685 A1 | 4/2004 |
| WO | 2004/044004 A2 | 5/2004 |
| WO | 2004/074322 A1 | 9/2004 |
| WO | 2005/113595 A2 | 12/2005 |
| WO | 2005/114215 A2 | 12/2005 |
| WO | 2006/000830 A2 | 1/2006 |
| WO | 2006/125962 A2 | 11/2006 |
| WO | 2008/038002 A2 | 4/2008 |
| WO | 2008/039818 A2 | 4/2008 |
| WO | 2009/012418 A2 | 1/2009 |
| WO | 2011/146862 A1 | 11/2011 |
| WO | 2012/058460 A2 | 5/2012 |
| WO | 2012/079000 A1 | 6/2012 |
| WO | 2013/039889 A1 | 3/2013 |
| WO | 2013/040371 A2 | 3/2013 |
| WO | 2013/044225 A1 | 3/2013 |
| WO | 2013/154760 A1 | 10/2013 |
| WO | 2013/166321 A1 | 11/2013 |
| WO | 2013/176915 A1 | 11/2013 |
| WO | 2014/011987 A1 | 1/2014 |
| WO | 2014/018863 A1 | 1/2014 |
| WO | 2014/047561 A1 | 3/2014 |
| WO | 2014/059173 A2 | 4/2014 |
| WO | 2014/083173 A1 | 6/2014 |
| WO | 2014/093622 A2 | 6/2014 |
| WO | 2014/133567 A1 | 9/2014 |
| WO | 2014/133568 A1 | 9/2014 |
| WO | 2014/134165 A1 | 9/2014 |
| WO | 2014/172606 A1 | 10/2014 |
| WO | 2014/184744 A1 | 11/2014 |
| WO | 2014/191128 A1 | 12/2014 |
| WO | 2014/204725 A1 | 12/2014 |
| WO | 2014/210353 A2 | 12/2014 |
| WO | 2015/057834 A1 | 4/2015 |
| WO | 2015/057852 A1 | 4/2015 |
| WO | 2015/120096 A2 | 8/2015 |
| WO | 2015/142675 A2 | 9/2015 |
| WO | 2015/158671 A1 | 10/2015 |
| WO | 2015/187528 A1 | 12/2015 |
| WO | 2016/000304 A1 | 1/2016 |
| WO | 2016/011210 A2 | 1/2016 |
| WO | 2016/014789 A2 | 1/2016 |
| WO | 2016/040476 A1 | 3/2016 |
| WO | 2016/070061 A1 | 5/2016 |
| WO | 2016/106236 A1 | 6/2016 |
| WO | 2016/168584 A1 | 10/2016 |
| WO | 2016/191756 A1 | 12/2016 |
| WO | 2016/196388 A1 | 12/2016 |
| WO | 2017/011804 A1 | 1/2017 |

(56) References Cited

FOREIGN PATENT DOCUMENTS

| WO | 2017/070395 A1 | 4/2017 |
|---|---|---|
| WO | 2017/156336 A1 | 9/2017 |
| WO | 2017/164936 A1 | 9/2017 |
| WO | 2017/211900 A1 | 12/2017 |
| WO | 2018/028647 A1 | 2/2018 |
| WO | 2018/191553 A1 | 10/2018 |
| WO | 2018/213708 A1 | 11/2018 |
| WO | 2018/213726 A1 | 11/2018 |
| WO | 2019/005884 A1 | 1/2019 |
| WO | 2019/005886 A1 | 1/2019 |
| WO | 2019/018423 A1 | 1/2019 |
| WO | 2019/060746 A1 | 3/2019 |
| WO | 2019/071048 A1 | 4/2019 |
| WO | 2019/094984 A1 | 5/2019 |
| WO | 2019/126709 A1 | 6/2019 |
| WO | 2019/126716 A1 | 6/2019 |
| WO | 2019/126762 A2 | 6/2019 |
| WO | 2020/033601 A1 | 2/2020 |
| WO | 2020/077236 A1 | 4/2020 |

OTHER PUBLICATIONS

Benci, et al., "Tumor Interferon Signaling Regulates a Multigenic Resistance Program to Immune Checkpoint Blockade", Cell, vol. 167, No. 6, Dec. 1, 2016, 28 pages.

Brewitz, et al., "CD8 + T Cells Orchestrate pDC-XCR1 + Dendritic Cell Spatial and Functional Cooperativity to Optimize Priming", Immunity, vol. 46, No. 2, Feb. 21, 2017, 205-219.

Chalabi, et al., "Neoadjuvant Immunotherapy Leads to Pathological Responses in MMR-proficient and MMR-Deficient Early-Stage Colon Cancers", Nature Medicine, vol. 26, No. 4, Apr. 6, 2020, 566-576.

Chow, et al., "Intratumoral Activity of the CXCR3 Chemokine System is Required for the Efficacy of Anti-PD-1 Therapy", Immunity, vol. 50, No. 6, Jun. 18, 2019, 21 pages.

Fankhauser, et al., "Tumor Lymphangiogenesis Promotes T Cell Infiltration and Potentiates Immunotherapy in Melanoma", Science Translational Medicine, vol. 9, No. 407, Sep. 13, 2017, 12 pages.

Helmink, et al., "B Cells and Tertiary Lymphoid Structures Promote Immunotherapy Response", Nature, vol. 577, No. 7791, Jan. 23, 2020, 28 pages.

House, et al., "Macrophage-Derived CXCL9 and CXCL 10 are Required for Antitumor Immune Responses following Immune Checkpoint Blockade", Clinical Cancer Research, vol. 26, No. 2, Oct. 21, 2019, 487-504.

Jansen, et al., "An Intra-Tumoral Niche Maintains and Differentiates Stem-Like CD8 T Cells", Nature, vol. 576, Dec. 2019, 28 pages.

Liu, et al., "Targeting the IDO1 Pathway in Cancer: from Bench to Bedside", Journal of Hematology & Oncology, vol. 11, No. 100, 2018, 12 pages.

Mlecnik, et al., "Integrative Analyses of Colorectal Cancer Show Immunoscore is a Stronger Predictor of Patient Survival Than Microsatellite Instability", Immunity, vol. 44, No. 3, Mar. 15, 2016, 698-711.

Petitprez, et al., "B Cells are Associated with Survival and Immunotherapy Response in Sarcoma", Nature, vol. 577, Jan. 23, 2020, 24 pages.

Pitzalis, et al., "Ectopic Lymphoid-like Structures in Infection, Cancer and Autoimmunity", Nature Reviews Immunology, vol. 14, Jul. 2014, 447-462.

Rao, et al., "Pathologically Expanded Peripheral T Helper Cell Subset Drives B Cells in Rheumatoid Arthritis", Nature, vol. 542, No. 7639, Feb. 2, 2017, 17 pages.

Sade-Feldman, et al., "Defining T Cell States Associated with Response to Checkpoint Immunotherapy in Melanoma", Cell, vol. 175, No. 4, Nov. 1, 2018, 37 pages.

Thommen, et al., "A Transcriptionally and Functionally Distinct Pd-1+ Cd8+ T Cell Pool with Predictive Potential in Non-small Cell Lung Cancer Treated with Pd-1 Blockade", Nature Medicine, vol. 24, No. 7, Jul. 2018, 28 pages.

Tsoi, et al., "Multi-stage Differentiation Defines Melanoma Subtypes with Differential Vulnerability to Drug-Induced Iron-Dependent Oxidative Stress", Cancer Cell, vol. 33, May 14, 2018, 21 pages.

Zhang, et al., "Lineage Tracking Reveals Dynamic Relationships of T Cells in Colorectal Cancer", Nature, vol. 564, Dec. 13, 2018, 30 pages.

\* cited by examiner

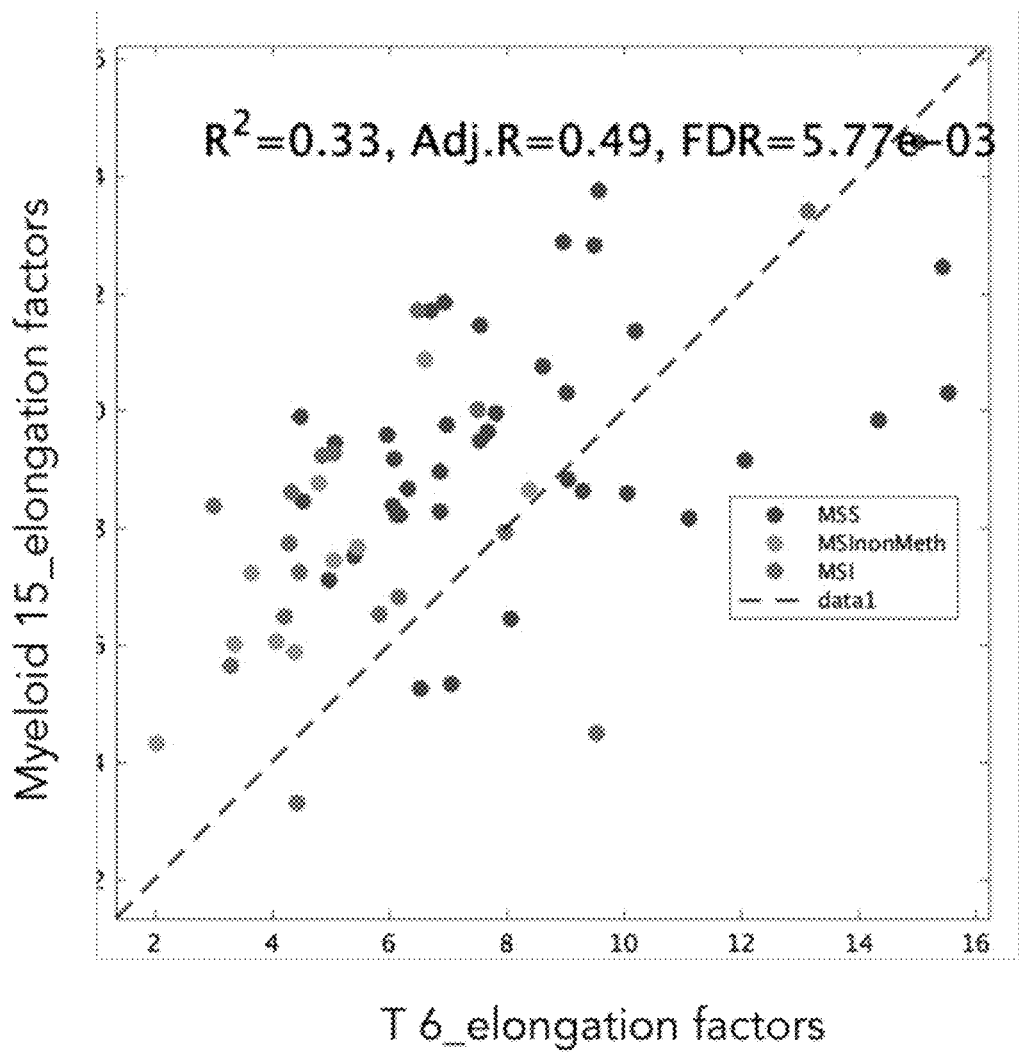
FIG. 20E

The immune composition of tumors varies across patients, activated CD8+ T cells are selectively enriched in a subset of MSI CRC

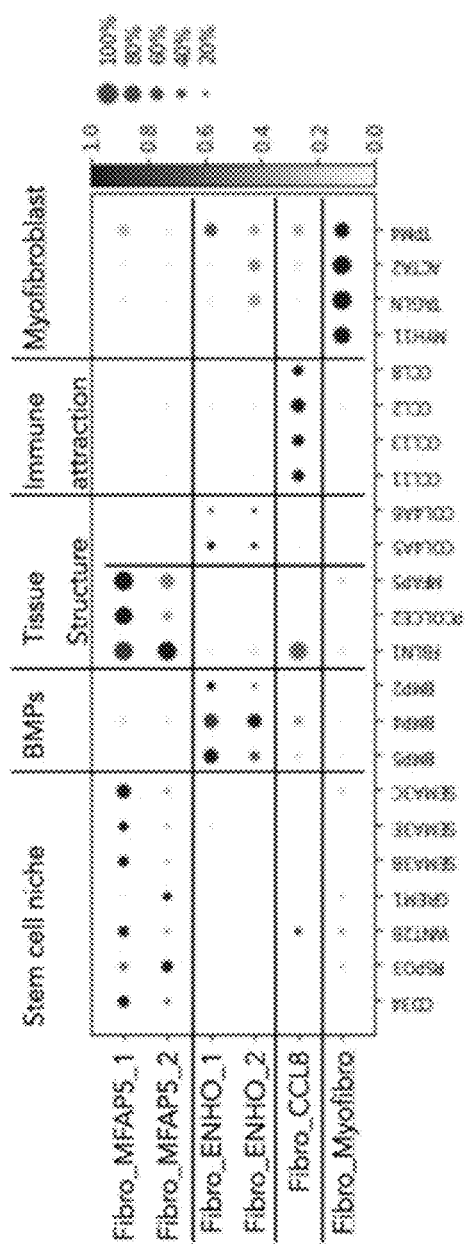
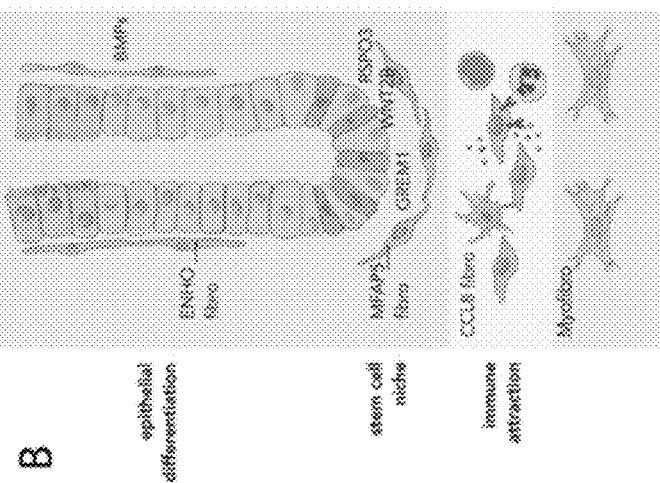
FIG. 79B

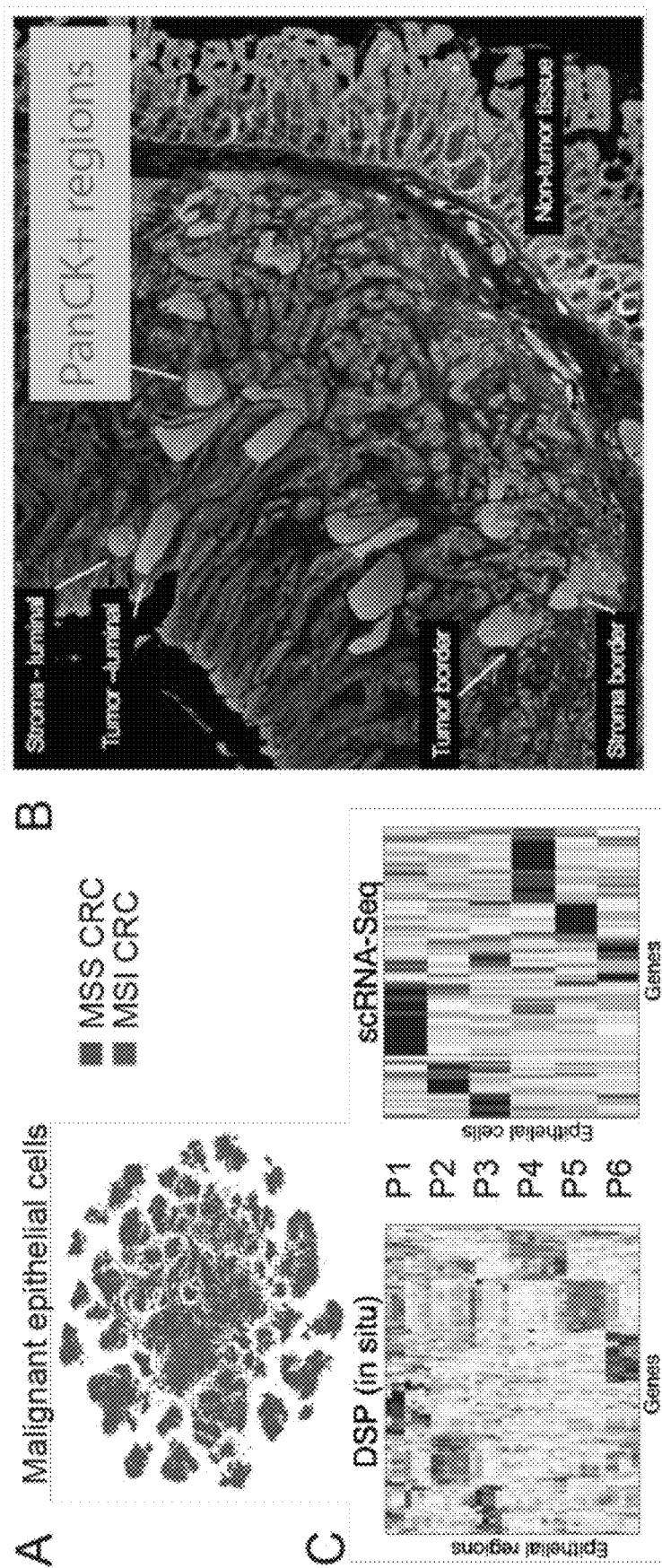
FIG. 80A-C

METHODS FOR PREDICTING OUTCOMES AND TREATING COLORECTAL CANCER USING A CELL ATLAS

CROSS-REFERENCE TO RELATED APPLICATIONS

This application claims the benefit of U.S. Provisional Application No. 62/888,347, filed Aug. 16, 2019. The entire contents of the above-identified application are hereby fully incorporated herein by reference.

REFERENCE TO AN ELECTRONIC SEQUENCE LISTING

The contents of the electronic sequence listing (BROD_4720US_ST25.txt"; Size is 9 Kilobytes and it was created on Aug. 14, 2020) is herein incorporated by reference in its entirety.

TECHNICAL FIELD

The subject matter disclosed herein is generally directed to a colorectal (CRC) cell atlas that provides methods of predicting outcomes of cancer patients and therapeutic targets for treating patients in need thereof.

BACKGROUND

New tools, such as single-cell genomics, have allowed for mapping single cell types in a tissue. Without maps of different cell types in a tumor, including the tumor microenvironment (TME), and the genes they express, we cannot describe all cellular activities and understand the biological networks that direct them. A comprehensive cell atlas would make it possible to catalog all cell types and even subtypes of cells in a tumor, and even distinguish different stages of differentiation and cell states, such as immune cell activation. A cell atlas has the potential to transform our approach to biomedicine. It would help identify markers and signatures for cancer, uncover new targets for therapeutic intervention, and provide a direct view of human biology in vivo, removing the distorting aspects of cell culture. Patient cohort studies using single cell analysis are therefore essential for identifying consistent and robust features that underlie cancer and response to therapy.

SUMMARY

In one aspect, the present invention provides for an isolated T cell comprising a CXCL13 gene program comprising expression of one or more genes selected from the group consisting of CXCL13, MT2A, RBPJ, SLA, PDCD1, FKBP5, NR3C1, NAP1L4, RAB27A, ITM2A, BST2, TGIF1, MTHFD2, PTMS, TOX, CHN1, TSHZ2, YWHAQ, NBL1, MIR155HG, CLPP, LY6E, ARL3, CD2BP2, ZBED2, HAVCR2, MT1E, FAM3C, DGUOK, LBH, TMEM173, DUSP4, SRGAP3, RNF19A, GALM, IFNG, SNAP47, PLSCR1, PDLIM4, SNX9, CD226, IL6ST, LAG3, TRAT1, AHI1, IFI44L, PAG1, GOLIM4, CBLB, BCL2L11, MYO7A, GNG4, NPDC1, SARDH, MX1, CD200, BTLA, TNS3, TSPO, SLC7A5, HTRA1, TSPAN14, KCNK5, PDE7B, TNFSF4, ELMO1, CAMK1, PRDX6, NUDT16, ITGAE, SOD1, DGKZ, ITPR1, LMO4, HECTD2, NMB, SLC4A2, CCDC6, LRMP, SLC27A2 and AGFG1. In certain embodiments, the T cell is a CD8+ T cell. In another aspect, the present invention provides for a population of T cells according to any embodiment herein. In certain embodiments, the population is expanded ex vivo. In certain embodiments, the T cells are isolated from a subject suffering from colorectal cancer (CRC). In certain embodiments, the T cells are modified to express a chimeric antigen receptor (CAR) or tumor specific T cell receptor (TCR). In another aspect, the present invention provides for a method of treating colorectal cancer in a subject in need thereof comprising administering the T cells according to any embodiment herein to the subject.

In another aspect, the present invention provides for a method of treating colorectal cancer in a subject in need thereof, comprising: detecting expression of a gene program comprising expression of one or more genes selected from the group consisting of CXCL13, MT2A, RBPJ, SLA, PDCD1, FKBP5, NR3C1, NAP1L4, RAB27A, ITM2A, BST2, TGIF1, MTHFD2, PTMS, TOX, CHN1, TSHZ2, YWHAQ, NBL1, MIR155HG, CLPP, LY6E, ARL3, CD2BP2, ZBED2, HAVCR2, MT1E, FAM3C, DGUOK, LBH, TMEM173, DUSP4, SRGAP3, RNF19A, GALM, IFNG, SNAP47, PLSCR1, PDLIM4, SNX9, CD226, IL6ST, LAG3, TRAT1, AHI1, IFI44L, PAG1, GOLIM4, CBLB, BCL2L11, MYO7A, GNG4, NPDC1, SARDH, MX1, CD200, BTLA, TNS3, TSPO, SLC7A5, HTRA1, TSPAN14, KCNK5, PDE7B, TNFSF4, ELMO1, CAMK1, PRDX6, NUDT16, ITGAE, SOD1, DGKZ, ITPR1, LMO4, HECTD2, NMB, SLC4A2, CCDC6, LRMP, SLC27A2 and AGFG1; and if the subject expresses the gene program, administering a checkpoint blockade (CPB) therapy and/or an IDO1 inhibitor. In certain embodiments, the gene program is detected in CD8+ T cells.

In another aspect, the present invention provides for a method of treating colorectal cancer in a subject in need thereof comprising: detecting expression of a gene program comprising an interferon-stimulated gene signature (ISG); and if the subject expresses the gene program, administering a CPB therapy and/or an IDO1 inhibitor. In certain embodiments, the program comprises one or more genes selected from the group consisting of CXCL10, CXCL11, IDO1 and PDL1. In certain embodiments, the gene program is detected in malignant, stromal, and/or myeloid cells.

In another aspect, the present invention provides for a method of shifting colorectal cancer (CRC) tumor microenvironment phenotypes comprising administering to a subject one or more agents capable of modulating a gene program selected from any of Tables 1-14. In certain embodiments, the program is a myeloid specific program. In certain embodiments, the program is a pDC program. In certain embodiments, the program is modulated by administering an agent targeting one or more transcription factors selected from the group consisting of IKZF1 and IRF4. In certain embodiments, the program is an interferon stimulated gene (ISG) program. In certain embodiments, the program is modulated by administering an agent targeting one or more transcription factors selected from the group consisting of STAT1, STAT2, IRF7, IRF1, IRF9 and IRF3. In certain embodiments, the program is a macrophage program. In certain embodiments, the program is selected from the group consisting of a M2-like, APO/CTS and C1Q program. In certain embodiments, the program is specific to myeloid-derived suppressor cells (MDSCs). In certain embodiments, the program is a CD8+ T cell specific program. In certain embodiments, the program is an activated CD8+ T cell program. In certain embodiments, the program is selected from the group consisting of a GNLY/KLRC2, HSP, and CXCL13 program. In certain embodiments, the program is a CD4+ T cell specific program. In certain embodiments, the program is expressed in Tregs. In certain embodiments, the program is a consensus malignant program selected from Table 14. In certain embodiments, the method is a method of treating a subject in need thereof, wherein shifting a program increases sensitivity of the CRC to an immunotherapy. In certain embodiments, the immunotherapy is checkpoint blockade (CPB) therapy. In certain embodiments, the CPB therapy comprises anti-PD-1, anti-CTLA4, anti-PD-L1, anti-TIM3, anti-TIGIT, anti-LAG3, or combinations thereof. In certain embodiments, the one or more agents comprises a small molecule, small molecule degrader, genetic modifying agent, antibody, antibody fragment, antibody-like protein scaffold, aptamer, protein, or any combination thereof. In certain embodiments, the genetic modifying agent comprises a CRISPR system, RNAi system, a zinc finger nuclease system, a TALE system, or a meganuclease. In certain embodiments, the CRISPR-Cas system comprises a CRISPR-Cas base editing system, a prime editor system, or a CAST system.

In another aspect, the present invention provides for a method of detecting or monitoring colorectal cancer (CRC) comprising measuring in a sample obtained from a subject one or more gene programs selected from any of Tables 1-14. In certain embodiments, the program is a CD8+ T cell specific program. In certain embodiments, the program is an activated CD8+ T cell program. In certain embodiments, the program is a CXCL13 program comprising one or more genes selected from the group consisting of CXCL13, MT2A, RBPJ, SLA, PDCD1, FKBP5, NR3C1, NAP1L4, RAB27A, ITM2A, BST2, TGIF1, MTHFD2, PTMS, TOX, CHN1, TSHZ2, YWHAQ, NBL1, MIR155HG, CLPP, LY6E, ARL3, CD2BP2, ZBED2, HAVCR2, MT1E, FAM3C, DGUOK, LBH, TMEM173, DUSP4, SRGAP3, RNF19A, GALM, IFNG, SNAP47, PLSCR1, PDLIM4, SNX9, CD226, IL6ST, LAG3, TRAT1, AHI1, IFI44L, PAG1, GOLIM4, CBLB, BCL2L11, MYO7A, GNG4, NPDC1, SARDH, MX1, CD200, BTLA, TNS3, TSPO, SLC7A5, HTRA1, TSPAN14, KCNK5, PDE7B, TNFSF4, ELMO1, CAMK1, PRDX6, NUDT16, ITGAE, SOD1, DGKZ, ITPR1, LMO4, HECTD2, NMB, SLC4A2, CCDC6, LRMP, SLC27A2 and AGFG1. In certain embodiments, detection of the program indicates response to checkpoint blockade (CPB) therapy. In certain embodiments, the program comprises an interferon stimulated gene signature comprising one or more genes selected from CXCL10, CXCL11, IDO1 and PDL1. In certain embodiments, detection of the program indicates response to checkpoint blockade (CPB) therapy. In certain embodiments, the program is selected from the group consisting of a GNLY/KLRC2, HSP, and/or CXCL13 program. In certain embodiments, the program is a myeloid specific program. In certain embodiments, the program is a pDC program. In certain embodiments, the program comprises one or more transcription factors selected from the group consisting of IKZF1 and IRF4. In certain embodiments, the program is an ISG program. In certain embodiments, the program comprises one or more transcription factors selected from the group consisting of STAT1, STAT2, IRF7, IRF1, IRF9 and IRF3. In certain embodiments, the program is a macrophage program. In certain embodiments, the program is selected from the group consisting of a M2-like, APO/CTS and C1Q program. In certain embodiments, the program is specific to myeloid-derived suppressor cells (MDSCs). In certain embodiments, the program is a CD4+ T cell specific program. In certain embodiments, the program is expressed in Tregs. In certain embodiments, the program is a consensus malignant program selected from Table 14.

In certain embodiments, a program is measured using immunohistochemistry, RNA sequencing, RT-PCR, fluorescently barcoded probes, FISH, FACS or any combination thereof. In certain embodiments, the one or more programs are monitored during treatment. In certain embodiments, the treatment is immunotherapy. In certain embodiments, the immunotherapy is checkpoint blockade (CPB) therapy. In certain embodiments, the CPB therapy comprises anti-PD-1, anti-CTLA4, anti-PD-L1, anti-TIM3, anti-TIGIT, anti-LAG3, or combinations thereof.

In another aspect, the present invention provides for a method of screening for agents capable of modulating tumor microenvironment phenotypes in colorectal cancer (CRC) comprising: applying a candidate agent to a CRC cell or cell population; and detecting modulation of one or more programs selected from any of Tables 1-14, thereby identifying the agent. In certain embodiments, the agent is applied to an animal model. In certain embodiments, the animal model is a patient-derived xenograft (PDX).

In another aspect, the present invention provides for a method of detecting or monitoring colorectal cancer (CRC) comprising measuring the composition of a tumor sample obtained from a subject in need thereof, wherein the composition comprises one or more cell types selected from the group consisting of myeloid cells, endothelial cells, pericytes, fibroblasts, Tregs, activated CD8+ T cells and proliferating CD8+ T cells. In certain embodiments, an increase in the one or more cell types indicates CRC. In certain embodiments, fibroblast cell types increase in CRC. In certain embodiments, the method further comprises measuring gene signatures to detect CRC subtypes, wherein a Strom12 gene signature, preferably comprising one or more genes selected from the group consisting of CXCL14, BMP4, CXCR4, FRZB and LSP1, and a Strom22 gene signature, preferably comprising one or more genes selected from the group consisting of MMP1, MMP3, CXCL1, CXCL5, CXCL6, CXCL8, IL6, IL11, IL24, MT1E, MT1F, MT1X and MT2A, are detected in the fibroblasts, wherein MSS has higher expression of Strom12 as compared to MSI and MSI has higher expression of Strom22 as compared to MSS, whereby MSI and MSS tumors can be identified.

In another aspect, the present invention provides for a method of classifying CRC tumors comprising projecting bulk expression data obtained from a tumor onto one or more NMF programs selected from Tables 1-14. In certain embodiments, the tumors are classified based on likelihood of survival. In certain embodiments, the tumors are classified based on response to CPB therapy. In certain embodiments, the tumors are classified based on response to IDO1 inhibition.

In another aspect, the present invention provides for a method of treating CRC comprising administering CPB therapy and/or an IDO1 inhibitor in combination with an agent capable of modulating a gene selected from Table 1-14.

In certain embodiments, the CRC according to any embodiment herein is MSS or MSI. In certain embodiments, the MSI has a methylator phenotype or a non-methylator phenotype.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIG. 20A-20E—Correlation of NMF program activities within tumor specimens. A. Correlation plot with cell programs indicated (correlation weights are indicated by color). B. NMF correlation for FosJun programs in T cell program 4 and Myeloid program 11. C. NMF correlation for HSP programs in myeloid program 7 and T cell program 17. D. NMF correlation for ISG programs in stromal program 11 and T cell program 19. E. NMF correlation for elongation factor programs in myeloid program 15 and T cell program 6.

FIG. 79A-79D—Dramatic remodeling of the stromal cell compartment and emergence of MSS- and MSI-specific cancer associated fibroblast cell states. A. Normal fibroblast cell states were depleted in tumors, tumor-specific cancer-associated fibroblast (CAF) cell states emerged. CAF1 was enriched in MSS tumors, CAF2 in MSI tumors, CAF3 was present in both. B. Fibroblasts serve critical functions in normal colon tissue. ENHO fibroblasts drive the differentiation of epithelial cells, MFAP5 fibroblasts provide the stem cell niche at the bottom of the crypt, CCL8 fibroblasts are likely involved in ensuring a homeostatic immune environment, myofibroblasts have contractile properties. C. Cancer-associated fibroblasts acquire novel features, including myofibroblast 'myCAF' and inflammatory fibroblast 'iCAF' features. D. CAF1, CAF2, and CAF3 occupy different niches in the tumor microenvironment. CAF1 are intimately associated with the basolateral surface of the tumor epithelium, CAF2 are predominantly in stromal bands, CAF3 localize to the luminal surface.

FIG. 80A-80C—Malignant cells in MSS and MSI CRC. A. Malignant cells largely separated by MSS and MSI CRC. B. GeoMx DSP enabled the sampling of multiple regions per patient specimen. C. scRNAseq-derived malignant cell signatures were patient-specific and found in multiple regions of the tumor in situ.

Figure 1:
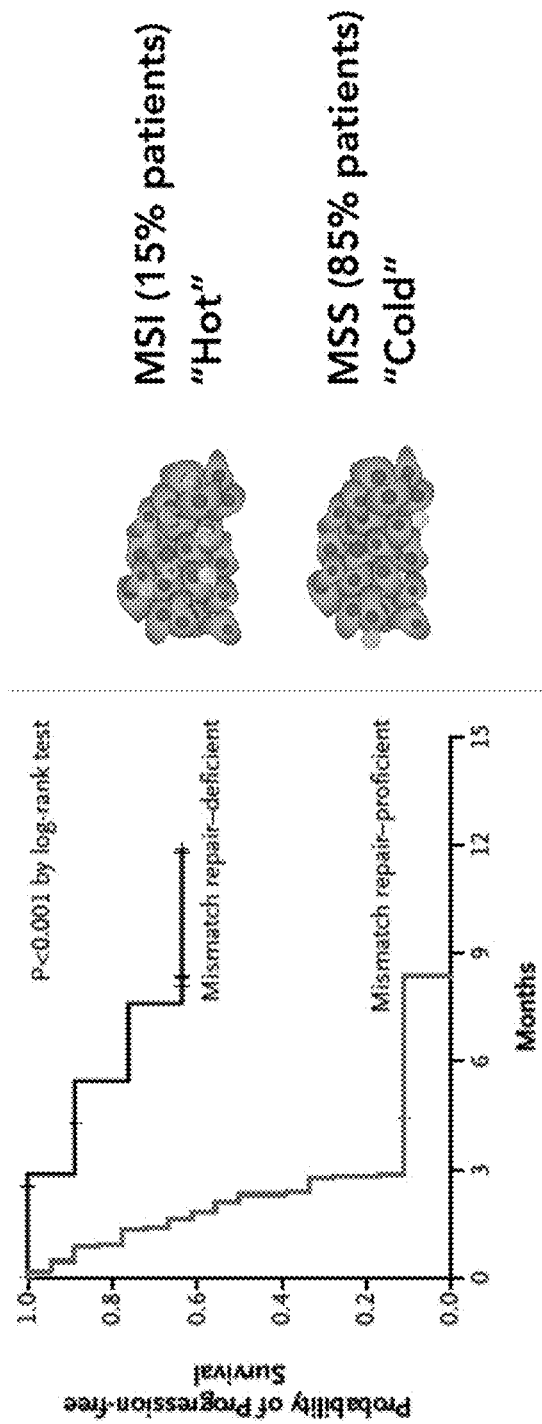
FIG. 1—Colorectal cancer (CRC) subtypes and their responses to immunotherapy. Plot and schematic showing CRC subtypes and their survival in response anti-PD1 therapy.

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlett, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a" "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

Colorectal cancer (CRC), also known as bowel cancer and colon cancer, is the development of cancer from the colon or rectum (parts of the large intestine). Colorectal cancer (CRC) can be separated into two molecularly and immunologically distinct types: 15% of patients have mismatch repair deficient (MSI) tumors with high mutational burden and high immunotherapy response rate, and 85% of patients have mismatch repair proficient (MSS) tumors with low mutational burden and either weak or no response to immunotherapy. MSI tumors differ in MMR deficiency due to hypermethylation induced silencing of the MLH1 gene or germline mutations in the DNA mismatch repair (MMR) genes (MLH1, MSH2, MSH6 and PMS2) or deletion of the 3' end of EPCAM. MSI tumors can be distinguished in that MSI tumors can have a CpG island methylator phenotype or a non-methylator phenotype (Lynch type).

The tumor microenvironment (TME) is the environment around a tumor, including the surrounding blood vessels, immune cells, fibroblasts, signaling molecules and the extracellular matrix (ECM). The tumor and the surrounding microenvironment are closely related and interact constantly. Tumors can influence the microenvironment by releasing extracellular signals, promoting tumor angiogenesis and inducing peripheral immune tolerance, while the immune cells in the microenvironment can affect the growth and evolution of cancerous cells.

Immunotherapy with checkpoint blockade (CPB) has improved survival and outcomes in melanoma and other tumor types, but still a majority of cancer patients do not respond. CRCs that are mismatch repair deficient (MSI) are responsive to CPB therapy in about 50% of the cases, while CRCs that are mismatch repair proficient (MSS) generally are non-responsive to CPB therapy. A small percentage of MSS tumors are hyper-responsive to immunotherapy (about 3%).

Here, Applicants analyzed 31 MSS and 34 MSI primary untreated CRC specimens by single cell RNA-Seq and multiplex microscopy to discover how immune, malignant and stromal cells are altered and interact in human CRC tumors. Some cell types acquired new polarization states across tumors of both subtypes, including myeloid cells, endothelial cells and pericytes, while others exhibited MSI- or MSS-specific states, such as T cells, myeloid cells, malignant cells and fibroblasts. The cooccurrence patterns of these programs across patient tumors highlighted two multicellular networks of interacting cells among the malignant, stromal, myeloid, and T cell populations. By visualizing their spatial locations in MSI and MSS tumors, Applicants found that the first network, which consisted of highly inflammatory MMP3+ fibroblasts, IL1B+ monocytes, CXCL1+ malignant cells, and neutrophils, occurred at the luminal interface of most tumors, at sites of epithelial damage and wound healing. The second multicellular network was largely restricted to MSI tumors and consisted of stromal, myeloid, and malignant cells with strong interferon-stimulated gene signatures that included the CXCR3 chemokines CXCL10/CXCL11 and inhibitory molecules such as IDO1 and PDL1. This network formed as foci around activated T cells expressing IFNG, CXCR3 and CXCL13 at the interface of malignant glands and stromal bundles. This study identifies cellular elements and gene programs, assembles them into multicellular interaction networks, and positions key immune hubs within the tumor.

Applicants have generated a single cell atlas for CRC using a large patient cohort of normal and tissue samples across CRC subtypes and single cell RNA sequencing (scRNA-seq). The single cell atlas of the present invention can provide for predicting response to therapy and predicting survival, and provides new therapeutic targets and methods of treatment. Moreover, the atlas provides for personalized therapy. The CRC atlas provides for novel biological programs, cell states and/or signature genes.

The CRC atlas identified the emergence of new fibroblast states with different phenotypes in MSS versus MSI CRC. In the normal colon, Applicants identified previously well described fibroblasts plus a novel immune attracting fibroblast type. In CRC, Applicants observed that 'normal' tissue supporting functions changed or were lost, especially in MSI CRC. In MSI CRC, Applicants observed the expression of neutrophil attracting chemokines.

The CRC atlas identified transcriptional correlates of vascular dysfunction in MSS and MSI CRC (endothelial cells and pericytes). This included angiogenesis, loss of vascular integrity, e.g., stiffness (upregulation of basement membrane components) and leakiness (loss of tight junctions), and changed immune attraction, adhesion, and trans-migration. Applicants identified regulators (e.g., transcription factors) responsible for normal tumor changes. These regulators may be targeted therapeutically.

The CRC atlas identified a strong myeloid infiltration in MSS and MSI CRC and a dramatic expansion of the phenotypic spectrum of monocytes/macrophages (different in MSS versus MSI). Applicants analyzed the myeloid compartment through the lens of NMF gene programs (inflammation, ISG, macrophage polarization states including M2-like program). Applicants used PHATE maps and other trajectory methods to determine which factors in the TME are inducing myeloid phenotypes (e.g. cytokine—NMF correlations).

The CRC atlas identified a CXCL13 T cell program that marks activated T cells in human tumors and is a superior marker compared to cytolytic programs. Applicants also identified programs related to IL17+CD4+ and CD8+ T cells. Applicants can compare the cell states identified with states from previous scRNAseq studies. The CXCL13+ T cell program may be a better indicator of anti-tumor immunity (e.g., predictor of anti-PD1 response) than current measurements (MMR status, immunoscore).

The CRC atlas identified that patient-specific and shared malignant programs correlate with histologic features, genetic drivers, and immunologic state.

The CRC atlas identified that the co-occurrence of gene programs identifies cellular interaction hubs (e.g, expression of programs in different cell types). The M2-like myeloid program may drive a malignant invasiveness program and potentially can predict nodal state. A chemokine/chemokine receptor feed forward loop may drive the accumulation of CXCL13+ T cells. Additionally, immunohistochemical/mRNA FISH staining shows the spatial co-occurrence of the identified programs.

Signature Genes

In certain embodiments, the CRC atlas includes gene signatures and/or biological programs (see, Tables 1-14). In one aspect, the embodiments disclosed herein relate to a method of detecting CRC signatures in tumor microenvironments (TME). Detection may indicate response to a specific treatment or be used to identify a therapeutic agent. In another aspect, the embodiments disclosed herein relate to a method of altering or shifting CRC tumor microenvironments (TME) by altering or shifting one or more of the gene signatures and/or biological programs.

As used herein a "signature" may encompass any gene or genes, protein or proteins, or epigenetic element(s) whose expression profile or whose occurrence is associated with a specific cell type, subtype, or cell state of a specific cell type or subtype within a population of cells. The gene signatures and/or biological programs are specific from stromal cell types, epithelial cell types, endothelial cell types, adaptive and innate immune cell types, and malignant cells. For ease of discussion, when discussing gene expression, any of gene or genes, protein or proteins, or epigenetic element(s) may be substituted. As used herein, the terms "signature", "expression profile", or "expression program" may be used interchangeably. As used herein the term "biological program" can be used interchangeably with "expression program" or "transcriptional program" and may refer to a set of genes that share a role in a biological function (e.g., an activation program, cell differentiation program, proliferation program). Biological programs can include a pattern of gene expression that result in a corresponding physiological event or phenotypic trait. Biological programs can include up to several hundred genes that are expressed in a spatially and temporally controlled fashion. Expression of individual genes can be shared between biological programs. Expression of individual genes can be shared among different single cell types; however, expression of a biological program may be cell type specific or temporally specific (e.g., the biological program is expressed in a cell type at a specific time). Expression of a biological program may be regulated by a master switch, such as a nuclear receptor or transcription factor. As used herein, the term "topic" refers to a biological program. The biological program can be modeled as a distribution over expressed genes. It is to be understood that also when referring to proteins (e.g. differentially expressed proteins), such may fall within the definition of "gene" signature. Levels of expression or activity or prevalence may be compared between different cells in order to characterize or identify, for instance, signatures specific for cell (sub)populations. Increased or decreased expression or activity or prevalence of signature genes may be compared between different cells in order to characterize or identify, for example, specific cell (sub)populations. The detection of a signature in single cells may be used to identify and quantitate, for example, specific cell (sub)populations. A signature may include a gene or genes, protein or proteins, or epigenetic element(s) whose expression or occurrence is specific to a cell (sub)population, such that expression or occurrence is exclusive to the cell (sub)population. A gene signature as used herein, may thus refer to any set of up- and down-regulated genes that are representative of a cell type or subtype. A gene signature as used herein, may also refer to any set of up- and down-regulated genes between different cells or cell (sub)populations derived from a gene-expression profile. For example, a gene signature may comprise a list of genes differentially expressed in a cell (sub)type or cell state of interest.

The signature as defined herein (being it a gene signature, protein signature or other genetic or epigenetic signature) can be used to indicate the presence of a cell type, a subtype of the cell type, the state of the microenvironment of a population of cells, a particular cell type population or subpopulation, and/or the overall status of the entire cell (sub)population. Furthermore, the signature may be indicative of cells within a population of cells in vivo. The signature may also be used to suggest for instance particular therapies, or follow up treatment, or to suggest ways to modulate immune systems. The signatures of the present invention may be discovered by analysis of expression profiles of single-cells within a population of cells from isolated samples (e.g. tumor samples), thus allowing the discovery of novel cell subtypes or cell states that were previously invisible or unrecognized. The presence of subtypes or cell states may be determined by subtype specific or cell state specific signatures. The presence of these specific cell (sub)types or cell states may be determined by applying the signature genes to bulk sequencing data in a sample. In certain example embodiments, the signatures of the present invention may be microenvironment specific, such as their expression in a particular spatio-temporal context. In certain example embodiments, signatures as discussed herein are specific to a particular pathological context. In certain example embodiments, a combination of cell subtypes having a particular signature may indicate an outcome. In certain example embodiments, the signatures can be used to deconvolute the network of cells present in a particular pathological condition. In certain example embodiments, the presence of specific cells and cell subtypes are indicative of a particular response to treatment, such as including increased or decreased susceptibility to treatment. The signature may indicate the presence of one particular cell type. In one embodiment, the novel signatures are used to detect multiple cell states or hierarchies that occur in subpopulations of cancer cells that are linked to particular pathological condition (e.g. cancer grade), or linked to a particular outcome or progression of the disease (e.g. metastasis), or linked to a particular response to treatment of the disease.

The signature according to certain embodiments of the present invention may comprise or consist of one or more genes, proteins and/or epigenetic elements, such as for instance 1, 2, 3, 4, 5, 6, 7, 8, 9, 10 or more. In certain embodiments, the signature may comprise or consist of two or more genes, proteins and/or epigenetic elements, such as for instance 2, 3, 4, 5, 6, 7, 8, 9, 10 or more. In certain embodiments, the signature may comprise or consist of three or more genes, proteins and/or epigenetic elements, such as for instance 3, 4, 5, 6, 7, 8, 9, 10 or more. In certain embodiments, the signature may comprise or consist of four or more genes, proteins and/or epigenetic elements, such as for instance 4, 5, 6, 7, 8, 9, 10 or more. In certain embodiments, the signature may comprise or consist of five or more genes, proteins and/or epigenetic elements, such as for instance 5, 6, 7, 8, 9, 10 or more. In certain embodiments, the signature may comprise or consist of six or more genes, proteins and/or epigenetic elements, such as for instance 6, 7, 8, 9, 10 or more. In certain embodiments, the signature may comprise or consist of seven or more genes, proteins and/or epigenetic elements, such as for instance 7, 8, 9, 10 or more. In certain embodiments, the signature may comprise or consist of eight or more genes, proteins and/or epigenetic elements, such as for instance 8, 9, 10 or more. In certain embodiments, the signature may comprise or consist of nine or more genes, proteins and/or epigenetic elements, such as for instance 9, 10 or more. In certain embodiments, the signature may comprise or consist of ten or more genes, proteins and/or epigenetic elements, such as for instance 10, 11, 12, 13, 14, 15, or more. It is to be understood that a signature according to the invention may for instance also include genes or proteins as well as epigenetic elements combined.

In certain embodiments, a signature is characterized as being specific for a particular tumor cell or tumor cell (sub)population if it is upregulated or only present, detected or detectable in that particular tumor cell or tumor cell (sub)population, or alternatively is downregulated or only absent, or undetectable in that particular tumor cell or tumor cell (sub)population. In this context, a signature consists of one or more differentially expressed genes/proteins or differential epigenetic elements when comparing different cells or cell (sub)populations, including comparing different tumor cells or tumor cell (sub)populations, as well as comparing tumor cells or tumor cell (sub)populations with non-tumor cells or non-tumor cell (sub)populations. It is to be understood that "differentially expressed" genes/proteins include genes/proteins which are up- or down-regulated as well as genes/proteins which are turned on or off. When referring to up- or down-regulation, in certain embodiments, such up- or down-regulation is preferably at least two-fold, such as two-fold, three-fold, four-fold, five-fold, or more, such as for instance at least ten-fold, at least 20-fold, at least 30-fold, at least 40-fold, at least 50-fold, or more. Alternatively, or in addition, differential expression may be determined based on common statistical tests, as is known in the art.

As discussed herein, differentially expressed genes/proteins, or differential epigenetic elements may be differentially expressed on a single cell level, or may be differentially expressed on a cell population level. Preferably, the differentially expressed genes/proteins or epigenetic elements as discussed herein, such as constituting the gene signatures as discussed herein, when as to the cell population level, refer to genes that are differentially expressed in all or substantially all cells of the population (such as at least 80%, preferably at least 90%, such as at least 95% of the individual cells). This allows one to define a particular subpopulation of tumor cells. As referred to herein, a "subpopulation" of cells preferably refers to a particular subset of cells of a particular cell type which can be distinguished or are uniquely identifiable and set apart from other cells of this cell type. The cell subpopulation may be phenotypically characterized, and is preferably characterized by the signature as discussed herein. A cell (sub)population as referred to herein may constitute of a (sub)population of cells of a particular cell type characterized by a specific cell state.

When referring to induction, or alternatively suppression of a particular signature, preferable is meant induction or alternatively suppression (or upregulation or downregulation) of at least one gene/protein and/or epigenetic element of the signature, such as for instance at least to, at least three, at least four, at least five, at least six, or all genes/proteins and/or epigenetic elements of the signature.

Signatures may be functionally validated as being uniquely associated with a particular immune responder phenotype. Induction or suppression of a particular signature may consequentially be associated with or causally drive a particular immune responder phenotype.

Various aspects and embodiments of the invention may involve analyzing gene signatures, protein signature, and/or other genetic or epigenetic signature based on single cell analyses (e.g. single cell RNA sequencing) or alternatively based on cell population analyses, as is defined herein elsewhere.

In further aspects, the invention relates to gene signatures, protein signature, and/or other genetic or epigenetic signature of particular tumor cell subpopulations, as defined herein elsewhere. The invention hereto also further relates to particular tumor cell subpopulations, which may be identified based on the methods according to the invention as discussed herein; as well as methods to obtain such cell (sub)populations and screening methods to identify agents capable of inducing or suppressing particular tumor cell (sub)populations.

The invention further relates to various uses of the gene signatures, protein signature, and/or other genetic or epigenetic signature as defined herein, as well as various uses of the tumor cells or tumor cell (sub)populations as defined herein. Particular advantageous uses include methods for identifying agents capable of inducing or suppressing particular tumor cell (sub)populations based on the gene signatures, protein signature, and/or other genetic or epigenetic signature as defined herein. The invention further relates to agents capable of inducing or suppressing particular tumor cell (sub)populations based on the gene signatures, protein signature, and/or other genetic or epigenetic signature as defined herein, as well as their use for modulating, such as inducing or repressing, a particular gene signature, protein signature, and/or other genetic or epigenetic signature. In one embodiment, genes in one population of cells may be activated or suppressed in order to affect the cells of another population. In related aspects, modulating, such as inducing or repressing, a particular gene signature, protein signature, and/or other genetic or epigenetic signature may modify overall tumor composition, such as tumor cell composition, such as tumor cell subpopulation composition or distribution, or functionality.

The signature genes of the present invention were discovered by analysis of expression profiles of single-cells within a population of cells from freshly isolated tumors, thus allowing the discovery of novel cell subtypes that were previously invisible in a population of cells within a tumor. The presence of subtypes may be determined by subtype specific signature genes. The presence of these specific cell types may be determined by applying the signature genes to bulk sequencing data in a patient tumor. Not being bound by a theory, a tumor is a conglomeration of many cells that make up a tumor microenvironment, whereby the cells communicate and affect each other in specific ways. As such, specific cell types within this microenvironment may express signature genes specific for this microenvironment. Not being bound by a theory the signature genes of the present invention may be microenvironment specific, such as their expression in a tumor. Not being bound by a theory, signature genes determined in single cells that originated in a tumor are specific to other tumors. Not being bound by a theory, a combination of cell subtypes in a tumor may indicate an outcome. Not being bound by a theory, the signature genes can be used to deconvolute the network of cells present in a tumor based on comparing them to data from bulk analysis of a tumor sample. Not being bound by a theory the presence of specific cells and cell subtypes may be indicative of tumor growth, invasiveness and resistance to treatment. The signature gene may indicate the presence of one particular cell type. In one embodiment, the signature genes may indicate that tumor infiltrating T-cells are present. The presence of cell types within a tumor may indicate that the tumor will be resistant to a treatment. In one embodiment, the signature genes of the present invention are applied to bulk sequencing data from a tumor sample obtained from a subject, such that information relating to disease outcome and personalized treatments is determined. In one embodiment, the novel signature genes are used to detect multiple cell states that occur in a subpopulation of tumor cells that are linked to resistance to targeted therapies and progressive tumor growth. In certain embodiments, one or more signature genes or gene programs in any of Tables 1-14 are detected or modulated.

All gene name symbols refer to the gene as commonly known in the art. The examples described herein that refer to the mouse gene names are to be understood to also encompasses human genes, as well as genes in any other organism (e.g., homologous, orthologous genes). The term, homolog, may apply to the relationship between genes separated by the event of speciation (e.g., ortholog). Orthologs are genes in different species that evolved from a common ancestral gene by speciation. Normally, orthologs retain the same function in the course of evolution. Gene symbols may be those referred to by the HUGO Gene Nomenclature Committee (HGNC) or National Center for Biotechnology Information (NCBI). Any reference to the gene symbol is a reference made to the entire gene or variants of the gene. The signature as described herein may encompass any of the genes described herein.

Diagnostic and Screening Methods

In certain embodiments, CRC programs are detected to determine if a tumor is responsive to an immunotherapy (adoptive cell transfer and/or checkpoint blockade therapy) or IDO1 inhibition. In certain embodiments, a malignant program that is immune suppressive (e.g., CXCR3 chemokines (CXCL10/CXCL11) or IDO1 and PDL1 indicates that a subject is responsive to an immunotherapy. For example, expression of PDL1 may indicate that a CPB therapy is effective. In certain embodiments a CXCL13 program (T_21 T cell program) indicates that the tumor has activated capable of anti-tumor activity. Thus, inhibition of repressive signals with CPB therapy and/or IDO1 inhibitors may allow the activated T cells to eliminate the tumor. In certain embodiments, a myeloid specific program is detected. In certain embodiments, the program is specific to myeloid-derived suppressor cells (MDSCs), such that the program indicates immune suppression. In certain embodiments, a program expressed in Tregs is detected to indicate levels of immune suppression. In certain embodiments, a consensus malignant program is detected to indicate if the tumor is sensitive to a standard treatment or a treatment described herein. In certain embodiments, transcription factors that are in the programs are detected. In certain embodiments, cell surface proteins in a program are detected (e.g., PDL1 or IDO1). In certain embodiments, an interferon stimulated gene program is detected to indicate interaction between malignant cells and the tumor microenvironment. In certain embodiments, detection of one or more programs indicates survival. In certain embodiments, the programs can be detected in response to a screen for therapeutic agents.

The invention provides biomarkers for the identification, diagnosis, prognosis and manipulation of tumor properties, for use in a variety of diagnostic and/or therapeutic indications. In certain embodiments, the one or more biomarkers are selected from one or more signature genes or signatures as described herein. In certain embodiments, the invention provides uses of the biomarkers for predicting tumor response to immunotherapy, such as checkpoint blockade (CPB) therapy or adoptive cell transfer, and for selecting cancer treatments. In certain embodiments, a tumor is classified as responsive or non-responsive to an immunotherapy (e.g., CPB therapy or adoptive cell transfer, described further herein). In preferred embodiments, the biomarkers indicate response to CBP therapy and can be used to select the appropriate treatment, preferably a treatment including an immunotherapy. In certain embodiments, biomarkers are analyzed before and after a treatment. Biomarkers in the context of the present invention encompasses, without limitation nucleic acids, proteins, reaction products, and metabolites, together with their polymorphisms, mutations, variants, modifications, subunits, fragments, and other analytes or sample-derived measures. In certain embodiments, biomarkers include the signature genes or signature gene products, and/or cells as described herein.

The terms "diagnosis" and "monitoring" are commonplace and well-understood in medical practice. By means of further explanation and without limitation the term "diagnosis" generally refers to the process or act of recognising, deciding on or concluding on a disease or condition in a subject on the basis of symptoms and signs and/or from results of various diagnostic procedures (such as, for example, from knowing the presence, absence and/or quantity of one or more biomarkers characteristic of the diagnosed disease or condition).

The terms "prognosing" or "prognosis" generally refer to an anticipation on the progression of a disease or condition and the prospect (e.g., the probability, duration, and/or extent) of recovery. A good prognosis of the diseases or conditions taught herein may generally encompass anticipation of a satisfactory partial or complete recovery from the diseases or conditions, preferably within an acceptable time period. A good prognosis of such may more commonly encompass anticipation of not further worsening or aggravating of such, preferably within a given time period. A poor prognosis of the diseases or conditions as taught herein may generally encompass anticipation of a substandard recovery and/or unsatisfactorily slow recovery, or to substantially no recovery or even further worsening of such.

The biomarkers of the present invention are useful in methods of identifying patient populations with a CPB responder or non-responder phenotype based on a detected level of expression, activity and/or function of one or more biomarkers. These biomarkers are also useful in monitoring subjects undergoing treatments and therapies for suitable or aberrant response(s) to determine efficaciousness of the treatment or therapy and for selecting or modifying therapies and treatments that would be efficacious in treating, delaying the progression of or otherwise ameliorating a symptom. The biomarkers provided herein are useful for selecting a group of patients at a specific state of a disease with accuracy that facilitates selection of treatments.

The term "monitoring" generally refers to the follow-up of a disease or a condition in a subject for any changes which may occur over time.

The terms also encompass prediction of a disease. The terms "predicting" or "prediction" generally refer to an advance declaration, indication or foretelling of a disease or condition in a subject not (yet) having said disease or condition. For example, a prediction of a disease or condition in a subject may indicate a probability, chance or risk that the subject will develop said disease or condition, for example within a certain time period or by a certain age. Said probability, chance or risk may be indicated inter alia as an absolute value, range or statistics, or may be indicated relative to a suitable control subject or subject population (such as, e.g., relative to a general, normal or healthy subject or subject population). Hence, the probability, chance or risk that a subject will develop a disease or condition may be advantageously indicated as increased or decreased, or as fold-increased or fold-decreased relative to a suitable control subject or subject population. As used herein, the term "prediction" of the conditions or diseases as taught herein in a subject may also particularly mean that the subject has a 'positive' prediction of such, i.e., that the subject is at risk of having such (e.g., the risk is significantly increased vis-à-vis a control subject or subject population). The term "prediction of no" diseases or conditions as taught herein as described herein in a subject may particularly mean that the subject has a 'negative' prediction of such, i.e., that the subject's risk of having such is not significantly increased vis-à-vis a control subject or subject population.

Hence, the methods may rely on comparing the quantity of biomarkers, or gene or gene product signatures measured in samples from patients with reference values, wherein said reference values represent known predictions, diagnoses and/or prognoses of diseases or conditions as taught herein.

For example, distinct reference values may represent the prediction of a risk (e.g., an abnormally elevated risk) of having a given disease or condition as taught herein vs. the prediction of no or normal risk of having said disease or condition. In another example, distinct reference values may represent predictions of differing degrees of risk of having such disease or condition.

In a further example, distinct reference values can represent the diagnosis of a given disease or condition as taught herein vs. the diagnosis of no such disease or condition (such as, e.g., the diagnosis of healthy, or recovered from said disease or condition, etc.). In another example, distinct reference values may represent the diagnosis of such disease or condition of varying severity.

In yet another example, distinct reference values may represent a good prognosis for a given disease or condition as taught herein vs. a poor prognosis for said disease or condition. In a further example, distinct reference values may represent varyingly favourable or unfavourable prognoses for such disease or condition.

Such comparison may generally include any means to determine the presence or absence of at least one difference and optionally of the size of such difference between values being compared. A comparison may include a visual inspection, an arithmetical or statistical comparison of measurements. Such statistical comparisons include, but are not limited to, applying a rule.

Reference values may be established according to known procedures previously employed for other cell populations, biomarkers and gene or gene product signatures. For example, a reference value may be established in an individual or a population of individuals characterised by a particular diagnosis, prediction and/or prognosis of said disease or condition (i.e., for whom said diagnosis, prediction and/or prognosis of the disease or condition holds true). Such population may comprise without limitation 2 or more, 10 or more, 100 or more, or even several hundred or more individuals.

A "deviation" of a first value from a second value may generally encompass any direction (e.g., increase: first value>second value; or decrease: first value<second value) and any extent of alteration.

For example, a deviation may encompass a decrease in a first value by, without limitation, at least about 10% (about 0.9-fold or less), or by at least about 20% (about 0.8-fold or less), or by at least about 30% (about 0.7-fold or less), or by at least about 40% (about 0.6-fold or less), or by at least about 50% (about 0.5-fold or less), or by at least about 60% (about 0.4-fold or less), or by at least about 70% (about 0.3-fold or less), or by at least about 80% (about 0.2-fold or less), or by at least about 90% (about 0.1-fold or less), relative to a second value with which a comparison is being made.

For example, a deviation may encompass an increase of a first value by, without limitation, at least about 10% (about 1.1-fold or more), or by at least about 20% (about 1.2-fold or more), or by at least about 30% (about 1.3-fold or more), or by at least about 40% (about 1.4-fold or more), or by at least about 50% (about 1.5-fold or more), or by at least about 60% (about 1.6-fold or more), or by at least about 70% (about 1.7-fold or more), or by at least about 80% (about 1.8-fold or more), or by at least about 90% (about 1.9-fold or more), or by at least about 100% (about 2-fold or more), or by at least about 150% (about 2.5-fold or more), or by at least about 200% (about 3-fold or more), or by at least about 500% (about 6-fold or more), or by at least about 700% (about 8-fold or more), or like, relative to a second value with which a comparison is being made.

Preferably, a deviation may refer to a statistically significant observed alteration. For example, a deviation may refer to an observed alteration which falls outside of error margins of reference values in a given population (as expressed, for example, by standard deviation or standard error, or by a predetermined multiple thereof, e.g., ±1×SD or ±2×SD or ±3×SD, or ±1×SE or ±2×SE or ±3×SE). Deviation may also refer to a value falling outside of a reference range defined by values in a given population (for example, outside of a range which comprises ≥40%, ≥50%, ≥60%, ≥70%, ≥75% or ≥80% or ≥85% or ≥90% or ≥95% or even ≥100% of values in said population).

In a further embodiment, a deviation may be concluded if an observed alteration is beyond a given threshold or cut-off. Such threshold or cut-off may be selected as generally known in the art to provide for a chosen sensitivity and/or specificity of the prediction methods, e.g., sensitivity and/or specificity of at least 50%, or at least 60%, or at least 70%, or at least 80%, or at least 85%, or at least 90%, or at least 95%.

For example, receiver-operating characteristic (ROC) curve analysis can be used to select an optimal cut-off value of the quantity of a given immune cell population, biomarker or gene or gene product signatures, for clinical use of the present diagnostic tests, based on acceptable sensitivity and specificity, or related performance measures which are well-knownper se, such as positive predictive value (PPV), negative predictive value (NPV), positive likelihood ratio (LR+), negative likelihood ratio (LR−), Youden index, or similar.

Detection of Biomarkers

In one embodiment, the signature genes, biomarkers, and/or cells may be detected or isolated by immunofluorescence, immunohistochemistry (IHC), fluorescence activated cell sorting (FACS), mass spectrometry (MS), mass cytometry (CyTOF), sequencing, RNA-seq, single cell RNA-seq (described further herein), quantitative RT-PCR, single cell qPCR, FISH, RNA-FISH, MERFISH (multiplex (in situ) RNA FISH) and/or by in situ hybridization. Other methods including absorbance assays and colorimetric assays are known in the art and may be used herein. Detection may comprise primers and/or probes or fluorescently bar-coded oligonucleotide probes for hybridization to RNA (see e.g., Geiss G K, et al., Direct multiplexed measurement of gene expression with color-coded probe pairs. Nat Biotechnol. 2008 March; 26(3):317-25). In certain embodiments, cancer is diagnosed, prognosed, or monitored. For example, a tissue sample may be obtained and analyzed for specific cell markers (IHC) or specific transcripts (e.g., RNA-FISH). In one embodiment, tumor cells are stained for cell subtype specific signature genes. In one embodiment, the cells are fixed. In another embodiment, the cells are formalin fixed and paraffin embedded. Not being bound by a theory, the presence of the tumor subtypes indicate outcome and personalized treatments.

The present invention also may comprise a kit with a detection reagent that binds to one or more biomarkers or can be used to detect one or more biomarkers.

Sequencing

In certain embodiments, sequencing comprises high-throughput (formerly "next-generation") technologies to generate sequencing reads. In DNA sequencing, a read is an inferred sequence of base pairs (or base pair probabilities) corresponding to all or part of a single DNA fragment. A typical sequencing experiment involves fragmentation of the genome into millions of molecules or generating complementary DNA (cDNA) fragments, which are size-selected and ligated to adapters. The set of fragments is referred to as a sequencing library, which is sequenced to produce a set of reads. Methods for constructing sequencing libraries are known in the art (see, e.g., Head et al., Library construction for next-generation sequencing: Overviews and challenges. Biotechniques. 2014; 56(2): 61-77). A "library" or "fragment library" may be a collection of nucleic acid molecules derived from one or more nucleic acid samples, in which fragments of nucleic acid have been modified, generally by incorporating terminal adapter sequences comprising one or more primer binding sites and identifiable sequence tags. In certain embodiments, the library members (e.g., genomic DNA, cDNA) may include sequencing adaptors that are compatible with use in, e.g., Illumina's reversible terminator method, long read nanopore sequencing, Roche's pyrosequencing method (454), Life Technologies' sequencing by ligation (the SOLiD platform) or Life Technologies' Ion Torrent platform. Examples of such methods are described in the following references: Margulies et al (Nature 2005 437: 376-80); Schneider and Dekker (Nat Biotechnol. 2012 Apr. 10; 30(4):326-8); Ronaghi et al (Analytical Biochemistry 1996 242: 84-9); Shendure et al (Science 2005 309: 1728-32); Imelfort et al (Brief Bioinform. 2009 10:609-18); Fox et al (Methods Mol. Biol. 2009; 553:79-108); Appleby et al (Methods Mol. Biol. 2009; 513:19-39); and Morozova et al (Genomics. 2008 92:255-64), which are incorporated by reference for the general descriptions of the methods and the particular steps of the methods, including all starting products, reagents, and final products for each of the steps.

In certain embodiments, the present invention includes whole genome sequencing. Whole genome sequencing (also known as WGS, full genome sequencing, complete genome sequencing, or entire genome sequencing) is the process of determining the complete DNA sequence of an organism's genome at a single time. This entails sequencing all of an organism's chromosomal DNA as well as DNA contained in the mitochondria and, for plants, in the chloroplast. "Whole genome amplification" ("WGA") refers to any amplification method that aims to produce an amplification product that is representative of the genome from which it was amplified. Non-limiting WGA methods include Primer extension PCR (PEP) and improved PEP (I-PEP), Degenerated oligonucleotide primed PCR (DOP-PCR), Ligation-mediated PCR (LMP), T7-based linear amplification of DNA (TLAD), and Multiple displacement amplification (MDA).

In certain embodiments, the present invention includes whole exome sequencing. Exome sequencing, also known as whole exome sequencing (WES), is a genomic technique for sequencing all of the protein-coding genes in a genome (known as the exome) (see, e.g., Ng et al., 2009, Nature volume 461, pages 272-276). It consists of two steps: the first step is to select only the subset of DNA that encodes proteins. These regions are known as exons—humans have about 180,000 exons, constituting about 1% of the human genome, or approximately 30 million base pairs. The second step is to sequence the exonic DNA using any high-throughput DNA sequencing technology. In certain embodiments, whole exome sequencing is used to determine somatic mutations in genes associated with disease (e.g., cancer mutations).

In certain embodiments, targeted sequencing is used in the present invention (see, e.g., Mantere et al., PLoS Genet 12 e1005816 2016; and Carneiro et al. BMC Genomics, 2012 13:375). Targeted gene sequencing panels are useful tools for analyzing specific mutations in a given sample. Focused panels contain a select set of genes or gene regions that have known or suspected associations with the disease or phenotype under study. In certain embodiments, targeted sequencing is used to detect mutations associated with a disease in a subject in need thereof. Targeted sequencing can increase the cost-effectiveness of variant discovery and detection.

In certain embodiments, multiple displacement amplification (MDA) is used to generate a sequencing library (e.g., single cell genome sequencing). Multiple displacement amplification (MDA, is a non-PCR-based isothermal method based on the annealing of random hexamers to denatured DNA, followed by strand-displacement synthesis at constant temperature (Blanco et al. J. Biol. Chem. 1989, 264, 8935-8940). It has been applied to samples with small quantities of genomic DNA, leading to the synthesis of high molecular weight DNA with limited sequence representation bias (Lizardi et al. Nature Genetics 1998, 19, 225-232; Dean et al., Proc. Natl. Acad. Sci. U.S.A 2002, 99, 5261-5266). As DNA is synthesized by strand displacement, a gradually increasing number of priming events occur, forming a network of hyper-branched DNA structures. The reaction can be catalyzed by enzymes such as the Phi29 DNA polymerase or the large fragment of the Bst DNA polymerase. The Phi29 DNA polymerase possesses a proofreading activity resulting in error rates 100 times lower than Taq polymerase (Lasken et al. Trends Biotech. 2003, 21, 531-535).

In certain embodiments, the invention involves the Assay for Transposase Accessible Chromatin sequencing (ATAC-seq) or single cell ATAC-seq as described (see, e.g., Buenrostro, et al., Transposition of native chromatin for fast and sensitive epigenomic profiling of open chromatin, DNA-binding proteins and nucleosome position. Nature methods 2013; 10 (12): 1213-1218; Buenrostro et al., Single-cell chromatin accessibility reveals principles of regulatory variation. Nature 523, 486-490 (2015); Cusanovich, D. A., Daza, R., Adey, A., Pliner, H., Christiansen, L., Gunderson, K. L., Steemers, F. J., Trapnell, C. & Shendure, J. Multiplex single-cell profiling of chromatin accessibility by combinatorial cellular indexing. Science. 2015 May 22; 348(6237): 910-4. doi: 10.1126/science.aab1601. Epub 2015 May 7; US20160208323A1; US20160060691A1; and WO2017156336A1). The term "tagmentation" refers to a step in the Assay for Transposase Accessible Chromatin using sequencing (ATAC-seq) as described. Specifically, a hyperactive Tn5 transposase loaded in vitro with adapters for high-throughput DNA sequencing, can simultaneously fragment and tag a genome with sequencing adapters. In certain embodiments, ATAC-seq is used on a bulk DNA sample to determine mitochondrial mutations.

In certain embodiments, a transcriptome is sequenced. The transcriptome may be used to genotype nuclear and mitochondrial genomes in addition to determining gene expression. As used herein the term "transcriptome" refers to the set of transcripts molecules. In some embodiments, transcript refers to RNA molecules, e.g., messenger RNA (mRNA) molecules, small interfering RNA (siRNA) molecules, transfer RNA (tRNA) molecules, ribosomal RNA (rRNA) molecules, and complimentary sequences, e.g., cDNA molecules. In some embodiments, a transcriptome refers to a set of mRNA molecules. In some embodiments, a transcriptome refers to a set of cDNA molecules. In some embodiments, a transcriptome refers to one or more of mRNA molecules, siRNA molecules, tRNA molecules, rRNA molecules, in a sample, for example, a single cell or a population of cells. In some embodiments, a transcriptome refers to cDNA generated from one or more of mRNA molecules, siRNA molecules, tRNA molecules, rRNA molecules, in a sample, for example, a single cell or a population of cells. In some embodiments, a transcriptome refers to 50%, 55, 60, 65, 70, 75, 80, 85, 90, 91, 92, 93, 94, 95, 96, 97, 98, 99, 99.9, or 100% of transcripts from a single cell or a population of cells. In some embodiments, transcriptome not only refers to the species of transcripts, such as mRNA species, but also the amount of each species in the sample. In some embodiments, a transcriptome includes each mRNA molecule in the sample, such as all the mRNA molecules in a single cell.

In certain embodiments, the invention involves single cell RNA sequencing (see, e.g., Kalisky, T., Blainey, P. & Quake, S. R. Genomic Analysis at the Single-Cell Level. Annual review of genetics 45, 431-445, (2011); Kalisky, T. & Quake, S. R. Single-cell genomics. Nature Methods 8, 311-314 (2011); Islam, S. et al. Characterization of the single-cell transcriptional landscape by highly multiplex RNA-seq. Genome Research, (2011); Tang, F. et al. RNA- Seq analysis to capture the transcriptome landscape of a single cell. Nature Protocols 5, 516-535, (2010); Tang, F. et al. mRNA-Seq whole-transcriptome analysis of a single cell. Nature Methods 6, 377-382, (2009); Ramskold, D. et al. Full-length mRNA-Seq from single-cell levels of RNA and individual circulating tumor cells. Nature Biotechnology 30, 777-782, (2012); and Hashimshony, T., Wagner, F., Sher, N. & Yanai, I. CEL-Seq: Single-Cell RNA-Seq by Multiplexed Linear Amplification. Cell Reports, Cell Reports, Volume 2, Issue 3, p 666-673, 2012).

In certain embodiments, the present invention involves single cell RNA sequencing (scRNA-seq). In certain embodiments, the invention involves plate based single cell RNA sequencing (see, e.g., Picelli, S. et al., 2014, "Full-length RNA-seq from single cells using Smart-seq2" Nature protocols 9, 171-181, doi:10.1038/nprot.2014.006).

In certain embodiments, the invention involves high-throughput single-cell RNA-seq where the RNAs from different cells are tagged individually, allowing a single library to be created while retaining the cell identity of each read. In this regard reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO2014210353A2; Zilionis, et al., 2017, "Single-cell barcoding and sequencing using droplet microfluidics" Nat Protoc. Jan; 12(1):44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; Rosenberg et al., 2017, "Scaling single cell transcriptomics through split pool barcoding" bioRxiv preprint first posted online Feb. 2, 2017, doi: dx.doi.org/10.1101/105163; Rosenberg et al., "Single-cell profiling of the developing mouse brain and spinal cord with split-pool barcoding" Science 15 Mar. 2018; Vitak, et al., "Sequencing thousands of single-cell genomes with combinatorial indexing" Nature Methods, 14(3):302-308, 2017; Cao, et al., Comprehensive single-cell transcriptional profiling of a multicellular organism. Science, 357(6352):661-667, 2017; Gierahn et al., "Seq-Well: portable, low-costRNA sequencing of single cells at high throughput" Nature Methods 14, 395-398 (2017); and Hughes, et al., "Highly Efficient, Massively-Parallel Single-Cell RNA-Seq Reveals Cellular States and Molecular Features of Human Skin Pathology" bioRxiv 689273; doi: doi.org/10.1101/689273, all the contents and disclosure of each of which are herein incorporated by reference in their entirety.

In certain embodiments, the invention involves single nucleus RNA sequencing. In this regard reference is made to Swiech et al., 2014, "In vivo interrogation of gene function in the mammalian brain using CRISPR-Cas9" Nature Biotechnology Vol. 33, pp. 102-106; Habib et al., 2016, "Div-Seq: Single-nucleus RNA-Seq reveals dynamics of rare adult newborn neurons" Science, Vol. 353, Issue 6302, pp. 925-928; Habib et al., 2017, "Massively parallel single-nucleus RNA-seq with DroNc-seq" Nat Methods. 2017 October; 14(10):955-958; International Patent Application No. PCT/US2016/059239, published as WO2017164936 on Sep. 28, 2017; International patent application number PCT/US2018/060860, published as WO/2019/094984 on May 16, 2019; International Patent Application No. PCT/US2019/055894, published as WO/2020/077236 on Apr. 16, 2020; and Drokhlyansky, et al., "The enteric nervous system of the human and mouse colon at a single-cell resolution," bioRxiv 746743; doi: doi.org/10.1101/746743, which are herein incorporated by reference in their entirety.

In certain embodiments, dimension reduction is used to cluster nuclei from single cells based on differentially expressed genes. In certain embodiments, the dimension reduction technique may be, but is not limited to, Uniform Manifold Approximation and Projection (UMAP) t-SNE, or PHATE (see, e.g., Becht et al., Evaluation of UMAP as an alternative to t-SNE for single-cell data, bioRxiv 298430; doi.org/10.1101/298430; Becht et al., 2019, Dimensionality reduction for visualizing single-cell data using UMAP, Nature Biotechnology volume 37, pages 38-44; and Moon et al., PHATE: A Dimensionality Reduction Method for Visualizing Trajectory Structures in High-Dimensional Biological Data, bioRxiv 120378; doi: doi.org/10.1101/120378).

The present invention may encompass incorporation of a unique molecular identifier (UMI) (see, e.g., Kivioja et al., 2012, Nat. Methods. 9 (1): 72-4 and Islam et al., 2014, Nat. Methods. 11 (2): 163-6) a unique sample barcode, a unique cell barcode (cell into the sequencing library, or a combination. The barcode as used herein refers to a short sequence of nucleotides (for example, DNA or RNA) that is used as an identifier for an associated molecule, such as a target molecule and/or target nucleic acid, or as an identifier of the source of an associated molecule, such as a sample or cell-of-origin. A barcode may also refer to any unique, non-naturally occurring, nucleic acid sequence that may be used to identify the originating source of a nucleic acid fragment.

Barcoding may be performed based on any of the compositions or methods disclosed in patent publication WO 2014047561 A1, Compositions and methods for labeling of agents, incorporated herein in its entirety. In certain embodiments barcoding uses an error correcting scheme (T. K. Moon, Error Correction Coding: Mathematical Methods and Algorithms (Wiley, New York, ed. 1, 2005)). Not being bound by a theory, amplified sequences from different sources can be sequenced together and resolved based on the barcode associated with each sequencing read.

In preferred embodiments, sequencing is performed using unique molecular identifiers (UMI). The term "unique molecular identifiers" (UMI) as used herein refers to a sequencing linker or a subtype of nucleic acid barcode used in a method that uses molecular tags to detect and quantify unique amplified products. A UMI is used to distinguish effects through a single clone from multiple clones. The term "clone" as used herein may refer to a single mRNA or target nucleic acid to be sequenced. Unique Molecular Identifiers may be short (usually 4-10 bp) random barcodes added to transcripts during reverse-transcription. They enable sequencing reads to be assigned to individual transcript molecules and thus the removal of amplification noise and biases from RNA-seq data. The UMI may also be used to determine the number of transcripts that gave rise to an amplified product.

MS Methods

Biomarker detection may also be evaluated using mass spectrometry methods. A variety of configurations of mass spectrometers can be used to detect biomarker values. Several types of mass spectrometers are available or can be produced with various configurations. In general, a mass spectrometer has the following major components: a sample inlet, an ion source, a mass analyzer, a detector, a vacuum system, and instrument-control system, and a data system. Difference in the sample inlet, ion source, and mass analyzer generally define the type of instrument and its capabilities. For example, an inlet can be a capillary-column liquid chromatography source or can be a direct probe or stage such as used in matrix-assisted laser desorption. Common ion sources are, for example, electrospray, including nanospray and microspray or matrix-assisted laser desorption. Common mass analyzers include a quadrupole mass filter, ion trap mass analyzer and time-of-flight mass analyzer. Additional mass spectrometry methods are well known in the art (see Burlingame et al., Anal. Chem. 70:647 R-716R (1998); Kinter and Sherman, New York (2000)).

Protein biomarkers and biomarker values can be detected and measured by any of the following: electrospray ionization mass spectrometry (ESI-MS), ESI-MS/MS, ESI-MS/(MS)n, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), tandem time-of-flight (TOF/TOF) technology, called ultraflex III TOF/TOF, atmospheric pressure chemical ionization mass spectrometry (APCI-MS), APCI-MS/MS, APCI-(MS).sup.N, atmospheric pressure photoionization mass spectrometry (APPI-MS), APPI-MS/MS, and APPI-(MS).sup.N, quadrupole mass spectrometry, Fourier transform mass spectrometry (FTMS), quantitative mass spectrometry, and ion trap mass spectrometry.

Sample preparation strategies are used to label and enrich samples before mass spectroscopic characterization of protein biomarkers and determination biomarker values. Labeling methods include but are not limited to isobaric tag for relative and absolute quantitation (iTRAQ) and stable isotope labeling with amino acids in cell culture (SILAC). Capture reagents used to selectively enrich samples for candidate biomarker proteins prior to mass spectroscopic analysis include but are not limited to aptamers, antibodies, nucleic acid probes, chimeras, small molecules, an F(ab')$_2$ fragment, a single chain antibody fragment, an Fv fragment, a single chain Fv fragment, a nucleic acid, a lectin, a ligand-binding receptor, affibodies, nanobodies, ankyrins, domain antibodies, alternative antibody scaffolds (e.g. diabodies, etc.) imprinted polymers, avimers, peptidomimetics, peptoids, peptide nucleic acids, threose nucleic acid, a hormone receptor, a cytokine receptor, and synthetic receptors, and modifications and fragments of these.

Immunoassays

Immunoassay methods are based on the reaction of an antibody to its corresponding target or analyte and can detect the analyte in a sample depending on the specific assay format. To improve specificity and sensitivity of an assay method based on immunoreactivity, monoclonal antibodies are often used because of their specific epitope recognition. Polyclonal antibodies have also been successfully used in various immunoassays because of their increased affinity for the target as compared to monoclonal antibodies. Immunoassays have been designed for use with a wide range of biological sample matrices. Immunoassay formats have been designed to provide qualitative, semi-quantitative, and quantitative results.

Quantitative results may be generated through the use of a standard curve created with known concentrations of the specific analyte to be detected. The response or signal from an unknown sample is plotted onto the standard curve, and a quantity or value corresponding to the target in the unknown sample is established.

Numerous immunoassay formats have been designed. ELISA or EIA can be quantitative for the detection of an analyte/biomarker. This method relies on attachment of a label to either the analyte or the antibody and the label component includes, either directly or indirectly, an enzyme. ELISA tests may be formatted for direct, indirect, competitive, or sandwich detection of the analyte. Other methods rely on labels such as, for example, radioisotopes ($I^{125}$) or fluorescence. Additional techniques include, for example, agglutination, nephelometry, turbidimetry, Western blot, immunoprecipitation, immunocytochemistry, immunohistochemistry, flow cytometry, Luminex assay, and others (see ImmunoAssay: A Practical Guide, edited by Brian Law, published by Taylor & Francis, Ltd., 2005 edition).

Exemplary assay formats include enzyme-linked immunosorbent assay (ELISA), radioimmunoassay, fluorescent, chemiluminescence, and fluorescence resonance energy transfer (FRET) or time resolved-FRET (TR-FRET) immunoassays. Examples of procedures for detecting biomarkers include biomarker immunoprecipitation followed by quantitative methods that allow size and peptide level discrimination, such as gel electrophoresis, capillary electrophoresis, planar electrochromatography, and the like.

Methods of detecting and/or quantifying a detectable label or signal generating material depend on the nature of the label. The products of reactions catalyzed by appropriate enzymes (where the detectable label is an enzyme; see above) can be, without limitation, fluorescent, luminescent, or radioactive or they may absorb visible or ultraviolet light. Examples of detectors suitable for detecting such detectable labels include, without limitation, x-ray film, radioactivity counters, scintillation counters, spectrophotometers, colorimeters, fluorometers, luminometers, and densitometers.

Any of the methods for detection can be performed in any format that allows for any suitable preparation, processing, and analysis of the reactions. This can be, for example, in multi-well assay plates (e.g., 96 wells or 384 wells) or using any suitable array or microarray. Stock solutions for various agents can be made manually or robotically, and all subsequent pipetting, diluting, mixing, distribution, washing, incubating, sample readout, data collection and analysis can be done robotically using commercially available analysis software, robotics, and detection instrumentation capable of detecting a detectable label.

Hybridization Assays

Such applications are hybridization assays in which a nucleic acid that displays "probe" nucleic acids for each of the genes to be assayed/profiled in the profile to be generated is employed. In these assays, a sample of target nucleic acids is first prepared from the initial nucleic acid sample being assayed, where preparation may include labeling of the target nucleic acids with a label, e.g., a member of a signal producing system. Following target nucleic acid sample preparation, the sample is contacted with the array under hybridization conditions, whereby complexes are formed between target nucleic acids that are complementary to probe sequences attached to the array surface. The presence of hybridized complexes is then detected, either qualitatively or quantitatively. Specific hybridization technology which may be practiced to generate the expression profiles employed in the subject methods includes the technology described in U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280. In these methods, an array of "probe" nucleic acids that includes a probe for each of the biomarkers whose expression is being assayed is contacted with target nucleic acids as described above. Contact is carried out under hybridization conditions, e.g., stringent hybridization conditions as described above, and unbound nucleic acid is then removed. The resultant pattern of hybridized nucleic acids provides information regarding expression for each of the biomarkers that have been probed, where the expression information is in terms of whether or not the gene is expressed and, typically, at what level, where the expression data, i.e., expression profile, may be both qualitative and quantitative.

Optimal hybridization conditions will depend on the length (e.g., oligomer vs. polynucleotide greater than 200 bases) and type (e.g., RNA, DNA, PNA) of labeled probe and immobilized polynucleotide or oligonucleotide. General parameters for specific (i.e., stringent) hybridization conditions for nucleic acids are described in Sambrook et al., supra, and in Ausubel et al., "Current Protocols in Molecular Biology", Greene Publishing and Wiley-interscience, NY (1987), which is incorporated in its entirety for all purposes. When the cDNA microarrays are used, typical hybridization conditions are hybridization in 5×SSC plus 0.2% SDS at 65 C for 4 hours followed by washes at 25° C. in low stringency wash buffer (1×SSC plus 0.2% SDS) followed by 10 minutes at 25° C. in high stringency wash buffer (0.1SSC plus 0.2% SDS) (see Shena et al., Proc. Natl. Acad. Sci. USA, Vol. 93, p. 10614 (1996)). Useful hybridization conditions are also provided in, e.g., Tijessen, Hybridization With Nucleic Acid Probes", Elsevier Science Publishers B.V. (1993) and Kricka, "Nonisotopic DNA Probe Techniques", Academic Press, San Diego, Calif. (1992).

In certain embodiments, a tumor can be categorized based on signature genes or gene programs expressed by the tumor. In certain embodiments, the tumor subtype is determined by bulk sequencing of a tumor, including the TME. In certain embodiments, single cell sequencing may be used to determine the expression of the signature genes in single cells of the tumor. In certain embodiments, tumor subtypes can be determined by determining the percentage of specific cell subtypes in the tumor that contribute to the average expression of the tumor. In certain embodiments, tumor samples contain different proportions of tumor cells and healthy cells. In certain embodiments, gene expression associated with the malignant cells are determined from bulk sequencing reads by deconvolution of the sample, such that gene expression associated with healthy tissue is subtracted from the overall gene expression (see, e.g., WO 2018/191553; and Puram et al., Cell. 2017 Dec. 14; 171(7):1611-1624.e24). For example, deconvoluting bulk gene expression data obtained from a tumor containing both malignant and non-malignant cells can include defining the relative frequency of a set of cell types in the tumor from the bulk gene expression data using cell type specific gene expression (e.g., cell types may be T cells, fibroblasts, macrophages, mast cells, B/plasma cells, endothelial cells, myocytes and dendritic cells); and defining a linear relationship between the frequency of the non-malignant cell types and the expression of a set of genes, wherein the set of genes comprises genes highly expressed by malignant cells and at most two non-malignant cell types, wherein the set of genes are derived from gene expression analysis of single cells in the tumor or the same tumor type, and wherein the residual of the linear relationship defines the malignant cell-specific (MCS) expression profile. Not being bound by a theory, subtracting non-malignant gene expression can allow the method to be used across different tumor samples obtained by different practitioners.

Screening for Modulating Agents

A further aspect of the invention relates to a method for identifying an agent capable of modulating one or more phenotypic aspects of a cell or cell population, e.g. a CRC cell population or program, as disclosed herein, comprising: a) applying a candidate agent to the cell or cell population; b) detecting modulation of one or more programs (e.g., Tables 1-14) or cell type composition of the cell or cell population by the candidate agent, thereby identifying the agent. The phenotypic aspects of the cell or cell population that is modulated may be a gene signature or biological program specific to a cell type or cell phenotype or phenotype specific to a population of cells (e.g., a responder phenotype). In certain embodiments, steps can include administering candidate modulating agents to cells, detecting identified cell (sub)populations for changes in signatures, or identifying relative changes in cell (sub) populations which may comprise detecting relative abundance of particular gene signatures.

The term "modulate" broadly denotes a qualitative and/or quantitative alteration, change or variation in that which is being modulated. Where modulation can be assessed quantitatively—for example, where modulation comprises or consists of a change in a quantifiable variable such as a quantifiable property of a cell or where a quantifiable variable provides a suitable surrogate for the modulation—modulation specifically encompasses both increase (e.g., activation) or decrease (e.g., inhibition) in the measured variable. The term encompasses any extent of such modulation, e.g., any extent of such increase or decrease, and may more particularly refer to statistically significant increase or decrease in the measured variable. By means of example, modulation may encompass an increase in the value of the measured variable by at least about 10%, e.g., by at least about 20%, preferably by at least about 30%, e.g., by at least about 40%, more preferably by at least about 50%, e.g., by at least about 75%, even more preferably by at least about 100%, e.g., by at least about 150%, 200%, 250%, 300%, 400% or by at least about 500%, compared to a reference situation without said modulation; or modulation may encompass a decrease or reduction in the value of the measured variable by at least about 10%, e.g., by at least about 20%, by at least about 30%, e.g., by at least about 40%, by at least about 50%, e.g., by at least about 60%, by at least about 70%, e.g., by at least about 80%, by at least about 90%, e.g., by at least about 95%, such as by at least about 96%, 97%, 98%, 99% or even by 100%, compared to a reference situation without said modulation. Preferably, modulation may be specific or selective, hence, one or more desired phenotypic aspects of an immune cell or immune cell population may be modulated without substantially altering other (unintended, undesired) phenotypic aspect(s).

The term "agent" broadly encompasses any condition, substance or agent capable of modulating one or more phenotypic aspects of a cell or cell population as disclosed herein. Such conditions, substances or agents may be of physical, chemical, biochemical and/or biological nature. The term "candidate agent" refers to any condition, substance or agent that is being examined for the ability to modulate one or more phenotypic aspects of a cell or cell population as disclosed herein in a method comprising applying the candidate agent to the cell or cell population (e.g., exposing the cell or cell population to the candidate agent or contacting the cell or cell population with the candidate agent) and observing whether the desired modulation takes place.

Agents may include any potential class of biologically active conditions, substances or agents, such as for instance antibodies, proteins, peptides, nucleic acids, oligonucleotides, small molecules, or combinations thereof, as described herein.

The methods of phenotypic analysis can be utilized for evaluating environmental stress and/or state, for screening of chemical libraries, and to screen or identify structural, syntenic, genomic, and/or organism and species variations. For example, a culture of cells, can be exposed to an environmental stress, such as but not limited to heat shock, osmolarity, hypoxia, cold, oxidative stress, radiation, starvation, a chemical (for example a therapeutic agent or potential therapeutic agent) and the like. After the stress is applied, a representative sample can be subjected to analysis, for example at various time points, and compared to a control, such as a sample from an organism or cell, for example a cell from an organism, or a standard value. By exposing cells, or fractions thereof, tissues, or even whole animals, to different members of the chemical libraries, and performing the methods described herein, different members of a chemical library can be screened for their effect on immune phenotypes thereof simultaneously in a relatively short amount of time, for example using a high throughput method.

Aspects of the present disclosure relate to the correlation of an agent with the spatial proximity and/or epigenetic profile of the nucleic acids in a sample of cells. In some embodiments, the disclosed methods can be used to screen chemical libraries for agents that modulate chromatin architecture epigenetic profiles, and/or relationships thereof.

In some embodiments, screening of test agents involves testing a combinatorial library containing a large number of potential modulator compounds. A combinatorial chemical library may be a collection of diverse chemical compounds generated by either chemical synthesis or biological synthesis, by combining a number of chemical "building blocks" such as reagents. For example, a linear combinatorial chemical library, such as a polypeptide library, is formed by combining a set of chemical building blocks (amino acids) in every possible way for a given compound length (for example the number of amino acids in a polypeptide compound). Millions of chemical compounds can be synthesized through such combinatorial mixing of chemical building blocks.

In certain embodiments, biomarkers are used to screen for therapeutic agents capable of shifting a tumor to a responsive state. In certain embodiments, biomarkers are screened in an animal model. In certain embodiments, a patient-derived xenograft (PDX) is used to screen cancer drugs and other types of treatment to see how they affect the biomarkers before they are given to the patient. A PDX model may also be used in the development of new cancer drugs. In certain embodiments, the biomarkers are the orthologues of the biomarkers in the animal model.

In certain embodiments, the present invention provides for gene signature screening. The concept of signature screening was introduced by Stegmaier et al. (Gene expression-based high-throughput screening (GE-HTS) and application to leukemia differentiation. Nature Genet. 36, 257-263 (2004)), who realized that if a gene-expression signature was the proxy for a phenotype of interest, it could be used to find small molecules that effect that phenotype without knowledge of a validated drug target. The signatures or biological programs of the present invention may be used to screen for drugs that reduce the signature or biological program in cells as described herein. The signature or biological program may be used for GE-HTS. In certain embodiments, pharmacological screens may be used to identify drugs that are selectively toxic to cells having a signature.

The Connectivity Map (cmap) is a collection of genome-wide transcriptional expression data from cultured human cells treated with bioactive small molecules and simple pattern-matching algorithms that together enable the discovery of functional connections between drugs, genes and diseases through the transitory feature of common gene-expression changes (see, Lamb et al., The Connectivity Map: Using Gene-Expression Signatures to Connect Small Molecules, Genes, and Disease. Science 29 Sep. 2006: Vol. 313, Issue 5795, pp. 1929-1935, DOI: 10.1126/science.1132939; and Lamb, J., The Connectivity Map: a new tool for biomedical research. Nature Reviews Cancer January 2007: Vol. 7, pp. 54-60). In certain embodiments, Cmap can be used to screen for small molecules capable of modulating a signature or biological program of the present invention in silico.

Cancer

In certain embodiments, the methods described herein are applicable to any cancer type. In preferred embodiments, the cancer is CRC. The cancer may include, without limitation, liquid tumors such as leukemia (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease, non-Hodgkin's disease), Waldenstrom's macroglobulinemia, heavy chain disease, or multiple myeloma.

The cancer may include, without limitation, solid tumors such as sarcomas and carcinomas. Examples of solid tumors include, but are not limited to fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, epithelial carcinoma, bronchogenic carcinoma, hepatoma, colorectal cancer (e.g., colon cancer, rectal cancer), anal cancer, pancreatic cancer (e.g., pancreatic adenocarcinoma, islet cell carcinoma, neuroendocrine tumors), breast cancer (e.g., ductal carcinoma, lobular carcinoma, inflammatory breast cancer, clear cell carcinoma, mucinous carcinoma), ovarian carcinoma (e.g., ovarian epithelial carcinoma or surface epithelial-stromal tumor including serous tumor, endometrioid tumor and mucinous cystadenocarcinoma, sex-cord-stromal tumor), prostate cancer, liver and bile duct carcinoma (e.g., hepatocellular carcinoma, cholangiocarcinoma, hemangioma), choriocarcinoma, seminoma, embryonal carcinoma, kidney cancer (e.g., renal cell carcinoma, clear cell carcinoma, Wilms' tumor, nephroblastoma), cervical cancer, uterine cancer (e.g., endometrial adenocarcinoma, uterine papillary serous carcinoma, uterine clear-cell carcinoma, uterine sarcomas and leiomyosarcomas, mixed mullerian tumors), testicular cancer, germ cell tumor, lung cancer (e.g., lung adenocarcinoma, squamous cell carcinoma, large cell carcinoma, bronchioloalveolar carcinoma, non-small-cell carcinoma, small cell carcinoma, mesothelioma), bladder carcinoma, signet ring cell carcinoma, cancer of the head and neck (e.g., squamous cell carcinomas), esophageal carcinoma (e.g., esophageal adenocarcinoma), tumors of the brain (e.g., glioma, glioblastoma, medulloblastoma, astrocytoma, medulloblastoma, craniopharyngioma, ependymoma, pinealoma, hemangioblastoma, acoustic neuroma, oligodendroglioma, schwannoma, meningioma), neuroblastoma, retinoblastoma, neuroendocrine tumor, melanoma, cancer of the stomach (e.g., stomach adenocarcinoma, gastrointestinal stromal tumor), or carcinoids. Lymphoproliferative disorders are also considered to be proliferative diseases.

Therapeutic Methods

In one aspect, the embodiments disclosed herein relate to a method of shifting CRC tumor microenvironments (TME). In certain embodiments, CRC programs are shifted to make a tumor more responsive to an immunotherapy (adoptive cell transfer and/or checkpoint blockade therapy) or IDO1 inhibition. As used herein, "shifting" a tumor microenvironment or a program refers to altering expression or activity of one or more genes expressed in the TME or gene program. Shifting a program may include altering a pattern of gene expression or activity, such that the program is enhanced or repressed. In certain embodiments, a malignant program that is immune suppressive is shifted (e.g., CXCR3 chemokines (CXCL10/CXCL11) or IDO1 and PDL1. In certain embodiments a CXCL13 program is enhanced (T_21 T cell program). In certain embodiments, a myeloid specific program is shifted. In certain embodiments, the program is specific to myeloid-derived suppressor cells (MDSCs), such that a program is shifted to prevent immune suppression. In certain embodiments, a program expressed in Tregs is shifted to prevent immune suppression. In certain embodiments, a consensus malignant program is shifted to make a tumor more sensitive to a standard treatment or a treatment described herein. In certain embodiments, transcription factors that are in the programs are targeted. In certain embodiments, cell surface proteins in a program are targeted (e.g., PDL1 or IDO1). In certain embodiments, an interferon stimulated gene program is shifted to prevent interaction between malignant cells and the tumor microenvironment. For example, to prevent malignant cells from interacting with activated T cells and suppressing an immune response or causing immune cells to be exhausted.

Therapeutic Agents

In certain embodiments, the present invention provides for one or more therapeutic agents (e.g., CPB therapy, IDO1 inhibitors, agonists or antagonists of a biological program). Targeting the identified combinations may provide for enhanced or otherwise previously unknown activity in the treatment of disease. In certain embodiments, targeting the combination may require less of the agent as compared to the current standard of care and provide for less toxicity and improved treatment. In certain embodiments, the agents are used to modulate cell types (e.g., shifting signatures in cancer subtypes). In certain embodiments, the one or more agents comprises a small molecule inhibitor, small molecule degrader (e.g., ATTEC, AUTAC, LYTAC, or PROTAC), genetic modifying agent, antibody, antibody fragment, antibody-like protein scaffold, aptamer, protein, or any combination thereof.

The terms "therapeutic agent", "therapeutic capable agent" or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested. As used herein "treating" includes ameliorating, curing, preventing it from becoming worse, slowing the rate of progression, or preventing the disorder from re-occurring (i.e., to prevent a relapse).

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The term also applies to a dose that will provide an image for detection by any one of the imaging methods described herein. The specific dose may vary depending on one or more of: the particular agent chosen, the dosing regimen to be followed, whether it is administered in combination with other compounds, timing of administration, the tissue to be imaged, and the physical delivery system in which it is carried.

For example, in methods for treating cancer in a subject, an effective amount of a combination of agents is any amount that provides an anti-cancer effect, such as reduces or prevents proliferation of a cancer cell or makes a cancer cell responsive to an immunotherapy.

Standard of Care

Aspects of the invention involve modifying the therapy within a standard of care based on the detection of any of the biomarkers as described herein. In one embodiment, therapy comprising an agent is administered within a standard of care where addition of the agent is synergistic within the steps of the standard of care. In one embodiment, the agent targets and/or shifts a tumor to an immunotherapy responder phenotype. In one embodiment, the agent inhibits expression or activity of one or more transcription factors capable of regulating a gene program. In one embodiment, the agent targets tumor cells expressing a gene program. The term "standard of care" as used herein refers to the current treatment that is accepted by medical experts as a proper treatment for a certain type of disease and that is widely used by healthcare professionals. Standard of care is also called best practice, standard medical care, and standard therapy. Standards of care for cancer generally include surgery, lymph node removal, radiation, chemotherapy, targeted therapies, antibodies targeting the tumor, and immunotherapy. Immunotherapy can include checkpoint blockers (CBP), chimeric antigen receptors (CARs), and adoptive T-cell therapy. The standards of care for the most common cancers can be found on the website of National Cancer Institute (www.cancer.gov/cancertopics). A treatment clinical trial is a research study meant to help improve current treatments or obtain information on new treatments for patients with cancer. When clinical trials show that a new treatment is better than the standard treatment, the new treatment may be considered the new standard treatment.

The term "Adjuvant therapy" as used herein refers to any treatment given after primary therapy to increase the chance of long-term disease-free survival. The term "Neoadjuvant therapy" as used herein refers to any treatment given before primary therapy. The term "Primary therapy" as used herein refers to the main treatment used to reduce or eliminate the cancer. In certain embodiments, an agent that shifts a tumor to a responder phenotype are provided as a neoadjuvant before CPB therapy.

Checkpoint Blockade Therapy

In certain embodiments, responsive subjects are treated with an immunotherapy. In certain embodiments, responsive subjects are detected using one or more of the gene programs described herein. In certain embodiments, a tumor is shifted to be responsive before or simultaneously with administration of an immunotherapy. Immunotherapy can include checkpoint blockers (CPB), chimeric antigen receptors (CARs), and adoptive T-cell therapy. Antibodies that block the activity of checkpoint receptors, including CTLA-4, PD-1, Tim-3, Lag-3, and TIGIT, either alone or in combination, have been associated with improved effector CD8+ T cell responses in multiple pre-clinical cancer models (Johnston et al., 2014. The immunoreceptor TIGIT regulates antitumor and antiviral CD8(+) T cell effector function. Cancer cell 26, 923-937; Ngiow et al., 2011. Anti-TIM3 antibody promotes T cell IFN-gamma-mediated antitumor immunity and suppresses established tumors. Cancer research 71, 3540-3551; Sakuishi et al., 2010. Targeting Tim-3 and PD-1 pathways to reverse T cell exhaustion and restore anti-tumor immunity. The Journal of experimental medicine 207, 2187-2194; and Woo et al., 2012. Immune inhibitory molecules LAG-3 and PD-1 synergistically regulate T-cell function to promote tumoral immune escape. Cancer research 72, 917-927). Similarly, blockade of CTLA-4 and PD-1 in patients (Brahmer et al., 2012. Safety and activity of anti-PD-L1 antibody in patients with advanced cancer. The New England journal of medicine 366, 2455-2465; Hodi et al., 2010. Improved survival with ipilimumab in patients with metastatic melanoma. The New England journal of medicine 363, 711-723; Schadendorf et al., 2015. Pooled Analysis of Long-Term Survival Data From Phase II and Phase III Trials of Ipilimumab in Unresectable or Metastatic Melanoma. Journal of clinical oncology. official journal of the American Society of Clinical Oncology 33, 1889-1894; Topalian et al., 2012. Safety, activity, and immune correlates of anti-PD-1 antibody in cancer. The New England journal of medicine 366, 2443-2454; and Wolchok et al., 2017. Overall Survival with Combined Nivolumab and Ipilimumab in Advanced Melanoma. The New England journal of medicine 377, 1345-1356) has shown increased frequencies of proliferating T cells, often with specificity for tumor antigens, as well as increased CD8+ T cell effector function (Ayers et al., 2017. IFN-gamma-related mRNA profile predicts clinical response to PD-1 blockade. The Journal of clinical investigation 127, 2930-2940; Das et al., 2015. Combination therapy with anti-CTLA-4 and anti-PD-1 leads to distinct immunologic changes in vivo. Journal of immunology 194, 950-959; Gubin et al., 2014. Checkpoint blockade cancer immunotherapy targets tumour-specific mutant antigens. Nature 515, 577-581; Huang et al., 2017. T-cell invigoration to tumour burden ratio associated with anti-PD-1 response. Nature 545, 60-65; Kamphorst et al., 2017. Proliferation of PD-1+ CD8 T cells in peripheral blood after PD-1-targeted therapy in lung cancer patients. Proceedings of the National Academy of Sciences of the United States of America 114, 4993-4998; Kvistborg et al., 2014. Anti-CTLA-4 therapy broadens the melanoma-reactive CD8+ T cell response. Science translational medicine 6, 254ra128; van Rooij et al., 2013. Tumor exome analysis reveals neoantigen-specific T-cell reactivity in an ipilimumab-responsive melanoma. Journal of clinical oncology. official journal of the American Society of Clinical Oncology 31, e439-442; and Yuan et al., 2008. CTLA-4 blockade enhances polyfunctional NY-ESO-1 specific T cell responses in metastatic melanoma patients with clinical benefit. Proceedings of the National Academy of Sciences of the United States of America 105, 20410-20415). Accordingly, the success of checkpoint receptor blockade has been attributed to the binding of blocking antibodies to checkpoint receptors expressed on dysfunctional CD8+ T cells and restoring effector function in these cells. The check point blockade therapy may be an inhibitor of any check point protein described herein. The checkpoint blockade therapy may comprise anti-TIM3, anti-CTLA4, anti-PD-L1, anti-PD1, anti-TIGIT, anti-LAG3, or combinations thereof. Anti-PD1 antibodies are disclosed in U.S. Pat. No. 8,735,553. Antibodies to LAG-3 are disclosed in U.S. Pat. No. 9,132,281. Anti-CTLA4 antibodies are disclosed in U.S. Pat. Nos. 9,327,014; 9,320,811; and 9,062,111. Specific check point inhibitors include, but are not limited to anti-CTLA4 antibodies (e.g., Ipilimumab and tremelimumab), anti-PD-1 antibodies (e.g., Nivolumab, Pembrolizumab), and anti-PD-L1 antibodies (e.g., Atezolizumab).

IDO1 Inhibitors

In certain embodiments, responsive subjects are treated with an IDO1 inhibitor. In certain embodiments, responsive subjects are detected using one or more of the gene programs described herein. In certain embodiments, a tumor is shifted to be responsive before or simultaneously with administration of an IDO1 inhibitor. In certain embodiments an IDO1 inhibitor is administered in combination with a CPB therapy.

IDO1 modulates immune cell function to a suppressive phenotype and is therefore partially accountable for tumor escape from host immune surveillance. The enzyme indoleamine 2, 3-dioxygenase 1 (IDO1) degrades the essential amino acid tryptophan into kynurenine and other metabolites. These metabolites and the paucity of tryptophan leads to suppression of effector T-cell function and augmented differentiation of regulatory T cells.

In certain embodiments, the IDO1 inhibitor includes, but is not limited to indoximod, epacadostat, navoximod, PF-06840003, BMS-986205, and microRNA-153 (miR-153) (see, e.g., Liu, M., Wang, X., Wang, L. et al. Targeting the IDO1 pathway in cancer: from bench to bedside. J Hematol Oncol 11, 100 (2018)). IDO1 inhibitors may also include any inhibitors as described in US patent publication US20170037125A1.

Small Molecules

In certain embodiments, the one or more agents is a small molecule. The term "small molecule" refers to compounds, preferably organic compounds, with a size comparable to those organic molecules generally used in pharmaceuticals. The term excludes biological macromolecules (e.g., proteins, peptides, nucleic acids, etc.). Preferred small organic molecules range in size up to about 5000 Da, e.g., up to about 4000, preferably up to 3000 Da, more preferably up to 2000 Da, even more preferably up to about 1000 Da, e.g., up to about 900, 800, 700, 600 or up to about 500 Da. In certain embodiments, the small molecule may act as an antagonist or agonist (e.g., blocking an enzyme active site or activating a receptor by binding to a ligand binding site).

One type of small molecule applicable to the present invention is a degrader molecule (see, e.g., Ding, et al., Emerging New Concepts of Degrader Technologies, Trends Pharmacol Sci. 2020 July; 41(7):464-474). The terms "degrader" and "degrader molecule" refer to all compounds capable of specifically targeting a protein for degradation (e.g., ATTEC, AUTAC, LYTAC, or PROTAC, reviewed in Ding, et al. 2020). Proteolysis Targeting Chimera (PROTAC) technology is a rapidly emerging alternative therapeutic strategy with the potential to address many of the challenges currently faced in modern drug development programs. PROTAC technology employs small molecules that recruit target proteins for ubiquitination and removal by the proteasome (see, e.g., Zhou et al., Discovery of a Small-Molecule Degrader of Bromodomain and Extra-Terminal (BET) Proteins with Picomolar Cellular Potencies and Capable of Achieving Tumor Regression. J. Med. Chem. 2018, 61, 462-481; Bondeson and Crews, Targeted Protein Degradation by Small Molecules, Annu Rev Pharmacol Toxicol. 2017 Jan. 6; 57: 107-123; and Lai et al., Modular PROTAC Design for the Degradation of Oncogenic BCR-ABL Angew Chem Int Ed Engl. 2016 Jan. 11; 55(2): 807-810). In certain embodiments, LYTACs are particularly advantageous for cell surface proteins as described herein.

Genetic Modifying Agents

In certain embodiments, the one or more modulating agents may be a genetic modifying agent (e.g., modifies a transcription factor). In certain embodiments, a genetic modifying agent is used to shift a gene program described herein. In certain embodiments, immune cells used for adoptive cell transfer are modified using a genetic modifying agent. The genetic modifying agent may comprise a CRISPR system, a zinc finger nuclease system, a TALEN, a meganuclease or RNAi system. In certain embodiments, a target gene is genetically modified. In certain embodiments, a target gene RNA is modified, such that the modification is temporary. Methods of modifying RNA is discussed further herein.

Crispr-Cas Modification

In some embodiments, a polynucleotide of the present invention described elsewhere herein can be modified using a CRISPR-Cas and/or Cas-based system (e.g., genomic DNA or mRNA, preferably, for a disease gene). The nucleotide sequence may be or encode one or more components of a CRISPR-Cas system. For example, the nucleotide sequences may be or encode guide RNAs. The nucleotide sequences may also encode CRISPR proteins, variants thereof, or fragments thereof.

In general, a CRISPR-Cas or CRISPR system as used herein and in other documents, such as WO 2014/093622 (PCT/US2013/074667), refers collectively to transcripts and other elements involved in the expression of or directing the activity of CRISPR-associated ("Cas") genes, including sequences encoding a Cas gene, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g., CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). See, e.g., Shmakov et al. (2015) "Discovery and Functional Characterization of Diverse Class 2 CRISPR-Cas Systems", Molecular Cell, DOI: dx.doi.org/10.1016/j.molcel.2015.10.008.

CRISPR-Cas systems can generally fall into two classes based on their architectures of their effector molecules, which are each further subdivided by type and subtype. The two class are Class 1 and Class 2. Class 1 CRISPR-Cas systems have effector modules composed of multiple Cas proteins, some of which form crRNA-binding complexes, while Class 2 CRISPR-Cas systems include a single, multi-domain crRNA-binding protein.

In some embodiments, the CRISPR-Cas system that can be used to modify a polynucleotide of the present invention described herein can be a Class 1 CRISPR-Cas system. In some embodiments, the CRISPR-Cas system that can be used to modify a polynucleotide of the present invention described herein can be a Class 2 CRISPR-Cas system.

Class 1 CRISPR-Cas Systems

In some embodiments, the CRISPR-Cas system that can be used to modify a polynucleotide of the present invention described herein can be a Class 1 CRISPR-Cas system. Class 1 CRISPR-Cas systems are divided into types I, II, and IV. Makarova et al. 2020. Nat. Rev. 18: 67-83., particularly as described in FIG. 1. Type I CRISPR-Cas systems are divided into 9 subtypes (I-A, I-B, I-C, I-D, I-E, I-F1, I-F2, I-F3, and IG). Makarova et al., 2020. Class 1, Type I CRISPR-Cas systems can contain a Cas3 protein that can have helicase activity. Type III CRISPR-Cas systems are divided into 6 subtypes (III-A, III-B, III-C, III-D, III-E, and III-F). Type III CRISPR-Cas systems can contain a Cas10 that can include an RNA recognition motif called Palm and a cyclase domain that can cleave polynucleotides. Makarova et al., 2020. Type IV CRISPR-Cas systems are divided into 3 subtypes. (IV-A, IV-B, and IV-C). Makarova et al., 2020. Class 1 systems also include CRISPR-Cas variants, including Type I-A, I-B, I-E, I-F and I-U variants, which can include variants carried by transposons and plasmids, including versions of subtype I-F encoded by a large family of Tn7-like transposon and smaller groups of Tn7-like transposons that encode similarly degraded subtype I-B systems. Peters et al., PNAS 114 (35) (2017); DOI: 10.1073/pnas.1709035114; see also, Makarova et al. 2018. The CRISPR Journal, v. 1, n5, FIG. 5.

The Class 1 systems typically use a multi-protein effector complex, which can, in some embodiments, include ancillary proteins, such as one or more proteins in a complex referred to as a CRISPR-associated complex for antiviral defense (Cascade), one or more adaptation proteins (e.g., Cas1, Cas2, RNA nuclease), and/or one or more accessory proteins (e.g., Cas4, DNA nuclease), CRISPR associated Rossman fold (CARF) domain containing proteins, and/or RNA transcriptase.

The backbone of the Class 1 CRISPR-Cas system effector complexes can be formed by RNA recognition motif domain-containing protein(s) of the repeat-associated mysterious proteins (RAMPs) family subunits (e.g., Cas5, Cas6, and/or Cas7). RAMP proteins are characterized by having one or more RNA recognition motif domains. In some embodiments, multiple copies of RAMPs can be present. In some embodiments, the Class I CRISPR-Cas system can include 1, 2, 3, 4, 5, 6, 7, 8, 9, 10, 11, 12 or more Cas5, Cas6, and/or Cas7 proteins. In some embodiments, the Cas6 protein is an RNAse, which can be responsible for pre-crRNA processing. When present in a Class 1 CRISPR-Cas system, Cas6 can be optionally physically associated with the effector complex.

Class 1 CRISPR-Cas system effector complexes can, in some embodiments, also include a large subunit. The large subunit can be composed of or include a Cas8 and/or Cas10 protein. See, e.g., FIGS. 1 and 2. Koonin E V, Makarova K S. 2019. Phil. Trans. R. Soc. B 374: 20180087, DOI: 10.1098/rstb.2018.0087 and Makarova et al. 2020.

Class 1 CRISPR-Cas system effector complexes can, in some embodiments, include a small subunit (for example, Cas11). See, e.g., FIGS. 1 and 2. Koonin E V, Makarova K S. 2019 Origins and Evolution of CRISPR-Cas systems. Phil. Trans. R. Soc. B 374: 20180087, DOI: 10.1098/rstb.2018.0087.

In some embodiments, the Class 1 CRISPR-Cas system can be a Type I CRISPR-Cas system. In some embodiments, the Type I CRISPR-Cas system can be a subtype I-A CRISPR-Cas system. In some embodiments, the Type I CRISPR-Cas system can be a subtype I-B CRISPR-Cas system. In some embodiments, the Type I CRISPR-Cas system can be a subtype I-C CRISPR-Cas system. In some embodiments, the Type I CRISPR-Cas system can be a subtype I-D CRISPR-Cas system. In some embodiments, the Type I CRISPR-Cas system can be a subtype I-E CRISPR-Cas system. In some embodiments, the Type I CRISPR-Cas system can be a subtype I-F1 CRISPR-Cas system. In some embodiments, the Type I CRISPR-Cas system can be a subtype I-F2 CRISPR-Cas system. In some embodiments, the Type I CRISPR-Cas system can be a subtype I-F3 CRISPR-Cas system. In some embodiments, the Type I CRISPR-Cas system can be a subtype I-G CRISPR-Cas system. In some embodiments, the Type I CRISPR-Cas system can be a CRISPR-Cas variant, such as a Type I-A, I-B, I-E, I-F and I-U variants, which can include variants carried by transposons and plasmids, including versions of subtype I-F encoded by a large family of Tn7-like transposon and smaller groups of Tn7-like transposons that encode similarly degraded subtype I-B systems as previously described.

In some embodiments, the Class 1 CRISPR-Cas system can be a Type III CRISPR-Cas system. In some embodiments, the Type III CRISPR-Cas system can be a subtype III-A CRISPR-Cas system. In some embodiments, the Type III CRISPR-Cas system can be a subtype III-B CRISPR-Cas system. In some embodiments, the Type III CRISPR-Cas system can be a subtype III-C CRISPR-Cas system. In some embodiments, the Type III CRISPR-Cas system can be a subtype III-D CRISPR-Cas system. In some embodiments, the Type III CRISPR-Cas system can be a subtype III-E CRISPR-Cas system. In some embodiments, the Type III CRISPR-Cas system can be a subtype III-F CRISPR-Cas system.

In some embodiments, the Class 1 CRISPR-Cas system can be a Type IV CRISPR-Cas-system. In some embodiments, the Type IV CRISPR-Cas system can be a subtype IV-A CRISPR-Cas system. In some embodiments, the Type IV CRISPR-Cas system can be a subtype IV-B CRISPR-Cas system. In some embodiments, the Type IV CRISPR-Cas system can be a subtype IV-C CRISPR-Cas system.

The effector complex of a Class 1 CRISPR-Cas system can, in some embodiments, include a Cas3 protein that is optionally fused to a Cas2 protein, a Cas4, a Cas5, a Cas6, a Cas7, a Cas8, a Cas10, a Cas11, or a combination thereof. In some embodiments, the effector complex of a Class 1 CRISPR-Cas system can have multiple copies, such as 1, 2, 3, 4, 5, 6, 7, 8, 9, 10, 11, 12, 13, or 14, of any one or more Cas proteins.

Class 2 CRISPR-Cas Systems

The compositions, systems, and methods described in greater detail elsewhere herein can be designed and adapted for use with Class 2 CRISPR-Cas systems. Thus, in some embodiments, the CRISPR-Cas system is a Class 2 CRISPR-Cas system. Class 2 systems are distinguished from Class 1 systems in that they have a single, large, multi-domain effector protein. In certain example embodiments, the Class 2 system can be a Type II, Type V, or Type VI system, which are described in Makarova et al. "Evolutionary classification of CRISPR-Cas systems: a burst of class 2 and derived variants" Nature Reviews Microbiology, 18:67-81 (February 2020), incorporated herein by reference. Each type of Class 2 system is further divided into subtypes. See Markova et al. 2020, particularly at Figure. 2. Class 2, Type II systems can be divided into 4 subtypes: II-A, II-B, II-C1, and II-C2. Class 2, Type V systems can be divided into 17 subtypes: V-A, V-B1, V-B2, V-C, V-D, V-E, V-F1, V-F1(V-U3), V-F2, V-F3, V-G, V-H, V-I, V-K (V-U5), V-U1, V-U2, and V-U4. Class 2, Type IV systems can be divided into 5 subtypes: VI-A, VI-B1, VI-B2, VI-C, and VI-D.

The distinguishing feature of these types is that their effector complexes consist of a single, large, multi-domain protein. Type V systems differ from Type II effectors (e.g., Cas9), which contain two nuclear domains that are each responsible for the cleavage of one strand of the target DNA, with the HNH nuclease inserted inside the Ruv-C like nuclease domain sequence. The Type V systems (e.g., Cas12) only contain a RuvC-like nuclease domain that cleaves both strands. Type VI (Cas13) are unrelated to the effectors of Type II and V systems and contain two HEPN domains and target RNA. Cas13 proteins also display collateral activity that is triggered by target recognition. Some Type V systems have also been found to possess this collateral activity with two single-stranded DNA in in vitro contexts.

In some embodiments, the Class 2 system is a Type II system. In some embodiments, the Type II CRISPR-Cas system is a II-A CRISPR-Cas system. In some embodiments, the Type II CRISPR-Cas system is a II-B CRISPR-Cas system. In some embodiments, the Type II CRISPR-Cas system is a II-C1 CRISPR-Cas system. In some embodiments, the Type II CRISPR-Cas system is a II-C2 CRISPR-Cas system. In some embodiments, the Type II system is a Cas9 system. In some embodiments, the Type II system includes a Cas9.

In some embodiments, the Class 2 system is a Type V system. In some embodiments, the Type V CRISPR-Cas system is a V-A CRISPR-Cas system. In some embodiments, the Type V CRISPR-Cas system is a V-B1 CRISPR-Cas system. In some embodiments, the Type V CRISPR-Cas system is a V-B2 CRISPR-Cas system. In some embodiments, the Type V CRISPR-Cas system is a V-C CRISPR-Cas system. In some embodiments, the Type V CRISPR-Cas system is a V-D CRISPR-Cas system. In some embodiments, the Type V CRISPR-Cas system is a V-E CRISPR-Cas system. In some embodiments, the Type V CRISPR-Cas system is a V-F1 CRISPR-Cas system. In some embodiments, the Type V CRISPR-Cas system is a V-F1 (V-U3) CRISPR-Cas system. In some embodiments, the Type V CRISPR-Cas system is a V-F2 CRISPR-Cas system. In some embodiments, the Type V CRISPR-Cas system is a V-F3 CRISPR-Cas system. In some embodiments, the Type V CRISPR-Cas system is a V-G CRISPR-Cas system. In some embodiments, the Type V CRISPR-Cas system is a V-H CRISPR-Cas system. In some embodiments, the Type V CRISPR-Cas system is a V-I CRISPR-Cas system. In some embodiments, the Type V CRISPR-Cas system is a V-K (V-U5) CRISPR-Cas system. In some embodiments, the Type V CRISPR-Cas system is a V-U1 CRISPR-Cas system. In some embodiments, the Type V CRISPR-Cas system is a V-U2 CRISPR-Cas system. In some embodiments, the Type V CRISPR-Cas system is a V-U4 CRISPR-Cas system. In some embodiments, the Type V CRISPR-Cas system includes a Cas12a (Cpf1), Cas12b (C2c1), Cas12c (C2c3), CasX, and/or Cas14.

In some embodiments the Class 2 system is a Type VI system. In some embodiments, the Type VI CRISPR-Cas system is a VI-A CRISPR-Cas system. In some embodiments, the Type VI CRISPR-Cas system is a VI-B1 CRISPR-Cas system. In some embodiments, the Type VI CRISPR-Cas system is a VI-B2 CRISPR-Cas system. In some embodiments, the Type VI CRISPR-Cas system is a VI-C CRISPR-Cas system. In some embodiments, the Type VI CRISPR-Cas system is a VI-D CRISPR-Cas system. In some embodiments, the Type VI CRISPR-Cas system includes a Cas13a (C2c2), Cas13b (Group 29/30), Cas13c, and/or Cas13d.

Specialized Cas-Based Systems

In some embodiments, the system is a Cas-based system that is capable of performing a specialized function or activity. For example, the Cas protein may be fused, operably coupled to, or otherwise associated with one or more functionals domains. In certain example embodiments, the Cas protein may be a catalytically dead Cas protein ("dCas") and/or have nickase activity. A nickase is a Cas protein that cuts only one strand of a double stranded target. In such embodiments, the dCas or nickase provide a sequence specific targeting functionality that delivers the functional domain to or proximate a target sequence. Example functional domains that may be fused to, operably coupled to, or otherwise associated with a Cas protein can be or include, but are not limited to a nuclear localization signal (NLS) domain, a nuclear export signal (NES) domain, a translational activation domain, a transcriptional activation domain (e.g. VP64, p65, MyoD1, HSF1, RTA, and SET7/9), a translation initiation domain, a transcriptional repression domain (e.g., a KRAB domain, NuE domain, NcoR domain, and a SID domain such as a SID4X domain), a nuclease domain (e.g., FokI), a histone modification domain (e.g., a histone acetyltransferase), a light inducible/controllable domain, a chemically inducible/controllable domain, a transposase domain, a homologous recombination machinery domain, a recombinase domain, an integrase domain, and combinations thereof. Methods for generating catalytically dead Cas9 or a nickase Cas9 (WO 2014/204725, Ran et al. Cell. 2013 Sep. 12; 154(6):1380-1389), Cas12 (Liu et al. Nature Communications, 8, 2095 (2017), and Cas13 (WO 2019/005884, WO2019/060746) are known in the art and incorporated herein by reference.

In some embodiments, the functional domains can have one or more of the following activities: methylase activity, demethylase activity, translation activation activity, translation initiation activity, translation repression activity, transcription activation activity, transcription repression activity, transcription release factor activity, histone modification activity, nuclease activity, single-strand RNA cleavage activity, double-strand RNA cleavage activity, single-strand DNA cleavage activity, double-strand DNA cleavage activity, molecular switch activity, chemical inducibility, light inducibility, and nucleic acid binding activity. In some embodiments, the one or more functional domains may comprise epitope tags or reporters. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporters include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and auto-fluorescent proteins including blue fluorescent protein (BFP).

The one or more functional domain(s) may be positioned at, near, and/or in proximity to a terminus of the effector protein (e.g., a Cas protein). In embodiments having two or more functional domains, each of the two can be positioned at or near or in proximity to a terminus of the effector protein (e.g., a Cas protein). In some embodiments, such as those where the functional domain is operably coupled to the effector protein, the one or more functional domains can be tethered or linked via a suitable linker (including, but not limited to, GlySer linkers) to the effector protein (e.g., a Cas protein). When there is more than one functional domain, the functional domains can be same or different. In some embodiments, all the functional domains are the same. In some embodiments, all of the functional domains are different from each other. In some embodiments, at least two of the functional domains are different from each other. In some embodiments, at least two of the functional domains are the same as each other.

Other suitable functional domains can be found, for example, in International Application Publication No. WO 2019/018423.

Split CRISPR-Cas Systems

In some embodiments, the CRISPR-Cas system is a split CRISPR-Cas system. See e.g., Zetche et al., 2015. Nat. Biotechnol. 33(2): 139-142 and WO 2019/018423, the compositions and techniques of which can be used in and/or adapted for use with the present invention. Split CRISPR-Cas proteins are set forth herein and in documents incorporated herein by reference in further detail herein. In certain embodiments, each part of a split CRISPR protein are attached to a member of a specific binding pair, and when bound with each other, the members of the specific binding pair maintain the parts of the CRISPR protein in proximity. In certain embodiments, each part of a split CRISPR protein is associated with an inducible binding pair. An inducible binding pair is one which is capable of being switched "on" or "off" by a protein or small molecule that binds to both members of the inducible binding pair. In some embodiments, CRISPR proteins may preferably split between domains, leaving domains intact. In particular embodiments, said Cas split domains (e.g., RuvC and HNH domains in the case of Cas9) can be simultaneously or sequentially introduced into the cell such that said split Cas domain(s) process the target nucleic acid sequence in the algae cell. The reduced size of the split Cas compared to the wild type Cas allows other methods of delivery of the systems to the cells, such as the use of cell penetrating peptides as described herein.

DNA and RNA Base Editing

In some embodiments, a polynucleotide of the present invention described elsewhere herein can be modified using a base editing system. In some embodiments, a Cas protein is connected or fused to a nucleotide deaminase. Thus, in some embodiments the Cas-based system can be a base editing system. As used herein "base editing" refers generally to the process of polynucleotide modification via a CRISPR-Cas-based or Cas-based system that does not include excising nucleotides to make the modification. Base editing can convert base pairs at precise locations without generating excess undesired editing byproducts that can be made using traditional CRISPR-Cas systems.

In certain example embodiments, the nucleotide deaminase may be a DNA base editor used in combination with a DNA binding Cas protein such as, but not limited to, Class 2 Type II and Type V systems. Two classes of DNA base editors are generally known: cytosine base editors (CBEs) and adenine base editors (ABEs). CBEs convert a C•G base pair into a T•A base pair (Komor et al. 2016. Nature. 533:420-424; Nishida et al. 2016. Science. 353; and Li et al. Nat. Biotech. 36:324-327) and ABEs convert an A•T base pair to a G•C base pair. Collectively, CBEs and ABEs can mediate all four possible transition mutations (C to T, A to G, T to C, and G to A). Rees and Liu. 2018.Nat. Rev. Genet. 19(12): 770-788, particularly at FIGS. 1b, 2a-2c, 3a-3f, and Table 1. In some embodiments, the base editing system includes a CBE and/or an ABE. In some embodiments, a polynucleotide of the present invention described elsewhere herein can be modified using a base editing system. Rees and Liu. 2018. Nat. Rev. Gent. 19(12):770-788. Base editors also generally do not need a DNA donor template and/or rely on homology-directed repair. Komor et al. 2016. Nature. 533: 420-424; Nishida et al. 2016. Science. 353; and Gaudeli et al. 2017. Nature. 551:464-471. Upon binding to a target locus in the DNA, base pairing between the guide RNA of the system and the target DNA strand leads to displacement of a small segment of ssDNA in an "R-loop". Nishimasu et al. Cell. 156:935-949. DNA bases within the ssDNA bubble are modified by the enzyme component, such as a deaminase. In some systems, the catalytically disabled Cas protein can be a variant or modified Cas can have nickase functionality and can generate a nick in the non-edited DNA strand to induce cells to repair the non-edited strand using the edited strand as a template. Komor et al. 2016. Nature. 533:420-424; Nishida et al. 2016. Science. 353; and Gaudeli et al. 2017. Nature. 551:464-471. Base editors may be further engineered to optimize conversion of nucleotides (e.g. A:T to G:C). Richter et al. 2020. Nature Biotechnology. doi.org/10.1038/s41587-020-0453-z.

Other Example Type V base editing systems are described in WO 2018/213708, WO 2018/213726, PCT/US2018/067207, PCT/US2018/067225, and PCT/US2018/067307 which are incorporated by referenced herein.

In certain example embodiments, the base editing system may be a RNA base editing system. As with DNA base editors, a nucleotide deaminase capable of converting nucleotide bases may be fused to a Cas protein. However, in these embodiments, the Cas protein will need to be capable of binding RNA. Example RNA binding Cas proteins include, but are not limited to, RNA-binding Cas9s such as *Francisella novicida* Cas9 ("FnCas9"), and Class 2 Type VI Cas systems. The nucleotide deaminase may be a cytidine deaminase or an adenosine deaminase, or an adenosine deaminase engineered to have cytidine deaminase activity. In certain example embodiments, the RNA based editor may be used to delete or introduce a post-translation modification site in the expressed mRNA. In contrast to DNA base editors, whose edits are permanent in the modified cell, RNA base editors can provide edits where finer temporal control may be needed, for example in modulating a particular immune response. Example Type VI RNA-base editing systems are described in Cox et al. 2017. Science 358: 1019-1027, WO 2019/005884, WO 2019/005886, WO 2019/071048, PCT/US20018/05179, PCT/US2018/067207, which are incorporated herein by reference. An example FnCas9 system that may be adapted for RNA base editing purposes is described in WO 2016/106236, which is incorporated herein by reference.

An example method for delivery of base-editing systems, including use of a split-intein approach to divide CBE and ABE into reconstitutable halves, is described in Levy et al. Nature Biomedical Engineering doi.org/10.1038/s41441-019-0505-5 (2019), which is incorporated herein by reference.

Prime Editors

In some embodiments, a polynucleotide of the present invention described elsewhere herein can be modified using a prime editing system (See e.g. Anzalone et al. 2019. Nature. 576: 149-157). Like base editing systems, prime editing systems can be capable of targeted modification of a polynucleotide without generating double stranded breaks and does not require donor templates. Further prime editing systems can be capable of all 12 possible combination swaps. Prime editing can operate via a "search-and-replace" methodology and can mediate targeted insertions, deletions, all 12 possible base-to-base conversion, and combinations thereof. Generally, a prime editing system, as exemplified by PE1, PE2, and PE3 (Id.), can include a reverse transcriptase fused or otherwise coupled or associated with an RNA-programmable nickase, and a prime-editing extended guide RNA (pegRNA) to facility direct copying of genetic information from the extension on the pegRNA into the target polynucleotide. Embodiments that can be used with the present invention include these and variants thereof. Prime editing can have the advantage of lower off-target activity than traditional CRISPR-Cas systems along with few byproducts and greater or similar efficiency as compared to traditional CRISPR-Cas systems.

In some embodiments, the prime editing guide molecule can specify both the target polynucleotide information (e.g. sequence) and contain a new polynucleotide cargo that replaces target polynucleotides. To initiate transfer from the guide molecule to the target polynucleotide, the PE system can nick the target polynucleotide at a target side to expose a 3'hydroxyl group, which can prime reverse transcription of an edit-encoding extension region of the guide molecule (e.g. a prime editing guide molecule or peg guide molecule) directly into the target site in the target polynucleotide. See e.g. Anzalone et al. 2019. Nature. 576: 149-157, particularly at FIGS. 1b, 1c, related discussion, and Supplementary discussion.

In some embodiments, a prime editing system can be composed of a Cas polypeptide having nickase activity, a reverse transcriptase, and a guide molecule. The Cas polypeptide can lack nuclease activity. The guide molecule can include a target binding sequence as well as a primer binding sequence and a template containing the edited polynucleotide sequence. The guide molecule, Cas polypeptide, and/or reverse transcriptase can be coupled together or otherwise associate with each other to form an effector complex and edit a target sequence. In some embodiments, the Cas polypeptide is a Class 2, Type V Cas polypeptide. In some embodiments, the Cas polypeptide is a Cas9 polypeptide (e.g. is a Cas9 nickase). In some embodiments, the Cas polypeptide is fused to the reverse transcriptase. In some embodiments, the Cas polypeptide is linked to the reverse transcriptase.

In some embodiments, the prime editing system can be a PE1 system or variant thereof, a PE2 system or variant thereof, or a PE3 (e.g. PE3, PE3b) system. See e.g., Anzalone et al. 2019. Nature. 576: 149-157, particularly at pgs. 2-3, FIGS. 2a, 3a-3f, 4a-4b, Extended data FIGS. 3a-3b, 4.

The peg guide molecule can be about 10 to about 200 or more nucleotides in length, such as 10 to/or 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 or more nucleotides in length. Optimization of the peg guide molecule can be accomplished as described in Anzalone et al. 2019. Nature. 576: 149-157, particularly at pg. 3, FIG. 2a-2b, and Extended Data FIGS. 5a-c.

CRISPR Associated Transposase (CAST) Systems

In some embodiments, a polynucleotide of the present invention described elsewhere herein can be modified using a CRISPR Associated Transposase ("CAST") system. CAST system can include a Cas protein that is catalytically inactive, or engineered to be catalytically active, and further comprises a transposase (or subunits thereof) that catalyze RNA-guided DNA transposition. Such systems are able to insert DNA sequences at a target site in a DNA molecule without relying on host cell repair machinery. CAST systems can be Class1 or Class 2 CAST systems. An example Class 1 system is described in Klompe et al. Nature, doi: 10.1038/s41586-019-1323, which is in incorporated herein by reference. An example Class 2 system is described in Strecker et al. Science. 10/1126/science. aax9181 (2019), and PCT/US2019/066835 which are incorporated herein by reference.

Guide Molecules

The CRISPR-Cas or Cas-Based system described herein can, in some embodiments, include one or more guide molecules. The terms guide molecule, guide sequence and guide polynucleotide, refer to polynucleotides capable of guiding Cas to a target genomic locus and are used interchangeably as in foregoing cited documents such as WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. The guide molecule can be a polynucleotide.

The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay (Qui et al. 2004. BioTechniques. 36(4)702-707). Similarly, cleavage of a target nucleic acid sequence may be evaluated in a test tube by providing the target nucleic acid sequence, components of a nucleic acid-targeting complex, including the guide sequence to be tested and a control guide sequence different from the test guide sequence, and comparing binding or rate of cleavage at the target sequence between the test and control guide sequence reactions. Other assays are possible and will occur to those skilled in the art.

In some embodiments, the guide molecule is an RNA. The guide molecule(s) (also referred to interchangeably herein as guide polynucleotide and guide sequence) that are included in the CRISPR-Cas or Cas based system can be any polynucleotide sequence having sufficient complementarity with a target nucleic acid sequence to hybridize with the target nucleic acid sequence and direct sequence-specific binding of a nucleic acid-targeting complex to the target nucleic acid sequence. In some embodiments, the degree of complementarity, when optimally aligned using a suitable alignment algorithm, can be about or more than about 50%, 60%, 75%, 80%, 85%, 90%, 95%, 97.5%, 99%, or more. Optimal alignment may be determined with the use of any suitable algorithm for aligning sequences, non-limiting examples of which include the Smith-Waterman algorithm, the Needleman-Wunsch algorithm, algorithms based on the Burrows-Wheeler Transform (e.g., the Burrows Wheeler Aligner), ClustalW, ClustalX, BLAT, Novoalign (Novocraft Technologies; available at www.novocraft.com), ELAND (Illumina, San Diego, CA), SOAP (available at soap.genomics.org.cn), and Maq (available at maq.sourceforge.net).

A guide sequence, and hence a nucleic acid-targeting guide, may be selected to target any target nucleic acid sequence. The target sequence may be DNA. The target sequence may be any RNA sequence. In some embodiments, the target sequence may be a sequence within an RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non-coding RNA (ncRNA), long non-coding RNA (lncRNA), and small cytoplasmatic RNA (scRNA). In some preferred embodiments, the target sequence may be a sequence within an RNA molecule selected from the group consisting of mRNA, pre-mRNA, and rRNA. In some preferred embodiments, the target sequence may be a sequence within an RNA molecule selected from the group consisting of ncRNA, and lncRNA. In some more preferred embodiments, the target sequence may be a sequence within an mRNA molecule or a pre-mRNA molecule.

In some embodiments, a nucleic acid-targeting guide is selected to reduce the degree secondary structure within the nucleic acid-targeting guide. In some embodiments, about or less than about 75%, 50%, 40%, 30%, 25%, 20%, 15%, 10%, 5%, 1%, or fewer of the nucleotides of the nucleic acid-targeting guide participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106(1): 23-24; and PA Carr and GM Church, 2009, Nature Biotechnology 27(12): 1151-62).

In certain embodiments, a guide RNA or crRNA may comprise, consist essentially of, or consist of a direct repeat (DR) sequence and a guide sequence or spacer sequence. In certain embodiments, the guide RNA or crRNA may comprise, consist essentially of, or consist of a direct repeat sequence fused or linked to a guide sequence or spacer sequence. In certain embodiments, the direct repeat sequence may be located upstream (i.e., 5') from the guide sequence or spacer sequence. In other embodiments, the direct repeat sequence may be located downstream (i.e., 3') from the guide sequence or spacer sequence.

In certain embodiments, the crRNA comprises a stem loop, preferably a single stem loop. In certain embodiments, the direct repeat sequence forms a stem loop, preferably a single stem loop.

In certain embodiments, the spacer length of the guide RNA is from 15 to 35 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27 to 30 nt, e.g., 27, 28, 29, or 30 nt, from 30 to 35 nt, e.g., 30, 31, 32, 33, 34, or 35 nt, or 35 nt or longer.

The "tracrRNA" sequence or analogous terms includes any polynucleotide sequence that has sufficient complementarity with a crRNA sequence to hybridize. In some embodiments, the degree of complementarity between the tracrRNA sequence and crRNA sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and crRNA sequence are contained within a single transcript, such that hybridization between the two produces a transcript having a secondary structure, such as a hairpin.

In general, degree of complementarity is with reference to the optimal alignment of the sca sequence and tracr sequence, along the length of the shorter of the two sequences. Optimal alignment may be determined by any suitable alignment algorithm, and may further account for secondary structures, such as self-complementarity within either the sca sequence or tracr sequence. In some embodiments, the degree of complementarity between the tracr sequence and sea sequence along the length of the shorter of the two when optimally aligned is about or more than about 25%, 30%, 40%, 50%, 60%, 70%, 80%, 90%, 95%, 97.5%, 99%, or higher.

In some embodiments, the degree of complementarity between a guide sequence and its corresponding target sequence can be about or more than about 50%, 60%, 75%, 80%, 85%, 90%, 95%, 97.5%, 99%, or 100%; a guide or RNA or sgRNA can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length; or guide or RNA or sgRNA can be less than about 75, 50, 45, 40, 35, 30, 25, 20, 15, 12, or fewer nucleotides in length; and tracr RNA can be 30 or 50 nucleotides in length. In some embodiments, the degree of complementarity between a guide sequence and its corresponding target sequence is greater than 94.5% or 95% or 95.5% or 96% or 96.5% or 97% or 97.5% or 98% or 98.5% or 99% or 99.5% or 99.9%, or 100%. Off target is less than 100% or 99.9% or 99.5% or 99% or 99% or 98.5% or 98% or 97.5% or 97% or 96.5% or 96% or 95.5% or 95% or 94.5% or 94% or 93% or 92% or 91% or 90% or 89% or 88% or 87% or 86% or 85% or 84% or 83% or 82% or 81% or 80% complementarity between the sequence and the guide, with it advantageous that off target is 100% or 99.9% or 99.5% or 99% or 99% or 98.5% or 98% or 97.5% or 97% or 96.5% or 96% or 95.5% or 95% or 94.5% complementarity between the sequence and the guide.

In some embodiments according to the invention, the guide RNA (capable of guiding Cas to a target locus) may comprise (1) a guide sequence capable of hybridizing to a genomic target locus in the eukaryotic cell; (2) a tracr sequence; and (3) a tracr mate sequence. All (1) to (3) may reside in a single RNA, i.e., an sgRNA (arranged in a 5' to 3' orientation), or the tracr RNA may be a different RNA than the RNA containing the guide and tracr sequence. The tracr hybridizes to the tracr mate sequence and directs the CRISPR/Cas complex to the target sequence. Where the tracr RNA is on a different RNA than the RNA containing the guide and tracr sequence, the length of each RNA may be optimized to be shortened from their respective native lengths, and each may be independently chemically modified to protect from degradation by cellular RNase or otherwise increase stability.

Many modifications to guide sequences are known in the art and are further contemplated within the context of this invention. Various modifications may be used to increase the specificity of binding to the target sequence and/or increase the activity of the Cas protein and/or reduce off-target effects. Example guide sequence modifications are described in PCT/US2019/045582, specifically paragraphs [0178]-[0333], which is incorporated herein by reference.

Target Sequences, PAMs, and PFSs
Target Sequences

In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise RNA polynucleotides. The term "target RNA" refers to an RNA polynucleotide being or comprising the target sequence. In other words, the target polynucleotide can be a polynucleotide or a part of a polynucleotide to which a part of the guide sequence is designed to have complementarity with and to which the effector function mediated by the complex comprising the CRISPR effector protein and a guide molecule is to be directed. In some embodiments, a target sequence is located in the nucleus or cytoplasm of a cell.

The guide sequence can specifically bind a target sequence in a target polynucleotide. The target polynucleotide may be DNA. The target polynucleotide may be RNA. The target polynucleotide can have one or more (e.g., 1, 2, 3, 4, 5, 6, 7, 8, 9, 10, etc. or more) target sequences. The target polynucleotide can be on a vector. The target polynucleotide can be genomic DNA. The target polynucleotide can be episomal. Other forms of the target polynucleotide are described elsewhere herein.

The target sequence may be DNA. The target sequence may be any RNA sequence. In some embodiments, the target sequence may be a sequence within an RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non-coding RNA (ncRNA), long non-coding RNA (lncRNA), and small cytoplasmatic RNA (scRNA). In some preferred embodiments, the target sequence (also referred to herein as a target polynucleotide) may be a sequence within an RNA molecule selected from the group consisting of mRNA, pre-mRNA, and rRNA. In some preferred embodiments, the target sequence may be a sequence within an RNA molecule selected from the group consisting of ncRNA, and lncRNA. In some more preferred embodiments, the target sequence may be a sequence within an mRNA molecule or a pre-mRNA molecule.

PAM and PFS Elements

PAM elements are sequences that can be recognized and bound by Cas proteins. Cas proteins/effector complexes can then unwind the dsDNA at a position adjacent to the PAM element. It will be appreciated that Cas proteins and systems that include them that target RNA do not require PAM sequences (Marraffini et al. 2010. Nature. 463:568-571). Instead, many rely on PFSs, which are discussed elsewhere herein. In certain embodiments, the target sequence should be associated with a PAM (protospacer adjacent motif) or PFS (protospacer flanking sequence or site), that is, a short sequence recognized by the CRISPR complex. Depending on the nature of the CRISPR-Cas protein, the target sequence should be selected, such that its complementary sequence in the DNA duplex (also referred to herein as the non-target sequence) is upstream or downstream of the PAM. In the embodiments, the complementary sequence of the target sequence is downstream or 3' of the PAM or upstream or 5' of the PAM. The precise sequence and length requirements for the PAM differ depending on the Cas protein used, but PAMs are typically 2-5 base pair sequences adjacent the protospacer (that is, the target sequence). Examples of the natural PAM sequences for different Cas proteins are provided herein below and the skilled person will be able to identify further PAM sequences for use with a given Cas protein.

The ability to recognize different PAM sequences depends on the Cas polypeptide(s) included in the system. See e.g., Gleditzsch et al. 2019. RNA Biology. 16(4):504-517. Table A below shows several Cas polypeptides and the PAM sequence they recognize.

TABLE A

Example PAM Sequences

| Cas Protein | PAM Sequence |
|---|---|
| SpCas9 | NGG/NRG |
| SaCas9 | NGRRT or NGRRN |
| NmeCas9 | NNNNGATT |
| CjCas9 | NNNNRYAC |
| StCas9 | NNAGAAW |
| Cas12a (Cpf1) (including LbCpf1 and AsCpf1) | TTTV |
| Cas12b (C2c1) | TTT, TTA, and TTC |
| Cas12c (C2c3) | TA |
| Cas12d (CasY) | TA |
| Cas12e (CasX) | 5'-TTCN-3' |

In a preferred embodiment, the CRISPR effector protein may recognize a 3' PAM. In certain embodiments, the CRISPR effector protein may recognize a 3' PAM which is 5'H, wherein H is A, C or U.

Further, engineering of the PAM Interacting (PI) domain on the Cas protein may allow programing of PAM specificity, improve target site recognition fidelity, and increase the versatility of the CRISPR-Cas protein, for example as described for Cas9 in Kleinstiver B P et al. Engineered CRISPR-Cas9 nucleases with altered PAM specificities. Nature. 2015 Jul. 23; 523(7561):481-5. Doi: 10.1038/nature14592. As further detailed herein, the skilled person will understand that Cas13 proteins may be modified analogously. Gao et al, "Engineered Cpf1 Enzymes with Altered PAM Specificities," bioRxiv 091611; doi: dx.doi.org/10.1101/091611 (Dec. 4, 2016). Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

PAM sequences can be identified in a polynucleotide using an appropriate design tool, which are commercially available as well as online. Such freely available tools include, but are not limited to, CRISPRFinder and CRISP-RTarget. Mojica et al. 2009. Microbiol. 155(Pt. 3):733-740; Atschul et al. 1990. J. Mol. Biol. 215:403-410; Biswass et al. 2013 RNA Biol. 10:817-827; and Grissa et al. 2007. Nucleic Acid Res. 35:W52-57. Experimental approaches to PAM identification can include, but are not limited to, plasmid depletion assays (Jiang et al. 2013. Nat. Biotechnol. 31:233-239; Esvelt et al. 2013. Nat. Methods. 10:1116-1121; Kleinstiver et al. 2015. Nature. 523:481-485), screened by a high-throughput in vivo model called PAM-SCNAR (Pattanayak et al. 2013. Nat. Biotechnol. 31:839-843 and Leenay et al. 2016.Mol. Cell. 16:253), and negative screening (Zetsche et al. 2015. Cell. 163:759-771).

As previously mentioned, CRISPR-Cas systems that target RNA do not typically rely on PAM sequences. Instead such systems typically recognize protospacer flanking sites (PFSs) instead of PAMs Thus, Type VI CRISPR-Cas systems typically recognize protospacer flanking sites (PFSs) instead of PAMs. PFSs represents an analogue to PAMs for RNA targets. Type VI CRISPR-Cas systems employ a Cas13. Some Cas13 proteins analyzed to date, such as Cas13a (C2c2) identified from Leptotrichia shahii (LshCAs13a) have a specific discrimination against G at the 3'end of the target RNA. The presence of a C at the corresponding crRNA repeat site can indicate that nucleotide pairing at this position is rejected. However, some Cas13 proteins (e.g., LwaCAs13a and PspCas13b) do not seem to have a PFS preference. See e.g., Gleditzsch et al. 2019. RNA Biology. 16(4):504-517.

Some Type VI proteins, such as subtype B, have 5'-recognition of D (G, T, A) and a 3'-motif requirement of NAN or NNA. One example is the Cas13b protein identified in Bergeyella zoohelcum (BzCas13b). See e.g., Gleditzsch et al. 2019. RNA Biology. 16(4):504-517.

Overall Type VI CRISPR-Cas systems appear to have less restrictive rules for substrate (e.g., target sequence) recognition than those that target DNA (e.g., Type V and type II).

Zinc Finger Nucleases

In some embodiments, the polynucleotide is modified using a Zinc Finger nuclease or system thereof. One type of programmable DNA-binding domain is provided by artificial zinc-finger (ZF) technology, which involves arrays of ZF modules to target new DNA-binding sites in the genome. Each finger module in a ZF array targets three DNA bases. A customized array of individual zinc finger domains is assembled into a ZF protein (ZFP).

ZFPs can comprise a functional domain. The first synthetic zinc finger nucleases (ZFNs) were developed by fusing a ZF protein to the catalytic domain of the Type IIS restriction enzyme FokI. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to Fok I cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79). ZFPs can also be designed as transcription activators and repressors and have been used to target many genes in a wide variety of organisms. Exemplary methods of genome editing using ZFNs can be found for example in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, all of which are specifically incorporated by reference.

TALE Nucleases

In some embodiments, a TALE nuclease or TALE nuclease system can be used to modify a polynucleotide. In some embodiments, the methods provided herein use isolated, non-naturally occurring, recombinant or engineered DNA binding proteins that comprise TALE monomers or TALE monomers or half monomers as a part of their organizational structure that enable the targeting of nucleic acid sequences with improved efficiency and expanded specificity.

Naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", "TALE monomers" or "monomers" will be used to refer to the highly conserved repetitive polypeptide sequences within the TALE nucleic acid binding domain and the term "repeat variable di-residues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA binding domain is $X_{1-11}$-$(X_{12}X_{13})$-$X_{14-33}$ or 34 or 35, where the subscript indicates the amino acid position and X represents any amino acid. $X_{12}X_{13}$ indicate the RVDs. In some polypeptide monomers, the variable amino acid at position 13 is missing or absent and in such monomers, the RVD consists of a single amino acid. In such cases the RVD may be alternatively represented as X*, where X represents $X_{12}$ and (*) indicates that $X_{13}$ is absent. The DNA binding domain comprises several repeats of TALE monomers and this may be represented as $(X_{1-11}$-$(X_{12}X_{13})$-$X_{14-33}$ or 34 or 35)$_z$, where in an advantageous embodiment, z is at least 5 to 40. In a further advantageous embodiment, z is at least 10 to 26.

The TALE monomers can have a nucleotide binding affinity that is determined by the identity of the amino acids in its RVD. For example, polypeptide monomers with an RVD of NI can preferentially bind to adenine (A), monomers with an RVD of NG can preferentially bind to thymine (T), monomers with an RVD of HD can preferentially bind to cytosine (C) and monomers with an RVD of NN can preferentially bind to both adenine (A) and guanine (G). In some embodiments, monomers with an RVD of IG can preferentially bind to T. Thus, the number and order of the polypeptide monomer repeats in the nucleic acid binding domain of a TALE determines its nucleic acid target specificity. In some embodiments, monomers with an RVD of NS can recognize all four base pairs and can bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011).

The polypeptides used in methods of the invention can be isolated, non-naturally occurring, recombinant or engineered nucleic acid-binding proteins that have nucleic acid or DNA binding regions containing polypeptide monomer repeats that are designed to target specific nucleic acid sequences.

As described herein, polypeptide monomers having an RVD of HN or NH preferentially bind to guanine and thereby allow the generation of TALE polypeptides with high binding specificity for guanine containing target nucleic acid sequences. In some embodiments, polypeptide monomers having RVDs RN, NN, NK, SN, NH, KN, HN, NQ, HH, RG, KH, RH and SS can preferentially bind to guanine. In some embodiments, polypeptide monomers having RVDs RN, NK, NQ, HH, KH, RH, SS and SN can preferentially bind to guanine and can thus allow the generation of TALE polypeptides with high binding specificity for guanine containing target nucleic acid sequences. In some embodiments, polypeptide monomers having RVDs HH, KH, NH, NK, NQ, RH, RN and SS can preferentially bind to guanine and thereby allow the generation of TALE polypeptides with high binding specificity for guanine containing target nucleic acid sequences. In some embodiments, the RVDs that have high binding specificity for guanine are RN, NH RH and KH. Furthermore, polypeptide monomers having an RVD of NV can preferentially bind to adenine and guanine. In some embodiments, monomers having RVDs of H*, HA, KA, N*, NA, NC, NS, RA, and S* bind to adenine, guanine, cytosine and thymine with comparable affinity.

The predetermined N-terminal to C-terminal order of the one or more polypeptide monomers of the nucleic acid or DNA binding domain determines the corresponding predetermined target nucleic acid sequence to which the polypeptides of the invention will bind. As used herein the monomers and at least one or more half monomers are "specifically ordered to target" the genomic locus or gene of interest. In plant genomes, the natural TALE-binding sites always begin with a thymine (T), which may be specified by a cryptic signal within the non-repetitive N-terminus of the TALE polypeptide; in some cases, this region may be referred to as repeat 0. In animal genomes, TALE binding sites do not necessarily have to begin with a thymine (T) and polypeptides of the invention may target DNA sequences that begin with T, A, G or C. The tandem repeat of TALE monomers always ends with a half-length repeat or a stretch of sequence that may share identity with only the first 20 amino acids of a repetitive full-length TALE monomer and this half repeat may be referred to as a half-monomer. Therefore, it follows that the length of the nucleic acid or DNA being targeted is equal to the number of full monomers plus two.

As described in Zhang et al., Nature Biotechnology 29:149-153 (2011), TALE polypeptide binding efficiency may be increased by including amino acid sequences from the "capping regions" that are directly N-terminal or C-terminal of the DNA binding region of naturally occurring TALEs into the engineered TALEs at positions N-terminal or C-terminal of the engineered TALE DNA binding region. Thus, in certain embodiments, the TALE polypeptides described herein further comprise an N-terminal capping region and/or a C-terminal capping region.

An exemplary amino acid sequence of a N-terminal capping region is:

(SEQ ID NO: 1)
M D P I R S R T P S P A R E L L S G P Q P D G V Q

P T A D R G V S P P A G G P L D G L P A R R T M S

R T R L P S P P A P S P A F S A D S F S D L L R Q

F D P S L F N T S L F D S L P P F G A H H T E A A

T G E W D E V Q S G L R A A D A P P P T M R V A V

T A A R P P R A K P A P R R R A A Q P S D A S P A

A Q V D L R T L G Y S Q Q Q Q E K I K P K V R S T

V A Q H H E A L V G H G F T H A H I V A L S Q H P

A A L G T V A V K Y Q D M I A A L P E A T H E A I

V G V G K Q W S G A R A L E A L L T V A G E L R G

P P L Q L D T G Q L L K I A K R G G V T A V E A V

H A W R N A L T G A P L N

An exemplary amino acid sequence of a C-terminal capping region is:

(SEQ ID NO: 2)
R P A L E S I V A Q L S R P D P A L A A L T N D H

L V A L A C L G G R P A L D A V K K G L P H A P A

L I K R T N R R I P E R T S H R V A D H A Q V V R

V L G F F Q C H S H P A Q A F D D A M T Q F G M S

R H G L L Q L F R R V G V T E L E A R S G T L P P

A S Q R W D R I L Q A S G M K R A K P S P T S T Q

T P D Q A S L H A F A D S L E R D L D A P S P M H

E G D Q T R A S

As used herein the predetermined "N-terminus" to "C terminus" orientation of the N-terminal capping region, the DNA binding domain comprising the repeat TALE monomers and the C-terminal capping region provide structural basis for the organization of different domains in the d-TALEs or polypeptides of the invention.

The entire N-terminal and/or C-terminal capping regions are not necessary to enhance the binding activity of the DNA binding region. Therefore, in certain embodiments, fragments of the N-terminal and/or C-terminal capping regions are included in the TALE polypeptides described herein.

In certain embodiments, the TALE polypeptides described herein contain a N-terminal capping region fragment that included at least 10, 20, 30, 40, 50, 54, 60, 70, 80, 87, 90, 94, 100, 102, 110, 117, 120, 130, 140, 147, 150, 160, 170, 180, 190, 200, 210, 220, 230, 240, 250, 260 or 270 amino acids of an N-terminal capping region. In certain embodiments, the N-terminal capping region fragment amino acids are of the C-terminus (the DNA-binding region proximal end) of an N-terminal capping region. As described in Zhang et al., Nature Biotechnology 29:149-153 (2011), N-terminal capping region fragments that include the C-terminal 240 amino acids enhance binding activity equal to the full length capping region, while fragments that include the C-terminal 147 amino acids retain greater than 80% of the efficacy of the full length capping region, and fragments that include the C-terminal 117 amino acids retain greater than 50% of the activity of the full-length capping region.

In some embodiments, the TALE polypeptides described herein contain a C-terminal capping region fragment that included at least 6, 10, 20, 30, 37, 40, 50, 60, 68, 70, 80, 90, 100, 110, 120, 127, 130, 140, 150, 155, 160, 170, 180 amino acids of a C-terminal capping region. In certain embodiments, the C-terminal capping region fragment amino acids are of the N-terminus (the DNA-binding region proximal end) of a C-terminal capping region. As described in Zhang et al., Nature Biotechnology 29:149-153 (2011), C-terminal capping region fragments that include the C-terminal 68 amino acids enhance binding activity equal to the full-length capping region, while fragments that include the C-terminal 20 amino acids retain greater than 50% of the efficacy of the full-length capping region.

In certain embodiments, the capping regions of the TALE polypeptides described herein do not need to have identical sequences to the capping region sequences provided herein. Thus, in some embodiments, the capping region of the TALE polypeptides described herein have sequences that are at least 50%, 60%, 70%, 80%, 85%, 90%, 91%, 92%, 93%, 94%, 95%, 96%, 97%, 98% or 99% identical or share identity to the capping region amino acid sequences provided herein. Sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the TALE polypeptides described herein have sequences that are at least 95% identical or share identity to the capping region amino acid sequences provided herein.

Sequence homologies can be generated by any of a number of computer programs known in the art, which include but are not limited to BLAST or FASTA. Suitable computer programs for carrying out alignments like the GCG Wisconsin Bestfit package may also be used. Once the software has produced an optimal alignment, it is possible to calculate % homology, preferably % sequence identity. The software typically does this as part of the sequence comparison and generates a numerical result.

In some embodiments described herein, the TALE polypeptides of the invention include a nucleic acid binding domain linked to the one or more effector domains. The terms "effector domain" or "regulatory and functional domain" refer to a polypeptide sequence that has an activity other than binding to the nucleic acid sequence recognized by the nucleic acid binding domain. By combining a nucleic acid binding domain with one or more effector domains, the polypeptides of the invention may be used to target the one or more functions or activities mediated by the effector domain to a particular target DNA sequence to which the nucleic acid binding domain specifically binds.

In some embodiments of the TALE polypeptides described herein, the activity mediated by the effector domain is a biological activity. For example, in some embodiments the effector domain is a transcriptional inhibitor (i.e., a repressor domain), such as an mSin interaction domain (SID). SID4X domain or a Kruppel-associated box (KRAB) or fragments of the KRAB domain. In some embodiments the effector domain is an enhancer of transcription (i.e. an activation domain), such as the VP16, VP64 or p65 activation domain. In some embodiments, the nucleic acid binding is linked, for example, with an effector domain that includes but is not limited to a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal.

In some embodiments, the effector domain is a protein domain which exhibits activities which include but are not limited to transposase activity, integrase activity, recombinase activity, resolvase activity, invertase activity, protease activity, DNA methyltransferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity. Other preferred embodiments of the invention may include any combination of the activities described herein.

Meganucleases

In some embodiments, a meganuclease or system thereof can be used to modify a polynucleotide. Meganucleases, which are endodeoxyribonucleases characterized by a large recognition site (double-stranded DNA sequences of 12 to 40 base pairs). Exemplary methods for using meganucleases can be found in U.S. Pat. Nos. 8,163,514, 8,133,697, 8,021,867, 8,119,361, 8,119,381, 8,124,369, and 8,129,134, which are specifically incorporated by reference.

Sequences Related to Nucleus Targeting and Transportation

In some embodiments, one or more components (e.g., the Cas protein and/or deaminase, Zn Finger protein, TALE, or meganuclease) in the composition for engineering cells may comprise one or more sequences related to nucleus targeting and transportation. Such sequence may facilitate the one or more components in the composition for targeting a sequence within a cell. In order to improve targeting of the CRISPR-Cas protein and/or the nucleotide deaminase protein or catalytic domain thereof used in the methods of the present disclosure to the nucleus, it may be advantageous to provide one or both of these components with one or more nuclear localization sequences (NLSs).

In some embodiments, the NLSs used in the context of the present disclosure are heterologous to the proteins. Non-limiting examples of NLSs include an NLS sequence derived from: the NLS of the SV40 virus large T-antigen, having the amino acid sequence PKKKRKV (SEQ ID NO: 3) or PKKKRKVEAS (SEQ ID NO: 4); the NLS from nucleoplasmin (e.g., the nucleoplasmin bipartite NLS with the sequence KRPAATKKAGQAKKKK (SEQ ID NO: 5)); the c-myc NLS having the amino acid sequence PAAKRVKLD (SEQ ID NO: 6) or RQRRNELKRSP (SEQ ID NO: 7); the hRNPA1 M9 NLS having the sequence NQSSNFGPMKGGNFGGRSSGPYGGGGQYFAK-PRNQGGY (SEQ ID NO: 8); the sequence RMRIZFKNKGKDTAELRRRRVEVSVELRKAKKD-EQILKRRNV (SEQ ID NO: 9) of the IBB domain from importin-alpha; the sequences VSRKRPRP (SEQ ID NO: 10) and PPKKARED (SEQ ID NO: 11) of the myoma T protein; the sequence PQPKKKPL (SEQ ID NO: 12) of human p53; the sequence SALIKKKKKMAP (SEQ ID NO: 13) of mouse c-abl IV; the sequences DRLRR (SEQ ID NO: 14) and PKQKKRK (SEQ ID NO: 15) of the influenza virus NS1; the sequence RKLKKKIKKL (SEQ ID NO: 16) of the Hepatitis virus delta antigen; the sequence REKKKFLKRR (SEQ ID NO: 17) of the mouse Mx1 protein; the sequence KRKGDEVDGVDEVAKKKSKK (SEQ ID NO: 18) of the human poly(ADP-ribose) polymerase; and the sequence RKCLQAGMNLEARKTKK (SEQ ID NO: 19) of the steroid hormone receptors (human) glucocorticoid. In general, the one or more NLSs are of sufficient strength to drive accumulation of the DNA-targeting Cas protein in a detectable amount in the nucleus of a eukaryotic cell. In general, strength of nuclear localization activity may derive from the number of NLSs in the CRISPR-Cas protein, the particular NLS(s) used, or a combination of these factors. Detection of accumulation in the nucleus may be performed by any suitable technique. For example, a detectable marker may be fused to the nucleic acid-targeting protein, such that location within a cell may be visualized, such as in combination with a means for detecting the location of the nucleus (e.g., a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of nucleic acid-targeting complex formation (e.g., assay for deaminase activity) at the target sequence, or assay for altered gene expression activity affected by DNA-targeting complex formation and/or DNA-targeting), as compared to a control not exposed to the CRISPR-Cas protein and deaminase protein, or exposed to a CRISPR-Cas and/or deaminase protein lacking the one or more NLSs.

The CRISPR-Cas and/or nucleotide deaminase proteins may be provided with 1 or more, such as with, 2, 3, 4, 5, 6, 7, 8, 9, 10, or more heterologous NLSs. In some embodiments, the proteins comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g., zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. In preferred embodiments of the CRISPR-Cas proteins, an NLS attached to the C-terminal of the protein.

In certain embodiments, the CRISPR-Cas protein and the deaminase protein are delivered to the cell or expressed within the cell as separate proteins. In these embodiments, each of the CRISPR-Cas and deaminase protein can be provided with one or more NLSs as described herein. In certain embodiments, the CRISPR-Cas and deaminase proteins are delivered to the cell or expressed with the cell as a fusion protein. In these embodiments one or both of the CRISPR-Cas and deaminase protein is provided with one or more NLSs. Where the nucleotide deaminase is fused to an adaptor protein (such as MS2) as described above, the one or more NLS can be provided on the adaptor protein, provided that this does not interfere with aptamer binding. In particular embodiments, the one or more NLS sequences may also function as linker sequences between the nucleotide deaminase and the CRISPR-Cas protein.

In certain embodiments, guides of the disclosure comprise specific binding sites (e.g. aptamers) for adapter proteins, which may be linked to or fused to an nucleotide deaminase or catalytic domain thereof. When such a guide forms a CRISPR complex (e.g., CRISPR-Cas protein binding to guide and target) the adapter proteins bind and, the nucleotide deaminase or catalytic domain thereof associated with the adapter protein is positioned in a spatial orientation which is advantageous for the attributed function to be effective.

The skilled person will understand that modifications to the guide which allow for binding of the adapter+nucleotide deaminase, but not proper positioning of the adapter+nucleotide deaminase (e.g. due to steric hindrance within the three dimensional structure of the CRISPR complex) are modifications which are not intended. The one or more modified guide may be modified at the tetra loop, the stem loop 1, stem loop 2, or stem loop 3, as described herein, preferably at either the tetra loop or stem loop 2, and in some cases at both the tetra loop and stem loop 2.

In some embodiments, a component (e.g., the dead Cas protein, the nucleotide deaminase protein or catalytic domain thereof, or a combination thereof) in the systems may comprise one or more nuclear export signals (NES), one or more nuclear localization signals (NLS), or any combinations thereof. In some cases, the NES may be an HIV Rev NES. In certain cases, the NES may be MAPK NES. When the component is a protein, the NES or NLS may be at the C terminus of component. Alternatively or additionally, the NES or NLS may be at the N terminus of component. In some examples, the Cas protein and optionally said nucleotide deaminase protein or catalytic domain thereof comprise one or more heterologous nuclear export signal(s) (NES(s)) or nuclear localization signal(s) (NLS(s)), preferably an HIV Rev NES or MAPK NES, preferably C-terminal.

Templates

In some embodiments, the composition for engineering cells comprise a template, e.g., a recombination template. A template may be a component of another vector as described herein, contained in a separate vector, or provided as a separate polynucleotide. In some embodiments, a recombination template is designed to serve as a template in homologous recombination, such as within or near a target sequence nicked or cleaved by a nucleic acid-targeting effector protein as a part of a nucleic acid-targeting complex.

In an embodiment, the template nucleic acid alters the sequence of the target position. In an embodiment, the template nucleic acid results in the incorporation of a modified, or non-naturally occurring base into the target nucleic acid.

The template sequence may undergo a breakage mediated or catalyzed recombination with the target sequence. In an embodiment, the template nucleic acid may include sequence that corresponds to a site on the target sequence that is cleaved by a Cas protein mediated cleavage event. In an embodiment, the template nucleic acid may include sequence that corresponds to both, a first site on the target sequence that is cleaved in a first Cas protein mediated event, and a second site on the target sequence that is cleaved in a second Cas protein mediated event.

In certain embodiments, the template nucleic acid can include sequence which results in an alteration in the coding sequence of a translated sequence, e.g., one which results in the substitution of one amino acid for another in a protein product, e.g., transforming a mutant allele into a wild type allele, transforming a wild type allele into a mutant allele, and/or introducing a stop codon, insertion of an amino acid residue, deletion of an amino acid residue, or a nonsense mutation. In certain embodiments, the template nucleic acid can include sequence which results in an alteration in a non-coding sequence, e.g., an alteration in an exon or in a 5' or 3' non-translated or non-transcribed region. Such alterations include an alteration in a control element, e.g., a promoter, enhancer, and an alteration in a cis-acting or trans-acting control element.

A template nucleic acid having homology with a target position in a target gene may be used to alter the structure of a target sequence. The template sequence may be used to alter an unwanted structure, e.g., an unwanted or mutant nucleotide. The template nucleic acid may include sequence which, when integrated, results in: decreasing the activity of a positive control element; increasing the activity of a positive control element; decreasing the activity of a negative control element; increasing the activity of a negative control element; decreasing the expression of a gene; increasing the expression of a gene; increasing resistance to a disorder or disease; increasing resistance to viral entry; correcting a mutation or altering an unwanted amino acid residue conferring, increasing, abolishing or decreasing a biological property of a gene product, e.g., increasing the enzymatic activity of an enzyme, or increasing the ability of a gene product to interact with another molecule.

The template nucleic acid may include sequence which results in: a change in sequence of 1, 2, 3, 4, 5, 6, 7, 8, 9, 10, 1 1, 12 or more nucleotides of the target sequence.

A template polynucleotide may be of any suitable length, such as about or more than about 10, 15, 20, 25, 50, 75, 100, 150, 200, 500, 1000, or more nucleotides in length. In an embodiment, the template nucleic acid may be 20+/−10, 30+/−10, 40+/−10, 50+/−10, 60+/−10, 70+/−10, 80+/−10, 90+/−10, 100+/−10, 1 10+/−10, 120+/−10, 130+/−10, 140+/−10, 150+/−10, 160+/−10, 170+/−10, 1 80+/−10, 190+/−10, 200+/−10, 210+/−10, of 220+/−10 nucleotides in length. In an embodiment, the template nucleic acid may be 30+/−20, 40+/−20, 50+/−20, 60+/−20, 70+/−20, 80+/−20, 90+/−20, 100+/−20, 1 10+/−20, 120+/−20, 130+/−20, 140+/−20, 150+/−20, 160+/−20, 170+/−20, 180+/−20, 190+/−20, 200+/−20, 210+/−20, of 220+/−20 nucleotides in length. In an embodiment, the template nucleic acid is 10 to 1,000, 20 to 900, 30 to 800, 40 to 700, 50 to 600, 50 to 500, 50 to 400, 50 to 300, 50 to 200, or 50 to 100 nucleotides in length.

In some embodiments, the template polynucleotide is complementary to a portion of a polynucleotide comprising the target sequence. When optimally aligned, a template polynucleotide might overlap with one or more nucleotides of a target sequences (e.g. about or more than about 1, 5, 10, 15, 20, 25, 30, 35, 40, 45, 50, 60, 70, 80, 90, 100 or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence.

The exogenous polynucleotide template comprises a sequence to be integrated (e.g., a mutated gene). The sequence for integration may be a sequence endogenous or exogenous to the cell. Examples of a sequence to be integrated include polynucleotides encoding a protein or a non-coding RNA (e.g., a microRNA). Thus, the sequence for integration may be operably linked to an appropriate control sequence or sequences. Alternatively, the sequence to be integrated may provide a regulatory function.

An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000.

An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000.

In certain embodiments, one or both homology arms may be shortened to avoid including certain sequence repeat elements. For example, a 5' homology arm may be shortened to avoid a sequence repeat element. In other embodiments, a 3' homology arm may be shortened to avoid a sequence repeat element. In some embodiments, both the 5' and the 3' homology arms may be shortened to avoid including certain sequence repeat elements.

In some methods, the exogenous polynucleotide template may further comprise a marker. Such a marker may make it easy to screen for targeted integrations. Examples of suitable markers include restriction sites, fluorescent proteins, or selectable markers. The exogenous polynucleotide template of the disclosure can be constructed using recombinant techniques (see, for example, Sambrook et al., 2001 and Ausubel et al., 1996).

In certain embodiments, a template nucleic acid for correcting a mutation may be designed for use as a single-stranded oligonucleotide. When using a single-stranded oligonucleotide, 5' and 3' homology arms may range up to about 200 base pairs (bp) in length, e.g., at least 25, 50, 75, 100, 125, 150, 175, or 200 bp in length.

In certain embodiments, a template nucleic acid for correcting a mutation may be designed for use with a homology-independent targeted integration system. Suzuki et al. describe in vivo genome editing via CRISPR/Cas9 mediated homology-independent targeted integration (2016, Nature 540:144-149). Schmid-Burgk, et al. describe use of the CRISPR-Cas9 system to introduce a double-strand break (DSB) at a user-defined genomic location and insertion of a universal donor DNA (Nat Commun. 2016 Jul. 28; 7:12338). Gao, et al. describe "Plug-and-Play Protein Modification Using Homology-Independent Universal Genome Engineering" (Neuron. 2019 Aug. 21; 103(4):583-597).

RNAi

In certain embodiments, the genetic modifying agent is RNAi (e.g., shRNA, interfering RNAs). As used herein, the term "RNAi" refers to any type of interfering RNA, including but not limited to, siRNAi, shRNAi, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein). The term "RNAi" can include both gene silencing RNAi molecules, and also RNAi effector molecules which activate the expression of a gene.

In certain embodiments, a modulating agent may comprise silencing one or more endogenous genes. As used herein, "gene silencing" or "gene silenced" in reference to an activity of an RNAi molecule, for example a siRNA or miRNA refers to a decrease in the mRNA level in a cell for a target gene by at least about 5%, about 10%, about 20%, about 30%, about 40%, about 50%, about 60%, about 70%, about 80%, about 90%, about 95%, about 99%, about 100% of the mRNA level found in the cell without the presence of the miRNA or RNA interference molecule. In one preferred embodiment, the mRNA levels are decreased by at least about 70%, about 80%, about 90%, about 95%, about 99%, about 100%.

As used herein, a "siRNA" refers to a nucleic acid that forms a double stranded RNA, which double stranded RNA has the ability to reduce or inhibit expression of a gene or target gene when the siRNA is present or expressed in the same cell as the target gene. The double stranded RNA siRNA can be formed by the complementary strands. In one embodiment, a siRNA refers to a nucleic acid that can form a double stranded siRNA. The sequence of the siRNA can correspond to the full-length target gene, or a subsequence thereof. Typically, the siRNA is at least about 15-50 nucleotides in length (e.g., each complementary sequence of the double stranded siRNA is 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The terms "microRNA" or "miRNA" are used interchangeably herein are endogenous RNAs, some of which are known to regulate the expression of protein-coding genes at the posttranscriptional level. Endogenous microRNAs are small RNAs naturally present in the genome that are capable of modulating the productive utilization of mRNA. The term artificial microRNA includes any type of RNA sequence, other than endogenous microRNA, which is capable of modulating the productive utilization of mRNA. MicroRNA sequences have been described in publications such as Lim, et al., Genes & Development, 17, p. 991-1008 (2003), Lim et al Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and/or RNAi pathways.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 1 16:281-297), comprises a dsRNA molecule.

Antibodies

In certain embodiments, the one or more agents is an antibody. The term "antibody" is used interchangeably with the term "immunoglobulin" herein, and includes intact antibodies, fragments of antibodies, e.g., Fab, F(ab')$_2$ fragments, and intact antibodies and fragments that have been mutated either in their constant and/or variable region (e.g., mutations to produce chimeric, partially humanized, or fully humanized antibodies, as well as to produce antibodies with a desired trait, e.g., enhanced binding and/or reduced FcR binding). The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')2, Fabc, Fd, dAb, $V_{HH}$ and scFv and/or Fv fragments.

As used herein, a preparation of antibody protein having less than about 50% of non-antibody protein (also referred to herein as a "contaminating protein"), or of chemical precursors, is considered to be "substantially free." 40%, 30%, 20%, 10% and more preferably 5% (by dry weight), of non-antibody protein, or of chemical precursors is considered to be substantially free. When the antibody protein or biologically active portion thereof is recombinantly produced, it is also preferably substantially free of culture medium, i.e., culture medium represents less than about 30%, preferably less than about 20%, more preferably less than about 10%, and most preferably less than about 5% of the volume or mass of the protein preparation.

The term "antigen-binding fragment" refers to a polypeptide fragment of an immunoglobulin or antibody that binds antigen or competes with intact antibody (i.e., with the intact antibody from which they were derived) for antigen binding (i.e., specific binding). As such these antibodies or fragments thereof are included in the scope of the invention, provided that the antibody or fragment binds specifically to a target molecule.

It is intended that the term "antibody" encompass any Ig class or any Ig subclass (e.g. the IgG1, IgG2, IgG3, and IgG4 subclasses of IgG) obtained from any source (e.g., humans and non-human primates, and in rodents, lagomorphs, caprines, bovines, equines, ovines, etc.).

The term "Ig class" or "immunoglobulin class", as used herein, refers to the five classes of immunoglobulin that have been identified in humans and higher mammals, IgG, IgM, IgA, IgD, and IgE. The term "Ig subclass" refers to the two subclasses of IgM (H and L), three subclasses of IgA (IgA1, IgA2, and secretory IgA), and four subclasses of IgG (IgG1, IgG2, IgG3, and IgG4) that have been identified in humans and higher mammals. The antibodies can exist in monomeric or polymeric form; for example, 1 gM antibodies exist in pentameric form, and IgA antibodies exist in monomeric, dimeric or multimeric form.

The term "IgG subclass" refers to the four subclasses of immunoglobulin class IgG-IgG1, IgG2, IgG3, and IgG4 that have been identified in humans and higher mammals by the heavy chains of the immunoglobulins, V1–γ4, respectively. The term "single-chain immunoglobulin" or "single-chain antibody" (used interchangeably herein) refers to a protein having a two-polypeptide chain structure consisting of a heavy and a light chain, said chains being stabilized, for example, by interchain peptide linkers, which has the ability to specifically bind antigen. The term "domain" refers to a globular region of a heavy or light chain polypeptide comprising peptide loops (e.g., comprising 3 to 4 peptide loops) stabilized, for example, by β pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions". The "constant" domains of an antibody light chain are referred to interchangeably as "light chain constant regions", "light chain constant domains", "CL" regions or "CL" domains. The "constant" domains of an antibody heavy chain are referred to interchangeably as "heavy chain constant regions", "heavy chain constant domains", "CH" regions or "CH" domains). The "variable" domains of an antibody light chain are referred to interchangeably as "light chain variable regions", "light chain variable domains", "VL" regions or "VL" domains). The "variable" domains of an antibody heavy chain are referred to interchangeably as "heavy chain constant regions", "heavy chain constant domains", "VH" regions or "VH" domains).

The term "region" can also refer to a part or portion of an antibody chain or antibody chain domain (e.g., a part or portion of a heavy or light chain or a part or portion of a constant or variable domain, as defined herein), as well as more discrete parts or portions of said chains or domains. For example, light and heavy chains or light and heavy chain variable domains include "complementarity determining regions" or "CDRs" interspersed among "framework regions" or "FRs", as defined herein.

The term "conformation" refers to the tertiary structure of a protein or polypeptide (e.g., an antibody, antibody chain, domain or region thereof). For example, the phrase "light (or heavy) chain conformation" refers to the tertiary structure of a light (or heavy) chain variable region, and the phrase "antibody conformation" or "antibody fragment conformation" refers to the tertiary structure of an antibody or fragment thereof.

The term "antibody-like protein scaffolds" or "engineered protein scaffolds" broadly encompasses proteinaceous non-immunoglobulin specific-binding agents, typically obtained by combinatorial engineering (such as site-directed random mutagenesis in combination with phage display or other molecular selection techniques). Usually, such scaffolds are derived from robust and small soluble monomeric proteins (such as Kunitz inhibitors or lipocalins) or from a stably folded extra-membrane domain of a cell surface receptor (such as protein A, fibronectin or the ankyrin repeat).

Such scaffolds have been extensively reviewed in Binz et al. (Engineering novel binding proteins from nonimmunoglobulin domains. Nat Biotechnol 2005, 23:1257-1268), Gebauer and Skerra (Engineered protein scaffolds as next-generation antibody therapeutics. Curr Opin Chem Biol. 2009, 13:245-55), Gill and Damle (Biopharmaceutical drug discovery using novel protein scaffolds. Curr Opin Biotechnol 2006, 17:653-658), Skerra (Engineered protein scaffolds for molecular recognition. J Mol Recognit 2000, 13:167-187), and Skerra (Alternative non-antibody scaffolds for molecular recognition. Curr Opin Biotechnol 2007, 18:295-304), and include without limitation affibodies, based on the Z-domain of staphylococcal protein A, a three-helix bundle of 58 residues providing an interface on two of its alpha-helices (Nygren, Alternative binding proteins: Affibody binding proteins developed from a small three-helix bundle scaffold. FEBS J 2008, 275:2668-2676); engineered Kunitz domains based on a small (ca. 58 residues) and robust, disulphide-crosslinked serine protease inhibitor, typically of human origin (e.g. LACI-D1), which can be engineered for different protease specificities (Nixon and Wood, Engineered protein inhibitors of proteases. Curr Opin Drug Discov Dev 2006, 9:261-268); monobodies or adnectins based on the 10th extracellular domain of human fibronectin III (1° fn3), which adopts an Ig-like beta-sandwich fold (94 residues) with 2-3 exposed loops, but lacks the central disulphide bridge (Koide and Koide, Monobodies: antibody mimics based on the scaffold of the fibronectin type III domain. Methods Mol Biol 2007, 352:95-109); anticalins derived from the lipocalins, a diverse family of eight-stranded beta-barrel proteins (ca. 180 residues) that naturally form binding sites for small ligands by means of four structurally variable loops at the open end, which are abundant in humans, insects, and many other organisms (Skerra, Alternative binding proteins: Anticalins harnessing the structural plasticity of the lipocalin ligand pocket to engineer novel binding activities. FEBS J 2008, 275:2677-2683); DARPins, designed ankyrin repeat domains (166 residues), which provide a rigid interface arising from typically three repeated beta-turns (Stumpp et al., DARPins: a new generation of protein therapeutics. Drug Discov Today 2008, 13:695-701); avimers (multimerized LDLR-A module) (Silverman et al., Multivalent avimer proteins evolved by exon shuffling of a family of human receptor domains. Nat Biotechnol 2005, 23:1556-1561); and cysteine-rich knottin peptides (Kolmar, Alternative binding proteins: biological activity and therapeutic potential of cystine-knot miniproteins. FEBS J 2008, 275:2684-2690).

"Specific binding" of an antibody means that the antibody exhibits appreciable affinity for a particular antigen or epitope and, generally, does not exhibit significant cross reactivity. "Appreciable" binding includes binding with an affinity of at least 25 µM. Antibodies with affinities greater than $1 \times 10^7$ $M^{-1}$ (or a dissociation coefficient of 1 M or less or a dissociation coefficient of 1 nm or less) typically bind with correspondingly greater specificity. Values intermediate of those set forth herein are also intended to be within the scope of the present invention and antibodies of the invention bind with a range of affinities, for example, 100 nM or less, 75 nM or less, 50 nM or less, 25 nM or less, for example 10 nM or less, 5 nM or less, 1 nM or less, or in embodiments 500 pM or less, 100 pM or less, 50 pM or less or 25 pM or less. An antibody that "does not exhibit significant crossreactivity" is one that will not appreciably bind to an entity other than its target (e.g., a different epitope or a different molecule). For example, an antibody that specifically binds to a target molecule will appreciably bind the target molecule but will not significantly react with non-target molecules or peptides. An antibody specific for a particular epitope will, for example, not significantly cross-react with remote epitopes on the same protein or peptide. Specific binding can be determined according to any art-recognized means for determining such binding. Preferably, specific binding is determined according to Scatchard analysis and/or competitive binding assays.

As used herein, the term "affinity" refers to the strength of the binding of a single antigen-combining site with an antigenic determinant. Affinity depends on the closeness of stereochemical fit between antibody combining sites and antigen determinants, on the size of the area of contact between them, on the distribution of charged and hydrophobic groups, etc. Antibody affinity can be measured by equilibrium dialysis or by the kinetic BIACORE™ method. The dissociation constant, Kd, and the association constant, Ka, are quantitative measures of affinity.

As used herein, the term "monoclonal antibody" refers to an antibody derived from a clonal population of antibody-producing cells (e.g., B lymphocytes or B cells) which is homogeneous in structure and antigen specificity. The term "polyclonal antibody" refers to a plurality of antibodies originating from different clonal populations of antibody-producing cells which are heterogeneous in their structure and epitope specificity but which recognize a common antigen. Monoclonal and polyclonal antibodies may exist within bodily fluids, as crude preparations, or may be purified, as described herein.

The term "binding portion" of an antibody (or "antibody portion") includes one or more complete domains, e.g., a pair of complete domains, as well as fragments of an antibody that retain the ability to specifically bind to a target molecule. It has been shown that the binding function of an antibody can be performed by fragments of a full-length antibody. Binding fragments are produced by recombinant DNA techniques, or by enzymatic or chemical cleavage of intact immunoglobulins. Binding fragments include Fab, Fab', F(ab')$_2$, Fabc, Fd, dAb, Fv, single chains, single-chain antibodies, e.g., scFv, and single domain antibodies.

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, FR residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin.

Examples of portions of antibodies or epitope-binding proteins encompassed by the present definition include: (i) the Fab fragment, having $V_L$, $C_L$, $V_H$ and $C_H1$ domains; (ii) the Fab' fragment, which is a Fab fragment having one or more cysteine residues at the C-terminus of the $C_H1$ domain; (iii) the Fd fragment having $V_H$ and $C_H1$ domains; (iv) the Fd' fragment having $V_H$ and $C_H1$ domains and one or more cysteine residues at the C-terminus of the CHI domain; (v) the Fv fragment having the $V_L$ and $V_H$ domains of a single arm of an antibody; (vi) the dAb fragment (Ward et al., 341 Nature 544 (1989)) which consists of a $V_H$ domain or a $V_L$ domain that binds antigen; (vii) isolated CDR regions or isolated CDR regions presented in a functional framework; (viii) F(ab')$_2$ fragments which are bivalent fragments including two Fab' fragments linked by a disulphide bridge at the hinge region; (ix) single chain antibody molecules (e.g., single chain Fv; scFv) (Bird et al., 242 Science 423 (1988); and Huston et al., 85 PNAS 5879 (1988)); (x) "diabodies" with two antigen binding sites, comprising a heavy chain variable domain ($V_H$) connected to a light chain variable domain ($V_L$) in the same polypeptide chain (see, e.g., EP 404,097; WO 93/11161; Hollinger et al., 90 PNAS 6444

(1993)); (xi) "linear antibodies" comprising a pair of tandem Fd segments ($V_H$-$C_h1$-$V_H$-$C_h1$) which, together with complementary light chain polypeptides, form a pair of antigen binding regions (Zapata et al., Protein Eng. 8(10): 1057-62 (1995); and U.S. Pat. No. 5,641,870).

As used herein, a "blocking" antibody or an antibody "antagonist" is one which inhibits or reduces biological activity of the antigen(s) it binds. In certain embodiments, the blocking antibodies or antagonist antibodies or portions thereof described herein completely inhibit the biological activity of the antigen(s).

Antibodies may act as agonists or antagonists of the recognized polypeptides. For example, the present invention includes antibodies which disrupt receptor/ligand interactions either partially or fully. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or of one of its down-stream substrates by immunoprecipitation followed by western blot analysis. In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex. Likewise, encompassed by the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides disclosed herein. The antibody agonists and antagonists can be made using methods known in the art. See, e.g., PCT publication WO 96/40281; U.S. Pat. No. 5,811,097; Deng et al., Blood 92(6):1981-1988 (1998); Chen et al., Cancer Res. 58(16): 3668-3678 (1998); Harrop et al., J. Immunol. 161(4):1786-1794 (1998); Zhu et al., Cancer Res. 58(15):3209-3214 (1998); Yoon et al., J. Immunol. 160(7):3170-3179 (1998); Prat et al., J. Cell. Sci. III (Pt2):237-247 (1998); Pitard et al., J. Immunol. Methods 205(2):177-190 (1997); Liautard et al., Cytokine 9(4):233-241 (1997); Carlson et al., J. Biol. Chem. 272(17):11295-11301 (1997); Taryman et al., Neuron 14(4): 755-762 (1995); Muller et al., Structure 6(9):1153-1167 (1998); Bartunek et al., Cytokine 8(1):14-20 (1996).

The antibodies as defined for the present invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

Simple binding assays can be used to screen for or detect agents that bind to a target protein, or disrupt the interaction between proteins (e.g., a receptor and a ligand). Because certain targets of the present invention are transmembrane proteins, assays that use the soluble forms of these proteins rather than full-length protein can be used, in some embodiments. Soluble forms include, for example, those lacking the transmembrane domain and/or those comprising the IgV domain or fragments thereof which retain their ability to bind their cognate binding partners. Further, agents that inhibit or enhance protein interactions for use in the compositions and methods described herein, can include recombinant peptido-mimetics.

Detection methods useful in screening assays include antibody-based methods, detection of a reporter moiety, detection of cytokines as described herein, and detection of a gene signature as described herein.

Another variation of assays to determine binding of a receptor protein to a ligand protein is through the use of affinity biosensor methods. Such methods may be based on the piezoelectric effect, electrochemistry, or optical methods, such as ellipsometry, optical wave guidance, and surface plasmon resonance (SPR).

Aptamers

In certain embodiments, the one or more agents is an aptamer. Nucleic acid aptamers are nucleic acid species that have been engineered through repeated rounds of in vitro selection or equivalently, SELEX (systematic evolution of ligands by exponential enrichment) to bind to various molecular targets such as small molecules, proteins, nucleic acids, cells, tissues and organisms. Nucleic acid aptamers have specific binding affinity to molecules through interactions other than classic Watson-Crick base pairing. Aptamers are useful in biotechnological and therapeutic applications as they offer molecular recognition properties similar to antibodies. In addition to their discriminate recognition, aptamers offer advantages over antibodies as they can be engineered completely in a test tube, are readily produced by chemical synthesis, possess desirable storage properties, and elicit little or no immunogenicity in therapeutic applications. In certain embodiments, RNA aptamers may be expressed from a DNA construct. In other embodiments, a nucleic acid aptamer may be linked to another polynucleotide sequence. The polynucleotide sequence may be a double stranded DNA polynucleotide sequence. The aptamer may be covalently linked to one strand of the polynucleotide sequence. The aptamer may be ligated to the polynucleotide sequence. The polynucleotide sequence may be configured, such that the polynucleotide sequence may be linked to a solid support or ligated to another polynucleotide sequence.

Aptamers, like peptides generated by phage display or monoclonal antibodies ("mAbs"), are capable of specifically binding to selected targets and modulating the target's activity, e.g., through binding, aptamers may block their target's ability to function. A typical aptamer is 10-15 kDa in size (30-45 nucleotides), binds its target with sub-nanomolar affinity, and discriminates against closely related targets (e.g., aptamers will typically not bind other proteins from the same gene family). Structural studies have shown that aptamers are capable of using the same types of binding interactions (e.g., hydrogen bonding, electrostatic complementarity, hydrophobic contacts, steric exclusion) that drives affinity and specificity in antibody-antigen complexes.

Aptamers have a number of desirable characteristics for use in research and as therapeutics and diagnostics including high specificity and affinity, biological efficacy, and excellent pharmacokinetic properties. In addition, they offer specific competitive advantages over antibodies and other protein biologics. Aptamers are chemically synthesized and are readily scaled as needed to meet production demand for research, diagnostic or therapeutic applications. Aptamers are chemically robust. They are intrinsically adapted to regain activity following exposure to factors such as heat and denaturants and can be stored for extended periods (>1 yr) at room temperature as lyophilized powders. Not being bound by a theory, aptamers bound to a solid support or beads may be stored for extended periods.

Oligonucleotides in their phosphodiester form may be quickly degraded by intracellular and extracellular enzymes such as endonucleases and exonucleases. Aptamers can include modified nucleotides conferring improved characteristics on the ligand, such as improved in vivo stability or improved delivery characteristics. Examples of such modifications include chemical substitutions at the ribose and/or phosphate and/or base positions. SELEX identified nucleic acid ligands containing modified nucleotides are described, e.g., in U.S. Pat. No. 5,660,985, which describes oligonucleotides containing nucleotide derivatives chemically modified at the 2' position of ribose, 5 position of pyrimidines, and 8 position of purines, U.S. Pat. No. 5,756,703 which describes oligonucleotides containing various 2'-modified pyrimidines, and U.S. Pat. No. 5,580,737 which describes highly specific nucleic acid ligands containing one or more nucleotides modified with 2'-amino (2'-$NH_2$), 2'-fluoro (2'-F), and/or 2'-O-methyl (2'-OMe) substituents. Modifications of aptamers may also include, modifications at exocyclic amines, substitution of 4-thiouridine, substitution of 5-bromo or 5-iodo-uracil; backbone modifications, phosphorothioate or allyl phosphate modifications, methylations, and unusual base-pairing combinations such as the isobases isocytidine and isoguanosine. Modifications can also include 3' and 5' modifications such as capping. As used herein, the term phosphorothioate encompasses one or more non-bridging oxygen atoms in a phosphodiester bond replaced by one or more sulfur atoms. In further embodiments, the oligonucleotides comprise modified sugar groups, for example, one or more of the hydroxyl groups is replaced with halogen, aliphatic groups, or functionalized as ethers or amines. In one embodiment, the 2'-position of the furanose residue is substituted by any of an O-methyl, O-alkyl, O-allyl, S-alkyl, S-allyl, or halo group. Methods of synthesis of 2-modified sugars are described, e.g., in Sproat, et al., Nucl. Acid Res. 19:733-738 (1991); Cotten, et al, Nucl. Acid Res. 19:2629-2635 (1991); and Hobbs, et al, Biochemistry 12:5138-5145 (1973). Other modifications are known to one of ordinary skill in the art. In certain embodiments, aptamers include aptamers with improved off-rates as described in International Patent Publication No. WO 2009012418, "Method for generating aptamers with improved off-rates," incorporated herein by reference in its entirety. In certain embodiments aptamers are chosen from a library of aptamers. Such libraries include, but are not limited to those described in Rohloff et al., "Nucleic Acid Ligands With Protein-like Side Chains: Modified Aptamers and Their Use as Diagnostic and Therapeutic Agents," Molecular Therapy Nucleic Acids (2014) 3, e201. Aptamers are also commercially available (see, e.g., SomaLogic, Inc., Boulder, Colorado). In certain embodiments, the present invention may utilize any aptamer containing any modification as described herein.

Adoptive Cell Transfer

In certain embodiments, the methods of the present invention may be used to predict a response to adoptive cell transfer methods. In certain embodiments, modulating gene program activity or treating with an agent that shifts a tumor to a responder phenotype may be used prior to or in conjunction with adoptive cell transfer to increase the effectiveness of adoptive cell transfer. As described further herein, the CXCL13 T cell program can mark activated T cells in human tumors and is a superior marker compared to cytolytic programs. In certain embodiments, T cells are used for adoptive transfer. The T cells may be a T cell expressing a biological program as described herein. In certain embodiments, T cells expressing a CXCL13 program may be used in adoptive cell transfer (T_21 in Table 10). The T cells may be isolated from a donor or subject and modified to express a CAR or TCR as described further herein. In certain embodiments, a population of T cells for transfer are treated with one or more agents to shift the T cells to express a CXCL13 program. In certain embodiments, adoptive cell transfer is used in combination with CPB therapy and/or IDO1 inhibition.

As used herein, "ACT", "adoptive cell therapy" and "adoptive cell transfer" may be used interchangeably. In certain embodiments, Adoptive cell therapy (ACT) can refer to the transfer of cells to a patient with the goal of transferring the functionality and characteristics into the new host by engraftment of the cells (see, e.g., Mettananda et al., Editing an α-globin enhancer in primary human hematopoietic stem cells as a treatment for β-thalassemia, Nat Commun. 2017 Sep. 4; 8(1):424). As used herein, the term "engraft" or "engraftment" refers to the process of cell incorporation into a tissue of interest in vivo through contact with existing cells of the tissue. Adoptive cell therapy (ACT) can refer to the transfer of cells, most commonly immune-derived cells, back into the same patient or into a new recipient host with the goal of transferring the immunologic functionality and characteristics into the new host. If possible, use of autologous cells helps the recipient by minimizing GVHD issues. The adoptive transfer of autologous tumor infiltrating lymphocytes (TIL) (Zacharakis et al., (2018) Nat Med. 2018 June; 24(6):724-730; Besser et al., (2010) Clin. Cancer Res 16 (9) 2646-55; Dudley et al., (2002) Science 298 (5594): 850-4; and Dudley et al., (2005) Journal of Clinical Oncology 23 (10): 2346-57) or genetically re-directed peripheral blood mononuclear cells (Johnson et al., (2009) Blood 114 (3): 535-46; and Morgan et al., (2006) Science 314(5796) 126-9) has been used to successfully treat patients with advanced solid tumors, including melanoma, metastatic breast cancer and colorectal carcinoma, as well as patients with CD19-expressing hematologic malignancies (Kalos et al., (2011) Science Translational Medicine 3 (95): 95ra73). In certain embodiments, allogenic cells immune cells are transferred (see, e.g., Ren et al., (2017) Clin Cancer Res 23 (9) 2255-2266). As described further herein, allogenic cells can be edited to reduce alloreactivity and prevent graft-versus-host disease. Thus, use of allogenic cells allows for cells to be obtained from healthy donors and prepared for use in patients as opposed to preparing autologous cells from a patient after diagnosis.

Aspects of the invention involve the adoptive transfer of immune system cells, such as T cells, specific for selected antigens, such as tumor associated antigens or tumor specific neoantigens (see, e.g., Maus et al., 2014, Adoptive Immunotherapy for Cancer or Viruses, Annual Review of Immunology, Vol. 32: 189-225; Rosenberg and Restifo, 2015, Adoptive cell transfer as personalized immunotherapy for human cancer, Science Vol. 348 no. 6230 pp. 62-68; Restifo et al., 2015, Adoptive immunotherapy for cancer: harnessing the T cell response. Nat. Rev. Immunol. 12(4): 269-281; and Jenson and Riddell, 2014, Design and implementation of adoptive therapy with chimeric antigen receptor-modified T cells. Immunol Rev. 257(1): 127-144; and Rajasagi et al., 2014, Systematic identification of personal tumor-specific neoantigens in chronic lymphocytic leukemia. Blood. 2014 Jul. 17; 124(3):453-62).

In certain embodiments, an antigen (such as a tumor antigen) to be targeted in adoptive cell therapy (such as particularly CAR or TCR T-cell therapy) of a disease (such as particularly of tumor or cancer) may be selected from a group consisting of: MR1 (see, e.g., Crowther, et al., 2020, Genome-wide CRISPR-Cas9 screening reveals ubiquitous T cell cancer targeting via the monomorphic MHC class I-related protein MR1, Nature Immunology volume 21, pages 178-185), B cell maturation antigen (BCMA) (see, e.g., Friedman et al., Effective Targeting of Multiple BCMA-Expressing Hematological Malignancies by Anti-BCMA CAR T Cells, Hum Gene Ther. 2018 Mar. 8; Berdeja J G, et al. Durable clinical responses in heavily pretreated patients with relapsed/refractory multiple myeloma: updated results from a multicenter study of bb2121 anti-Bcma CAR T cell therapy. Blood. 2017; 130:740; and Mouhieddine and Ghobrial, Immunotherapy in Multiple Myeloma: The Era of CAR T Cell Therapy, Hematologist, May-June 2018, Volume 15, issue 3); PSA (prostate-specific antigen); prostate-specific membrane antigen (PSMA); PSCA (Prostate stem cell antigen); Tyrosine-protein kinase transmembrane receptor ROR1; fibroblast activation protein (FAP); Tumor-associated glycoprotein 72 (TAG72); Carcinoembryonic antigen (CEA); Epithelial cell adhesion molecule (EPCAM); Mesothelin; Human Epidermal growth factor Receptor 2 (ERBB2 (Her2/neu)); Prostase; Prostatic acid phosphatase (PAP); elongation factor 2 mutant (ELF2M); Insulin-like growth factor 1 receptor (IGF-1R); gp1OO; BCR-ABL (breakpoint cluster region-Abelson); tyrosinase; New York esophageal squamous cell carcinoma 1 (NY-ESO-1); x-light chain, LAGE (L antigen); MAGE (melanoma antigen); Melanoma-associated antigen 1 (MAGE-A1); MAGE A3; MAGE A6; legumain; Human papillomavirus (HPV) E6; HPV E7; prostein; survivin; PCTA1 (Galectin 8); Melan-A/MART-1; Ras mutant; TRP-1 (tyrosinase related protein 1, or gp75); Tyrosinase-related Protein 2 (TRP2); TRP-2/INT2 (TRP-2/intron 2); RAGE (renal antigen); receptor for advanced glycation end products 1 (RAGE1); Renal ubiquitous 1, 2 (RU1, RU2); intestinal carboxyl esterase (iCE); Heat shock protein 70-2 (HSP70-2) mutant; thyroid stimulating hormone receptor (TSHR); CD123; CD171; CD19; CD20; CD22; CD26; CD30; CD33; CD44v7/8 (cluster of differentiation 44, exons 7/8); CD53; CD92; CD100; CD148; CD150; CD200; CD261; CD262; CD362; CS-1 (CD2 subset 1, CRACC, SLAMF7, CD319, and 19A24); C-type lectin-like molecule-1 (CLL-1); ganglioside GD3 (aNeu5Ac (2-8)aNeu5Ac(2-3)bDGalp(1-4)bDGlcp(1-1)Cer); Tn antigen (Tn Ag); Fms-Like Tyrosine Kinase 3 (FLT3); CD38; CD138; CD44v6; B7H3 (CD276); KIT (CD117); Interleukin-13 receptor subunit alpha-2 (IL-13Ra2); Interleukin 11 receptor alpha (IL-11Ra); prostate stem cell antigen (PSCA); Protease Serine 21 (PRSS21); vascular endothelial growth factor receptor 2 (VEGFR2); Lewis(Y) antigen; CD24; Platelet-derived growth factor receptor beta (PDGFR-beta); stage-specific embryonic antigen-4 (SSEA-4); Mucin 1, cell surface associated (MUC1); mucin 16 (MUC16); epidermal growth factor receptor (EGFR); epidermal growth factor receptor variant III (EGFRvIII); neural cell adhesion molecule (NCAM); carbonic anhydrase IX (CAIX); Proteasome (Prosome, Macropain) Subunit, Beta Type, 9 (LMP2); ephrin type-A receptor 2 (EphA2); Ephrin B2; Fucosyl GM1; sialyl Lewis adhesion molecule (sLe); ganglioside GM3 (aNeu5Ac(2-3)bDGalp(1-4)bDGlcp(1-1) Cer); TGS5; high molecular weight-melanoma-associated antigen (HMWMAA); o-acetyl-GD2 ganglioside (OAcGD2); Folate receptor alpha; Folate receptor beta; tumor endothelial marker 1 (TEM1/CD248); tumor endothelial marker 7-related (TEM7R); claudin 6 (CLDN6); G protein-coupled receptor class C group 5, member D (GPRC5D); chromosome X open reading frame 61 (CX-ORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); ETS translocation-variant gene 6, located on chromosome 12p (ETV6-AML); sperm protein 17 (SPA17); X Antigen Family, Member IA (XAGE1); angiopoietin-binding cell surface receptor 2 (Tie 2); CT (cancer/testis (antigen)); melanoma cancer testis antigen-1 (MAD-CT-1); melanoma cancer testis antigen-2 (MAD-CT-2); Fos-related antigen 1; p53; p53 mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; Cyclin D1; v-myc avian myelocytomatosis viral oncogene neuroblastoma derived homolog (MYCN); Ras Homolog Family Member C (RhoC); Cytochrome P450 1B1 (CYP1B1); CCCTC-Binding Factor (Zinc Finger Protein)-Like (BORIS); Squamous Cell Carcinoma Antigen Recognized By T Cells-1 or 3 (SART1, SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint-1, -2, -3 or -4 (SSX1, SSX2, SSX3, SSX4); CD79a; CD79b; CD72; Leukocyte-associated immunoglobulin-like receptor 1 (LAIR1); Fc fragment of IgA receptor (FCAR); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); mouse double minute 2 homolog (MDM2); livin; alphafetoprotein (AFP); transmembrane activator and CAML Interactor (TACI); B-cell activating factor receptor (BAFF-R); V-Ki-ras2 Kirsten rat sarcoma viral oncogene homolog (KRAS); immunoglobulin lambda-like polypeptide 1 (IGLL1); 707-AP (707 alanine proline); ART-4 (adenocarcinoma antigen recognized by T4 cells); BAGE (B antigen; b-catenin/m, b-catenin/mutated); CAMEL (CTL-recognized antigen on melanoma); CAP1 (carcinoembryonic antigen peptide 1); CASP-8 (caspase-8); CDC27m (cell-division cycle 27 mutated); CDK4/m (cyclin-dependent kinase 4 mutated); Cyp-B (cyclophilin B); DAM (differentiation antigen melanoma); EGP-2 (epithelial glycoprotein 2); EGP-40 (epithelial glycoprotein 40); Erbb2, 3, 4 (erythroblastic leukemia viral oncogene homolog-2, -3, 4); FBP (folate binding protein); fAchR (Fetal acetylcholine receptor); G250 (glycoprotein 250); GAGE (G antigen); GnT-V (N-acetylglucosaminyltransferase V); HAGE (helicase antigen); ULA-A (human leukocyte antigen-A); HST2 (human signet ring tumor 2); KIAA0205; KDR (kinase insert domain receptor); LDLR/FUT (low density lipid receptor/GDP L-fucose: b-D-galactosidase 2-a-L fucosyltransferase); L1CAM (L1 cell adhesion molecule); MC1R (melanocortin 1 receptor); Myosin/m (myosin mutated); MUM-1, -2, -3 (melanoma ubiquitous mutated 1, 2, 3); NA88-A (NA cDNA clone of patient M88); KG2D (Natural killer group 2, member D) ligands; oncofetal antigen (h5T4); p190 minor bcr-abl (protein of 190KD bcr-abl); Pml/RARa (promyelocytic leukaemia/retinoic acid receptor a); PRAME (preferentially expressed antigen of melanoma); SAGE (sarcoma antigen); TEL/AML1 (translocation Ets-family leukemia/acute myeloid leukemia 1); TPI/m (triosephosphate isomerase mutated); CD70; and any combination thereof.

In certain embodiments, an antigen to be targeted in adoptive cell therapy (such as particularly CAR or TCR T-cell therapy) of a disease (such as particularly of tumor or cancer) is a tumor-specific antigen (TSA).

In certain embodiments, an antigen to be targeted in adoptive cell therapy (such as particularly CAR or TCR T-cell therapy) of a disease (such as particularly of tumor or cancer) is a neoantigen.

In certain embodiments, an antigen to be targeted in adoptive cell therapy (such as particularly CAR or TCR T-cell therapy) of a disease (such as particularly of tumor or cancer) is a tumor-associated antigen (TAA).

In certain embodiments, an antigen to be targeted in adoptive cell therapy (such as particularly CAR or TCR T-cell therapy) of a disease (such as particularly of tumor or cancer) is a universal tumor antigen. In certain preferred embodiments, the universal tumor antigen is selected from the group consisting of: a human telomerase reverse transcriptase (hTERT), survivin, mouse double minute 2 homolog (MDM2), cytochrome P450 1B1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53, cyclin (Dl), and any combinations thereof.

In certain embodiments, an antigen (such as a tumor antigen) to be targeted in adoptive cell therapy (such as particularly CAR or TCR T-cell therapy) of a disease (such as particularly of tumor or cancer) may be selected from a group consisting of: CD19, BCMA, CD70, CLL-1, MAGE A3, MAGE A6, HPV E6, HPV E7, WT1, CD22, CD171, ROR1, MUC16, and SSX2. In certain preferred embodiments, the antigen may be CD19. For example, CD19 may be targeted in hematologic malignancies, such as in lymphomas, more particularly in B-cell lymphomas, such as without limitation in diffuse large B-cell lymphoma, primary mediastinal b-cell lymphoma, transformed follicular lymphoma, marginal zone lymphoma, mantle cell lymphoma, acute lymphoblastic leukemia including adult and pediatric ALL, non-Hodgkin lymphoma, indolent non-Hodgkin lymphoma, or chronic lymphocytic leukemia. For example, BCMA may be targeted in multiple myeloma or plasma cell leukemia (see, e.g., 2018 American Association for Cancer Research (AACR) Annual meeting Poster: Allogeneic Chimeric Antigen Receptor T Cells Targeting B Cell Maturation Antigen). For example, CLL1 may be targeted in acute myeloid leukemia. For example, MAGE A3, MAGE A6, SSX2, and/or KRAS may be targeted in solid tumors. For example, HPV E6 and/or HPV E7 may be targeted in cervical cancer or head and neck cancer. For example, WT1 may be targeted in acute myeloid leukemia (AML), myelodysplastic syndromes (MDS), chronic myeloid leukemia (CML), non-small cell lung cancer, breast, pancreatic, ovarian or colorectal cancers, or mesothelioma. For example, CD22 may be targeted in B cell malignancies, including non-Hodgkin lymphoma, diffuse large B-cell lymphoma, or acute lymphoblastic leukemia. For example, CD171 may be targeted in neuroblastoma, glioblastoma, or lung, pancreatic, or ovarian cancers. For example, ROR1 may be targeted in ROR1+ malignancies, including non-small cell lung cancer, triple negative breast cancer, pancreatic cancer, prostate cancer, ALL, chronic lymphocytic leukemia, or mantle cell lymphoma. For example, MUC16 may be targeted in MUC16ecto+ epithelial ovarian, fallopian tube or primary peritoneal cancer. For example, CD70 may be targeted in both hematologic malignancies as well as in solid cancers such as renal cell carcinoma (RCC), gliomas (e.g., GBM), and head and neck cancers (HNSCC). CD70 is expressed in both hematologic malignancies as well as in solid cancers, while its expression in normal tissues is restricted to a subset of lymphoid cell types (see, e.g., 2018 American Association for Cancer Research (AACR) Annual meeting Poster: Allogeneic CRISPR Engineered Anti-CD70 CAR-T Cells Demonstrate Potent Preclinical Activity Against Both Solid and Hematological Cancer Cells).

Various strategies may for example be employed to genetically modify T cells by altering the specificity of the T cell receptor (TCR) for example by introducing new TCR a and R chains with selected peptide specificity (see U.S. Pat. No. 8,697,854; PCT Patent Publications: WO2003020763, WO2004033685, WO2004044004, WO2005114215, WO2006000830, WO2008038002, WO2008039818, WO2004074322, WO2005113595, WO2006125962, WO2013166321, WO2013039889, WO2014018863, WO2014083173; U.S. Pat. No. 8,088,379).

As an alternative to, or addition to, TCR modifications, chimeric antigen receptors (CARs) may be used in order to generate immunoresponsive cells, such as T cells, specific for selected targets, such as malignant cells, with a wide variety of receptor chimera constructs having been described (see U.S. Pat. Nos. 5,843,728; 5,851,828; 5,912,170; 6,004, 811; 6,284,240; 6,392,013; 6,410,014; 6,753,162; 8,211, 422; and, PCT Publication WO9215322).

In general, CARs are comprised of an extracellular domain, a transmembrane domain, and an intracellular domain, wherein the extracellular domain comprises an antigen-binding domain that is specific for a predetermined target. While the antigen-binding domain of a CAR is often an antibody or antibody fragment (e.g., a single chain variable fragment, scFv), the binding domain is not particularly limited so long as it results in specific recognition of a target. For example, in some embodiments, the antigen-binding domain may comprise a receptor, such that the CAR is capable of binding to the ligand of the receptor. Alternatively, the antigen-binding domain may comprise a ligand, such that the CAR is capable of binding the endogenous receptor of that ligand.

The antigen-binding domain of a CAR is generally separated from the transmembrane domain by a hinge or spacer. The spacer is also not particularly limited, and it is designed to provide the CAR with flexibility. For example, a spacer domain may comprise a portion of a human Fc domain, including a portion of the CH3 domain, or the hinge region of any immunoglobulin, such as IgA, IgD, IgE, IgG, or IgM, or variants thereof. Furthermore, the hinge region may be modified so as to prevent off-target binding by FcRs or other potential interfering objects. For example, the hinge may comprise an IgG4 Fc domain with or without a S228P, L235E, and/or N297Q mutation (according to Kabat numbering) in order to decrease binding to FcRs. Additional spacers/hinges include, but are not limited to, CD4, CD8, and CD28 hinge regions.

The transmembrane domain of a CAR may be derived either from a natural or from a synthetic source. Where the source is natural, the domain may be derived from any membrane bound or transmembrane protein. Transmembrane regions of particular use in this disclosure may be derived from CD8, CD28, CD3, CD45, CD4, CD5, CDS, CD9, CD16, CD22, CD33, CD37, CD64, CD80, CD86, CD 134, CD137, CD 154, TCR. Alternatively, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

Alternative CAR constructs may be characterized as belonging to successive generations. First-generation CARs typically consist of a single-chain variable fragment of an antibody specific for an antigen, for example comprising a VL linked to a VH of a specific antibody, linked by a flexible linker, for example by a CD8a hinge domain and a CD8a transmembrane domain, to the transmembrane and intracellular signaling domains of either CD3ζ or FcRγ (scFv-CD3ζ or scFv-FcRγ; see U.S. Pat. Nos. 7,741,465; 5,912,172; U.S. Pat. No. 5,906,936). Second-generation CARs incorporate the intracellular domains of one or more costimulatory molecules, such as CD28, OX40 (CD134), or 4-1BB (CD137) within the endodomain (for example scFv-CD28/ OX40/4-1BB-CD3ζ; see U.S. Pat. Nos. 8,911,993; 8,916, 381; 8,975,071; 9,101,584; 9,102,760; 9,102,761). Third-generation CARs include a combination of costimulatory endodomains, such a CD3ζ-chain, CD97, GDI 1a-CD18, CD2, ICOS, CD27, CD154, CDS, OX40, 4-1BB, CD2, CD7, LIGHT, LFA-1, NKG2C, B7-H3, CD30, CD40, PD-1, or CD28 signaling domains (for example scFv-CD28-4-1BB-CD3ζ or scFv-CD28-OX40-CD3ζ; see U.S. Pat. Nos. 8,906,682; 8,399,645; 5,686,281; PCT Publication No. WO2014134165; PCT Publication No. WO2012079000). In certain embodiments, the primary signaling domain comprises a functional signaling domain of a protein selected from the group consisting of CD3 zeta, CD3 gamma, CD3 delta, CD3 epsilon, common FcR gamma (FCERIG), FcR beta (Fc Epsilon Rib), CD79a, CD79b, Fc gamma RIIa, DAP10, and DAP12. In certain preferred embodiments, the primary signaling domain comprises a functional signaling domain of CD3ζ or FcRγ. In certain embodiments, the one or more costimulatory signaling domains comprise a functional signaling domain of a protein selected, each independently, from the group consisting of: CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8 alpha, CD8 beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D. In certain embodiments, the one or more costimulatory signaling domains comprise a functional signaling domain of a protein selected, each independently, from the group consisting of: 4-1BB, CD27, and CD28. In certain embodiments, a chimeric antigen receptor may have the design as described in U.S. Pat. No. 7,446,190, comprising an intracellular domain of CD3ζ chain (such as amino acid residues 52-163 of the human CD3 zeta chain, as shown in SEQ ID NO: 14 of U.S. Pat. No. 7,446,190), a signaling region from CD28 and an antigen-binding element (or portion or domain; such as scFv). The CD28 portion, when between the zeta chain portion and the antigen-binding element, may suitably include the transmembrane and signaling domains of CD28 (such as amino acid residues 114-220 of SEQ ID NO: 10, full sequence shown in SEQ ID NO: 6 of U.S. Pat. No. 7,446,190; these can include the following portion of CD28 as set forth in Genbank identifier NM_006139 (sequence version 1, 2 or 3): IEVMYPPPYLD-NEKSNGTIIHVKGKHLCPSPLFPGPSKPFWVLVVV-GGVLACYSLLVTVA FIIFWVRSKRSRLLHSDYMNMT-PRRPGPTRKHYQPYAPPRDFAAYRS)) (SEQ ID NO: 20). Alternatively, when the zeta sequence lies between the CD28 sequence and the antigen-binding element, intracellular domain of CD28 can be used alone (such as amino sequence set forth in SEQ ID NO: 9 of U.S. Pat. No. 7,446,190). Hence, certain embodiments employ a CAR comprising (a) a zeta chain portion comprising the intracellular domain of human CD3ζ chain, (b) a costimulatory signaling region, and (c) an antigen-binding element (or portion or domain), wherein the costimulatory signaling region comprises the amino acid sequence encoded by SEQ ID NO: 6 of U.S. Pat. No. 7,446,190.

Alternatively, costimulation may be orchestrated by expressing CARs in antigen-specific T cells, chosen so as to be activated and expanded following engagement of their native αβTCR, for example by antigen on professional antigen-presenting cells, with attendant costimulation. In addition, additional engineered receptors may be provided on the immunoresponsive cells, for example to improve targeting of a T-cell attack and/or minimize side effects.

By means of an example and without limitation, Kochenderfer et al., (2009) J Immunother. 32 (7): 689-702 described anti-CD19 chimeric antigen receptors (CAR). FMC63-28Z CAR contained a single chain variable region moiety (scFv) recognizing CD19 derived from the FMC63 mouse hybridoma (described in Nicholson et al., (1997) Molecular Immunology 34: 1157-1165), a portion of the human CD28 molecule, and the intracellular component of the human TCR-ζ molecule. FMC63-CD828BBZ CAR contained the FMC63 scFv, the hinge and transmembrane regions of the CD8 molecule, the cytoplasmic portions of CD28 and 4-1BB, and the cytoplasmic component of the TCR-ζ molecule. The exact sequence of the CD28 molecule included in the FMC63-28Z CAR corresponded to Genbank identifier NM_006139; the sequence included all amino acids starting with the amino acid sequence IEVMYPPPY (SEQ. I.D. No. 2) and continuing all the way to the carboxy-terminus of the protein. To encode the anti-CD19 scFv component of the vector, the authors designed a DNA sequence which was based on a portion of a previously published CAR (Cooper et al., (2003) Blood 101: 1637-1644). This sequence encoded the following components in frame from the 5' end to the 3' end: an XhoI site, the human granulocyte-macrophage colony-stimulating factor (GM-CSF) receptor α-chain signal sequence, the FMC63 light chain variable region (as in Nicholson et al., supra), a linker peptide (as in Cooper et al., supra), the FMC63 heavy chain variable region (as in Nicholson et al., supra), and a NotI site. A plasmid encoding this sequence was digested with XhoI and NotI. To form the MSGV-FMC63-28Z retroviral vector, the XhoI and NotI-digested fragment encoding the FMC63 scFv was ligated into a second XhoI and NotI-digested fragment that encoded the MSGV retroviral backbone (as in Hughes et al., (2005) Human Gene Therapy 16: 457-472) as well as part of the extracellular portion of human CD28, the entire transmembrane and cytoplasmic portion of human CD28, and the cytoplasmic portion of the human TCR-ζ molecule (as in Maher et al., 2002) Nature Biotechnology 20: 70-75). The FMC63-28Z CAR is included in the KTE-C19 (axicabtagene ciloleucel) anti-CD19 CAR-T therapy product in development by Kite Pharma, Inc. for the treatment of inter alia patients with relapsed/refractory aggressive B-cell non-Hodgkin lymphoma (NHL). Accordingly, in certain embodiments, cells intended for adoptive cell therapies, more particularly immunoresponsive cells such as T cells, may express the FMC63-28Z CAR as described by Kochenderfer et al. (supra). Hence, in certain embodiments, cells intended for adoptive cell therapies, more particularly immunoresponsive cells such as T cells, may comprise a CAR comprising an extracellular antigen-binding element (or portion or domain; such as scFv) that specifically binds to an antigen, an intracellular signaling domain comprising an intracellular domain of a CD3ζ chain, and a costimulatory signaling region comprising a signaling domain of CD28. Preferably, the CD28 amino acid sequence is as set forth in Genbank identifier NM_006139 (sequence version 1, 2 or 3) starting with the amino acid sequence IEVMYPPPY (SEQ ID NO: 21) and continuing all the way to the carboxy-terminus of the protein. The sequence is reproduced herein: IEVMYPP-PYLDNEKSNGTIIHVKGKHLCPSPL-FPGPSKPFWVLVVVGGVLACYSLLVTVA FIIFWVR-SKRSRLLHSDYMNMTPRRPGPTRKHYQPYAPPRD-FAAYRS (SEQ ID NO: 20). Preferably, the antigen is CD19, more preferably the antigen-binding element is an anti-CD19 scFv, even more preferably the anti-CD19 scFv as described by Kochenderfer et al. (supra).

Additional anti-CD19 CARs are further described in WO2015187528. More particularly Example 1 and Table 1 of WO2015187528, incorporated by reference herein, demonstrate the generation of anti-CD19 CARs based on a fully human anti-CD19 monoclonal antibody (47G4, as described in US20100104509) and murine anti-CD19 monoclonal antibody (as described in Nicholson et al. and explained above). Various combinations of a signal sequence (human CD8-alpha or GM-CSF receptor), extracellular and transmembrane regions (human CD8-alpha) and intracellular T-cell signaling domains (CD28-CD3ζ; 4-1BB-CD3ζ; CD27-CD3ζ; CD28-CD27-CD3ζ, 4-1BB-CD27-CD3ζ; CD27-4-1BB-CD3ζ; CD28-CD27-FcεRI gamma chain; or CD28-FcεRI gamma chain) were disclosed. Hence, in certain embodiments, cells intended for adoptive cell therapies, more particularly immunoresponsive cells such as T cells, may comprise a CAR comprising an extracellular antigen-binding element that specifically binds to an antigen, an extracellular and transmembrane region as set forth in Table 1 of WO2015187528 and an intracellular T-cell signaling domain as set forth in Table 1 of WO2015187528. Preferably, the antigen is CD19, more preferably the antigen-binding element is an anti-CD19 scFv, even more preferably the mouse or human anti-CD19 scFv as described in Example 1 of WO2015187528. In certain embodiments, the CAR comprises, consists essentially of or consists of an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13 as set forth in Table 1 of WO2015187528.

By means of an example and without limitation, chimeric antigen receptor that recognizes the CD70 antigen is described in WO2012058460A2 (see also, Park et al., CD70 as a target for chimeric antigen receptor T cells in head and neck squamous cell carcinoma, Oral Oncol. 2018 March; 78:145-150; and Jin et al., CD70, a novel target of CAR T-cell therapy for gliomas, Neuro Oncol. 2018 Jan. 10; 20(1):55-65). CD70 is expressed by diffuse large B-cell and follicular lymphoma and also by the malignant cells of Hodgkins lymphoma, Waldenstrom's macroglobulinemia and multiple myeloma, and by HTLV-1- and EBV-associated malignancies. (Agathanggelou et al. Am. J. Pathol. 1995; 147: 1152-1160; Hunter et al., Blood 2004; 104:4881. 26; Lens et al., J Immunol. 2005; 174:6212-6219; Baba et al., J Virol. 2008; 82:3843-3852.) In addition, CD70 is expressed by non-hematological malignancies such as renal cell carcinoma and glioblastoma. (Junker et al., J Urol. 2005; 173:2150-2153; Chahlavi et al., Cancer Res 2005; 65:5428-5438) Physiologically, CD70 expression is transient and restricted to a subset of highly activated T, B, and dendritic cells.

By means of an example and without limitation, chimeric antigen receptor that recognizes BCMA has been described (see, e.g., U.S. Patent Publication No. US20160046724A1; and International Patent Publication Nos. WO2016014789A2; WO2017211900A1; WO2015158671A1; US20180085444A1; WO2018028647A1; US20170283504A1; and WO2013154760A1).

In certain embodiments, the immune cell may, in addition to a CAR or exogenous TCR as described herein, further comprise a chimeric inhibitory receptor (inhibitory CAR) that specifically binds to a second target antigen and is capable of inducing an inhibitory or immunosuppressive or repressive signal to the cell upon recognition of the second target antigen. In certain embodiments, the chimeric inhibitory receptor comprises an extracellular antigen-binding element (or portion or domain) configured to specifically bind to a target antigen, a transmembrane domain, and an intracellular immunosuppressive or repressive signaling domain. In certain embodiments, the second target antigen is an antigen that is not expressed on the surface of a cancer cell or infected cell or the expression of which is downregulated on a cancer cell or an infected cell. In certain embodiments, the second target antigen is an MHC-class I molecule. In certain embodiments, the intracellular signaling domain comprises a functional signaling portion of an immune checkpoint molecule, such as for example PD-1 or CTLA4. Advantageously, the inclusion of such inhibitory CAR reduces the chance of the engineered immune cells attacking non-target (e.g., non-cancer) tissues.

Alternatively, T-cells expressing CARs may be further modified to reduce or eliminate expression of endogenous TCRs in order to reduce off-target effects. Reduction or elimination of endogenous TCRs can reduce off-target effects and increase the effectiveness of the T cells (U.S. Pat. No. 9,181,527). T cells stably lacking expression of a functional TCR may be produced using a variety of approaches. T cells internalize, sort, and degrade the entire T cell receptor as a complex, with a half-life of about 10 hours in resting T cells and 3 hours in stimulated T cells (von Essen, M. et al. 2004. J. Immunol. 173:384-393). Proper functioning of the TCR complex requires the proper stoichiometric ratio of the proteins that compose the TCR complex. TCR function also requires two functioning TCR zeta proteins with ITAM motifs. The activation of the TCR upon engagement of its MHC-peptide ligand requires the engagement of several TCRs on the same T cell, which all must signal properly. Thus, if a TCR complex is destabilized with proteins that do not associate properly or cannot signal optimally, the T cell will not become activated sufficiently to begin a cellular response.

Accordingly, in some embodiments, TCR expression may eliminated using RNA interference (e.g., shRNA, siRNA, miRNA, etc.), CRISPR, or other methods that target the nucleic acids encoding specific TCRs (e.g., TCR-α and TCR-β) and/or CD3 chains in primary T cells. By blocking expression of one or more of these proteins, the T cell will no longer produce one or more of the key components of the TCR complex, thereby destabilizing the TCR complex and preventing cell surface expression of a functional TCR.

In some instances, CAR may also comprise a switch mechanism for controlling expression and/or activation of the CAR. For example, a CAR may comprise an extracellular, transmembrane, and intracellular domain, in which the extracellular domain comprises a target-specific binding element that comprises a label, binding domain, or tag that is specific for a molecule other than the target antigen that is expressed on or by a target cell. In such embodiments, the specificity of the CAR is provided by a second construct that comprises a target antigen binding domain (e.g., an scFv or a bispecific antibody that is specific for both the target antigen and the label or tag on the CAR) and a domain that is recognized by or binds to the label, binding domain, or tag on the CAR. See, e.g., WO 2013/044225, WO 2016/000304, WO 2015/057834, WO 2015/057852, WO 2016/070061, U.S. Pat. No. 9,233,125, US 2016/0129109. In this way, a T-cell that expresses the CAR can be administered to a subject, but the CAR cannot bind its target antigen until the second composition comprising an antigen-specific binding domain is administered.

Alternative switch mechanisms include CARs that require multimerization in order to activate their signaling function (see, e.g., US 2015/0368342, US 2016/0175359, US 2015/0368360) and/or an exogenous signal, such as a small molecule drug (US 2016/0166613, Yung et al., Science, 2015), in order to elicit a T-cell response. Some CARs may also comprise a "suicide switch" to induce cell death of the CAR T-cells following treatment (Buddee et al., PLoS One, 2013) or to downregulate expression of the CAR following binding to the target antigen (WO 2016/011210).

Alternative techniques may be used to transform target immunoresponsive cells, such as protoplast fusion, lipofection, transfection or electroporation. A wide variety of vectors may be used, such as retroviral vectors, lentiviral vectors, adenoviral vectors, adeno-associated viral vectors, plasmids or transposons, such as a Sleeping Beauty transposon (see U.S. Pat. Nos. 6,489,458; 7,148,203; 7,160,682; 7,985,739; 8,227,432), may be used to introduce CARs, for example using 2nd generation antigen-specific CARs signaling through CD3ζ and either CD28 or CD137. Viral vectors may for example include vectors based on HIV, SV40, EBV, HSV or BPV.

Cells that are targeted for transformation may for example include T cells, Natural Killer (NK) cells, cytotoxic T lymphocytes (CTL), regulatory T cells, human embryonic stem cells, tumor-infiltrating lymphocytes (TIL) or a pluripotent stem cell from which lymphoid cells may be differentiated. T cells expressing a desired CAR may for example be selected through co-culture with γ-irradiated activating and propagating cells (AaPC), which co-express the cancer antigen and co-stimulatory molecules. The engineered CAR T-cells may be expanded, for example by co-culture on AaPC in presence of soluble factors, such as IL-2 and IL-21. This expansion may for example be carried out so as to provide memory CAR+ T cells (which may for example be assayed by non-enzymatic digital array and/or multi-panel flow cytometry). In this way, CAR T cells may be provided that have specific cytotoxic activity against antigen-bearing tumors (optionally in conjunction with production of desired chemokines such as interferon-γ). CAR T cells of this kind may for example be used in animal models, for example to treat tumor xenografts.

In certain embodiments, ACT includes co-transferring CD4+ Th1 cells and CD8+ CTLs to induce a synergistic antitumor response (see, e.g., Li et al., Adoptive cell therapy with CD4+ T helper 1 cells and CD8+ cytotoxic T cells enhances complete rejection of an established tumor, leading to generation of endogenous memory responses to non-targeted tumor epitopes. Clin Transl Immunology. 2017 October; 6(10): e160).

In certain embodiments, Th17 cells are transferred to a subject in need thereof. Th17 cells have been reported to directly eradicate melanoma tumors in mice to a greater extent than Th1 cells (Muranski P, et al., Tumor-specific Th17-polarized cells eradicate large established melanoma. Blood. 2008 Jul. 15; 112(2):362-73; and Martin-Orozco N, et al., T helper 17 cells promote cytotoxic T cell activation in tumor immunity. Immunity. 2009 Nov. 20; 31(5):787-98). Those studies involved an adoptive T cell transfer (ACT) therapy approach, which takes advantage of CD4+ T cells that express a TCR recognizing tyrosinase tumor antigen. Exploitation of the TCR leads to rapid expansion of Th17 populations to large numbers ex vivo for reinfusion into the autologous tumor-bearing hosts.

In certain embodiments, ACT may include autologous iPSC-based vaccines, such as irradiated iPSCs in autologous anti-tumor vaccines (see e.g., Kooreman, Nigel G. et al., Autologous iPSC-Based Vaccines Elicit Anti-tumor Responses In Vivo, Cell Stem Cell 22, 1-13, 2018, doi.org/10.1016/j.stem.2018.01.016).

Unlike T-cell receptors (TCRs) that are MHC restricted, CARs can potentially bind any cell surface-expressed antigen and can thus be more universally used to treat patients (see Irving et al., Engineering Chimeric Antigen Receptor T-Cells for Racing in Solid Tumors: Don't Forget the Fuel, Front. Immunol., 3 Apr. 2017, doi.org/10.3389/fimmu.2017.00267). In certain embodiments, in the absence of endogenous T-cell infiltrate (e.g., due to aberrant antigen processing and presentation), which precludes the use of TIL therapy and immune checkpoint blockade, the transfer of CAR T-cells may be used to treat patients (see, e.g., Hinrichs CS, Rosenberg SA. Exploiting the curative potential of adoptive T-cell therapy for cancer. Immunol Rev (2014) 257(1):56-71. doi:10.1111/imr.12132).

Approaches such as the foregoing may be adapted to provide methods of treating and/or increasing survival of a subject having a disease, such as a neoplasia, for example by administering an effective amount of an immunoresponsive cell comprising an antigen recognizing receptor that binds a selected antigen, wherein the binding activates the immunoresponsive cell, thereby treating or preventing the disease (such as a neoplasia, a pathogen infection, an autoimmune disorder, or an allogeneic transplant reaction).

In certain embodiments, the treatment can be administered after lymphodepleting pretreatment in the form of chemotherapy (typically a combination of cyclophosphamide and fludarabine) or radiation therapy. Initial studies in ACT had short lived responses and the transferred cells did not persist in vivo for very long (Houot et al., T-cell-based immunotherapy: adoptive cell transfer and checkpoint inhibition. Cancer Immunol Res (2015) 3(10):1115-22; and Kamta et al., Advancing Cancer Therapy with Present and Emerging Immuno-Oncology Approaches. Front. Oncol. (2017) 7:64). Immune suppressor cells like Tregs and MDSCs may attenuate the activity of transferred cells by outcompeting them for the necessary cytokines. Not being bound by a theory lymphodepleting pretreatment may eliminate the suppressor cells allowing the TILs to persist.

In one embodiment, the treatment can be administrated into patients undergoing an immunosuppressive treatment (e.g., glucocorticoid treatment). The cells or population of cells, may be made resistant to at least one immunosuppressive agent due to the inactivation of a gene encoding a receptor for such immunosuppressive agent. In certain embodiments, the immunosuppressive treatment provides for the selection and expansion of the immunoresponsive T cells within the patient.

In certain embodiments, the treatment can be administered before primary treatment (e.g., surgery or radiation therapy) to shrink a tumor before the primary treatment. In another embodiment, the treatment can be administered after primary treatment to remove any remaining cancer cells.

In certain embodiments, immunometabolic barriers can be targeted therapeutically prior to and/or during ACT to enhance responses to ACT or CAR T-cell therapy and to support endogenous immunity (see, e.g., Irving et al., Engineering Chimeric Antigen Receptor T-Cells for Racing in Solid Tumors: Don't Forget the Fuel, Front. Immunol., 3 Apr. 2017, doi.org/10.3389/fimmu.2017.00267).

The administration of cells or population of cells, such as immune system cells or cell populations, such as more particularly immunoresponsive cells or cell populations, as disclosed herein may be carried out in any convenient manner, including by aerosol inhalation, injection, ingestion, transfusion, implantation or transplantation. The cells or population of cells may be administered to a patient subcutaneously, intradermally, intratumorally, intranodally, intramedullary, intramuscularly, intrathecally, by intravenous or intralymphatic injection, or intraperitoneally. In some embodiments, the disclosed CARs may be delivered or administered into a cavity formed by the resection of tumor tissue (i.e. intracavity delivery) or directly into a tumor prior to resection (i.e. intratumoral delivery). In one embodiment, the cell compositions of the present invention are preferably administered by intravenous injection.

The administration of the cells or population of cells can consist of the administration of $10^4$-$10^9$ cells per kg body weight, preferably $10^1$ to $10^6$ cells/kg body weight including all integer values of cell numbers within those ranges. Dosing in CAR T cell therapies may for example involve administration of from $10^6$ to $10^9$ cells/kg, with or without a course of lymphodepletion, for example with cyclophosphamide. The cells or population of cells can be administrated in one or more doses. In another embodiment, the effective amount of cells are administrated as a single dose. In another embodiment, the effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions are within the skill of one in the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, the effective amount of cells or composition comprising those cells are administrated parenterally. The administration can be an intravenous administration. The administration can be directly done by injection within a tumor.

To guard against possible adverse reactions, engineered immunoresponsive cells may be equipped with a transgenic safety switch, in the form of a transgene that renders the cells vulnerable to exposure to a specific signal. For example, the herpes simplex viral thymidine kinase (TK) gene may be used in this way, for example by introduction into allogeneic T lymphocytes used as donor lymphocyte infusions following stem cell transplantation (Greco, et al., Improving the safety of cell therapy with the TK-suicide gene. Front. Pharmacol. 2015; 6: 95). In such cells, administration of a nucleoside prodrug such as ganciclovir or acyclovir causes cell death. Alternative safety switch constructs include inducible caspase 9, for example triggered by administration of a small-molecule dimerizer that brings together two nonfunctional icasp9 molecules to form the active enzyme. A wide variety of alternative approaches to implementing cellular proliferation controls have been described (see U.S. Patent Publication No. 20130071414; PCT Patent Publication WO2011146862; PCT Patent Publication WO2014011987; PCT Patent Publication WO2013040371; Zhou et al. BLOOD, 2014, 123/25:3895-3905; Di Stasi et al., The New England Journal of Medicine 2011; 365:1673-1683; Sadelain M, The New England Journal of Medicine 2011; 365:1735-173; Ramos et al., Stem Cells 28(6):1107-15 (2010)).

In a further refinement of adoptive therapies, genome editing may be used to tailor immunoresponsive cells to alternative implementations, for example providing edited CAR T cells (see Poirot et al., 2015, Multiplex genome edited T-cell manufacturing platform for "off-the-shelf" adoptive T-cell immunotherapies, Cancer Res 75 (18): 3853; Ren et al., 2017, Multiplex genome editing to generate universal CAR T cells resistant to PD1 inhibition, Clin Cancer Res. 2017 May 1; 23(9):2255-2266. doi: 10.1158/1078-0432.CCR-16-1300. Epub 2016 Nov. 4; Qasim et al., 2017, Molecular remission of infant B-ALL after infusion of universal TALEN gene-edited CAR T cells, Sci Transl Med. 2017 Jan. 25; 9(374); Legut, et al., 2018, CRISPR-mediated TCR replacement generates superior anticancer transgenic T cells. Blood, 131(3), 311-322; and Georgiadis et al., Long Terminal Repeat CRISPR-CAR-Coupled "Universal" T Cells Mediate Potent Anti-leukemic Effects, Molecular Therapy, In Press, Corrected Proof, Available online 6 Mar. 2018). Cells may be edited using any CRISPR system and method of use thereof as described herein. CRISPR systems may be delivered to an immune cell by any method described herein. In preferred embodiments, cells are edited ex vivo and transferred to a subject in need thereof. Immunoresponsive cells, CAR T cells or any cells used for adoptive cell transfer may be edited. Editing may be performed for example to insert or knock-in an exogenous gene, such as an exogenous gene encoding a CAR or a TCR, at a preselected locus in a cell (e.g. TRAC locus); to eliminate potential alloreactive T-cell receptors (TCR) or to prevent inappropriate pairing between endogenous and exogenous TCR chains, such as to knock-out or knock-down expression of an endogenous TCR in a cell; to disrupt the target of a chemotherapeutic agent in a cell; to block an immune checkpoint, such as to knock-out or knock-down expression of an immune checkpoint protein or receptor in a cell; to knock-out or knock-down expression of other gene or genes in a cell, the reduced expression or lack of expression of which can enhance the efficacy of adoptive therapies using the cell; to knock-out or knock-down expression of an endogenous gene in a cell, said endogenous gene encoding an antigen targeted by an exogenous CAR or TCR; to knock-out or knock-down expression of one or more IHC constituent proteins in a cell; to activate a T cell; to modulate cells such that the cells are resistant to exhaustion or dysfunction; and/or increase the differentiation and/or proliferation of functionally exhausted or dysfunctional CD8+ T-cells (see PCT Patent Publications: WO2013176915, WO2014059173, WO2014172606, WO2014184744, and WO2014191128).

In certain embodiments, editing may result in inactivation of a gene. By inactivating a gene, it is intended that the gene of interest is not expressed in a functional protein form. In a particular embodiment, the CRISPR system specifically catalyzes cleavage in one targeted gene thereby inactivating said targeted gene. The nucleic acid strand breaks caused are commonly repaired through the distinct mechanisms of homologous recombination or non-homologous end joining (NHEJ). However, NHEJ is an imperfect repair process that often results in changes to the DNA sequence at the site of the cleavage. Repair via non-homologous end joining (NHEJ) often results in small insertions or deletions (Indel) and can be used for the creation of specific gene knockouts. Cells in which a cleavage induced mutagenesis event has occurred can be identified and/or selected by well-known methods in the art. In certain embodiments, homology directed repair (HDR) is used to concurrently inactivate a gene (e.g., TRAC) and insert an endogenous TCR or CAR into the inactivated locus.

Hence, in certain embodiments, editing of cells (such as by CRISPR/Cas), particularly cells intended for adoptive cell therapies, more particularly immunoresponsive cells such as T cells, may be performed to insert or knock-in an exogenous gene, such as an exogenous gene encoding a CAR or a TCR, at a preselected locus in a cell. Conventionally, nucleic acid molecules encoding CARs or TCRs are transfected or transduced to cells using randomly integrating vectors, which, depending on the site of integration, may lead to clonal expansion, oncogenic transformation, variegated transgene expression and/or transcriptional silencing of the transgene. Directing of transgene(s) to a specific locus in a cell can minimize or avoid such risks and advantageously provide for uniform expression of the transgene(s) by the cells. Without limitation, suitable 'safe harbor' loci for directed transgene integration include CCR5 or AAVS1. Homology-directed repair (HDR) strategies are known and described elsewhere in this specification allowing to insert transgenes into desired loci (e.g., TRAC locus).

Further suitable loci for insertion of transgenes, in particular CAR or exogenous TCR transgenes, include without limitation loci comprising genes coding for constituents of endogenous T-cell receptor, such as T-cell receptor alpha locus (TRA) or T-cell receptor beta locus (TRB), for example T-cell receptor alpha constant (TRAC) locus, T-cell receptor beta constant 1 (TRBC1) locus or T-cell receptor beta constant 2 (TRBC1) locus. Advantageously, insertion of a transgene into such locus can simultaneously achieve expression of the transgene, potentially controlled by the endogenous promoter, and knock-out expression of the endogenous TCR. This approach has been exemplified in Eyquem et al., (2017) Nature 543: 113-117, wherein the authors used CRISPR/Cas9 gene editing to knock-in a DNA molecule encoding a CD19-specific CAR into the TRAC locus downstream of the endogenous promoter; the CAR-T cells obtained by CRISPR were significantly superior in terms of reduced tonic CAR signaling and exhaustion.

T cell receptors (TCR) are cell surface receptors that participate in the activation of T cells in response to the presentation of antigen. The TCR is generally made from two chains, $\alpha$ and $\beta$, which assemble to form a heterodimer and associates with the CD3-transducing subunits to form the T cell receptor complex present on the cell surface. Each $\alpha$ and $\beta$ chain of the TCR consists of an immunoglobulin-like N-terminal variable (V) and constant (C) region, a hydrophobic transmembrane domain, and a short cytoplasmic region. As for immunoglobulin molecules, the variable region of the $\alpha$ and $\beta$ chains are generated by V(D)J recombination, creating a large diversity of antigen specificities within the population of T cells. However, in contrast to immunoglobulins that recognize intact antigen, T cells are activated by processed peptide fragments in association with an MHC molecule, introducing an extra dimension to antigen recognition by T cells, known as MHC restriction. Recognition of MHC disparities between the donor and recipient through the T cell receptor leads to T cell proliferation and the potential development of graft versus host disease (GVHD). The inactivation of TCR$\alpha$ or TCR$\beta$ can result in the elimination of the TCR from the surface of T cells preventing recognition of alloantigen and thus GVHD. However, TCR disruption generally results in the elimination of the CD3 signaling component and alters the means of further T cell expansion.

Hence, in certain embodiments, editing of cells (such as by CRISPR/Cas), particularly cells intended for adoptive cell therapies, more particularly immunoresponsive cells such as T cells, may be performed to knock-out or knock-down expression of an endogenous TCR in a cell. For example, NHEJ-based or HDR-based gene editing approaches can be employed to disrupt the endogenous TCR alpha and/or beta chain genes. For example, gene editing system or systems, such as CRISPR/Cas system or systems, can be designed to target a sequence found within the TCR beta chain conserved between the beta 1 and beta 2 constant region genes (TRBC1 and TRBC2) and/or to target the constant region of the TCR alpha chain (TRAC) gene.

Allogeneic cells are rapidly rejected by the host immune system. It has been demonstrated that, allogeneic leukocytes present in non-irradiated blood products will persist for no more than 5 to 6 days (Boni, Muranski et al. 2008 Blood 1; 112(12):4746-54). Thus, to prevent rejection of allogeneic cells, the host's immune system usually has to be suppressed to some extent. However, in the case of adoptive cell transfer the use of immunosuppressive drugs also have a detrimental effect on the introduced therapeutic T cells. Therefore, to effectively use an adoptive immunotherapy approach in these conditions, the introduced cells would need to be resistant to the immunosuppressive treatment. Thus, in a particular embodiment, the present invention further comprises a step of modifying T cells to make them resistant to an immunosuppressive agent, preferably by inactivating at least one gene encoding a target for an immunosuppressive agent. An immunosuppressive agent is an agent that suppresses immune function by one of several mechanisms of action. An immunosuppressive agent can be, but is not limited to a calcineurin inhibitor, a target of rapamycin, an interleukin-2 receptor α-chain blocker, an inhibitor of inosine monophosphate dehydrogenase, an inhibitor of dihydrofolic acid reductase, a corticosteroid or an immunosuppressive antimetabolite. The present invention allows conferring immunosuppressive resistance to T cells for immunotherapy by inactivating the target of the immunosuppressive agent in T cells. As non-limiting examples, targets for an immunosuppressive agent can be a receptor for an immunosuppressive agent such as: CD52, glucocorticoid receptor (GR), a FKBP family gene member and a cyclophilin family gene member.

In certain embodiments, editing of cells (such as by CRISPR/Cas), particularly cells intended for adoptive cell therapies, more particularly immunoresponsive cells such as T cells, may be performed to block an immune checkpoint, such as to knock-out or knock-down expression of an immune checkpoint protein or receptor in a cell. Immune checkpoints are inhibitory pathways that slow down or stop immune reactions and prevent excessive tissue damage from uncontrolled activity of immune cells. In certain embodiments, the immune checkpoint targeted is the programmed death-1 (PD-1 or CD279) gene (PDCD1). In other embodiments, the immune checkpoint targeted is cytotoxic T-lymphocyte-associated antigen (CTLA-4). In additional embodiments, the immune checkpoint targeted is another member of the CD28 and CTLA4 Ig superfamily such as BTLA, LAG3, ICOS, PDL1 or KIR. In further additional embodiments, the immune checkpoint targeted is a member of the TNFR superfamily such as CD40, OX40, CD137, GITR, CD27 or TIM-3.

Additional immune checkpoints include Src homology 2 domain-containing protein tyrosine phosphatase 1 (SHP-1) (Watson H A, et al., SHP-1: the next checkpoint target for cancer immunotherapy?Biochem Soc Trans. 2016 Apr. 15; 44(2):356-62). SHP-1 is a widely expressed inhibitory protein tyrosine phosphatase (PTP). In T-cells, it is a negative regulator of antigen-dependent activation and proliferation. It is a cytosolic protein, and therefore not amenable to antibody-mediated therapies, but its role in activation and proliferation makes it an attractive target for genetic manipulation in adoptive transfer strategies, such as chimeric antigen receptor (CAR) T cells. Immune checkpoints may also include T cell immunoreceptor with Ig and ITIM domains (TIGIT/Vstm3/WUCAM/VSIG9) and VISTA (Le Mercier I, et al., (2015) Beyond CTLA-4 and PD-1, the generation Z of negative checkpoint regulators. Front. Immunol. 6:418).

WO2014172606 relates to the use of MT1 and/or MT2 inhibitors to increase proliferation and/or activity of exhausted CD8+ T-cells and to decrease CD8+ T-cell exhaustion (e.g., decrease functionally exhausted or unresponsive CD8+ immune cells). In certain embodiments, metallothioneins are targeted by gene editing in adoptively transferred T cells.

In certain embodiments, targets of gene editing may be at least one targeted locus involved in the expression of an immune checkpoint protein. Such targets may include, but are not limited to CTLA4, PPP2CA, PPP2CB, PTPN6, PTPN22, PDCD1, ICOS (CD278), PDL1, KIR, LAG3, HAVCR2, BTLA, CD160, TIGIT, CD96, CRTAM, LAIR1, SIGLEC7, SIGLEC9, CD244 (2B4), TNFRSF10B, TNFRSF10A, CASP8, CASP10, CASP3, CASP6, CASP7, FADD, FAS, TGFBRII, TGFRBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, VISTA, GUCY1A2, GUCY1A3, GUCY1B2, GUCY1B3, MT1, MT2, CD40, OX40, CD137, GITR, CD27, SHP-1, TIM-3, CEACAM-1, CEACAM-3, or CEACAM-5. In preferred embodiments, the gene locus involved in the expression of PD-1 or CTLA-4 genes is targeted. In other preferred embodiments, combinations of genes are targeted, such as but not limited to PD-1 and TIGIT.

By means of an example and without limitation, WO2016196388 concerns an engineered T cell comprising (a) a genetically engineered antigen receptor that specifically binds to an antigen, which receptor may be a CAR; and (b) a disrupted gene encoding a PD-L1, an agent for disruption of a gene encoding a PD-L1, and/or disruption of a gene encoding PD-L1, wherein the disruption of the gene may be mediated by a gene editing nuclease, a zinc finger nuclease (ZFN), CRISPR/Cas9 and/or TALEN. WO2015142675 relates to immune effector cells comprising a CAR in combination with an agent (such as CRISPR, TALEN or ZFN) that increases the efficacy of the immune effector cells in the treatment of cancer, wherein the agent may inhibit an immune inhibitory molecule, such as PD1, PD-L1, CTLA-4, TIM-3, LAG-3, VISTA, BTLA, TIGIT, LAIR1, CD160, 2B4, TGFR beta, CEACAM-1, CEACAM-3, or CEACAM-5. Ren et al., (2017) Clin Cancer Res 23 (9) 2255-2266 performed lentiviral delivery of CAR and electro-transfer of Cas9 mRNA and gRNAs targeting endogenous TCR, β-2 microglobulin (B2M) and PD1 simultaneously, to generate gene-disrupted allogeneic CAR T cells deficient of TCR, HLA class I molecule and PD1.

In certain embodiments, cells may be engineered to express a CAR, wherein expression and/or function of methylcytosine dioxygenase genes (TET1, TET2 and/or TET3) in the cells has been reduced or eliminated, such as by CRISPR, ZNF or TALEN (for example, as described in WO201704916).

In certain embodiments, editing of cells (such as by CRISPR/Cas), particularly cells intended for adoptive cell therapies, more particularly immunoresponsive cells such as T cells, may be performed to knock-out or knock-down expression of an endogenous gene in a cell, said endogenous gene encoding an antigen targeted by an exogenous CAR or TCR, thereby reducing the likelihood of targeting of the engineered cells. In certain embodiments, the targeted antigen may be one or more antigen selected from the group consisting of CD38, CD138, CS-1, CD33, CD26, CD30, CD53, CD92, CD100, CD148, CD150, CD200, CD261, CD262, CD362, human telomerase reverse transcriptase (hTERT), survivin, mouse double minute 2 homolog (MDM2), cytochrome P450 1B1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53, cyclin (D1), B cell maturation antigen (BCMA), transmembrane activator and CAML Interactor (TACI), and B-cell activating factor receptor (BAFF-R) (for example, as described in WO2016011210 and WO2017011804).

In certain embodiments, editing of cells (such as by CRISPR/Cas), particularly cells intended for adoptive cell therapies, more particularly immunoresponsive cells such as T cells, may be performed to knock-out or knock-down expression of one or more MHC constituent proteins, such as one or more HLA proteins and/or beta-2 microglobulin (B2M), in a cell, whereby rejection of non-autologous (e.g., allogeneic) cells by the recipient's immune system can be reduced or avoided. In preferred embodiments, one or more HLA class I proteins, such as HLA-A, B and/or C, and/or B2M may be knocked-out or knocked-down. Preferably, B2M may be knocked-out or knocked-down. By means of an example, Ren et al., (2017) Clin Cancer Res 23 (9) 2255-2266 performed lentiviral delivery of CAR and electro-transfer of Cas9 mRNA and gRNAs targeting endogenous TCR, β-2 microglobulin (B2M) and PD1 simultaneously, to generate gene-disrupted allogeneic CAR T cells deficient of TCR, HLA class I molecule and PD1.

In other embodiments, at least two genes are edited. Pairs of genes may include, but are not limited to PD1 and TCRα, PD1 and TCRβ, CTLA-4 and TCRα, CTLA-4 and TCRβ, LAG3 and TCRα, LAG3 and TCRβ, Tim3 and TCRα, Tim3 and TCRβ, BTLA and TCRα, BTLA and TCRβ, BY55 and TCRα, BY55 and TCRβ, TIGIT and TCRα, TIGIT and TCRβ, B7H5 and TCRα, B7H5 and TCRβ, LAIR1 and TCRα, LAIR1 and TCRβ, SIGLEC10 and TCRα, SIGLEC10 and TCRβ, 2B4 and TCRα, 2B4 and TCRβ, B2M and TCRα, B2M and TCRβ.

In certain embodiments, a cell may be multiply edited (multiplex genome editing) as taught herein to (1) knock-out or knock-down expression of an endogenous TCR (for example, TRBC1, TRBC2 and/or TRAC), (2) knock-out or knock-down expression of an immune checkpoint protein or receptor (for example PD1, PD-L1 and/or CTLA4); and (3) knock-out or knock-down expression of one or more MHC constituent proteins (for example, HLA-A, B and/or C, and/or B2M, preferably B2M).

Whether prior to or after genetic modification of the T cells, the T cells can be activated and expanded generally using methods as described, for example, in U.S. Pat. Nos. 6,352,694; 6,534,055; 6,905,680; 5,858,358; 6,887,466; 6,905,681; 7,144,575; 7,232,566; 7,175,843; 5,883,223; 6,905,874; 6,797,514; 6,867,041; and 7,572,631. T cells can be expanded in vitro or in vivo.

Immune cells may be obtained using any method known in the art. In one embodiment, allogenic T cells may be obtained from healthy subjects. In one embodiment T cells that have infiltrated a tumor are isolated. T cells may be removed during surgery. T cells may be isolated after removal of tumor tissue by biopsy. T cells may be isolated by any means known in the art. In one embodiment, T cells are obtained by apheresis. In one embodiment, the method may comprise obtaining a bulk population of T cells from a tumor sample by any suitable method known in the art. For example, a bulk population of T cells can be obtained from a tumor sample by dissociating the tumor sample into a cell suspension from which specific cell populations can be selected. Suitable methods of obtaining a bulk population of T cells may include, but are not limited to, any one or more of mechanically dissociating (e.g., mincing) the tumor, enzymatically dissociating (e.g., digesting) the tumor, and aspiration (e.g., as with a needle).

The bulk population of T cells obtained from a tumor sample may comprise any suitable type of T cell. Preferably, the bulk population of T cells obtained from a tumor sample comprises tumor infiltrating lymphocytes (TILs).

The tumor sample may be obtained from any mammal. Unless stated otherwise, as used herein, the term "mammal" refers to any mammal including, but not limited to, mammals of the order Lagomorpha, such as rabbits; the order Carnivora, including Felines (cats) and Canines (dogs); the order Artiodactyla, including Bovines (cows) and Swines (pigs); or of the order Perissodactyla, including Equines (horses). The mammals may be non-human primates, e.g., of the order Primates, Ceboids, or Simoids (monkeys) or of the order Anthropoids (humans and apes). In some embodiments, the mammal may be a mammal of the order Rodentia, such as mice and hamsters. Preferably, the mammal is a non-human primate or a human. An especially preferred mammal is the human.

T cells can be obtained from a number of sources, including peripheral blood mononuclear cells (PBMC), bone marrow, lymph node tissue, spleen tissue, and tumors. In certain embodiments of the present invention, T cells can be obtained from a unit of blood collected from a subject using any number of techniques known to the skilled artisan, such as Ficoll separation. In one preferred embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor) according to the manufacturer's instructions. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient. A specific subpopulation of T cells, such as CD28+, CD4+, CDC, CD45RA+, and CD45RO+ T cells, can be further isolated by positive or negative selection techniques. For example, in one preferred embodiment, T cells are isolated by incubation with anti-CD3/anti-CD28 (i.e., 3×28)-conjugated beads, such as DYNABEADS® M-450 CD3/CD28 T, or XCYTE DYNABEADS™ for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells.

Enrichment of a T cell population by negative selection can be accomplished with a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

Further, monocyte populations (i.e., CD14+ cells) may be depleted from blood preparations by a variety of methodologies, including anti-CD14 coated beads or columns, or utilization of the phagocytotic activity of these cells to facilitate removal. Accordingly, in one embodiment, the invention uses paramagnetic particles of a size sufficient to be engulfed by phagocytotic monocytes. In certain embodiments, the paramagnetic particles are commercially available beads, for example, those produced by Life Technologies under the trade name Dynabeads™. In one embodiment, other non-specific cells are removed by coating the paramagnetic particles with "irrelevant" proteins (e.g., serum proteins or antibodies). Irrelevant proteins and antibodies include those proteins and antibodies or fragments thereof that do not specifically target the T cells to be isolated. In certain embodiments, the irrelevant beads include beads coated with sheep anti-mouse antibodies, goat anti-mouse antibodies, and human serum albumin.

In brief, such depletion of monocytes is performed by preincubating T cells isolated from whole blood, apheresed peripheral blood, or tumors with one or more varieties of irrelevant or non-antibody coupled paramagnetic particles at any amount that allows for removal of monocytes (approximately a 20:1 bead:cell ratio) for about 30 minutes to 2 hours at 22 to 37 degrees C., followed by magnetic removal of cells which have attached to or engulfed the paramagnetic particles. Such separation can be performed using standard methods available in the art. For example, any magnetic separation methodology may be used including a variety of which are commercially available, (e.g., DYNAL® Magnetic Particle Concentrator (DYNAL MPC®)). Assurance of requisite depletion can be monitored by a variety of methodologies known to those of ordinary skill in the art, including flow cytometric analysis of CD14 positive cells, before and after depletion.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc). Such populations of cells may have therapeutic value and would be desirable to obtain. For example, using high concentration of cells allows more efficient selection of CD8+ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one embodiment, the concentration of cells used is $5\times10^6$/ml. In other embodiments, the concentration used can be from about $1\times10^5$/ml to $1\times10^6$/ml, and any integer value in between.

T cells can also be frozen. Wishing not to be bound by theory, the freeze and subsequent thaw step provides a more uniform product by removing granulocytes and to some extent monocytes in the cell population. After a washing step to remove plasma and platelets, the cells may be suspended in a freezing solution. While many freezing solutions and parameters are known in the art and will be useful in this context, one method involves using PBS containing 20% DMSO and 8% human serum albumin, or other suitable cell freezing media, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

T cells for use in the present invention may also be antigen-specific T cells. For example, tumor-specific T cells can be used. In certain embodiments, antigen-specific T cells can be isolated from a patient of interest, such as a patient afflicted with a cancer or an infectious disease. In one embodiment, neoepitopes are determined for a subject and T cells specific to these antigens are isolated. Antigen-specific cells for use in expansion may also be generated in vitro using any number of methods known in the art, for example, as described in U.S. Patent Publication No. US 20040224402 entitled, Generation and Isolation of Antigen-Specific T Cells, or in U.S. Pat. Nos. 6,040,177. Antigen-specific cells for use in the present invention may also be generated using any number of methods known in the art, for example, as described in Current Protocols in Immunology, or Current Protocols in Cell Biology, both published by John Wiley & Sons, Inc., Boston, Mass.

In a related embodiment, it may be desirable to sort or otherwise positively select (e.g. via magnetic selection) the antigen specific cells prior to or following one or two rounds of expansion. Sorting or positively selecting antigen-specific cells can be carried out using peptide-MHC tetramers (Altman, et al., Science. 1996 Oct. 4; 274(5284):94-6). In another embodiment, the adaptable tetramer technology approach is used (Andersen et al., 2012 Nat Protoc. 7:891-902). Tetramers are limited by the need to utilize predicted binding peptides based on prior hypotheses, and the restriction to specific HLAs. Peptide-MHC tetramers can be generated using techniques known in the art and can be made with any MHC molecule of interest and any antigen of interest as described herein. Specific epitopes to be used in this context can be identified using numerous assays known in the art. For example, the ability of a polypeptide to bind to MHC class I may be evaluated indirectly by monitoring the ability to promote incorporation of $^{125}$I labeled β2-microglobulin (β2m) into MHC class I/β2m/peptide heterotrimeric complexes (see Parker et al., J. Immunol. 152:163, 1994).

In one embodiment cells are directly labeled with an epitope-specific reagent for isolation by flow cytometry followed by characterization of phenotype and TCRs. In one embodiment, T cells are isolated by contacting with T cell specific antibodies. Sorting of antigen-specific T cells, or generally any cells of the present invention, can be carried out using any of a variety of commercially available cell sorters, including, but not limited to, MoFlo sorter (Dako-Cytomation, Fort Collins, Colo.), FACSAria™, FACSArray™, FACSVantage™, BD™ LSR II, and FACSCalibur™ (BD Biosciences, San Jose, Calif.).

In a preferred embodiment, the method comprises selecting cells that also express CD3. The method may comprise specifically selecting the cells in any suitable manner. Preferably, the selecting is carried out using flow cytometry. The flow cytometry may be carried out using any suitable method known in the art. The flow cytometry may employ any suitable antibodies and stains. Preferably, the antibody is chosen such that it specifically recognizes and binds to the particular biomarker being selected. For example, the specific selection of CD3, CD8, TIM-3, LAG-3, 4-1BB, or PD-1 may be carried out using anti-CD3, anti-CD8, anti-TIM-3, anti-LAG-3, anti-4-1BB, or anti-PD-1 antibodies, respectively. The antibody or antibodies may be conjugated to a bead (e.g., a magnetic bead) or to a fluorochrome. Preferably, the flow cytometry is fluorescence-activated cell sorting (FACS). TCRs expressed on T cells can be selected based on reactivity to autologous tumors. Additionally, T cells that are reactive to tumors can be selected for based on markers using the methods described in patent publication Nos. WO2014133567 and WO2014133568, herein incorporated by reference in their entirety. Additionally, activated T cells can be selected for based on surface expression of CD107a.

In one embodiment of the invention, the method further comprises expanding the numbers of T cells in the enriched cell population. Such methods are described in U.S. Pat. No. 8,637,307 and is herein incorporated by reference in its entirety. The numbers of T cells may be increased at least about 3-fold (or 4-, 5-, 6-, 7-, 8-, or 9-fold), more preferably at least about 10-fold (or 20-, 30-, 40-, 50-, 60-, 70-, 80-, or 90-fold), more preferably at least about 100-fold, more preferably at least about 1,000 fold, or most preferably at least about 100,000-fold. The numbers of T cells may be expanded using any suitable method known in the art. Exemplary methods of expanding the numbers of cells are described in patent publication No. WO 2003057171, U.S. Pat. No. 8,034,334, and U.S. Patent Application Publication No. 2012/0244133, each of which is incorporated herein by reference.

In one embodiment, ex vivo T cell expansion can be performed by isolation of T cells and subsequent stimulation or activation followed by further expansion. In one embodiment of the invention, the T cells may be stimulated or activated by a single agent. In another embodiment, T cells are stimulated or activated with two agents, one that induces a primary signal and a second that is a co-stimulatory signal. Ligands useful for stimulating a single signal or stimulating a primary signal and an accessory molecule that stimulates a second signal may be used in soluble form. Ligands may be attached to the surface of a cell, to an Engineered Multivalent Signaling Platform (EMSP), or immobilized on a surface. In a preferred embodiment both primary and secondary agents are co-immobilized on a surface, for example a bead or a cell. In one embodiment, the molecule providing the primary activation signal may be a CD3 ligand, and the co-stimulatory molecule may be a CD28 ligand or 4-1BB ligand.

In certain embodiments, T cells comprising a CAR or an exogenous TCR, may be manufactured as described in WO2015120096, by a method comprising: enriching a population of lymphocytes obtained from a donor subject; stimulating the population of lymphocytes with one or more T-cell stimulating agents to produce a population of activated T cells, wherein the stimulation is performed in a closed system using serum-free culture medium; transducing the population of activated T cells with a viral vector comprising a nucleic acid molecule which encodes the CAR or TCR, using a single cycle transduction to produce a population of transduced T cells, wherein the transduction is performed in a closed system using serum-free culture medium; and expanding the population of transduced T cells for a predetermined time to produce a population of engineered T cells, wherein the expansion is performed in a closed system using serum-free culture medium. In certain embodiments, T cells comprising a CAR or an exogenous TCR, may be manufactured as described in WO2015120096, by a method comprising: obtaining a population of lymphocytes; stimulating the population of lymphocytes with one or more stimulating agents to produce a population of activated T cells, wherein the stimulation is performed in a closed system using serum-free culture medium; transducing the population of activated T cells with a viral vector comprising a nucleic acid molecule which encodes the CAR or TCR, using at least one cycle transduction to produce a population of transduced T cells, wherein the transduction is performed in a closed system using serum-free culture medium; and expanding the population of transduced T cells to produce a population of engineered T cells, wherein the expansion is performed in a closed system using serum-free culture medium. The predetermined time for expanding the population of transduced T cells may be 3 days. The time from enriching the population of lymphocytes to producing the engineered T cells may be 6 days. The closed system may be a closed bag system. Further provided is population of T cells comprising a CAR or an exogenous TCR obtainable or obtained by said method, and a pharmaceutical composition comprising such cells.

In certain embodiments, T cell maturation or differentiation in vitro may be delayed or inhibited by the method as described in WO2017070395, comprising contacting one or more T cells from a subject in need of a T cell therapy with an AKT inhibitor (such as, e.g., one or a combination of two or more AKT inhibitors disclosed in claim 8 of WO2017070395) and at least one of exogenous Interleukin-7 (IL-7) and exogenous Interleukin-15 (IL-15), wherein the resulting T cells exhibit delayed maturation or differentiation, and/or wherein the resulting T cells exhibit improved T cell function (such as, e.g., increased T cell proliferation; increased cytokine production; and/or increased cytolytic activity) relative to a T cell function of a T cell cultured in the absence of an AKT inhibitor.

In certain embodiments, a patient in need of a T cell therapy may be conditioned by a method as described in WO2016191756 comprising administering to the patient a dose of cyclophosphamide between 200 $mg/m^2$/day and 2000 mg/m²/day and a dose of fludarabine between 20 mg/m²/day and 900 mg/m²/day.

In certain embodiments, a patient in need of adoptive cell transfer may be administered a TLR agonist to enhance anti-tumor immunity (see, e.g., Urban-Wojciuk, et al., The Role of TLRs in Anti-cancer Immunity and Tumor Rejection, Front Immunol. 2019; 10: 2388; and Kaczanowska et al., TLR agonists: our best frenemy in cancer immunotherapy, J Leukoc Biol. 2013 June; 93(6): 847-863). In certain embodiments, TLR agonists are delivered in a nanoparticle system (see, e.g., Buss and Bhatia, Nanoparticle delivery of immunostimulatory oligonucleotides enhances response to checkpoint inhibitor therapeutics, Proc Natl Acad Sci USA. 2020 Jun. 3; 202001569). In certain embodiments, the agonist is a TLR9 agonist. Id.

The invention is further described in the following examples, which do not limit the scope of the invention described in the claims.

EXAMPLES

Example 1—CRC Tumor Microenvironment (TME)

Figure 2:
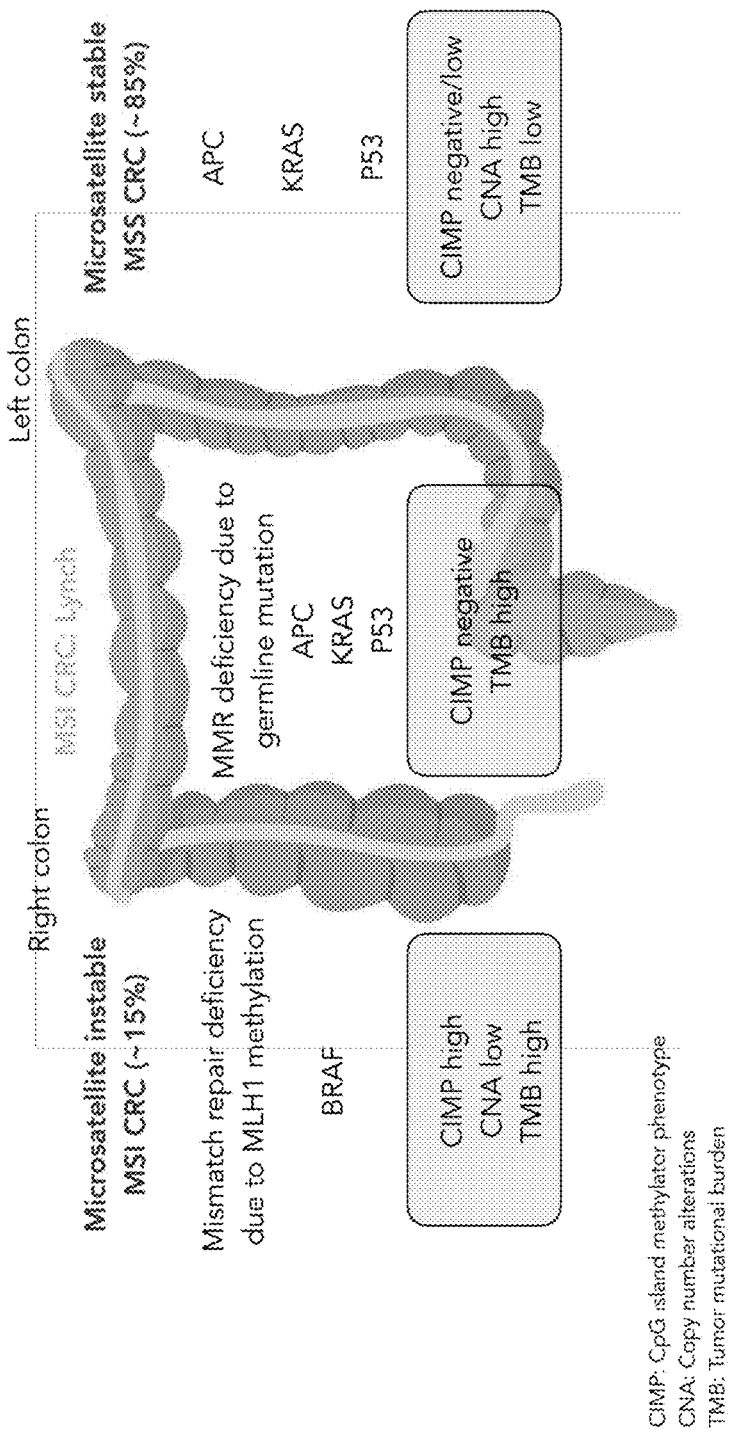
FIG. 2—Schematic showing that MSS and MSI tumors are genetically and epigenetically different.

Colorectal cancer (CRC) can be classified into different subtypes based on mismatch repair (MMR) function in the tumor (FIG. 1). About half of microsatellite instable (MSI) CRC tumors are responsive to anti-PD1 and most microsatellite stable (MSS) CRC tumors are not responsive. A small percentage of MSS tumors are hyper-responsive to immunotherapy (about 3%). MSI tumors differ in MMR deficiency due to deficiency due to MLH1 methylation or germline mutations (FIG. 2). MSI tumors can be differentiated in that MSI tumors can have a CpG island methylator phenotype or a non-methylator phenotype (Lynch type).

Figure 3:
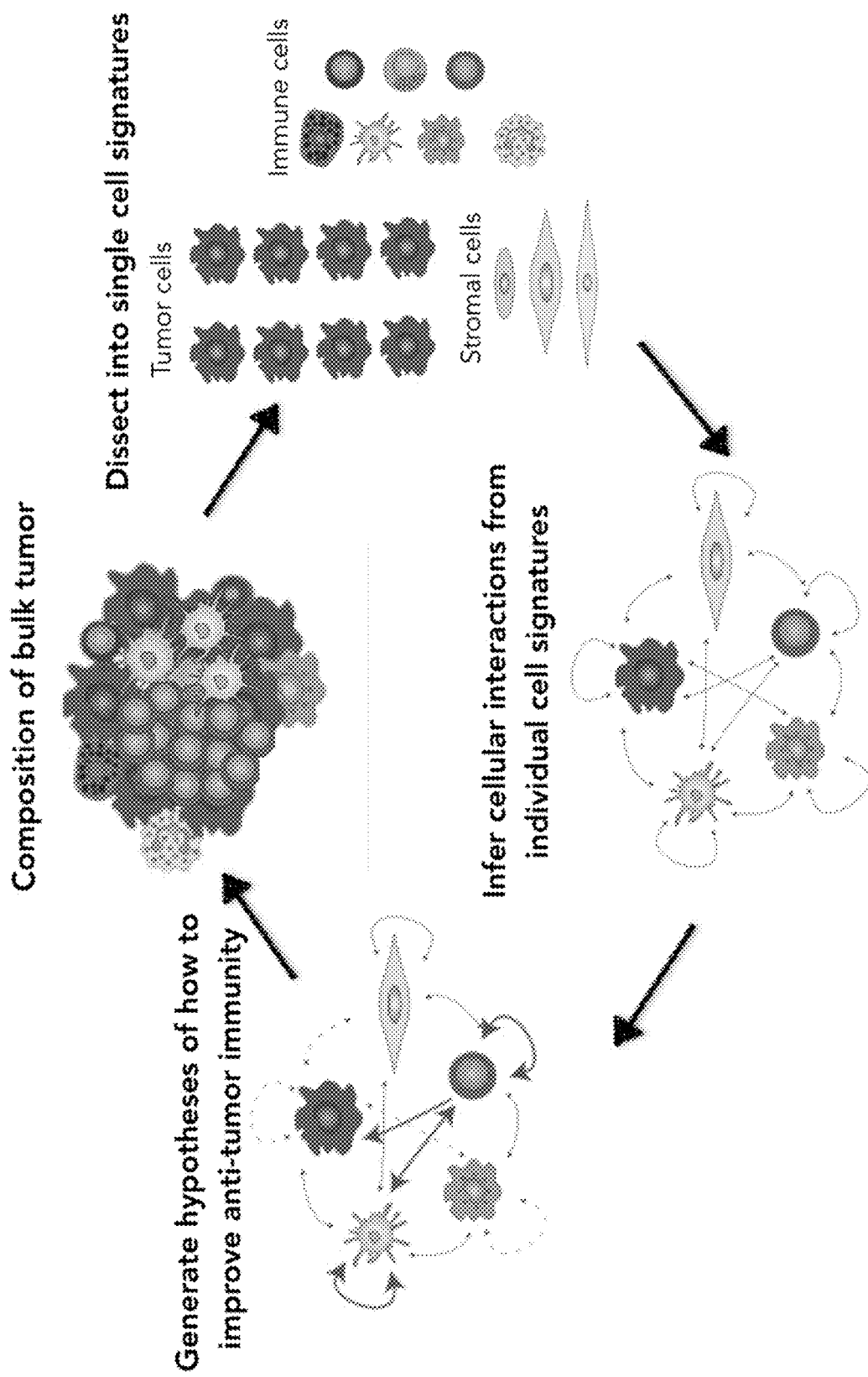
FIG. 3—Schematic showing experimental methodology for identifying mechanisms to target for increasing anti-tumor immunity.
Figure 4:
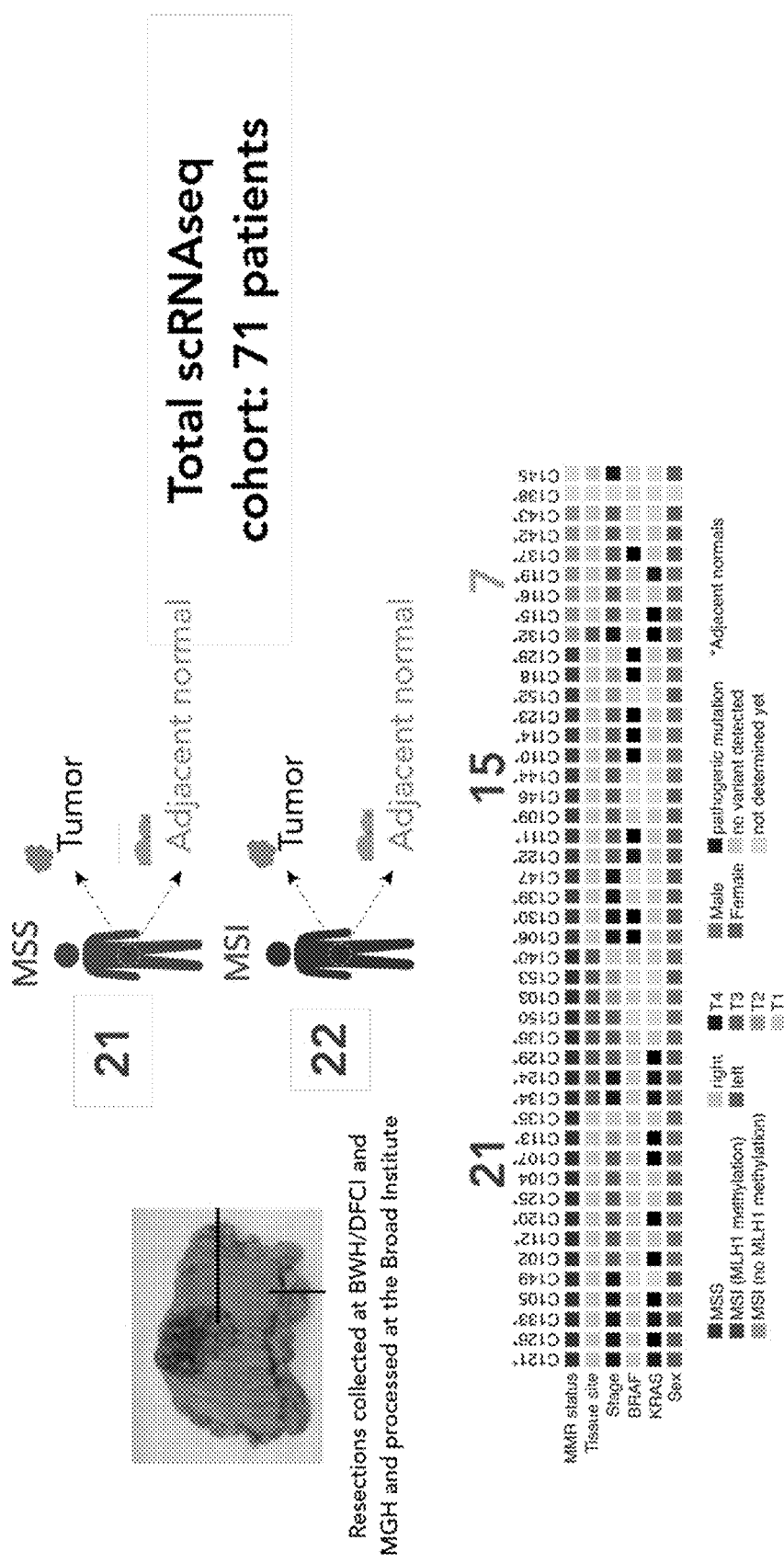
FIG. 4—Schematic representing the patient cohort for the present study.
Figure 5:
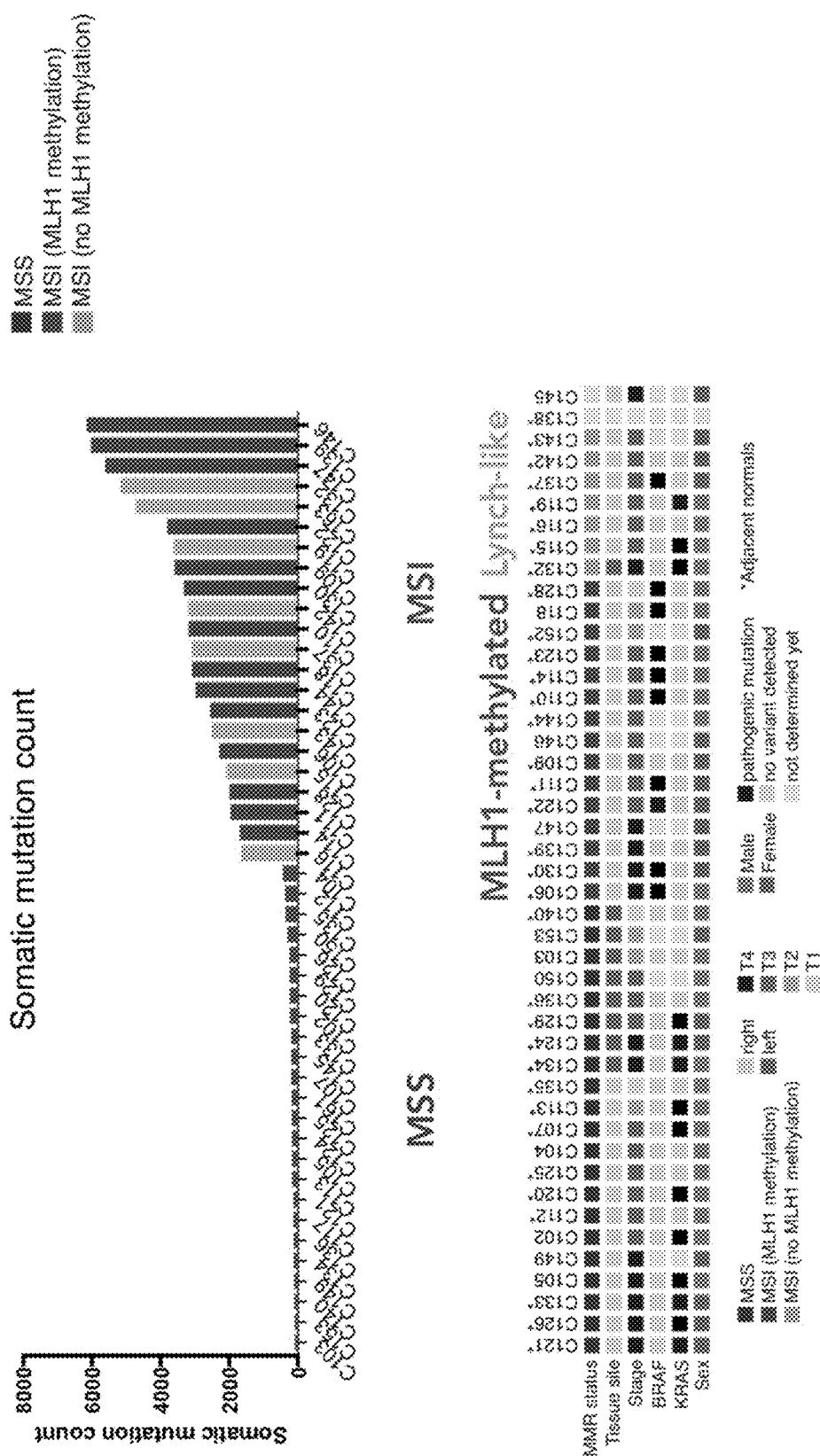
FIG. 5—Graph showing tumor mutational load in MSS and MSI tumors.
Figure 41:
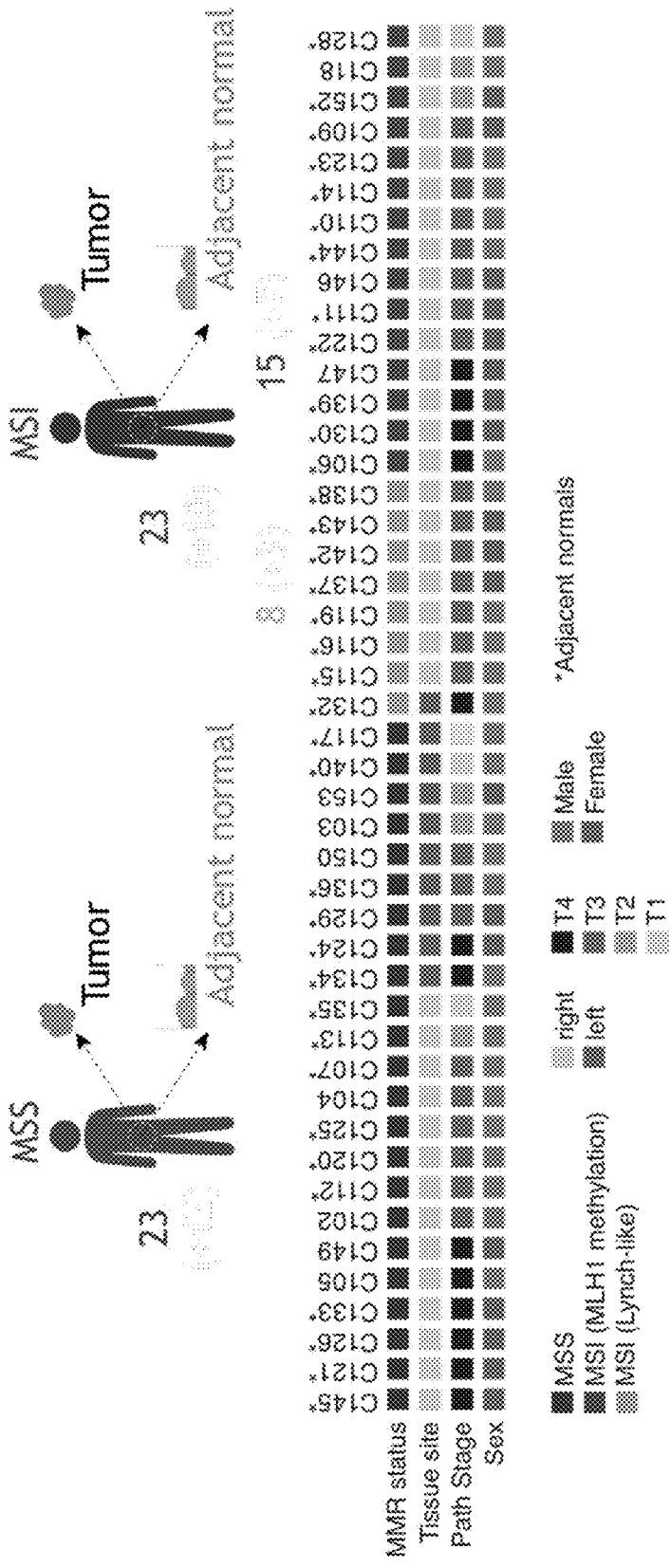
FIG. 41—Schematic and chart representing the updated patient cohort for the present study.
Figure 42:
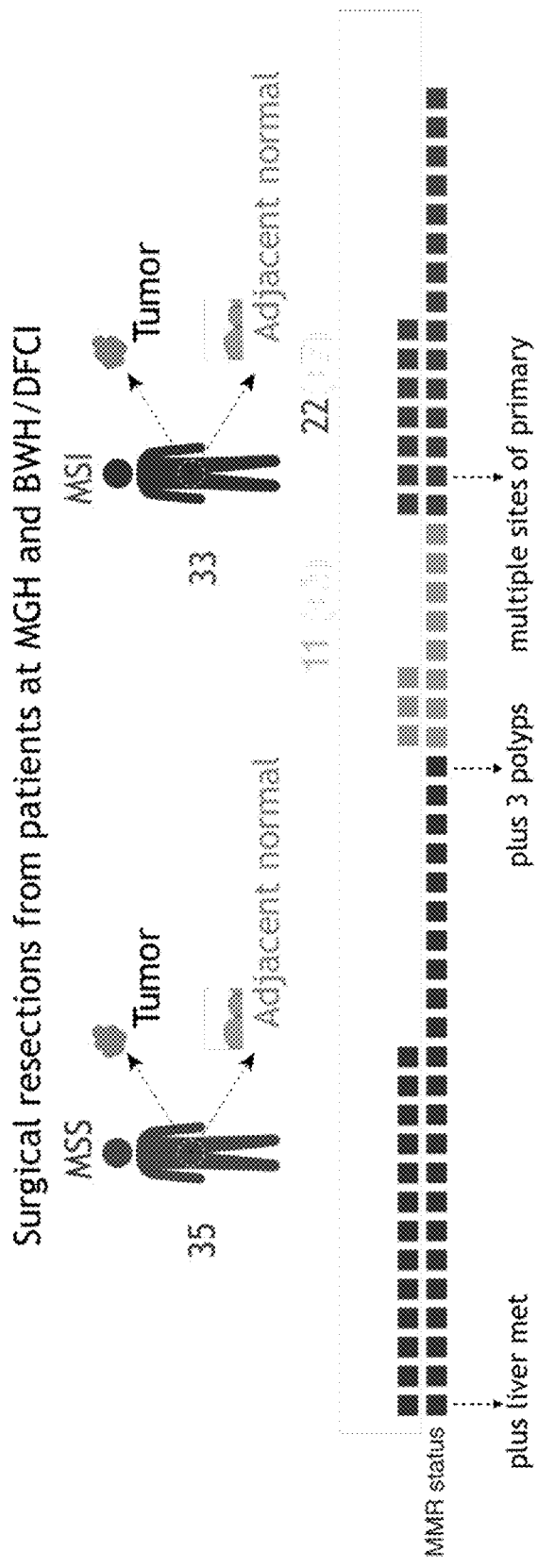
FIG. 42—Schematic and chart representing the updated specimens profiled in the present study.
Figure 43:
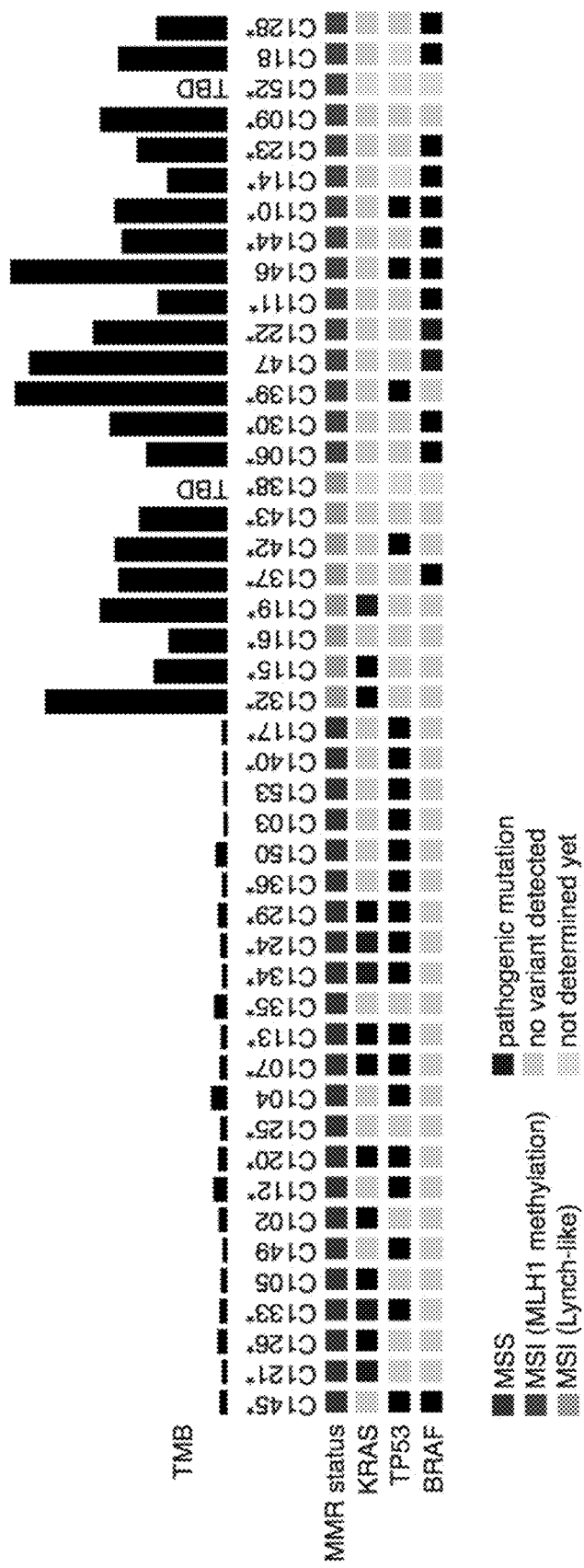
FIG. 43—Graph showing tumor mutational load in MSS and MSI tumors.
Figure 44:
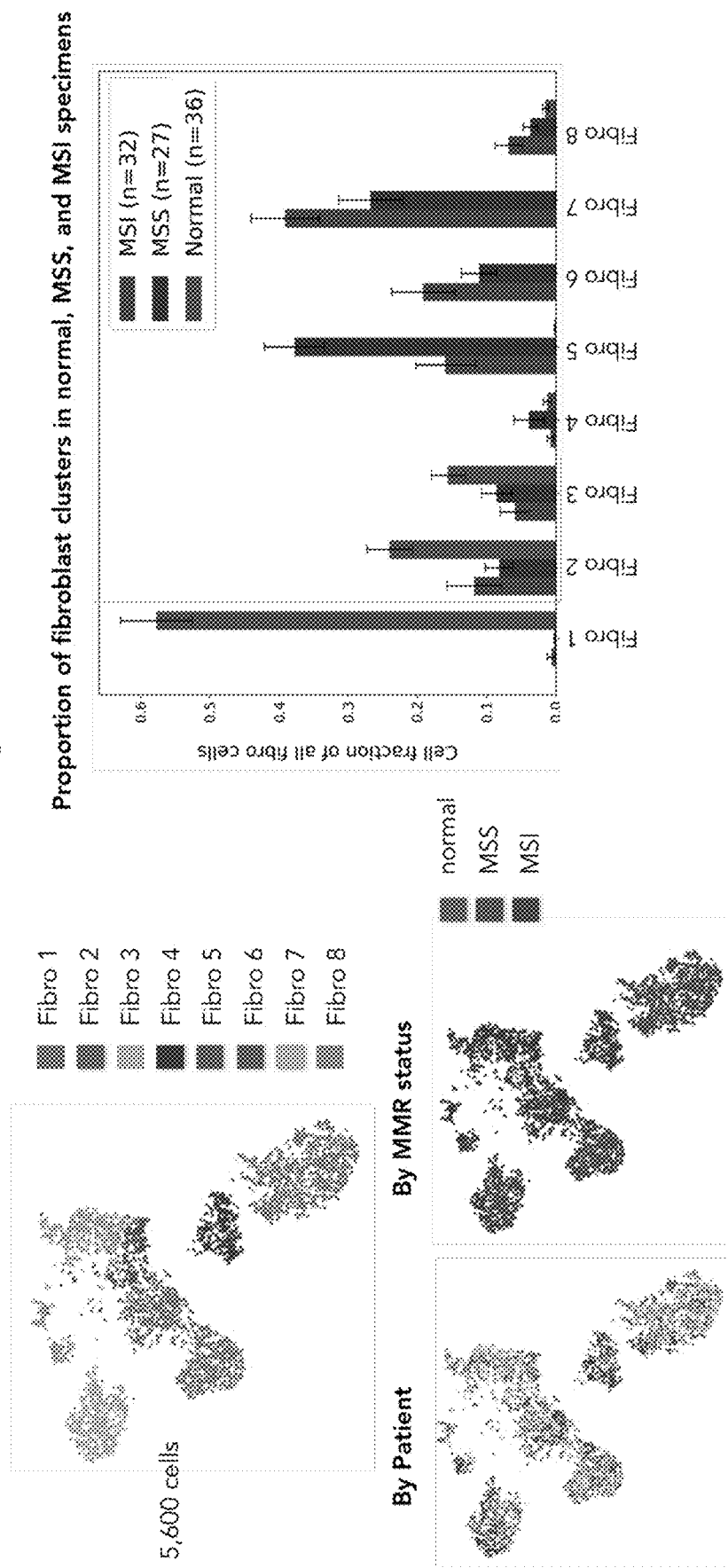
FIG. 44—tSNE plots and bar graph showing fibroblast clusters identified in normal and CRC cancers.
Figure 45:
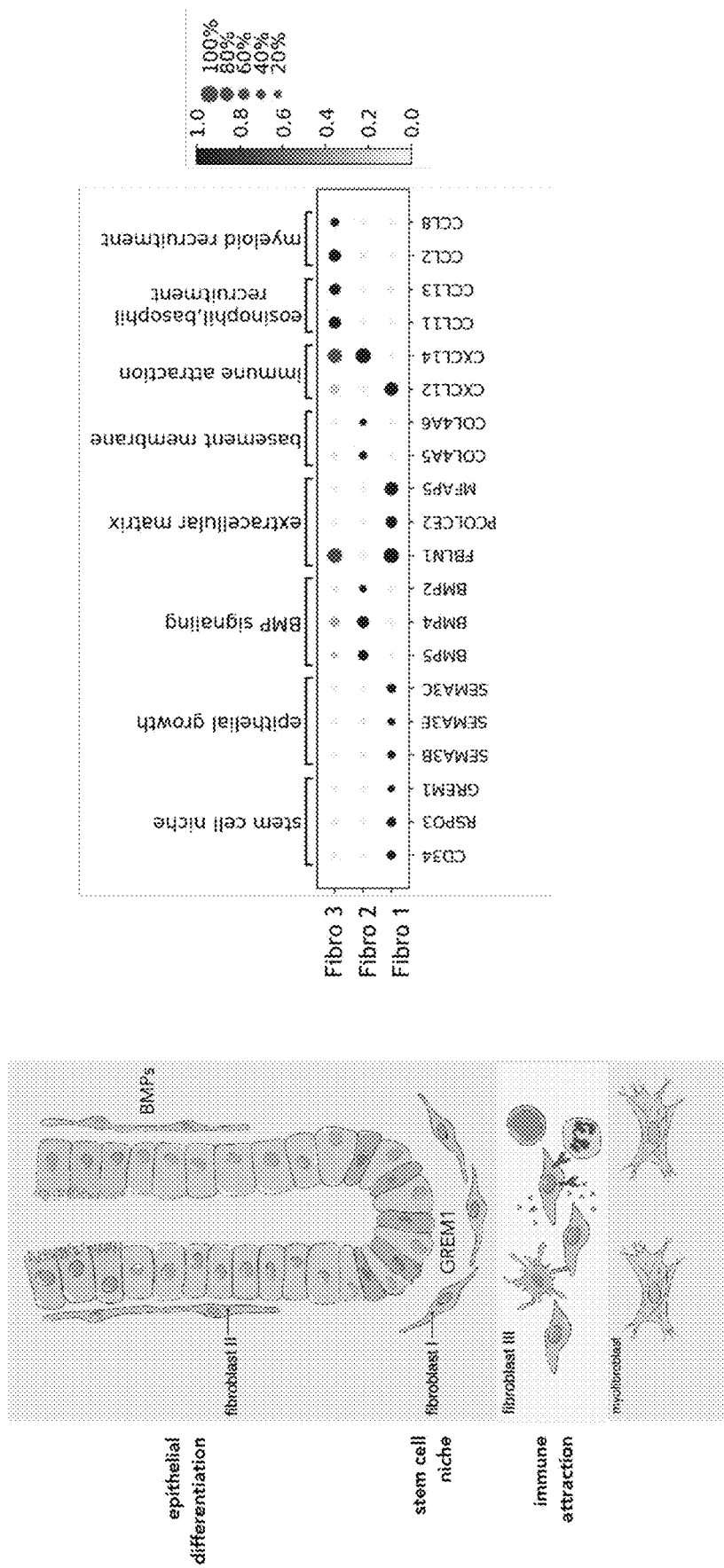
FIG. 45—shows gene expression for Fibro1, 2 and 3.
Figure 46:
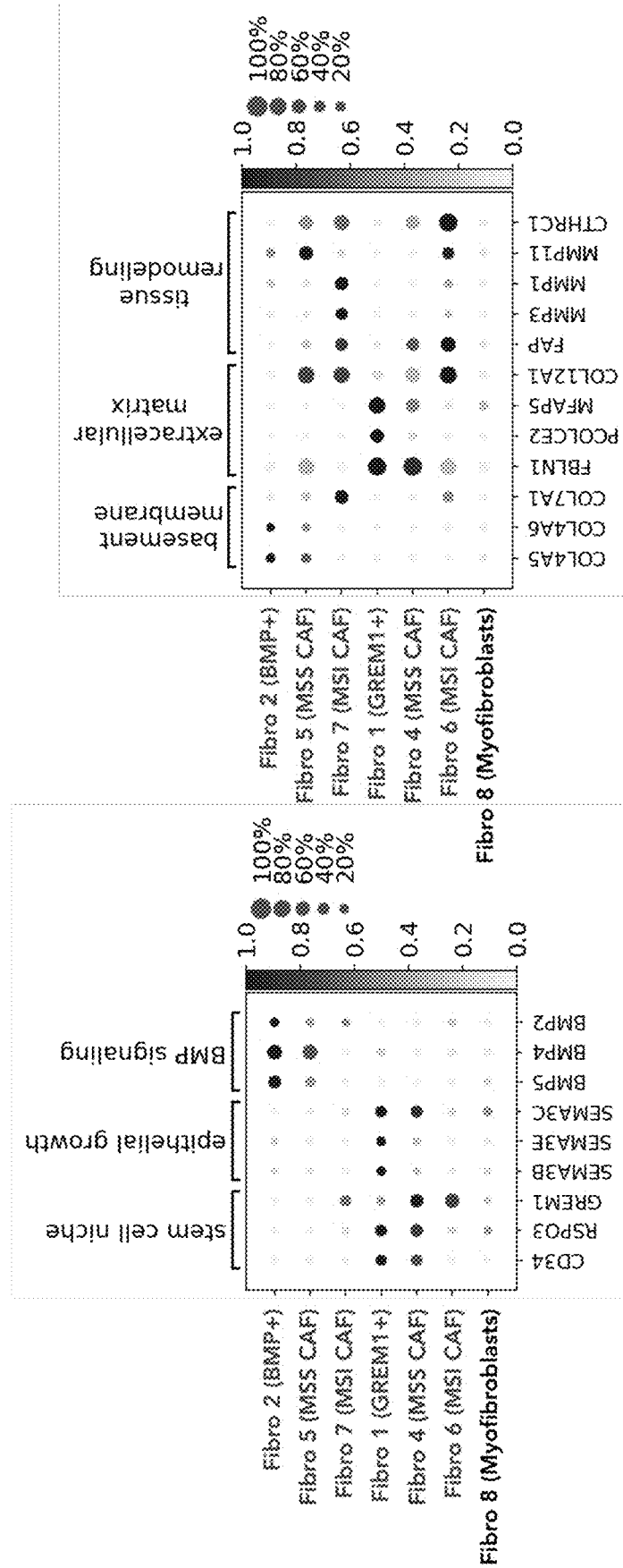
FIG. 46—shows gene expression for fibroblast clusters.
Figure 47:
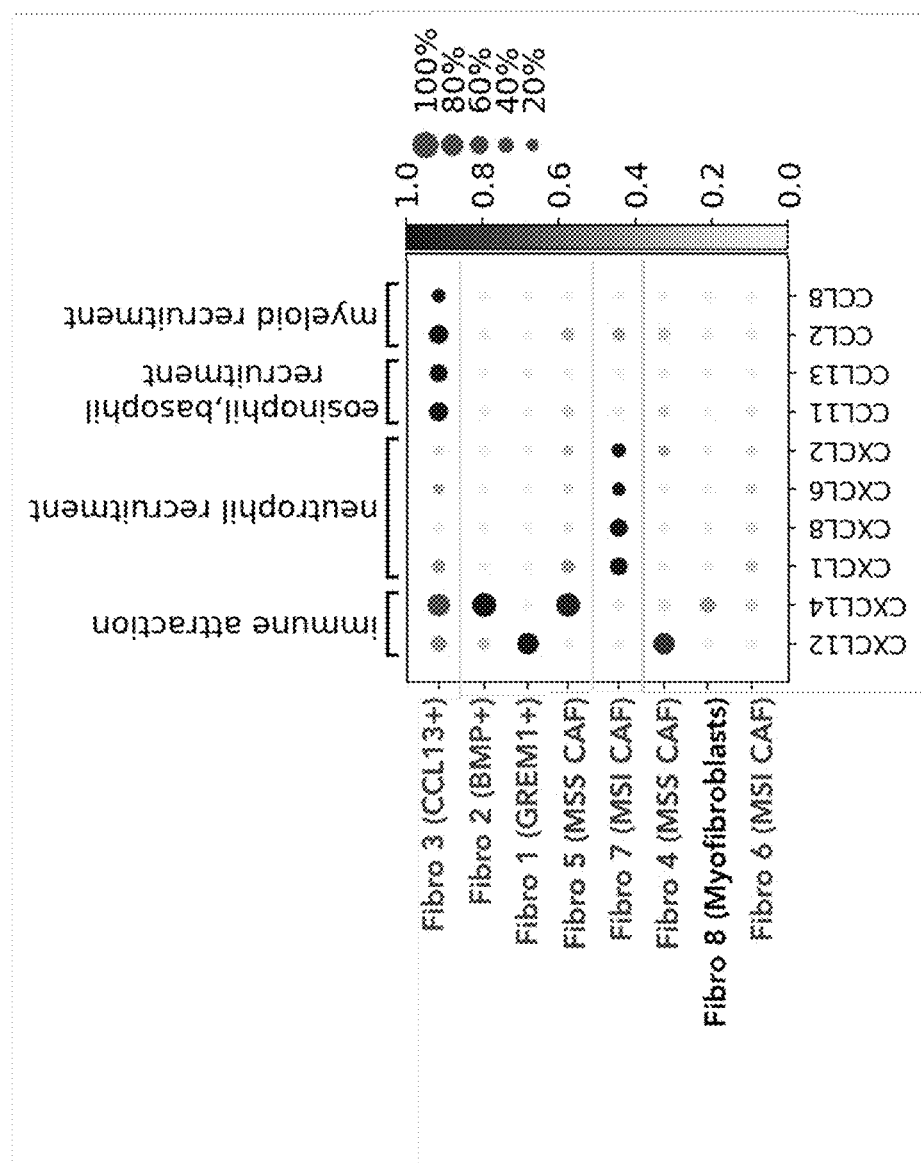
FIG. 47—shows gene expression of chemokines for fibroblast clusters.
Figure 48:
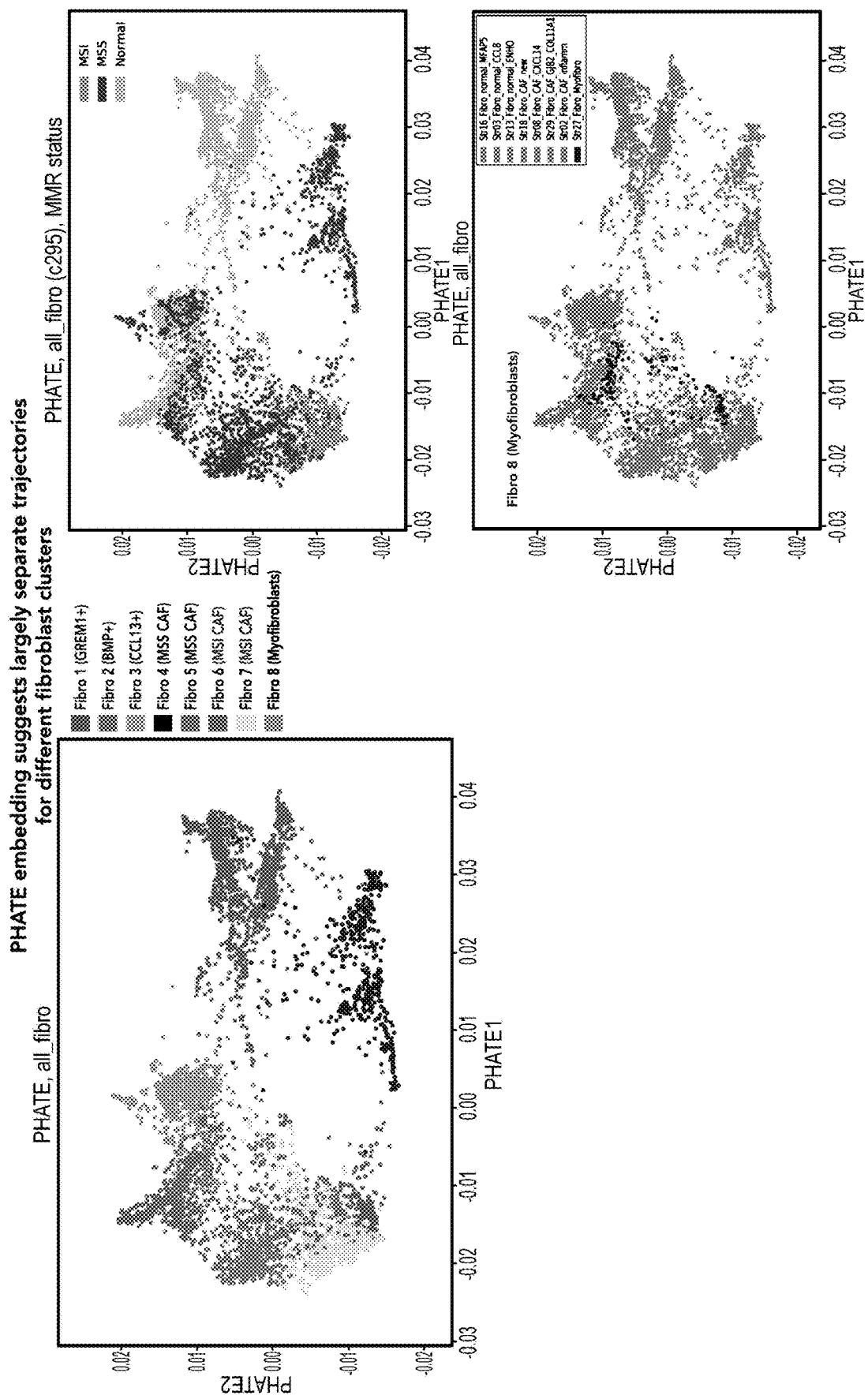
FIG. 48—PHATE embedding of fibroblast clusters.
Figure 49:
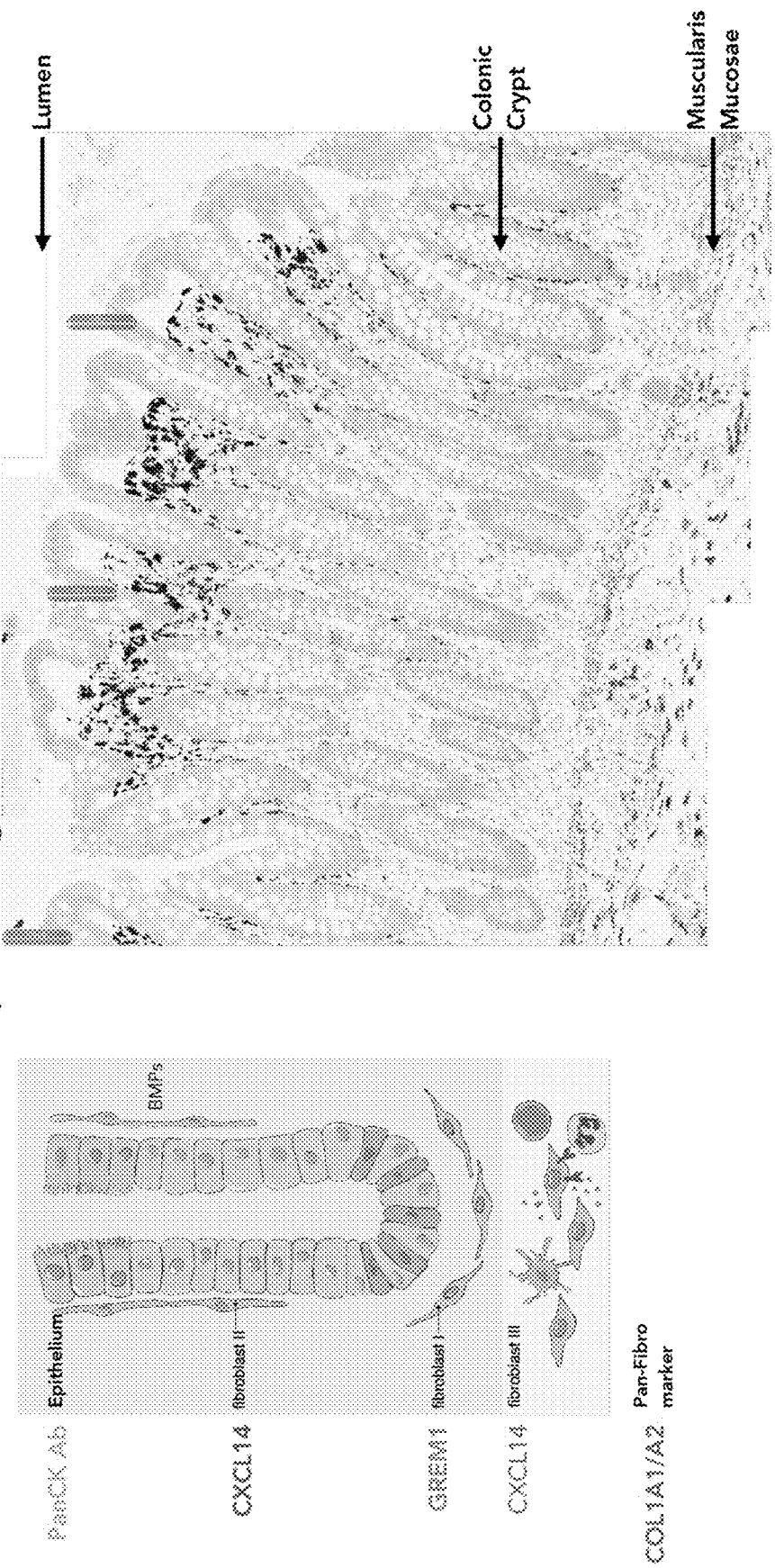
FIGS. 49-52—Quantitative mRNA FISH/IF imaging in FFPE specimens.
Figure 50:
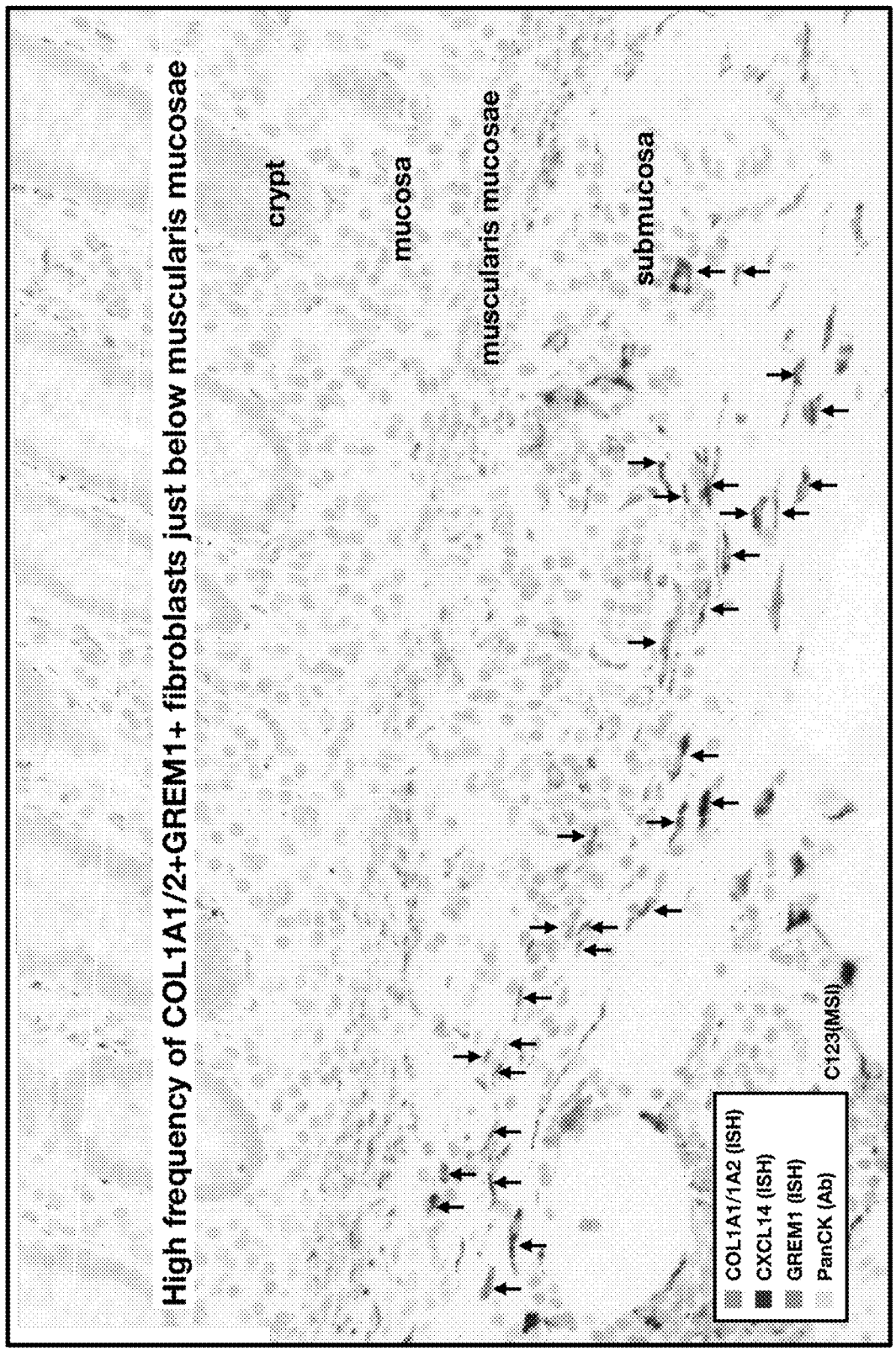
Figure 51:
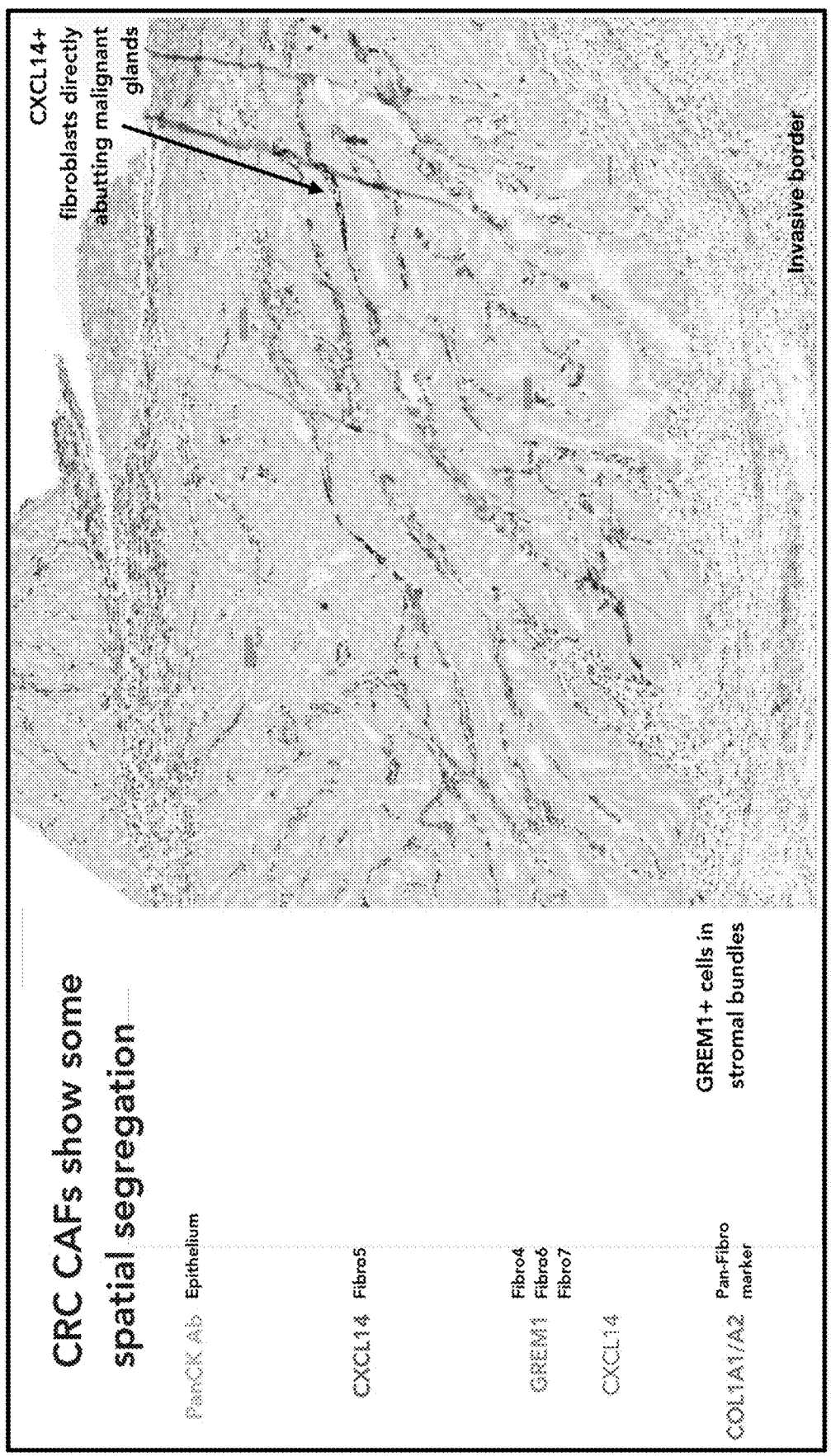
Figure 52:
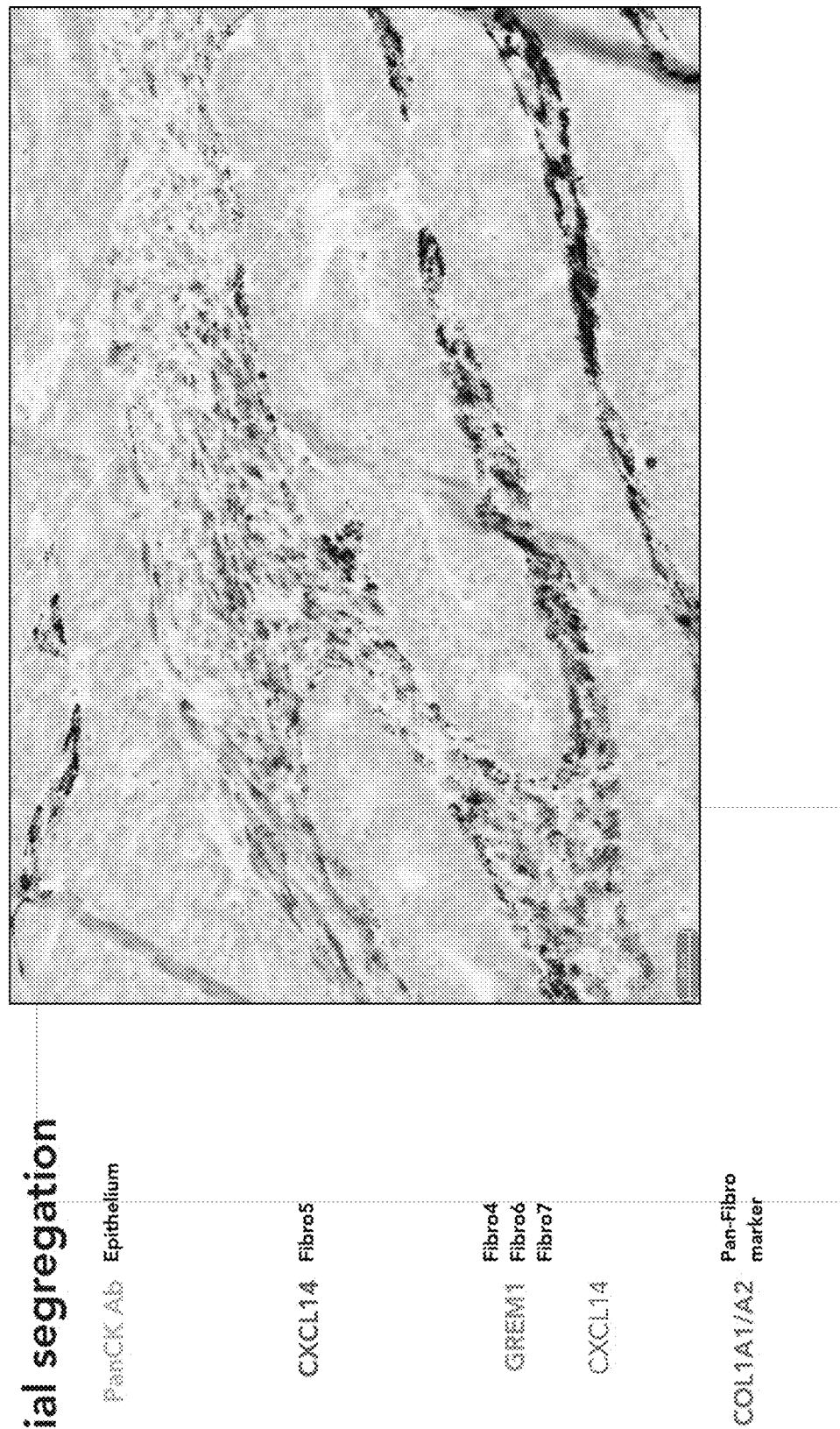
Figure 53:
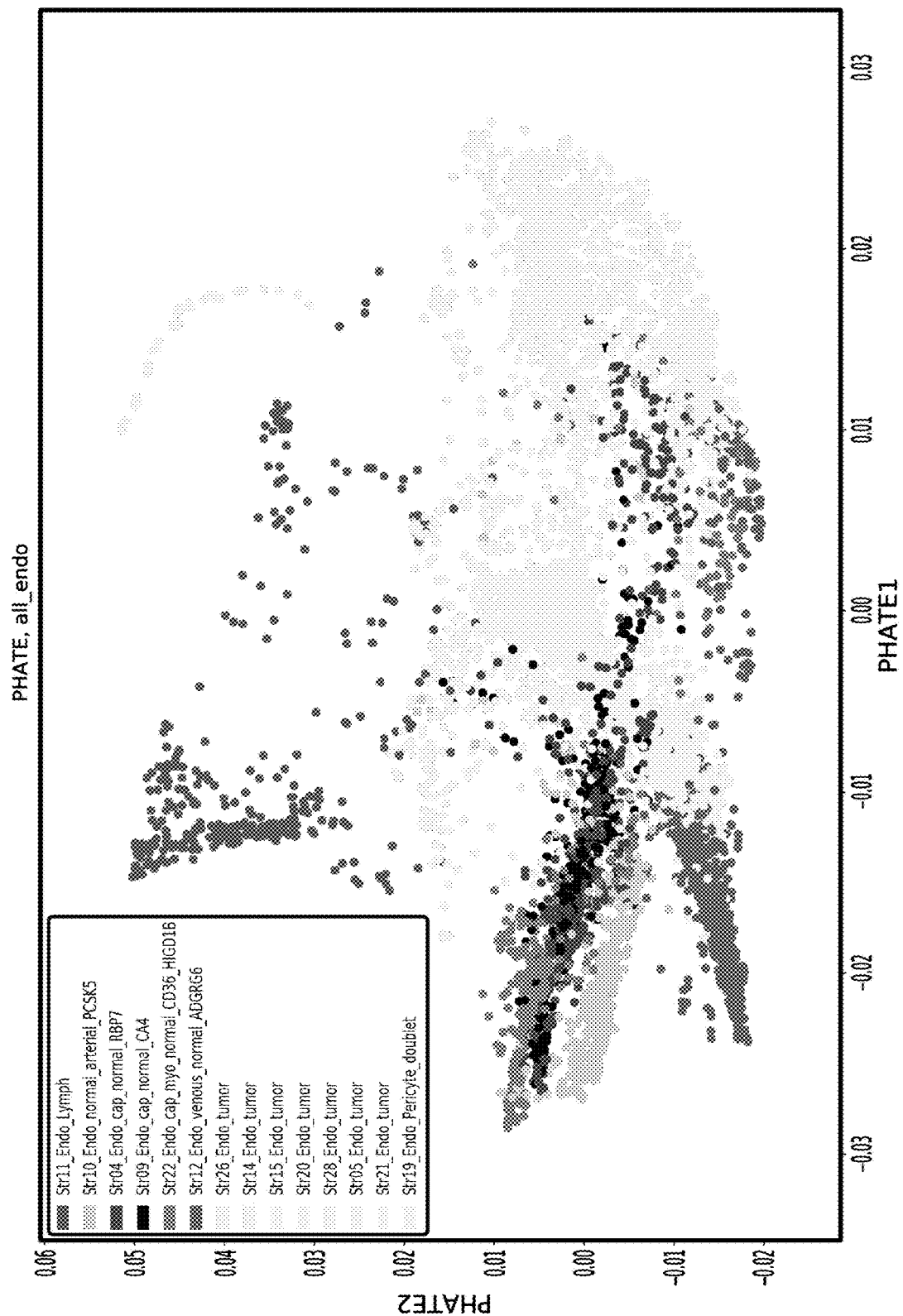
FIG. 53—PHATE embedding of endothelial cells.
Figure 54:
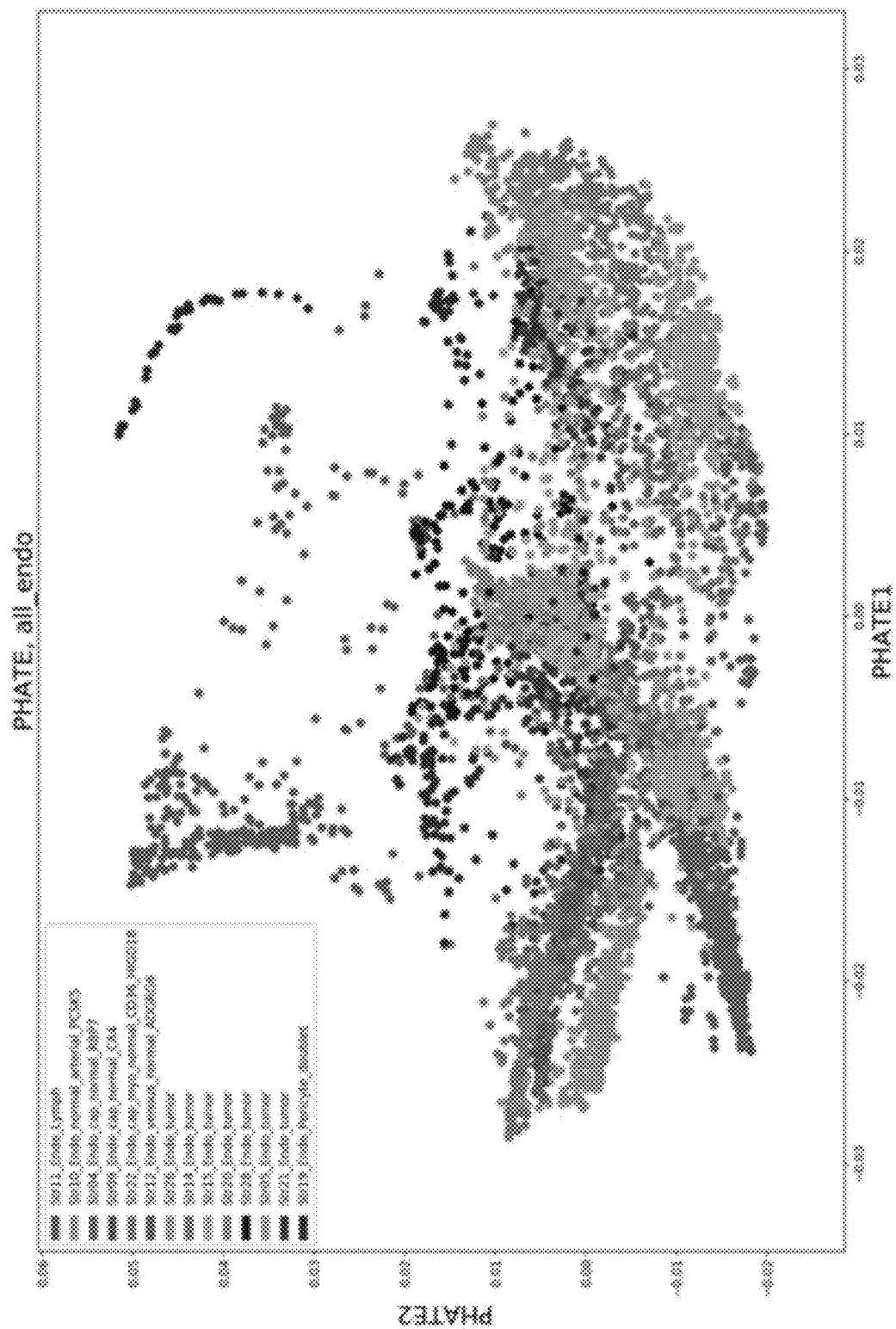
FIG. 54—PHATE embedding of endothelial cells.
Figure 55:
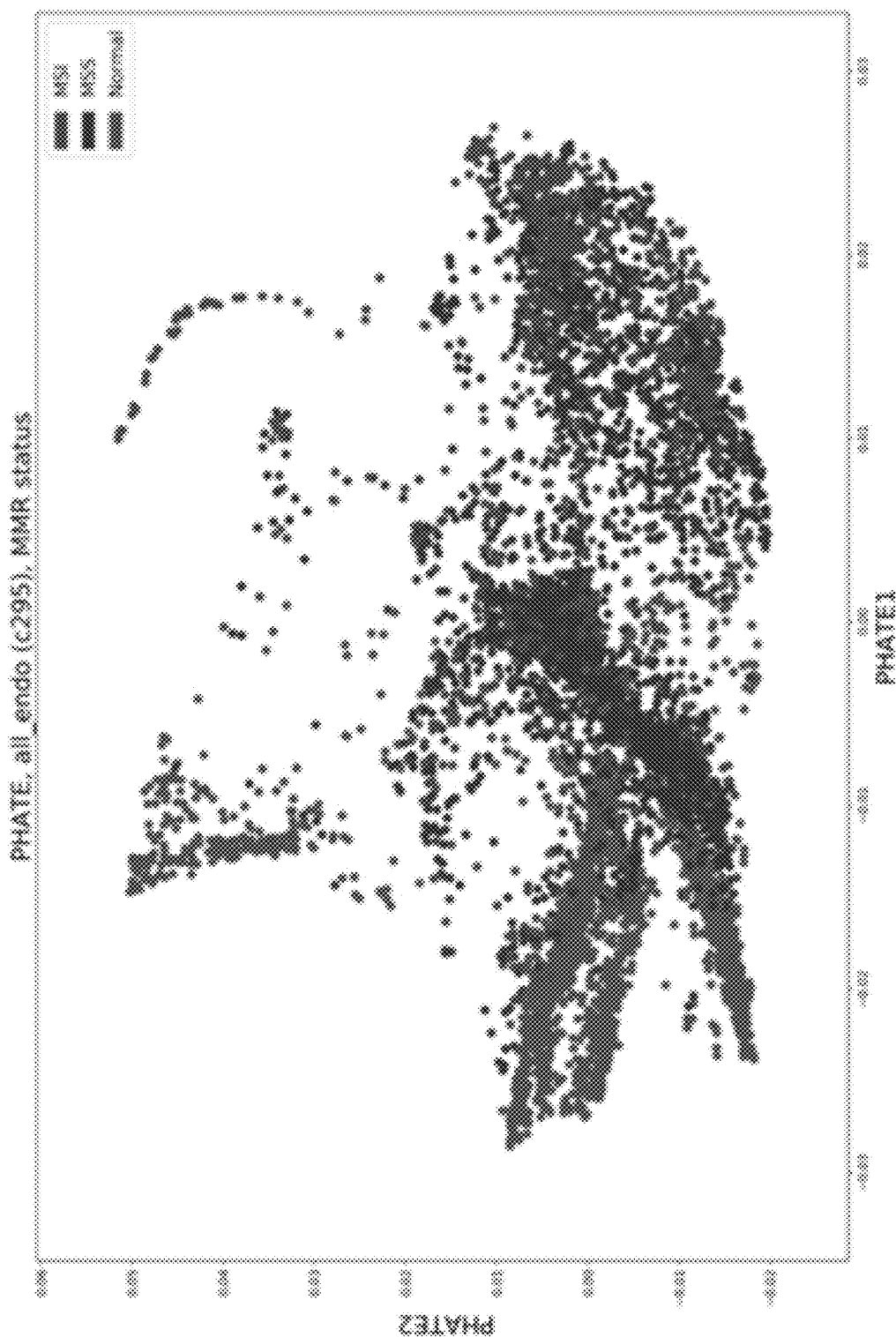
FIG. 55—PHATE embedding of endothelial cells labeled by MMR status.
Figure 56:
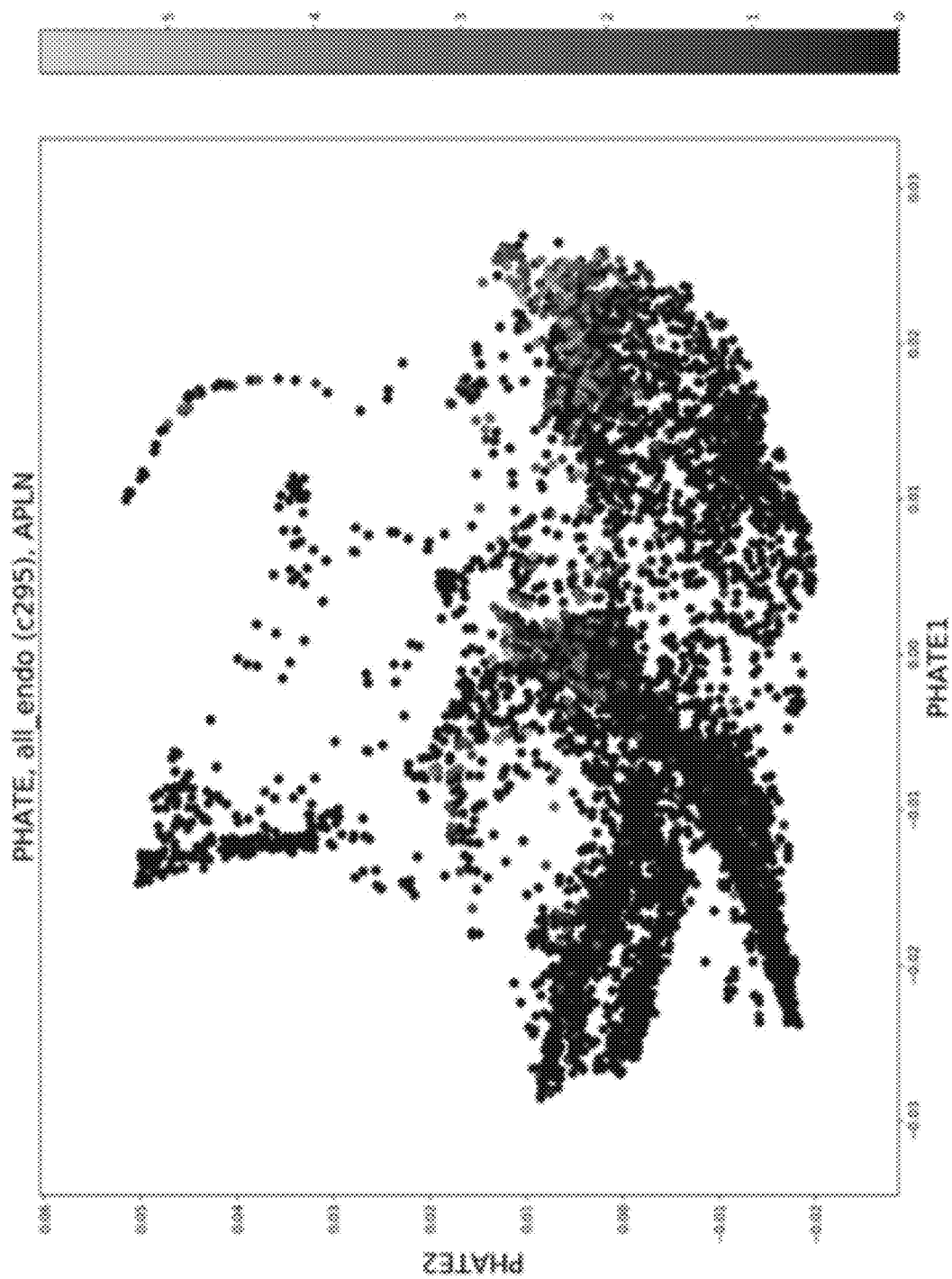
FIG. 56—PHATE embedding of endothelial cells labeled by APLN expression.
Figure 57:
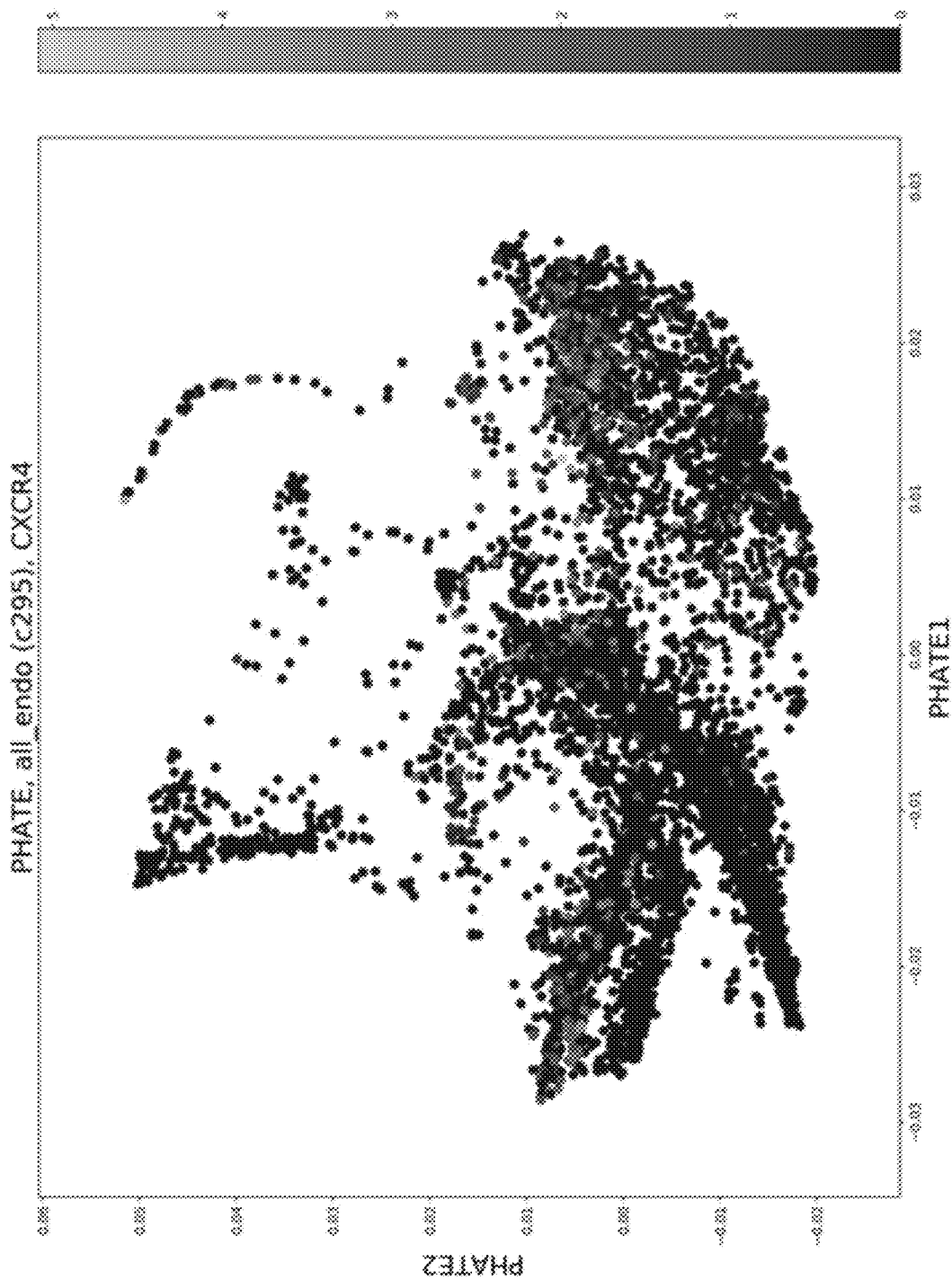
FIG. 57—PHATE embedding of endothelial cells labeled by CXCR4 expression.
Figure 58:
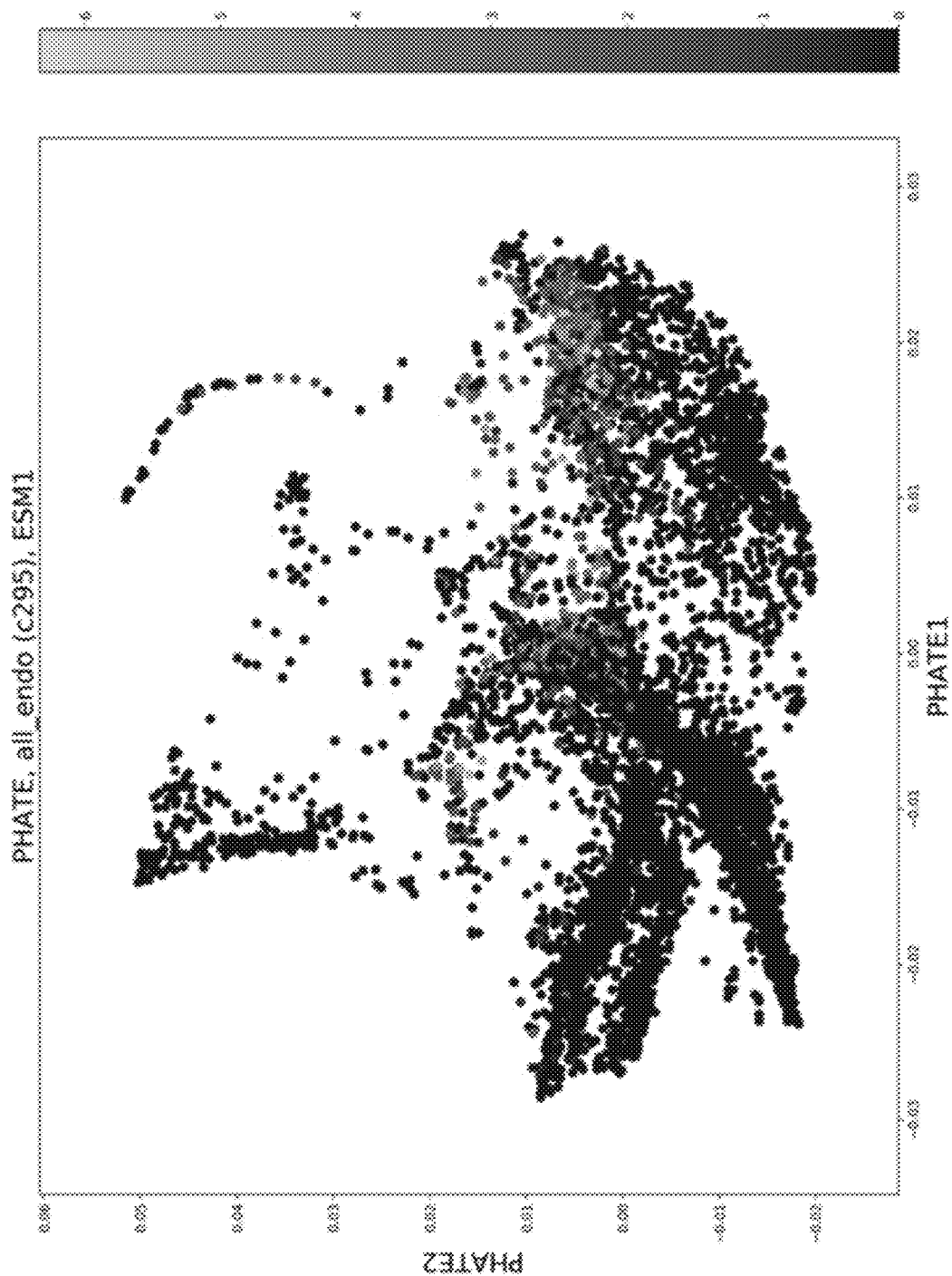
FIG. 58—PHATE embedding of endothelial cells labeled by ESM1 expression.
Figure 59:
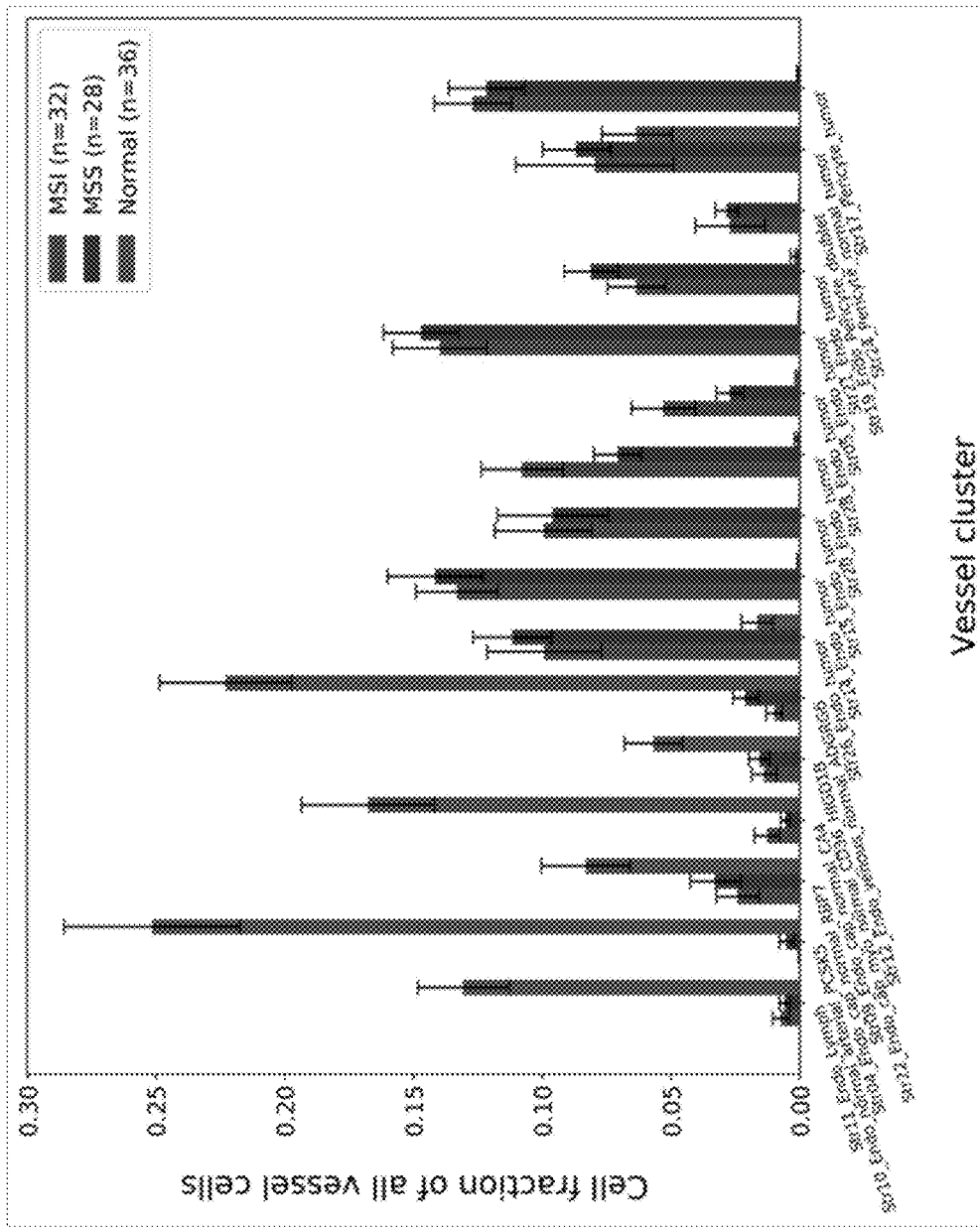
FIG. 59—Bar graph showing endothelial cell vessel cluster cell fraction in normal and CRC.
Figure 60:
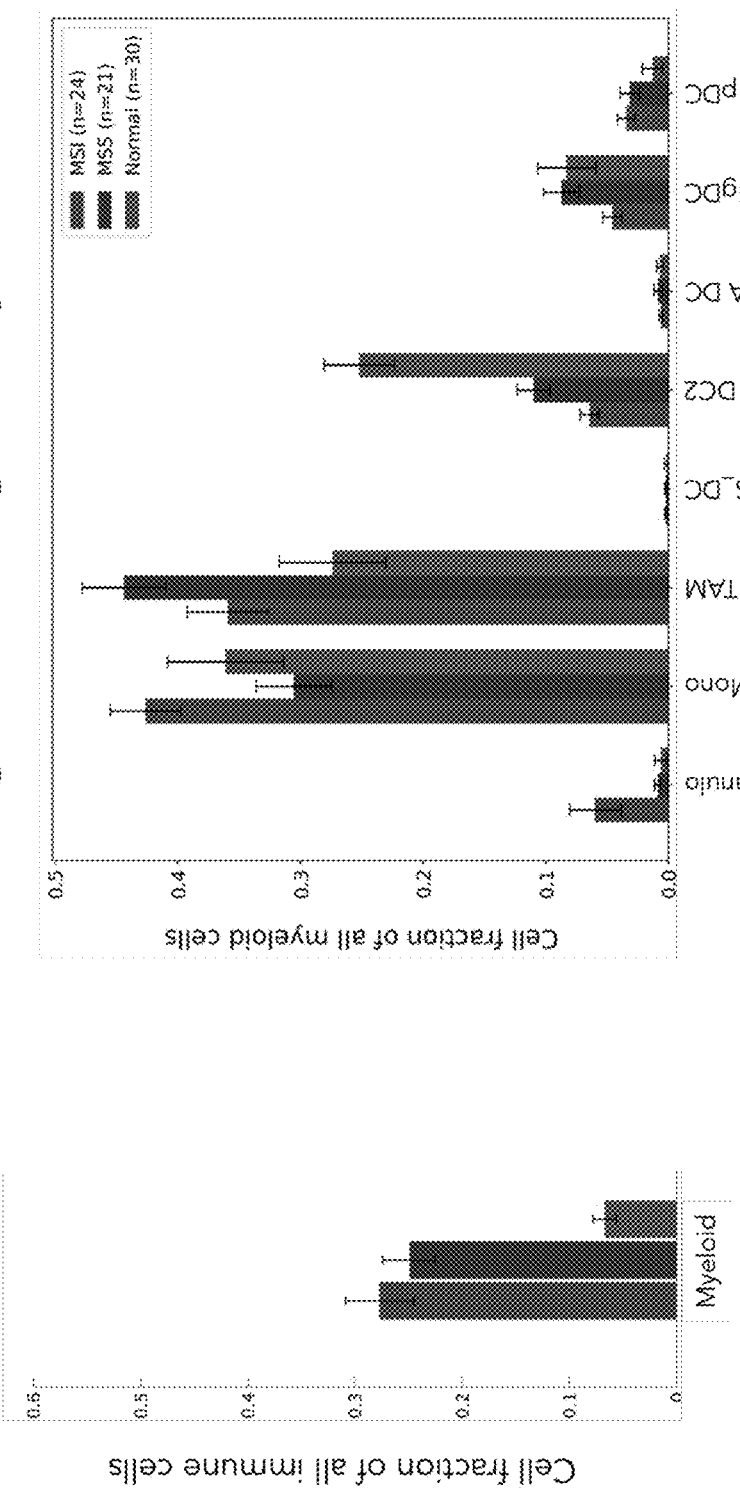
FIG. 60—Bar graphs showing percentage of myeloid cells out of all immune cells and the individual myeloid cells in normal and CRC.
Figure 61:
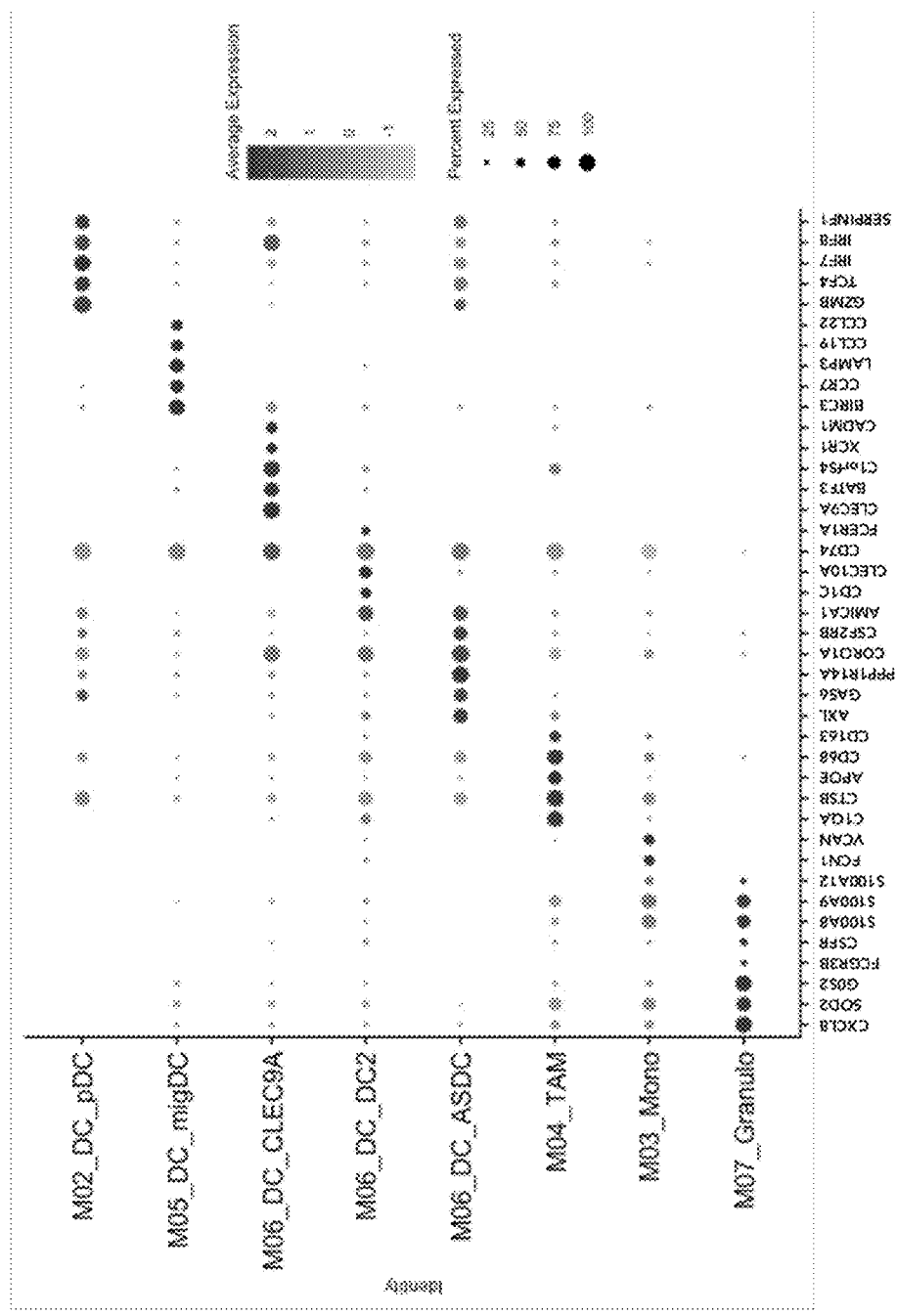
FIG. 61—Graph showing gene expression of known markers for the myeloid clusters.
Figure 62:
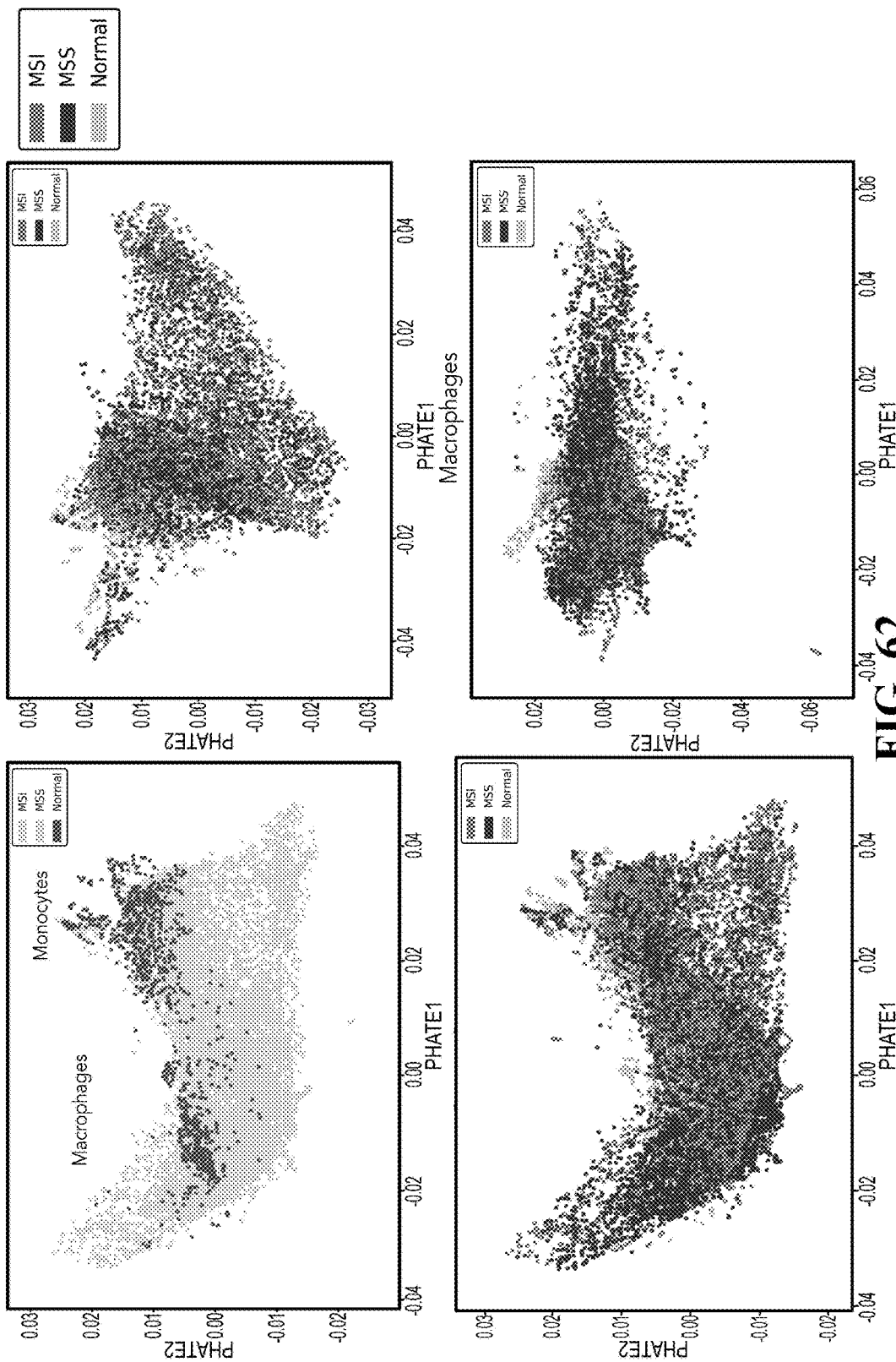
FIG. 62—PHATE maps of monocytes and macrophages in normal and CRC.
Figure 63:
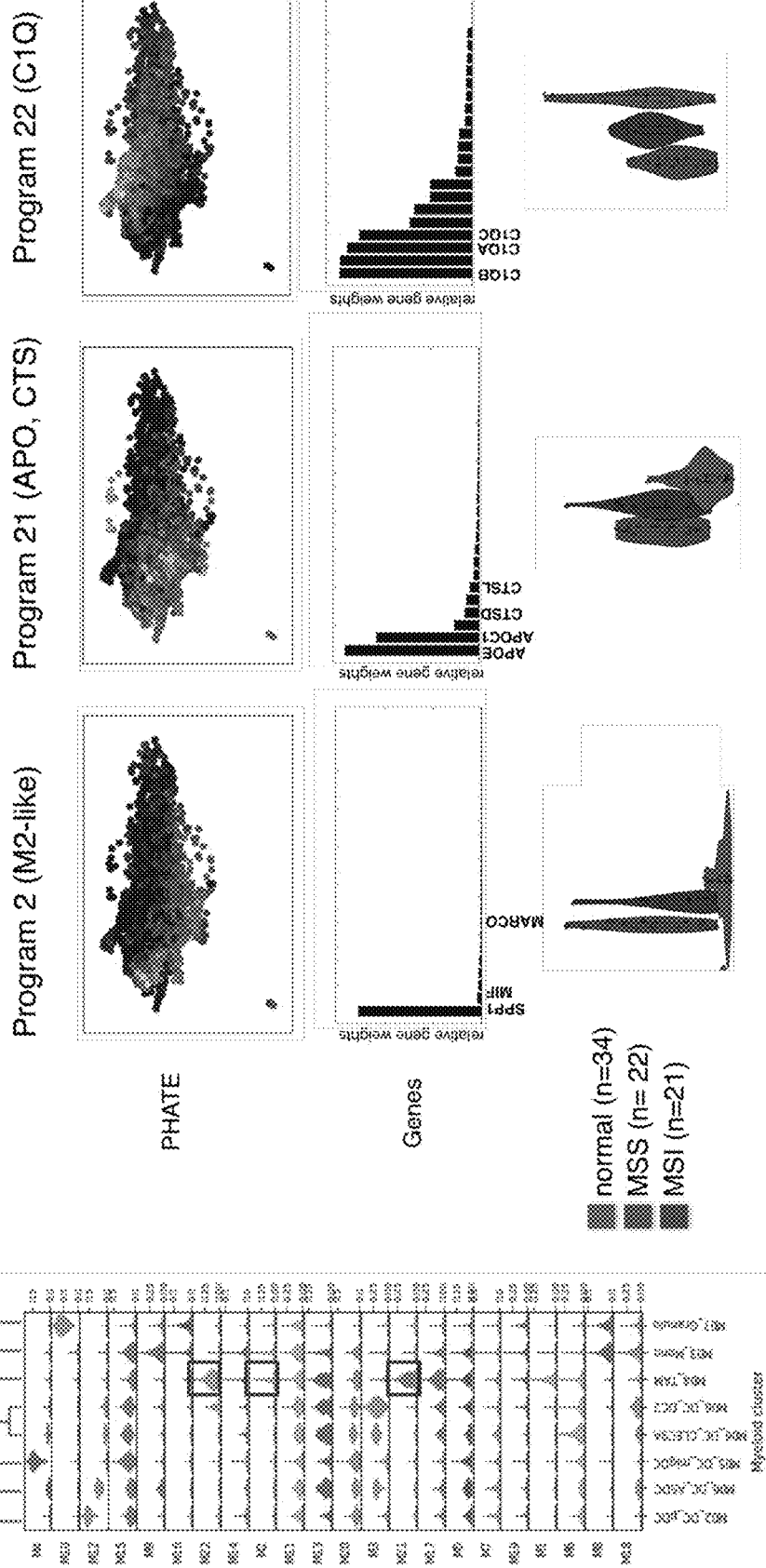
FIG. 63—Expression of myeloid gene programs across myeloid clusters. Violin plots for all programs (left). PHATE maps labeled for each program indicated are shown. Expression of key genes for each program are shown. Expression of indicated programs in normal and CRC is shown.

Applicants aim to identify mechanisms to target for increasing anti-tumor immunity. Applicants obtained patient tumor samples and (1) determined the composition of the tumor, (2) characterized single cells in the tumor, (3) inferred cell interactions from individual cell signatures (e.g., by determining receptor ligand pairs expressed in individual cells), and (4) generated hypotheses of how to improve anti-tumor immunity (FIG. 3). For example, a tumor cell may be interacting with an immune cell to suppress an immune response. Immune cells may also be interacting with specific stromal cells. Tumor cells may also be interacting with stromal cells or altering the composition of the tumor microenvironment. Applicants initially obtained tumor and adjacent normal tissue from 21 MSS and 22 MSI patients (FIG. 4). Applicants obtained additional tumor and adjacent normal tissue resulting in the analysis of tissue from 23 MSS and 23 MSI patients (FIGS. 41-43). The MSI patients were further classified by DNA methylation status. The patients were further characterized based on their tumor, including tissue site, mutation status and stage. Applicants observed that MSI tumors have a much higher tumor mutational load as compared to MSS (FIGS. 5 and 43).

Applicants can generate a roadmap for CRC (e.g., a "Google Map" of patient tumors). The map can be generated by providing: Biological information, including medical records, histology, cell profiles, and genetic information, and Data, including multiplexed ion beam imaging (MIBI) (see, e.g., Angelo et al., Nat Med. 2014 April; 20(4): 436-442), NanoString (DSP, digital spatial profiling) (see e.g., Geiss G K, et al., Direct multiplexed measurement of gene expression with color-coded probe pairs. Nat Biotechnol. 2008 March; 26(3):317-25), microbiome, immunoprofiling, and sequencing (e.g., bulk and/or single cell sequencing). Tumors for the study were obtained at the clinical site by a surgery team. Pathology was performed at the clinical site. Tumor samples were brought to the experimental site. At the experimental site tumors were dissociated for scRNA-seq, flow cytometry and cell culture. Tissues were also snap frozen for analysis of DNA by WES, bulk RNA-seq, and epigenetics. Tissue was also OCT frozen for multiplex imaging. The data obtained was computationally analyzed.

Figure 6:
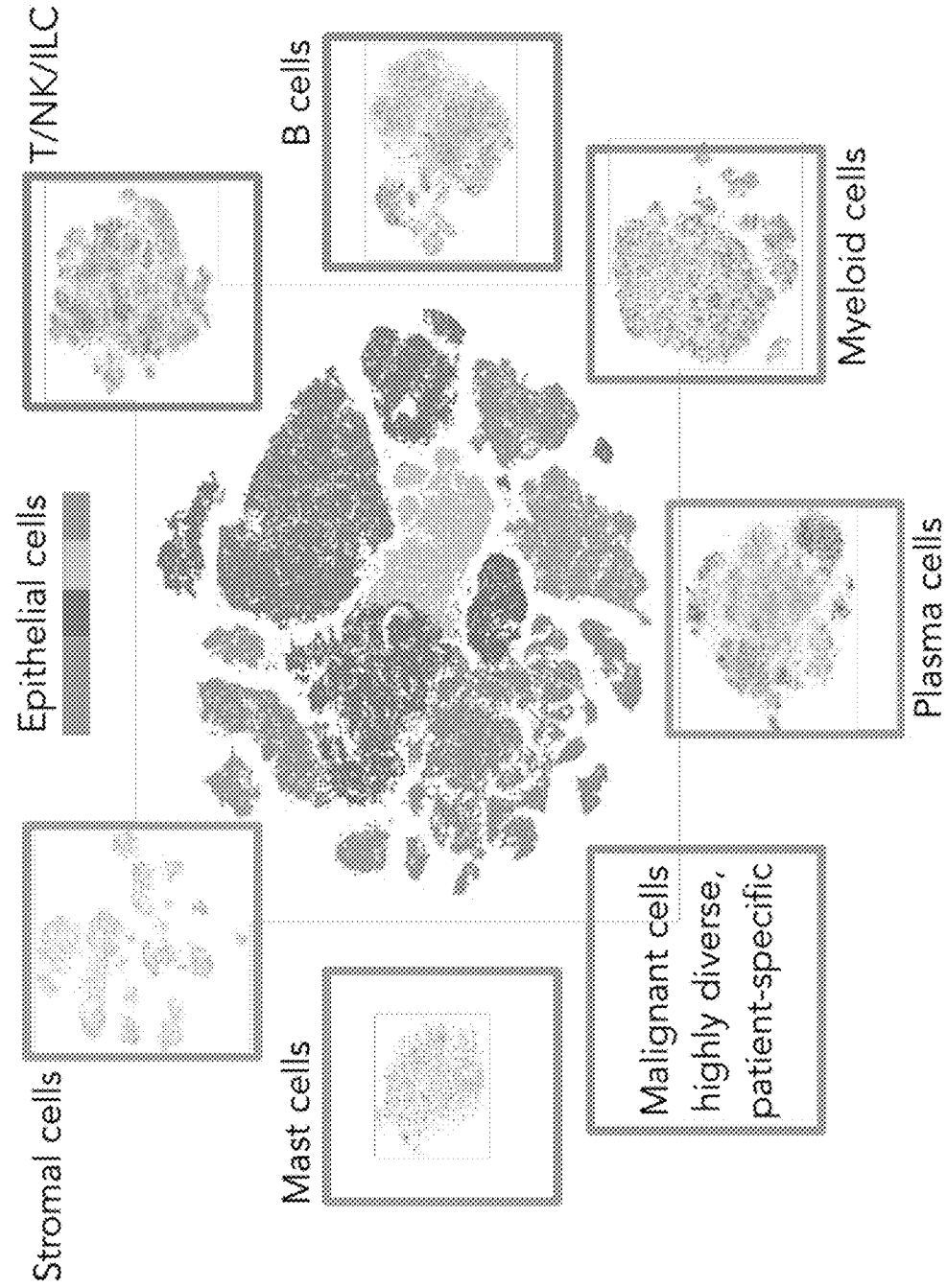
FIG. 6—Plots showing clustering of single cells obtained from the patient cohort.
Figure 7:
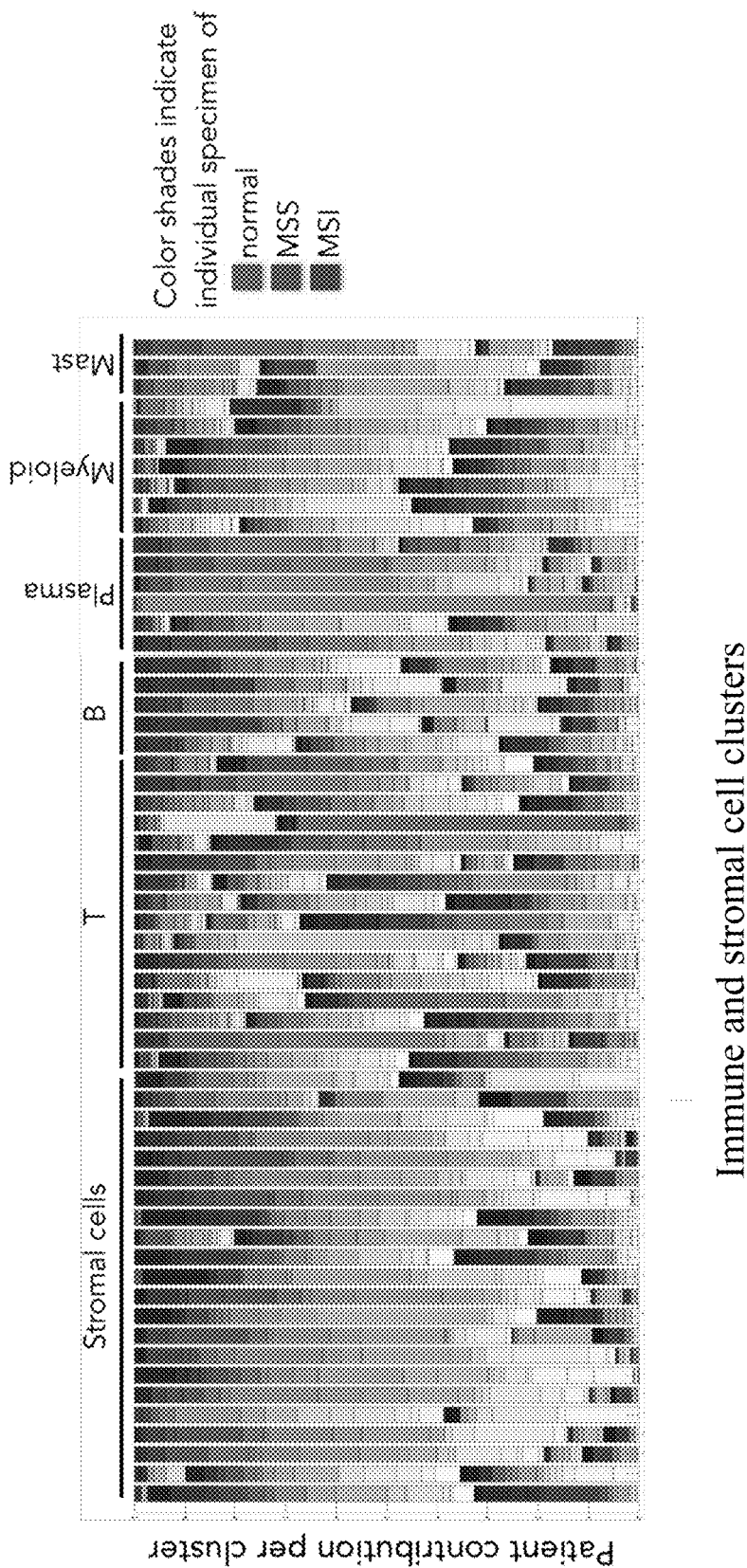
FIG. 7—Graph showing the compositions of immune and stromal cell states across the patients.
Figure 8:
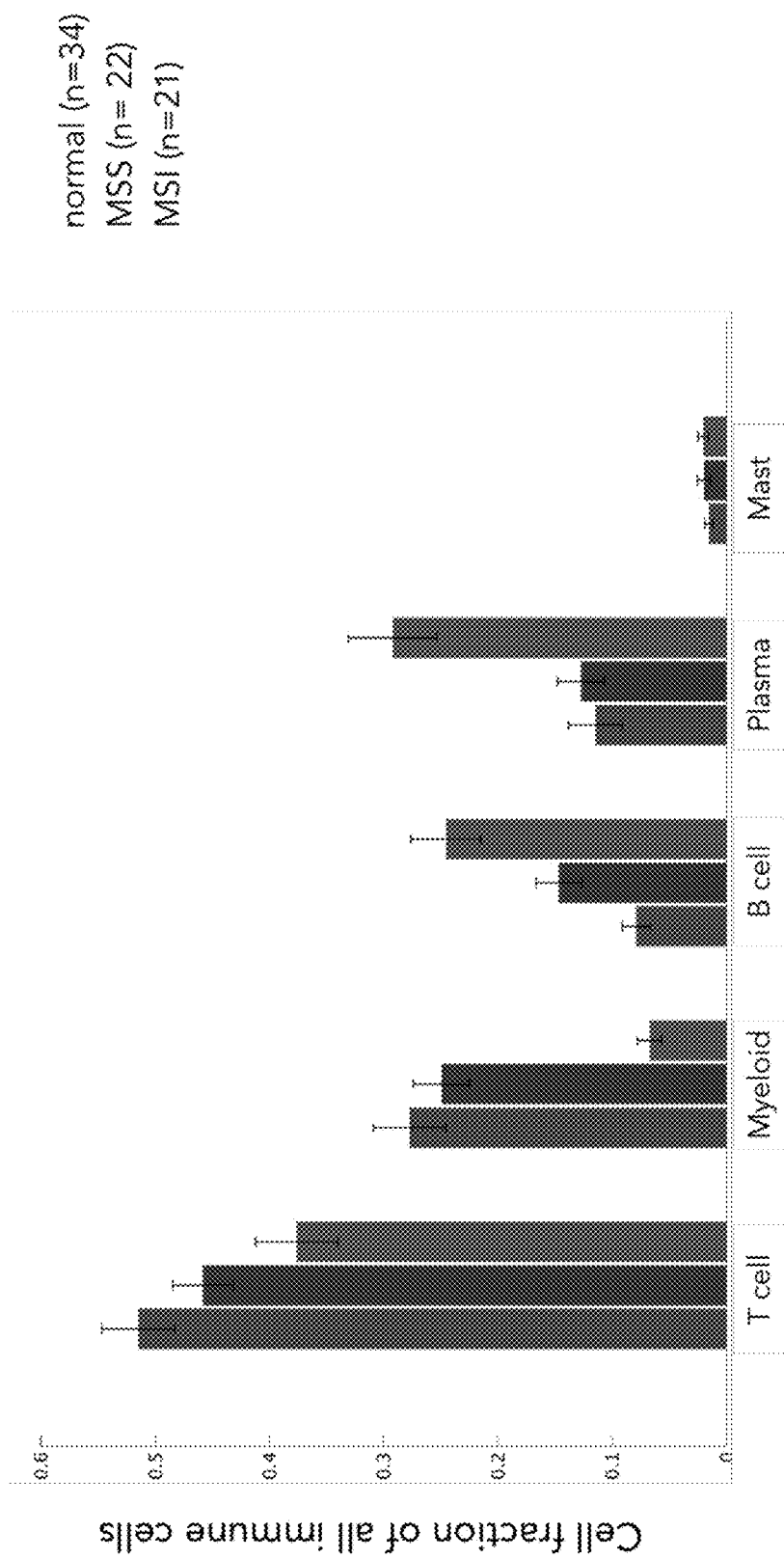
FIG. 8—Graph showing the percentage of all immune subtypes in normal, MSS and MSI tissues.
Figure 9:
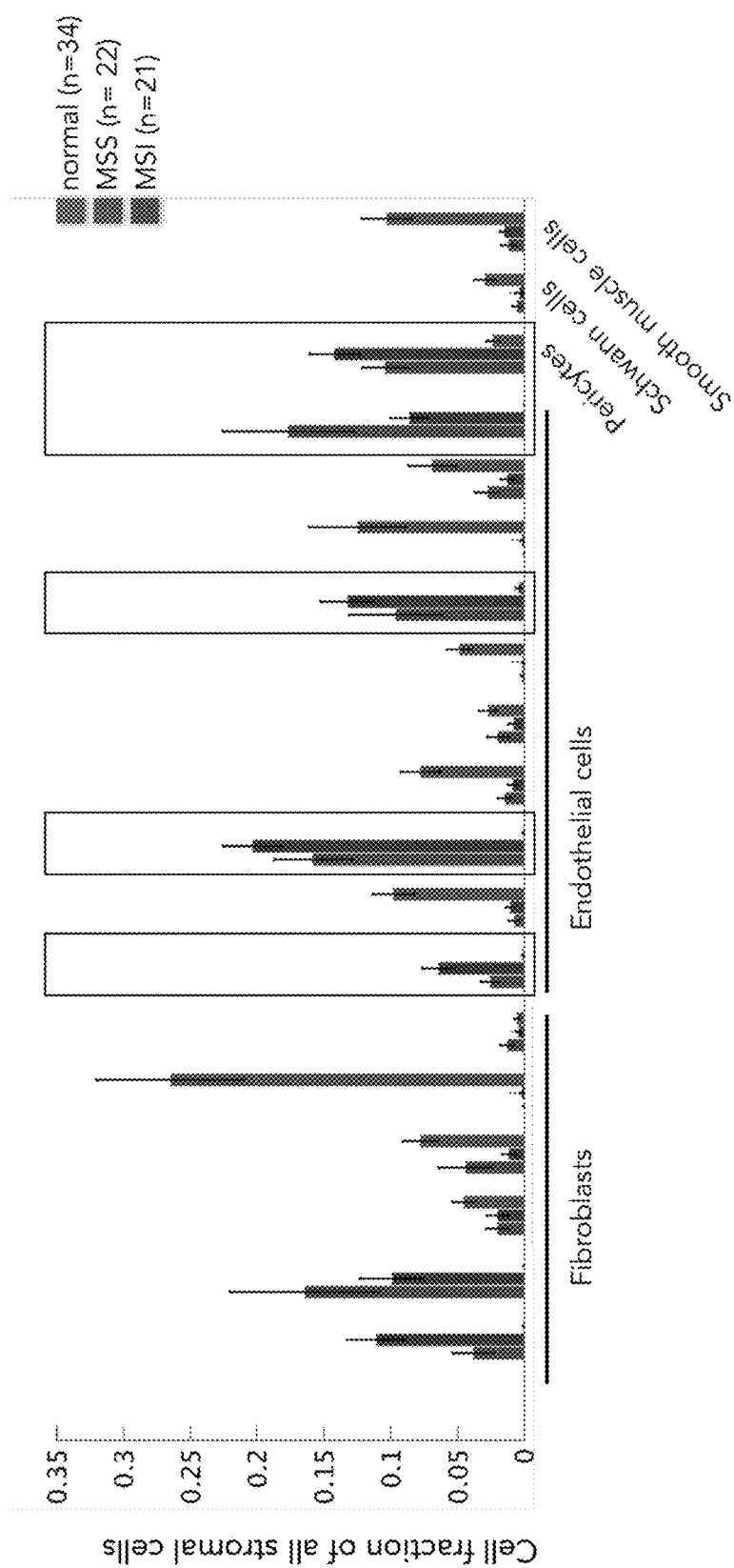
FIG. 9—Graph showing the percentage of stromal subtypes in normal, MSS and MSI tissues.
Figure 10:
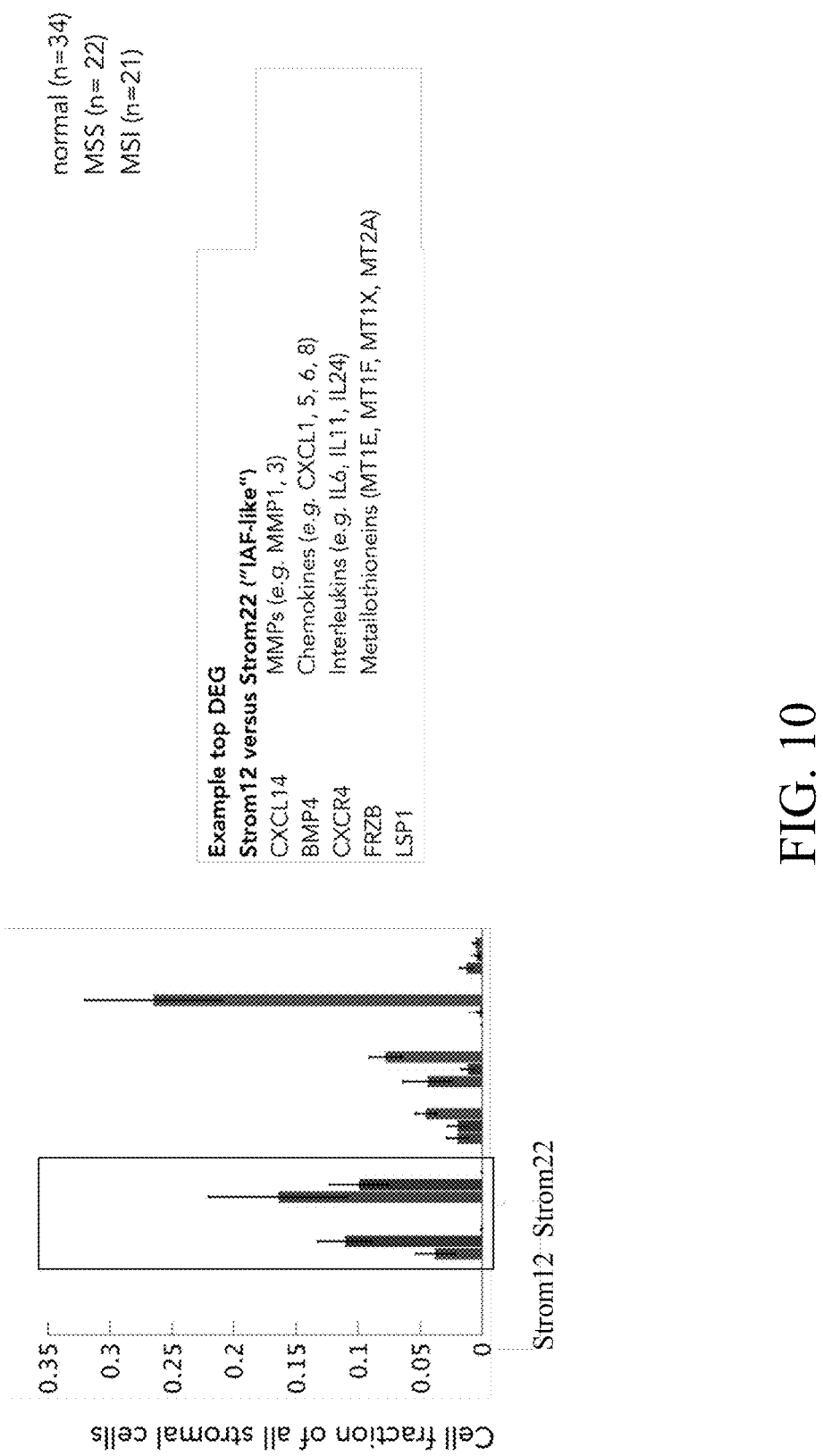
FIG. 10—Graph showing the percentage of fibroblasts in normal, MSS and MSI tissues. Also shown are exemplary genes differentially expressed between MSS and MSI.
Figure 11:
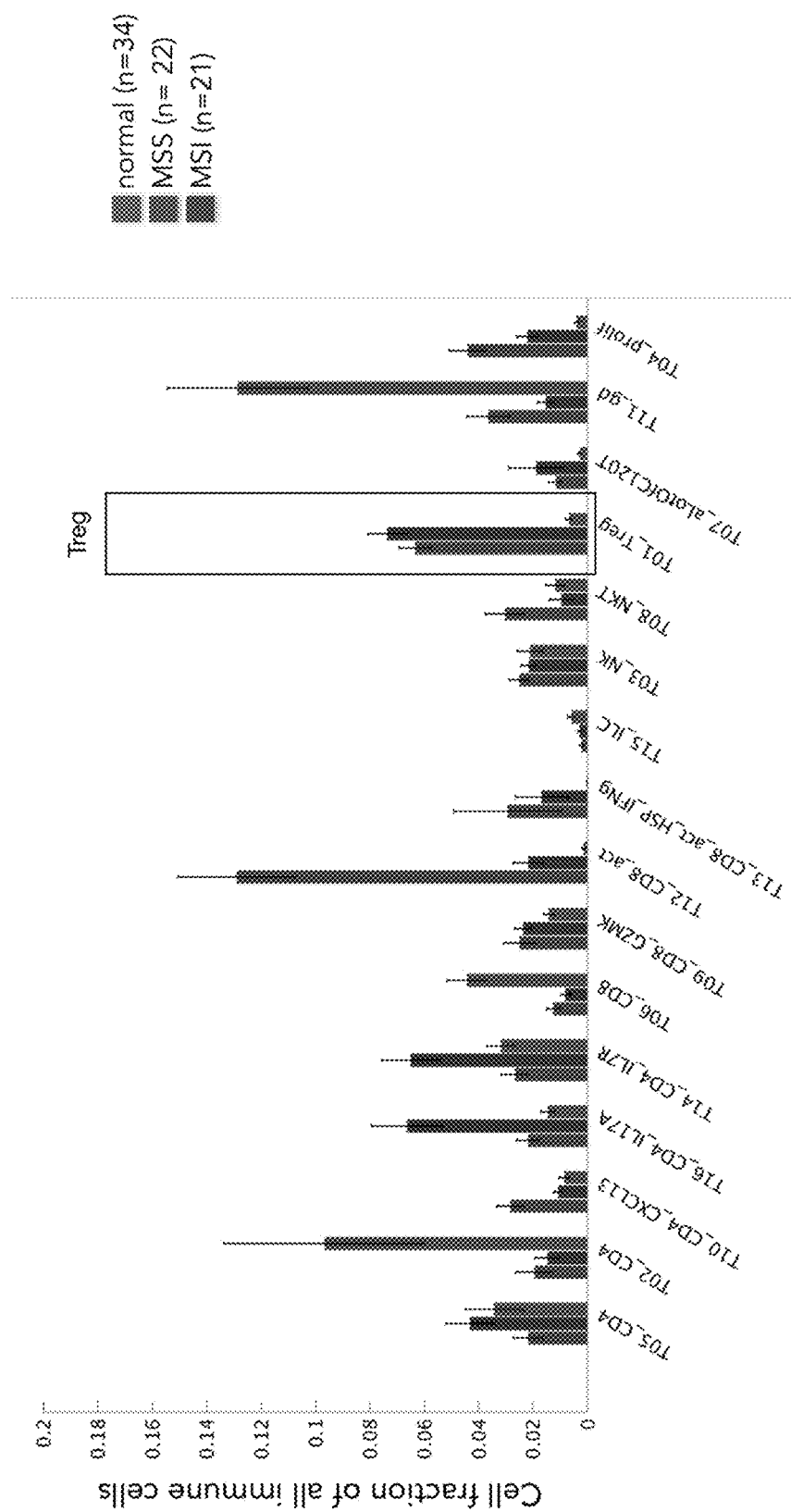
FIG. 11—Graph showing the percentage of T cells in normal, MSS and MSI tissues (Tregs are highlighted).
Figure 12:
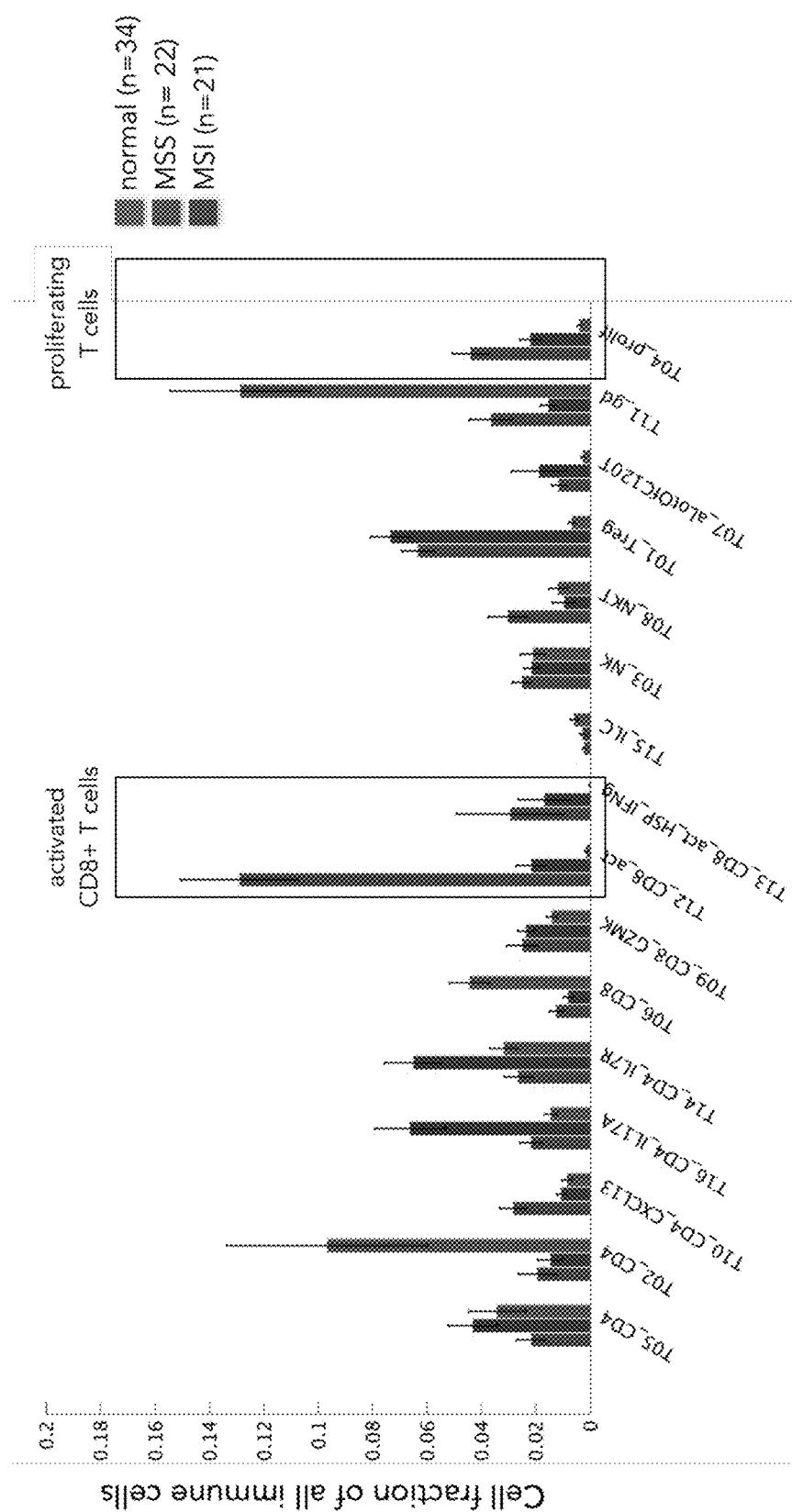
FIG. 12—Graph showing the percentage of T cells in normal, MSS and MSI tissues (Activated and proliferating T cells are highlighted).
Figure 13:
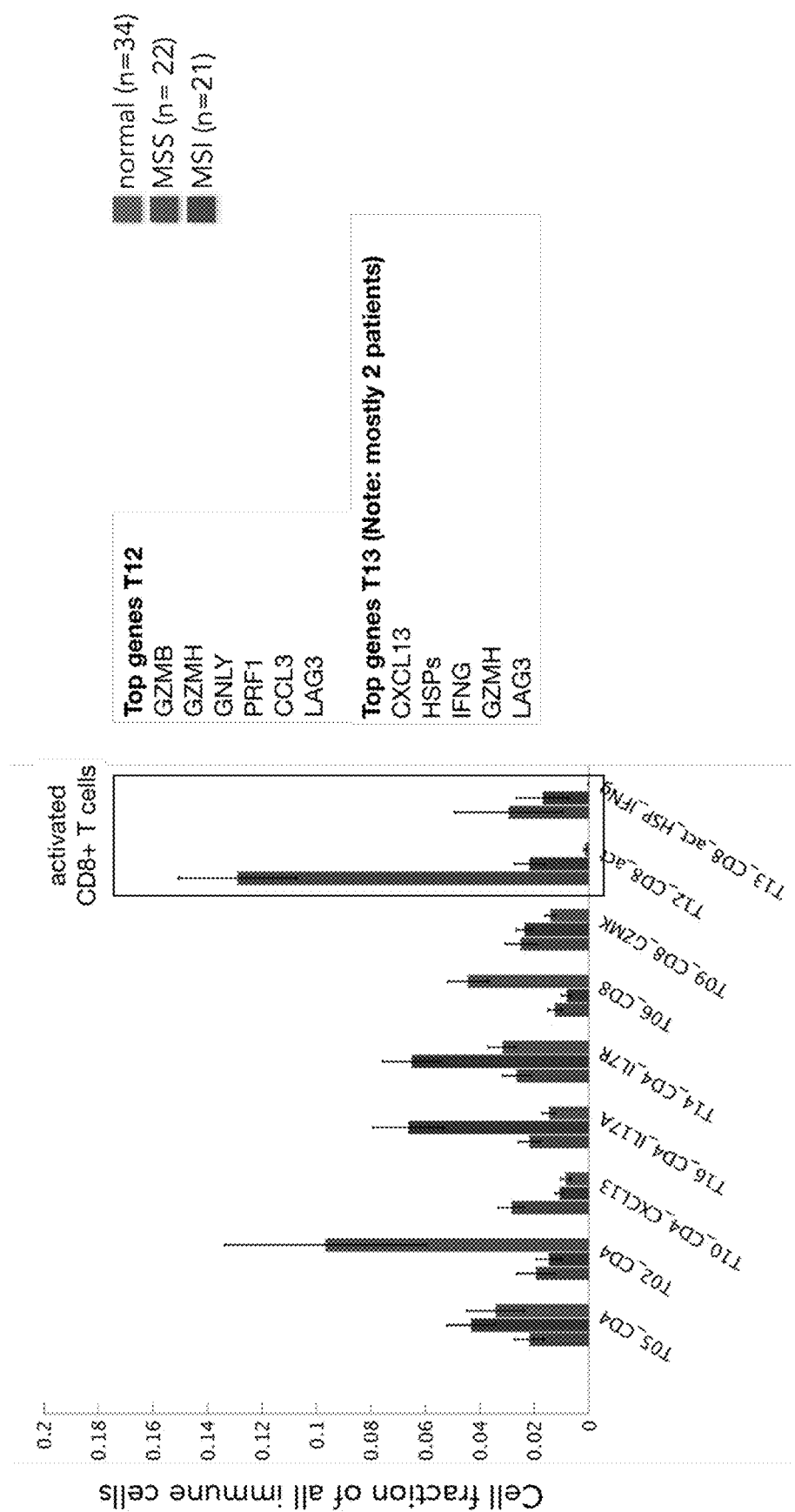
FIG. 13—Graph showing the percentage of T cells in normal, MSS and MSI tissues (Activated T cells are highlighted). The top genes for the activated CD8+ T cells are indicated (see also, Tables).

Applicants generated a single cell atlas from 381,214 single cells across all compartments from the 45 patient tumors (FIG. 6). The atlas uncovered diverse malignant, epithelial, stromal and immune cells. Applicants observed that the immune and stromal cell states are reproducible across patients (FIG. 7). The immune and stromal clusters present in normal, MSS and MSI samples was observed. For example, certain T cells clusters were enriched in MSI tumors. Applicants observed that myeloid cells are highly infiltrated in both MSS and MSI tumors (FIG. 8). Applicants also observed that B and plasma cells are relatively depleted in both MSS and MSI tumors (FIG. 8). Applicants observed dramatic remodeling in the stromal cell compartment between normal, MSS and MSI (FIG. 9). For example, pericytes, certain endothelial cells and certain fibroblasts were enriched in CRC. Applicants observed that tumor-associated fibroblast (TAF, also referred to as CAF) signatures differ in MSS vs MSI (FIG. 10). The top differentially expressed genes for the two gene signature programs are shown (see, also Tables). Applicants observed that Tregs are enriched in both MSS and MSI tumors (FIG. 11). Applicants observed that activated and proliferating T cells are especially enriched in MSI tumors (FIG. 12). Applicants observed that activated T cells are especially enriched in MSI tumors (FIG. 13). The activated cluster T12 includes expression of GZMB, GZMH, GNLY, PRF1, CCL3 and LAG3. The activated cluster T13 includes expression of CXCL13, HSPs, IFNG, GZMH and LAG3.

Figure 14:
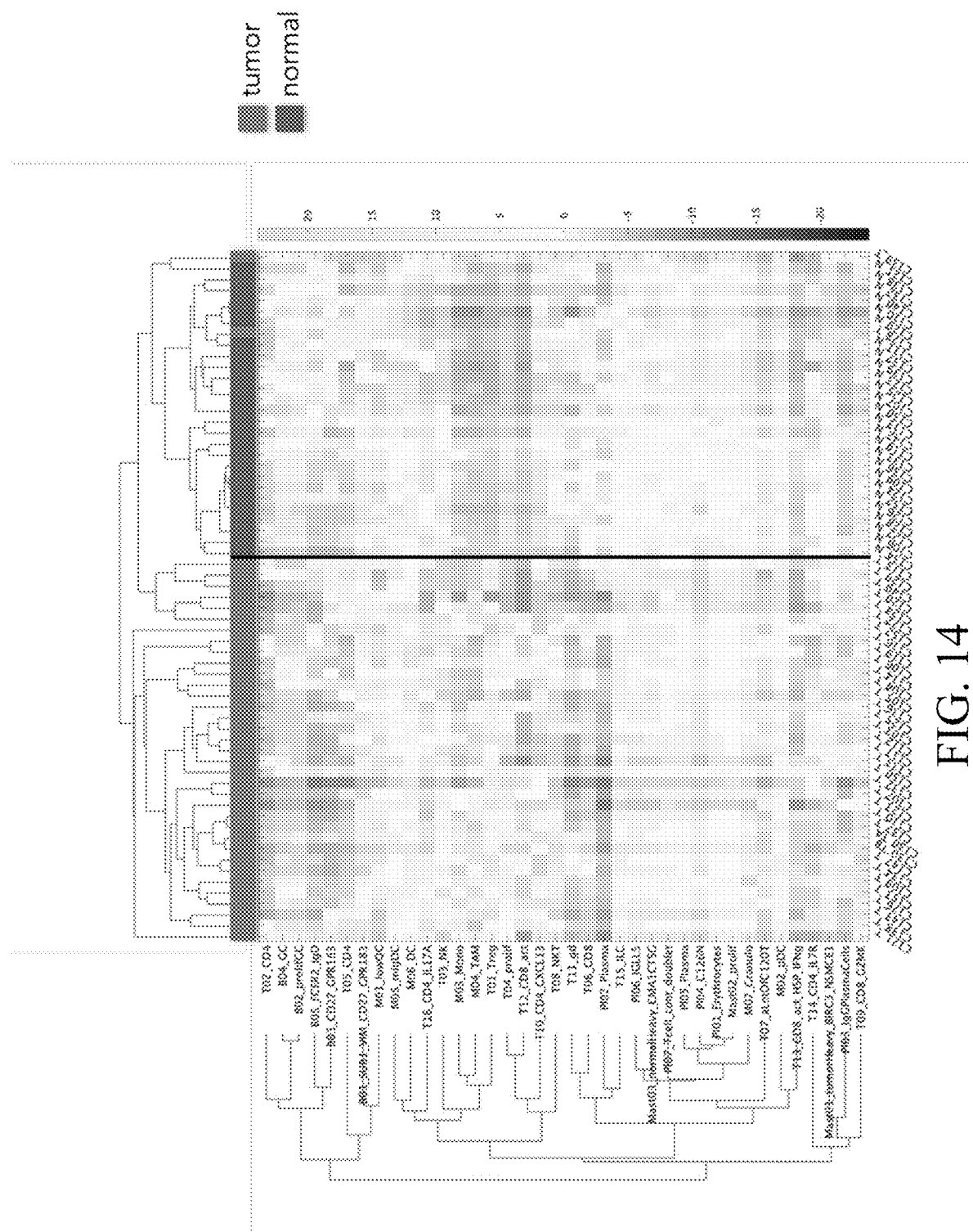
FIG. 14—Unsupervised clustering by immune composition. x-axis=patient samples (N=normal, T=tumor); y-axis=immune clusters.
Figure 15:
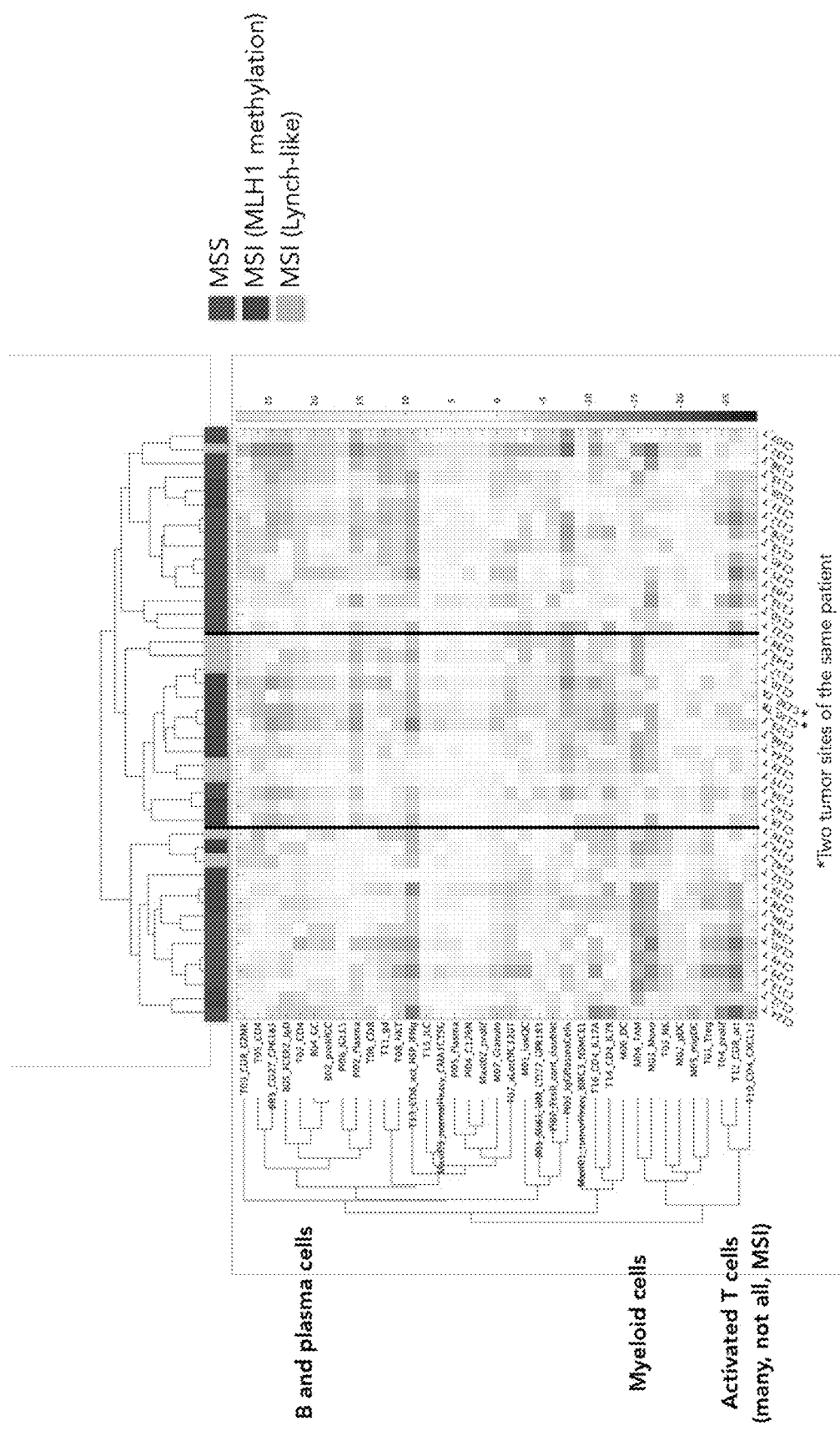
FIG. 15—Unsupervised clustering by immune composition. x-axis=patient tumor samples, y-axis=immune clusters.
Figure 16A:
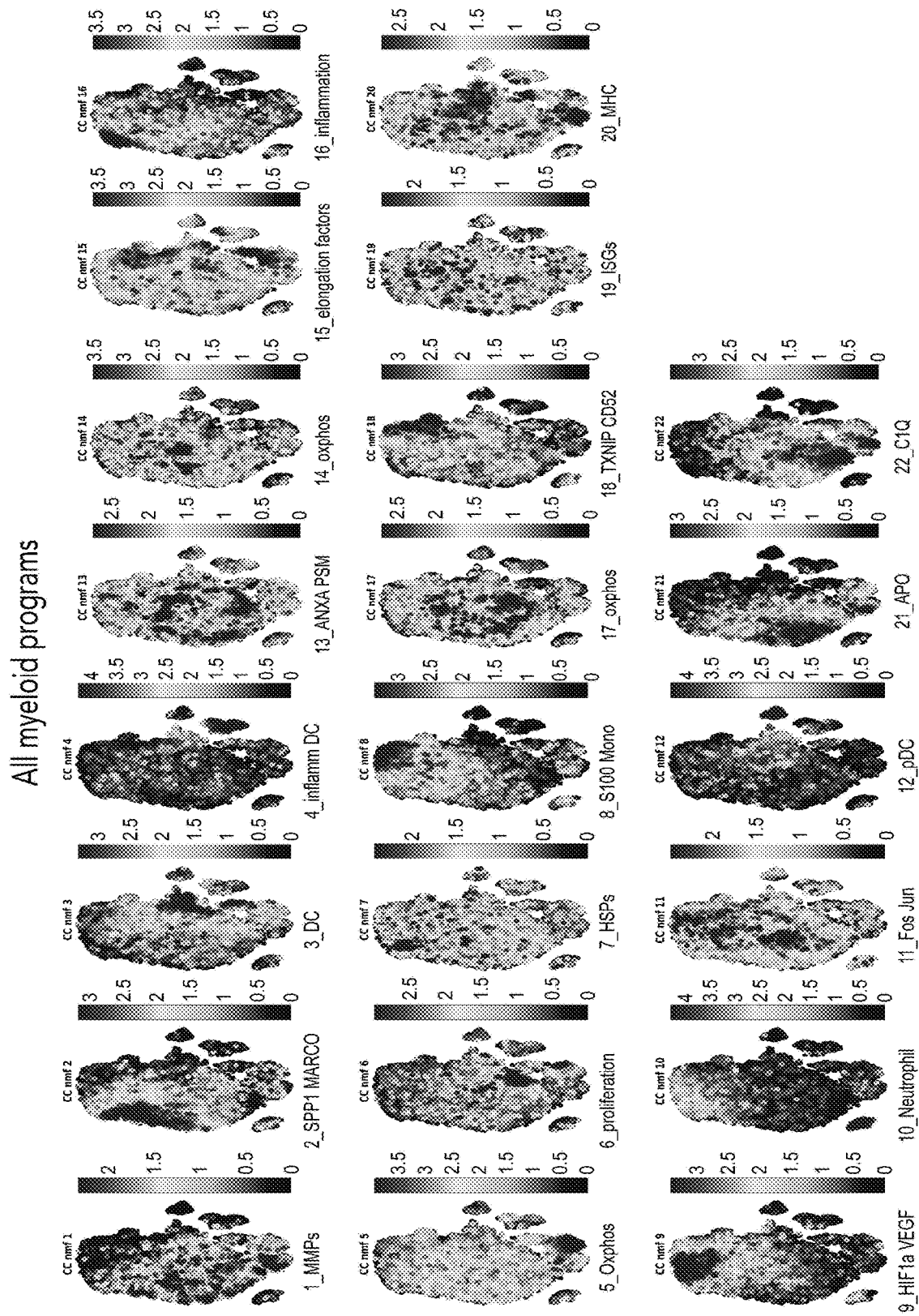
FIG. 16A-16E—Myeloid cell programs. A. All myeloid programs projected on myeloid cell clusters (tSNE) B. Illustrative myeloid cell programs (pDC and ISG cell programs). Graphs showing program genes and inferred transcription factors. C. Macrophage programs in tumor versus normal tissue. tSNE and graphs showing program genes. Violin plots showing expression in normal, MSS and MSI tissues. D. Example myeloid programs in tumor versus normal tissue. tSNE and graphs showing program genes. Violin plots showing expression in normal, MSS and MSI tissues. E. Example myeloid NMFs.
Figure 16B:
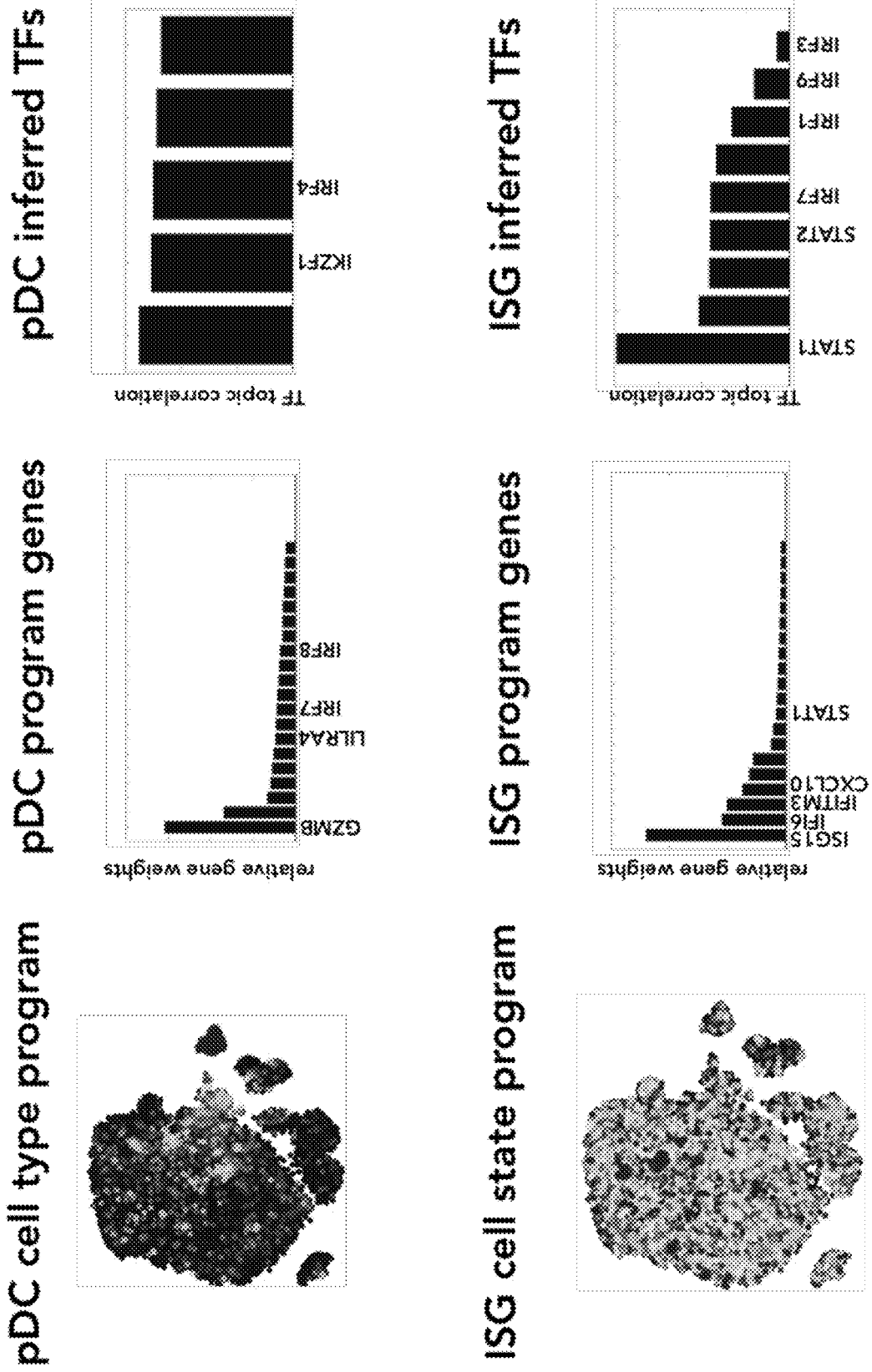
Figure 16C:
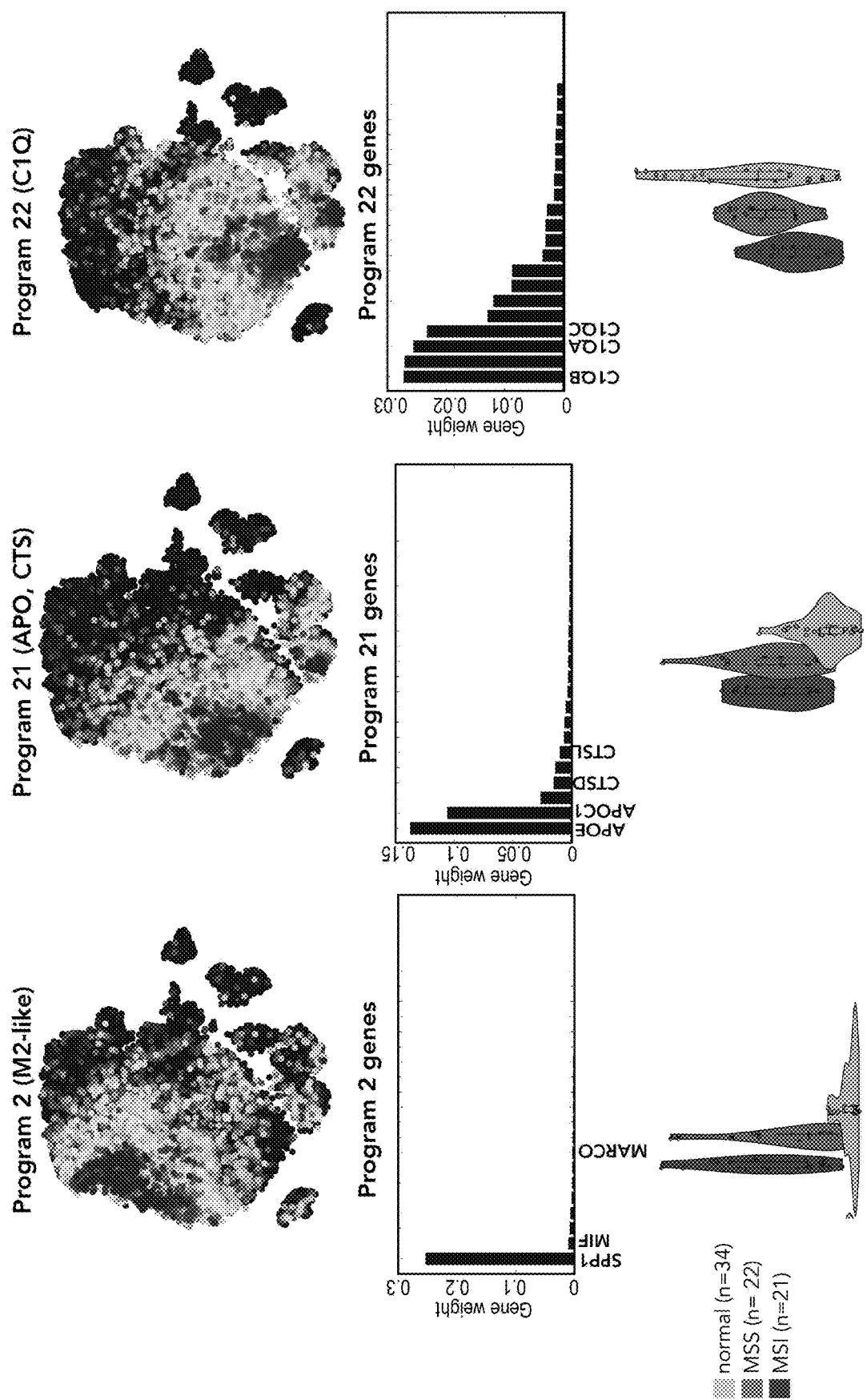
Figure 16D:
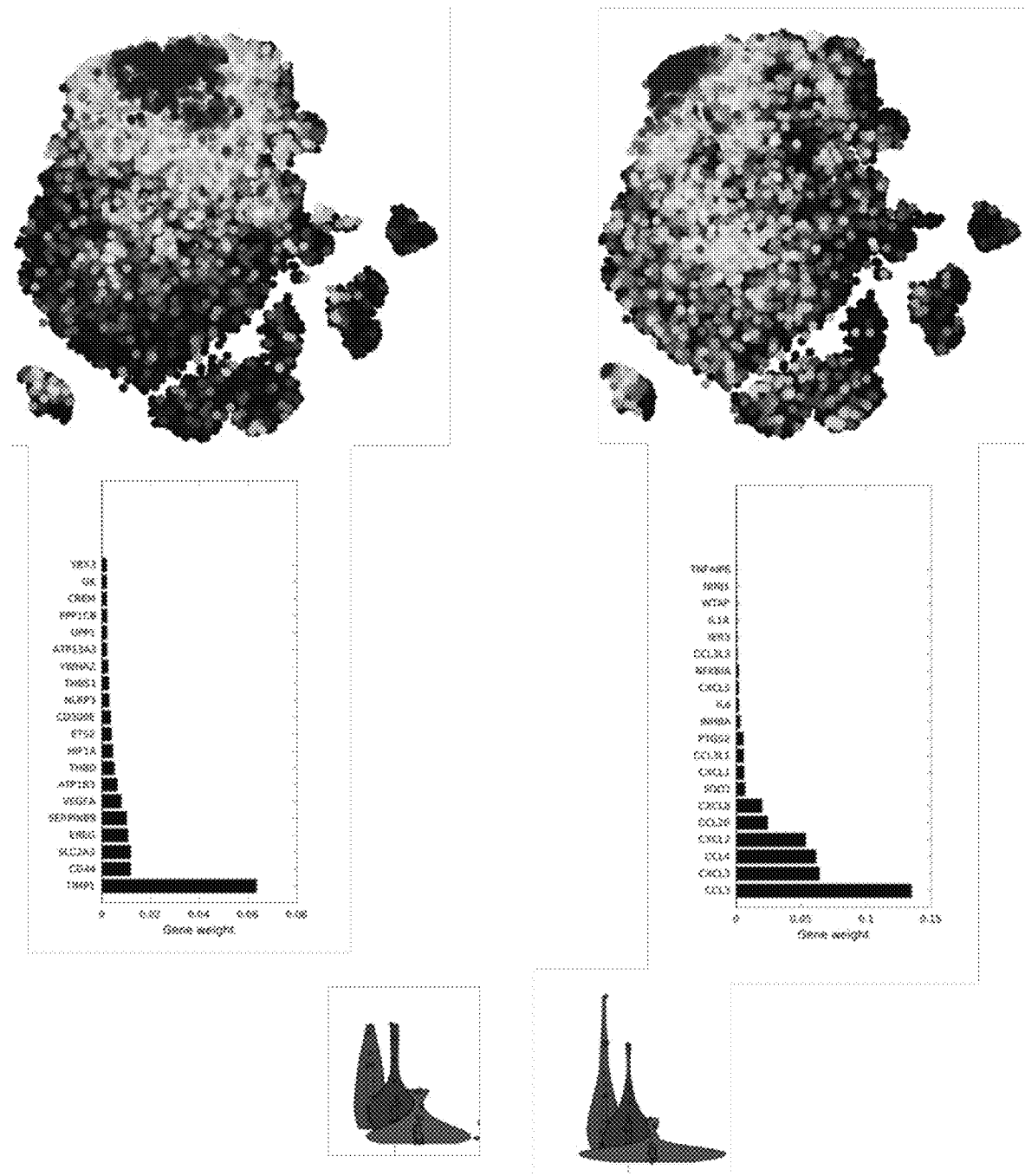
Figure 16E:
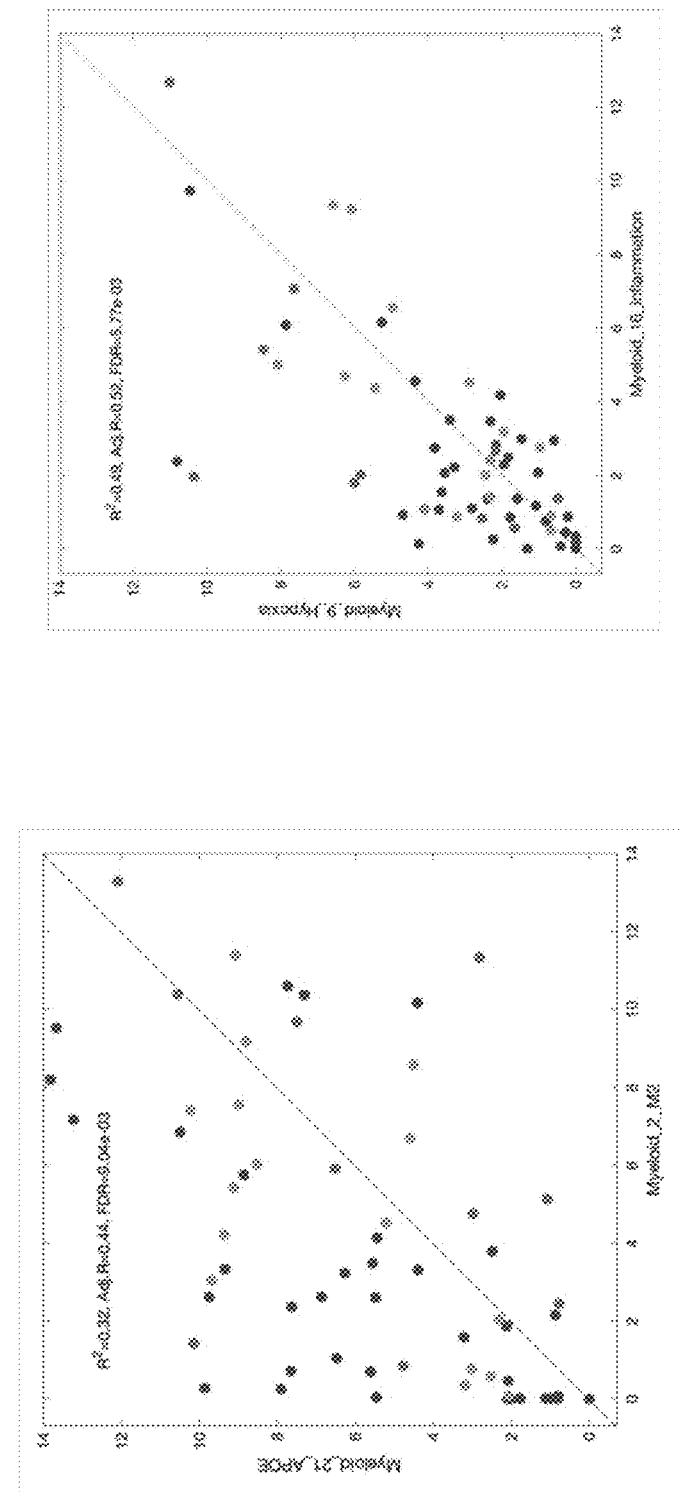
Figure 17A:
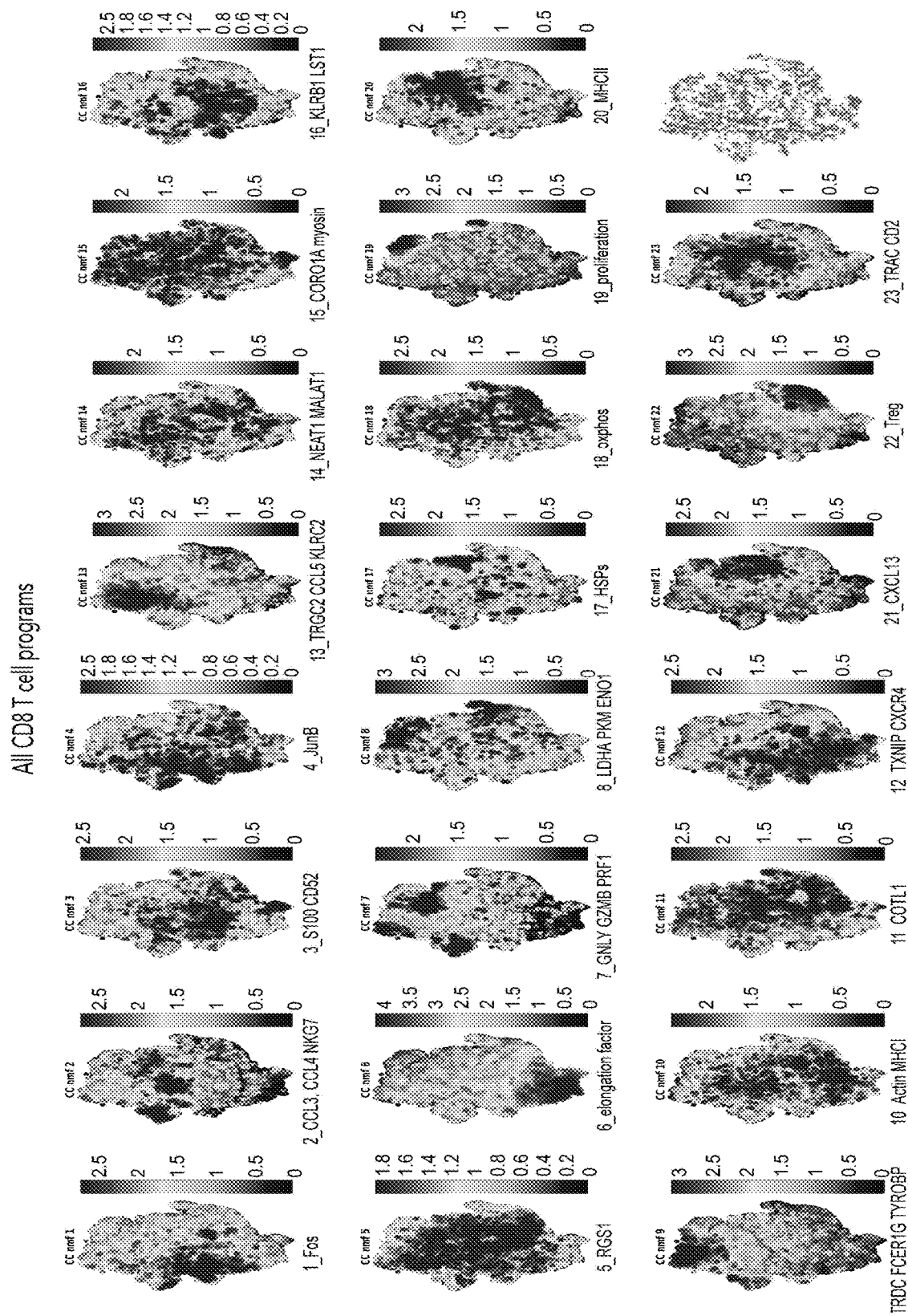
FIG. 17A-17D—CD8+ T cell programs. A. All CD8 T cell programs projected on T cell clusters (tSNE) B. Illustrative T cell programs and graphs showing program genes. C. T cell programs in tumor versus normal tissue. tSNE and graphs showing program genes. Violin plots showing expression in normal, MSS and MSI tissues. D. NMFs for T21 (CXCL13 program) compared to other programs in MSI and MSS tissues.
Figure 17B:
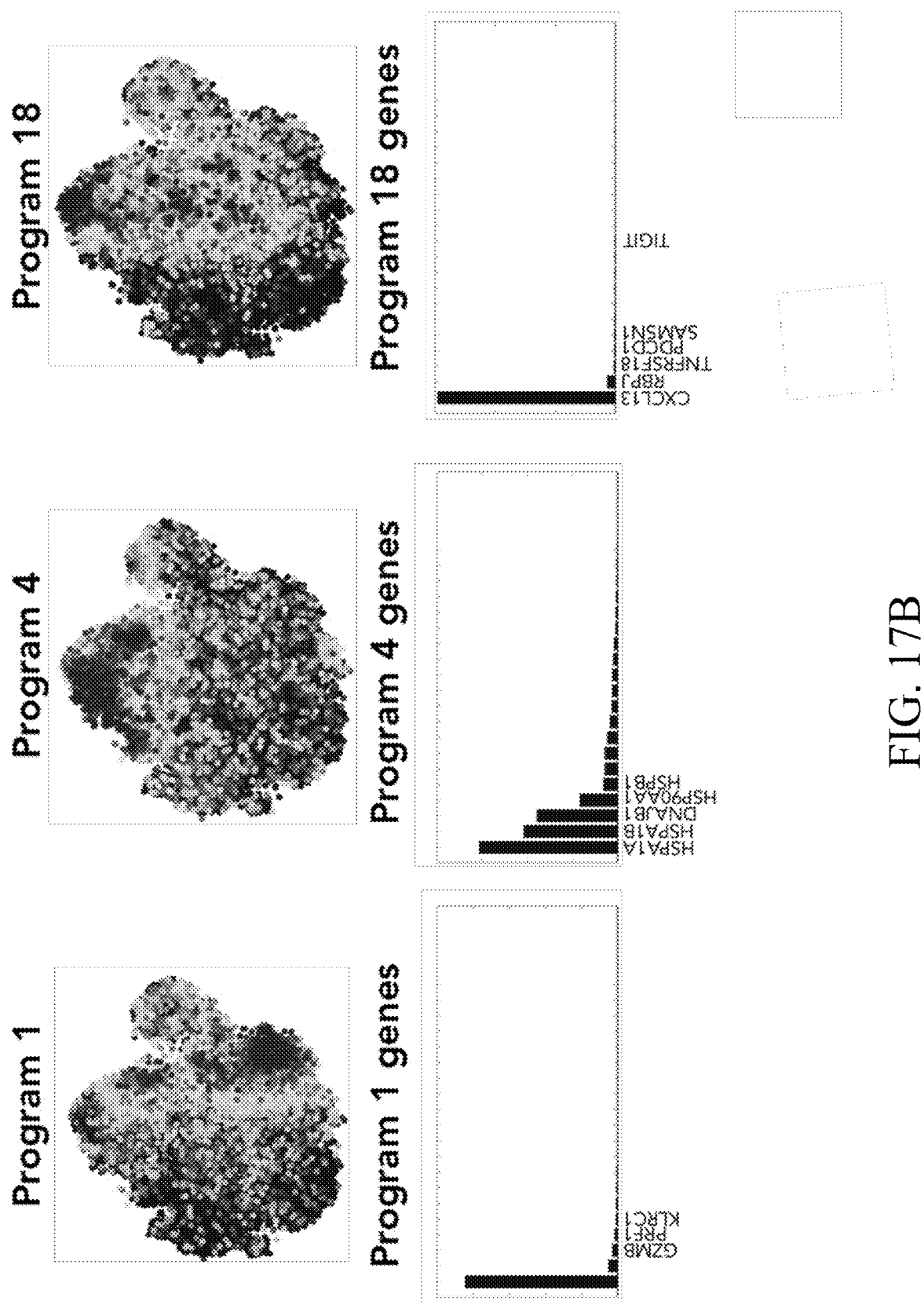
Figure 17C:
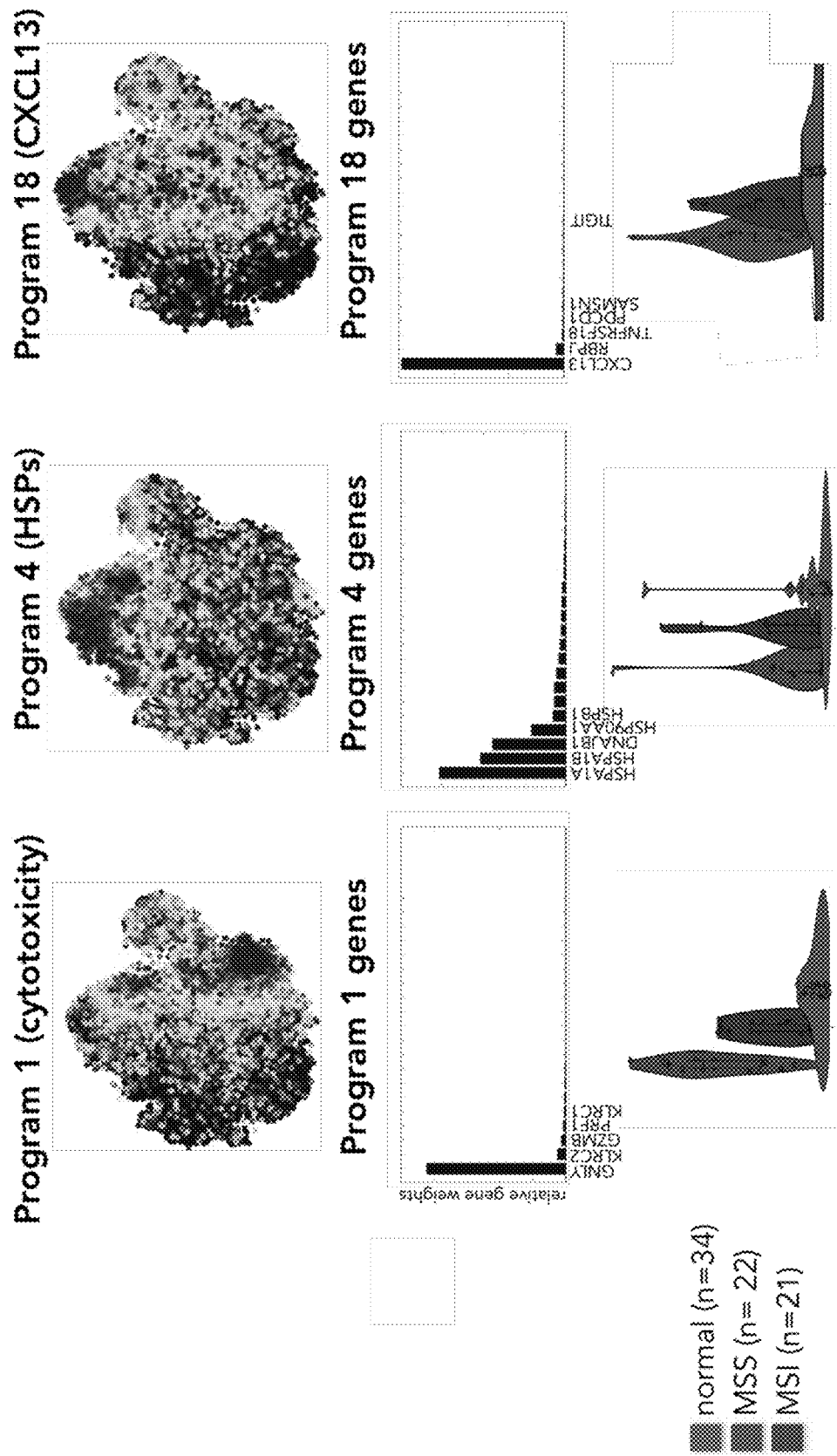
Figure 17D:
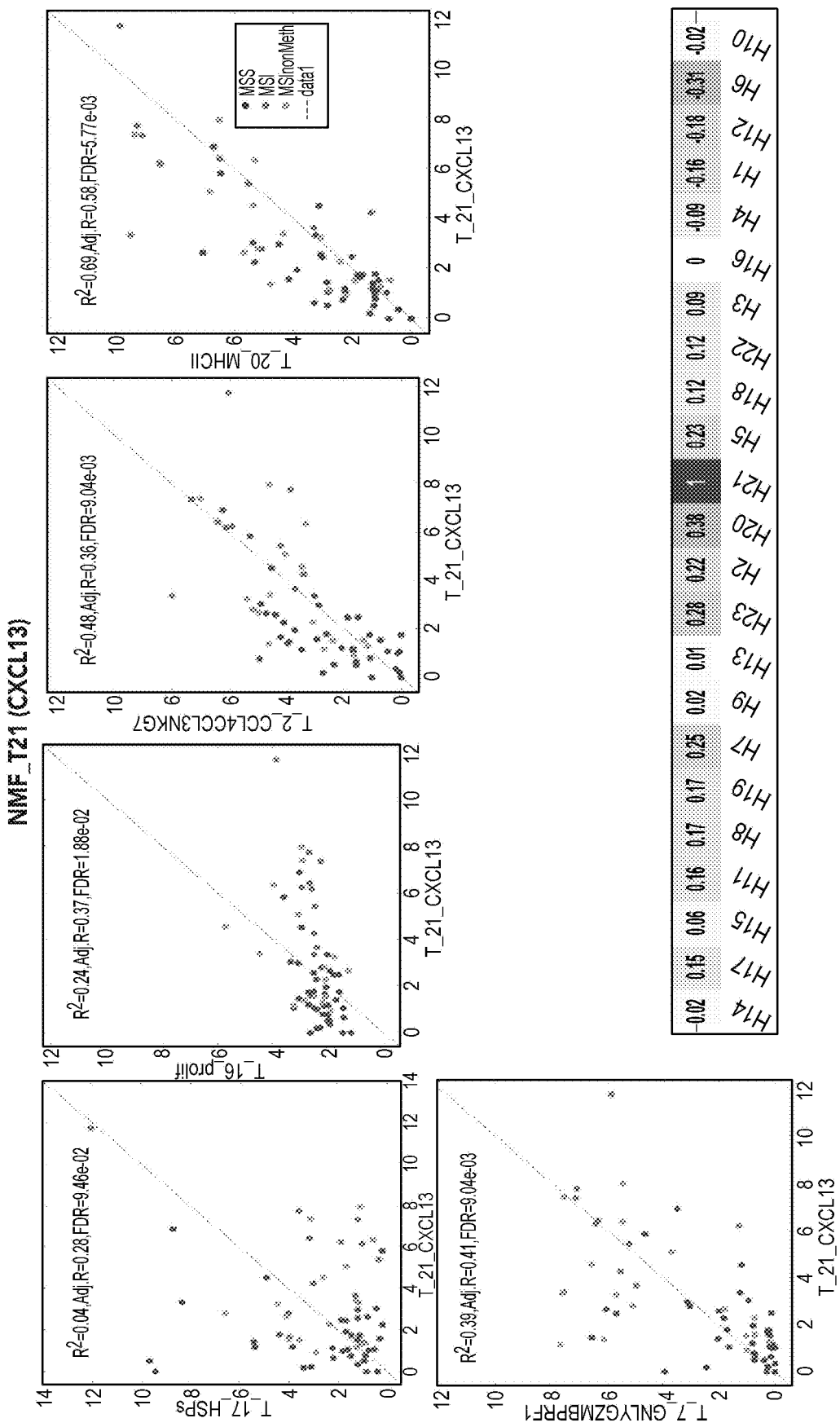

Applicants observed that unsupervised clustering by immune composition separates tumor from normal patient samples (FIG. 14). Applicants observed that unsupervised clustering by immune composition does not separate CRC tumor types (FIG. 15). Not all MSI tumors fell into the same immune category.

Figure 18:
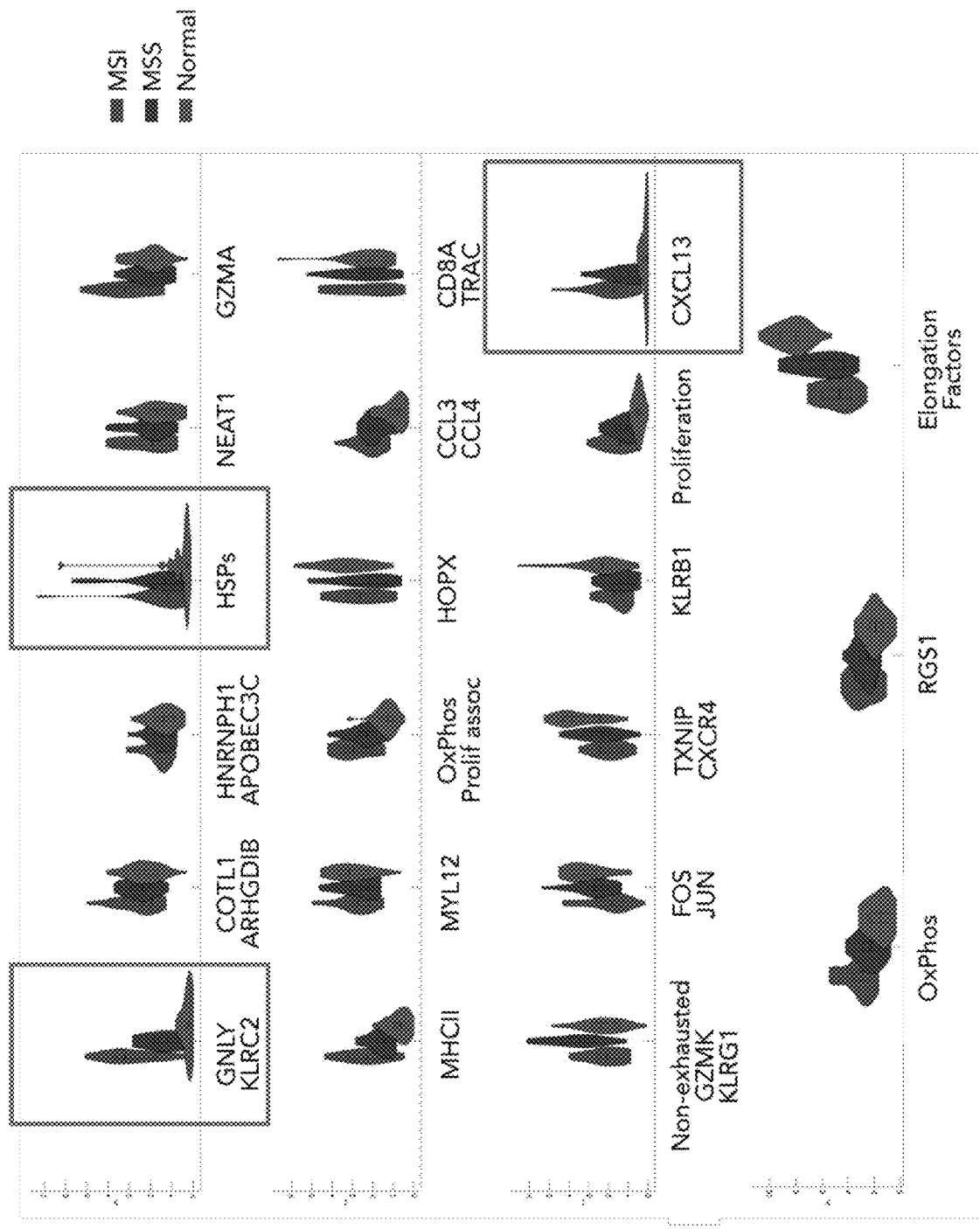
FIG. 18—Violin plots showing expression of CD8 activation states in normal, MSS and MSI tissues.
Figure 19:
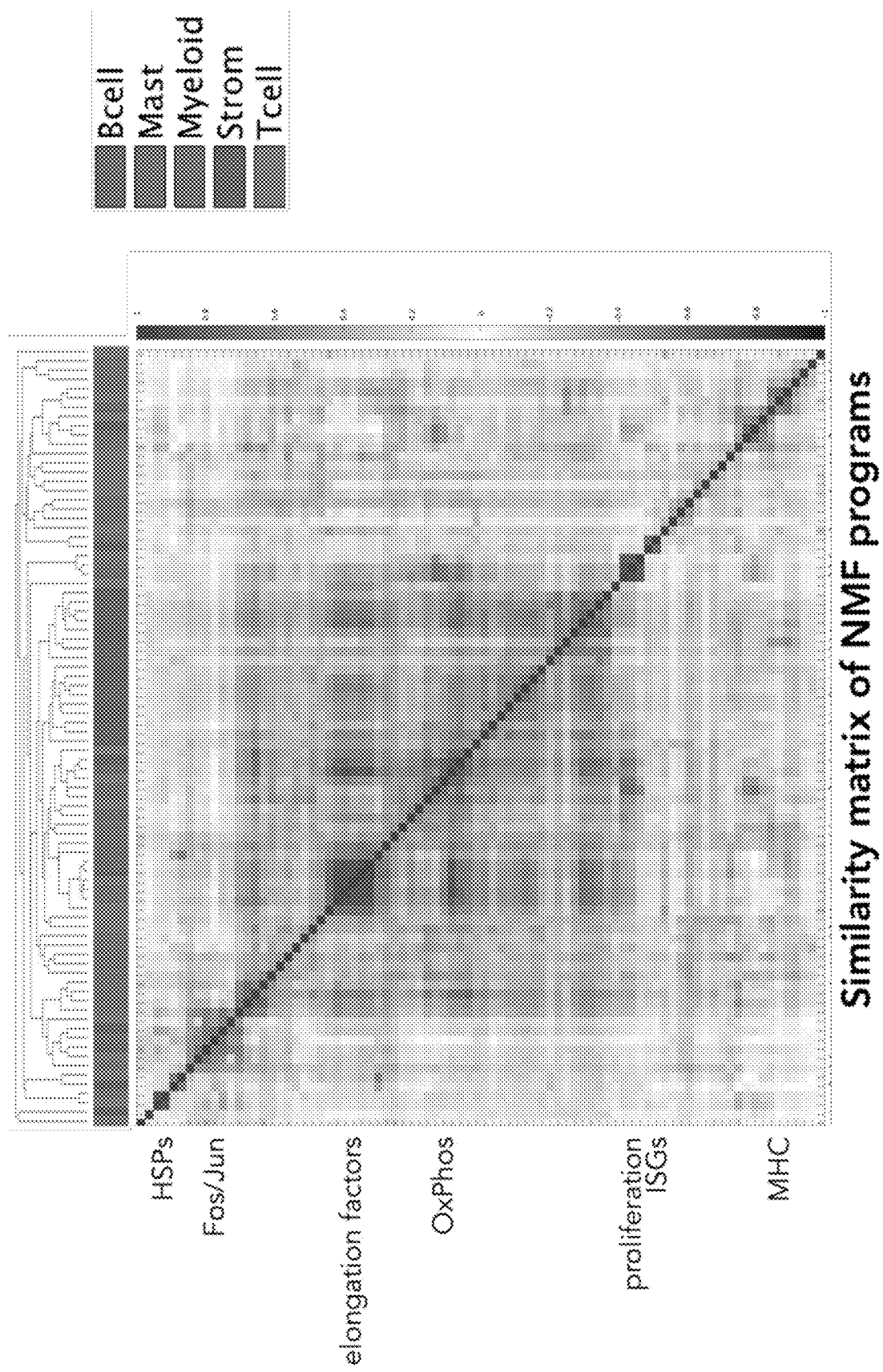
FIG. 19—Similarity matrix of NMF programs.

One cell type may span a range of continuous cell states (see, e.g., Shekhar et al., Comprehensive Classification of Retinal Bipolar Neurons by Single-Cell Transcriptomics Cell. 2016 Aug. 25; 166(5):1308-1323.e30; and Bielecki, Riesenfeld, Kowalczyk, et al., 2018 Skin inflammation driven by differentiation of quiescent tissue-resident ILCs into a spectrum of pathogenic effectors. bioRxiv 461228). One method to identify cell programs is non-negative matrix factorization (NMF) (see, e.g., Lee D D and Seung H S, Learning the parts of objects by non-negative matrix factorization, Nature. 1999 Oct. 21; 401(6755):788-91). Other approaches are topic models (Bielecki, Riesenfeld, Kowalczyk, et al., 2018) and word embeddings. Identifying cell programs can recover cell states and bridge differences between cells. Applicants generated a "dictionary" of programs in the CRC tumor microenvironment (TME) (see, Tables 1-14). Applicants identified myeloid, CD8 T cell and stromal cell programs. Applicants also identified consensus CRC malignant programs. Applicants further characterized myeloid cell programs (FIG. 16). Applicants further characterized CD8 T cell programs (FIG. 17). Applicants observed that CD8 activation states are different between MSS, MSI, and normal tissues (FIG. 18). Applicants observed that some gene programs are conserved across cell types (FIG. 19) and tend to occur together (FIG. 20).

Figure 20A:
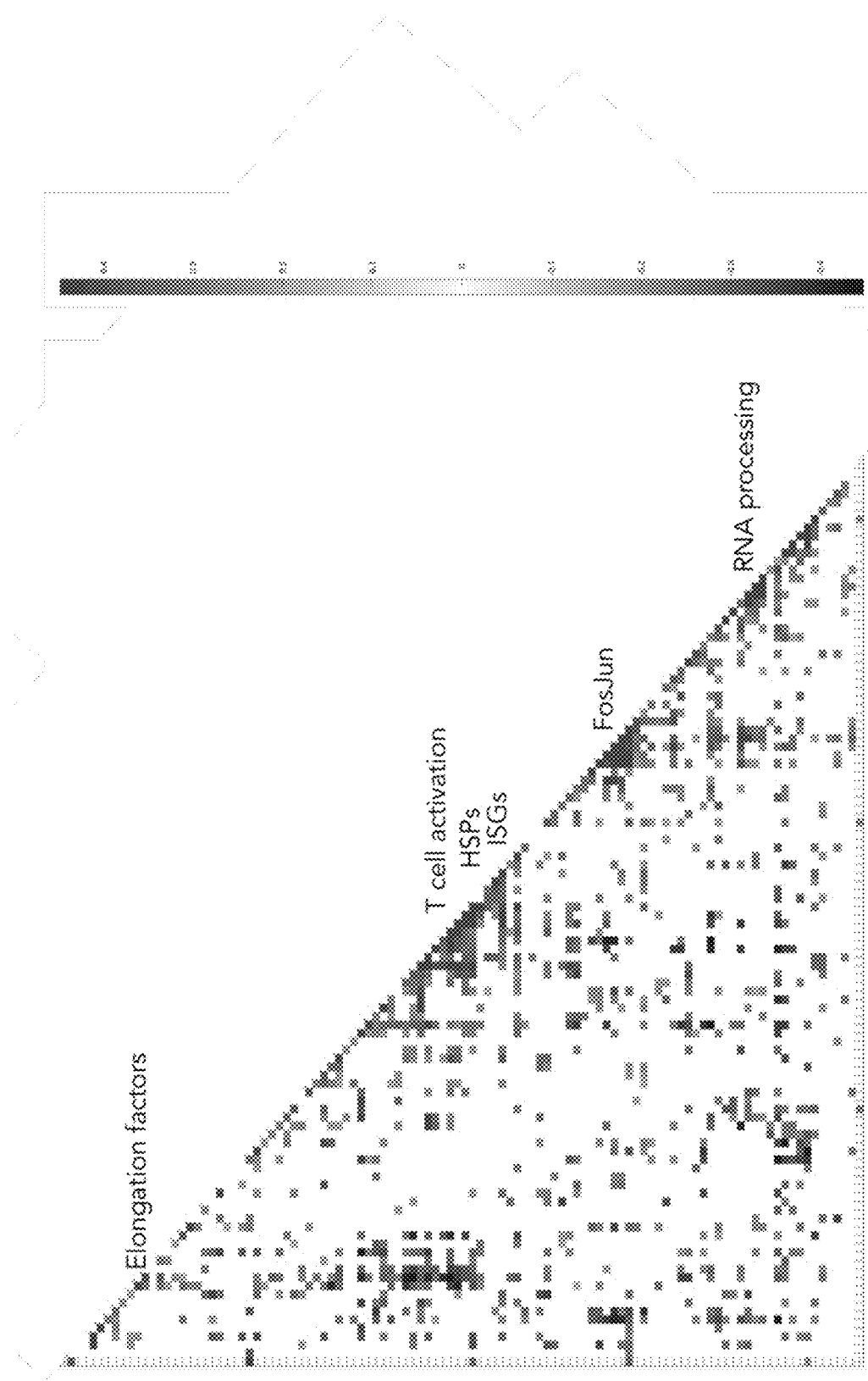
Figure 20B:
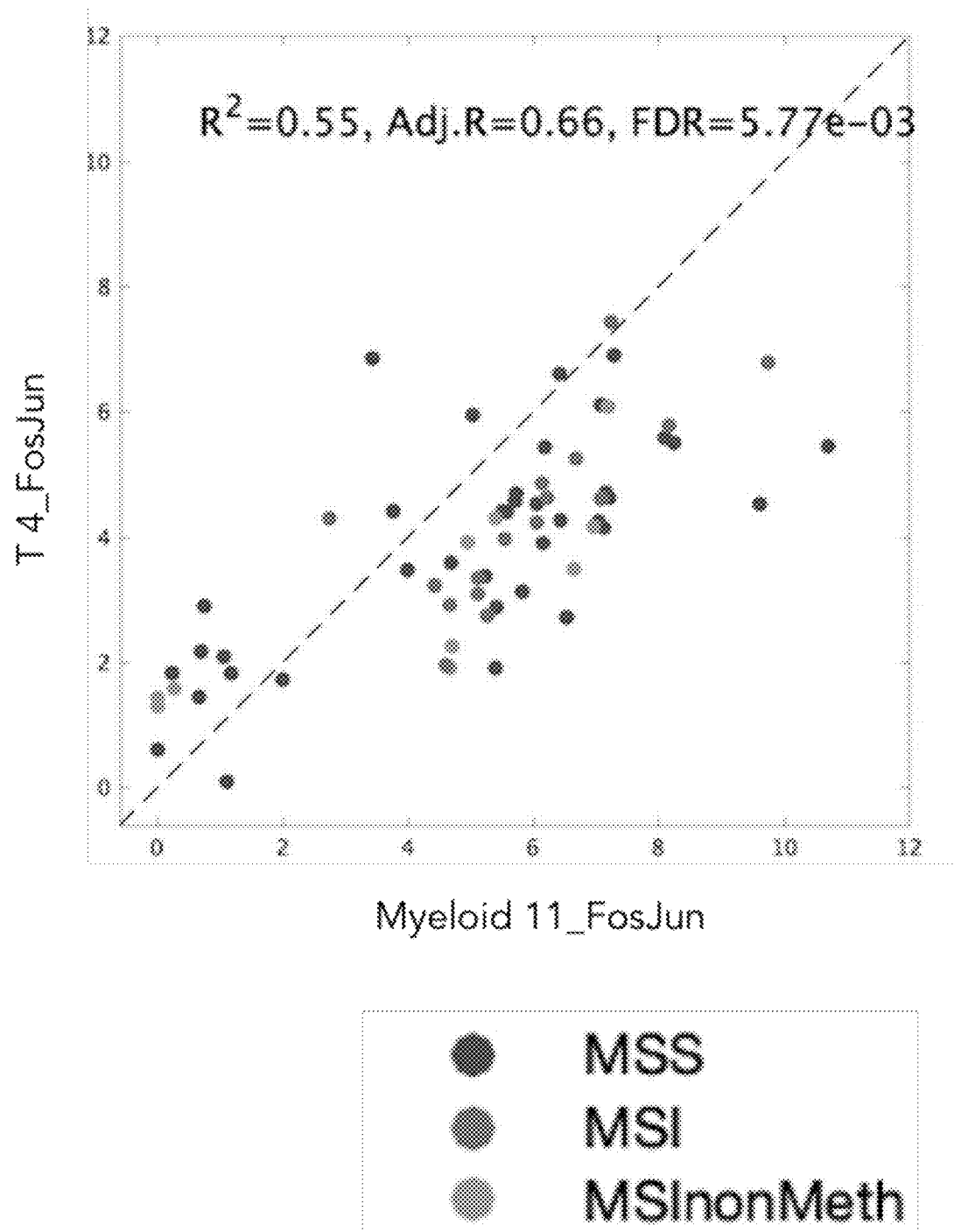
Figure 20C:
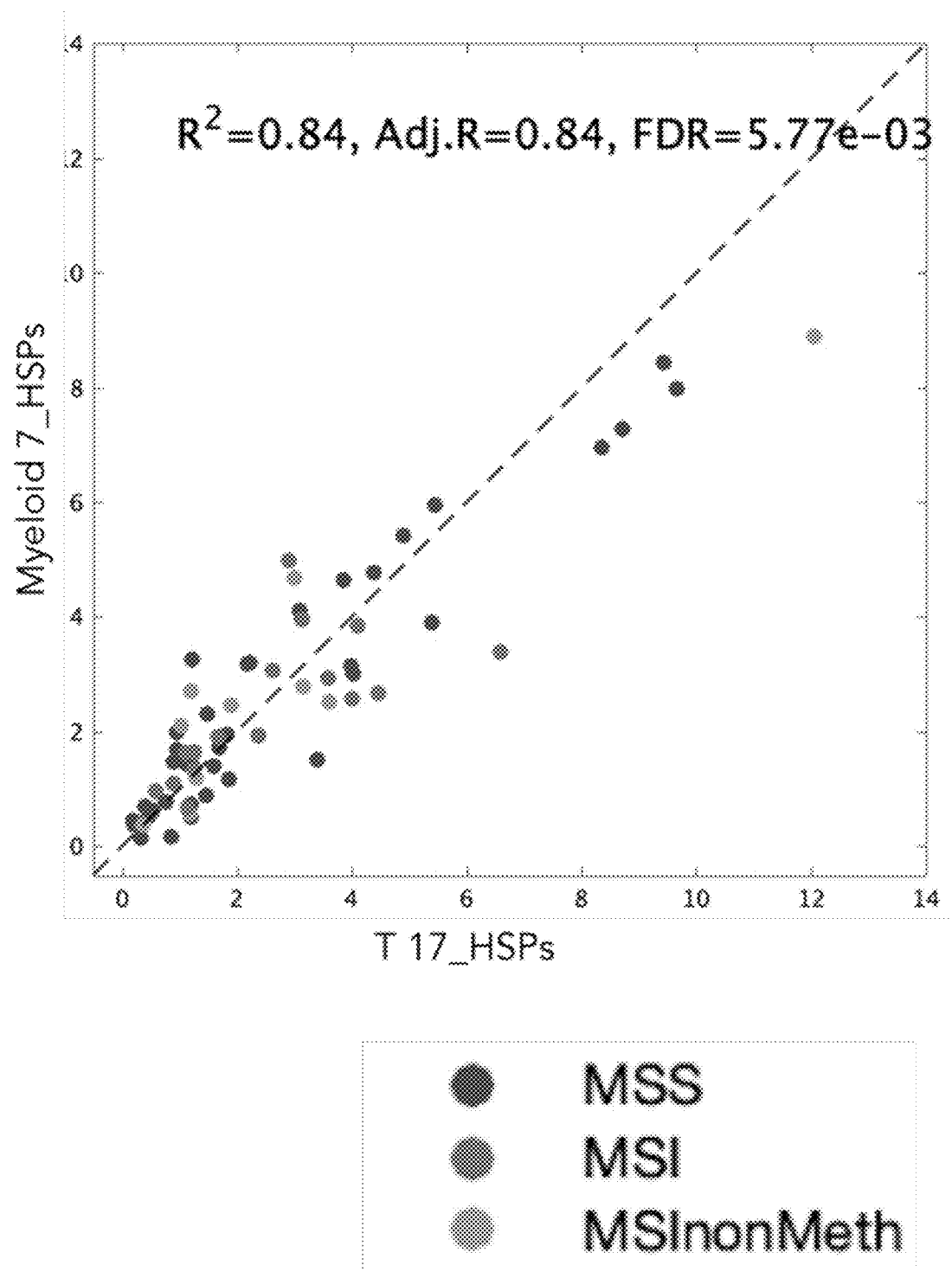
Figure 20D:
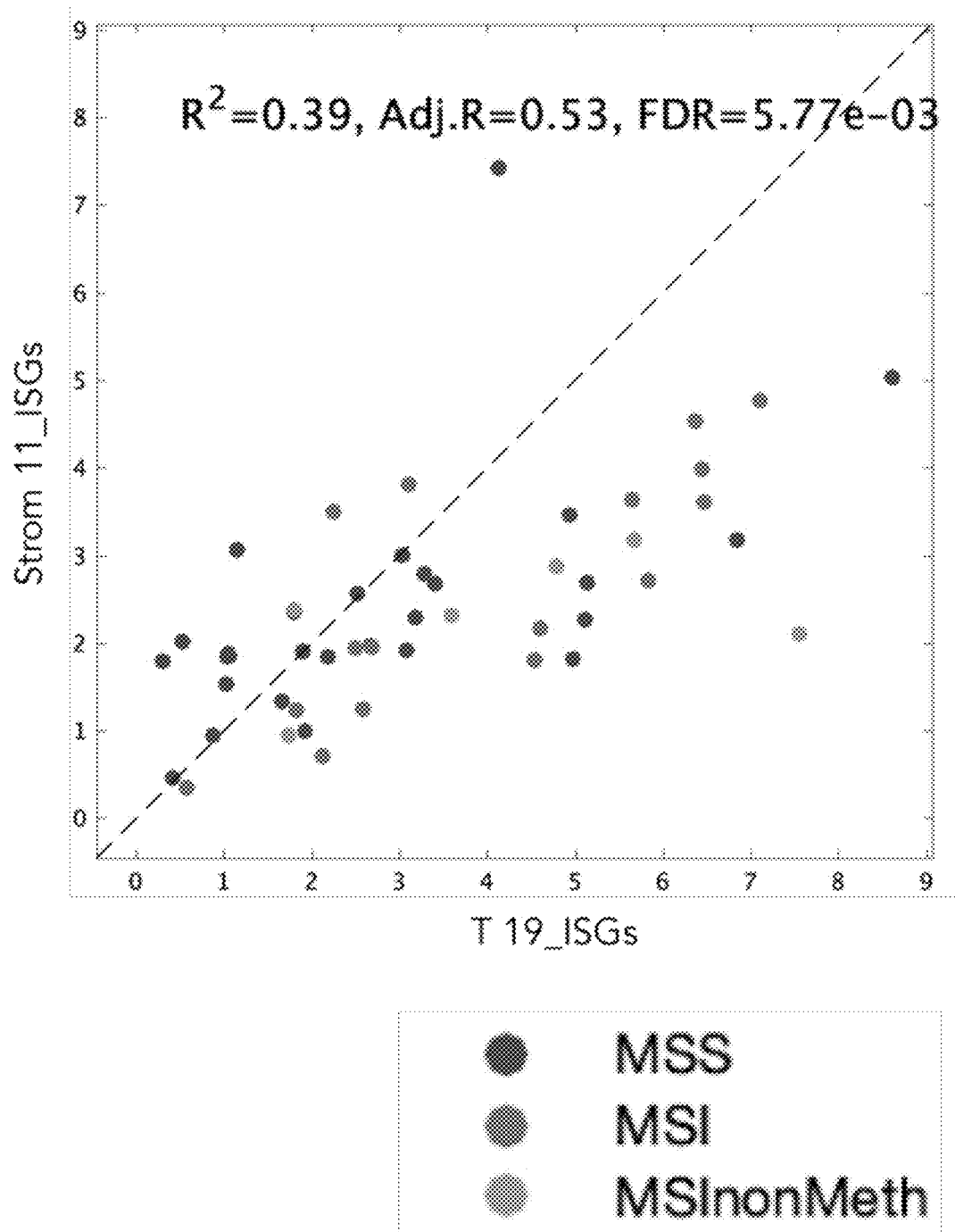

Applicants can also determine how gene programs are related to each other. Correlation plots show gene programs that go up or down together (FIG. 20A). Comparisons of specific programs in MSS, MSI and MSI non-methylator were also performed (FIG. 20B-E).

In summary, Applicants have identified the building blocks and gene programs of the MSS and MSI CRC TME. There is substantial remodeling of cellular composition in MSS and MSI CRC vs. normal and each other. The stromal compartment is dramatically changed in CRC and there are MSS vs. MSI-specific fibroblast signatures. These signatures may be useful in designing treatments for each subtype. Activated T cells are specifically enriched in MSI CRC. Tregs and myeloid cells are enriched in both MSS and MSI CRC compared to normal tissue. The immune cell composition defines three tissue categories; one specific for MSI, but not all MSI. The NMF-based approach identifies gene programs within and across cell types, their upstream regulators and their co-occurence in tumors. The present disclosure resolves T cell and myeloid states, some of which are differential between CRC and normal and MSS vs. MSI.

Example 2—CRC Malignant Compartment

Figure 21A:
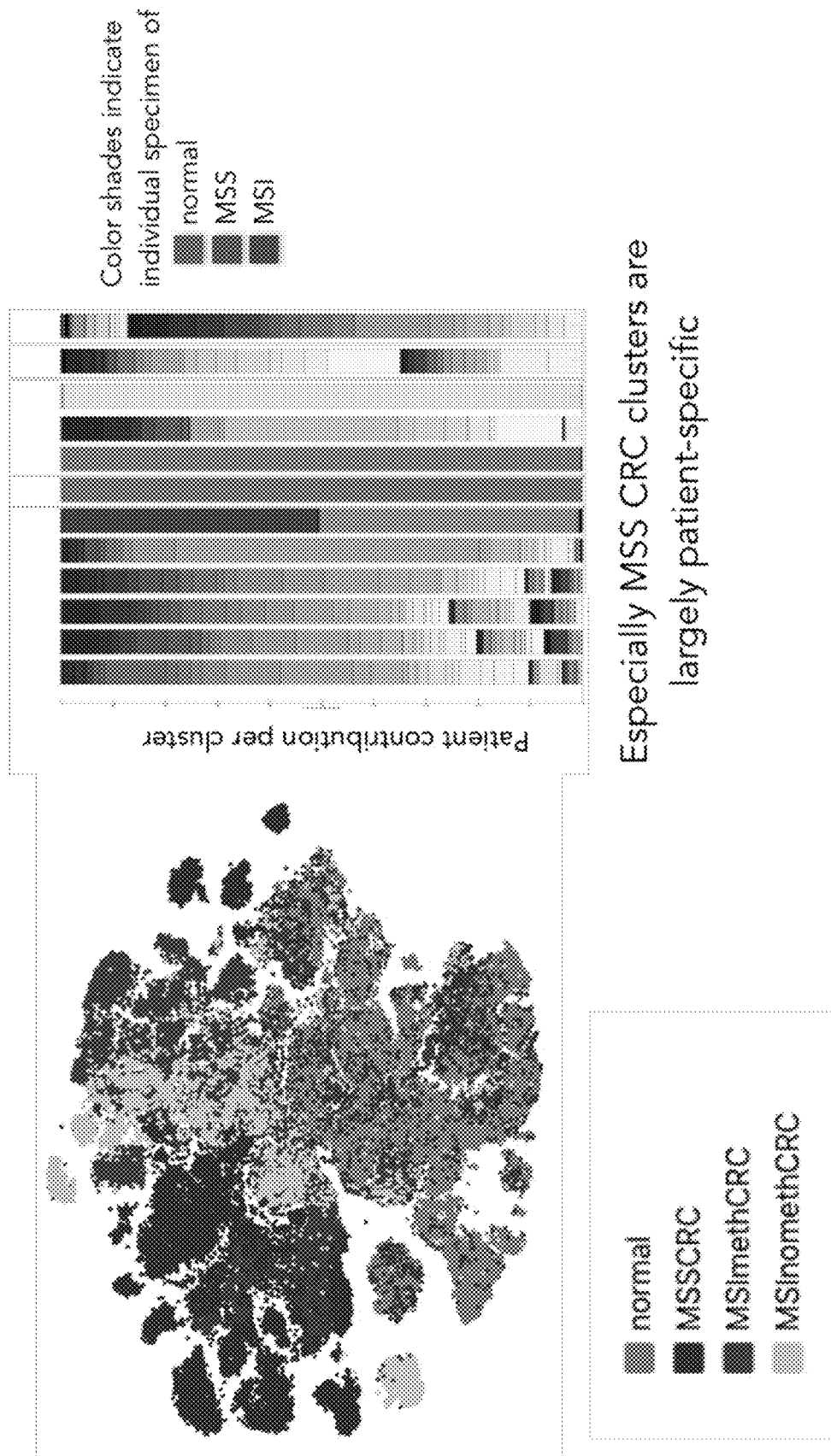
FIG. 21A-21B—A. Clustering of epithelial cells by CRC type or normal tissue. Graph showing the compositions of malignant epithelial cell states across the patients. B. Heat map showing malignant epithelial cell gene expression across the patients.
Figure 21B:
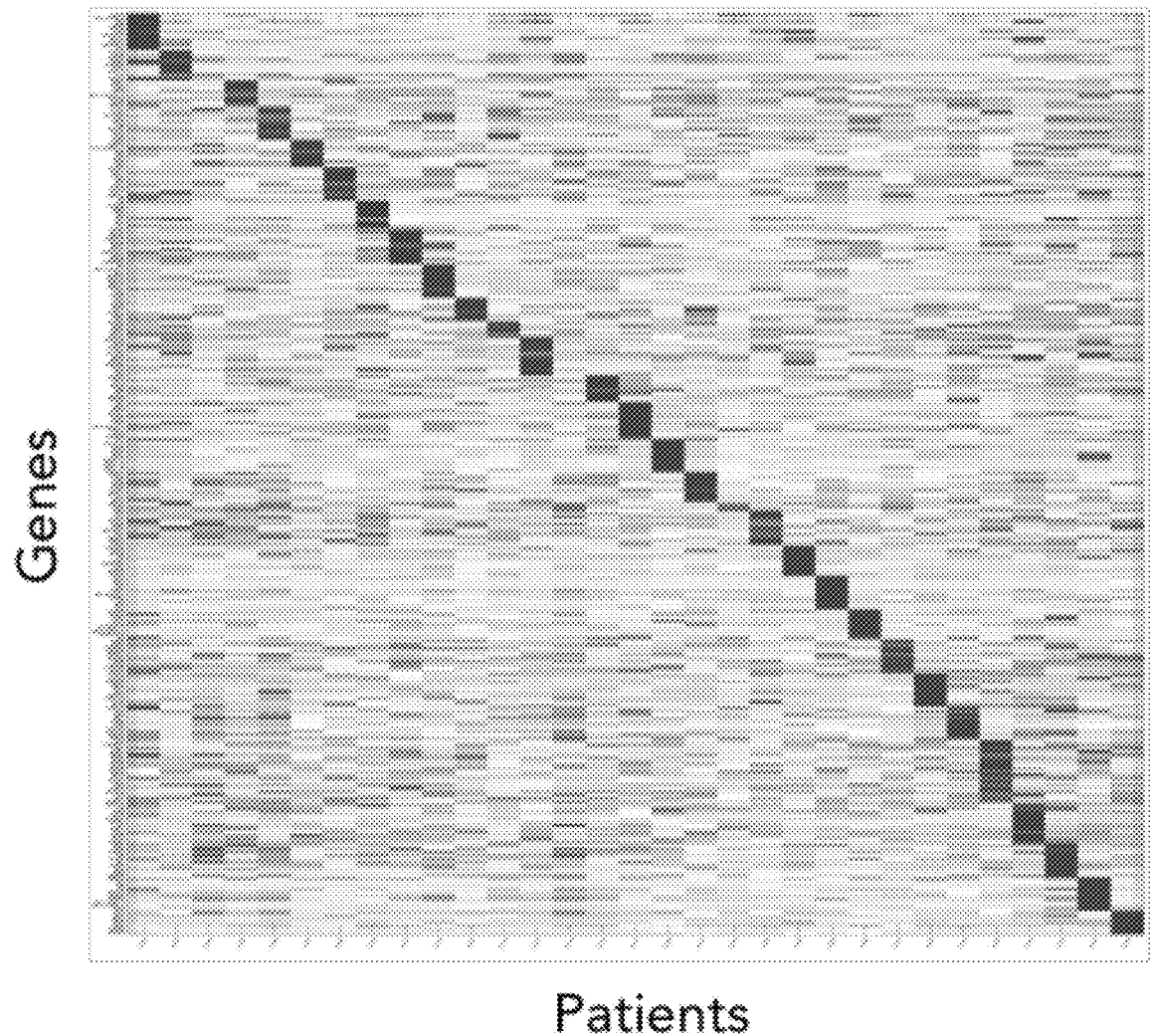
Figure 22:
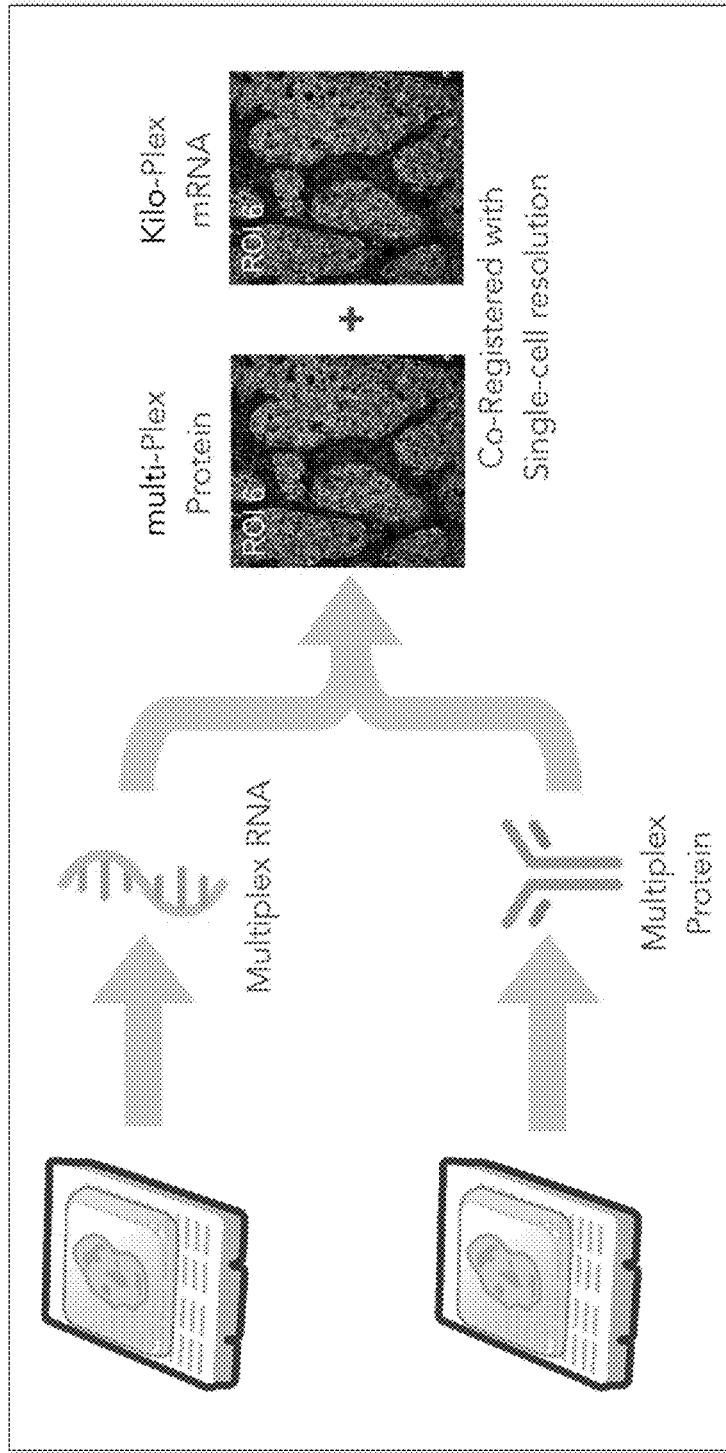
FIG. 22—Diagrams showing in situ analysis of tissue samples.
Figure 23A:
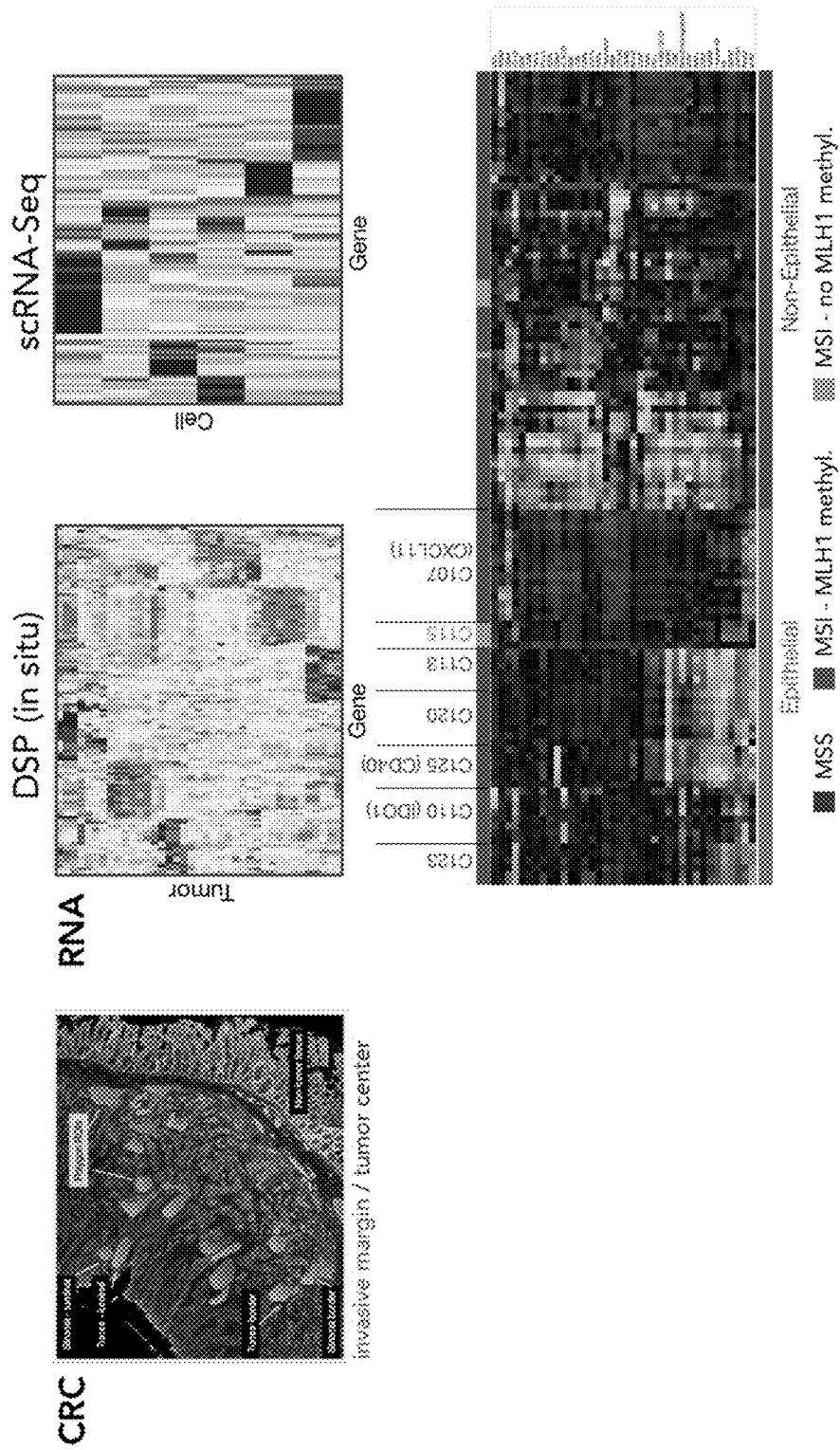
FIG. 23A-23C—In situ analysis of patient samples as compared to RNA and protein analysis. A. IHC, DSP and scRNA-seq analysis of tissue samples. B. IHC, DSP and scRNA-seq analysis of tissue samples. IDO1 expression is indicated in epithelial regions of interest (ROIs) for each patient and in clusters for the patients. C. Graphs showing expression of the indicated genes across patients.
Figure 23B:
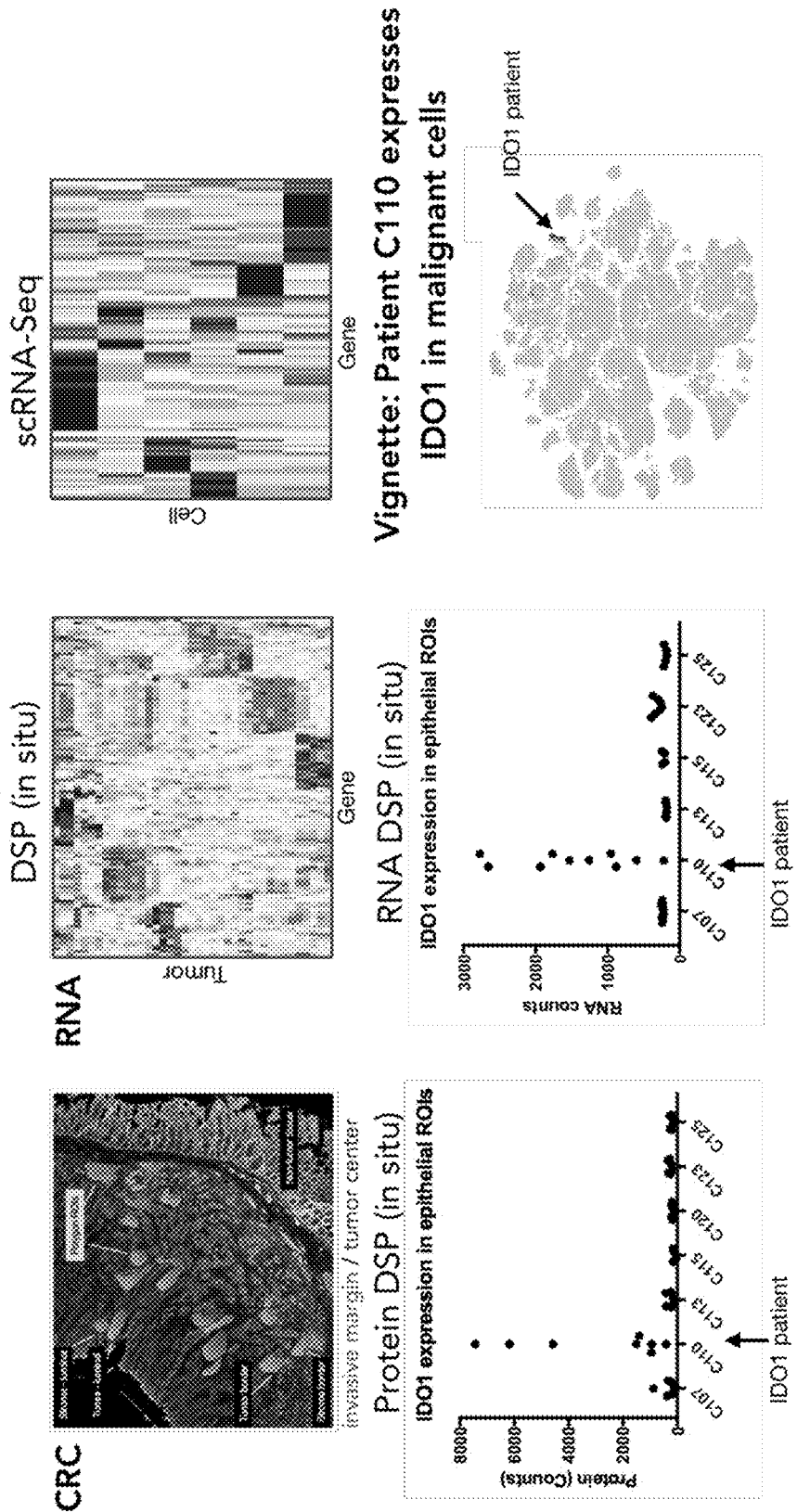
Figure 23C:
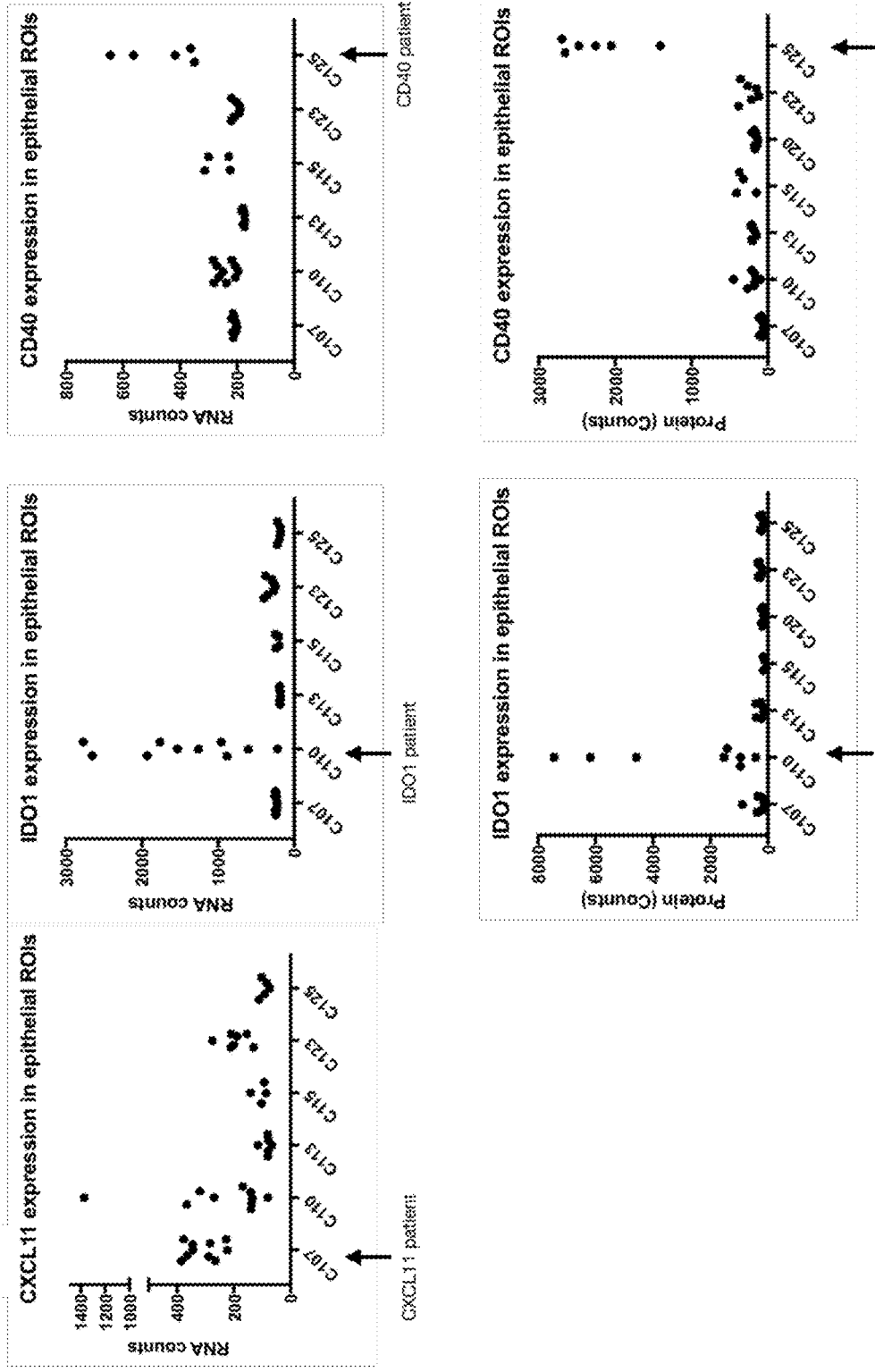
Figure 24:
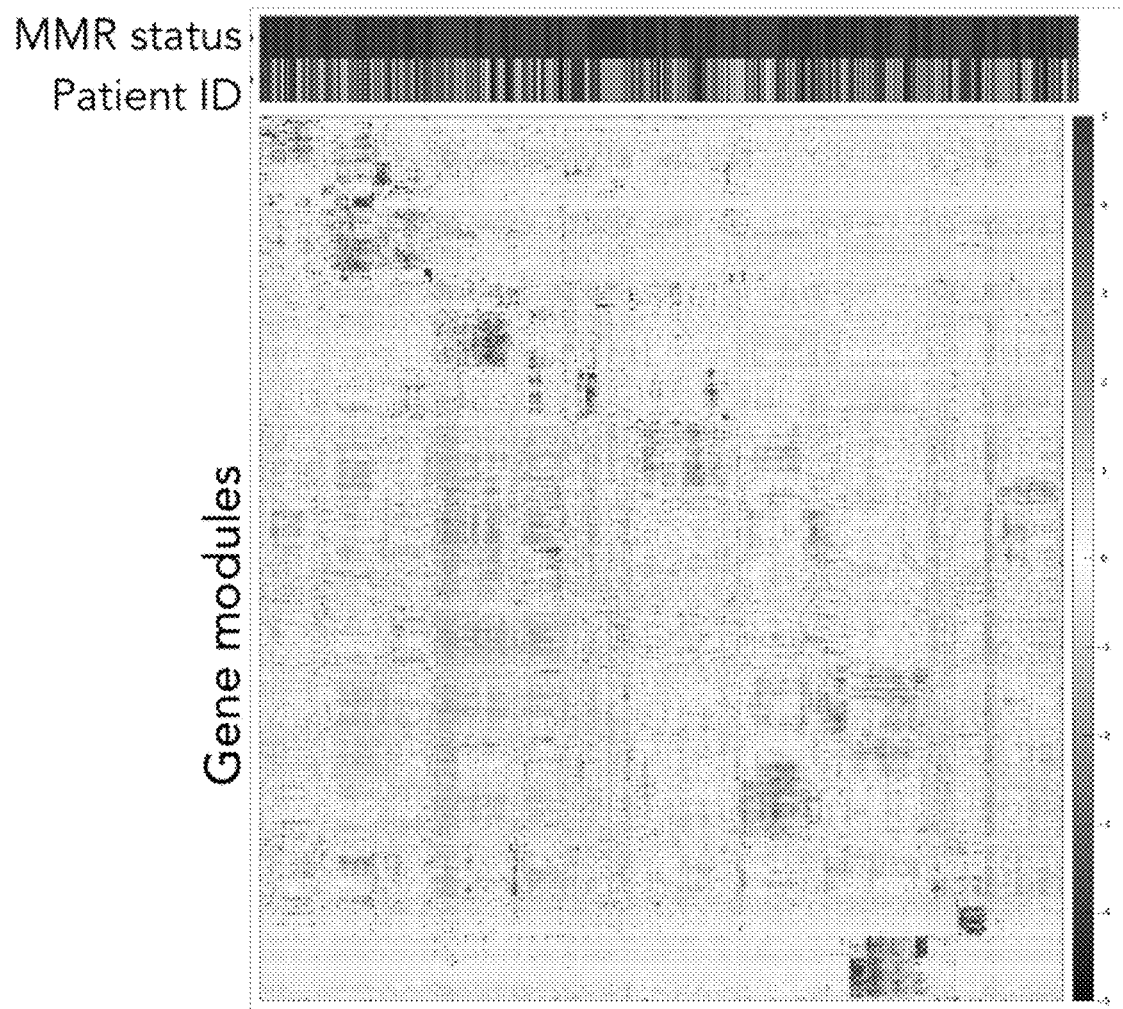
FIG. 24—Heat map showing clustering of NMF vectors to identify consensus programs in malignant cells across patients.
Figure 25:
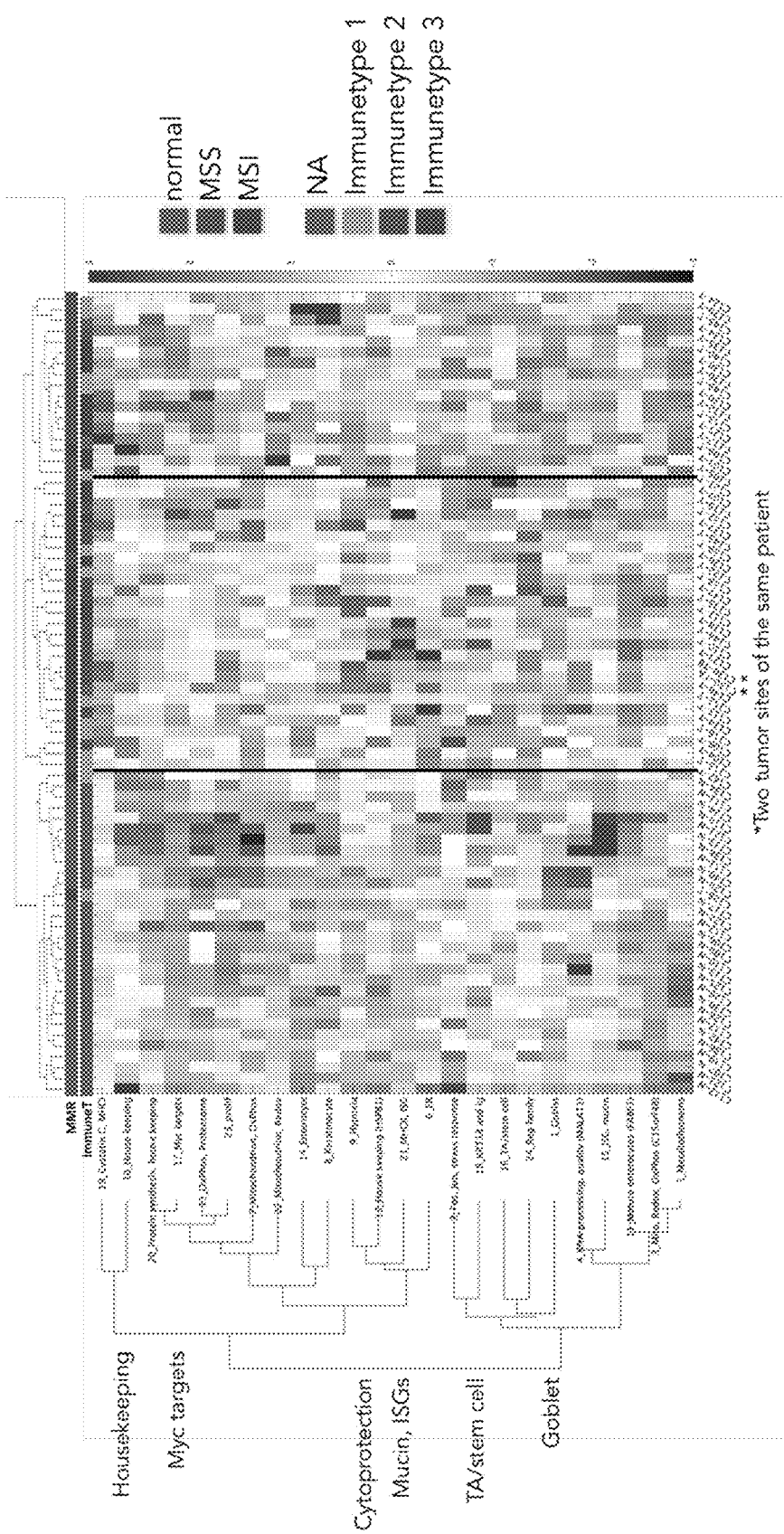
FIG. 25—Heat map showing clustering of normal and tumor patient samples using the consensus malignant programs.
Figure 26:
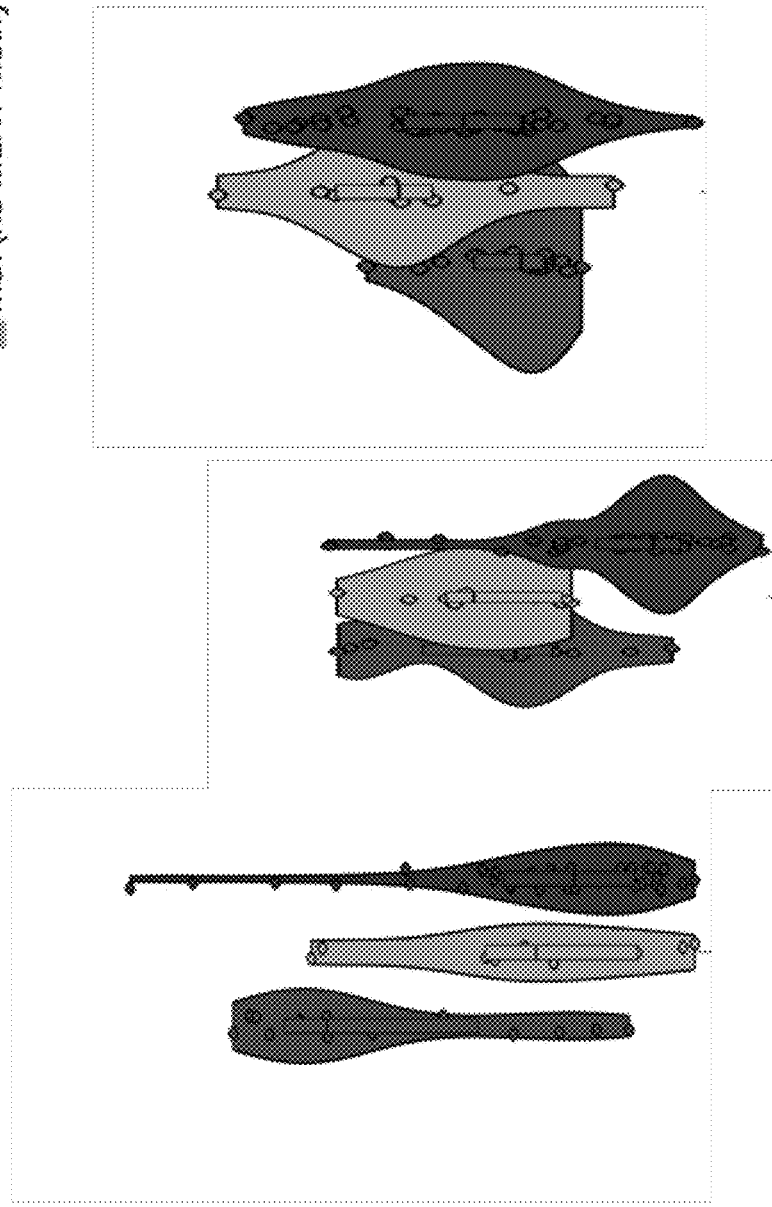
FIG. 26—Violin plots showing differential expression of consensus malignant programs between CRC types (MSI non-methylated Lynch-like, MSI methylated and MSS).
Figure 27:
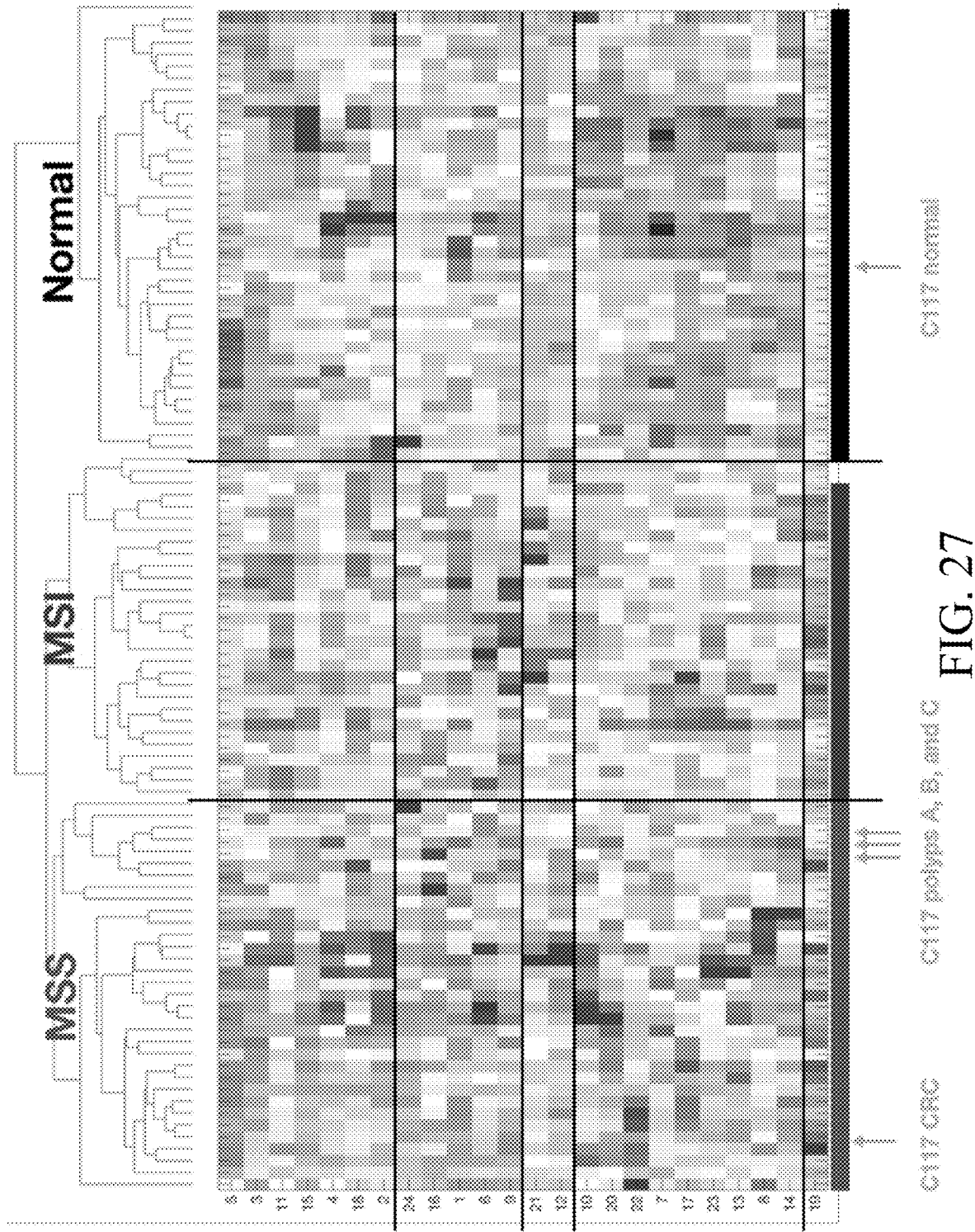
FIG. 27—Heatmap showing malignant program expression across patient samples. CRC and polyps are indicated.

Applicants observed that malignant epithelial cells separate by MMR status and enter patient-specific states (FIG. 21). Patient-specific signatures were confirmed in situ on both the RNA and protein level (FIG. 23). Applicants used an NMF-based to reveal consensus programs in malignant cells across patients (FIG. 24). The consensus malignant programs stratify patient samples to MSS, MSI and normal (FIGS. 25, 26). Some exceptions highlight unusual tumors. For example, tumor sample C133-T and C126-T are examples of mucinous adenocarcinoma and C107-T is an example of an MSS patient with activated T cell infiltrates. Applicants observed that there is differential program regulation in progression from polyp to CRC (FIG. 27).

In summary, Applicants characterized the CRC malignant compartment. Malignant cells enter patient-specific cell states. Despite this, NMF is able to uncover the set of shared transcriptional programs. CRC clustering by programs largely separates MSS from MSI CRC (with notable exceptions). Malignant programs and immune TME composition define distinct categorizations. There is differential program activity between MSS versus MSI (MLH1 methylated) versus Lynch-like MSI.

Example 3—Identifying Associations in CRC Using the Cell Atlas

Figure 28:
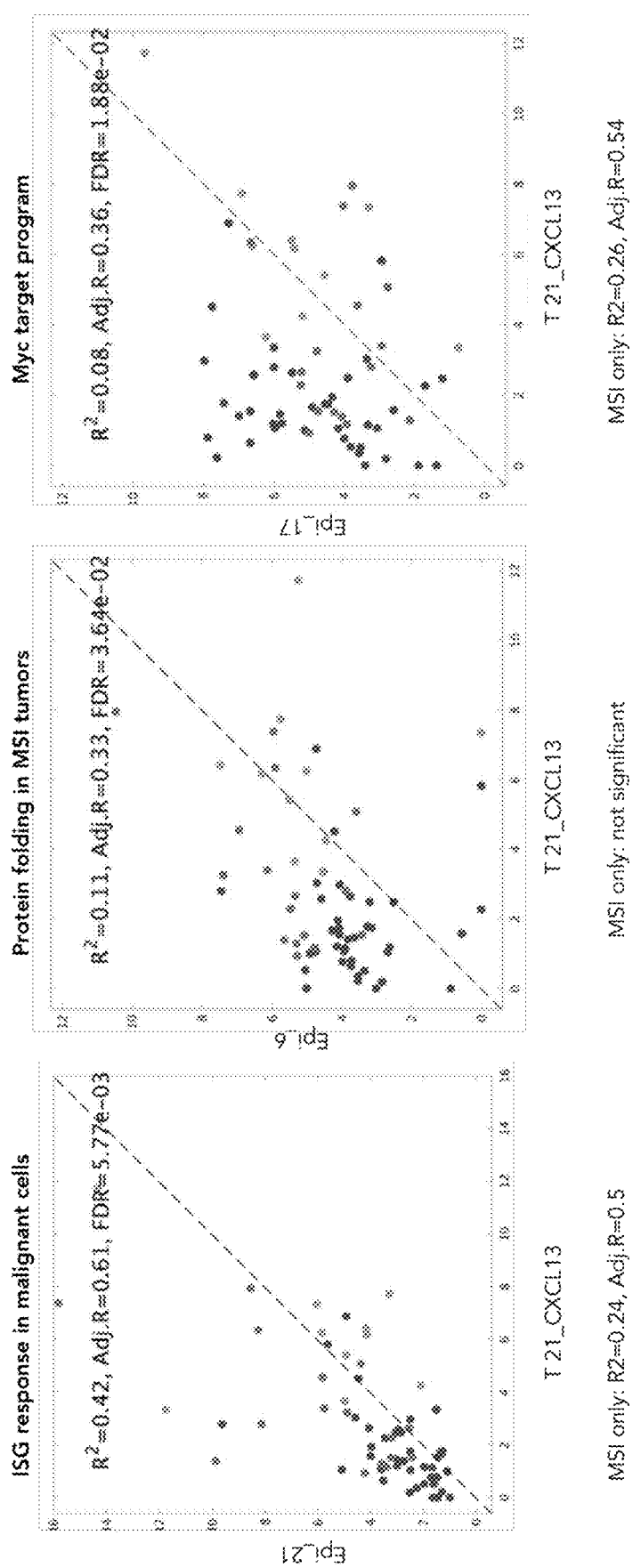
FIG. 28—NMFs for T21 (CXCL13 program) compared to malignant programs in MSI and MSS tissues.
Figure 29:
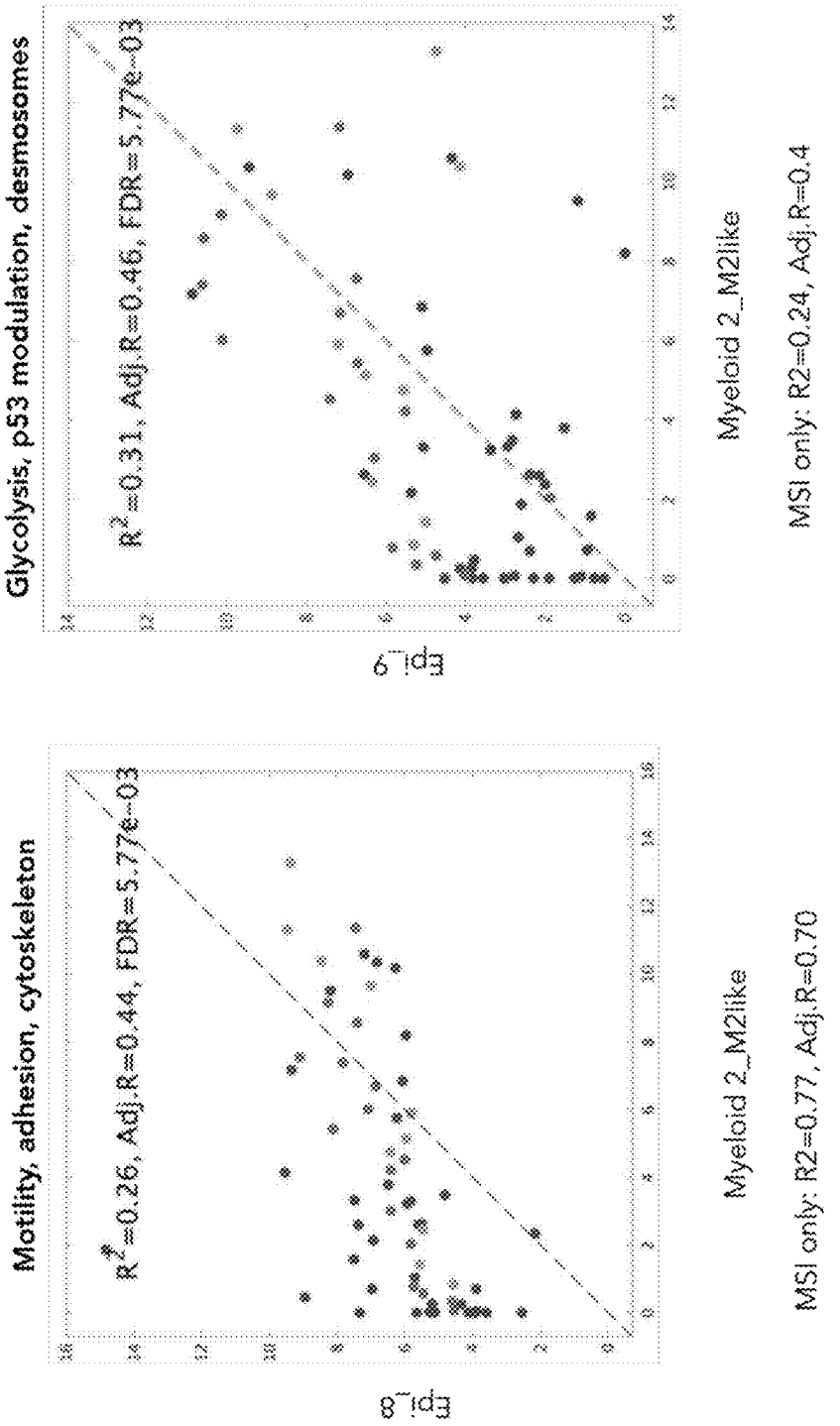
FIG. 29—NMFs for Myeloid 2_M2 like program compared to malignant programs in MSI and MSS tissues.
Figure 30:
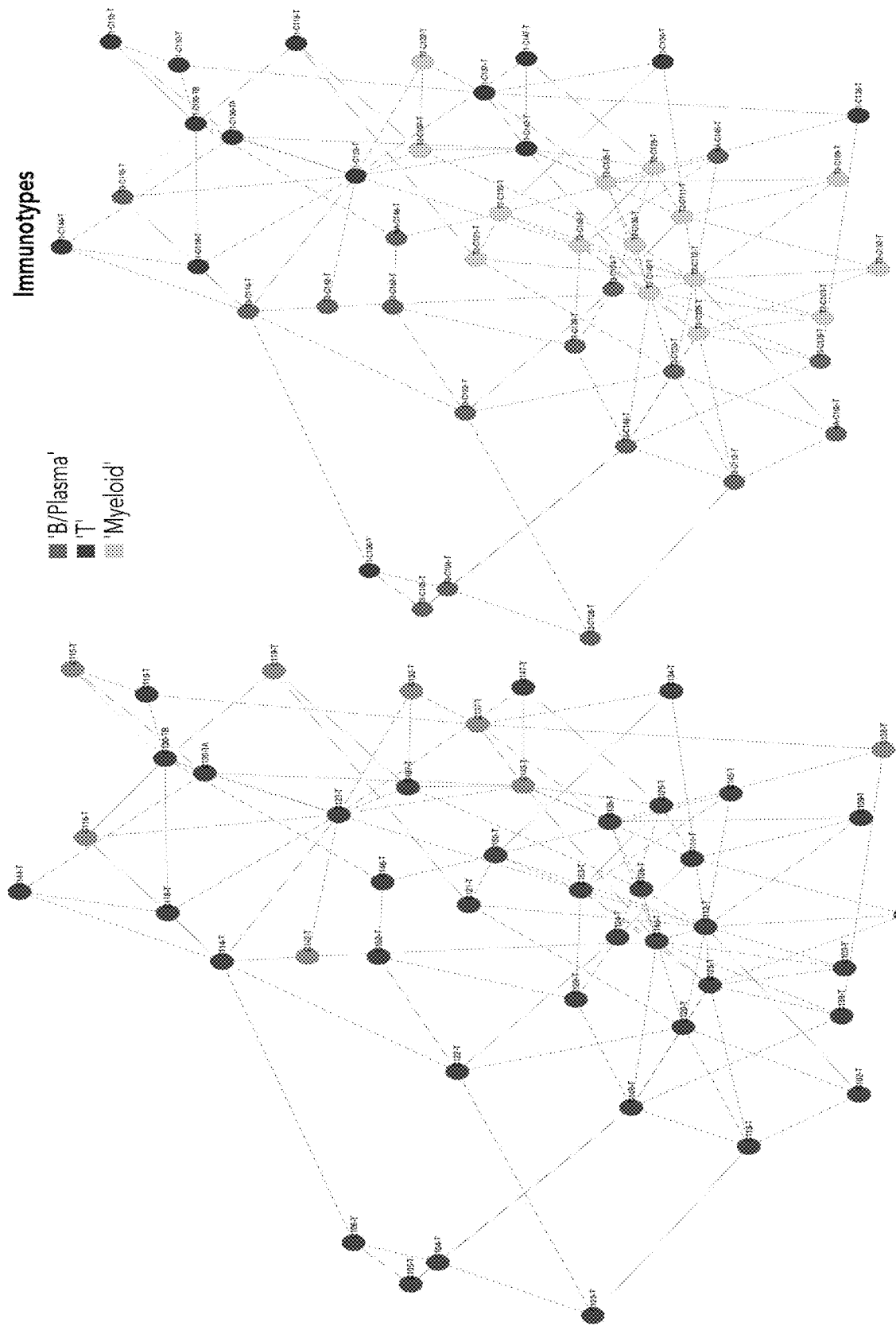
FIG. 30—Plot showing classification of tumors into immunotypes based on NMF gene programs.
Figure 31:
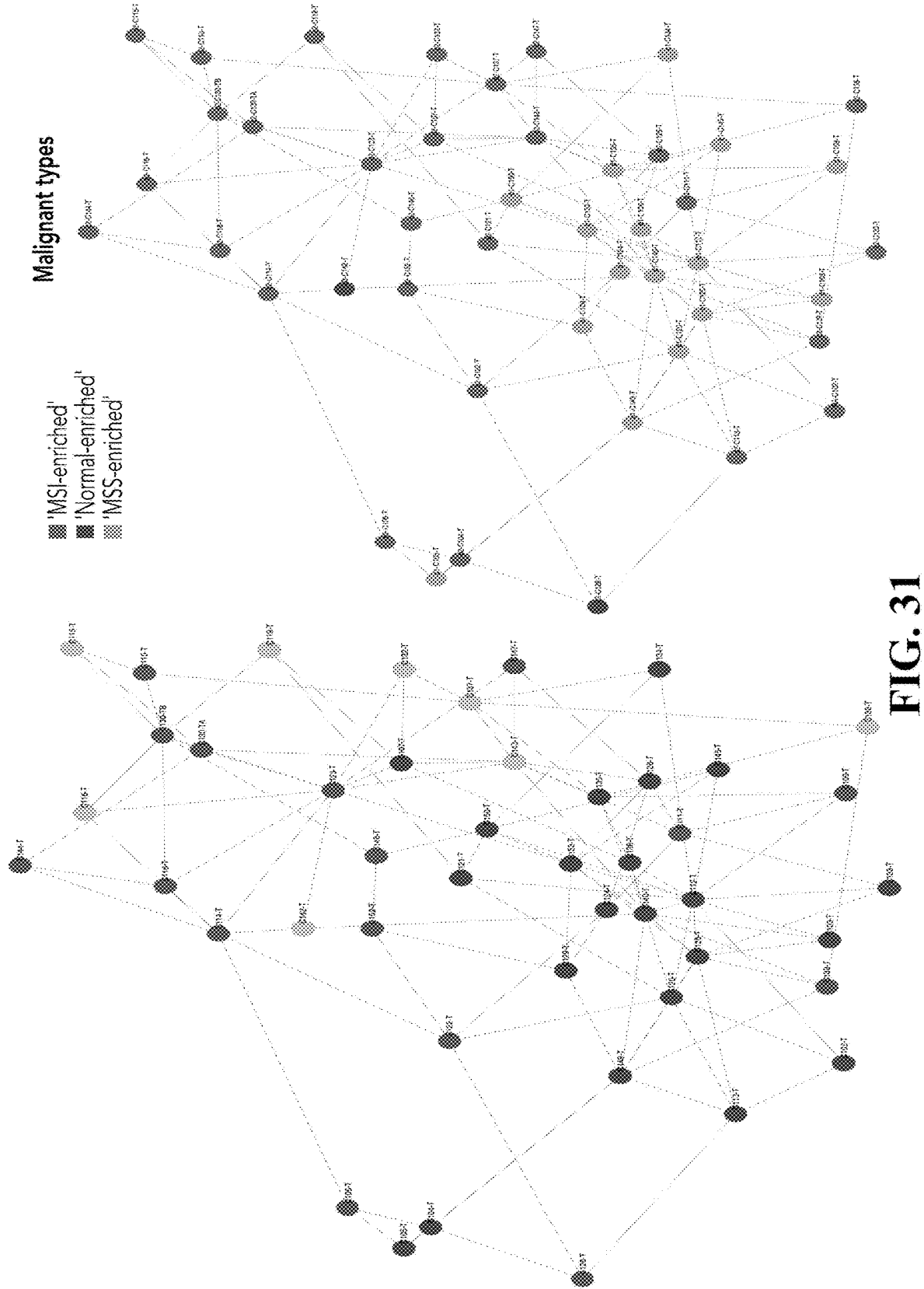
FIG. 31—Plot showing classification of tumors into malignant types based on NMF gene programs.
Figure 32:
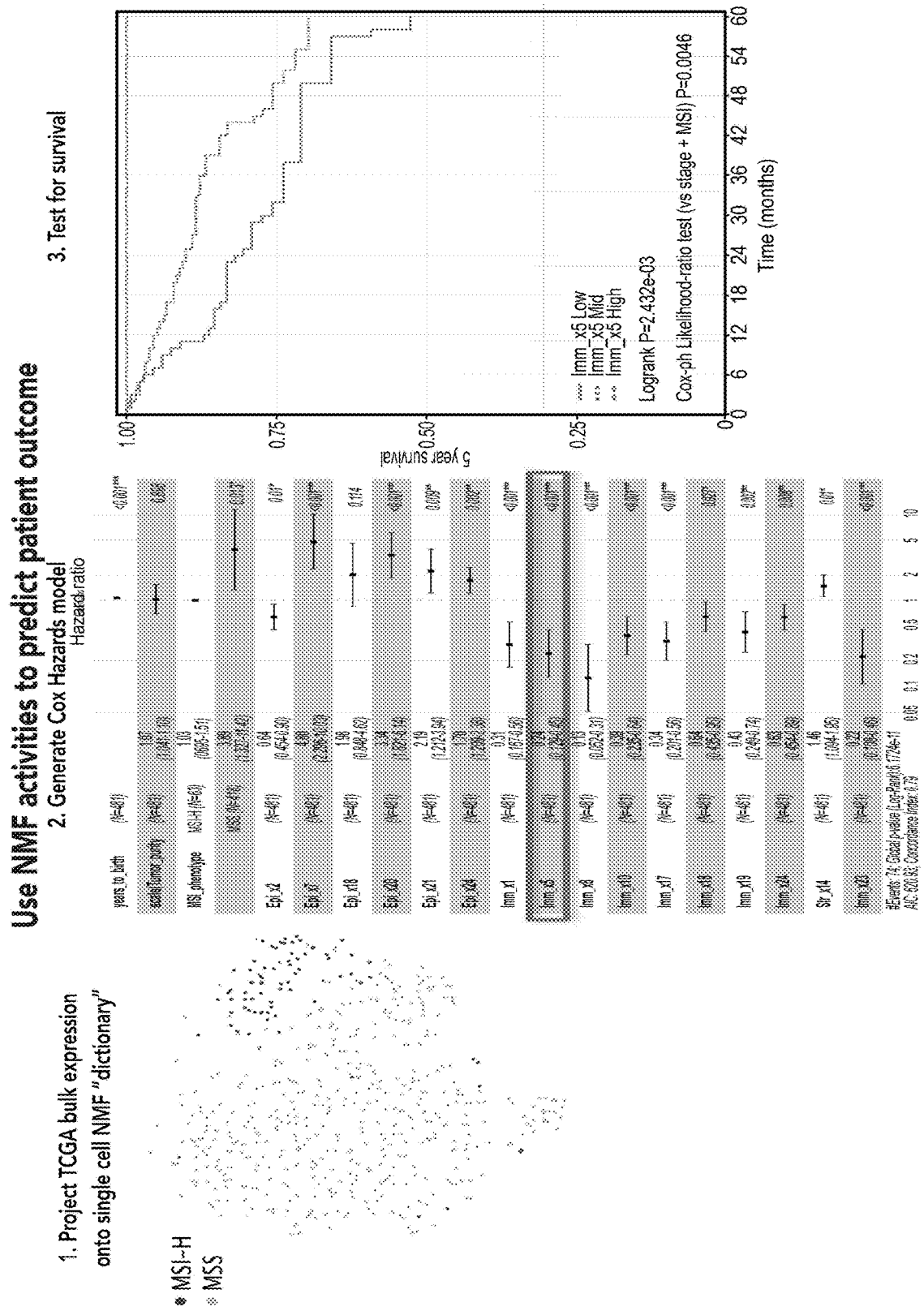
FIG. 32—Workflow for using NMF programs to predict patient outcomes.
Figure 33:
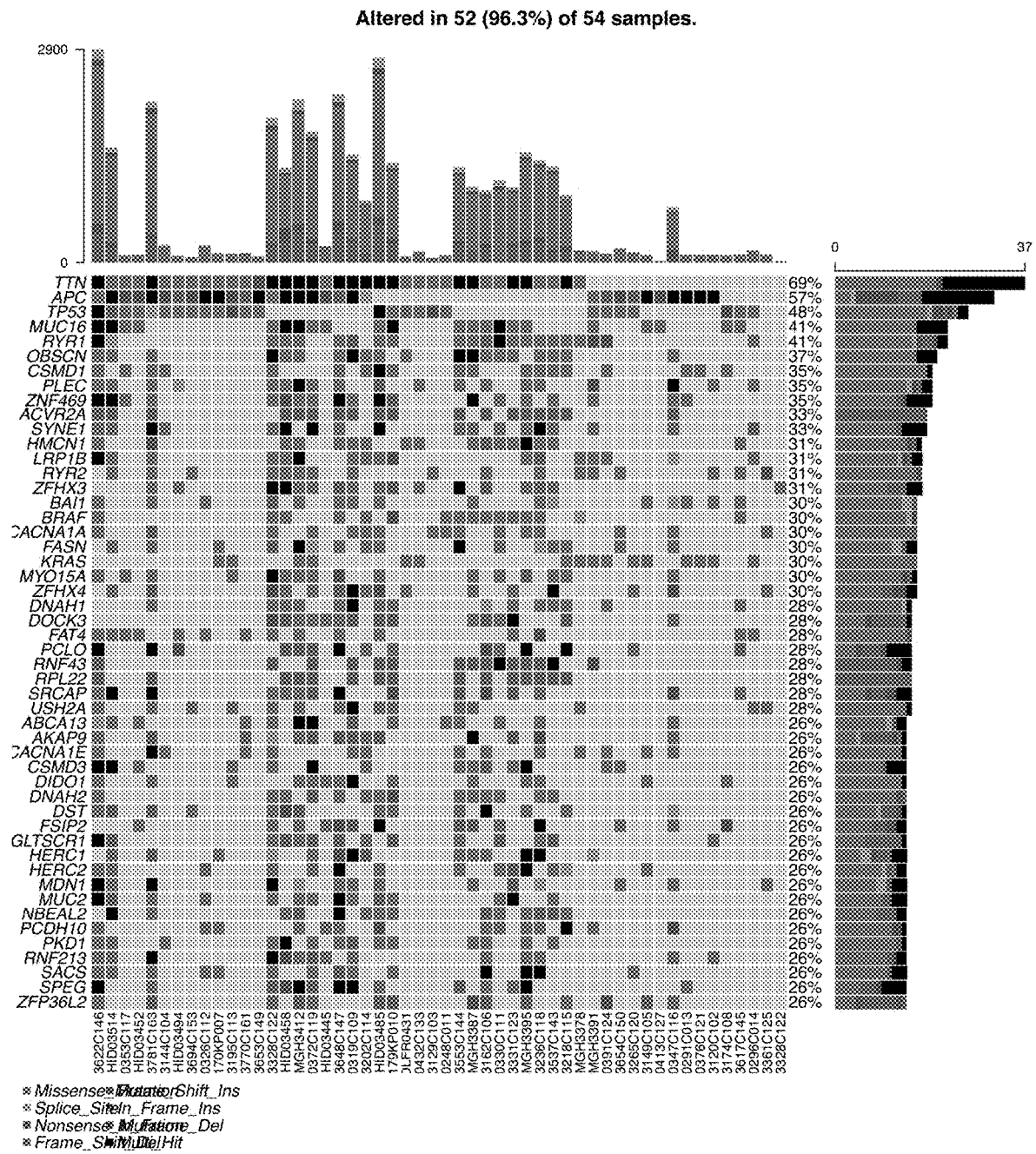
FIG. 33—Chart showing different mutation types present in 54 patient samples.

Applicants observed associations between CXCL13 T cell and malignant programs (ISG response, protein folding, and Myc targets) (FIG. 28). Applicants observed associations between M2-like and malignant programs (motility, adhesion, cytoskeleton and glycolysis, p53 modulation, desmosomes) (FIG. 29). Applicants can classify tumors using the dictionary of cell programs identified using NMF (FIGS. 30, 31). The NMF programs can be used to predict patient outcome by projecting bulk expression onto the single cell NMF "dictionary." Applicants provide proof of concept by projecting bulk expression data available on The Cancer Genome Atlas (TCGA) onto the single cell NMF "dictionary" and generating Hazard models based on the known survival available for the TCGA samples (FIG. 32). The dictionary allows for predicting survival in the patients as different groups have different survival curves.

Figure 34:
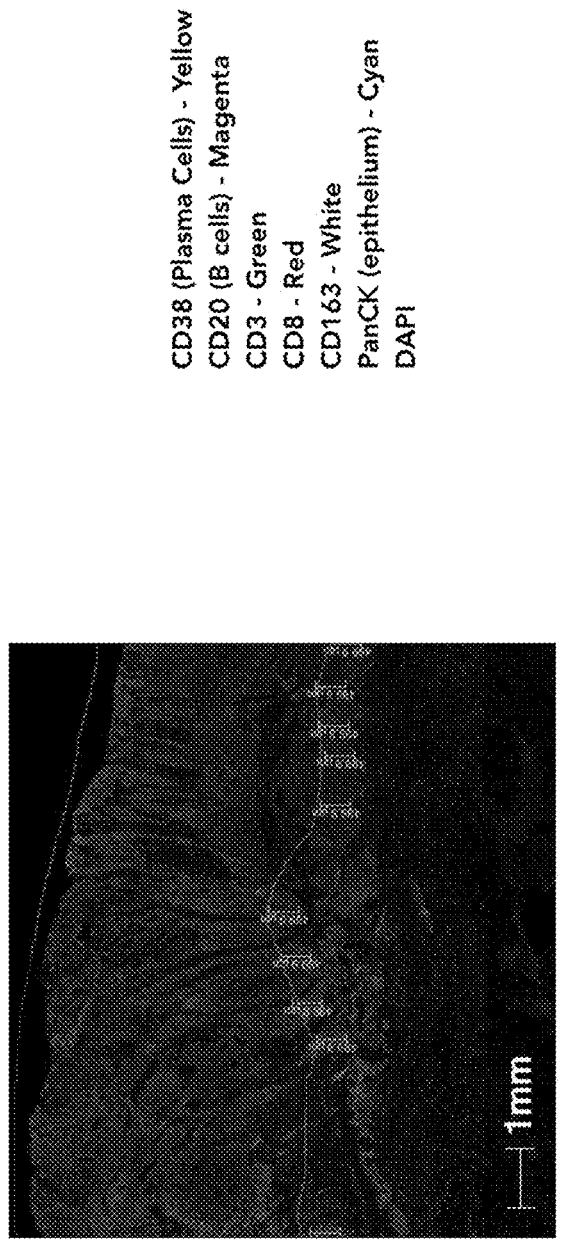
FIG. 34—Immunohistochemistry (IHC) of tumor tissues.
Figure 35:
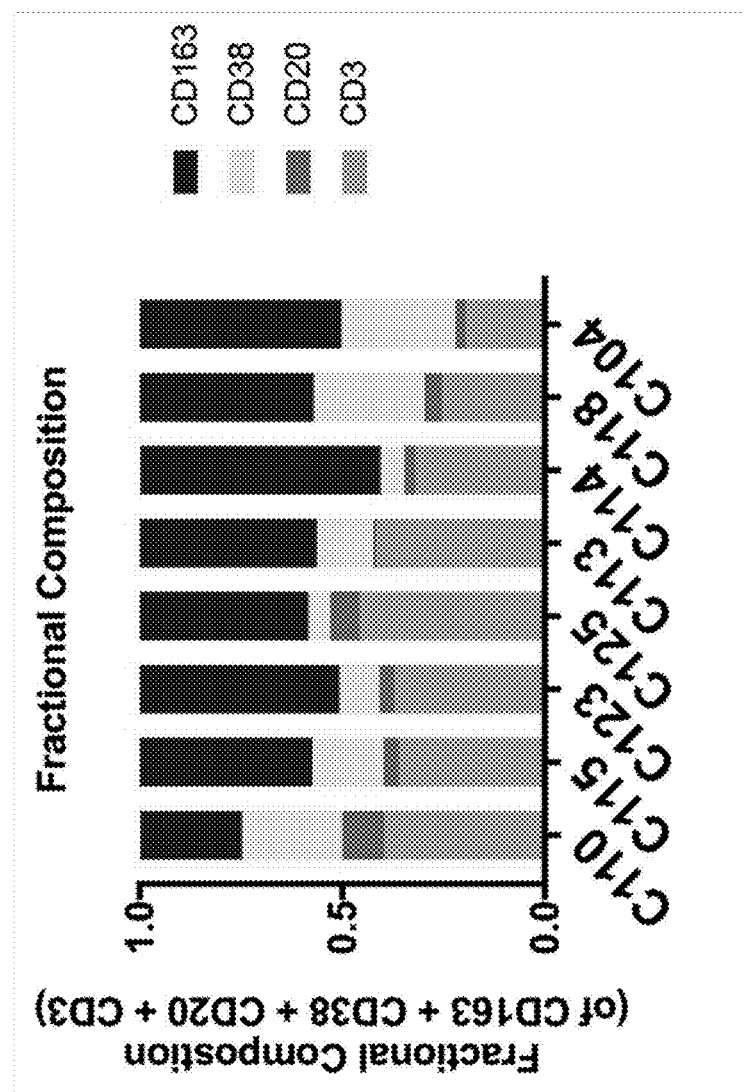
FIG. 35—Graph showing compositional differences observed in situ for the indicated patients.
Figure 36:
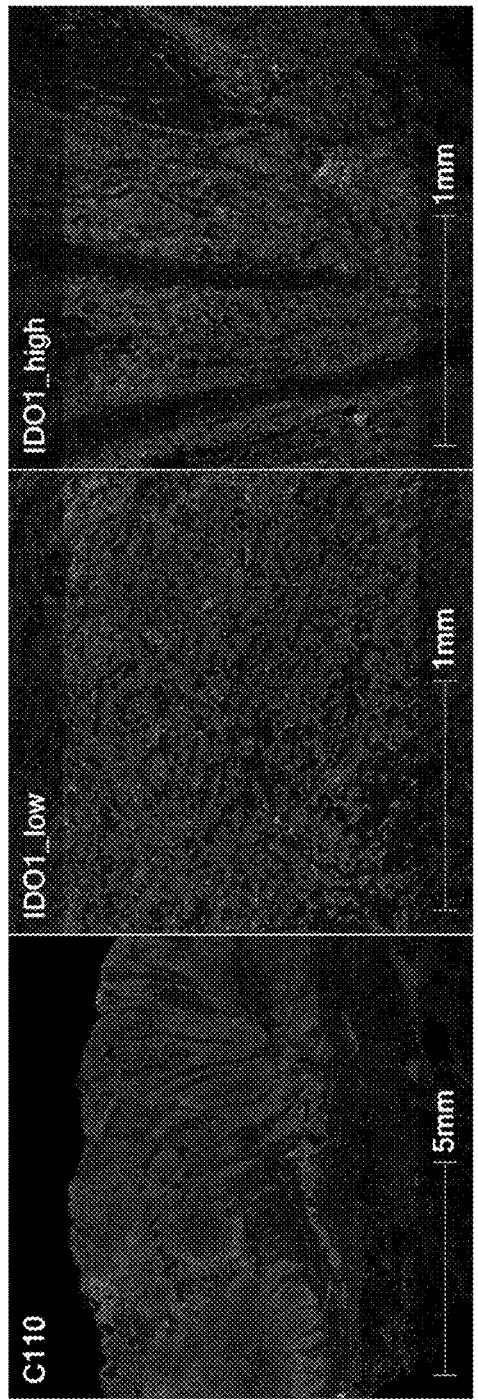
FIG. 36—IHC of tissue samples having IDO1 low or high expression.
Figure 37:
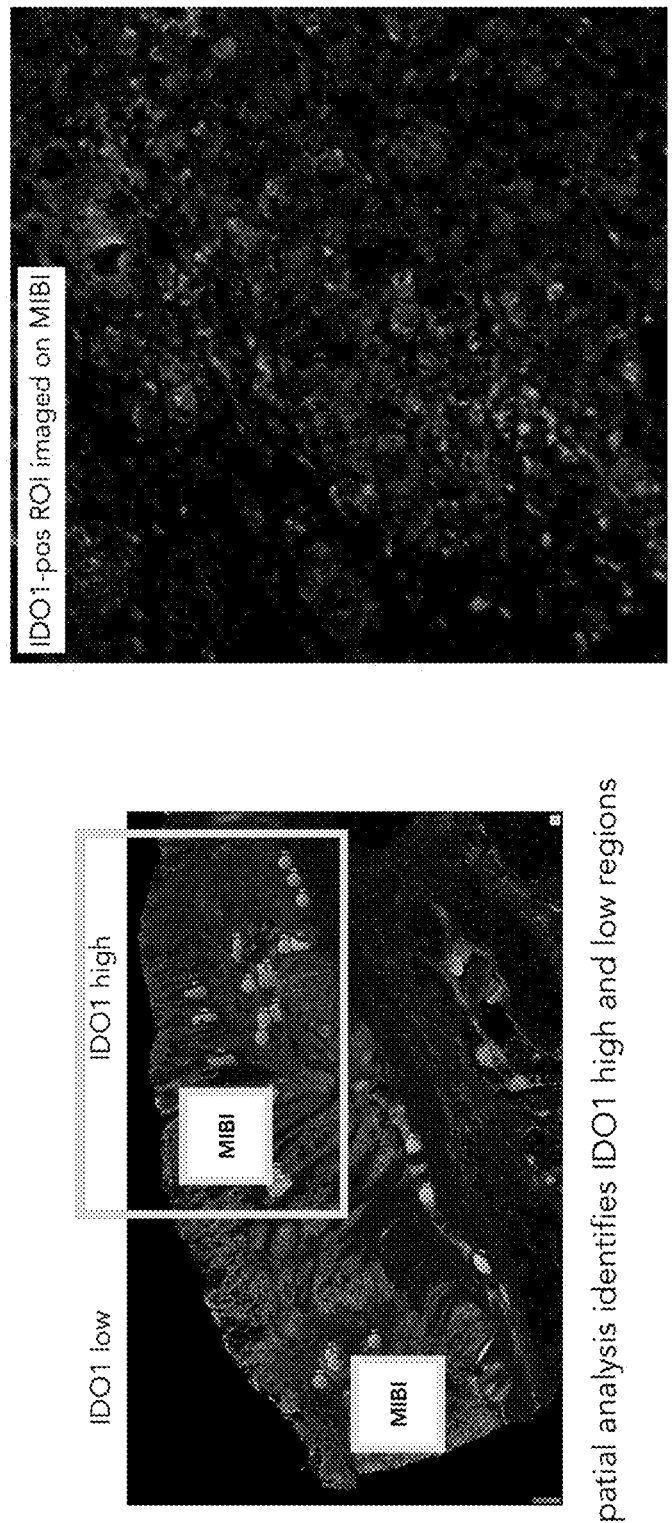
FIG. 37—Spatial analysis of IDO1 patient using MIBI.
Figure 38:
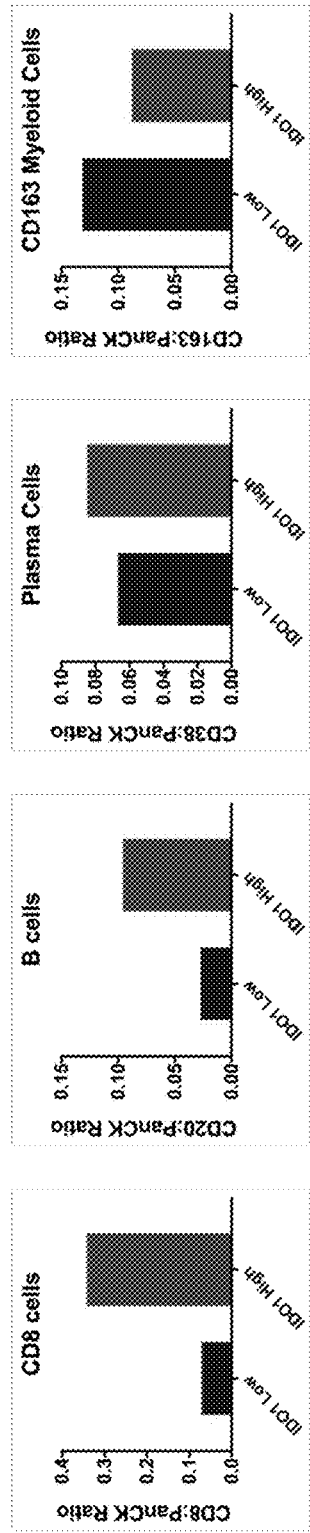
FIG. 38—Graphs showing density of immune cells in IDO1 high and low regions.
Figure 39:
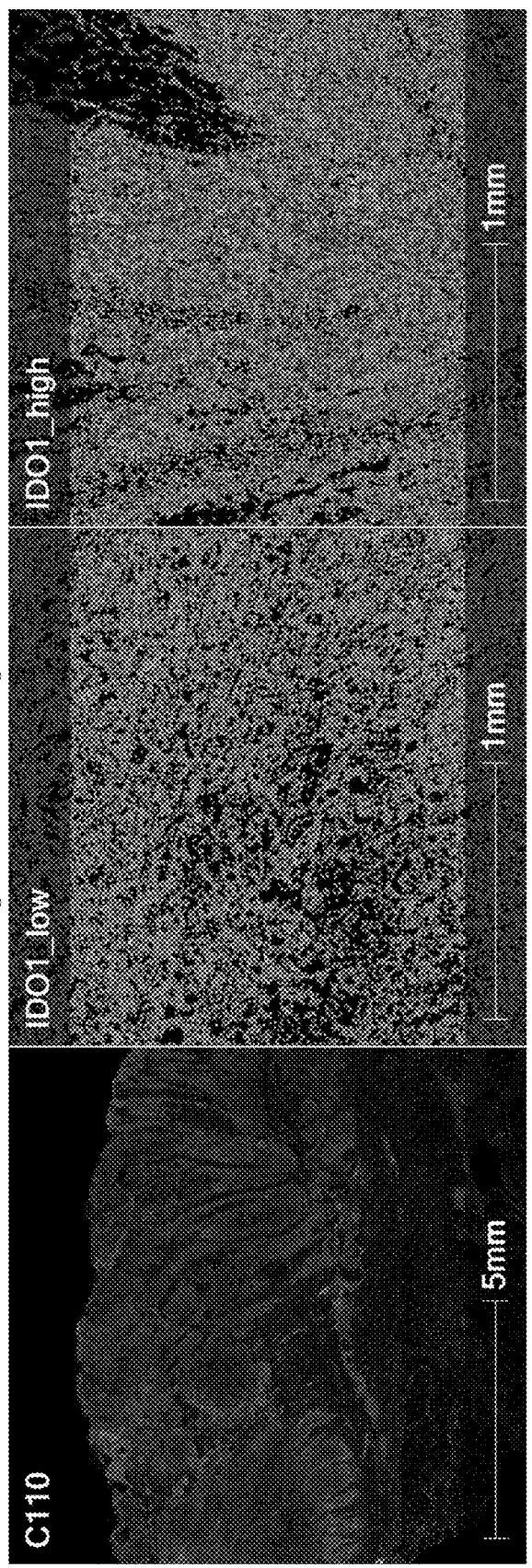
FIG. 39—Spatial analysis of IDO1 low and high regions.
Figure 40:
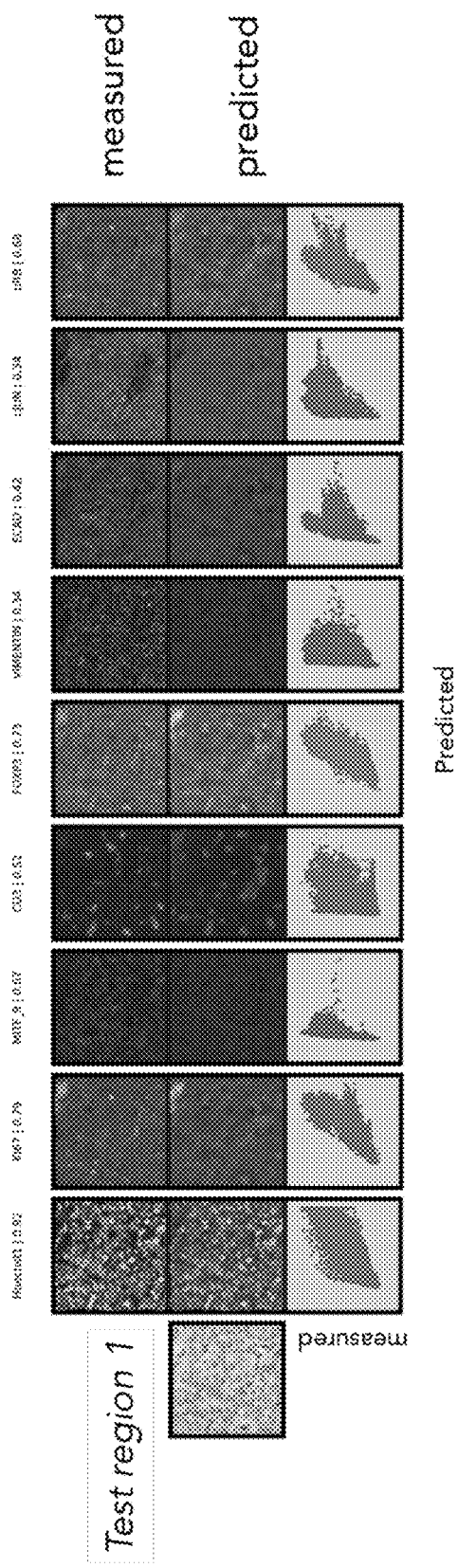
FIG. 40—Example of relating profiles and histological features in melanoma.

Additionally, Applicants validated compositional differences in situ (FIGS. 34, 35). Applicants observed that areas detected to have high IDO1 expression had a profound CD8 infiltrate (FIGS. 36, 38, 39). Applicants observed IDO1 high and low regions in CRC tissue (FIG. 37).

Example 4—High-Plex Profiling of MSS and MSI Human CRC Reveals Cellular Interaction Networks Between Malignant Cells and the Immune System The CRC atlas identified the emergence of new fibroblast states with different phenotypes in MSS versus MSI CRC (FIGS. 44-52). In the normal colon, Applicants identified previously well described fibroblasts plus a novel immune attracting fibroblast type. In CRC, Applicants observed that 'normal' tissue supporting functions changed or were lost, especially in MSI CRC. In MSI CRC, Applicants observed the expression of neutrophil attracting chemokines.

The CRC atlas identified transcriptional correlates of vascular dysfunction in MSS and MSI CRC (endothelial cells and pericytes) (FIGS. 53-59). This included angiogenesis, loss of vascular integrity, e.g., stiffness (upregulation of basement membrane components) and leakiness (loss of tight junctions), and changed immune attraction, adhesion, and transmigration. Applicants identified regulators (e.g., transcription factors) responsible for normal to tumor changes. These regulators may be targeted therapeutically.

The CRC atlas identified a strong myeloid infiltration in MSS and MSI CRC and a dramatic expansion of the phenotypic spectrum of monocytes/macrophages (different in MSS versus MSI) (FIGS. 60-63). Applicants analyzed the myeloid compartment through the lens of NMF gene programs (inflammation, ISG, macrophage polarization states including M2-like program). Applicants used PHATE maps and other trajectory methods to determine which factors in the TME are inducing myeloid phenotypes (e.g. cytokine—NMF correlations).

Figure 64:
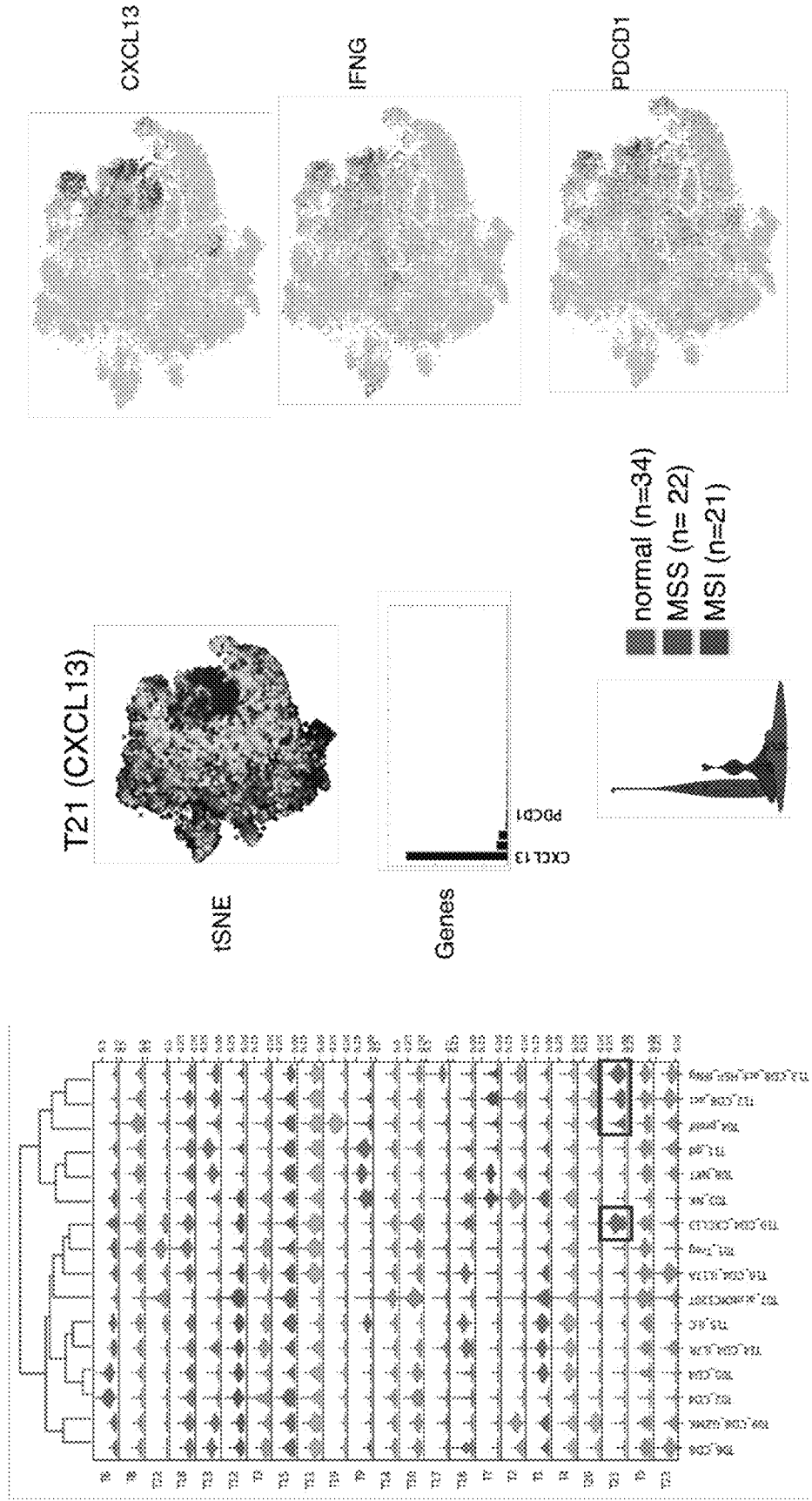
FIG. 64—Expression of T cell gene programs across T cell clusters. tSNE maps labeled for the T21 program and individual genes in the program are shown. Expression of key genes for the T21 program is shown. Expression of the T21 program in normal and CRC is shown.
Figure 65:
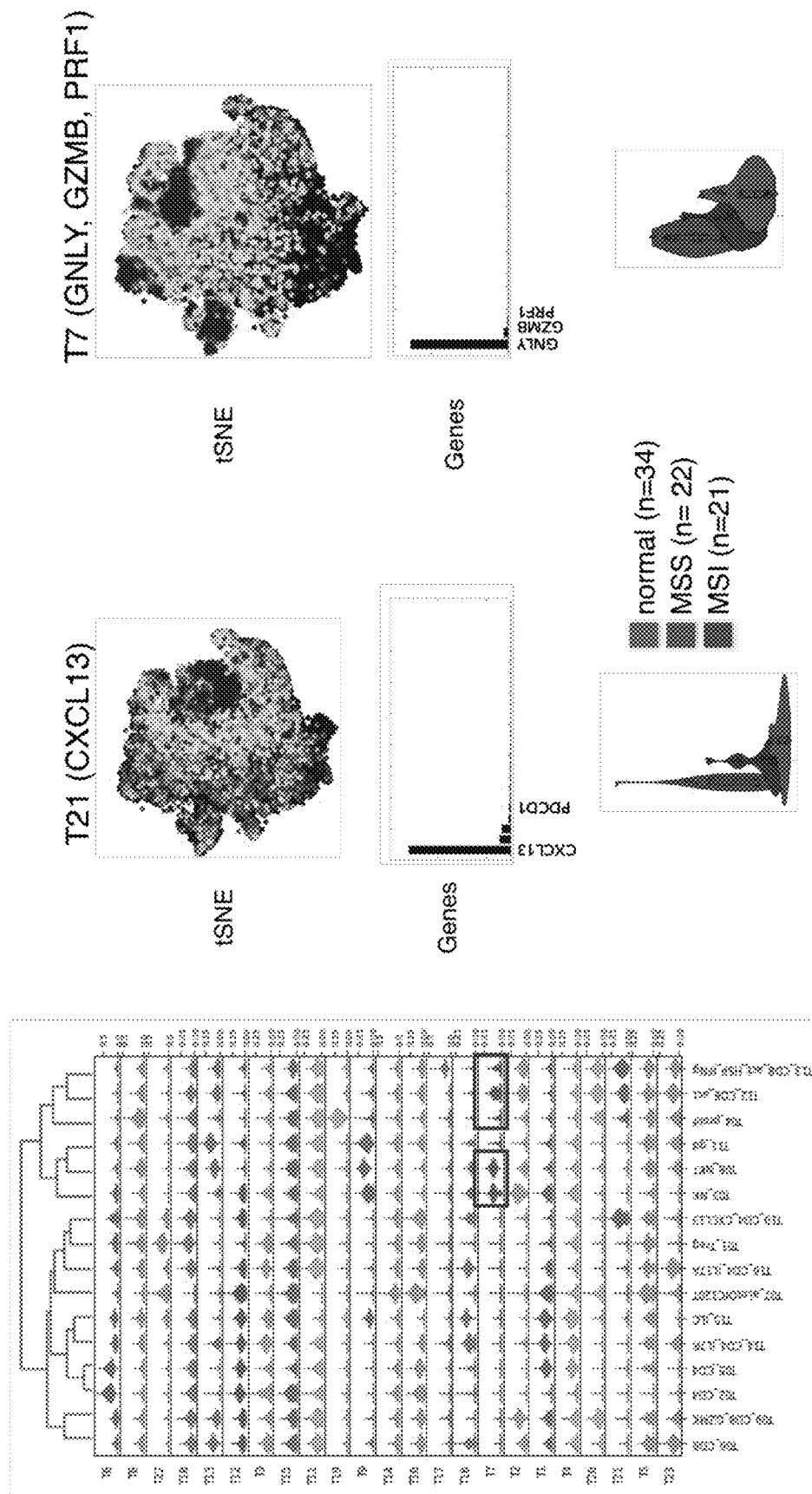
FIG. 65—Expression of T cell gene programs across T cell clusters. tSNE maps labeled for the T21 and T7 programs are shown. Expression of key genes for each program are shown. Expression of indicated programs in normal and CRC is shown.
Figure 66:
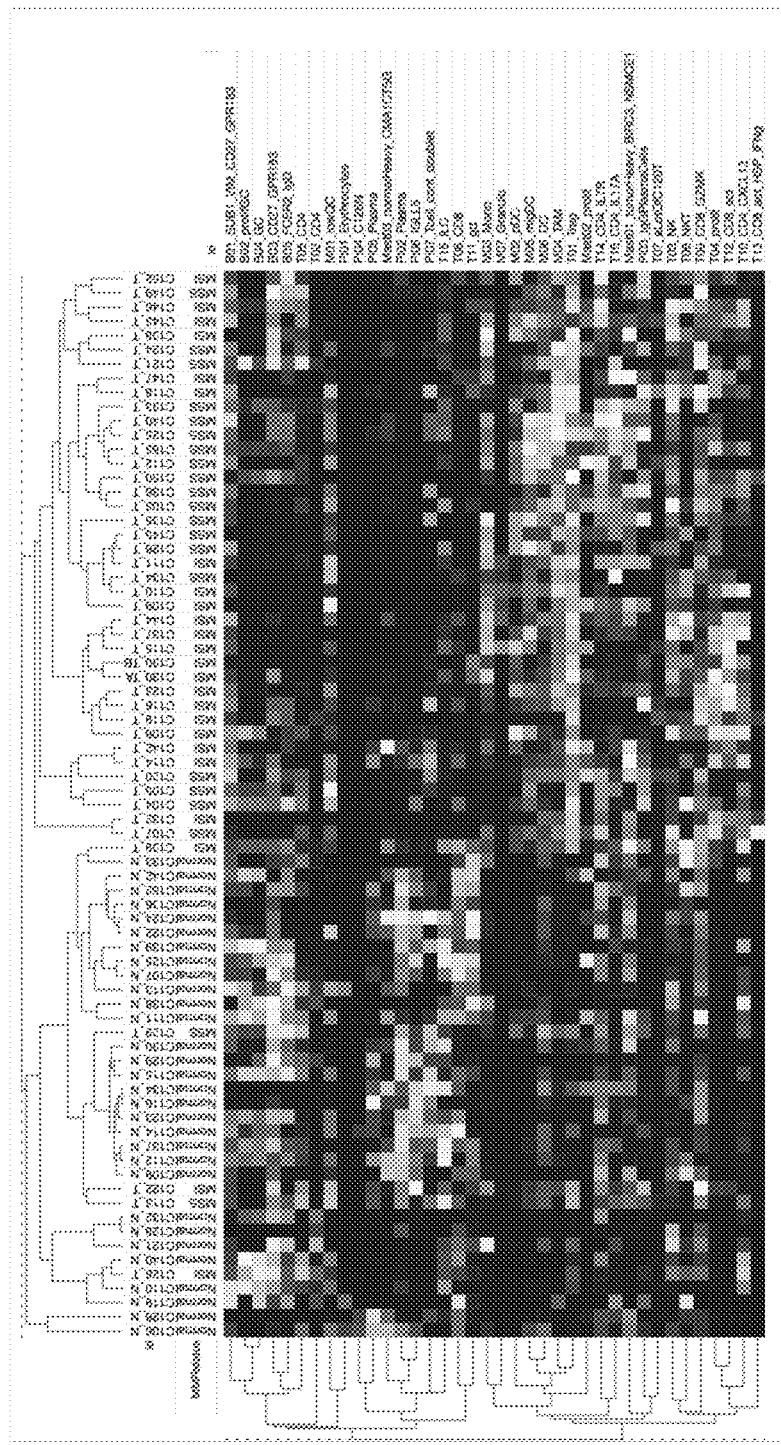
FIG. 66—Heatmap showing immune cell composition across patients.

The CRC atlas identified a CXCL13 T cell program that marks activated T cells in human tumors and is a superior marker compared to cytolytic programs (FIGS. 64-66). Applicants also identified programs related to IL17+CD4+ and CD8+ T cells. Applicants can compare the cell states identified with states from previous scRNAseq studies. The CXCL13+ T cell program may be a better indicator of anti-tumor immunity (e.g., predictor of anti-PD1 response) than current measurements (MMR status, immunoscore).

Figure 67:
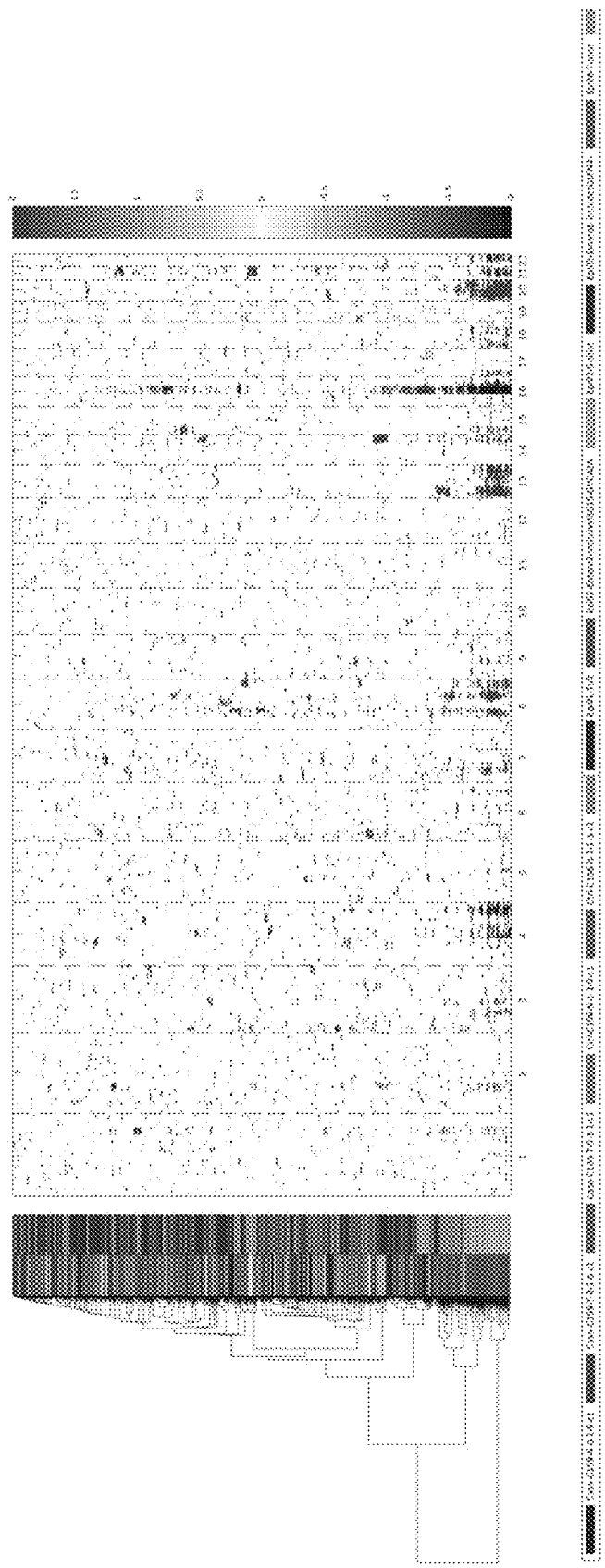
FIG. 67—Heatmap showing copy number variation (CNV) in sample C109 MSI.
Figure 68:
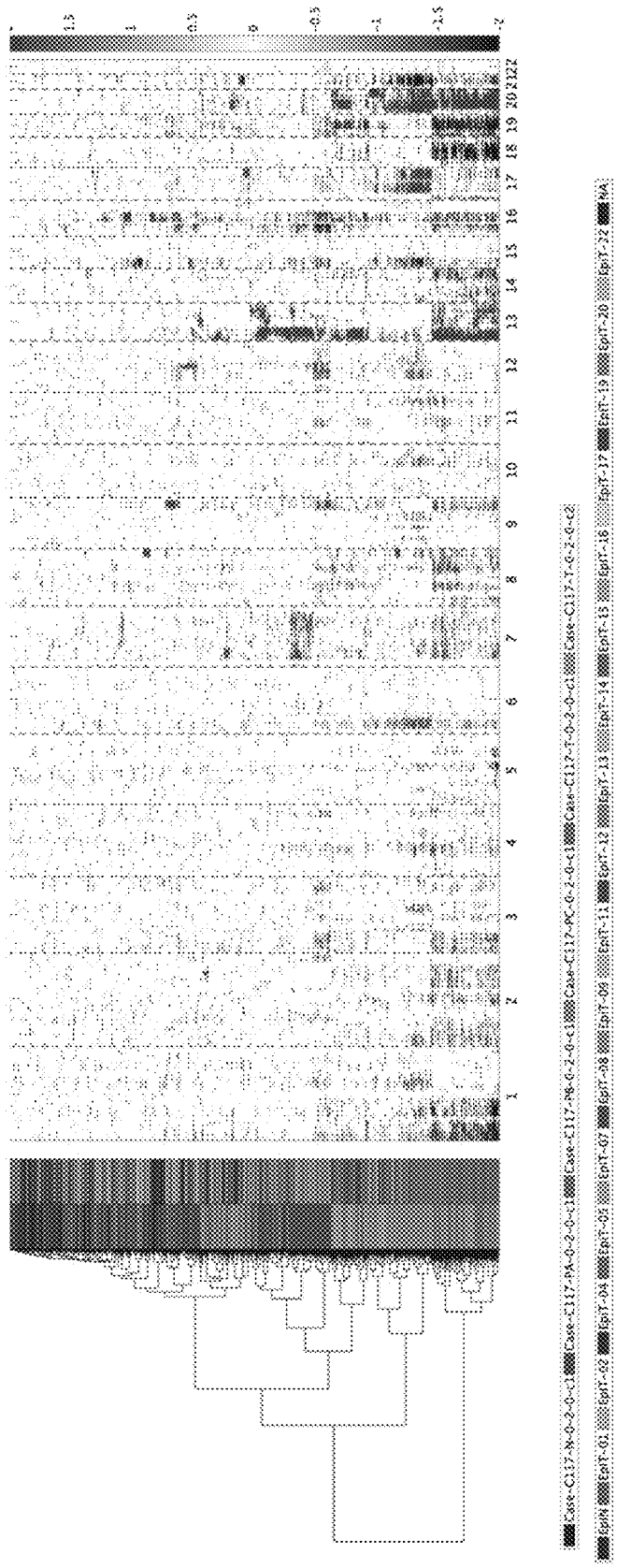
FIG. 68—Heatmap showing copy number variation (CNV) in sample C117.
Figure 69:
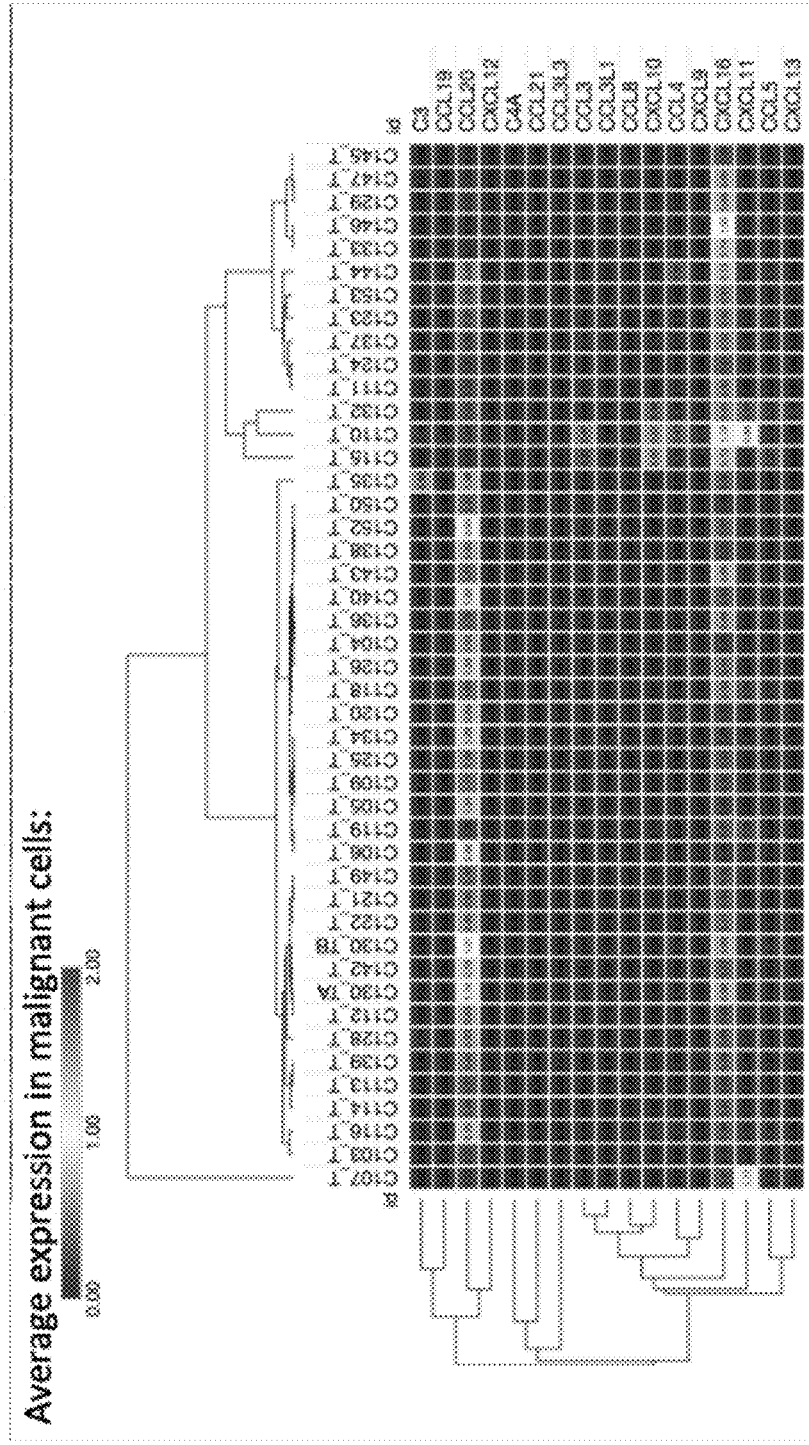
FIG. 69—Heatmap showing expression of chemokines across CRC samples.
Figure 70:
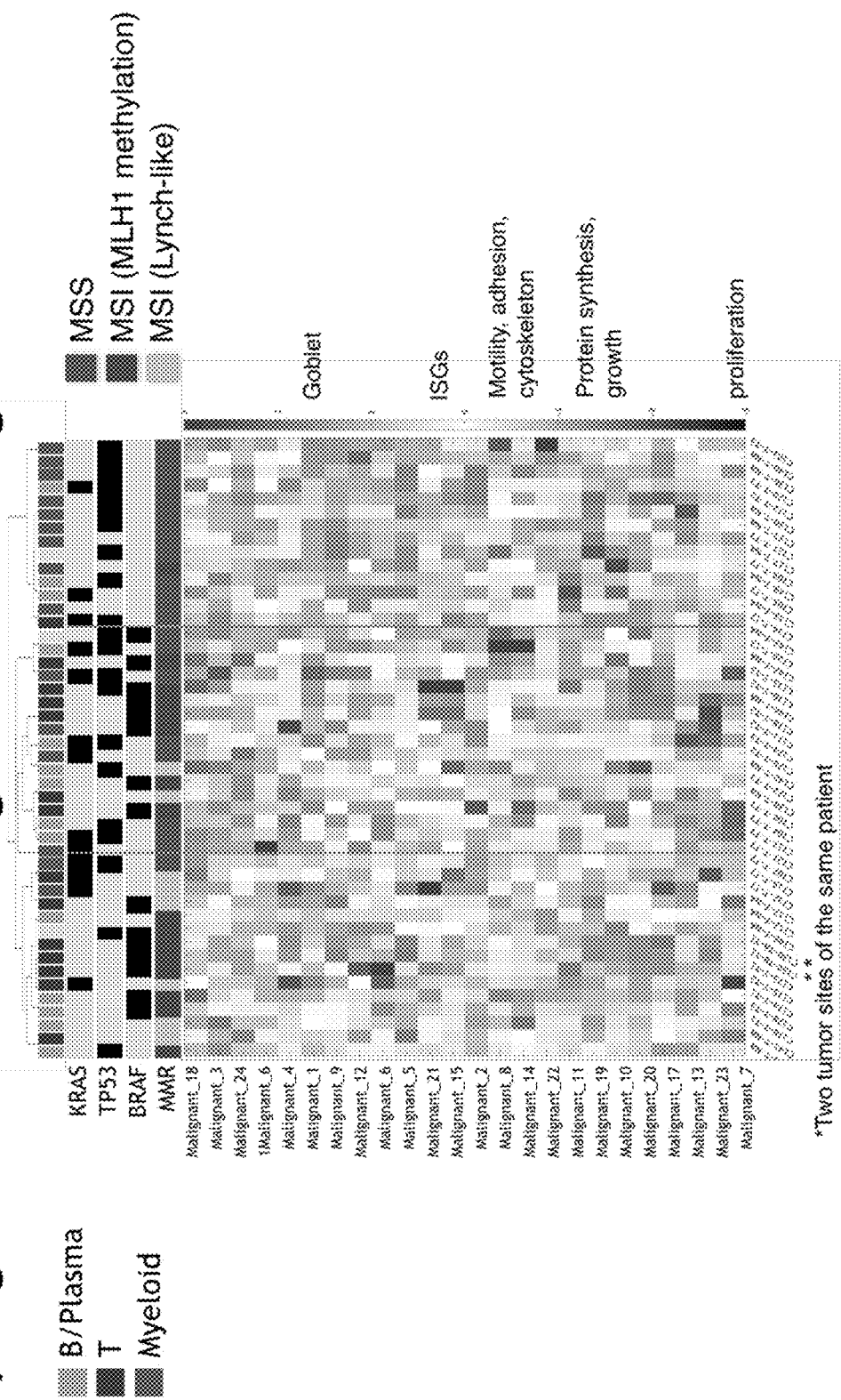
FIG. 70—Heat map showing expression of malignant programs across patient samples.
Figure 71:
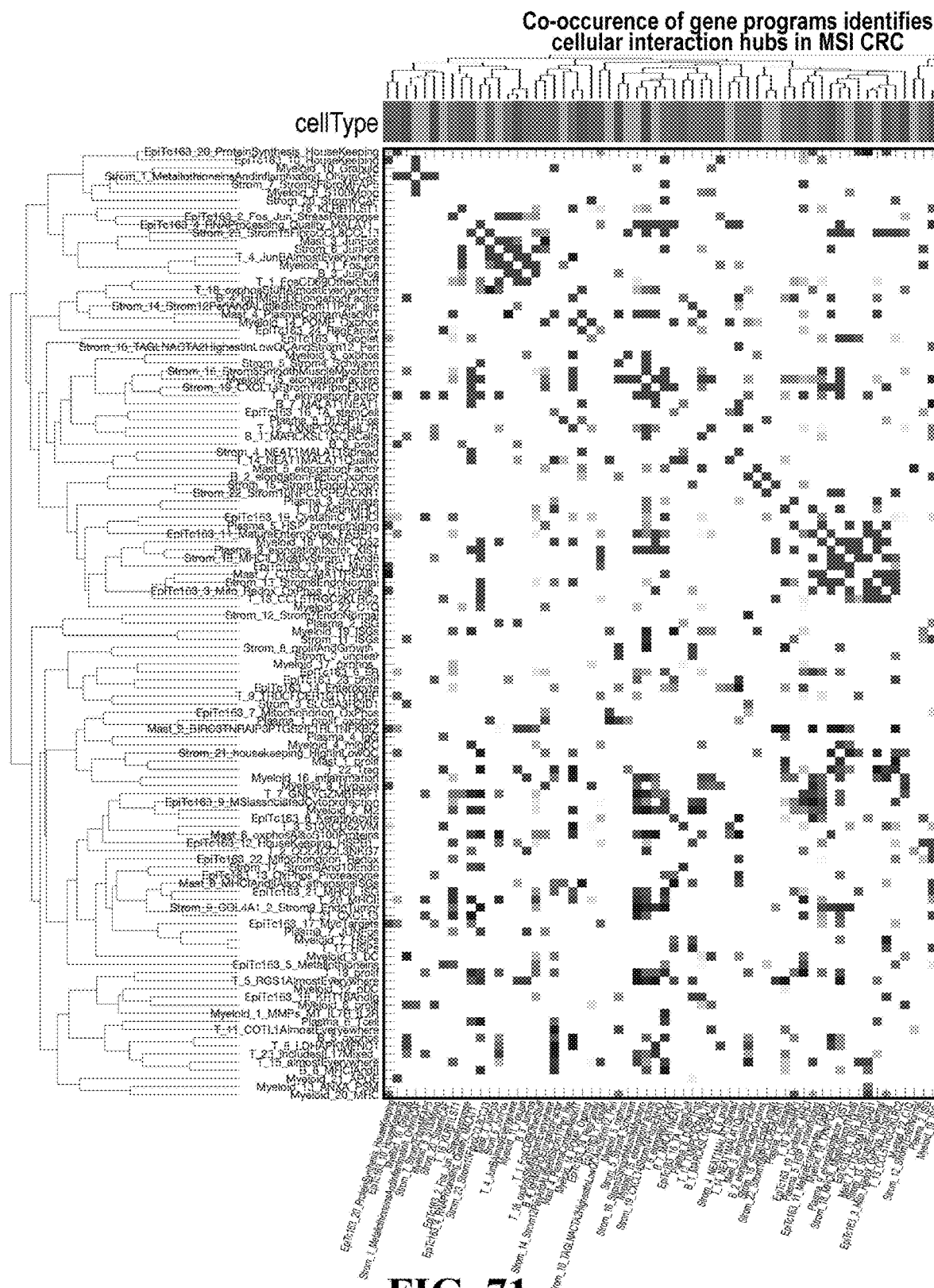
FIG. 71—Heatmap showing co-occurrence of gene programs. The gene programs are shown on the x and y axis. The myeloid_2 and T_21 programs co-occur.
Figure 71:
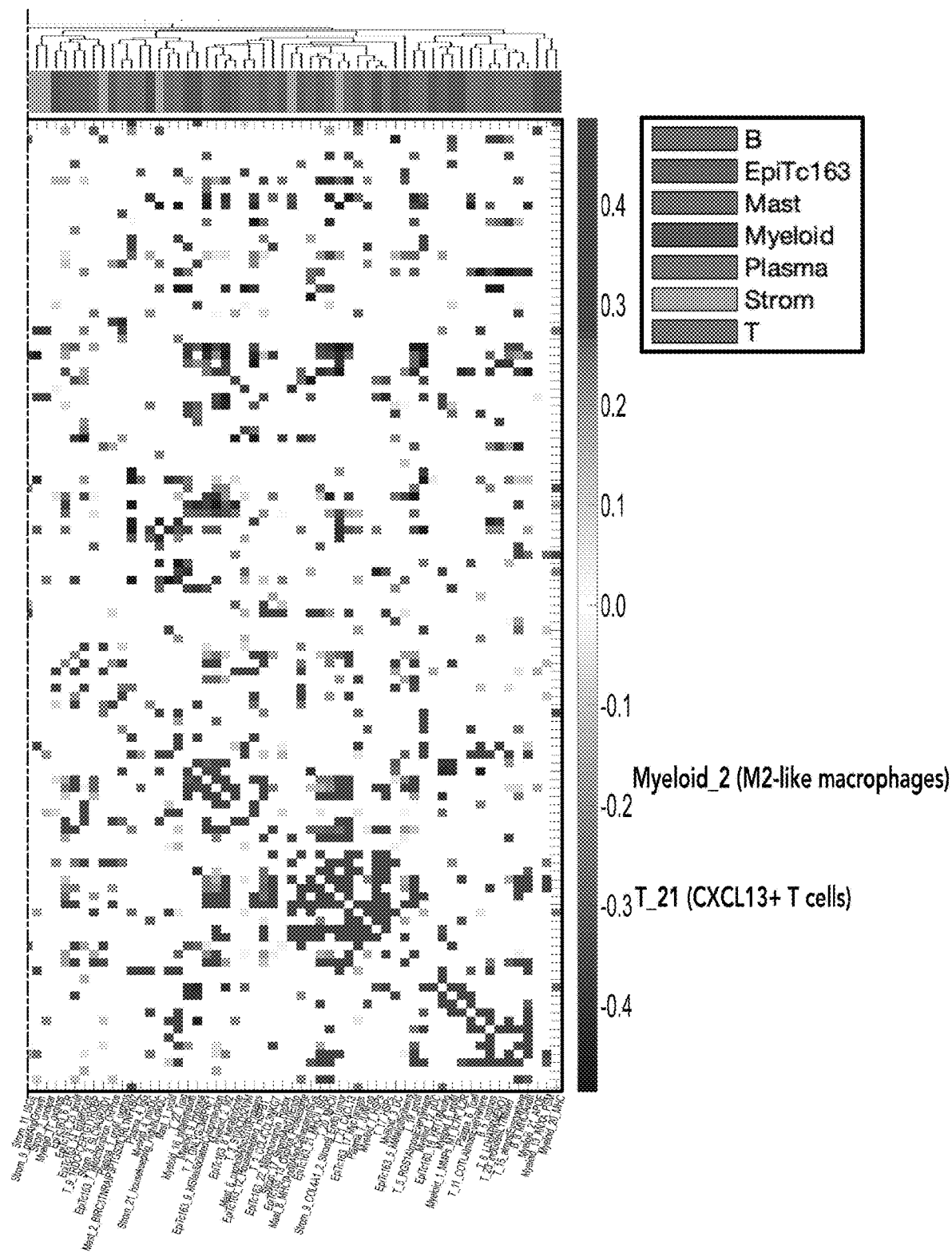
Figure 72:
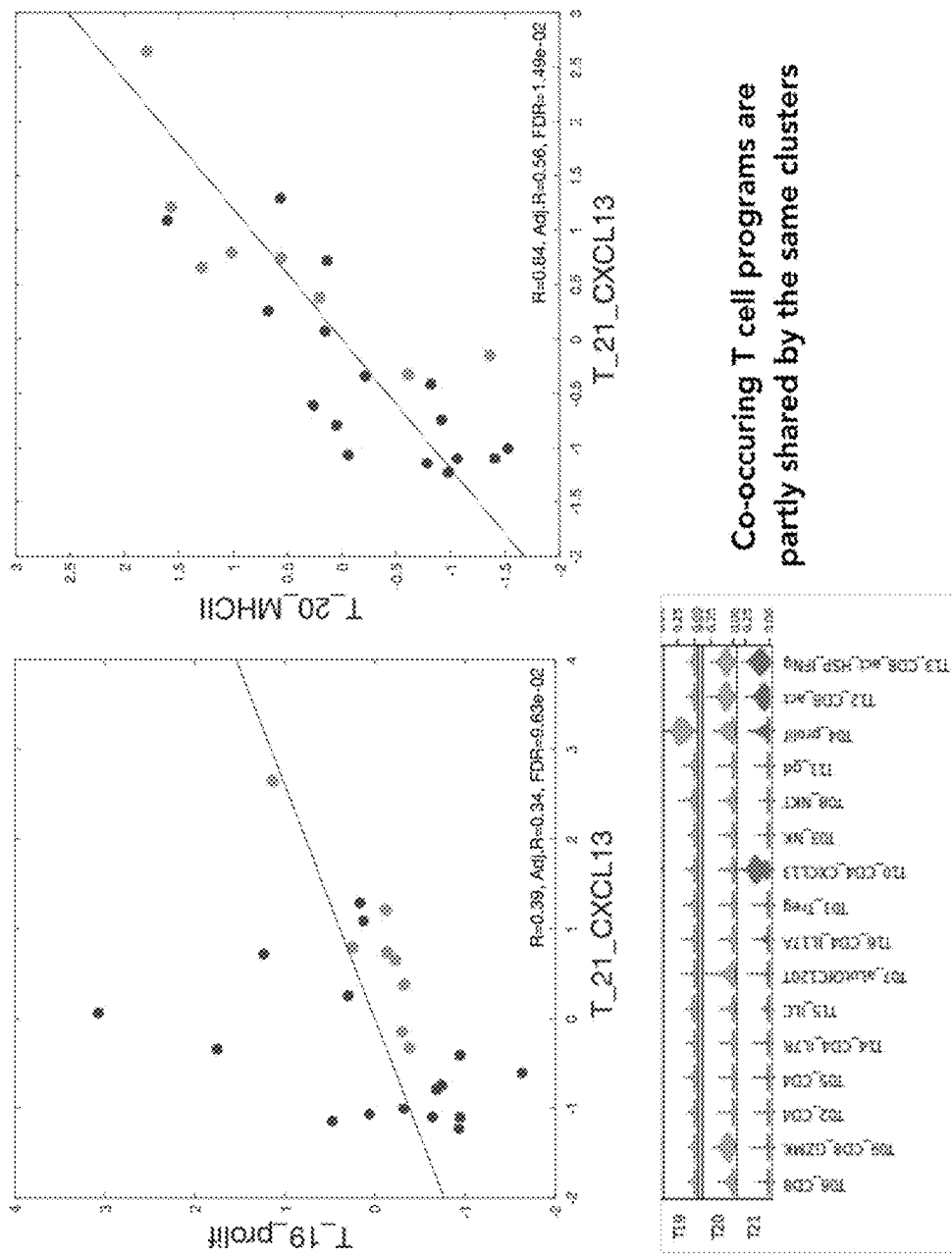
FIG. 72—NMFs for T21 (CXCL13 program) compared to T_19 and T_20 programs. Expression of programs across T cell types identified by atlas.
Figure 73:
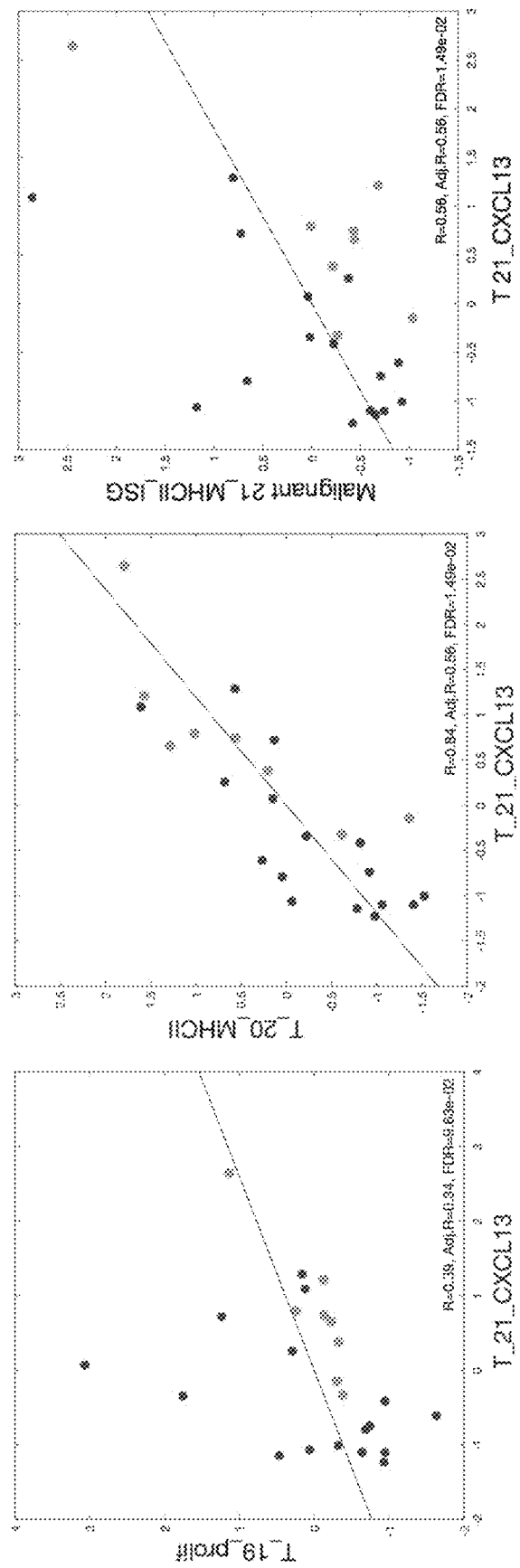
FIG. 73—NMFs for T21 (CXCL13 program) compared to T_19, T_20 and Malignant_21 T_19 and T_20 programs.

The CRC atlas identified that patient-specific and shared malignant programs correlate with histologic features, genetic drivers, and immunologic state (FIGS. 67-68, 70). Applicants also identified that malignant cells can produce cytokines (FIG. 69).

Figure 74:
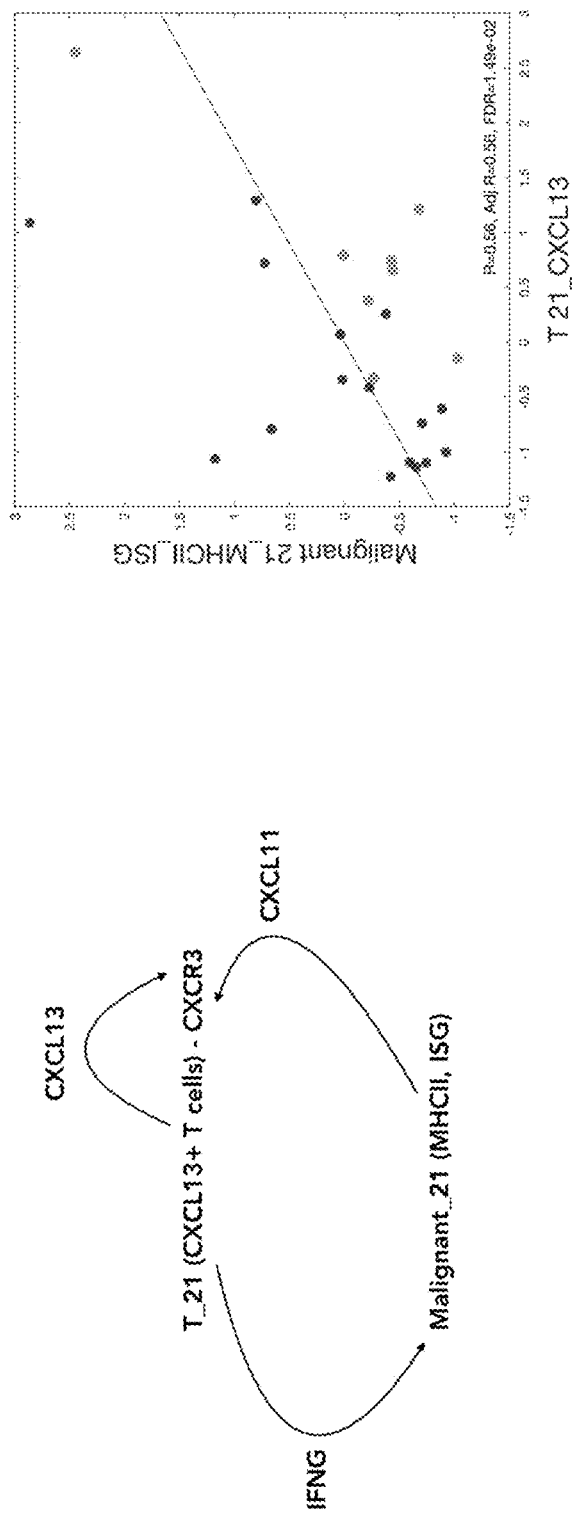
FIG. 74—Diagram showing a feed forward loop driving accumulation of CXCL13+ T cells. NMF comparing Malignant_21 and T_21 programs.
Figure 75:
FIG. 75—Tissue from C110 (MSI) stained for CXCL13 and CD3E.
Figure 76:
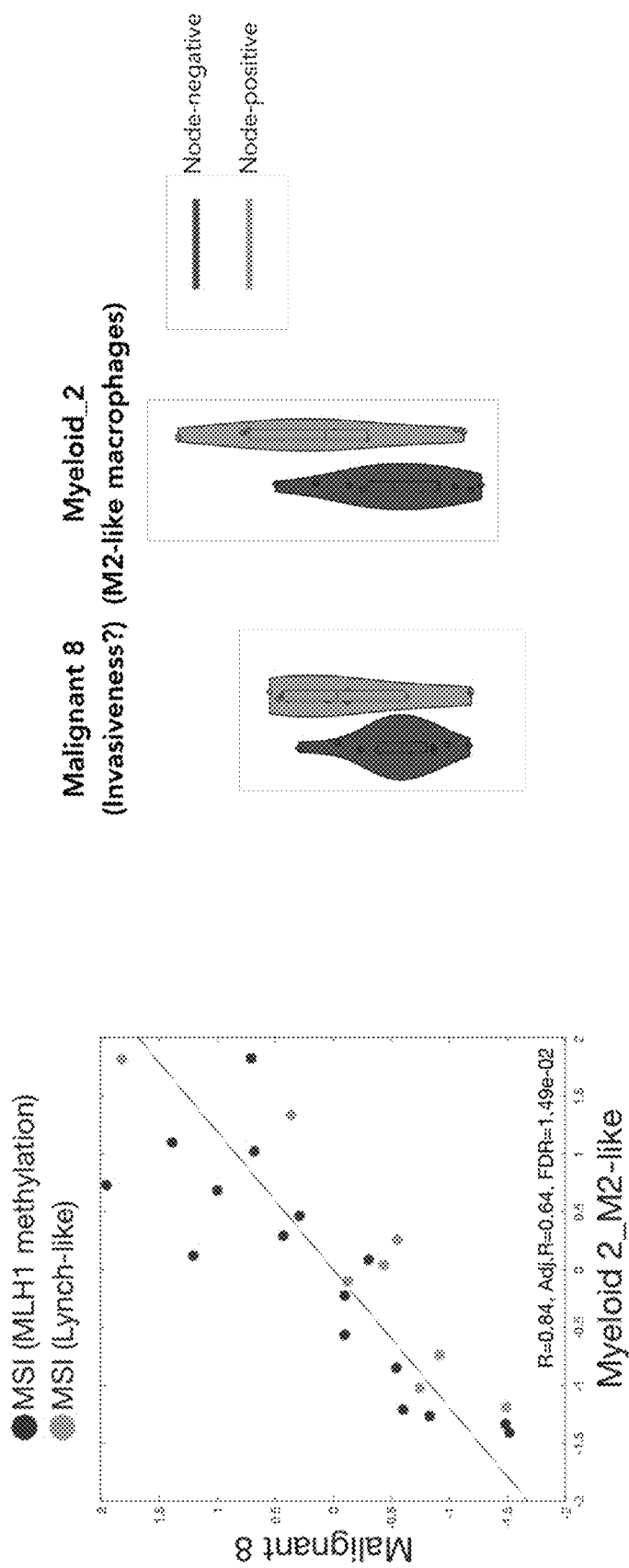
FIG. 76—NMF comparing Malignant_8 and Myeloid_2 programs in MSI CRC. Violin plots showing Malignant_8 and Myeloid_2 program expression in nodal negative and nodal positive cells.
Figure 77:
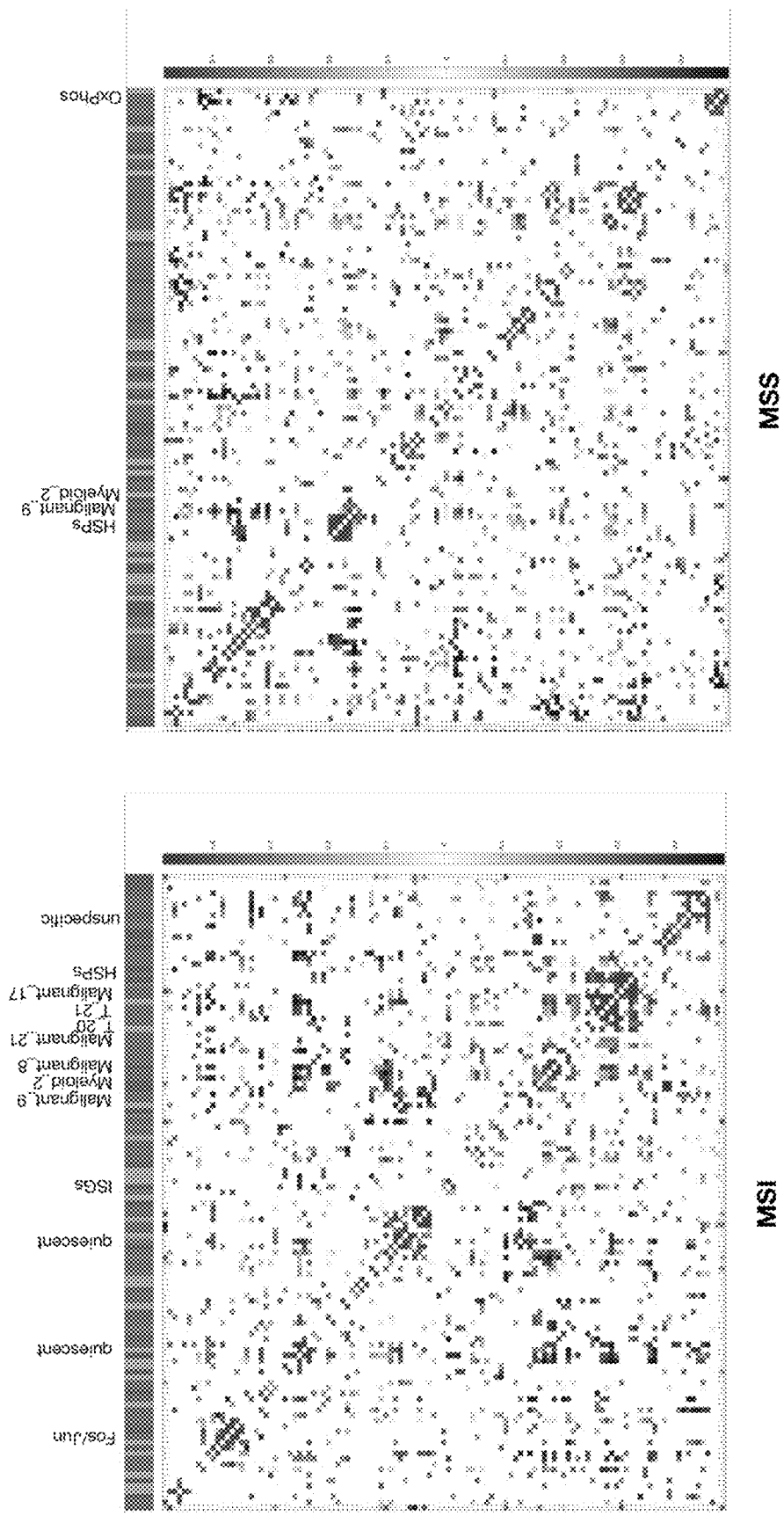
FIG. 77—Heatmaps showing correlation of programs in MSI and MSS.

The CRC atlas identified that the co-occurrence of gene programs identifies cellular interaction hubs (e.g, expression of programs in different cell types) (FIGS. 71-77). The M2-like myeloid program may drive a malignant invasiveness program and potentially can predict nodal state (FIG. 76). A chemokine/chemokine receptor feed forward loop may drive the accumulation of CXCL13+ T cells (FIG. 74). Additionally, immunohistochemical and mRNA staining shows the spatial co-occurrence of the identified programs.

Figure 78A:
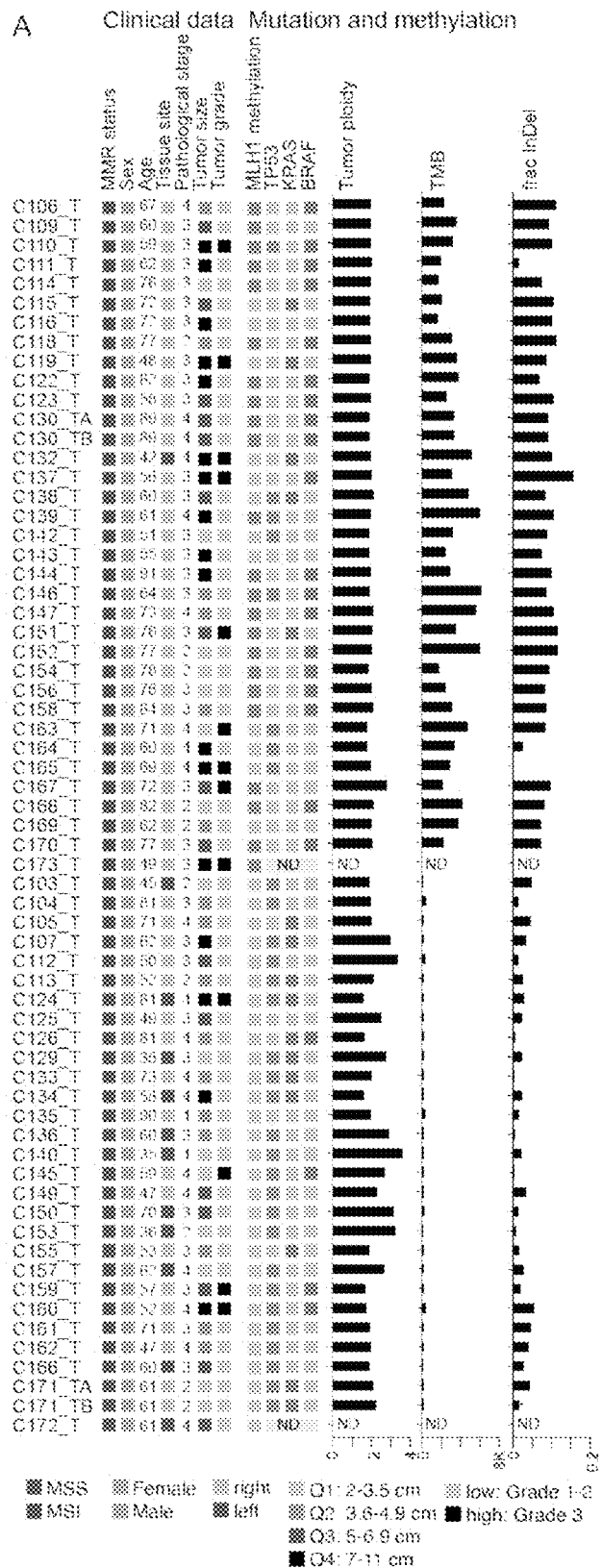
FIG. 78A-78C—scRNAseq cohort of 65 patients with primary untreated CRC. A. Clinical and genetic features of Applicants' cohort comprising 34 MSI and 31 MSS patients. B. ScRNAseq revealed the cellular elements and gene programs of CRC and C. compositional differences between normal colon tissue, MSS CRC, and MSI CRC specimens.
Figure 78B:
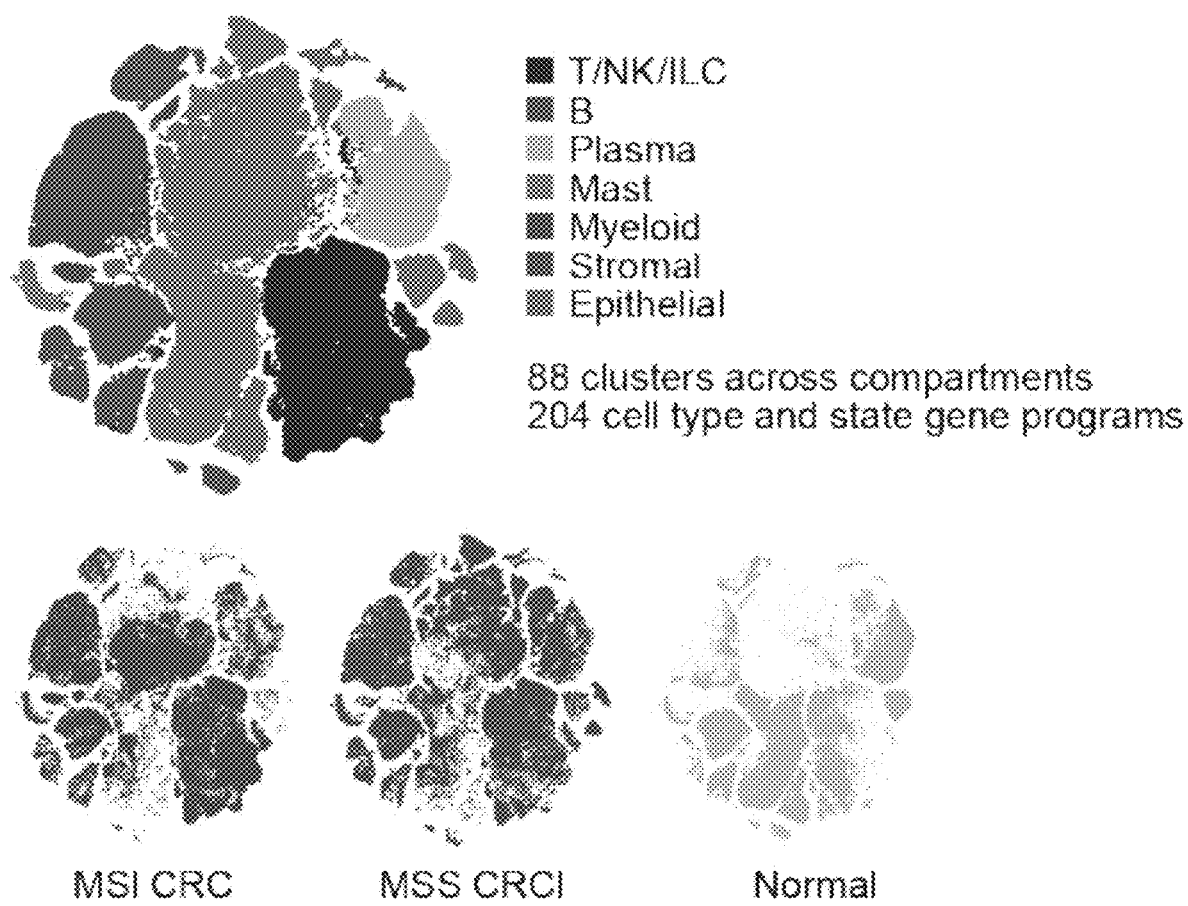
Figure 78C:
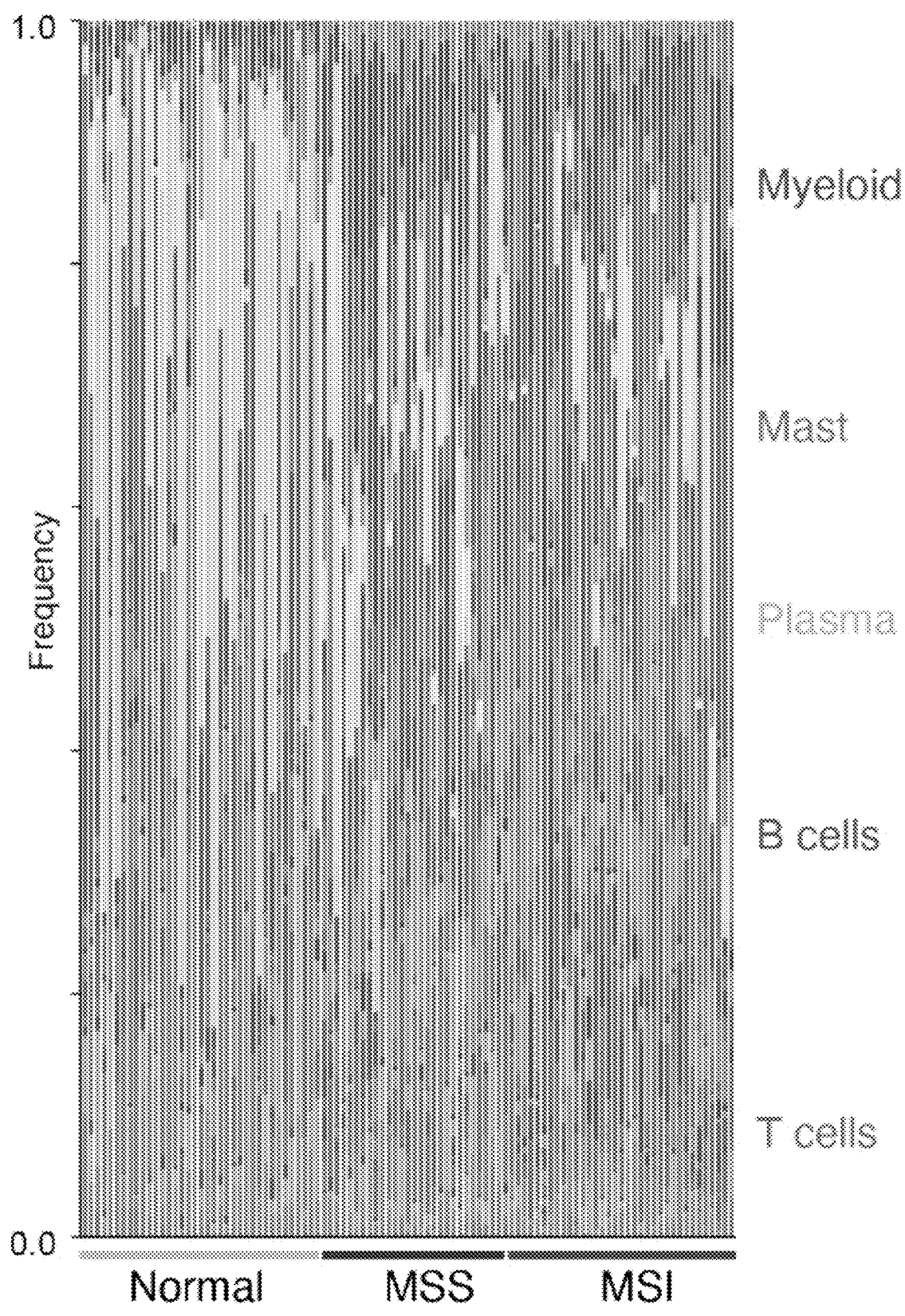
Figure 79A:
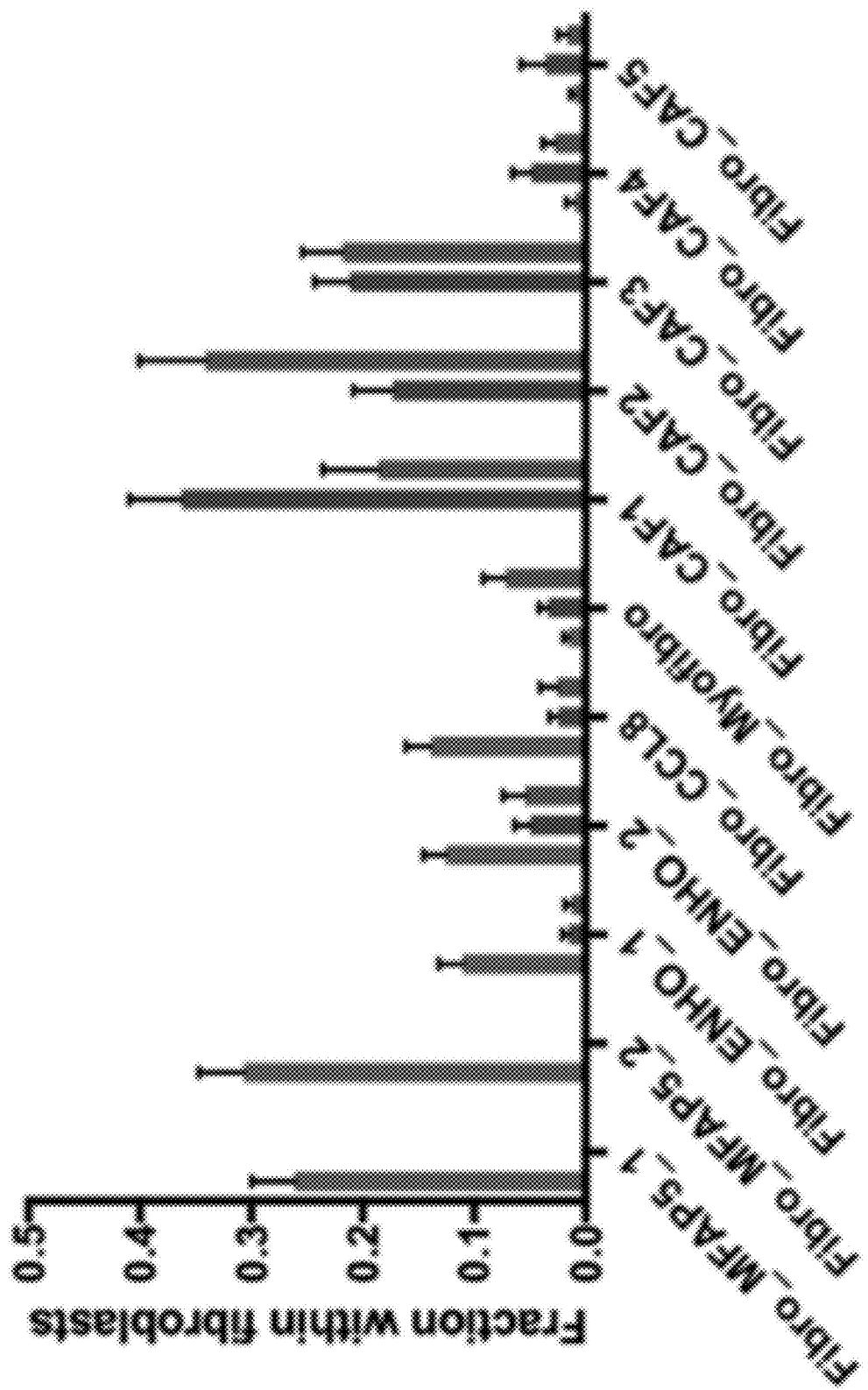
Figure 79C:
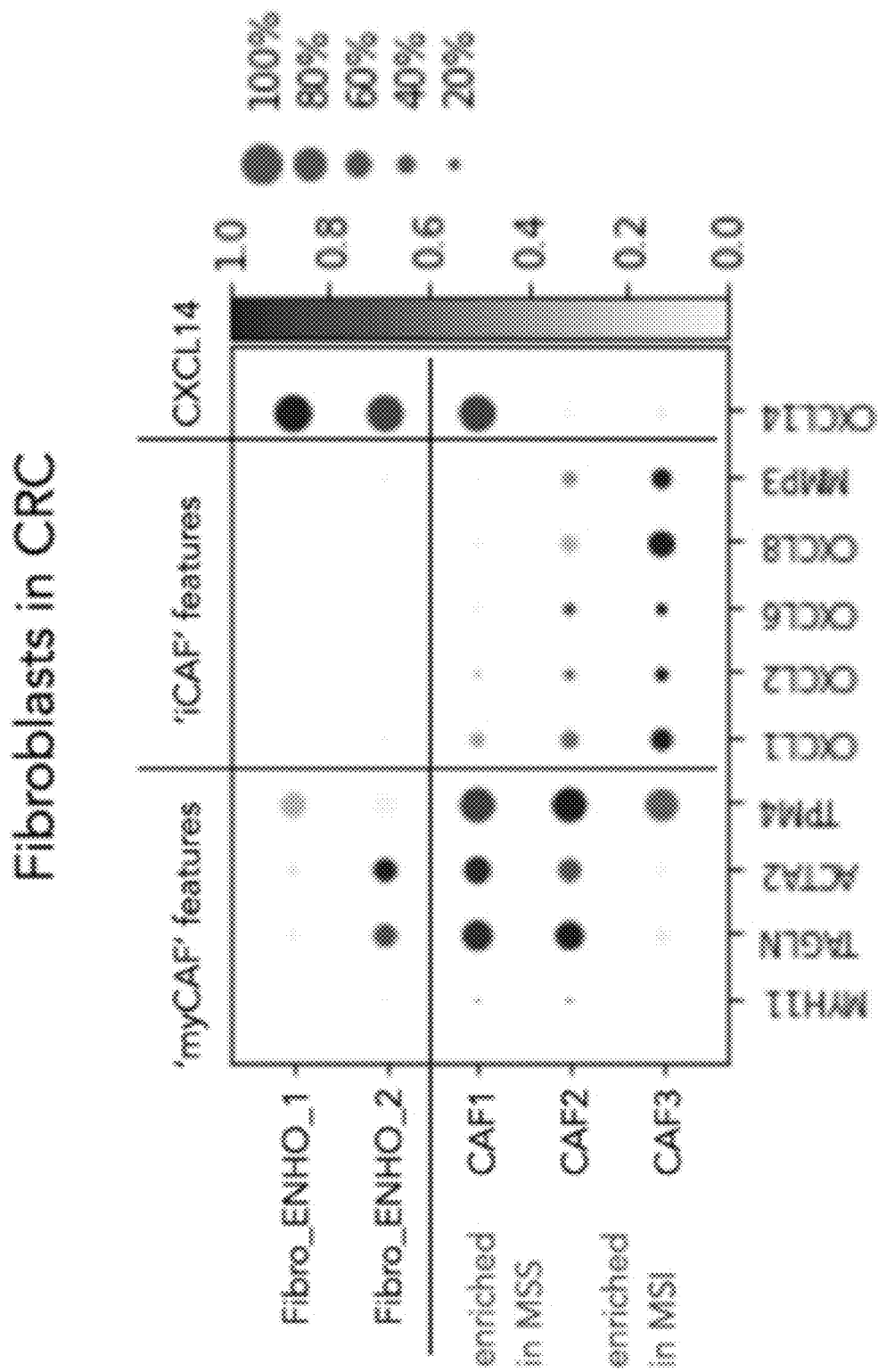
Figure 79D:
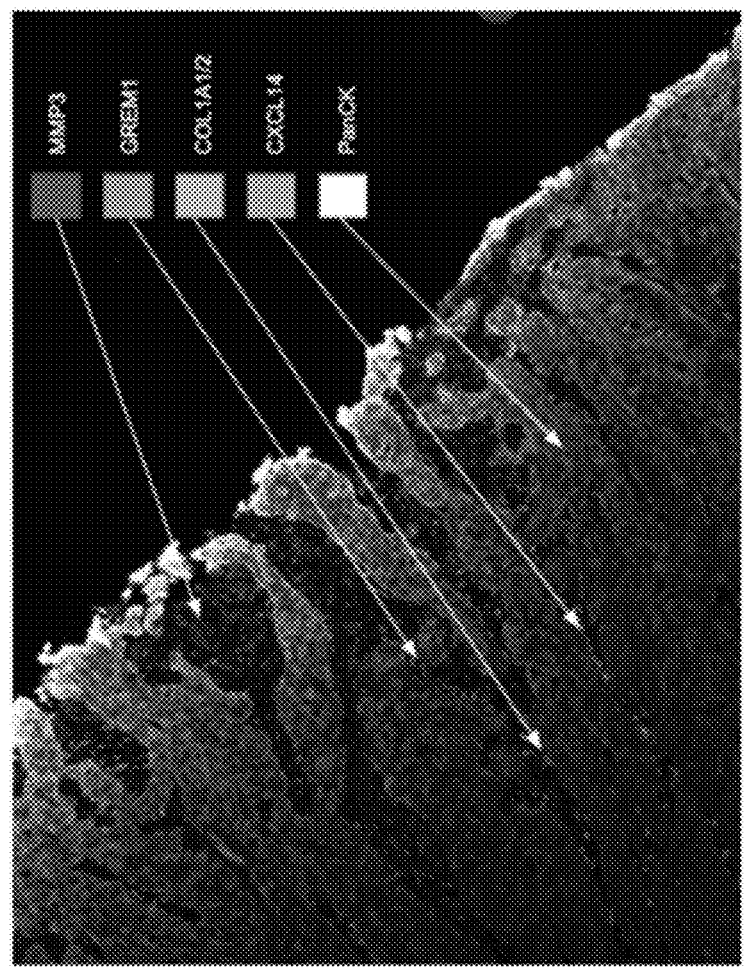

Example 5—Cellular Elements and Spatially-Organized Multicellular Immune Hubs in MSI and MSS Colorectal Cancer Applicants performed multiple analyses on fresh, frozen, and fixed tumor and adjacent normal colon specimens from 65 patients with primary untreated CRC, among them 31 patients with MSS and 34 patients with MSI tumors (FIG. 78A). These analyses included droplet-based and plate-based single-cell RNA sequencing, bulk RNA sequencing, whole exome sequencing, transcriptional and proteomic tissue profiling using the GeoMx Digital Spatial Profiling technology from NanoString, and multiplex ISH/IF imaging. The size of the cohort enabled Applicants to do correlational analyses across patients in order to reveal multicellular interaction networks. By profiling ~400,000 single immune, stromal, and malignant cell transcriptomes (FIG. 78B) and defining 88 clusters and 204 nonnegative matrix factorization-based gene programs, Applicants discovered what is unique in tumor vs normal tissue and in MSI vs MSS tumors (FIG. 78C). In accordance with previous findings[1], activated CD8+ T cells were largely restricted to MSI CRC. Myeloid cells, endothelial cells and pericytes were commonly enriched in both MSS and MSI CRC and acquired tumor-specific polarization states. In addition, Applicants discovered several tumor-specific fibroblast cell states with distinct localization patterns in the tumor tissue as visualized by multiplex ISH/IF imaging (FIG. 79).

Malignant cells largely segregated into MSS versus MSI CRC (FIG. 80A) and often acquired highly patient-specific signatures (in contrast to immune and stromal cell types and states which were preserved across patients). To understand the degree of intra-patient heterogeneity and whether the patient specific malignant cell signatures that Applicants had discovered by single cell RNA sequencing were indeed representative for the respective tumor, Applicants profiled multiple PanCK+ regions for each of six formalin-fixed specimens from the cohort by GeoMx Digital Spatial Profiling (FIG. 80B). Using this independent approach, Applicants confirmed that the transcriptional profiles of malignant cells were more similar within a patient than across patients and indeed resembled the profiles from the single cell RNA sequencing data (FIG. 80C). In addition, Applicants discovered that transcriptionally distinct malignant cell signatures within a patient were not randomly distributed across the tumor, but often occurred in a spatially organized manner.

Figure 81:
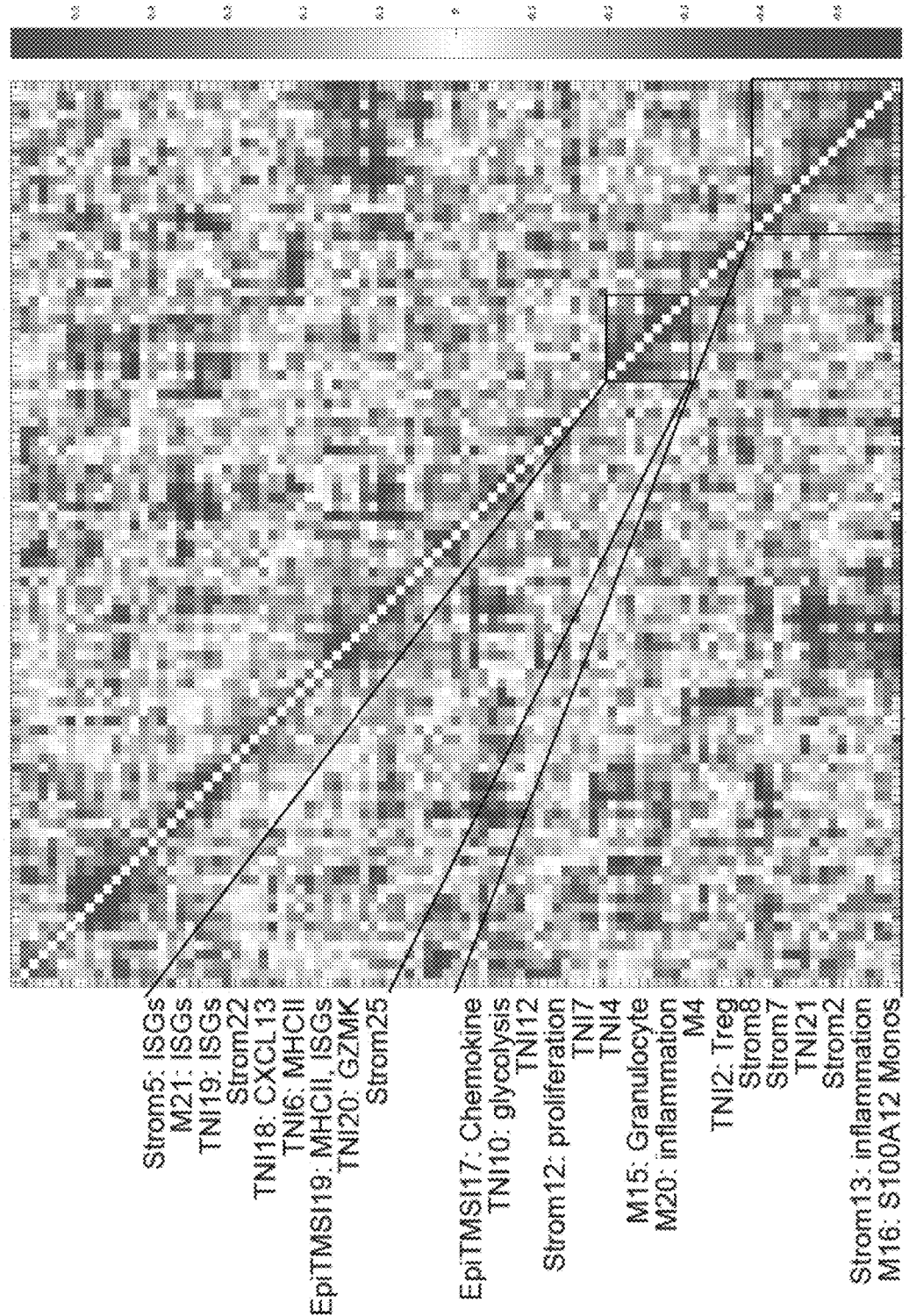
FIG. 81—Correlational analysis of malignant, stromal, myeloid and T cell programs in MSI CRC revealed cellular interaction nodes. Applicants focused on the CXCL13 T cell—malignant ISG interaction node and the malignant chemokine—inflammation interaction node.

In order to understand how malignant cells interacted with their tumor microenvironment, Applicants applied a nonnegative matrix factorization-based approach to define a set of shared malignant programs and performed a correlational analysis of all gene programs across malignant, stromal, myeloid and T cell populations. This approach pointed Applicants to two main cellular interaction networks in MSI CRC (FIG. 81). The first interaction network between malignant cells and the tumor microenvironment contained a gene program in the malignant cells that was characterized by granulocyte-attracting chemokines, which co-occurred with IL1B+ monocytes, and highly inflammatory fibroblasts. This network is still under investigation, but seems to localize to the luminal interface of most MSS and MSI tumors at sites of epithelial damage and active wound healing.

Figure 82:
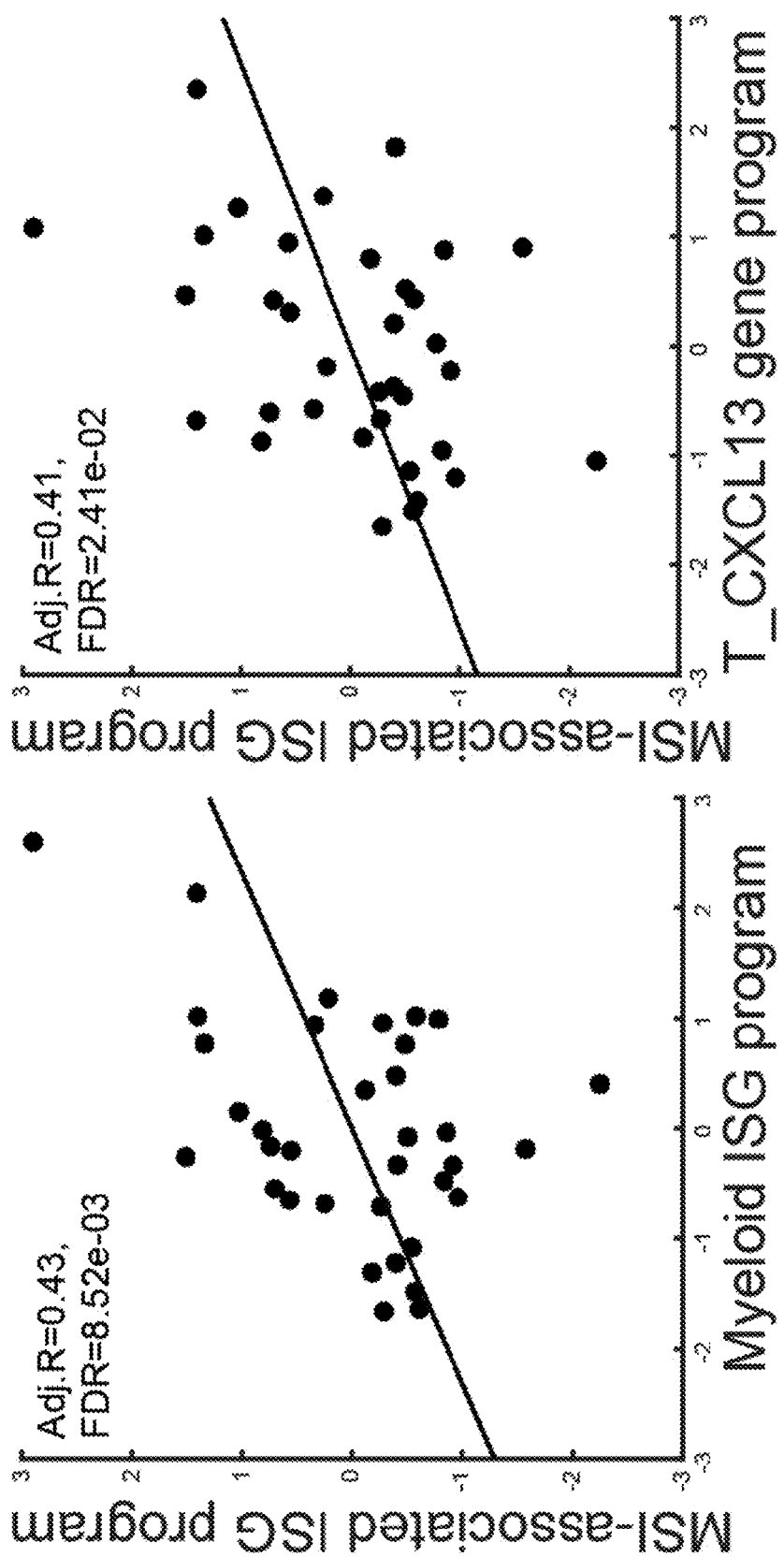
FIG. 82—Pairwise correlations of the MSI-associated ISG program activity with the myeloid ISG and the CXCL13+ T cell program activities. Each dot represents one MSI CRC specimen.
Figure 83:
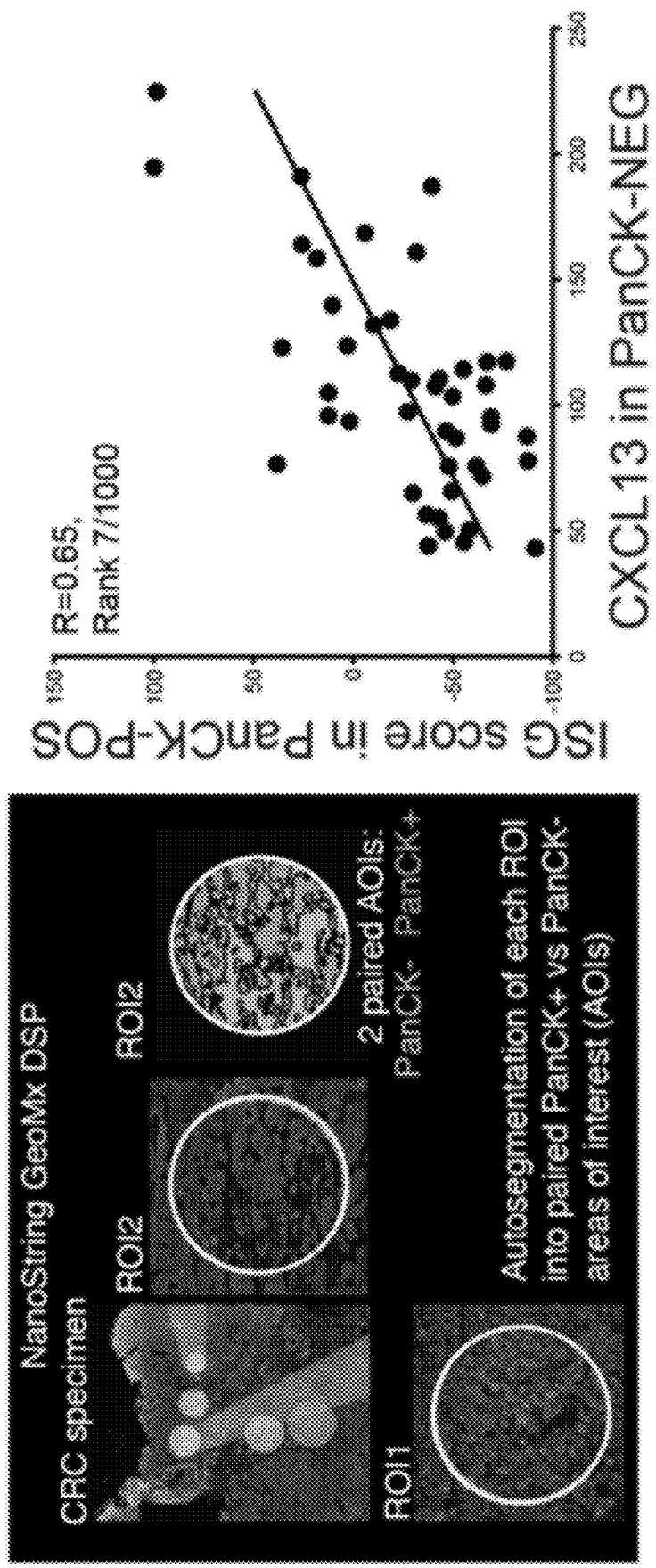
FIG. 83—Spatial proximity of ISGs in malignant cells and CXCL13 in stromal cell regions. Nanostring GeoMx DSP analysis enabled autosegmentation of ROIs into paired PanCK+ and PanCK− AOIs and revealed spatial association between CXCL13 in stromal cell regions and ISGs in malignant cells.
Figure 84A:
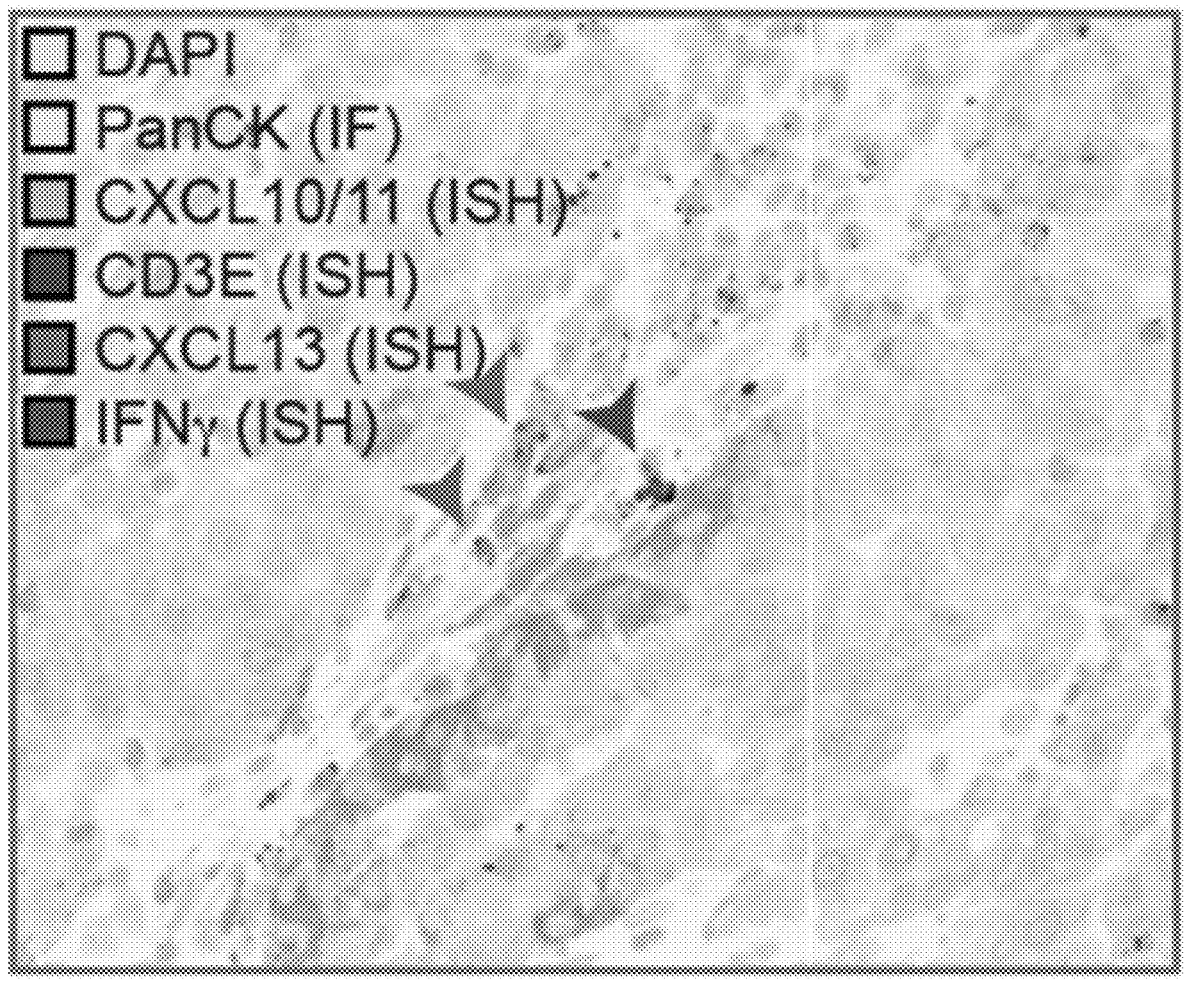
FIG. 84A-84B—Quantitative IF/ISH microscopy revealed foci of CXCL10/CXCL11+ malignant cells in close proximity to IFNγ+ and CXCL13+CD3+ T cells. A. CXCL10/CXCL11+ PanCK+ malignant cells, IFNγ+ and CXCL13+CD3+ T cells were visualized by combined IF/ISH stainings of human CRC specimens. B. Quantitative analysis of whole tissue scans revealed close proximity of CXCL10/CXCL11+ malignant cells with IFNγ+ and CXCL13+CD3+ T cells.
Figure 84B:
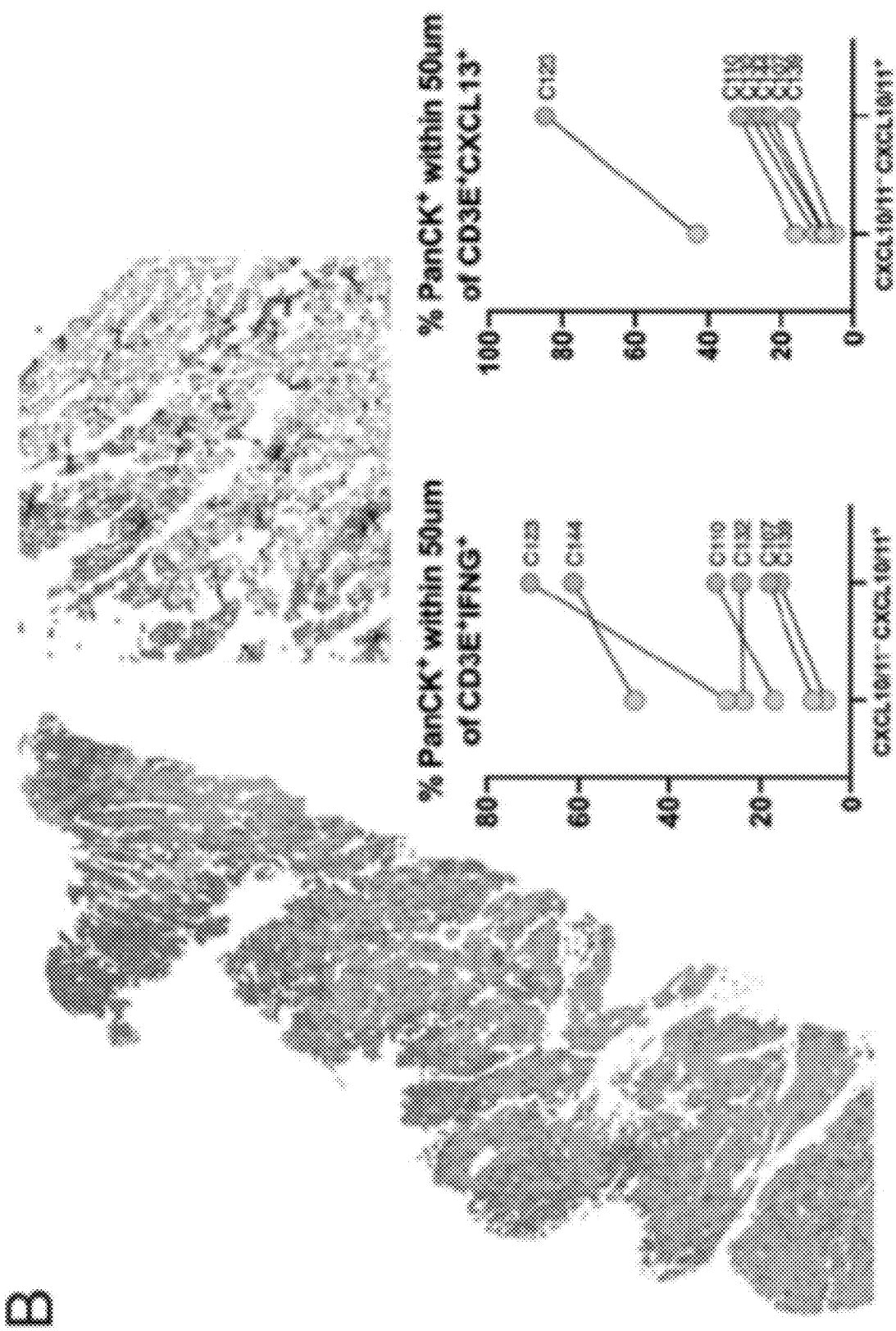
Figure 85:
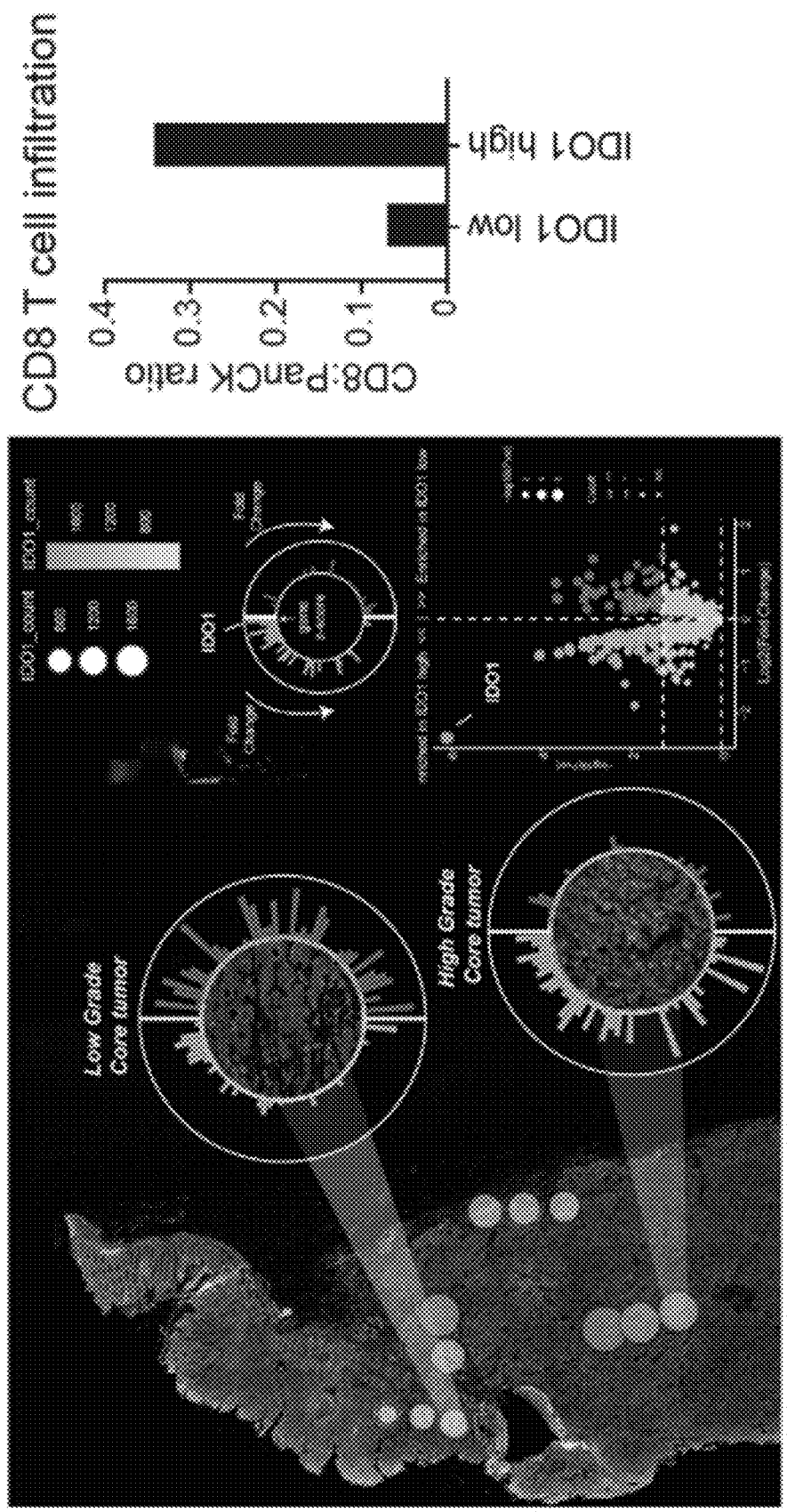
FIG. 85—Upregulation of inhibitory molecules such as IDO1 in high grade areas with high densities of CD8+ T cells.

The second network contained ISG programs in malignant, myeloid, and stromal cells and was associated with an activated T cell program characterized by CXCL13, RBPJ, and PD-1. This T cell program was present in both CD4+ and CD8+ T cells and highly enriched in a subset of MSI specimens. FIG. 82 shows pairwise correlations between the activities of the malignant ISG program, the myeloid ISG and the CXCL13 T cell program across all MSI CRC specimens. Of note, CD8+CXCL13+PD-1-high T cells emerge as T cell subset with anti-tumor potential in human tumors[2]. CD4+CXCL13+ T cells were recently described as peripheral T helper cells in rheumatoid arthritis[3] and in MSI CRC[4] (consistent with the observations). Based on receptor/ligand analyses, Applicants predicted the following intra-tumoral feedforward loop: IFNγ from CXCR3+CXCL13+ T cells induces ISG expression in malignant cells. Among these ISGs are the CXCR3 ligands CXCL10 and CXCL11 which further attract CXCR3+CXCL13+ T cells, thus driving accumulation and potentially exhaustion of T cells. Profiling of selected MSI CRC specimens by NanoString GeoMx DSP confirmed spatial association of CXCL13+ T cells and ISG+ malignant cells within the tumor tissue (FIG. 83). Intra-tumoral activity of the CXCR3 system was recently shown to be required for the efficacy of anti-PD-1 therapy in the MC38 tumor model[5,6]. Furthermore, a recent neoadjuvant immunotherapy study of early-stage colon cancer found both IFNγ scores and CXCL13 expression upregulated posttreatment[7], suggesting that the CXCL13+ T cell—malignant ISG circuit might indicate active antitumor responses. To visualize and quantify this cellular interaction network with single cell resolution, Applicants stained the CRC specimens by multiplex ISH/IF and revealed how CXCL10/CXCL11+ malignant cells formed focal structures at the interface between malignant glands and stromal bundles within the tumor body, around either CXCL13+, IFNγ+ or double-positive T cells (FIG. 84). In some patients, these structures expanded to large regions which were associated with high grade medullary morphology. Of note, these high-grade areas with high densities of CXCL13+ T cells were also associated with an upregulation of inhibitory molecules such as PD-L1 and IDO1 (FIG. 85), suggesting that these regional areas of ongoing but insufficient anti-tumor responses might promote immune evasion. In summary, this work uncovers the cellular elements of human colorectal cancer and reveals how malignant cells, stromal cells, and immune cells engage in spatially organized immune responses.

Example 6—Discussion

Single cell RNA sequencing has unlocked insights into the cell types and transcriptional programs of many human healthy and diseased tissues. However, removed from the spatial context, the interpretation of transcriptional signatures and the prediction of cellular interactions has been challenging. By integrating single cell RNA sequencing with spatial profiling, Applicants were able to discover how and where in human colorectal cancer malignant cells engaged in interactions with stromal cells and the immune system: In a subset of MSI CRC, ISG-positive malignant cells formed focal structures around putative anti-tumor CXCL13+ and IFNγ+ T cells. In both MSS and MSI CRC, CXCL1+ malignant cells localized with inflammatory fibroblasts, monocytes, and granulocytes to the luminal surface, which could represent an inflammatory wound healing response associated with epithelial damage, mechanical stress and/or microbial contact. While immune responses in tumors have been studied for decades, several aspects of human tumor biology emerge that are not fully recapitulated in mouse models. Of note, CXCL13+ T cells which formed the center of the IFNγ driven interaction hub do not exist in mice. CXCL13 is classically known as B cell attracting chemokine and critical for the germinal center formation in lymphoid structures[8]. Recent reports suggest that tertiary lymphoid structures (TLS) and B cells promote immunotherapy response[9,10].

Figure 86:
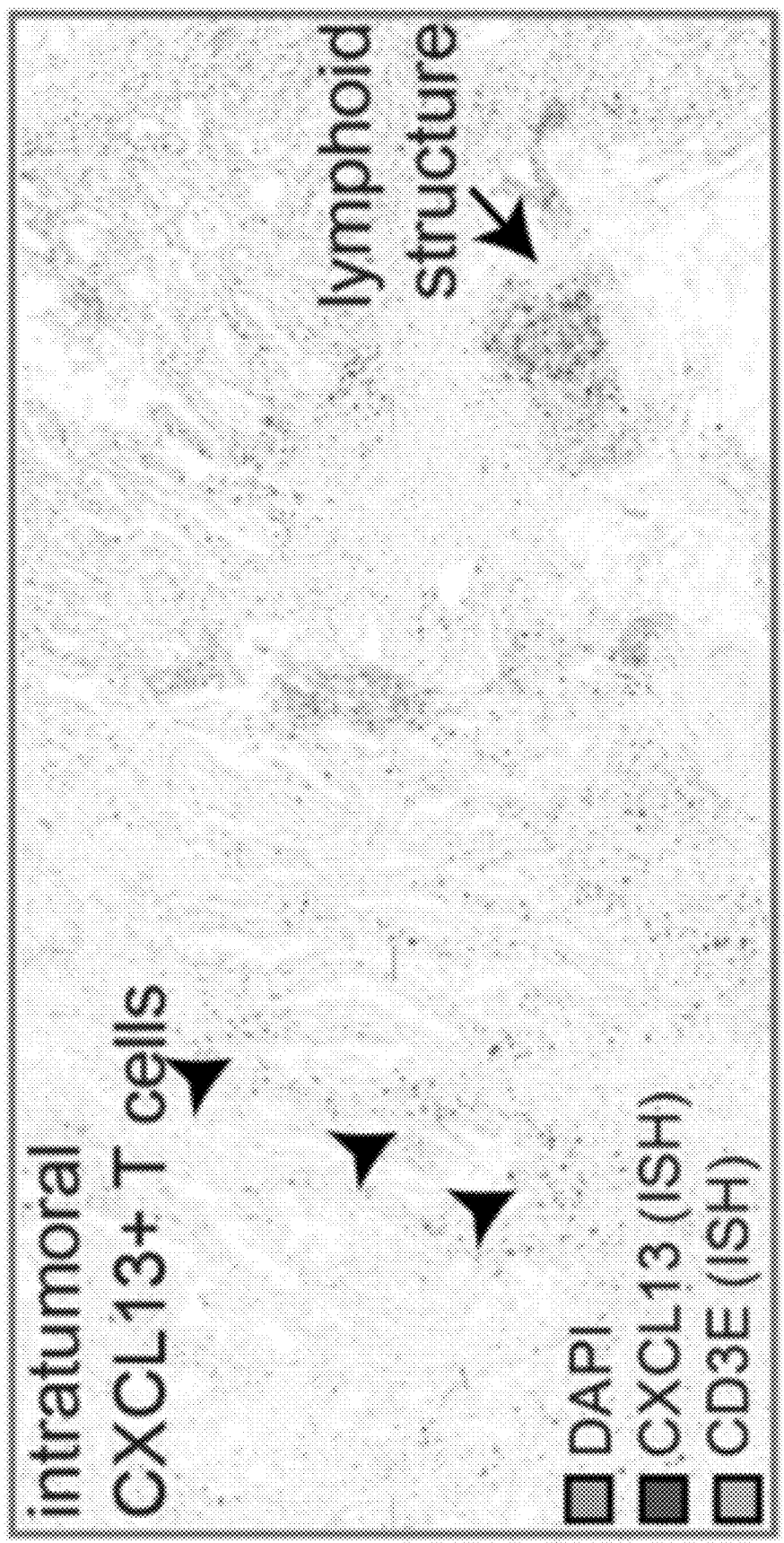
FIG. 86—CXCL13+ T cells were found in the tumor bed, far away from CXCL13+ lymphoid structures.
Figure 87:
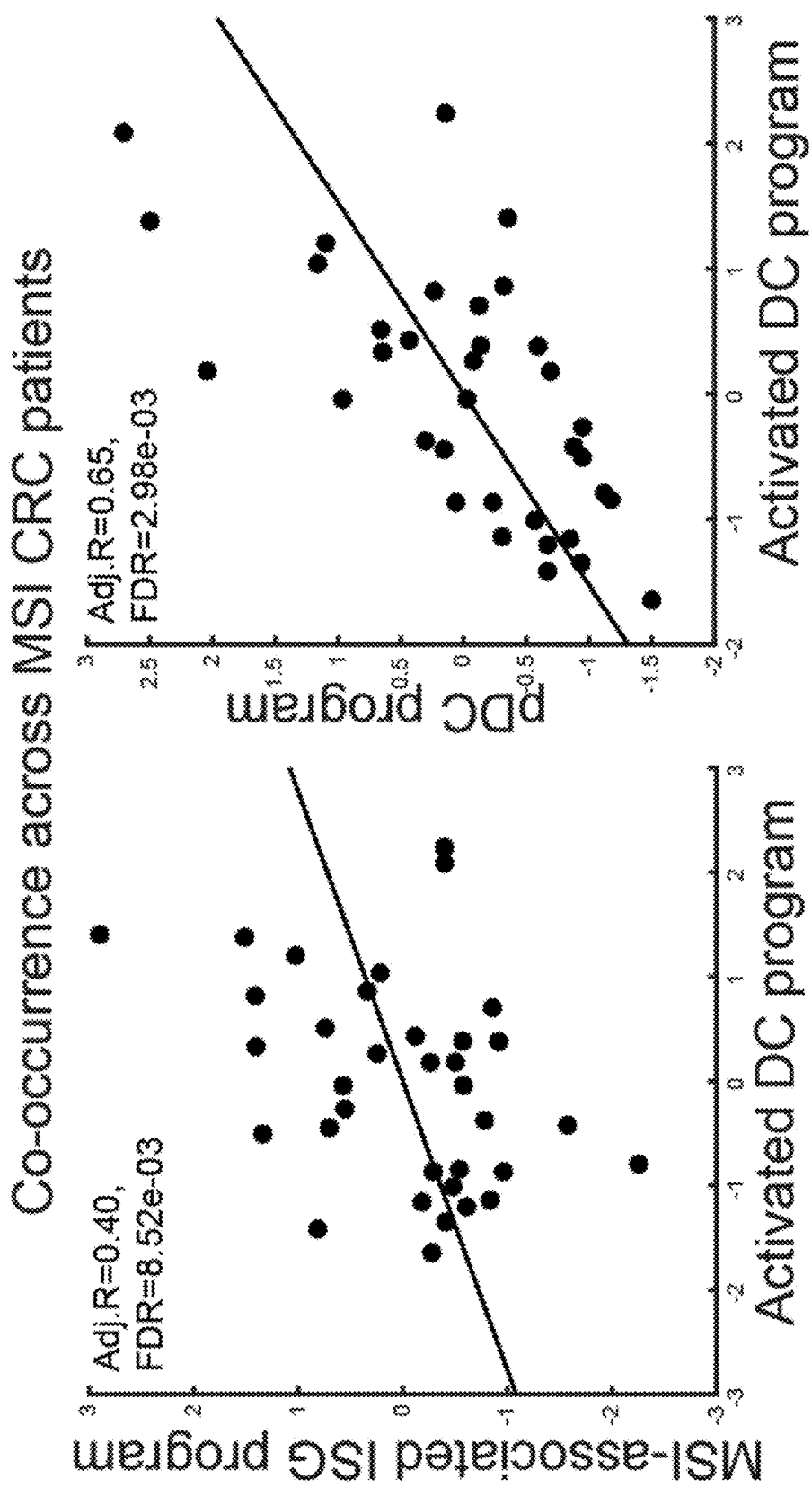
FIG. 87—Correlation between the activities of the activated DC program, the MSI-associated ISG program in malignant cells and the pDC program. Each dot is one MSI CRC specimen.

However, TLS are difficult to study since they do not form in transplantable mouse models. Thus, the mechanisms by which TLS promote anti-tumor immunity are still unknown. Intriguingly, the data suggests that CXCL13+ T cells accumulated in the tumor bed far away from TLS, which are normally found at the invasive margin (FIG. 86). Whether the intratumoral accumulations of CXCL13+ T cells might represent more primitive precursors of lymphoid-like structures remains to be determined. Interestingly, Jansen et al.[11] recently described intra-tumoral niches of MHCII+ cells in prostate, kidney, and bladder cancer. These niches resembled T cell zones of lymphatic tissue and were proposed to maintain and differentiate stem-like TCF7+CD8+ T cells, the T cell subset that is enriched in patients and essential in mice responding to immunotherapy[12]. The identity of the MHCII+ cells was not further assessed in this study. MHCII genes can be upregulated by IFNγ and were strongly expressed in the ISG+ malignant and myeloid cells that co-occurred with CXCL13+ T cells in the scRNAseq data set. Moreover, CXCL13+ T cells produce high levels of IL-21 based on the scRNAseq data, which could serve as a niche factor for the TCF7+ T cell pool. Thus, the intratumoral structures that Applicants identified in MSI CRC tumors could have the potential to serve as an intratumoral niche for stem-like T cells. Another (not mutually exclusive) hypothesis is that these organized cellular networks are required for optimal T cell priming or re-stimulation of T cells in the tumor. Activated DCs were rare in the tumors, but interestingly co-occurred with ISG+ malignant cells and pDCs (FIG. 87). pDCs showed the by far highest expression of CXCR3 in the scRNAseq data. Thus, recruitment of pDCs by CXCR3 ligand expressing malignant and myeloid cells, leading to spatial coordination with activated DCs is an intriguing hypothesis. Of note, functional collaboration between CD8+ T cells, pDCs, and XCR1+ DCs for optimal T cell priming was described in viral infections[13] and a previous study pointed to the possibility, that naïve T cells can get activated within the tumor in the absence of lymphocyte trafficking from lymphnodes[14]. Apart from these potential roles of the malignant ISG—CXCL13 T cell interaction network in the formation of anti-tumor immunity, it will be equally important to understand if and how these structures might become hotspots for the development of immune evasion, immunosuppression, and T cell exhaustion. Importantly, the ISG programs in myeloid and malignant cells included immunosuppressive molecules such as PD-L1 or IDO1 that can protect malignant cells from T cell attacks. Of note, IFNγ, was proposed to epigenetically imprint B16 melanoma cells, thereby driving a multigenic resistance program" and shown to cause de-differentiation of melanoma cells[16], thus promoting transcriptional plasticity and tumor evolution. Whether or not these processes occur in human CRC remains to be determined and will be subject of mechanistic follow-up studies.

REFERENCES

1 Mlecnik, B. et al. Integrative Analyses of Colorectal Cancer Show Immunoscore Is a Stronger Predictor of Patient Survival Than Microsatellite Instability. Immunity 44, 698-711, doi:10.1016/j.immuni.2016.02.025 (2016).
2 Thommen, D. S. et al. A transcriptionally and functionally distinct PD-1+CD8+ T cell pool with predictive potential in non-small-cell lung cancer treated with PD-1 blockade. Nat. Med. 24, 994-1004, doi:10.1038/s41591-018-0057-z (2018).
3 Rao, D. A. et al. Pathologically expanded peripheral T helper cell subset drives B cells in rheumatoid arthritis. Nature 542, 110-114, doi:10.1038/nature20810 (2017).
4 Zhang, L. et al. Lineage tracking reveals dynamic relationships of T cells in colorectal cancer. Nature 564, 268-272, doi:10.1038/s41586-018-0694-x (2018).
5 Chow, M. T. et al. Intratumoral Activity of the CXCR3 Chemokine System Is Required for the Efficacy of Anti-PD-1 Therapy. Immunity 50, 1498-1512.e1495, doi:10.1016/j.immuni.2019.04.010 (2019).
6 House, I. G. et al. Macrophage-Derived CXCL9 and CXCL10 Are Required for Antitumor Immune Responses Following Immune Checkpoint Blockade. Clin. Cancer Res. 26, 487-504, doi:10.1158/1078-0432.CCR-19-1868 (2020).
7 Chalabi, M. et al. Neoadjuvant immunotherapy leads to pathological responses in MMR-proficient and MMR-deficient early-stage colon cancers. Nat. Med. 26, 566-576, doi:10.1038/s41591-020-0805-8 (2020).
8 Pitzalis, C., Jones, G. W., Bombardieri, M. & Jones, S. A. Ectopic lymphoid-like structures in infection, cancer and autoimmunity. Nat. Rev. Immunol. 14, 447-462, doi:10.1038/nri3700 (2014).
9 Helmink, B. A. et al. B cells and tertiary lymphoid structures promote immunotherapy response. Nature 577, 549-555, doi:10.1038/s41586-019-1922-8 (2020).
10 Petitprez, F. et al. B cells are associated with survival and immunotherapy response in sarcoma. Nature 577, 556-560, doi:10.1038/s41586-019-1906-8 (2020).
11 Jansen, C. S. et al. An intra-tumoral niche maintains and differentiates stem-like CD8 T cells. Nature, doi:10.1038/s41586-019-1836-5 (2019).
12 Sade-Feldman, M. et al. Defining T Cell States Associated with Response to Checkpoint Immunotherapy in Melanoma. Cell 175, 998-1013 e1020, doi:10.1016/j.cell.2018.10.038 (2018).
13 Brewitz, A. et al. CD8+ T Cells Orchestrate pDC-XCR1+ Dendritic Cell Spatial and Functional Cooperativity to Optimize Priming. Immunity 46, 205-219, doi:10.1016/j.immuni.2017.01.003 (2017).
14 Fankhauser, M. et al. Tumor lymphangiogenesis promotes T cell infiltration and potentiates immunotherapy in melanoma. Sci Transl Med 9, doi:10.1126/scitranslmed.aal4712 (2017).
15 Benci, J. L. et al. Tumor Interferon Signaling Regulates a Multigenic Resistance Program to Immune Checkpoint Blockade. Cell 167, 1540-1554 e1512, doi:10.1016/j.cell.2016.11.022 (2016).
16 Tsoi, J. et al. Multi-stage Differentiation Defines Melanoma Subtypes with Differential Vulnerability to Drug-Induced Iron-Dependent Oxidative Stress. Cancer Cell 33, 890-904.e895, doi:10.1016/j.ccell.2018.03.017 (2018).

Tables

TABLE 1

| All immune NMF programs | | | | | | | |
|---|---|---|---|---|---|---|---|
| outTop-Genes1 | outTop-Genes2 | outTop-Genes3 | outTop-Genes4 | outTop-Genes5 | outTop-Genes6 | outTop-Genes7 | outTop-Genes8 |
| TNFRSF4 | TXNIP | IL7R | HLA-B | ENO1 | IL1B | CD7 | EEF1A1 |
| TNFRSF18 | ZFP36L2 | LTB | HLA-C | PSME2 | G0S2 | GZMA | EEF1B2 |
| BATF | CXCR4 | CD3E | HLA-A | PKM | FTH1 | CCL5 | EEF2 |
| RGS1 | BTG1 | CD3D | B2M | CALR | SOD2 | HOPX | TPT1 |
| IL32 | TSC22D3 | GIMAP7 | HLA-E | ATP5B | CXCL2 | TMIGD2 | NACA |
| TIGIT | CIRBP | CD40LG | HLA-F | PDIA3 | C15orf48 | KLRC2 | NPM1 |
| CTLA4 | DDIT4 | LEPROTL1 | PSME1 | PGK1 | CCL3 | CD160 | HNRNPA1 |
| IL2RA | CYTIP | RORA | BSG | PSMB1 | BCL2A1 | ID2 | NBEAL1 |
| DUSP4 | PIK3IP1 | GIMAP4 | PSMB9 | PSMA4 | IL1RN | ITGA1 | GLTSCR2 |
| BIRC3 | CALM2 | AAK1 | TMBIM6 | SERBP1 | CXCL3 | KIR2DL4 | FAU |
| ICOS | H3F3B | CD3G | TFF3 | ATP5G3 | CCL20 | HCST | UBA52 |

TABLE 1-continued

All immune NMF programs

| | | | | | | | |
|---|---|---|---|---|---|---|---|
| PHLDA1 | SKP1 | ODF2L | KRT18 | PSMA7 | NAMPT | CKLF | EIF3E |
| CORO1B | KLF2 | ACAP1 | PIGT | TPI1 | IER3 | SPRY1 | PABPC1 |
| CARD16 | VAMP2 | CD6 | NUCB1 | PSMB3 | PLAUR | CD96 | EEF1D |
| TNFRSF1B | PPP1R2 | MGAT4A | GPR108 | XRCC6 | PTGS2 | CD247 | SLC25A6 |
| SOD1 | MYL12A | BCL11B | TFF1 | HNRNPK | CD44 | RHOC | TOMM7 |
| GBP2 | CNBP | TRAF3IP3 | OS9 | PSMA3 | SLC2A3 | C9orf142 | PFDN5 |
| SPOCK2 | YPEL3 | ABRACL | KRT8 | HNRNPM | CXCL1 | OSTF1 | BTF3 |
| LAIR2 | SMAP2 | TRAT1 | IGSF8 | ATP5A1 | SAT1 | ABI3 | NAP1L1 |
| FOXP3 | IFI16 | FLT3LG | HLA-G | PSMD8 | CCL3L1 | PTPN22 | COX4I1 |
| SH2D2A | CIR1 | TC2N | B3GALT4 | C1QBP | IVNS1ABP | SSBP4 | EIF3L |
| ARID5B | RCSD1 | EVL | MAGED2 | PSMA5 | PNRC1 | ARHGAP9 | EIF3F |
| IL2RG | EAPP | SEPT1 | PPP1R1B | LDHA | TNFAIP6 | SCML4 | UQCRB |
| ICA1 | PTGES3 | GIMAP2 | BTD | PGAM1 | PLEK | STK17A | EIF3K |
| PTPN7 | SESN1 | TTC39C | LENG1 | SSBP1 | TREM1 | STOM | C6orf48 |
| SLA | RSBN1 | AQP3 | P4HTM | CCT5 | NINJ1 | GPR82 | EIF3H |
| PMAIP1 | ANAPC16 | ITK | SOD3 | HNRNPA2B1 | AQP9 | PCID2 | ATP5G2 |
| TBC1D4 | ELF1 | RCAN3 | PRSS8 | PSMB6 | ADM | METTL9 | HINT1 |
| MAGEH1 | TRIM22 | OCIAD2 | CDX1 | HSPA5 | PPIF | RARRES3 | COX7C |
| CREM | C11orf58 | AMICA1 | STOML1 | PSMA1 | SLC25A37 | PRKCH | EIF4B |
| MAF | CCNDBP1 | TNFAIP8 | AP1M2 | SNRPB2 | INHBA | RGL4 | EIF3G |
| UGP2 | MEAF6 | SERINC5 | ADCK3 | PSMA2 | GK | FYN | SNHG8 |
| RTKN2 | SBDS | SEPT6 | CKMT1B | GHITM | ICAM1 | UBASH3B | SSR2 |
| GADD45A | HBP1 | ETS1 | DFFB | XRCC5 | BNIP3L | KRT81 | CD48 |
| NDFIP1 | SRSF8 | CAMK4 | RBM14-RBM4 | PSMD7 | VEGFA | SYTL3 | FXYD5 |
| TNFRSF9 | SP100 | PTGER4 | FUT3 | CCT7 | HIF1A | PITPNC1 | COMMD6 |
| BTG3 | MED6 | IL17A | TPD52L1 | CCT6A | NFKBIA | P2RY11 | EIF3D |
| ISCU | KLF9 | RBL2 | ENTPD2 | MYL12B | ATP13A3 | CAPN12 | UXT |
| LCK | TARSL2 | EMB | HOXD-AS2 | RAN | PFKFB3 | PELO | PCBP2 |
| SLAMF1 | TRIM4 | CD2 | FAM209B | PARK7 | OLR1 | COMMD7 | CCNI |
| MAP1LC3A | SUCLG2 | IKZF1 | PDX1 | CCT4 | IL1A | GNAS | LDHB |
| ARL6IP5 | TBCC | TCF7 | SEMA3B | PSMC5 | HILPDA | PRKACB | ST13 |
| GALM | ALDH9A1 | OXNAD1 | PLA2G4F | MDH2 | TIMP1 | MSH3 | YBX1 |
| RASSF5 | CHMP7 | ARHGAP15 | SNORA80 | CCT2 | LITAF | LAT2 | RSL24D1 |
| PRDX2 | MKRN1 | CCR6 | TUBA3C | PSMB2 | CYSTM1 | STARD3NL | C19orf43 |
| IL1R2 | ASB8 | DENND2D | MSH5-SAPCD1 | ATP5C1 | CXCL5 | CCDC85B | UBXN1 |
| CUL9 | PDCD7 | PERP | CXCL17 | MDH1 | ETS2 | APOBR | TOMM20 |
| CD70 | RNF113A | NMRK1 | SLC22A3 | VDAC1 | NFKBIZ | SLC25A39 | FBL |
| TMEM173 | LIX1L | ZAP70 | | PA2G4 | HCAR2 | EPS8L2 | RSL1D1 |
| GATA3 | ZSCAN18 | GZMM | | PHB | OSM | RNF187 | EIF1 |
| CD28 | CDC37L1 | MAL | | SSB | EREG | FAM173A | NSA2 |
| EID1 | GGPS1 | PRR5 | | PSMB8 | IL6 | ATP8B4 | ERP29 |
| RAP1A | SNAI3 | TOB1 | | UBE2L3 | NDRG1 | SLC9A3R1 | ALKBH7 |
| ENTPD1 | CGRRF1 | RGS14 | | NME1 | MXD1 | DZIP3 | EVI2B |
| FAS | POLR2C | TECR | | EIF3I | EHD1 | OBFC1 | EDF1 |
| ZNRF1 | FBXO8 | STAT4 | | CCT3 | UBE2B | HIC1 | ZNF90 |
| LAPTM4B | ZNF559 | PTGER2 | | TUFM | CCL3L3 | ABCB1 | HIGD2A |
| RHOF | GGNBP2 | C14orf64 | | RBM8A | CCRL2 | UBAC2 | CMPK1 |
| TNIP2 | ZNF766 | IF144 | | SAP18 | PI3 | KRT86 | EIF3M |
| GLRX | TLE4 | TRAPPC6A | | COPE | ZNF267 | PTPN4 | OXA1L |
| NINJ2 | CDC40 | SUN2 | | CCT8 | FCGR2A | AKAP5 | COX7A2L |
| LAYN | ANKRD46 | PASK | | PRMT1 | LCP2 | S100A13 | SNRPD2 |
| PMVK | KBTBD3 | DPP4 | | CDC37 | INSIG1 | NARF | EIF4A2 |
| FANK1 | METTL18 | SORL1 | | HNRNPF | BEST1 | FAM3C | LINC00493 |
| HTATIP2 | AMN1 | | | PSMB7 | SDCBP | GYG1 | EIF2S3 |
| CFLAR | TBC1D10A | | | PSMC4 | BHLHE40 | PLA2G16 | ATP5O |
| IL21R | PPIL4 | | | EIF6 | MAP1LC3B | CD244 | ARL6IP4 |
| ARID5A | ORC4 | | | COX5A | PHLDA2 | FSD1 | CSDE1 |
| EPSTI1 | DUSP11 | | | VCP | UPP1 | ISYNA1 | EIF2A |
| CCND2 | TUBD1 | | | EIF2S2 | ARL5B | EFCAB4A | ABHD14B |
| SNX9 | PHF1 | | | PUF60 | FLT1 | FBXO2 | UFC1 |
| ARPP19 | ANKZF1 | | | NUDC | PDE4B | ZBTB16 | ATP5D |
| GBP5 | TCEANC | | | PSMD4 | RIPK2 | GFOD1 | EPB41L4A-AS1 |
| TANK | ZNF230 | | | ARF1 | NBN | ABHD15 | IGBP1 |
| | ZNF540 | | | SLC25A3 | ATP2B1 | APBB1IP | CCNG1 |
| | SUPV3L1 | | | RNH1 | GPR84 | HAGHL | CLNS1A |
| | MED7 | | | CYC1 | S100P | ADRB1 | HADHA |
| | PNPLA2 | | | PSMD13 | SNAPC1 | | POLR1D |
| | ZNF180 | | | PTPN6 | FNDC3B | | PEBP1 |
| | BBS2 | | | ADRM1 | NLRP3 | | SEC11A |
| | IFIT5 | | | ATP5F1 | AZIN1 | | PRKCSH |
| | LIPT1 | | | WDR1 | PLEKHB2 | | NACA2 |
| | PPCS | | | NDUFB8 | HK2 | | NDUFB5 |
| | ARMCX5 | | | HSPA9 | TNF | | IMPDH2 |
| | KCTD6 | | | NDUFAB1 | HES4 | | ZFAND1 |
| | TUT1 | | | TALDO1 | RNF19B | | SSU72 |
| | SNAPC3 | | | PSMB10 | FLOT1 | | LETMD1 |
| | ZNF639 | | | HSD17B10 | LPCAT1 | | TNFRSF14 |
| | ZNF181 | | | | IRAK2 | | PPDPF |

TABLE 1-continued

All immune NMF programs

| | | | | | | PROK2 | CASP4 |
|---|---|---|---|---|---|---|---|
| | | | | | | FCGR3B | EEF1G |
| ZNF211 | | | | | | ERRFI1 | NHSL2 |
| ZNF671 | | | | | | MMP19 | SNHG7 |
| | | | | | | ANGPTL4 | C8orf59 |
| | | | | | | TNFSF15 | CAMLG |
| | | | | | | GADD45B | TIMM9 |
| | | | | | | CCL4L2 | PHB2 |
| | | | | | | EIF1B | DPH5 |
| | | | | | | ANPEP | DAP3 |
| | | | | | | LIMS1 | MAF1 |

| outTop-Genes9 | outTop-Genes10 | outTop-Genes11 | outTop-Genes12 | outTop-Genes13 | outTop-Genes14 | outTop-Genes15 | outTop-Genes16 |
|---|---|---|---|---|---|---|---|
| SPP1 | S100A4 | CXCL13 | TXN | ACTG1 | HSPA1A | GNLY | CD74 |
| APOC1 | SH3BGRL3 | CD8A | HLA-DQA1 | HMGN1 | HSPA1B | GZMB | CD37 |
| CSTB | CLIC1 | CD8B | PPA1 | LIMD2 | HSP90AA1 | CCL4 | VPREB3 |
| APOE | S100A11 | IFNG | HLA-DPA1 | ARPC2 | DNAJB1 | PRF1 | HLA-DRA |
| CTSD | ARHGDIB | GZMH | GSTP1 | MARCKSL1 | HSPB1 | KLRD1 | CD79A |
| CTSB | VIM | LAG3 | HLA-DPB1 | ARPC3 | JUN | CST7 | MS4A1 |
| GPNMB | ARPC1B | RBPJ | FSCN1 | H3F3A | HSPE1 | CMC1 | CD52 |
| LGALS1 | COTL1 | ITM2A | LSP1 | TCEA1 | UBC | KLRC1 | TNFRSF13C |
| LGALS3 | MYL6 | GZMK | CCL19 | TCL1A | HSPH1 | KLRF1 | CD79B |
| FABP5 | PFN1 | PDCD1 | GSN | LRMP | HSPA8 | IFITM2 | BANK1 |
| RNASE1 | S100A6 | RAB27A | LAMP3 | ACTB | HSPA6 | CLIC3 | LAPTM5 |
| CCL18 | TAGLN2 | MT2A | CCL22 | UCP2 | DNAJA1 | SPON2 | ARHGAP24 |
| ANXA2 | CALM1 | CXCR6 | IDO1 | HMGA1 | CACYBP | CHST12 | MEF2C |
| NUPR1 | PLP2 | CRTAM | GPX4 | ATP5L | RHOB | SAMD3 | MARCH1 |
| IFI6 | GPSM3 | CLEC2B | HLA-DRB1 | CORO1A | HSPD1 | C1orf21 | BCL11A |
| GLUL | EMP3 | CLEC2D | ALDH2 | BASP1 | ZFAND2A | BIN2 | HLA-DQB1 |
| CCL2 | PPP1R18 | VCAM1 | CSF2RA | NEIL1 | IER5 | MAPK1 | FCER2 |
| MMP9 | DRAP1 | SUPT3H | CCR7 | METAP2 | DNAJA4 | PYHIN1 | CD19 |
| LAMP1 | CAPZB | TUBA4A | GABARAPL2 | BRK1 | RGS2 | ARPC5L | DRAM2 |
| MGST3 | TPM3 | ZNF683 | GPR183 | PPP1CC | DNAJB4 | LYAR | ADAM28 |
| FBP1 | LY6E | SH2D1A | HLA-DQA2 | BCAS4 | SERPINH1 | TBX21 | POU2F2 |
| GSTO1 | CIB1 | MIR155HG | LGALS2 | RHOA | BAG3 | PTGDR | LY86 |
| TREM2 | PPP1CA | TNFSF4 | SYNGR2 | PARP1 | CLK1 | TTC38 | ORAI2 |
| MT1G | CFL1 | OASL | CCL17 | UBE2D3 | DEDD2 | NCR3 | HVCN1 |
| ATP6V1F | TSPO | APOBEC3H | EBI3 | SRSF7 | UBB | YPEL1 | IRF8 |
| MT1X | GNB2 | PTMS | PPP1R14A | ARPC5 | NEU1 | MATK | HLA-DOB |
| CD68 | TPM4 | CPNE7 | RAB9A | EZR | GADD45G | PTGDS | PDLIM1 |
| BRI3 | CRIP1 | APOBEC3G | LAD1 | LYPLA1 | ABHD3 | MCTP2 | SELL |
| CAPG | TBCB | F2R | GRSF1 | SLC25A5 | MYLIP | XCL1 | RALGPS2 |
| MMP12 | ZYX | CCR5 | CLIC2 | MOB1A | ID3 | SH2D1B | BLK |
| MARCO | RAC2 | TBCD | CD1E | SERPINA9 | FKBP4 | PRSS23 | CD72 |
| ASAH1 | RHOG | HAVCR2 | NUB1 | DAAM1 | CDC42EP3 | NCAM1 | PKIG |
| LILRB4 | RGS19 | CARS | RAMP1 | BCL7A | DNAJB6 | IGFBP7 | GAPT |
| RAB13 | ARPC4 | MAP4K1 | DAPP1 | ZFAND6 | ANKRD37 | AKR1C3 | BLNK |
| MSR1 | FKBP8 | NBL1 | HLA-DRB5 | ZCCHC7 | SQSTM1 | FCRL6 | RASGRP2 |
| FCGR3A | CD99 | TOX | CDKN1A | LSM10 | IFI44L | IGFBP2 | LY9 |
| SDC2 | CNN2 | CBLB | PKIB | LMO2 | RGS16 | EOMES | FCRLA |
| BCAP31 | ARRB2 | ARL3 | GPR157 | GMDS | DDIT3 | BPGM | LYL1 |
| PDXK | ARHGDIA | SNAP47 | PEA15 | DBI | CHORDC1 | GTF3C1 | TSPAN13 |
| MT1H | ETHE1 | C19orf66 | CD86 | BIK | SLC5A3 | TSPAN32 | CLECL1 |
| SDS | CAPN2 | NELL2 | RELB | LPP | TSPYL2 | GNPTAB | TLR10 |
| ACP5 | RAB5C | PSTPIP1 | MAP3K13 | ISG20 | IRF7 | AFAP1L2 | TCF4 |
| IL4I1 | DOK2 | MYO7A | CD83 | SNX3 | RABGGTB | IFITM1 | MYC |
| CYP27A1 | PDLIM2 | GABARAPL1 | TUBA1A | MBD4 | MB21D1 | PDGFRB | CD22 |
| SNX10 | CALHM2 | FASLG | CLEC10A | STAG3 | GEM | GK5 | FAM129C |
| MMP14 | MYO1G | TNIP3 | RASSF4 | PTPN18 | C17orf67 | KLHDC4 | HHEX |
| CORO1C | MIEN1 | SHISA5 | NFKB1 | C14orf166 | HSD17B7 | C11orf21 | TNFRSF13B |
| ATP6V0B | PYCARD | GALNT2 | SPINT2 | RRAS2 | ISG15 | TGFBR3 | NCF1 |
| NPL | CMTM3 | JAKMIP1 | MTHFD2 | ACY3 | NFKBIE | CARD11 | CHI3L2 |
| HMOX1 | MAPKAPK3 | MSC | RAB11A | PGLS | HIST2H2AA3 | SELPLG | PPM1K |
| FN1 | | ZFYVE28 | POGLUT1 | PPP2CA | DNAJB2 | SIRT2 | TRAF5 |
| CXCL16 | | DAPK2 | TUBB6 | OGG1 | CDKN2AIP | OSBPL5 | FCRL1 |
| HEXB | | ZNRD1 | KYNU | CSK | MX1 | KIR3DX1 | QRSL1 |
| S100A10 | | PDLIM4 | NCCRP1 | GGA2 | MID1IP1 | PRR5L | RIC3 |
| SLC16A3 | | PPP2R2B | REPIN1 | RFTN1 | ARL4D | FEZ1 | CXXC5 |
| ANXA5 | | REC8 | NET1 | SIAH2 | PHYH | SPTSSB | FCRL2 |
| GM2A | | SLAMF6 | HLA-DQB2 | SMARCB1 | GBP3 | PLEKHA1 | SCIMP |
| SCARB2 | | ANKRD35 | MGLL | RAP1B | IER5L | TFDP2 | CR2 |
| LIPA | | CHN1 | IL13RA1 | TBCA | MLKL | C9orf139 | TFEB |
| CHI3L1 | | LINC00158 | HMSD | GDI2 | CPA5 | MIB2 | AFF3 |
| TIMP2 | | BTN3A1 | FLT3 | GRHPR | TNFSF14 | TSPAN2 | GPR18 |
| RALA | | SRGAP3 | CERS6 | ZNF581 | TMEM140 | HBA1 | CXCR5 |
| CNIH4 | | ETV1 | TRIP10 | PRDX6 | CNOT8 | MVD | RABEP2 |

TABLE 1-continued

| All immune NMF programs | | | | | | |
|---|---|---|---|---|---|---|
| SCD | GFI1 | PAK1 | LYPLAL1 | ACTRT3 | LRRC28 | CNR2 |
| ATOX1 | CD2BP2 | BATF3 | RGS13 | MAP7D1 | WDSUB1 | PRKCB |
| LHFPL2 | METTL23 | TNFAIP2 | CD53 | RNF114 | RNF165 | PAWR |
| GNS | CLSTN3 | OPN3 | WDR66 | HIST1H3H | PLCXD2 | PAX5 |
| LGMN | BIN1 | IL15 | LSM14A | BBC3 | TMED1 | SYS1 |
| CCL7 | SARDH | FYTTD1 | POLD4 | EPS8 | ADAMTS10 | CEPT1 |
| PLIN2 | ZNF80 | KIF2A | VNN2 | NKR | LIM2 | SP140 |
| CD81 | TIMD4 | BCL2L14 | SH3BGRL | SPINK4 | FAM8A1 | FAM177B |
| VAT1 | DGKZ | CD80 | ATPIF1 | HERC5 | MLC1 | LPAR5 |
|  | CD200R1 | LY75 | SNAP23 | SERTAD3 | LGALS9B | SYPL1 |
|  | RBCK1 | KDM2B | KLHL6 | POMC | GNAL |  |
|  | WIPF3 | ZFAND5 | ODC1 | MICA | PLEKHG3 |  |
|  | CPNE2 | TRAFD1 | S1PR2 | YPEL2 | BCO2 |  |
|  | KCNK5 | FAM60A | TRAPPC1 | SNORA81 | SBK1 |  |
|  | RNF167 | LIMCH1 | DEF8 | KBTBD6 | MIR181A2HG |  |
|  | CLIC5 | ACOT9 | UBE2E1 | CLK3 | SLC1A7 |  |
|  | SLC27A2 | TREML1 | SRP9 | HSPA2 | BOK |  |
|  | AUH | TSPAN33 | CCDC144A | HSP90AB1 | ADAMTS1 |  |
|  | BTN3A3 |  | SELT | RASD1 | ESM1 |  |
|  | PRKD2 |  |  | PIK3R3 | EFNA5 |  |
|  | DDX60 |  |  | ING1 | PDZD4 |  |
|  | PLEKHF1 |  |  | HIST1H2BN |  |  |
|  | TSPAN14 |  |  | OLFM4 |  |  |
|  | ARHGEF3 |  |  | RND1 |  |  |
|  | KLRC4 |  |  | FRAT2 |  |  |
|  | CCDC64 |  |  | CCDC130 |  |  |
|  | HECTD2 |  |  | SLC2A1 |  |  |
|  | ARHGEF1 |  |  | C3orf38 |  |  |
|  | B3GNT2 |  |  | HIST3H2BB |  |  |
|  | KIF21A |  |  | RXRB |  |  |
|  | TGIF1 |  |  | SCRG1 |  |  |
|  |  |  |  | MKNK2 |  |  |
|  |  |  |  | KCTD11 |  |  |

| outTopGenes17 | outTopGenes18 | outTopGenes19 | outTopGenes20 | outTopGenes21 | outTopGenes22 | outTopGenes23 | outTopGenes24 |
|---|---|---|---|---|---|---|---|
| SSR4 | S100A9 | C1QB | TMSB4X | STMN1 | FOS | MALAT1 | TPSB2 |
| MZB1 | S100A8 | C1QC | ATP5E | HMGB2 | JUNB | NEAT1 | TPSAB1 |
| XBP1 | LYZ | MS4A6A | UQCR11 | H2AFZ | DUSP1 | HNRNPH1 | CPA3 |
| HERPUD1 | FCN1 | NPC2 | POLR2L | TUBA1B | ZFP36 | SET | HPGDS |
| DERL3 | LST1 | SEPP1 | PTMA | TUBB | BTG2 | CDC42 | LTC4S |
| FKBP11 | TYROBP | GRN | ATP5I | HIST1H4C | CD69 | C1orf56 | MS4A2 |
| SEC11C | VCAN | FCGRT | SERF2 | HMGN2 | FOSB | CDC42SE1 | CLU |
| FKBP2 | CTSS | TMEM176B | COX7A2 | HMGB1 | IER2 | STK17B | LAPTM4A |
| TNFRSF17 | MNDA | CST3 | TMSB10 | DUT | KLF6 | RBM39 | CTSG |
| SPCS1 | S100A12 | SLC40A1 | USMG5 | H2AFV | DUSP2 | MDM4 | VWA5A |
| SPCS2 | CSTA | HLA-DMA | C14orf2 | CKS1B | PPP1R15A | CTNNB1 | SAMSN1 |
| SSR3 | FCER1G | HLA-DMB | UQCRQ | TYMS | MYADM | TNRC6B | CD9 |
| HSP90B1 | TYMP | MS4A7 | UQCR10 | UBE2C | YPEL5 | SON | KIT |
| IGHG3 | SERPINA1 | RNASE6 | COX6B1 | DEK | ATF3 | PPP1CB | HPGD |
| CYBA | C1orf162 | IGSF6 | COX6C | CKS2 | EGR1 | SRSF5 | GATA2 |
| PRDX4 | FPR1 | CD14 | UBL5 | NUSAP1 | NR4A2 | ARGLU1 | SLC18A2 |
| DNAJB9 | AIF1 | MS4A4A | NDUFB2 | TUBB4B | ZNF331 | DDX17 | ALOX5AP |
| ITM2C | THBS1 | CTSC | POMP | RRM2 | RGCC | N4BP2L2 | C1orf186 |
| TMEM59 | AP1S2 | TMEM176A | NDUFA4 | SMC4 | NR4A1 | FUS | ANXA1 |
| SDF2L1 | STXBP2 | ITM2B | COX7B | TOP2A | TNFAIP3 | TRA2A | CD63 |
| SEC61B | GCA | YWHAH | SEC61G | BIRC5 | FAM53C | HNRNPU | TSC22D1 |
| SPCS3 | CFD | CSF1R | COX5B | TK1 | CSRNP1 | YWHAZ | IL1RL1 |
| MANF | IFITM3 | C1orf54 | NDUFA3 | MKI67 | SERTAD1 | XIST | MAOB |
| RABAC1 | CEBPB | RNASET2 | ATP5J2 | PTTG1 | IFRD1 | CAPZA1 | NSMCE1 |
| UBE2J1 | ATP1B3 | STAB1 | CHCHD2 | PCNA | PLK3 | DDX5 | HDC |
| TRAM1 | CEBPD | RGS10 | NDUFA11 | CDK1 | INTS6 | PNISR | SOCS1 |
| CRELD2 | HBEGF | MAFB | SNRPG | UBE2S | ZSWIM4 | STK4 | ADCYAP1 |
| TMED2 | CD55 | ITGB2 | NDUFB1 | CARHSP1 | MCL1 | PRRC2C | GPR65 |
| KRTCAP2 | APOBEC3A | MGST2 | OST4 | SIVA1 | TAGAP | WSB1 | CNRIP1 |
| C19orf10 | RNF149 | AKR1B1 | NDUFA1 | RPA3 | EGR2 | SRRM2 | SDPR |
| SERP1 | CLEC7A | FUCA1 | FTL | ZWINT | ZBTB10 | PRDM1 | SLC26A2 |
| SEC62 | IFI30 | AXL | COX17 | MZT2B | HEXIM1 | POLR2J3 | SRGN |
| ERLEC1 | FGR | PLD3 | MINOS1 | CDKN3 | COQ7 | LUC7L3 | KRT1 |
| KDELR2 | TNFSF13B | PSAP | NOP10 | ANP32B | MTRNR2L1 | DDX6 | BEX4 |
| PDIA4 | FGL2 | SLCO2B1 | ROMO1 | AURKB | SNHG9 | MBNL1 | TNFSF10 |
| ANKRD28 | KLF4 | DAB2 | NDUFB7 | CENPM | MEPCE | SF1 | CMA1 |
| ATF4 | CD36 | TGFBI | PPIA | RANBP1 | FAM43A | KTN1 | LMO4 |
| TMED10 | PTPRE | RNF130 | C19orf53 | H2AFX | SPATA2L | RNF213 | ALDH1A1 |
| TXNDC15 | C5AR1 | RB1 | NEDD8 | KPNA2 | ZNF250 | RBM6 | BACE2 |
| FAM46C | VAMP5 | PPT1 | NDUFS5 | MAD2L1 | TNFSF11 | JUND | ACSL4 |
| SDC1 | THBD | ADAP2 | RBX1 | CENPF | PLK2 | AKAP13 | PTGS1 |

TABLE 1-continued

| All immune NMF programs | | | | | | | | |
|---|---|---|---|---|---|---|---|---|
| ERGIC3 | CYBB | GPR34 | SRP14 | TMEM106C | RNF139 | SRSF7 | LMNA | |
| RRBP1 | NUP214 | VSIG4 | MYEOV2 | NUCKS1 | ID1 | ZFP36L1 | SLC45A3 | |
| LMAN2 | RETN | A2M | NDUFS6 | TMPO | ERF | B4GALT1 | SVOPL | |
| PIM2 | CFP | C3AR1 | COX8A | CENPW | EGR4 | CDC42SE2 | FCER1A | |
| LMAN1 | CD93 | MFSD1 | NDUFA13 | HN1 | MIR3188 | C6orf62 | ADRB2 | |
| JTB | RAB31 | CD300A | C11orf31 | ARL6IP1 | KIAA1683 | FNBP1 | FAM46A | |
| H1FX | CLEC4A | HEXA | APRT | SMC2 | CYGB | CCNL1 | SMYD3 | |
| CNPY2 | FAM45A | MARCKS | ATP5J | NUDT1 | TMPRSS4 | MGEA5 | STX3 | |
| KDELR1 | PLSCR1 | LAIR1 | DYNLL1 | MCM7 | BAMBI | GPBP1 | TPSD1 | |
| DNAJC1 | MAT2A | ENPP2 | PHPT1 | UBE2T | FAM71A | ARID1B | GALC | |
| FCRL5 | WARS | FAM26F | CYCS | CCNA2 | C10orf111 | LRRFIP1 | TIMP3 | |
| NUCB2 | DYNLT1 | SGK1 | TRMT112 | LSM4 | C3orf33 | SCAF11 | LIF | |
| CHPF | CLEC12A | SCPEP1 | FKBP1A | ANP32E | SYT5 | PTP4A2 | SEPT2 | |
| TXNDC11 | CLEC4E | AKR1A1 | MIF | CALM3 | SEZ6 | ANKRD11 | CADPS | |
| ALG5 | UBE2D1 | LY96 | COX14 | DNAJC9 | PTH2 | PRPF38B | ACOT7 | |
| PDIA6 | RBP7 | IL18 | TIMM8B | SKA2 | SHF | RBM25 | CRBN | |
| P4HB | GLIPR1 | SLC7A7 | UQCRH | DTYMK | PDZK1 | PPP3CA | ALOX5 | |
| CUTA | CASP1 | CTSZ | NDUFA2 | ASF1B | | EIF3A | GMPR | |
| RPN1 | ASGR1 | OAZ2 | COX6A1 | CDT1 | | PTPRC | STXBP6 | |
| CCR10 | LTA4H | PLTP | POLR2I | MZT2A | | NKTR | HS3ST1 | |
| HIST1H1C | ABHD5 | PDK4 | TIMM13 | DHFR | | ARID4B | AREG | |
| CITED2 | EFHD2 | CD4 | AP2S1 | CDC20 | | ANKRD12 | CTNNBL1 | |
| CCPG1 | NCF2 | TBXAS1 | C17orf89 | KIF22 | | PNN | RAB27B | |
| MEI1 | SOCS3 | TSPAN4 | OAZ1 | TPX2 | | ATRX | LEO1 | |
| CISD2 | CSF3R | C2 | LAMTOR2 | CCNB2 | | BCLAF1 | PBX1 | |
| CREB3L2 | IRS2 | | GTF2H5 | CENPA | | DDX3X | AKAP12 | |
| ERGIC2 | PICALM | | POLR2K | ANAPC11 | | APOBEC3C | BST2 | |
| JSRP1 | TMEM167A | | ATP5G1 | GTSE1 | | ACTR2 | RENBP | |
| HDLBP | DAZAP2 | | CAMTA1 | | | CSNK1A1 | ALAS1 | |
| SPAG4 | GNAQ | | ZNHIT1 | | | ADAR | P2RY14 | |
| | LYN | | NDUFS7 | | | TSPYL1 | CATSPER1 | |
| | | | C4orf48 | | | SRSF6 | RHOBTB3 | |
| | | | C19orf60 | | | FAM133B | SLC44A1 | |
| | | | TXNL4A | | | IQGAP1 | | |
| | | | LSM7 | | | AKAP9 | | |
| | | | C19orf79 | | | PCSK7 | | |
| | | | COX20 | | | SRRM1 | | |
| | | | RNF181 | | | TCF25 | | |
| | | | TMEM230 | | | REL | | |
| | | | CISD3 | | | | | |
| | | | C16orf13 | | | | | |
| | | | ATP6V1G1 | | | | | |

TABLE 2

| B cell NMF programs | | | | | | | |
|---|---|---|---|---|---|---|---|
| outTopGenes1 | outTopGenes2 | outTopGenes3 | outTopGenes4 | outTopGenes5 | outTopGenes6 | outTopGenes7 | outTopGenes8 |
| MARCKSL1 | B2M | JUNB | TMSB10 | PFN1 | H2AFZ | MALAT1 | HLA-DRB1 |
| ATP5L | TOMM7 | DUSP1 | CD52 | ATP5E | HMGB2 | MS4A1 | HLA-B |
| ISG20 | NAP1L1 | FOS | EEF1D | ACTB | STMN1 | HNRNPH1 | HLA-DPA1 |
| LIMD2 | EEF2 | CD69 | FAU | SH3BGRL3 | TUBB | MEF2C | HLA-C |
| UCP2 | TXNIP | JUN | PTMA | COTL1 | TUBA1B | MDM4 | HLA-DRB5 |
| SERF2 | UQCRB | H3F3B | HLA-DPB1 | UQCRH | HMGB1 | SET | HLA-A |
| LTB | SLC25A6 | TSC22D3 | EEF1A1 | SNRPD2 | HMGN2 | STK17B | CD79A |
| OAZ1 | EIF4A2 | KLF2 | TMSB4X | ATP5G2 | DUT | ZFP36L1 | CYBA |
| HMGN1 | TNFRSF13B | BTG2 | HLA-DRA | SUB1 | HIST1H4C | TNFRSF13C | HLA-DQB1 |
| NEIL1 | COX7C | KLF6 | UBA52 | YBX1 | H2AFV | BCL11A | HLA-E |
| CD79B | EVI2B | RGS1 | NACA | PRELID1 | DEK | PNISR | HLA-DQA1 |
| RGS13 | NPM1 | CXCR4 | BTG1 | UQCR11 | CKS2 | NEAT1 | CORO1A |
| TCEA1 | TPT1 | NR4A2 | GLTSCR2 | OST4 | RANBP1 | POU2F2 | CD53 |
| LAPTM5 | PABPC1 | ZFP36 | CD37 | CHCHD10 | PTTG1 | CDC42 | MYL12A |
| ACTG1 | ARHGAP24 | FOSB | RNASE6 | MYL6 | UBE2C | POLR2J3 | HLA-DMA |
| BASP1 | COMMD6 | PPP1R15A | PFDN5 | BTF3 | RAN | ARGLU1 | HLA-DQA2 |
| BCAS4 | FTL | SAT1 | FCER2 | APRT | TUBB4B | FUS | UBB |
| H3F3A | DRAM2 | CD83 | EIF3E | USMG5 | CALM2 | REL | PTPN6 |
| TPD52 | ZFP36L2 | GPR183 | PLAC8 | CFL1 | CKS1B | RBM6 | LSP1 |
| UBE2J1 | SSR2 | EIF1 | HNRNPA1 | PPA1 | HNRNPA2B1 | RBM39 | CD19 |
| LSM10 | VPREB3 | RGS2 | C1orf162 | NDUFB2 | RPA3 | DDX17 | CLIC1 |
| POU2AF1 | COX4I1 | SLC2A3 | CD200 | COX6B1 | COX8A | TNRC6B | ANXA6 |
| SNX3 | CD48 | YPEL5 | RASGRP2 | C9orf16 | TK1 | KTN1 | RAC2 |
| BRK1 | CMPK1 | IER2 | SESN1 | NBEAL1 | SNRPG | PNN | ARL6IP5 |
| NCF1 | C6orf48 | PNRC1 | RCSD1 | GAPDH | SNRPD1 | TRA2A | TMBIM6 |
| EZR | MARCH1 | SERTAD1 | TSPAN13 | NHP2 | RRM2 | SEL1L3 | CAP1 |

TABLE 2-continued

| B cell NMF programs | | | | | | | |
|---|---|---|---|---|---|---|---|
| outTopGenes1 | outTopGenes2 | outTopGenes3 | outTopGenes4 | outTopGenes5 | outTopGenes6 | outTopGenes7 | outTopGenes8 |
| C4orf3 | SERP1 | SRGN | ANAPC16 | S100A11 | NUSAP1 | SON | HLA-DMB |
| TBCA | ORAI2 | PMAIP1 | BTLA | C14orf2 | H2AFY | MGEA5 | DDIT4 |
| SLC25A5 | CD44 | NFKBIA | HINT1 | RBM3 | SMC4 | N4BP2L2 | HLA-DOB |
| IRF8 | ERP29 | CHMP1B | C12orf57 | MIF | CALM3 | PTPRC | SYNGR2 |
| EIF3H | YPEL3 | HERPUD1 | ZBTB16 | TXN | BIRC5 | PRRC2C | SPCS2 |
| SRSF9 | PPDPF | TUBA1A | LTA4H | C19orf53 | TYMS | ARID1B | CTSH |
| ATP6V1G1 | TOMM20 | DNAJB1 | TSTD1 | COX7A2 | SIVA1 | LUC7L3 | RNASET2 |
| GYPC | CLECL1 | SOCS3 | PIK3IP1 | ATP5D | CARHSP1 | PCSK7 | PPIB |
| SERPINA9 | ST13 | CD55 | CD72 | COX6C | GSTP1 | CDC425E1 | PSMB9 |
| ZNF581 | VIM | ZNF331 | SPRY1 | ARPC5 | LSM5 | SF1 | PDIA3 |
| DYNLL1 | S100A4 | CYTIP | FAM26F | NOP10 | HNRNPA3 | TAF1D | CTSS |
| ARPC3 | EIF4B | FAM53C | UXT | NDUFS5 | PCNA | IKZF1 | MYL12B |
| BCL7A | RARRES3 | JUND | GMFG | C1QBP | HN1 | CTNNB1 | ITGB2 |
| ALOX5AP | SSPN | CYCS | FOXP1 | GTF3A | PKM | NKTR | SEPT7 |
| CD81 | CXXC5 | RHOB | FAM129C | GPX4 | SNRPB | DDX6 | UBC |
| TCL1A | ALKBH7 | TAGAP | C16orf74 | EIF3G | YWHAH | C1orf56 | HSP90AB1 |
| POLR1D | ABHD14B | DDIT3 | EEF1B2 | GADD45GIP1 | CDK1 | PIP4K2A | DAD1 |
| CSTB | ISCU | NR4A1 | GAPT | CCDC85B | CDKN3 | PRKD3 | HVCN1 |
| FKBP1A | METTL8 | GADD45B | FBL | POLR2L | ANAPC11 | SLC38A1 | PSME1 |
| TKT | MARCKS | IRF1 | PCDH9 | GUK1 | UBE2S | CD22 | IL2RG |
| P2RX5 | SAMSN1 | EIF4A1 | FABP1 | COX5B | TOP2A | MBNL1 | PGK1 |
| TRAPPC1 | CUTA | EGR1 | RP9 | ATP5G1 | SUMO2 | LPIN1 | ICAM3 |
| GGA2 | SMARCB1 | CITED2 | GALNT2 | COX7B | CENPM | SCAF11 | HCLS1 |
| PTPN18 | PLP2 | ARL4A | LAIR1 | UBL5 | LDHA | GPBP1 | IFNGR1 |
| WDR66 | S100A6 | VPS37B | LHPP | PARK7 | MKI67 | WSB1 | EVL |
| STAG3 | PRKCB | CCR7 | CHI3L2 | EDF1 | ERH | PPP1CB | SP100 |
| PLEKHF2 | PDCD4 | MCL1 | LBH | C19orf70 | PPIA | CAPZA1 | TPM3 |
| DAAM1 | EIF3K | DNAJA1 | C12orf42 | PHPT1 | AURKB | TRIM38 | IFITM2 |
| ZCCHC7 | CSDE1 | LY9 | OPN3 | TIMM13 | MZT2B | ADAM19 | TMEM59 |
| SIT1 | SP110 | IDS | STRADB | ATP5I | LSM3 | SWAP70 | CAPZB |
| UBE2D2 | C19orf60 | IFRD1 | S1PR4 | HIGD2A | MCM7 | ARID4B | FCRLA |
| LYPLAL1 | DERL3 | DNAJB9 | SH3BP2 | NDUFA11 | PSIP1 | SRRM2 | TMBIM4 |
| GCHFR | ATP5O | VAMP2 | TMEM2 | SRM | SRSF3 | AKAP13 | ACTR3 |
| CD38 | HSD17B11 | ATF4 | GLO1 | TOMM22 | HMGA1 | XIST | BANK1 |
| CCDC69 | TMEM219 | TGIF1 | ANXA2R | NME1 | TPI1 | LCP1 | ITM2B |
| LYPLA1 | SKP1 | IER5 | NCK2 | RWDD1 | CBX3 | CCNL1 | ECH1 |
| RFTN1 | TNFAIP8 | TYMP | ZNF677 | MYEOV2 | TFDP1 | RBM25 | ACAP1 |
| IGBP1 | AIM2 | KDM6B | NPC2 | SEC61B | COX17 | APOBEC3C | LY86 |
| SPI1 | C10orf128 | EIF5 | AMN1 | PRDX5 | LSM4 | FNBP1 | STK17A |
| LMO2 | MEAF6 | RNF139 | | UQCR10 | C12orf75 | MYCBP2 | CAPG |
| PPP1CC | ARL6IP4 | HSP90AA1 | | ARPC2 | YWHAQ | SRSF6 | TBC1D10C |
| EIF3F | CNBP | BCAS2 | | SRI | SLBP | SRSF2 | PSAP |
| LPP | ITM2C | FAM46C | | VAMP8 | KPNA2 | ATRX | ATP6V0E1 |
| PGLS | GNG7 | MYADM | | ARPC4 | PRDX2 | UPF2 | IL16 |
| SYNE2 | SNRPN | SNHG8 | | APEX1 | NUCKS1 | PPP3CA | BST2 |
| MOB1A | PPM1K | PDE4B | | TIMM8B | ZWINT | ACTR2 | EMP3 |
| | VOPP1 | SDCBP | | TESC | DDX39A | ATM | HLA-F |
| | KLK1 | BIRC3 | | NDUFA4 | CDT1 | | PSMB8 |
| | TRAF5 | RBM8A | | PRR13 | CCDC167 | | CD99 |
| | DUSP22 | SIDT1 | | SEC61G | DNMT1 | | LMAN2 |
| | CORO1B | PIM2 | | UFC1 | | | TMED9 |
| | FXYD5 | CDKN1B | | ARPC1B | | | SF3B2 |
| | NSA2 | PTP4A1 | | MT2A | | | |
| | TBC1D9 | SBDS | | PSMA1 | | | |
| | PEBP1 | CLK1 | | LSM2 | | | |
| | SVIP | GPR65 | | NDUFA1 | | | |
| | PRKCSH | CXCR5 | | ATOX1 | | | |
| | CHPT1 | MYLIP | | FIS1 | | | |
| | HAGHL | NFKBID | | GTF3C6 | | | |
| | MGST3 | CLEC2B | | TRMT112 | | | |
| | RSL1D1 | COQ7 | | HSPE1 | | | |
| | FAM173A | MYC | | | | | |
| | GNPTAB | ATP1A1 | | | | | |
| | GUCY2C | | | | | | |
| | RILPL2 | | | | | | |

TABLE 3

| All epithelial NMF programs | | | | | | | |
|---|---|---|---|---|---|---|---|
| outTop-Genes1 | outTop-Genes2 | outTop-Genes3 | outTop-Genes4 | outTop-Genes6 | outTop-Genes7 | outTop-Genes8 | outTop-Genes9 |
| OLFM4 | TUBA1B | NPM1 | EEF2 | FABP1 | S100P | ZG16 | PSMA7 |
| SLC12A2 | H2AFZ | ENO1 | JTB | SLC26A2 | S100A11 | TFF3 | EIF3E |
| LYZ | HMGN2 | C1QBP | TOMM7 | CA1 | S100A14 | FCGBP | FTL |
| ATP1B1 | HMGB2 | ATP5B | SLC25A6 | CA2 | CEACAM6 | MUC2 | EIF2S2 |
| CBX3 | HMGB1 | ATP5C1 | C19orf53 | CKB | ANXA2 | SPINK4 | TNNC2 |
| HNRNPH1 | PTMA | ATP5A1 | NACA | FXYD3 | ACTB | CLCA1 | ROMO1 |
| APP | STMN1 | HSP90AB1 | GTF3A | LGALS4 | CD55 | ITLN1 | PFDN4 |
| RNF43 | TUBB | TPI1 | NENF | ETHE1 | S100A16 | KLK1 | EEF1D |
| CD46 | PTTG1 | HSPA8 | PPP1R14B | SELENBP1 | TFF1 | GSN | YWHAB |
| SOX4 | CKS2 | PSMB1 | PCBD1 | KRT8 | PERP | SERPINA1 | C8orf59 |
| IRF2BP2 | TUBB4B | HSPD1 | CHCHD2 | TMEM54 | FHL2 | REP15 | ATP5E |
| TGFBI | RANBP1 | EIF3I | GLTSCR2 | CES2 | MAL2 | NPDC1 | POLR2K |
| XIST | CENPW | PKM | PDCD5 | HSD11B2 | TPM4 | MUC1 | CXCL14 |
| PABPC1 | CKS1B | PRDX2 | TMEM147 | PRDX6 | S100A10 | ST6GALNAC1 | MYC |
| ETS2 | HIST1H4C | TUFM | SEC11C | BSG | TM4SF1 | TPSG1 | SLC39A4 |
| ITGA6 | UBE2C | SLC25A3 | KRT10 | CALM1 | HSPB1 | BCAS1 | HSPE1 |
| CTNNB1 | UBE2S | TKT | PRELID1 | KRT19 | RAC1 | RETNLB | ENY2 |
| HOXB9 | BIRC5 | PRDX1 | SSR2 | CYCS | SLPI | RAB27A | EIF6 |
| TFRC | CDKN3 | HNRNPA1 | PGLS | CDKN2B-AS1 | PHLDA2 | LRRC26 | EREG |
| TM9SF3 | DEK | ATP5F1 | CNPY2 | TST | CYSTM1 | RNASE1 | UQCRB |
| ATP1A1 | HNRNPA2B1 | CCT8 | C19orf24 | CHP1 | CSTB | XBP1 | UBE2V2 |
| TMEM123 | SNRPD1 | LDHB | MZT2B | TDP2 | CLIC1 | SYTL2 | LAPTM4B |
| GOLIM4 | CCNB1 | PHB | C19orf43 | AKR1B10 | GPRC5A | ATOH1 | DYNLRB1 |
| KTN1 | ARL6IP1 | PSMA4 | EEF1B2 | DHRS11 | CLTB | TPM1 | DDX27 |
| DDX17 | LSM5 | EIF4A1 | NDUFB9 | C10orf99 | EIF1 | TSPAN13 | PRPF6 |
| ZKSCAN1 | NUCKS1 | UQCRC2 | C19orf10 | SULT1A1 | VDAC2 | CREB3L1 | BNIP3 |
| ZFP36L1 | CDC20 | MDH2 | POLR1D | LIMA1 | PLAUR | AGR2 | YBX1 |
| ADD3 | H2AFV | C14orf166 | NAA10 | MALL | SH3BGRL3 | SPDEF | GPX4 |
| METTL12 | HMGN1 | CCT5 | RAD23A | SCP2 | LGALS3 | MLPH | ADRM1 |
| CERS6 | TUBA1C | PSMA5 | SRSF9 | FABP2 | EZR | FOXA3 | LYPLA1 |
| PDIA4 | TOP2A | CCT7 | SNHG7 | CHP2 | SERPINB1 | WFDC2 | CHCHD7 |
| MLEC | RPA3 | EIF3M | POLR2J | PAPSS2 | LDHA | BEST2 | RALY |
| FERMT1 | SRSF3 | ALDH2 | TXNL4A | METTL7A | RHOC | MLLT3 | TATDN1 |
| CDH1 | ANP32B | HSP90AA1 | NAP1L1 | SLC4A4 | PDZK1IP1 | TBX10 | EIF3H |
| CANX | MKI67 | TALDO1 | C1orf43 | ETNK1 | MYL12B | SCNN1A | KRT23 |
| PYGB | MAD2L1 | PSMA1 | SEC61B | TSC22D1 | C12orf75 | CDC42EP3 | RNF114 |
| SOX9 | SNRPF | NDUFV2 | ALKBH7 | FLNB | C4orf3 | MB | C20orf24 |
| CDCA7 | RRM2 | GMDS | C11orf31 | SQRDL | CIB1 | GLUL | DPM1 |
| SDC1 | CDK1 | GSTO1 | ATP6V1F | MVP | CD59 | NEDD4L | MAPRE1 |
| CMTM6 | LSM3 | PSMA3 | UFC1 | GNA11 | TIMP1 | HEPACAM2 | CCDC85B |
| TRIM2 | PCNA | PPA2 | MIEN1 | ABRACL | CAPG | STARD10 | RAB2A |
| FAM84A | KPNA2 | PSMB7 | EIF3F | AHCYL2 | TNFRSF12A | SCGB2A1 | C8orf33 |
| SCD | UBE2T | ECH1 | GUK1 | AMN | MYL12A | MUC4 | CTNNBL1 |
| PABPC4 | DTYMK | IMPDH2 | EI24 | MAOA | KDELR2 | CDC42EP5 | ZNF706 |
| TMBIM6 | SMC4 | CCT3 | POLR2I | UGDH | SERPINB6 | MINPP1 | EXOSC4 |
| SRRM2 | HMGB3 | PEBP1 | SLC25A39 | C2orf88 | PRSS3 | ANG | STAU1 |
| SNHG9 | TK1 | PSMA2 | SNF8 | CA12 | ARF4 | GPR153 | FNTA |
| PLCB4 | CENPF | CCT2 | TOMM20 | MGLL | ARPC2 | IL1R2 | GAL |
| PDXDC1 | SNRPG | PSMD8 | BAG1 | ENTPD5 | GLRX | ATP2A3 | GPR160 |
| PSAP | ZWINT | UQCRFS1 | BRK1 | PADI2 | RBCK1 | ERI3 | TOP1 |
| PTPRF | SNRPB | MDH1 | MSRB2 | HINT1 | SERP1 | RASEF | EIF4EBP1 |
| KIF5B | DUT | SUCLG1 | LAMTOR1 | GPT | TSPAN3 | KCNMA1 | PUF60 |
| FAM120A | CCNB2 | PSMB5 | TSTA3 | PRR15 | HEBP2 | RAP1GAP | MED30 |
| GFPT1 | NUSAP1 | PRMT1 | CENPV | SLC22A18AS | CHMP5 | CAPN9 | DCAF13 |
| NFIA | MZT1 | TXNL1 | MLF2 | MARCKS | ARF6 | RASD1 | ZC3H15 |
| SERINC5 | SKA2 | GDI2 | RAMP1 | ATP6V0D1 | MAP1LC3B | FAM107B | GZMB |
| EIF1AX | TYMS | EIF3K | C1orf122 | SPPL2A | TSPAN8 | MAN1A1 | PTP4A3 |
| STT3B | SRP9 | NANS | TMED3 | SLC25A5 | F3 | GALNT12 | PCAT1 |
| TBL1XR1 | NASP | SERBP1 | PAFAH1B3 | IQGAP2 | TPD52 | HSPA2 | GTF2E2 |
| DSP | WDR34 | REG1A | TIMM13 | ADTRP | CD164 | FAM177B | SUMO1 |
| MYH9 | STRA13 | NDUFA9 | COMMD6 | CALM2 | DDIT4 | PLA2G10 | ZFAND1 |
| CD44 | MCM7 | NDUFB5 | SSU72 | ACAA1 | BNIP3L | ANO7 | COMMD7 |
| CD81 | TPX2 | PPIB | ZNF593 | TP53I3 | ANXA11 | SPINK1 | ATOX1 |
| EIF4G2 | BUB3 | ESD | SRM | ACAA2 | TMBIM1 | ENTPD8 | TPD52L2 |
| EPHB2 | ERH | ECHS1 | TBCB | ACOX1 | LAMC2 | SLC50A1 | FAM49B |
| GTF2I | PBK | CCT4 | HES6 | PLCD3 | SLC2A1 | SLC2A10 | TIMP3 |
| SON | NCL | PSMB6 | FXYD5 | AKR1C3 | CXCL16 | FAM101A | MGMT |
| EIF3A | CCNA2 | PSMB2 | DUSP23 | SLC16A1 | CRB3 | LGALS9B | DNTTIP1 |
| NUDT4 | CCDC34 | TCP1 | CHCHD8 | MAPK3 | TAGLN2 | SLC9A3R2 | ATP6V1C1 |
| LEFTY1 | AURKB | SDHB | ISCU | MPST | SNX3 | SLC39A7 | C11orf58 |
| DYNC1I2 | CENPM | CCT6A | ANAPC11 | EPB41L4B | ANXA1 | GPRIN2 | MAF1 |
|  | SMC2 | NDUFS3 | LAMTOR2 | MYO1A | ATP6V1G1 | EIF2AK3 | QPRT |
|  | CENPN | MTCH2 | MAP2K2 | CMBL |  | KAZALD1 | C16orf13 |
|  | NUDT1 | XRCC6 | C6orf48 | PIGZ |  | WNK4 | SHARPIN |
|  | TMEM106C | RSL24D1 | CHCHD5 | PAQR8 |  | FGFR2 | PSPH |

TABLE 3-continued

| All epithelial NMF programs | | | | |
|---|---|---|---|---|
| PPA1 | EPB41L4A-AS1 | PRR13 | | NDUFAF6 |
| VDAC1 | FBL | GIPC1 | | DCTN6 |
| AHSA1 | TMEM219 | ANKRD9 | | |
| APEX1 | | OAF | | |
| PSMD7 | | ARF3 | | |
| AIMP1 | | GOLM1 | | |
| ST13 | | TPRN | | |
| SPCS1 | | MYO1D | | |

| | outTopGenes5 | |
|---|---|---|
| RSL1D1 | EEF1A1 |
| ATP5O | TPT1 |
| NDUFV1 | NBEAL1 |
| PGAM1 | NHSL2 |
| SNRPB2 | EEF1G |
| DECR1 | IGF2 |
| CNBP | FUT7 |
| SSBP1 | BPI |
| PSMB3 | HBG2 |
| BTF3 | MYL3 |
| CLTA | MYOZ1 |
| STRAP | MAL |
| HNRNPF | |

| outTopGenes10 | outTopGenes11 | outTopGenes12 | outTopGenes13 | outTopGenes14 | outTopGenes15 | outTopGenes16 | outTopGenes17 |
|---|---|---|---|---|---|---|---|
| TXN | MT1E | CD74 | MALAT1 | AQP8 | GUCA2B | FOS | HLA-A |
| ATP5J2 | MT1X | HLA-DRA | KRT18 | SEPP1 | CA7 | NEAT1 | HLA-B |
| TMSB4X | MT1G | IFITM3 | TMSB10 | FTH1 | OTOP2 | JUN | CST3 |
| DBI | PIGR | IFI6 | S100A6 | CEACAM7 | GUCA2A | JUNB | TMEM59 |
| PFN1 | C15orf48 | HLA-DRB1 | ATP5D | IL32 | CA4 | IER2 | ITM2B |
| NDUFB2 | ADH1C | PSMB9 | MUC5B | EMP1 | FKBP1A | KLF6 | EPCAM |
| COX7B | MT2A | BST2 | GADD45GIP1 | HPGD | SPIB | DUSP1 | CD63 |
| NDUFS5 | MT1F | HLA-DPA1 | GAPDH | PLAC8 | MT1H | EGR1 | CLDN3 |
| SERF2 | COX5A | PSME2 | UQCRC1 | ANPEP | SRI | FOSB | HLA-C |
| COX6B1 | UGT2B17 | HLA-E | CDC37 | MUC12 | HES4 | ELF3 | CD9 |
| C14orf2 | TCEA3 | RARRES3 | ACADVL | TRIM31 | PCSK1N | ZFP36 | B2M |
| USMG5 | CHCHD10 | TAP1 | NDUFB7 | CDHR5 | HRCT1 | ATF3 | TMEM176B |
| COX5B | MGST1 | HLA-DPB1 | EDF1 | SMPDL3A | CCNYL1 | RHOB | GRN |
| ATP5L | ATP5G1 | ISG15 | FKBP2 | HIST1H1C | KRT20 | CLDN4 | SPINT2 |
| COX7A2 | PPP1R1B | HLA-DMA | RRBP1 | SLC26A3 | SEPW1 | IER3 | UBB |
| UQCR10 | DDT | HLA-DQB1 | LLGL2 | SLC9A3 | METTL21A | BTG2 | FCGRT |
| NDUFS6 | QTRT1 | PSME1 | HOOK2 | CEACAM1 | CTSE | ZFP36L2 | TMEM176A |
| NDUFA4 | LGALS2 | LY6E | ARGLU1 | TMPRSS2 | ITM2C | NR4A1 | SSR4 |
| MINOS1 | SUCLG2 | UBE2L6 | GNAS | MXD1 | DMBT1 | MCL1 | NDUFC2 |
| ATP5J | C2orf82 | HLA-DRB5 | ASL | CTSD | NOTCH2NL | KLF4 | CYBA |
| COX7C | ATP5G2 | HLA-F | ECI1 | SPATS2L | SDCBP2 | PPP1R15A | LAPTM4A |
| COX6C | ATP8B1 | STAT1 | COMTD1 | TSPAN1 | ADRA2A | DNAJB1 | AZGP1 |
| UBL5 | IMPA2 | TYMP | TRABD | MUC3 | FABP5 | HSPA1B | NPC2 |
| ATPIF1 | NDRG2 | PSMB8 | PFKL | DHRS9 | MYOM1 | C8orf4 | MGST2 |
| UQCR11 | FAM162A | WARS | AES | TXNIP | CCL15 | VMP1 | BCAP31 |
| MYL6 | CDX1 | PLA2G2A | TRIM28 | CLDN23 | ST3GAL4 | JUND | H3F3A |
| NDUFB3 | CISD3 | LGALS3BP | NT5C | PRSS8 | CARD16 | UBC | NDUFA13 |
| ATP5G3 | B3GNT7 | CXCL3 | ETFB | CEACAM5 | PPP3CA | CCNL1 | EIF1B |
| PPIA | HSBP1L1 | RNF213 | LTBP4 | SGK1 | FRMD1 | HSPA1A | RNASET2 |
| NDUFA1 | GAS6 | CXCL1 | RASSF7 | TMEM37 | GPRC5C | NFKBIA | SH2D6 |
| OST4 | PNKD | SAA1 | PKP3 | RFK | SAMD9L | MIDN | LSR |
| ATP5I | MT1A | REG4 | PRRC2C | RSAD2 | CDK18 | TRIB1 | ATP6AP2 |
| UQCRQ | NEO1 | LAP3 | RSBN1L | SECTM1 | GUCY2C | SAT1 | LRMP |
| NDUFC1 | AFG3L2 | HLA-DQA1 | DPP7 | MIER3 | DDAH2 | IFRD1 | VPS28 |
| PRDX5 | SMAGP | IFITM2 | PHF14 | DST | HSD17B2 | TOB1 | HOTAIRM1 |
| CFL1 | GLIPR2 | IFI35 | SCAND1 | IL2RG | C2orf54 | RAB11FIP1 | TMBIM4 |
| APRT | EPHX2 | TAPBP | WDR60 | MEP1A | MEIS1 | DDX5 | TSPAN6 |
| SEC61G | ARHGAP44 | EPSTI1 | RNPEPL1 | VAMP8 | FUCA1 | WSB1 | ALOX5AP |
| NDUFB1 | MESP1 | MIF | UPF2 | SMPD1 | HIGD1A | HBEGF | ERP29 |
| SUB1 | SLC9A2 | IFITM1 | FBXW5 | ARL14 | OTOP3 | NFKBIZ | COX6A1 |
| TXNDC17 | FAM96A | EIF5A | AHI1 | ABHD3 | GNPTAB | INTS6 | PYCARD |
| ATP5H | RARRES1 | PSMB10 | TMEM160 | BIRC3 | CEACAM3 | BRD2 | GGH |
| TIMM8B | DDC | IFI44L | C19orf60 | OASL | SLC2A5 | H3F3B | SPCS2 |
| NDUFA3 | SIPA1L2 | PARP14 | IRF3 | TNFSF10 | PPP1R14C | BTG1 | HPGDS |
| NDUFA11 | NDUFV3 | TFF2 | PLXNB2 | TMIGD1 | ID3 | GDF15 | WDR83OS |
| HSBP1 | ECI2 | GBP1 | CCDC124 | PEX26 | MSLN | KLF3 | MGST3 |
| NDUFA6 | PTGDR | TAP2 | PHPT1 | ABCG2 | ADCY5 | SLC38A2 | TECR |
| ZNHIT1 | CAMTA1 | APOL1 | LONP1 | C11orf86 | LXN | HERPUD1 | N4BP2L2 |
| UBA52 | FOXD2 | MUC5AC | AURKAIP1 | PLS1 | CDX2 | ATF4 | PIGT |

TABLE 3-continued

All epithelial NMF programs

| | | | | | | | |
|---|---|---|---|---|---|---|---|
| POLC1 | LMO4 | ERICH1 | LRP10 | CPNE8 | IER5 | PGRMC1 | |
| PLA2G12A | IRF1 | NUDT8 | MYO15B | GADD45A | CYP3A5 | HCK | |
| CCNG1 | HLA-DMB | DGAT1 | MYH14 | VIPR1 | RND3 | REEP5 | |
| SLC39A5 | POLR2L | METRN | OAS1 | PRR15L | LDLR | SAP18 | |
| EDIL3 | CXCL11 | CCDC12 | NLN | NOTCH2 | SLC20A1 | RTN4 | |
| PFKFB2 | MANF | CDK11A | CD177 | NAE1 | LMNA | SH3BGRL | |
| TNFRSF11A | ASS1 | C1orf35 | DDX60 | TMEM120B | PMAIP1 | NDUFB11 | |
| ZDHHC2 | IFI44 | VARS | PRSS23 | PRKG2 | GADD45B | LMAN2 | |
| H5D17B8 | GBP4 | SNRNP70 | CTSZ | CDC42BPA | ZC3H12A | PBXIP1 | |
| ZNF814 | IFIT3 | NOXO1 | CGN | CPM | DNAJA1 | PTGS1 | |
| DHRS4L2 | CXCL10 | MVD | CLIC5 | EXD3 | NR4A2 | | |
| PROM2 | ODF3B | DNM2 | PDCD6IP | PROX1 | DDX3X | | |
| SCN9A | PARP9 | ELMO3 | LITAF | SI | SERTAD1 | | |
| UBAC1 | OAS2 | MICALL2 | TMCC3 | C4BPA | ID2 | | |
| NAA38 | ETV7 | SIL1 | CAB39 | MALT1 | KLF2 | | |
| C2orf72 | PDIA3 | ABCC3 | RIOK3 | | NCOA7 | | |
| AIM1 | PML | CD320 | PKIB | | HES1 | | |
| SYCE1L | CALR | SIGIRR | PLOD2 | | ERRFI1 | | |
| FRAT2 | CDC42EP1 | EFCAB4A | HRASLS2 | | ID1 | | |
| ECSIT | MDK | PNKP | ATP1B3 | | HSPH1 | | |
| NIPAL1 | | SLC25A1 | HHLA2 | | IRS2 | | |
| PTEN | | LTBR | SPINT1 | | FOSL2 | | |
| GSTZ1 | | ABHD11 | RCAN1 | | CLK1 | | |
| ISX | | ARHGEF16 | C1orf115 | | HEXIM1 | | |
| ZADH2 | | MPDU1 | EPS8 | | STAT3 | | |
| DNAJC4 | | TRPM4 | MXI1 | | CEBPD | | |
| PPARGC1B | | RPPH1 | PTPRH | | SRSF5 | | |
| BCL2 | | AP3D1 | TP53INP2 | | PLK3 | | |
| YBEY | | GPI | CTSA | | TMC5 | | |
| FKBP5 | | | GPA33 | | LIPH | | |
| ACVR1C | | | SLC17A4 | | CEBPB | | |
| FAM46C | | | APPL2 | | ANKRD37 | | |
| DPF3 | | | CFDP1 | | FAM53C | | |
| PDCD4 | | | SQSTM1 | | KCNQ1OT1 | | |
| ENOSF1 | | | BLOC1S1 | | PNRC1 | | |
| | | | LRRC1 | | FAM133B | | |
| | | | ABCB1 | | NEDD9 | | |
| | | | TJP3 | | MYADM | | |
| | | | IFNGR2 | | RBM39 | | |
| | | | ST14 | | | | |
| | | | PLSCR1 | | | | |

TABLE 4

Epithelial normal NMF programs

| outTop-Genes1 | outTop-Genes2 | outTop-Genes3 | outTop-Genes4 | outTop-Genes5 | outTop-Genes6 | outTop-Genes8 | outTop-Genes9 |
|---|---|---|---|---|---|---|---|
| ATP1B1 | SLC9A3 | ATP5I | SH2D6 | MLXIP | ZG16 | ATP5C1 | HIST1H4C |
| PIGR | ANPEP | NDUFB1 | AZGP1 | IRF2BP2 | GZMA | ATP5A1 | DUT |
| CTNNB1 | ETNK1 | NDUFA13 | KRT18 | APP | HOPX | EPCAM | RANBP1 |
| HNF4A | BSG | C19orf79 | LRMP | ZKSCAN1 | IGFBP5 | ATP5B | STRA13 |
| EIF5A | CDHR5 | UQCR11 | MARCKSL1 | SLC12A2 | FAM71D | SUCLG1 | TUBB |
| HNRNPH1 | CEACAM1 | NDUFA7 | HPGDS | ZFP36L2 | ITGA5 | LGALS4 | PCNA |
| GOLIM4 | SEN | POLR2L | HCK | HNRNPU | AEBP1 | TSPAN8 | SIVA1 |
| CDC42 | SLC20A1 | MYEOV2 | ALOX5AP | DDX17 | PDGFB | ATP5F1 | TK1 |
| PPP1CB | C19orf33 | NDUFA3 | PTGS1 | HNRNPA3 | FBLN2 | CD9 | DEK |
| B4GALT1 | C11orf86 | ROMO1 | EIF1B | FRYL | PCDH10 | ECH1 | TYMS |
| C1orf56 | ACAA2 | EEF1G | HOTAIRM1 | KLF5 | DBNDD2 | UQCRC2 | CARHSP1 |
| SET | TST | ZNF90 | PLCG2 | EIF3A | CDC20B | MDH1 | RPA3 |
| CDC42SE1 | TMEM120A | GABARAP | BMX | MUC5B | PAMR1 | MDH2 | RRM2 |
| PADI2 | TP53I3 | RPP21 | GNG13 | MLEC | APOB | NDUFA9 | CENPM |
| WTAP | CTSD | EIF4EBP3 | PTPN18 | SRRM2 | DES | MGST1 | LDHB |
| CTTN | FAM3B | CBX7 | PSTPIP2 | FOXP1 | POU6F2 | NANS | MCM7 |
| TRA2A | POLD4 | PIK3R2 | CST3 | ITGA6 | CD53 | PRDX1 | NAP1L1 |
| BCL10 | VILL | ACY1 | AVIL | PABPN1 | FBN1 | UBB | WDR34 |
| INSR | ACAA1 | APOE | ANXA13 | CCND2 | POU3F1 | ENO1 | NASP |
| PHKG1 | AK1 | CD69 | SH2D7 | HNRNPK | HPX | PSMB1 | MIF |
| TMED4 | RETSAT | TRAPPC5 | DEFB1 | CANX | NTRK3 | DECR1 | GGCT |
| YWHAE | FBXW5 | EGLN2 | PBXIP1 | PTPRF | GNG11 | TUFM | DHFR |
| EPPK1 | PKP3 | NDST2 | TPM1 | PNISR | TEX101 | UQCRFS1 | SNRPB |
| PPP3CA | CHMP1A | POMC | MATK | CELF1 | ZNF831 | NDUFV1 | HELLS |
| SRSF6 | SLC37A2 | CST7 | ALOX5 | CERS6 | LCP1 | C1QBP | MZT2A |
| TSPYL1 | SLC27A4 | DUSP26 | IL17RB | HSP90B1 | CHST11 | PSMA7 | SNRPD1 |

TABLE 4-continued

Epithelial normal NMF programs

| | | | | | | | |
|---|---|---|---|---|---|---|---|
| SUMF2 | PDE9A | SPEG | ATP2A3 | PDXDC1 | CYP3A43 | SQRDL | CDT1 |
| RNF152 | MAPK3 | ALDH4A1 | HTR3E | LENG8 | RGMA | PHB | GCHFR |
| SDC4 | PLIN2 | ISLR | KRT8 | REPIN1 | EBF1 | NDUFS3 | GINS2 |
| NHSL1 | SFXN1 | CCL13 | CALM2 | MUC4 | MYCT1 | PSME2 | RRM1 |
| ARPC4 | TMEM171 | | BIK | DSP | IGSF11 | AKR1C3 | RMI2 |
| DOCK5 | CAPN1 | | H3F3A | HNRNPD | DPH1 | PSMA4 | TMEM106C |
| CAPZA1 | TMEM82 | | ANXA4 | ERBB3 | ITGAX | PSME1 | DNMT1 |
| RASSF3 | SLC25A37 | | SPTLC2 | FAM84A | LOXL2 | PRDX2 | POLD2 |
| LETM1 | FAM43A | | LYZ | HOXB6 | CLEC10A | CYC1 | CDK4 |
| RREB1 | CYBRD1 | | RGS13 | ZBTB38 | RNF224 | ALDH2 | LSM2 |
| GIPC2 | LGALS1 | | TUBA1A | PAWR | | TALDO1 | ZWINT |
| SEC22B | HSPG2 | | RASSF6 | LRPPRC | | MGST2 | MCM3 |
| MDM4 | USP2 | | POU2F3 | ILF3 | | SPCS2 | UBE2T |
| AMFR | PEPD | | ANXA1 | HOXB9 | | PSMA2 | TFDP1 | outTop-Genes7

| | | | | | | |
|---|---|---|---|---|---|---|
| PDGFA | HKDC1 | TLE4 | FERMT1 | UBA52 | SDHB | FEN1 |
| C2orf68 | NR1H4 | H1FX | MAZ | CD52 | NDUFS2 | H2AFZ |
| LRRC16A | JOSD2 | PSAP | EML4 | LTB | PGK1 | ASF1B |
| CALR | ALDOB | PLEKHB1 | ZRANB2 | HCST | COPE | IDH2 |
| TMEM159 | ARSA | CIRBP | RNF43 | | PPA2 | CCDC34 |
| EIF5AL1 | SGK2 | BCAM | AKAP1 | | ECHS1 | MCM5 |
| FOXD2 | SH3BP1 | H3F3B | SF1 | | PPIB | RNASEH2C |
| TNRC6B | GGT6 | TMEM176B | TM9SF3 | | GSTO1 | MYBL2 |
| AP1G1 | MEP1B | CRIP1 | D2HGDH | | TPI1 | SLBP |
| EIF2S3 | METTL7B | SNRNP27 | FAM120A | | PSMA3 | HNRNPF |
| SYNC | PITX2 | AFAP1L2 | SRSF11 | | HSP90AA1 | PAFAH1B3 |
| DNAJC3 | HBB | TMEM176A | RHOBTB3 | | SLC25A3 | BCL7C |
| SAR1A | TMEM8A | FURIN | BPTF | | GHITM | USP1 |
| RNF2 | ASS1 | S100A6 | WNK2 | | HSPD1 | DNAJC9 |
| HSPA4 | RNPEPL1 | SKAP2 | SYNE2 | | CKMT1B | SNRNP25 |
| MTA2 | GBA | SOX9 | ATP2C2 | | PDHA1 | EIF4EBP1 |
| ADAM17 | CBLC | VAMP2 | NRIP1 | | ETFB | C9orf142 |
| KCNJ2 | GDPD2 | CREG1 | SNRNP70 | | LAPTM4A | COMMD4 |
| AFMID | STXBP2 | DDX5 | EPHB2 | | TECR | POLR2I |
| HNRNPL | LGI4 | ZFHX3 | TMEM123 | | ETFA | RFC2 |
| RQCD1 | VPS16 | MAP7 | ZNF207 | | CCT8 | NUDT8 |
| IAH1 | SLC6A9 | COL27A1 | SATB2 | | MGST3 | PSIP1 |
| PGGT1B | ALAS1 | DKK3 | TAF1D | | NDUFA10 | PAICS |
| DCUN1D1 | PSMD11 | CD14 | NUMA1 | | SSBP1 | HPRT1 |
| PER2 | CORO1B | ITPR2 | HOXB5 | | PSMA5 | NUDT1 |
| TLK1 | AARSD1 | PIK3CG | HNRNPM | | ESD | SNRPG |
| FLCN | CYP2B6 | ABHD2 | SPG7 | | FH | LIG1 |
| R3HDM2 | SLC52A3 | EID1 | OGT | | ECI1 | RBBP7 |
| ANKRD40 | SULT1A2 | CNN3 | SON | | CD63 | |
| MAP3K12 | IL10RB | CD300LF | HNRNPA2B1 | | PSMB7 | |
| RIT1 | DPEP1 | TIMP1 | CTBP2 | | CKMT1A | |
| GRHL2 | SLC25A1 | PAK3 | PUM1 | | AIMP1 | |
| FAM76A | NUCB1 | MYL6 | ABR | | PSMB3 | |
| DCAKD | NUDT14 | IL13RA1 | EPHX2 | | XRCC6 | |
| IRF2BPL | SLC14A2 | ZNF428 | PILRB | | CCT7 | |
| BRSK1 | GLYCTK | CCDC14 | | | IDH3B | |
| STRN3 | COQ4 | OGDHL | | | ERP29 | |
| SAMD12 | ARG2 | H2AFJ | | | PSMC5 | |
| LRRK1 | TOM1 | REEP5 | | | CCT5 | |
| RASGEF1B | PSD4 | | | | UQCRC1 | |
| THAP5 | ZNF341 | | | | PSMA1 | |
| ZC3H4 | OSGIN1 | | | | ITM2B | |
| CCDC58 | RAB6B | | | | HSP90AB1 | |
| RAB12 | | | | | ADH5 | |
| RIN2 | | | | | | |
| LYSMD1 | | | | | | |
| DEDD | | | | | | |
| GIGYF1 | | | | | | |
| ZNF557 | | | | | | |

TABLE 4-continued

Epithelial normal NMF programs

EXOSC6
UBE2W
ZFX
BROX
TAF13
C1orf174
MGP
DCN
TCTN2
COCH
LUM

| outTop-Genes10 | outTop-Genes11 | outTop-Genes12 | outTop-Genes13 | outTop-Genes14 | outTop-Genes15 | outTop-Genes16 | outTop-Genes17 |
|---|---|---|---|---|---|---|---|
| CA7 | AQP8 | ISG15 | NEAT1 | SDF2L1 | GUCA2B | MT1H | CLCA1 |
| CA4 | SEPP1 | MX1 | MALAT1 | C19orf10 | GUCA2A | MT1F | TFF3 |
| SPIB | FCGRT | 1F16 | ELF3 | CDX1 | MYOM1 | MT1G | ITLN1 |
| FKBP1A | B2M | OAS1 | VMP1 | HSPA5 | DDAH2 | MT1X | SPINK4 |
| TMSB10 | HLA-A | IFITM3 | CCNL1 | MANF | CCNYL1 | MT1A | KLK1 |
| DMBT1 | CLDN3 | HRASLS2 | WSB1 | SEC61B | METTL21A | MZB1 | SPINK1 |
| OTOP2 | MDK | IFI35 | N4BP2L2 | APRT | ANXA11 | TNFRSF17 | RETNLB |
| HES4 | CD177 | IFIT3 | HOOK2 | PPP1R14B | CFD | C1orf50 | RNASE1 |
| CARD16 | HLA-C | IRF7 | PCSK7 | NCL | REN | CD38 | ST6GALNAC1 |
| NOTCH2NL | SMPDL3A | TYMP | ANKRD12 | JTB | C4BPA | RGS1 | WFDC2 |
| ADRA2A | PI3 | MX2 | CCDC64B | PDCD5 | PRKG2 | SLC30A2 | LRRC26 |
| ITM2C | HIST1H1C | PLSCR1 | LLGL2 | P4HB | CD55 | IL18R1 | XBP1 |
| CDK18 | AMN | ISG20 | SIRT7 | TMED9 | FABP3 | CD79A | SSR4 |
| GNPTAB | IL32 | XAF1 | FAM133B | SRM | CITED2 | ZNF749 | HPCAL1 |
| HSD17B11 | HLA-B | OASL | CYP3A5 | TOMM22 | C2orf54 | TNFRSF18 | GMDS |
| GPRC5C | TMEM59 | EPSTI1 | RAD9A | LRRC59 | SCRN1 | FCRL5 | ATOH1 |
| MEIS1 | CLDN7 | IFI44L | AKAP13 | TXNL4A | UNC13D | IRF4 | RAP1GAP |
| MSLN | SERINC2 | RSAD2 | SRSF5 | DDX21 | ABCC5 | TNFRSF13B | CDC42EP5 |
| NOTCH2 | LSR | OAS3 | AAK1 | SRSF9 | ATP13A2 | PLAT | SERPINA1 |
| GUCY2C | PCK1 | UBE2L6 | C19orf25 | EIF4A1 | MFSD12 | IL16 | REP15 |
| GRN | NOSIP | OAS2 | FNIP1 | NME1 | RHCG | POSTN | TSPAN13 |
| PCSK1N | EFNA1 | CMPK2 | FAM160A2 | CHCHD8 | RAB31 | MEI1 | NPDC1 |
| C1orf21 | TMEM37 | IFITM1 | VPS13A | CRELD2 | FHL1 | RORA | REG4 |
| ADCY5 | SLC3A2 | USP18 | OFD1 | C17orf89 | MALT1 | HCLS1 | SLC4A7 |
| VIPR1 | CTSA | IFIT2 | MPHOSPH8 | PARK7 | TNFAIP2 | CTAG2 | BEST2 |
| ASAH1 | NAALADL1 | RNF213 | SH2D3A | RWDD1 | OTOP3 | SLAMF1 | KCNMA1 |
| HSPB1 | TMIGD1 | IFI44 | SHROOM1 | NAA10 | DOCK4 | CLECL1 | HES6 |
| EXD3 | HSPB3 | HERC6 | B3GAT2 | E124 | HYI | SMN2 | AGR2 |
| SULF2 | TCN2 | PSMB9 | SCAMP4 | C19orf24 | PPCDC | STAB1 | ITM2A |
| DNASE2 | NBL1 | SPATS2L | TMEM44 | PDIA6 | GADD45A | | RASD1 |
| FNIP2 | BRMS1 | C19orf66 | IRF9 | TOMM40 | SAMD9L | | TSTA3 |
| TTC39B | LEAP2 | LAP3 | ARRDC1 | C19orf53 | RALGDS | | SLC50A1 |
| FRMD1 | SLC6A19 | PARP9 | FBLIM1 | ZNF593 | PDLIM4 | | SPDEF |
| NAE1 | CDIPT | STAT1 | GGA1 | GPX2 | SSTR1 | | ASPH |
| UNC5C | NEU1 | TRIM22 | LUZP1 | GSPT1 | RABEP1 | | KIAA1324 |
| SAMHD1 | DIO3OS | PARP14 | CSNK1D | TIMM13 | VRK3 | | FRZB |
| RNF186 | HSD17B2 | LGALS9 | POMGNT1 | TMED3 | KRT13 | | FMOD |
| SMPDL3B | C8G | EIF2AK2 | WDR60 | DCTPP1 | DUOXA1 | | FKBP11 |
| SLC2A5 | MCOLN2 | SP110 | DLG1 | PDIA4 | RDX | | FOXA2 |
| TMC6 | HEBP1 | IFIH1 | MTMR11 | RRP7A | SLC6A6 | | DLL1 |
| ATG16L2 | PINK1 | HERC5 | PNKP | FABP4 | FABP4 | | ERI3 |
| PPP1R14C | XPNPEP2 | DDX60 | KCNQ1OT1 | KRT10 | FGF13 | | ERGIC1 |
| EEF2K | FXYD1 | ZBP1 | LPIN3 | SSR2 | USH1G | | TNNC2 |
| CCNJL | LGMN | ADAR | RNF207 | SSR3 | LBH | | SLC39A11 |
| LUZP2 | NDN | GSDMB | MARVELD3 | SERBP1 | EEF1A2 | | KDELR1 |
| PROX1 | AQP7 | RTP4 | MAFG | RAD23A | RAB24 | | DNAJC10 |
| PRKG1 | VAMP5 | APOL1 | PRRT2 | NHP2 | DKK1 | | GNE |
| SLC2A6 | SLC16A3 | SP100 | HOOK3 | SEC11C | CCDC153 | | RGS10 |
| TOM1L2 | TAPBPL | CNP | PPP1R10 | ODC1 | MPP6 | | RAB26 |
| PBX1 | POR | DDX58 | CWC25 | ARF1 | ARL4C | | ANO7 |
| CPNE2 | GABRA2 | TAP1 | BNIP2 | GTF3A | VANGL1 | | MB |
| NPY1R | KCNG1 | SHISA5 | ELMOD3 | PSMG3 | SPTBN5 | | FAM174B |
| PIK3AP1 | EDN2 | ETV7 | ABCC3 | C11orf83 | RAPGEF1 | | DNAJC12 |
| SPG21 | GLRA4 | PARP10 | CDK11A | TIMM17A | NLRX1 | | CREB3L4 |
| HR | GGT1 | RARRES3 | ITSN2 | ZNF511 | BTBD19 | | TRPT1 |
| FAM60A | PRRG2 | ODF3B | PLXNA2 | FAM96B | PAX6 | | EFCAB4A |
| TBCB | RILP | NAPA | ASCC2 | SRSF7 | MAP7D2 | | RAB15 |
| KCNIP4 | ALPI | HSH2D | PPFIA1 | IFRD2 | NT5DC4 | | ANO1 |
| NBPF10 | SLC7A7 | TAP2 | TMEM184A | ENSA | PHLDA3 | | WIPI1 |
| NT5E | TM6SF2 | PHF11 | HEXIM1 | C7orf50 | ALPK2 | | DERL1 |
| HES1 | ALDOC | PML | RDH5 | SRPRB | STX11 | | MAGED1 |
| PDK1 | APOM | PRKD2 | GON4L | MTDH | PPP1R3C | | ANXA5 |
| A1CF | MED29 | IFI16 | RDH13 | SRP72 | DCLRE1A | | SLC35A1 |

TABLE 4-continued

| Epithelial normal NMF programs | | | | | | |
|---|---|---|---|---|---|---|
| CTSC | HAAO | STAT2 | CLN8 | ISOC2 | PHEX | KLK3 |
| OSBPL8 | CYP2D6 | NLRC5 | CNKSR1 | POLR2E | CNR2 | SLC16A7 |
| P4HA2 | ARRB1 | DHX58 | NCOR1 | SRSF2 | ERP27 | SYTL1 |
| GLDN | GBP2 | NUB1 | SAT2 | PDCD6 | CCL22 | CA8 |
| NCOA1 | PPP1R14A | ZC3HAV1 | ZNF224 | SLC35B1 | IQCH | TOX |
| STK25 | SLC30A10 | SLFN5 | FUS | DRAP1 | NCCRP1 | DYRK4 |
| EDN3 | SLC31A2 | EXOC3L1 | | MPG | DCSTAMP | ATP6V0E2 |
| PDE3B | SLC5A11 | HLA-F | | PPA1 | CCL1 | KLK15 |
| TWSG1 | BAMBI | SLC15A3 | | HYOU1 | PAEP | SLC12A8 |
| AKAP7 | KRT14 | MOV10 | | TMED2 | NKX2-1 | C12orf57 |
| SLC16A5 | PIWIL2 | NMI | | PFDN2 | TFPI | HES2 |
| ARL8A | MOB2 | STARD5 | | C1orf122 | KRT80 | NUCB2 |
| RHOV | CIDEB | TRIM21 | | PDAP1 | LURAP1 | SLC36A4 |
| CHPT1 | DBP | BATF2 | | PYCR1 | DUSP27 | PTPRN2 |
| CNTFR | PLCL1 | TRIM5 | | MLF2 | FAM131B | MARVELD1 |
| RAP1GAP2 | PLA2G12B | SLC25A28 | | TMEM165 | THPO | TCEAL3 |
| NBPF14 | RBP2 | CXCL11 | | HOXB13 | IL17C | C14orf64 |
| B9D2 | FADS6 | UBA7 | | ARPC5L | PCDH11X | FERMT3 |
| POLD1 | FLVCR1-AS1 | TRIM69 | | POLR2K | SLC25A47 | SLC7A8 |
| GFOD1 | PLB1 | GBP4 | | CCT6A | | PLXDC2 |
| CASP1 | PRSS36 | LY6E | | TMEM134 | | FGFR2 |
| LGALS8 | SYT8 | CXCL10 | | TRMT112 | | RAMP1 |
| TGFB1 | HMHA1 | C17orf67 | | PCBD1 | | PDIA5 |
| ADAMTS14 | KNG1 | SAA1 | | LSM10 | | COL16A1 |
| | MYBPC1 | LAMP3 | | GNPNAT1 | | MYRIP |
| | ANKRD20A3 | CFB | | | | SYNE1 |
| | NAGS | MOB3C | | | | KLK4 |
| | DIO3 | SAA2 | | | | TRIQK |
| | FMN2 | PXK | | | | COPG1 |
| | RELL1 | BTC | | | | CKAP4 |
| | ENPEP | SP140L | | | | CADPS |
| | FAM27A | LMO2 | | | | SPINK2 |
| | ZBTB16 | SOCS1 | | | | TCEAL8 |
| | ADAT3 | RASGRP3 | | | | ARSJ |
| | FITM1 | CD274 | | | | |
| | FGF22 | BST2 | | | | |
| | AMICA1 | DNAJC6 | | | | |

| outTop-Genes18 | outTop-Genes19 | outTop-Genes21 | outTop-Genes22 | outTop-Genes23 | outTop-Genes24 | outTop-Genes25 | outTop-Genes26 |
|---|---|---|---|---|---|---|---|
| FABP1 | CA1 | NACA | TXNIP | ARL6IP1 | S100A11 | EEF1A1 | FOS |
| GOLM1 | SELENBP1 | EEF1B2 | MXD1 | HMGB1 | ID1 | C15orf48 | JUN |
| HMGCS2 | CA2 | HNRNPA1 | EMP1 | PTTG1 | S100P | YBX1 | IER2 |
| UGT2B17 | SULT1A1 | BTF3 | CEACAM6 | HMGN2 | ID3 | USMG5 | DUSP1 |
| CHP2 | AKR1B10 | NPM1 | TRIM31 | TUBA1B | ID2 | ATP5E | JUNB |
| C10orf99 | CHCHD10 | NBEAL1 | MUC13 | HMGB2 | ANXA2 | PABPC1 | EGR1 |
| CISD3 | CLDN8 | SLC25A6 | TP53INP2 | CKS2 | S100A16 | NDUFA5 | FOSB |
| CES2 | ITPKA | EIF3L | LITAF | CCNB1 | KRT20 | C14orf2 | ATF3 |
| TMEM141 | ARL2 | EEF2 | BIRC3 | TUBB4B | VSIG2 | EFHC2 | BTG2 |
| ADH1C | AKR7A3 | EIF3F | ARRDC4 | CDC20 | CCL15 | COMMD10 | RHOB |
| TP53TG1 | TMEM72 | GLTSCR2 | SECTM1 | UBE2C | S100A14 | CTTNBP2 | ZFP36 |
| SLC39A5 | ZNF57 | EIF3H | MIER3 | NUCKS1 | ST3GAL4 | DMRTA1 | IER3 |
| HSD11B2 | NPL | EIF3E | CLDN23 | LSM5 | SERPINB1 | KCNS3 | KLF4 |
| FAM195A | FSIP1 | EIF3D | EPS8 | CENPF | PERP | SELL | CLDN4 |
| TCEA3 | SNX15 | PPP1R1B | RAB11FIP1 | TOP2A | CDX2 | UBE2E2 | NR4A1 |
| PYCARD | PSCA | RSL24D1 | DUOX2 | BIRC5 | PHLDA2 | AIF1 | PPP1R15A |
| C4orf48 | SAMD4A | IMPDH2 | TNFRSF21 | CDKN3 | ACTG1 | TYROBP | UBC |
| PKP2 | SENP8 | RSL1D1 | RCAN1 | PTMS | CLIC1 | PLEKHO1 | KLF6 |
| SOD2 | CNPY4 | PEBP1 | DUSP5 | CCNB2 | MAL2 | SAMSN1 | C8orf4 |
| MGAT4B | PHLDB3 | COX7A2L | SQSTM1 | KPNA2 | PRR15L | IL7R | DNAJB1 |
| CMBL | B3GNT4 | SEC11A | IFNGR2 | CENPW | ACTR3 | SASH3 | IFRD1 |
| COX14 | TMEM116 | POLR1D | SAMD9 | RAD21 | BRI3 | ZNF257 | TRIB1 |
| PXMP2 | APBA1 | IGBP1 | TMCC3 | UBE2S | CAP1 | ZNF501 | JUND |
| CD99 | NHEJ1 | CCNI | HPGD | HMGB3 | ARPC2 | KCNA3 | TOB1 |
| ESRRA | UGT2B10 | NSA2 | OCLN | MKI67 | CHMP2B | PYHIN1 | MCL1 |
| HADH | SMPD2 | C6orf48 | ZFAND5 | RAN | TPD52 | ZAP70 | SERTAD1 |
| SUCLG2 | XAGE3 | EIF2A | TNFSF10 | STMN1 | LXN | DPEP2 | ANKRD37 |
| CAPNS1 | ANKRD45 | TOMM20 | C1orf106 | HMMR | DNAJC15 | COX7A1 | HERPUD1 |
| MAOA | SRPX2 | RBM3 | ARL14 | MAD2L1 | RAB10 | SYNJ2BP-COX16 | HSPA1B |
| MAP2K6 | MDP1 | FBL | TNFAIP3 | SKA2 | HSPA8 | PTPRCAP | ATF4 |
| AES | NID1 | EIF3G | NLN | CCNA2 | AGR3 | | NR4A2 |
| FAM213A | ACOT1 | CLNS1A | PRSS23 | CALM3 | RAB2A | | DNAJA1 |
| PFKL | RMRP | QARS | RFK | CENPA | CAPG | | BRD2 |
| B4GALNT2 | TNMD | TMEM230 | LMO7 | HMGN1 | ANXA3 | | GADD45B |
| MESP1 | ALPPL2 | ST13 | DAZAP2 | NUSAP1 | CTSE | | INTS6 |
| SIAE | CYYR1 | SH3YL1 | TNFRSF1A | H2AFV | FGFBP1 | | HBEGF |
| BCL2L15 | TIMD4 | SMAGP | DST | PTGES3 | ARPC3 | | PMAIP1 |

TABLE 4-continued

| Epithelial normal NMF programs | | | | | | | |
|---|---|---|---|---|---|---|---|
| PLEKHJ1 | OR9Q1 | APEX1 | PDCD6IP | GPSM2 | SH3KBP1 | | IER5 |
| ICAM3 | SULT2A1 | CCNB1IP1 | RIOK3 | PLK1 | CMAS | | LMNA |
| QTRT1 | | NOB1 | RMND5A | TROAP | TPM3 | | MYADM |
| FAM177A1 | | ABHD14B | CXCL16 | KIF20B | SERPINB6 | | KLF2 |
| PLCE1 | | CCNG1 | ABHD3 | MZT1 | ARF4 | | ZC3H12A |
| GPI | | TATDN1 | CD2AP | NEK2 | ATP6V0B | | TSC22D3 |
| | outTop-Genes20 | | | | | | |
| CFTR | MT1E | GDI2 | TRANK1 | TPX2 | HRCT1 | | KLF3 |
| FAM96A | MT2A | CNBP | CGN | ANP32E | FABP5 | | CEBPB |
| KIF1C | TCL1A | ERGIC3 | TICAM1 | DTYMK | VDAC2 | | FAM53C |
| CES3 | RTEL1-TNFRSF6B | TIMM9 | UBE2B | CEP55 | PPARG | | LDLR |
| SLC38A1 | PTX3 | GPR160 | TMPRSS2 | SMC4 | SDCBP2 | | MIDN |
| RTN3 | | EPB41L4A-AS1 | SDCBP | DLGAP5 | ARPC1B | | PIM3 |
| FAM45A | | NACA2 | TMEM56 | SAPCD2 | SLC22A18 | | CBX4 |
| PFKFB2 | | OLA1 | F11R | NUDCD2 | TPMT | | DDIT3 |
| MATN2 | | UBXN1 | IRF1 | CENPE | OSTF1 | | SOCS3 |
| PPARGC1A | | ZNF22 | RAP2B | AURKA | SI | | CSRNP1 |
| CYP27A1 | | PCNP | FEM1C | DEPDC1 | CSNK1A1 | | PLK2 |
| RAB32 | | PHB2 | CAB39 | CKAP2 | FAM107B | | SLC38A2 |
| DUSP23 | | TGIF1 | JUP | GTSE1 | CAST | | EGR2 |
| PRKAR2A | | OXA1L | PLOD2 | ECT2 | GNB2 | | COW |
| BDH1 | | CAMLG | GBP3 | PBK | NPC2 | | POLG2 |
| GFPT1 | | C11orf1 | LIPH | SRSF3 | SOD3 | | ZFP36L1 |
| GCNT2 | | GBAS | TMBIM1 | RBM8A | TSPAN15 | | DUSP8 |
| UBAC1 | | PDZK1IP1 | RNF103 | PTMA | CAPZB | | ZNF296 |
| PRADC1 | | FUNDC2 | NCOA7 | SFPQ | CDKN1A | | SIK1 |
| | | SNHG7 | ACHE | LBR | KDELR2 | | MNT |
| | | LETMD1 | ERRFI1 | RACGAP1 | VASP | | PER1 |
| | | CCDC59 | STOM | TPRKB | SLC16A9 | | SLC25A25 |
| | | RPIA | C12orf36 | ARHGAP11A | TNFRSF12A | | DUSP2 |
| | | DNAJC4 | PTP4A1 | DCTN3 | ORMDL2 | | ERF |
| | | UFC1 | ST14 | RBMX | SERPINB5 | | TOB2 |
| | | MED28 | NDFIP2 | CDC25B | C20orf24 | | OVOL1 |
| | | PFN2 | F2RL1 | AURKB | KRAS | | DNAJB4 |
| | | NOA1 | HK2 | PLP2 | PON2 | | KIAA1683 |
| | | | CASP10 | TIMM10 | RAB1A | | FBXL12 |
| | | | RHPN2 | DDX39A | SFT2D1 | | HOXD1 |
| | | | | HMGN3 | ARPC1A | | SNHG12 |
| | | | | PRR11 | MORF4L1 | | FAM71A |
| | | | | TNFAIP8L1 | AGPAT2 | | SEMA4A |
| | | | | | KIF5B | | SRGN |
| | | | | | VBP1 | | ING1 |
| | | | | | ATP6V1D | | SPATA2 |
| | | | | | GALE | | CDKN1C |
| | | | | | | | TPSAB1 |
| | | | | | | | RNF223 |
| | | | | | | | TPSB2 |
| | | | | | | | EGR3 |
| | | | | | | | TPPP3 |
| | | | | | | | JMJD6 |
| | | | | | | | CXCR4 |
| | | | | | | | SERTAD3 |
| | | | | | | | RGCC |
| | | | | | | | ZSWIM4 |
| | | | | | | | SRF |
| | | | | | | | FOSL1 |
| | | | | | | | IGHG3 |
| | | | | | | | LSP1 |
| | | | | | | | IGFBP3 |
| | | | | | | | CYTIP |
| | | | | | | | COL1A1 |
| | | | | | | | RGS16 |
| | | | | | | | LY6G6C |
| outTop-Genes27 | outTop-Genes28 | outTop-Genes29 | outTop-Genes30 | outTop-Genes31 | outTop-Genes32 | outTop-Genes33 | outTop-Genes34 |
| CKB | NDUF55 | PLAC8 | OLFM4 | PLA2G2A | TM4SF1 | SLC26A2 | TFF1 |
| MIR210HG | NDUFA4 | PKIB | LEFTY1 | CYBA | ACTB | CEACAM7 | MUC2 |
| PIGZ | ATP5G3 | CDKN2B-AS1 | HIGD1A | STARD10 | FDPS | ATP1B3 | GSN |
| C11orf49 | COX6C | HIGD1A | CD74 | GAPDH | HMGCS1 | NDRG1 | CDC42EP3 |
| C8orf33 | ATP5G1 | TMSB4X | REG1A | SPINK5 | MUC12 | MALL | QSOX1 |
| NSMCE4A | TXN | ETHE1 | HLA-DRA | SLPI | MSMO1 | SLC26A3 | TBX10 |
| TMEM191C | ATPIF1 | S100A10 | EPHB3 | B3GNT7 | C12orf75 | CEACAM5 | MLLT3 |
| CCL21 | COX5B | PRR13 | ALDH1B1 | PKM | IDI1 | PLS1 | GLUL |

TABLE 4-continued

Epithelial normal NMF programs

| | | | | | | | | |
|---|---|---|---|---|---|---|---|---|
| CAV1 | PRDX5 | SLC25A5 | KCNE3 | NQO1 | RHOF | GNA11 | SYTL2 |
| POU5F1 | ATP5J2 | FTL | ETS2 | ATP5D | CD59 | LIMA1 | RASEF |
| CCL4 | COX7A2 | FTH1 | RCN1 | LGALS2 | CDA | PAG1 | TSPAN1 |
| PDXP | NDUFB2 | CFL1 | RNF130 | NDUFS7 | TPM4 | SLC4A4 | BCAS1 |
| NPR1 | COX7B | MYL12B | PCCA | SLC44A4 | EZR | CAMK2N1 | HLA-E |
| FBXW10 | COX6A1 | VAMP8 | MYC | AURKAIP1 | INSIG1 | CAPN2 | MINPP1 |
| LGALS14 | ATP5H | PRSS3 | ZNF814 | EEF1D | GPRC5A | PAQR8 | MUC1 |
| PPFIA2 | ATP5J | TPT1 | HSPH1 | ASL | DHRS9 | MARCKS | FCGBP |
| MAMDC2 | COX5A | SH3BGRL3 | SMOC2 | TSPO | FAM46A | SPPL2A | MLPH |
| RELN | MINOS1 | LDHA | CTSH | GIPC1 | CTGF | CDH17 | ATP6V1G1 |
| APCDD1L | TXNDC17 | RHOC | PTPRO | PLA2G10 | TINAGL1 | SLC6A8 | ENTPD8 |
| BARHL1 | COX4I1 | FABP2 | AGTRAP | DGAT1 | SSFA2 | AHNAK | RAB27A |
| TGM4 | ATP5L | SRI | TMC8 | PGAM1 | SERP1 | MEP1A | FOXA3 |
| ASPDH | COX6B1 | TAX1BP3 | SLC5A1 | APOBR | YWHAZ | ACOX1 | CAPN8 |
| SLC32A1 | NDUFA1 | PPP1R14D | SERPINH1 | RNF145 | PLEC | EIF4G2 | GPR153 |
| MAP3K15 | DDT | PFN1 | HLA-DPB1 | CD151 | PLIN3 | APLP2 | TAGLN2 |
| CFC1B | EIF3K | CSTB | HLA-DPA1 | FKBP2 | TXNRD1 | EPB41L4B | CREB3L1 |
| AFF3 | UQCR10 | ABRACL | C12orf45 | NDUFB7 | RAP1B | TGOLN2 | FAM177B |
| C14orf178 | NDUFB3 | HN1 | ALDH1L1 | LGALS3BP | ACTN4 | TSC22D1 | IL3RA |
| ENOX1 | FAM162A | CLTB | GPC3 | APEH | TMEM120B | SLC35A3 | NEDD4L |
| GIPC3 | UQCRQ | PPDPF | LIPA | NOXO1 | FAM32A | COL17A1 | TUBB2A |
| | ATP5O | CYCS | TRIM54 | C9orf16 | RBCK1 | GNG12 | ANG |
| | C19orf70 | HINT1 | AGMAT | HLA-DRB1 | FHL2 | KTN1 | LGALS9B |
| | NDUFC1 | DYNLL1 | OXGR1 | LDHD | SLC20A2 | ACTR2 | FXYD3 |
| | NDUFS6 | MYL12A | RHBDF2 | PRSS8 | RBP4 | TMCO1 | EIF2AK3 |
| | DBI | TMEM54 | EBF4 | HSPA1A | VIL1 | HHLA2 | LGALS9C |
| | NDUFB9 | CYSTM1 | HENMT1 | DENND2A | SCNN1B | IVNS1ABP | NAAA |
| | NDUFA6 | SAT1 | MSI1 | APIP | EIF6 | FLNB | ZG16B |
| | NDUFC2 | SCP2 | NMB | RAB25 | RAB8A | METTL7A | TMCO3 |
| | NDUFB11 | EIF1 | VSNL1 | BAD | DNAJC5 | TRPM6 | GPRIN2 |
| | NDUFA11 | TDP2 | HSD3B7 | ACVRL1 | TIMP2 | GALNT7 | TPSG1 |
| | COX7C | HIGD2A | NHS | NDUFV3 | EFHD2 | SLC44A1 | SCGB2A1 |
| | ATP5G2 | GUK1 | CFI | RHBDL2 | RHOD | SLC16A1 | RAB3B |
| | NDUFAB1 | VAPA | C2 | BAK1 | CRB3 | AHCYL2 | FAM101A |
| | SNRPD2 | SNX3 | MPV17L | GSDMD | ARHGAP5 | DSG2 | GALNT5 |
| | NDUFA2 | RNF7 | ADA | SCD | LCOR | MYH9 | CLIC4 |
| | UQCRH | RAC1 | WNT5A | GPT | SIRT6 | CTNND1 | PTGER4 |
| | NAA38 | PRDX6 | ASB9 | INPP1 | GLRX | YWHAB | GDPD3 |
| | NDUFB10 | CHMP5 | FOXQ1 | KRT19 | THRB | CDH1 | SYT7 |
| | GSTP1 | UBE2A | CAPN6 | BAG3 | SMPD1 | CTSS | SPNS2 |
| | TBCA | SUMO1 | CD40 | CCND3 | LAMA1 | EPAS1 | FAM114A1 |
| | | SEPW1 | HLA-DQA1 | MVP | EREG | LASP1 | DNPEP |
| | | PDLIM1 | NOP2 | SHARPIN | VPS4B | HEPH | F3 |
| | | GNG5 | ZW10 | MFSD2A | TMEM220 | CNNM4 | ACOT7 |
| | | SKP1 | ST7 | ENDOG | LRP10 | ALDH18A1 | HSPA2 |
| | | AP3S1 | RAB11FIP3 | SDHA | C6orf132 | RBM47 | SDR16C5 |
| | | PRELID1 | RASAL1 | NUDT22 | WDR1 | GNAQ | MAN1A1 |
| | | CHMP4B | CLDN2 | TCIRG1 | WFDC3 | MXI1 | TFF2 |
| | | C2orf88 | SLC7A5 | ACE | SEMA3B | PYGB | CAPN9 |
| | | OAZ1 | PF4 | RNPEP | TJP3 | WASL | DDR1 |
| | | VDAC1 | SHISA9 | GPR35 | MVD | PRKACB | SLC7A11 |
| | | GABARAPL2 | CPXM2 | PITX1 | PPP2CB | SORL1 | TMEM173 |
| | | SERF2 | SLC28A3 | CCDC124 | PSORS1C1 | TM9SF2 | MICAL1 |
| | | ARPC5 | CPS1 | COQ9 | PMP22 | PAPSS2 | ADM |
| | | SDHD | ESRRG | PPIC | TOP1 | | EDEM1 |
| | | OCIAD2 | AR | TRIM7 | RTN4 | | MIA3 |
| | | CIB1 | ADAMTS15 | COMTD1 | | | DHDDS |
| | | OST4 | C5orf38 | GPS1 | | | YIPF3 |
| | | LGALS3 | SLC39A2 | SLC35C1 | | | KCNK6 |
| | | MPST | ROBO1 | GJB3 | | | RASD2 |
| | | PPP1CA | FAM26F | EHBP1L1 | | | SNAP23 |
| | | ARL4A | ABCG5 | OPLAH | | | NPW |
| | | MAP1LC3B | LIPT2 | LRFN4 | | | WNK4 |
| | | TSTD1 | FREM1 | PPP1R12B | | | FRMD3 |
| | | EDF1 | PDE4B | RRAS | | | DHX32 |
| | | DYNLT1 | IQCG | JAG1 | | | SPECC1 |
| | | PPCS | C1orf95 | ABCB8 | | | GALNT3 |
| | | SUMO2 | PGM2 | IL1RN | | | IL1R2 |
| | | SUB1 | CIITA | NADSYN1 | | | RHOBTB1 |
| | | YWHAQ | CITED4 | PGD | | | BACE2 |
| | | ZNF706 | STXBP6 | STX4 | | | CACFD1 |
| | | PRR15 | CYP4X1 | PPP6R1 | | | RAB27B |
| | | TMEM219 | RAB38 | C19orf60 | | | MCF2L |
| | | DHRS11 | SH3BP5 | HYAL1 | | | |
| | | CFDP1 | TRPM2 | MICALL2 | | | |
| | | SBDS | | SNX8 | | | |
| | | RHOA | | MESDC1 | | | |
| | | CHP1 | | NAGLU | | | |

TABLE 4-continued

| Epithelial normal NMF programs | |
|---|---|
| C1D | PMVK |
| ANAPC16 | |
| CAPZA2 | |

TABLE 5

ILC NMF programs

| outTopGenes1 | outTopGenes2 | outTopGenes3 | outTopGenes4 | outTopGenes5 |
|---|---|---|---|---|
| CD7 | LTB | MALAT1 | JUNB | CFL1 |
| TRDC | HLA-B | EEF1A1 | IER2 | TPI1 |
| IFITM2 | IL32 | IGHA2 | JUN | OST4 |
| XCL2 | HLA-A | IGKC | BTG2 | HMGN1 |
| XCL1 | UBC | IL7R | DUSP2 | CHCHD2 |
| CTSW | HLA-C | TSC22D3 | EGR1 | SEC61B |
| TMSB4X | GSN | TXNIP | FOSB | POLR2L |
| FCER1G | TNFSF13B | JCHAIN | CD69 | ARPC2 |
| HCST | ITM2B | TPT1 | NFKBIA | FTH1 |
| VIM | BST2 | B2M | FOS | H3F3A |
| ATP5E | LST1 | KLRB1 | TNFAIP3 | SNRPD2 |
| TMSB10 | HNRNPA2B1 | IGHA1 | ZFP36L1 | UQCR11 |
| TNFRSF18 | SKP1 | H1FX | PRMT9 | GAPDH |
| HOPX | UBB | FTL | ID2 | CKLF |
| KLRD1 | MYL12B | EEF1D | NR4A1 | C9orf16 |
| PTPRC | PRPF6 | RACK1 | NR4A2 | SRP14 |
| KLRC1 | HNRNPK | FAU | CD83 | GPX4 |
| EMP3 | ENO1 | CXCR4 | CHMP1B | OAZ1 |
| S100A10 | CD2 | HNRNPA1 | MCL1 | C19orf53 |
| TNFRSF4 | PSME1 | CITED2 | PPP1R15A | SERF2 |
| CLIC1 | MYL12A | EEF2 | NFKBIZ | HSPB1 |
| ANXA1 | ALDOC | ZFP36L2 | BIRC3 | CALM1 |
| NDUFA1 | CD74 | BTG1 | PHLDA1 | NDUFB2 |
| SELL | IL4I1 | UBA52 | C12orf57 | CORO1A |
| DDIT4 | IL2RG | PFDN5 | ZFP36 | C11orf31 |
| CD99 | ARHGDIB | NBEAL1 | GADD45B | NAA38 |
| SOX4 | LTA4H | NACA | HERPUD1 | PPIA |
| C1orf162 | CD37 | DUSP1 | SAT1 | COX7A2 |
| SF3B5 | HLA-E | GLTSCR2 | SERTAD1 | DYNLL1 |
| COX8A | PEBP1 | SEC11A | DNAJB1 | H2AFV |
| STK17B | LSP1 | PTMA | NFKBID | BRK1 |
| ITGB2 | ATP5A1 | EEF1B2 | ZNF331 | NEDD8 |
| PPP1R2 | TIMP1 | PABPC1 | ATF3 | C14orf2 |
| PGK1 | HSPA8 | COMMD6 | AREG | PYURF |
| CARD19 | CD164 | FXYD5 | DNAJA1 | GSTP1 |
| TUFM | STK17A | UQCRB | SRSF7 | PPP1CA |
| TNFSF10 | TMBIM6 | EIF3E | MAP3K8 | SFPQ |
| UQCRQ | LDHB | CCNI | INTS6 | CTNNB1 |
| POMP | ARL6IP5 | ATP5G2 | YME1L1 | ISG15 |
| GPR171 | SLC25A3 | IGLC3 | IRF1 | RGS1 |
| GMFG | YWHAH | BTF3 | PIM3 | KRT81 |
| S100A4 | AMICA1 | CCND3 | CREM | ARPC1B |
| S100A6 | EIF3L | KLF6 | SRSF2 | UBL5 |
| ADGRE5 | AQP3 | COX4I1 | KDM6B | RBX1 |
| ARHGAP15 | ATP5B | IGLC2 | SRSF3 | SIVA1 |
| MORF4L1 | XRCC5 | TYROBP | OTUD5 | SUMO2 |
| FMNL1 | IFNGR1 | SRGN | FNBP1 | YBX1 |
| CEBPB | HSPA5 | RNASET2 | HNRNPU | H2AFY |
| IFITM3 | EID1 | PPDPF | NCOA7 | SF3B6 |
| HNRNPM | HLA-DRB1 | RSL24D1 | RHOB | ACTB |
| TRGC1 | P4HB | PCBP2 | EIF4A1 | GPSM3 |
| SAMSN1 | IGFBP4 | CIRBP | SNHG9 | UQCR10 |
| FYB1 | RGS10 | SLC25A6 | ATF4 | WDR83OS |
| TRAPPC1 | HNRNPA0 | VAMP2 | C1orf56 | COTL1 |
| MYO1F | ATP5O | N4BP2L2 | TMEM107 | CDC42 |
| ENY2 | TMBIM4 | PNRC1 | ITPR1 | HINT1 |
| MT2A | HNRNPA3 | EIF3H | RSRP1 | SUB1 |
| LGALS1 | LAMP1 | DEK | FRY | NDUFB7 |
| SH3GLB1 | ANXA6 | PCDH9 | BRD2 | PARK7 |
| COX6A1 | VWA5A | HNRNPUL1 | SEPT2 | DRAP1 |
| SP100 | ERP29 | CAT | MYADM | NDUFS5 |
| DDX5 | PDIA3 | EIF1 | KLF4 | MINOS1 |
| TMEM258 | ITM2A | NPM1 | TAGAP | ATP5G1 |
| ICAM3 | ARPC3 | GIMAP6 | METTL15 | RHOC |
| UBE2N | SQSTM1 | EIF3F | H3F3B | SMS |

TABLE 5-continued

ILC NMF programs

| outTopGenes1 | outTopGenes2 | outTopGenes3 | outTopGenes4 | outTopGenes5 |
|---|---|---|---|---|
| APOBEC3G | NCL | ODF2L | RORA | ATP5G3 |
| JAK1 | HNRNPC | EIF3D | CXCL2 | HNRNPDL |
| HSPA1A | | COX7C | TIPARP | MYL6 |
| CWC15 | | XIST | SKIL | TIMM8B |
| GLIPR2 | | SSR2 | YPEL5 | COX17 |
| CLEC2D | | CLK1 | FOSL2 | ARHGDIA |
| CD247 | | TOMM7 | CDKN1A | GYPC |
| PTGES3 | | ATP5D | SMDT1 | PSMB9 |
| RBM39 | | SERP1 | HNRNPH1 | |
| PFN1 | | CD44 | HSPA1B | |
| RGS16 | | SRSF5 | KRT8 | |
| LAMTOR2 | | FKBP5 | RNF139 | |
| ANAPC11 | | PRR13 | IER5 | |
| RHOH | | UQCRH | EML4 | |
| | | RBMS1 | CSRNP1 | |
| | | C6orf48 | REL | |
| | | IL1R1 | SLC2A3 | |
| | | IGHM | MAFF | |
| | | TNRC6B | ARL4A | |
| | | YPEL3 | ICOS | |
| | | HSD17B11 | BHLHE40 | |
| | | CMPK1 | ZFAND5 | |
| | | TSPYL1 | SRSF6 | |
| | | DHRS7 | IFRD1 | |
| | | ATP5L | B3GNT7 | |
| | | UBXN1 | FUS | |
| | | CSDE1 | | |
| | | EIF3G | | |
| | | HMGB1 | | |
| | | SEC62 | | |
| | | HMGN3 | | |
| | | UXT | | |

TABLE 6

Mast cell NMF programs

| outTop-Genes1 | outTop-Genes2 | outTop-Genes3 | outTop-Genes4 | outTop-Genes5 | outTop-Genes6 | outTop-Genes7 | outTop-Genes8 |
|---|---|---|---|---|---|---|---|
| LGALS1 | BIRC3 | JUNB | CPA3 | EEF1A1 | SH3BGRL3 | CTSG | HLA-B |
| GAPDH | TNFAIP3 | JUN | MS4A2 | NACA | SERF2 | CMA1 | HLA-C |
| TUBB | PTGS2 | IER2 | SKP1 | TPT1 | TMSB4X | TPSAB1 | HLA-A |
| ACTG1 | BTG2 | FOS | B2M | GLTSCR2 | TMSB10 | FTH1 | CLU |
| PPIA | KLF6 | CD69 | RGS1 | EEF1B2 | S100A11 | MALAT1 | CTSD |
| ACTB | SLC26A2 | PPP1R15A | SRGN | EEF2 | ATP5E | TSC22D3 | HLA-E |
| CFL1 | IL1RL1 | DUSP1 | EIF4A2 | HNRNPA1 | UQCR11 | CD63 | PSAP |
| ARPC2 | NFKBIZ | UBB | RGS13 | BTF3 | LTC4S | H3F3B | CD74 |
| TUBA1B | NFKBIA | GATA2 | PTMA | SNHG8 | NDUFB2 | LAPTM4A | HSPA1A |
| VIM | CXCR4 | GADD45B | MYL12A | EIF3E | FTL | HPGD | TIMP1 |
| PRDX1 | MCL1 | SRSF5 | CALM2 | SLC25A6 | CD52 | DAD1 | HSPB1 |
| RAN | CSF1 | DDIT4 | KIT | UBA52 | TYROBP | C1orf186 | IFITM3 |
| YBX1 | THBS1 | INTS6 | SPCS1 | CCNI | MYL6 | NPC2 | BST2 |
| HINT1 | NEAT1 | SON | ITM2B | RGS10 | POLR2L | CAPG | HSPA1B |
| H2AFZ | REL | LMNA | H3F3A | ATP5G2 | C14orf2 | CLIC1 | LAPTM5 |
| SLC25A5 | CREM | GPR65 | ALOX5AP | EIF3L | S100A4 | TPSB2 | ARHGDIB |
| CHCHD2 | AREG | SERTAD1 | DDX5 | TOMM7 | UQCRQ | LGALS3 | HSP90AA1 |
| LDHA | DUSP6 | FOSB | TXNIP | EIF4B | COX7A2 | GSTP1 | HLA-DRB1 |
| CALM1 | GALC | SGK1 | SUMO2 | EIF3H | ATP6V1F | ANXA1 | HLA-DPB1 |
| HMGB2 | AHR | TUBA1A | CD9 | C6orf48 | USMG5 | SSR4 | HLA-DPA1 |
| PSMA7 | DUSP2 | H1FX | SLC18A2 | SEC11A | NDUFA4 | FCER1A | HLA-DRA |
| H2AFV | SOCS1 | HNRNPH1 | EEF1D | SERP1 | OST4 | SERPINB1 | PSME1 |
| DBI | VMP1 | TLE4 | RTN4 | EIF3F | COX17 | SRP14 | TNFSF10 |
| EXD3 | TPM4 | NR4A2 | BTG1 | LINC00493 | COX5B | EIF1 | IFI6 |
| ARPC5 | GLUL | SOX4 | GABARAPL2 | TOMM20 | ATP5I | HSPA5 | PTGS1 |
| TPI1 | LIF | SAT1 | PPDPF | EIF3D | CKLF | VWA5A | RGS2 |
| ATP5G3 | NR4A1 | DDX18 | SAMSN1 | PABPC1 | COX6B1 | PLIN2 | CTNNBL1 |
| CALR | ID2 | SRSF7 | TMEM59 | EPB41L4A-AS1 | UBL5 | KRT10 | PSMB9 |
| PKM | RHOH | EIF4A1 | VAMP2 | SSR2 | COMMD6 | VAMP8 | CD53 |
| HSP90B1 | SRSF2 | UBE2S | TSC22D1 | NSA2 | UQCR10 | SPCS2 | NSMCE1 |
| PARK7 | CD83 | SRSF6 | SDPR | EIF3K | CST3 | DYNLL1 | TMEM176B |
| ENO1 | KDM6B | SNHG9 | STMN1 | SNHG7 | PFDN5 | DNAJB9 | IFITM2 |
| S100A10 | STK17B | DNAJA1 | BEX4 | C19orf43 | COX6A1 | DYNLT1 | BTK |

TABLE 6-continued

Mast cell NMF programs

| | | | | | | | |
|---|---|---|---|---|---|---|---|
| SNRPD1 | FOSL2 | CLK1 | ASAH1 | EIF3G | FAU | APLP2 | HSD17B12 |
| CKS2 | JUND | ARGLU1 | CD44 | COX4I1 | COX7C | PRDX6 | ALOX5 |
| SNRPE | NR4A3 | IRF1 | TMBIM4 | UBXN1 | TMED2 | IFNGR1 | DNAJB1 |
| DUT | SLC2A3 | CITED2 | HMGN1 | EDF1 | MYEOV2 | HERPUD1 | TMBIM6 |
| RANBP1 | ZC3H12A | DDIT3 | NPM1 | ST13 | S100A6 | EAPP | UBE2L6 |
| SEC61B | HCST | SRRM1 | ADRB2 | POLR1D | NDUFA1 | FCER1G | CTSS |
| PPP1CA | PAG1 | ZG16 | LMO4 | UFC1 | OAZ1 | VAT1 | CD82 |
| COX5A | MT2A | FABP1 | SDCBP | EVI2B | SNX3 | CCL23 | ACTR3 |
| HIST1H4C | BCL2A1 | PIGR | MORF4L1 | FBL | NDUFA13 | GNAI1 | CAP1 |
| CKS1B | AKAP12 | KLF4 | ELF1 | IGBP1 | WDR83OS | NDUFB8 | NUCB1 |
| PDIA6 | ACSL4 | HAX1 | ATP6V1G1 | HADHA | NEDD8 | ATP5L | LY6E |
| MZT2B | C1orf56 | CSDE1 | EIF1B | ALKBH7 | C19orf53 | SLA | GSN |
| MYL12B | PTPN7 | C12orf57 | HNRNPA2B1 | IL1B | NDUFS5 | PEPD | ALAS1 |
| TXN | NFE2L2 | ARRDC3 | HPGDS | TMED4 | C4orf48 | PDCD4 | GRN |
| PCNA | IDS | HEXIM1 | ATP6V0E1 | LSM2 | DRAP1 | HDC | ITM2C |
| HMGB1 | LEO1 | ZNF331 | ESD | POLR2J3 | ROMO1 | CCDC90B | AP2M1 |
| TPM3 | NFKBID | DDX3X | CRBN | HIGD2A | ATP5G1 | CDK5RAP3 | DPP7 |
| PGAM1 | ELL2 | CHMP1B | UQCRB | CHMP3 | SEC61G | LDHB | CEBPB |
| PPIB | CD48 | KRT8 | HNRNPU | ARL6IP4 | NOP10 | COX7A1 | CHST12 |
| SNRPG | IER3 | ZRANB2 | LITAF | MRFAP1 | CSTB | ATP6AP2 | ANXA11 |
| PTTG1 | ZFP36 | MT1G | SYPL1 | AP1S2 | NDUFA3 | POP5 | ANXA6 |
| GNG5 | PLAUR | FUS | NBEAL1 | ZFP36L2 | GUK1 | SNX2 | CD68 |
| YWHAB | HIF1A | WSB1 | SUB1 | PNISR | PFN1 | MGST3 | HSP90AB1 |
| HN1 | SKIL | C15orf48 | HS3ST1 | C8orf59 | C4orf3 | PLGRKT | RENBP |
| SNRPF | GPR183 | POLR2A | LEPROTL1 | PABPC4 | NDUFB1 | MAD1L1 | RNASET2 |
| SNRPB | PIM1 | EMP3 | RALB | ZFAND1 | SUMO1 | XAB2 | CARD16 |
| CALM3 | EGR3 | HNRNPH2 | CCT8 | ABHD14B | RNF181 | CST7 | RARRES3 |
| HNRNPF | ANKRD28 | POMGNT1 | PPIG | RWDD1 | POLR2K | ORC4 | PLAT |
| DEK | DUSP10 | METTL15 | NDUFB5 | DPH5 | C19orf70 | TIMM17B | GMPR |
| HMGN2 | CDC42SE1 | PRPF6 | DSTN | SDCCAG8 | TRMT112 | MPLKIP | STAT1 |
| PDIA3 | B4GALT5 | TOB1 | XBP1 | TDRD3 | MT1X | KLHDC2 | PTPN6 |
| NDUFS6 | FOXP1 | GUCA2A | C14orf166 | HNRNPA0 | RSL24D1 | SPTLC1 | MBOAT7 |
| | EPAS1 | SLC45A3 | EIF3M | SNX5 | C11orf31 | H1F0 | PEF1 |
| | YWHAZ | TTPAL | BNIP3L | RHOF | LAGE3 | DNAAF2 | TAGLN2 |
| | STK4 | GUCA2B | TMED10 | LUC7L3 | NENF | NQO2 | ISG15 |
| | SYAP1 | CEBPZ | C11orf58 | DHRS4L2 | COX14 | CHMP4A | PLD3 |
| | VEGFA | TCF7 | HMGN3 | PPP1R11 | SELT | WDR33 | MAGED2 |
| | IGHG3 | TSPYL2 | FAM46A | NACA2 | FAM96B | METTL12 | HLA-F |
| | PHLDA1 | TFF3 | | CCNG1 | C9orf16 | DPF2 | PCMT1 |
| | ARHGEF6 | ATP1B1 | | CCDC59 | TSTD1 | SPRYD7 | VPS28 |
| | RASSF5 | MEPCE | | SURF1 | SDF2L1 | RABAC1 | ECH1 |
| | CNRIP1 | TGIF1 | | YBEY | SEPW1 | C2orf74 | HSPA6 |
| | EIF5 | A1BG | | ZNF90 | CLTB | STX5 | LAT2 |
| | DTNBP1 | SBDS | | TIMM9 | MINOS1 | ANKRD49 | ARF1 |
| | LCP2 | | | EIF2S3 | APOC1 | FBXL15 | RSAD2 |
| | TSEN54 | | | ELMO1 | SPNS1 | TAF9 | ACADVL |
| | UBE2D3 | | | GPATCH8 | PRR13 | PPIL4 | LAMP1 |
| | CCL4 | | | CCNB1IP1 | POLR2J | RPAIN | IDH3G |
| | ADCYAP1 | | | ZNF22 | CAMTA1 | C15orf61 | |
| | MAFF | | | JAGN1 | NDUFAF3 | N4BP2L1 | |
| | IL13 | | | SUPT4H1 | TP53TG1 | YAE1D1 | |
| | ZFP36L1 | | | THAP7 | POLE4 | GLRX2 | |
| | | | | FAM175A | POLR2I | | |
| | | | | TXN2 | FKBP2 | | |
| | | | | ZNF791 | KCNMB1 | | |
| | | | | ARHGEF40 | | | |

TABLE 7

Myeloid NMF programs

| outTop-Genes1 | outTop-Genes2 | outTop-Genes3 | outTop-Genes4 | outTop-5Genes | outTop-Genes6 | outTop-Genes7 | outTop-Genes8 |
|---|---|---|---|---|---|---|---|
| MMP12 | SPP1 | COTL1 | BIRC3 | FTL | H2AFZ | HSPA1A | S100A8 |
| MMP9 | MIF | YWHAH | TXN | S100A11 | HMGN2 | HSPA1B | S100A9 |
| IL7R | VIM | PKIB | FSCN1 | MYL6 | HMGB1 | HSP90AA1 | S100A12 |
| MT1G | LDHA | AMICA1 | CCR7 | SERF2 | STMN1 | DNAJB1 | LYZ |
| C1orf54 | S100A10 | GDI2 | CCL19 | PFN1 | TUBA1B | HSPB1 | S100A6 |
| MMP14 | GAPDH | FCER1A | CCL22 | LGALS1 | TUBB | HSPH1 | VCAN |
| IL4I1 | SDC2 | CD1C | LAMP3 | TMSB10 | HMGB2 | HSPE1 | S100A4 |
| MT1H | MARCO | CORO1A | MARCKSL1 | ACTB | HIST1H4C | UBC | MNDA |
| FCGR2A | FN1 | SPI1 | GSTP1 | VAMP8 | CKS1B | JUN | CSTA |
| MT1X | TPI1 | ACTR3 | CSF2RA | PRDX1 | DUT | IER5 | FCN1 |
| LMNA | CLEC5A | CLEC10A | ID2 | OAZ1 | RANBP1 | HSPA6 | TSPO |

TABLE 7-continued

| Myeloid NMF programs | | | | | | | |
|---|---|---|---|---|---|---|---|
| MT1E | FBP1 | FAM49B | RGS1 | ATP5J2 | H2AFV | HSPD1 | TYROBP |
| H2AFJ | RGCC | ARPC1B | IDO1 | CFL1 | NUCKS1 | UBB | H3F3A |
| CCL5 | PGK1 | CKLF | BASP1 | DBI | TYMS | HSP90AB1 | GCA |
| TMEM176A | SLC11A1 | SPINT2 | ANXA6 | COX5B | DEK | ZFAND2A | FPR1 |
| MT1F | SLAMF9 | CAP1 | CRIP1 | SH3BGRL3 | ANP32B | DNAJA1 | CD55 |
| ENPP2 | BNIP3 | GSN | RAB9A | ATP6V1F | PCNA | HSPA8 | RETN |
| ATP6AP2 | EMP3 | PPA1 | CFLAR | CSTB | UBE2C | DNAJA4 | RBP7 |
| VMO1 | FCGR2B | H2AFY | LSP1 | COX6B1 | RPA3 | PLIN2 | MGST1 |
| S100B | VKORC1 | CD1E | GRSF1 | YBX1 | MZT2B | BAG3 | METTL9 |
| IL2RG | SLC16A3 | NDRG2 | IL32 | PPDPF | TK1 | CACYBP | CLEC4E |
| PGD | RAB13 | PAK1 | EBI3 | UQCR10 | RAN | CLK1 | RNASE2 |
| IL2RA | FAM162A | ABI3 | CCL17 | AIF1 | PTTG1 | SLC5A3 | CD36 |
| SLAMF7 | ALDOA | VASP | LAD1 | UBL5 | CKS2 | HMOX1 | CDA |
| COL6A2 | P4HA1 | ACTG1 | GADD45A | ATP5E | TOP2A | SERPINH1 | BLVRB |
| COL6A1 | GPI | ARHGDIB | STK4 | UQCR11 | CDK1 | DNAJB6 | CYP1B1 |
| PPIC | CALM1 | ARPC2 | DUSP4 | NDUFB2 | BIRC5 | FKBP4 | NCF1 |
| TNFRSF9 | BCAT1 | LGALS2 | FNBP1 | NDUFA1 | LDHB | ANKRD37 | PLBD1 |
| NFKBIE | BNIP3L | CIB1 | SYNGR2 | NOP10 | SNRPD1 | FAM46A | QPCT |
| C1orf21 | VDAC1 | ARF6 | DUSP5 | FCER1G | CHCHD2 | HILPDA | BST1 |
| RCAN1 | PGAM1 | CNN2 | NUB1 | TMSB4X | RRM2 | NDRG1 | RTN3 |
| ITGB7 | LPL | PRELID1 | RAMP1 | FKBP1A | CARHSP1 | DNAJB4 | LRRK2 |
| CHST2 | MATK | PYCARD | CST7 | PPIA | KPNA2 | MYLIP | NDUFB1 |
| PDPN | SLC16A10 | ENTPD1 | RASSF4 | RHOA | MZT2A | GADD45G | GLIPR2 |
| RABAC1 | CD109 | FAM89B | DAPP1 | CAPZA2 | LSM4 | SLC38A2 | CLEC4D |
| OLFML2B | HPCAL1 | UCP2 | ALDH2 | RNF181 | SMC4 | SQSTM1 | SELL |
| ADAM8 | HCFC1R1 | RHOG | GPX4 | ARPC3 | NUSAP1 | EIF5 | VNN2 |
| NQO1 | ITGB1 | PRR13 | ISCU | DYNLRB1 | CENPW | RHOB | ASGR1 |
| ATP6V0D2 | GBE1 | DBNL | RELB | CALM2 | ANP32E | TCP1 | RAB27A |
| NBL1 | ENO2 | ARPC5 | GPR157 | RAC1 | HMGN1 | CHORDC1 | C19orf79 |
| ATP2C1 | RALA | KCNMB1 | SIAH2 | CYCS | SRSF3 | PTP4A1 | FBXL5 |
| SUCNR1 | NT5E | BID | CLIC2 | ATOX1 | SNRNP25 | TRA2B | FAM200B |
| AIFM2 | TMEM45A | TPM3 | GABARAPL2 | BLOC1S1 | DTYMK | PTGES3 | CRISPLD2 |
| TPD52 | CST6 | CD207 | OSTF1 | SNRPD2 | SNRPG | CITED2 | FOLR3 |
| GSTM4 | DARS | RUNX3 | TAGLN2 | GNG5 | MKI67 | MKNK2 | AGTRAP |
| PPM1N | COLEC12 | SAMHD1 | ERICH1 | NDUFS5 | SKA2 | SNAPC1 | CES1 |
| MMP10 | HTRA1 | CLNS1A | POGLUT1 | OST4 | CENPM | DEDD2 | CCR2 |
| ACVRL1 | KCNN4 | SNX3 | KIF2A | TRAPPC1 | CDKN3 | ATP6V1H | PYGL |
| ALOX15B | PFKP | KCNK6 | CDKN1A | PRDX5 | ZWINT | STIP1 | CREB5 |
| SEMA4A | PDLIM7 | FAM110A | NMRK1 | COX17 | HNRNPA2B1 | BHLHE40 | FAM45A |
| LAG3 | ANGPTL4 | ACAA1 | CIRBP | TMEM230 | HN1 | PIM1 | ITGAM |
| SGPP1 | QSOX1 | PTPN6 | MYO1G | NDUFC1 | HMGB3 | CRYAB | LTB4R |
| TSPAN15 | IGFBP2 | LCP1 | VOPP1 | NDUFA5 | SNRPB | ALAS1 | DPYD |
| CYP27B1 | TNS1 | GLIPR1 | RFTN1 | GABARAP | SIVA1 | EIF4A2 | TMEM170B |
| P4HA2 | TMEM38B | ATG3 | TNFAIP2 | TXNDC17 | SNRPF | RGS16 | ASGR2 |
| CLDN7 | PPBP | PLEKHO1 | MGLL | NDUFB3 | TMEM106C | SNHG12 | CR1 |
| SPTAN1 | CDCP1 | UBE2E2 | TBC1D4 | FAM96B | UBE2S | NXF1 | ZDHHC20 |
| PRKCDBP | UGP2 | AXL | NCCRP1 | SCAND1 | MCM7 | BCL10 | TMEM91 |
| CD40 | CLLU1OS | ZNF385A | PTPN1 | NDUFA11 | MAD2L1 | ARRDC2 | TLR4 |
| MMP25 | SCG5 | CLIC1 | MAP3K13 | VAMP3 | PARP1 | AHSA1 | CCNY |
| PROCR | PHLDA1 | IL22RA2 | TRADD | NDUFA6 | GGH | FAM210A | PSTPIP1 |
| MLLT6 | CD151 | SPATS2L | GPBP1 | POLR2L | NUDT1 | RSRC2 | SGMS2 |
| ARID5B | NMB | TCTN3 | LY75 | AP3S1 | SET | NUDT4 | ARHGEF40 |
| TPSB2 | TM4SF19 | MYL12A | FAM118A | PIN4 | LSM3 | PDK1 | F5 |
| HVCN1 | ANG | CLTB | CD200 | AP2S1 | NASP | FEM1C | NFE2 |
| TRIM47 | SLC2A5 | RGS19 | FAM60A | ROMO1 | SMC2 | EAF1 | SMARCD3 |
| HTATIP2 | ZGLP1 | RAP1A | HMSD | SCOC | TUBB4B | DDX3Y | CLU |
| PIR | CSF1 | LPXN | NFKB1 | TRAPPC2L | STRA13 | RNMT | HP |
| ACO1 | NRIP3 | HCLS1 | KDM2B | SUMO2 | LSM5 | ING1 | MEGF9 |
| DTX2 | PLOD2 | ARF3 | TRAF1 | FXYD3 | IDH2 | ENGASE | NFAM1 |
| AK8 | RAI14 | CACNA2D3 | FYTTD1 | MORN2 | H2AFX | ABHD3 | RAB3D |
| ECM1 | CA12 | CCND3 | RHOF | NDUFA2 | SLC25A5 | FAM13A | MARC1 |
| APOO | MIR210HG | ASB2 | ANXA7 | FABP4 | CDC20 | MID1IP1 | PXN |
| SMOX | LAT | CA2 | RAB11A | UPRT | CCNB1 | ZBTB43 | SLC16A6 |
| STEAP1B | AK4 | SRSF9 | LIMCH1 | CETN2 | | TSPYL2 | RASSF3 |
| PDLIM4 | ZNF395 | HIC1 | | DYNLT3 | | INSIG2 | TNNT1 |
| CDC42EP1 | MMP8 | SNX20 | | GNG10 | | ID3 | CD300LB |
| EMILIN1 | H1F0 | HLA-DQB2 | | MOSPD1 | | IER5L | DYSF |
| LSS | MMP7 | EID1 | | SLC22A18AS | | HK2 | NRG1 |
| SLC39A13 | PAM | RAB32 | | AKR7A3 | | IMP3 | |
| FGD5 | SEMA3C | CAT | | TMEM125 | | PLEKHF2 | |
| CERCAM | DPCD | CD1D | | VIL1 | | WDFY1 | |
| STARD10 | AGRP | HNRNPK | | NCBP2 | | | |
| PTRF | SPAG4 | PARM1 | | HKDC1 | | | |
| PCGF2 | TNFRSF12A | ZYX | | SERPINB5 | | | |
| NNMT | EGFL7 | CCR6 | | S100A2 | | | |
| NCK1 | ESYT2 | MLF2 | | FABP1 | | | |
| TTC39B | ASPH | DOK1 | | WDR72 | | | |
| IL21R | PPARG | MTMR14 | | MTMR2 | | | |

TABLE 7-continued

| Myeloid NMF programs | | | | | |
|---|---|---|---|---|---|
| AIM2 | RAPH1 | TPMT | | RNF186 | |
| | FCRLB | DENND1B | | ZNF503-AS2 | |
| | SLC28A3 | PON2 | | ARL14 | |
| | ADSSL1 | ALOX5 | | DNAL1 | |
| | SPOCD1 | DEF6 | | | |
| | PCOLCE2 | PRCP | | | |
| | C3 | UNC119 | | | |
| | PLXNA3 | SUPT4H1 | | | |
| | SEMA4B | TMEM14C | | | |
| | CLDN1 | | | | |

| outTop-Genes9 | outTop-Genes10 | outTop-Genes11 | outTop-Genes12 | outTop-Genes13 | outTop-Genes14 | outTop-Genes15 |
|---|---|---|---|---|---|---|
| TIMP1 | G0S2 | FOS | GZMB | ANXA2 | POMP | EEF1A1 |
| CD44 | FTH1 | DUSP1 | CLIC3 | CD63 | ATP6V0E1 | TPT1 |
| SLC2A3 | BCL2A1 | JUNB | PLAC8 | PPIB | MINOS1 | EEF1B2 |
| EREG | IFITM2 | ZFP36 | ITM2C | ATP5B | SEC61G | NACA |
| SERPINB9 | B2M | NEAT1 | TSPAN13 | PDIA3 | SUB1 | UBA52 |
| VEGFA | H3F3B | NR4A2 | IRF7 | PSMB1 | NPC2 | BTF3 |
| ATP1B3 | ALOX5AP | FOSB | C12orf75 | RNH1 | DYNLL1 | SLC25A6 |
| THBD | SAT1 | IER2 | PPP1R14B | GSTO1 | TMBIM6 | PABPC1 |
| HIF1A | PLEK | ATF3 | TCF4 | ENO1 | RBX1 | NBEAL1 |
| ETS2 | CYSTM1 | KLF6 | IRF8 | ATP5A1 | NDUFA4 | FAU |
| NLRP3 | OSM | SGK1 | SEC61B | TALDO1 | TMBIM4 | EIF3E |
| THBS1 | TREM1 | EGR1 | MZB1 | RPN2 | SFT2D1 | EEF2 |
| YWHAZ | HCAR2 | BTG2 | HERPUD1 | PKM | COX7A2 | ATP5G2 |
| ATP13A3 | RHOH | ZFP36L1 | BCL11A | PDIA6 | C14orf2 | HNRNPA1 |
| UPP1 | ANP32A | MCL1 | CXCR3 | HSPA5 | HSP90B1 | TOMM7 |
| PPP1CB | SDCBP | SOCS3 | SERPINF1 | SLC3A2 | ATP5I | PFDN5 |
| CREM | PI3 | KLF4 | TCL1A | ANXA5 | ATP6V1G1 | NAP1L1 |
| GK | AQP9 | CHMP1B | UGCG | ATP6V0D1 | LY96 | NPM1 |
| HBEGF | S100P | ZNF331 | PLD4 | ERP44 | SPCS3 | EIF1 |
| SRGN | MAP1LC3B | RGS2 | CLN8 | CTSH | USMG5 | EEF1D |
| PFKFB3 | CD69 | DUSP2 | SPCS1 | CCT5 | SKP1 | EIF3H |
| OLR1 | UBE2B | JUND | SOX4 | IGSF6 | TMEM50A | COX7C |
| LCP2 | FCGR3B | NR4A1 | IRF4 | REEP5 | NDUFA13 | ATP5L |
| TNFAIP3 | ADM | NFKBIZ | CCDC50 | COPE | MYL12B | COX4I1 |
| TPM4 | PROK2 | HNRNPU | DERL3 | UQCRC1 | TBCA | GLTSCR2 |
| CD93 | MALAT1 | CCNL1 | SSR4 | PSMB6 | COX7B | EIF3F |
| CEBPB | CMTM2 | GADD45B | LTB | PSMD8 | NDUFB11 | COMMD6 |
| BTG1 | IL1R2 | XIST | SCT | PSMD7 | VPS29 | UQCRH |
| PLAUR | CSF3R | ZFAND5 | SMPD3 | TUFM | TMEM59 | SEC11A |
| VMP1 | CLEC2B | DDX5 | C9orf142 | NAGK | CAMTA1 | EIF3L |
| SLC25A37 | HLA-E | DDX3X | PTGDS | EIF31 | CD163 | PTMA |
| LITAF | CD53 | PNRC1 | SPIB | PSMA7 | FABP5 | C6orf48 |
| DSE | PHACTR1 | C5AR1 | SEL1L3 | GHITM | SEC62 | PCBP2 |
| EMP1 | SLPI | CD83 | ERP29 | ATP5G3 | COX6C | UQCRB |
| SLC44A1 | IL1RN | NFE2L2 | PLP2 | PSMA5 | ABRACL | HIGD2A |
| FAM49A | PLAU | RASGEF1B | SLC20A1 | FERMT3 | HSBP1 | POLR1D |
| ACTN1 | PPIF | MAT2A | PTCRA | LMAN2 | NDUFC2 | EIF4B |
| HPSE | FLOT1 | EGR2 | APP | MGST3 | CNIH4 | COX7A2L |
| TNFRSF1B | USP10 | ABHD5 | SLC15A4 | XRCC6 | CISD2 | SERPI. |
| RNF19B | GNG2 | NR4A3 | MAP1A | SSR2 | LSM6 | TOMM20 |
| NAMPT | HES4 | NFKBID | OPN3 | EIF4A1 | HNRNPA3 | C9orf16 |
| ITGAX | TAGAP | TGIF1 | GPR183 | CAPG | VPS35 | EIF2S3 |
| DDX21 | FFAR2 | RBPJ | LRRC26 | PSMB7 | GTF3C6 | NSA2 |
| ADAM19 | FAM177A1 | OTUD1 | IL3RA | NANS | TMED10 | CCNI |
| TOP1 | BEST1 | PRDM1 | SRP14 | MANF | ATP5O | LINC00493 |
| PICALM | ZNF267 | PPP1R15A | OFD1 | ARM | UFM1 | ALKBH7 |
| ANPEP | CCRL2 | CSRNP1 | TPM2 | CYC1 | PPIG | RSL24D1 |
| TLR2 | TFF3 | MIDN | GAS6 | MDH2 | GTF2H5 | SNHG8 |
| FNDC3B | DDIT3 | PER1 | RAB11FIP1 | PSMC5 | MFSD1 | NHSL2 |
| MAP3K8 | PIM3 | KLF2 | IRF2BP2 | CCT7 | ACTR2 | ST13 |
| DUSP6 | MXD1 | TCOF1 | DCK | AP2M1 | SEPT7 | EIF3M |
| JARID2 | CDC42EP3 | WSB1 | IKZF1 | PSMB3 | PCBP1 | RSL1D1 |
| BACH1 | CXCR2 | KDM6B | ERN1 | HM13 | C4orf3 | EBL |
| SFPQ | LRG1 | GNAQ | NR3C1 | TMED9 | PAPOLA | UXT |
| PRNP | IDI1 | MYADM | LAMPS | LAPTM4A | TAX1BP1 | CMPK1 |
| MMP19 | TNFSF14 | GNA13 | CD164 | SLC25A3 | FAM96A | IGBP1 |
| SLC43A2 | KCNJ15 | ABL2 | SIDT1 | VCP | ENY2 | NACA2 |
| SAMSN1 | CMTM6 | PCF11 | GNAS | CLTA | NDUFAB1 | EIF3G |
| PNP | PGS1 | CIITA | CLEC4C | PSMD4 | GTF2A2 | ZFAND1 |
| IL1RAP | LPCAT1 | TMEM107 | LPIN1 | NDUFS2 | C8orf59 | PTRHD1 |
| SH3BP5 | EXOSC4 | IFI30 | PPP1R14A | UQCRC2 | CDC26 | PIGR |
| FLNA | MAP2K3 | JMJD1C | HINT1 | SDHB | TMEM126A | EPB41L4A-AS1 |
| ELL2 | PELI1 | IL10RA | FUZ | ORMDL2 | ATP5F1 | LYRM4 |
| TGM2 | IFRD1 | TIPARP | INPP4A | AKR1A1 | RPN1 | EEF1G |

TABLE 7-continued

| Myeloid NMF programs | | | | | | | |
|---|---|---|---|---|---|---|---|
| GPCPD1 | RNF149 | IRS2 | SNHG7 | OS9 | CDC42 | CCNG1 | |
| VDR | NSMAF | IGHG3 | | | ELF1 | TIMM9 | |
| BZW1 | UBE2W | STAT3 | | | PFDN4 | CLDN3 | |
| METRNL | HIST2H2AA3 | YME1L1 | | | ERH | THG1L | |
| SYAP1 | DGAT2 | REL | | | GADD45GIP1 | DPH5 | |
| GABARAPL1 | RNF13 | SATB1 | | | C11orf73 | OLA1 | |
| ATP6V1B2 | IFITM1 | PTGER4 | | | CHURC1 | LGALS4 | |
| CCDC109B | CPD | AFF4 | | | NDUFB5 | EIF2D | |
| STARD4 | MAP1LC3B2 | ATRX | | | MORF4L1 | CHP1 | |
| RASSF5 | | BRD2 | | | SHOC2 | DYM | |
| ACSL3 | | PHIP | | | DPY30 | EIF2A | |
| MPHOSPH6 | | IL10 | | | SNRPB2 | RAB4A | |
| GK5 | | ANKRD28 | | | SS18L2 | C19orf33 | |
| XBP1 | | RANBP2 | | | SSR3 | ZNF277 | |
| SNAI1 | | SORL1 | | | C14orf166 | QARS | |
| KYNU | | C16orf72 | | | CISD1 | ELF3 | |
| ACSL1 | | ZBTB20 | | | BTF3L4 | CDC42EP5 | |
| IVNS1ABP | | FAM133B | | | PSMA2 | CEACAM5 | |
| INSIG1 | | SGK3 | | | ISCA2 | PRSS3 | |
| ACSL4 | | ASH1L | | | | | |
| TLE3 | | FOXN3 | | | | | |
| EPB41L3 | | ZFHX3 | | | | | |
| | | SERTAD1 | | | | | |
| | | MEF2A | | | | | |
| | | BAZ2B | | | | | |
| | | FOXO3 | | | | | |

| outTop-Genes16 | outTop-Genes17 | outTop-Genes18 | outTop-Genes19 | outTop-Genes20 | outTop-Genes21 | outTop-Genes22 |
|---|---|---|---|---|---|---|
| CCL3 | BRI3 | TXNIP | ISG15 | HLA-DRB1 | APOE | C1QB |
| CXCL3 | CALR | CD52 | IFI6 | CD74 | APOC1 | SEPP1 |
| CCL4 | CTSB | LST1 | IFITM3 | HLA-DRA | GPNMB | C1QC |
| CXCL2 | GNAI2 | CD37 | CXCL10 | HLA-DPB1 | CTSD | ITM2B |
| CCL20 | SDF2L1 | CTSS | MT2A | HLA-DRB5 | NUPR1 | MS4A6A |
| SOD2 | TGFBI | C1orf162 | LY6E | HLA-DPA1 | ASAH1 | SLC40A1 |
| CXCL1 | CANX | CFD | GBP1 | HLA-DQA1 | LGMN | FCGRT |
| CCL3L1 | FKBP2 | TSC22D3 | VAMP5 | HLA-DQB1 | CCL18 | GPR34 |
| PTGS2 | MTDH | EVI2B | STAT1 | HLA-DQA2 | LIPA | MS4A7 |
| INHBA | GRINA | CEBPD | TYMP | HLA-DMA | TREM2 | RNASE6 |
| IL6 | EFHD2 | SERPINA1 | EPSTI1 | HLA-A | PLD3 | MS4A4A |
| CXCL5 | PSAP | CFP | TNFSF13B | HLA-B | CD68 | HLA-DMB |
| NFKBIA | TIMM13 | FGR | IFIT3 | CST3 | CD9 | CTSC |
| CCL3L3 | TMED2 | LIMD2 | PSMB9 | HLA-C | LAMP1 | AKR1B1 |
| IER3 | CYBB | FKBP5 | PSME2 | CPVL | GCHFR | RNASET2 |
| IL1A | COX6A1 | CD48 | MX1 | CYBA | MSR1 | FUCA1 |
| WTAP | C19orf10 | SMAP2 | IFI44L | TFF1 | CYP27A1 | STAB1 |
| NINJ1 | TTYH3 | TKT | TNFSF10 | ZNF774 | CXCL16 | CD14 |
| TNFAIP6 | P4HB | PTPRC | LAP3 | H5D17B2 | GM2A | VSIG4 |
| TNF | TPP1 | FXYD5 | IFI35 | C1orf116 | CD59 | RB1 |
| DRAM1 | C19orf24 | STXBP2 | UBE2L6 | C14orf37 | NPL | DAB2 |
| SLC39A8 | TLN1 | STK17B | IFIT2 | UGT2B17 | SDS | LPAR6 |
| RIPK2 | C19orf53 | NUDT16 | WARS | OR5H14 | CTSZ | MGST2 |
| IL23A | TMEM147 | CLEC12A | BST2 | | KCNMA1 | SLCO2B1 |
| TNIP3 | SIRPA | ARL4A | ISG20 | | CREG1 | GATM |
| CSF3 | MGAT1 | PILRA | CCL8 | | ACP5 | NCF4 |
| TNIP1 | PMP22 | FGL2 | CXCL11 | | OTOA | ADORA3 |
| TNFSF15 | MYEOV2 | POU2F2 | DYNLT1 | | GLUL | IGF1 |
| ITGB8 | LAPTM5 | CYTIP | IFI44 | | LILRB4 | PDK4 |
| IL1B | GUK1 | ZFP36L2 | FAM26F | | GPX3 | A2M |
| CCL4L2 | LAMTOR1 | HSD17B11 | SAMD9L | | SCD | HNMT |
| CCL4L1 | JTB | NAAA | RSAD2 | | LAMP2 | PLTP |
| EIF1B | ATP6VOB | AP152 | GBP5 | | FABP3 | DNASE1L3 |
| F3 | EIF5A | GIMAP4 | MX2 | | VAT1 | LTC4S |
| ATP2B1 | C11orf31 | CARD16 | GBP4 | | DNASE2 | OLFML3 |
| C15orf48 | KCTD12 | CELF2 | OAS2 | | CHI3L1 | CD209 |
| SERPINB2 | KDELR2 | CASP1 | RARRES3 | | RNASE1 | LY86 |
| FLT1 | M6PR | SYF2 | RNF213 | | TSC22D1 | GAL3ST4 |
| TM45F1 | C1orf43 | MTPN | PARP14 | | ACP2 | CD302 |
| MMP1 | C19orf60 | RCSD1 | OAS1 | | TIMP2 | FRMD4B |
| GPR84 | ZNF706 | CECR1 | XAF1 | | TCN2 | HLA-DOA |
| DNAAF1 | CDV3 | GPBAR1 | PLSCR1 | | SMPDL3A | MAF |
| AZIN1 | CISD3 | SLA | TAP1 | | RARRES1 | F13A1 |
| IRAK2 | GLT25D1 | SSH2 | EIF2AK2 | | HAMP | CAPZB |
| MPZL1 | EML4 | MARCH1 | GCH1 | | SLC38A6 | BEX4 |
| MTF1 | GNB1 | PQLC3 | SP110 | | CPM | RGS10 |
| TNFAIP8 | COX14 | ICAM3 | SNX10 | | ABCA1 | DRAM2 |
| AMPD3 | JOSD2 | TESC | ANKRD22 | | CD84 | CXCL12 |

TABLE 7-continued

| Myeloid NMF programs | | | | | | | |
|---|---|---|---|---|---|---|---|
| NBN | ARHGDIA | RIN3 | DRAP1 | | APLP2 | | ADAM28 |
| DLL1 | TMEM219 | GMFG | CCL2 | | SCARB2 | | AIG1 |
| ACSL5 | NDUFA3 | GIMAP2 | CMPK2 | | TFRC | | NAIP |
| BTG3 | CDC42SE1 | MYO1F | OAS3 | | HSD17B14 | | NCOA4 |
| SEC24A | NDUFB7 | YPEL3 | PARP9 | | SCCPDH | | IGSF21 |
| RAPGEF2 | RNF7 | ICAM2 | HERC5 | | GNS | | LACC1 |
| MSANTD3 | CHCHD10 | NOTCH2 | CHMP5 | | APOC2 | | AP2A2 |
| PLD1 | DUSP23 | GIMAP7 | TRIM22 | | TDP2 | | IGFBP4 |
| PIK3CB | RAP2B | LYL1 | NMI | | SCPEP1 | | ATG4C |
| CSGALNACT2 | SSU72 | TRAF3IP3 | CXCL9 | | KLHDC8B | | NDFIP1 |
| KMO | MYH9 | LTA4H | OASL | | MPP1 | | QPRT |
| ZP3 | ADAP2 | LYST | FCGR3A | | RBP1 | | IL18 |
| SAV1 | CAPZA1 | PTP4A2 | GBP2 | | SOAT1 | | SNX6 |
| HIVEP2 | MLEC | TCF7L2 | SAMD9 | | FDX1 | | WWP1 |
| MAP3K4 | LAT2 | NUP214 | IFIH1 | | SPARC | | CRYL1 |
| VAMP4 | MKNK1 | DOK2 | DEFB1 | | TSPAN4 | | GPR160 |
| IL24 | ST14 | MKRN1 | ATF5 | | CD81 | | NINJ2 |
| PTX3 | SPG21 | PRAM1 | RABGAP1L | | NR1H3 | | TMEM37 |
| SLAMF1 | ARL6IP4 | PTEN | PSMA4 | | RNF130 | | TNFRSF1A |
| FAM124A | FNIP2 | MTSS1 | SERPING1 | | HEXA | | TM6SF1 |
| SLCO4A1 | CTDNEP1 | UBXN1 | STAT2 | | PDE4DIP | | GPR155 |
| TFF2 | TNFSF12 | AHNAK | USP18 | | TNS3 | | EMP2 |
| DUSP16 | MFSD12 | WAC | LYSMD2 | | DPP7 | | WLS |
| HEY1 | SLC25A39 | VAMP2 | LYN | | ALDH1A1 | | PDGFC |
| GJB2 | NDUFV3 | | IFI16 | | HS3ST2 | | EPB41L2 |
| IL36G | CMTM3 | | LGALS9 | | ACOT13 | | CNRIP1 |
| MET | CORO1C | | APOBEC3A | | TMBIM1 | | FEZ2 |
| C7orf60 | FAM195B | | FCGR1B | | LGALS3 | | TMEM176B |
| NEU4 | LAIR1 | | NAPA | | RAB20 | | MGAT4A |
| CRADD | | | RAB8A | | FMNL2 | | SESN1 |
| TDRD9 | | | PHF11 | | ATP1B1 | | USP53 |
| AGPAT4 | | | CD38 | | CADM1 | | C10orf11 |
| ELOVL7 | | | DTX3L | | DNAJC5B | | LPAR5 |
| BTBD19 | | | PML | | FAM195A | | ITGB5 |
| STC1 | | | SIGLEC1 | | SLC15A3 | | GFRA2 |
| GLIS3 | | | APOL3 | | CHCHD6 | | LYRM5 |
| PPP2R5B | | | APOL2 | | EPHX1 | | STX12 |
| DNER | | | DDX60 | | CTSK | | TCEAL8 |
| OPTN | | | | | RRAGD | | SLC46A3 |
| LINC00346 | | | | | SLC7A8 | | ITGA9 |
| TRAF3IP2 | | | | | | | FRMD4A |
| SLC9B2 | | | | | | | GDE1 |
| C2CD4B | | | | | | | CRHBP |
| PTGES | | | | | | | CCDC28A |
| CDKN2B | | | | | | | ALDH9A1 |
| IL19 | | | | | | | CREBL2 |
| BCL6 | | | | | | | ST6GAL1 |
| KREMEN1 | | | | | | | TCEAL1 |
| LRRC69 | | | | | | | DIRC2 |
| C2CD4A | | | | | | | CD72 |
| LPAR4 | | | | | | | GCNT1 |
| PPP4R4 | | | | | | | STAU1 |

TABLE 8

| Plasma cell NMF programs | | | | | | | | |
|---|---|---|---|---|---|---|---|---|
| outTop-Genes 1 | outTop-Genes 2 | outTop-Genes 3 | outTop-Genes 4 | outTop-Genes 5 | outTop-Genes 6 | outTop-Genes 7 | outTop-Genes 8 | outTop-Genes 9 |
| CHCHD2 | ISG15 | ZFP36L2 | XBP1 | HSP90B1 | ACTB | JUN | DUSP1 | NBEAL1 |
| C19orf10 | IFI6 | H1FX | IGHG3 | IGLC3 | CD52 | IER2 | FOS | VIM |
| H2AFZ | IFI35 | DDIT4 | IGHG1 | HSPA5 | CXCR4 | HSP90AA1 | RGS1 | EEF1A1 |
| SDF2L1 | IGHA1 | TXNIP | IGHG4 | DERL3 | HLA-DRA | JUNB | KLF6 | GLTSCR2 |
| UQCRQ | LY6E | TSC22D3 | IGKC | PDIA3 | HLA-DPB1 | HSPA1B | ANKRD28 | EEF2 |
| SERF2 | B2M | IGHA2 | IGHGP | PDIA4 | IL32 | BTG2 | NEAT1 | CIRBP |
| SRM | STAT1 | ABCB9 | IGHG2 | CYBA | HBB | HSPA1A | YPEL5 | EEF1D |
| SEC61G | BST2 | SRGN | ITM2C | RPN2 | CD74 | NFKBIA | MCL1 | EIF4A2 |
| MTDH | MX1 | ID3 | JSRP1 | TMEM59 | CCL5 | EGR1 | HERPUD1 | PABPC4 |
| SEC11C | PRDM1 | TIMP1 | PIM2 | TMBIM6 | HBA2 | FOSB | UBC | IGKV3-20 |
| LGALS1 | ISG20 | CREB3L2 | SDC1 | NUCB2 | ACTG1 | PPP1R15A | TP53INP1 | SLC25A6 |
| SUB1 | DUSP5 | HMCES | TPST2 | PSAP | BTG1 | DNAJB1 | ZFP36 | IGHV3-23 |
| COX7A2 | IRF7 | RNASET2 | IGLV3-1 | CD63 | LAPTM5 | HSPB1 | JUND | EIF4B |
| PRELID1 | MT2A | PTK2B | IGLV6-57 | HLA-C | HLA-A | SQSTM1 | MYADM | TOMM7 |
| KDELR2 | S100A6 | KLF2 | LAX1 | SSR4 | HBA1 | NR4A1 | RGCC | IGHV4-39 |

TABLE 8-continued

Plasma cell NMF programs

| outTop-Genes 1 | outTop-Genes 2 | outTop-Genes 3 | outTop-Genes 4 | outTop-Genes 5 | outTop-Genes 6 | outTop-Genes 7 | outTop-Genes 8 | outTop-Genes 9 |
|---|---|---|---|---|---|---|---|---|
| ATP5E | ADAR | AP3S1 | GRN | SLC3A2 | HLA-DPA1 | GADD45B | LMNA | NPM1 |
| CYCS | IEI16 | TARSL2 | IGHV1-24 | PDIA6 | ARHGDIB | RHOB | TRIB1 | XIST |
| SEC61B | UBE2L6 | TNFRSF18 | PTP4A3 | S100A4 | MALAT1 | SOCS3 | TPT1 | |
| SRSF9 | OAS1 | KIAA0125 | TMEM19 | LAMP2 | LTB | DDX3X | DDX5 | HNRNPA1 |
| ATP5G1 | CD38 | SNHG7 | GAS6 | ICAM2 | SH3BGRL3 | WDR74 | ZNF791 | EEF1B2 |
| OAZ1 | PARP14 | GLO1 | FAM92B | ERP44 | MYL12A | HSP90AB1 | BIRC3 | IGHV4-59 |
| COX6A1 | EIF2AK2 | IL6ST | CADM1 | OS9 | CD3D | DUSP2 | FNBP1 | BTF3 |
| MZT2B | SP100 | SPAG4 | DNAAF1 | CCPG1 | CD37 | CITED2 | CD55 | CSDE1 |
| OSTC | IFI27 | TNFRSF4 | TXNDC11 | TECR | HLA-DRB1 | BRD2 | CXorf21 | PFDN5 |
| COX6B1 | TYMP | NOTCH2NL | SEL1L3 | CCR10 | CD69 | FAM53C | AHNAK | IGKV4-1 |
| POLR2L | XAF1 | ARID5B | CPEB4 | LAPTM4A | KLRB1 | RNU12 | FAM46C | EIF3E |
| ATP5J | EPSTI1 | TGFB1 | FAM174A | PRDX4 | TRBC2 | ATF3 | CD18 | RACK1 |
| GUK1 | PSMB9 | COL9A3 | QPRT | ITM2B | CORO1A | NFKBIZ | VPS37B | H3F3B |
| NDUFA4 | SAMD9L | QTRT1 | NDUFAF6 | HEXB | CD7 | PPP1R10 | LPIN1 | ZG16 |
| NDUFA11 | IFITM1 | SNORD3B-1 | CD79A | SIL1 | ID2 | ANKRD37 | STK4 | IGKV3-11 |
| CRELD2 | TNFSF10 | KANK1 | SMPDL3B | IGLC6 | CFL1 | SRSF7 | CCNH | TNFRSF17 |
| TXN | CHMP5 | YPEL3 | RILP | PRDX1 | PFN1 | DNAJA1 | HNRNPUL1 | IGKV1-39 |
| ATP5G3 | LAP3 | ZC3H12A | KCNN3 | IGLC2 | GZMA | TMEM107 | PELI1 | KRTCAP2 |
| COX8A | MEF2C | CTHRC1 | LTC4S | TM9SF2 | HCST | INTS6 | CRIP1 | PCBP2 |
| TMED2 | HERC5 | SNAI3 | C11orf80 | EDEM2 | EVL | HSPH1 | RGS2 | GNG7 |
| OST4 | NT5C3A | PLEKHH3 | FUT8 | DDOST | COTL1 | HEXIM1 | LENG8 | MT1G |
| PHPT1 | DRAP1 | RIC3 | SERPINI1 | TMEM205 | HLA-DQB1 | CCNL1 | RBM33 | EIF3D |
| PTMA | PPM1K | SERTAD2 | EFCAB4A | ALG5 | CCL4 | HIST2H2AA3 | RALGPS2 | PPDPF |
| POMP | HLA-E | HOMER2 | SPINK4 | C1GALT1C1 | HLA-DQA1 | GLA | TTPAL | EIF3L |
| USMG5 | PHGR1 | RHBDF2 | C10orf10 | GUSB | CD3E | IER3 | MSI2 | SEC11A |
| TMEM258 | USP18 | CD81 | DPEP1 | ICAM3 | NKG7 | SERTAD1 | BCL2L11 | JCHAIN |
| UQCRH | C19orf66 | LILRB1 | FUCA2 | NEU1 | ARPC1B | SLC38A2 | SEC31A | IGHV1-2 |
| NDUFA1 | ODF3B | SPON2 | CSNK1E | TAPBPL | IL7R | HSPA6 | RUBCN | IGKV1-5 |
| COX7B | RRBP1 | ANKRD53 | TM7SF2 | DHRS7 | CD53 | KCNQ10T1 | TBCEL | IGHV3-21 |
| NDUFB7 | IRF9 | EIF2AK4 | P2RX1 | HSPA13 | PTPRC | DNAJB4 | EHMT1 | RSL24D1 |
| RABAC1 | TNRC6B | PRKCA | IGKV2D-28 | LY96 | CD2 | CCDC144A | RBM23 | EVI2B |
| AURKAIP1 | OAS2 | PFKFB2 | GPX2 | MAGED2 | ALOX5AP | HIST2H2BE | WSB1 | PNRC1 |
| GAPDH | HNRNPH1 | BMF | CLDN14 | PIGK | MYL12B | TUBB4B | ZSWIM4 | IGLV2-8 |
| YBX1 | SP110 | HNRNPL | GNB3 | AGA | IGHM | IFRD1 | CCDC88A | IGHV3-15 |
| MZB1 | N4BP2L2 | LRRK1 | CNKSR1 | REEP5 | LIMD2 | HIST1H4E | COQ7 | IGLV7-46 |
| CHCHD10 | MYCBP2 | CCDC102A | IGHV6-1 | ITGB7 | FYB1 | IER5 | E2E5 | CD48 |
| NDUFS6 | SMCHD1 | AREG | IGLC4 | SEC23B | COMMD1 | TSPYL2 | GLCCI1 | IGLV2-14 |
| SNRPG | STAT2 | CSAD | PI3 | ALG8 | UCP2 | IFI30 | KLHL6 | EIF2A |
| UBL5 | TAP1 | ASB2 | SSTR2 | MGST3 | ACAP1 | HIST1H2BG | SAMD4B | IGHV3-9 |
| SPCS3 | CDV3 | RNU4-2 | C2 | PLTP | STK17A | SAT1 | NSMCE3 | IGLL5 |
| ATP5I | IFIT1 | SPINK2 | TSHR | SDHA | GNLY | NFKBID | TIPARP | ST13 |
| FKBP2 | FBXW7 | MIAT | DEFA5 | PRCP | HLA-B | GUCA2B | LONP2 | IGLC7 |
| TMA7 | XRN1 | POLR1E | PRDM15 | IGLL1 | TMSB4X | SNORD3A | FHIT | PABPC1 |
| UQCR11 | MDM4 | GTF2IRD2B | KIF3C | MDH1 | CALM2 | RASD1 | DUSP6 | TNFRSF14 |
| P4HB | TRIM69 | RNF122 | FRZB | RNF6AP1 | GZMB | PLK3 | WDR6 | EIF253 |
| ANAPC11 | UBALD2 | BEX5 | IGKV6-21 | ARSA | ARL6IP5 | PTCH2 | FOXN3 | IGBP1 |
| EIF5A | CECR1 | PPOX | HSDL1 | ATP6AP2 | GPSM3 | YMEQLQ | LGMN | EIF3F |
| MANF | RAB30 | MYBPC2 | CPTP | SCNN1B | RARRES3 | RNU5B-1 | ZMYM2 | PIGR |
| GLRX | RABGAP1L | PDCD7 | SMIM5 | HSD17B4 | IFITM2 | ZNF296 | DLG1 | IGLV3-21 |
| NME1 | PLSCR1 | SLC16A3 | CD99L2 | GPR108 | LSP1 | HIST1H2AE | VEZT | EIF3H |
| GTF3A | APOL2 | CRYL1 | IL5RA | NCSTN | VPREB3 | MKNK2 | IDS | IGHV3-7 |
| CCDC167 | C6orf62 | LYPD6B | HSD3B7 | QPCT | | ARRDC3 | B3GAT2 | IGHV5-51 |
| PRDX5 | CD164 | RFNG | AMIGO2 | PEPD | | | TRAM2 | IGHV3-74 |
| ATP6V0B | RBCK1 | IGLVI-70 | TAS1R3 | DPAGT1 | | | UBQLN2 | CCNI |
| SNU13 | FABP1 | GAB1 | SLC16A14 | UNC50 | | | NCK1 | TOMM20 |
| SSR3 | KPNB1 | CNOT10 | BTD | LMF1 | | | KIZ | IGHV1-18 |
| ZNF706 | LAMP3 | IRF2BP1 | PLA2G2D | ALDH16A1 | | | THEMIS2 | PPP1CC |
| NDUFB11 | AKAP9 | DEPTOR | CNTN4 | NAGK | | | ST6GAL1 | PAIP2B |
| UQCR10 | PARP9 | B3GALT6 | IGKV1D-33 | VCP | | | GALNT2 | ZBTB38 |
| EIF1 | WARS | ASCC1 | ZBP1 | MAGED1 | | | SLC35F5 | ZNF581 |
| PPIB | OAS3 | LSR | FASTKD1 | PDIA5 | | | CLK1 | IRF4 |
| LSM3 | HELZ2 | LCN8 | CUL7 | | | | ATHL1 | BTN3A2 |
| FTL | HERC6 | GALNT3 | HIST1H2BF | | | | KDM2A | DNAJB9 |
| NDUFB4 | UPF2 | ZFPM1 | ACOXL | | | | | MARCKS |
| C14orf2 | N4BP2L1 | IDUA | C1R | | | | | A1BG |
| NOP10 | IRF1 | CITED4 | DEFA6 | | | | | FXYD3 |
| FTH1 | FBXO6 | THAP11 | SAMD11 | | | | | UBE2J1 |
| SERPI | PPP2R5C | TMEM52 | HOXB7 | | | | | CLECL1 |
| NDUFV2 | FAM133B | JDP2 | CAMKMT | | | | | GPR160 |
| IDH2 | RICTOR | TIMP2 | SPR | | | | | IGHV4-34 |
| EIF252 | GLS | DDIT3 | PIK3CG | | | | | UBXN1 |
| | MX2 | FBXL12 | OVOL3 | | | | | IGLV1-40 |
| | CSF2RB | MARCH9 | CPED1 | | | | | CAMLG |
| | GPBP1 | TMEM115 | ENC1 | | | | | IGLV3-19 |
| | | IGLV3-27 | BSPRY | | | | | PCMTD1 |

TABLE 8-continued

Plasma cell NMF programs

| outTop-Genes 1 | outTop-Genes 2 | outTop-Genes 3 | outTop-Genes 4 | outTop-Genes 5 | outTop-Genes 6 | outTop-Genes 7 | outTop-Genes 8 | outTop-Genes 9 |
|---|---|---|---|---|---|---|---|---|
| | | CTSF | TMSB4Y | | | | | GPX4 |
| | | PMEPA1 | KCNMB3 | | | | | PPP1R2 |
| | | PTCRA | GALNT5 | | | | | MANEA |
| | | GON4L | IGLV5-48 | | | | | CCNG1 |
| | | CEACAM21 | | | | | | IGHV3-48 |
| | | ANKRD54 | | | | | | CD27 |
| | | | | | | | | RSL1D1 |
| | | | | | | | | IGKV1-9 |
| | | | | | | | | PDK1 |
| | | | | | | | | SRSF5 |

TABLE 9

Stroma NMF programs

| outTop-Genes1 | outTop-Genes2 | outTop-Genes3 | outTop-Genes4 | outTop-Genes5 | outTop-Genes6 | outTop-Genes7 | outTop-Genes8 |
|---|---|---|---|---|---|---|---|
| MT2A | CTGF | SLC9A3R2 | NEAT1 | CRYAB | JUNB | MFAP5 | TUBA1B |
| FTH1 | CYR61 | ID1 | MALAT1 | S100B | JUN | IGFBP6 | HSPA8 |
| MT1E | KLF6 | PODXL | CTNNB1 | GPM6B | FOS | SFRP2 | PDIA3 |
| MT1X | THBS1 | ID3 | HNRNPH1 | ALDH1A1 | ZFP36 | DCN | HSPA5 |
| SOD2 | C8orf4 | CXCL12 | DDX17 | PMP22 | IER2 | CCDC80 | HSP90AB1 |
| MMP1 | ARID5B | FCN3 | XIST | PLP1 | EGR1 | MGP | ENO1 |
| MMP3 | EDN1 | HEG1 | WSB1 | FXYD1 | FOSB | CFD | HSP90B1 |
| CXCL1 | NCOA7 | SOX18 | ARGLU1 | SPP1 | PPP1R15A | DPT | HSP90AA1 |
| NNMT | VMP1 | PIK3R3 | JUND | PRNP | SOCS3 | CST3 | UBB |
| CEBPB | RHOB | NPDC1 | TCF4 | CD9 | BTG2 | TNXB | PRDX1 |
| IER3 | RCAN1 | SGK1 | ZBTB20 | MPZ | HSPA1A | PCOLCE2 | CD63 |
| NAMPT | CITED2 | IFITM2 | AHNAK | NRXN1 | GADD45B | SFRP1 | ANXA5 |
| CHI3L1 | FEZ2 | AQP1 | NUCKS1 | LGI4 | NR4A1 | SLPI | ATP5B |
| IL24 | DNAJB4 | RAMP2 | N4BP2L2 | SCN7A | ATF3 | ADH1B | PSMB1 |
| CXCL3 | EMP1 | AES | PNISR | MATN2 | IRF1 | CD55 | PDIA6 |
| ADM | LDLR | CRIP2 | DPYSL2 | PEBP1 | HSPA1B | EFEMP1 | LAPTM4A |
| G0S2 | MCL1 | SWAP70 | HNRNPU | SEMA3B | SERTAD1 | GPX3 | PKM |
| ANGPTL4 | SERPINE1 | STC1 | SPTBN1 | PMEPA1 | BTG1 | C1QTNF3 | TMEM59 |
| PHLDA1 | FILIP1L | MPZL2 | TNRC6B | MARCKS | DNAJB1 | OGN | PPIB |
| CXCL5 | DLC1 | FLT1 | ZFP36L1 | S100A4 | CDKN1A | PI16 | CALR |
| IL6 | ADSS | INSR | RBM39 | MYOT | NFKBIZ | MGST1 | UBC |
| CXCL6 | PIM1 | CYYR1 | TRIM56 | CALM2 | SNHG9 | GPNMB | RPN2 |
| MT1F | MCTP1 | SLC6A6 | LUC7L3 | CDH19 | ATM | OSR2 | PGK1 |
| SLC16A3 | OSTM1 | NAA10 | FOXP1 | DKK3 | NFKBIA | FBN1 | PSMA4 |
| HILPDA | SAMD4A | SRP14 | SRRM2 | AP1S2 | PNRC1 | SERPING1 | PSMD8 |
| CXCL2 | FAM174A | LDB2 | SET | MAL | DUSP1 | OLFML3 | ATP5A1 |
| AKR1B1 | WEE1 | TBC1D1 | MACF1 | GFRA3 | KLF4 | CILP | MAGED2 |
| IL11 | RAB32 | PRKCDBP | HP1BP3 | ERBB3 | NR4A2 | CYBRD1 | TUBB4B |
| FGF7 | ABHD13 | ALPL | MDM4 | XKR4 | INTS6 | C3 | TMED9 |
| PLIN2 | GOLGA5 | PTP4A3 | POLR2J3 | ANK3 | MYADM | CLEC3B | TUBB |
| BNIP3 | WDYHV1 | UBE2J1 | TACC1 | PCSK2 | IER5 | KRT24 | LDHB |
| MT1G | EGR3 | PTTG1IP | KTN1 | GPR155 | SLC2A3 | FBLN2 | RTN4 |
| ACSL4 | MAFK | CDC37 | IQGAP1 | OLFML2A | CCNL1 | UAP1 | LMNA |
| GLRX | PPP1R3B | STOM | ANKRD11 | COL9A3 | IFRD1 | CD99 | XRCC5 |
| CCL20 | AMOTL2 | PEA15 | ACTR2 | TSPAN11 | HEXIM1 | CES1 | CCT3 |
| CA12 | FOSL1 | CD59 | MAP4 | H3F3B | KLF2 | PLA2G2A | XRCC6 |
| BNIP3L | VTA1 | DDIT4 | ATRX | PHLDA3 | SRSF7 | F10 | PSMA3 |
| SAT1 | SLC25A32 | STMN1 | GOLIM4 | TUBB2B | CSRNP1 | SCARA5 | RAN |
| WTAP | MAP3K13 | LIMS2 | CFLAR | S100A1 | PLK3 | PRELP | GSTO1 |
| MMP10 | RFK | HSPA12B | RBM25 | COMT | BRD2 | EMP3 | SPCS2 |
| C15orf48 | RRP8 | RILPL2 | SF1 | CAPS | STAT3 | CD248 | SSB |
| SLC39A14 | HMGCR | APOLD1 | NCL | HAND2 | FAM53C | SHISA3 | CCT5 |
| CD82 | KLHL12 | SYNPO | ARID1B | PLEKHB1 | DDIT3 | WISP2 | VCP |
| PTGES | DCUN1D3 | ESAM | TGOLN2 | NDRG2 | METTL12 | CLDN11 | HNRNPA2B1 |
| CD44 | LAMC2 | CASKIN2 | DDX3X | ARHGAP15 | MAFB | NUPR1 | CAPZB |
| COL7A1 | NUP153 | C9orf142 | CELF1 | RASSF4 | TOB1 | DDAH2 | CCT7 |
| TNFAIP3 | KRCC1 | SLC44A2 | PURA | CADM1 | SQSTM1 | SLIT3 | DNAJA1 |
| GK | ZNF263 | TMEM173 | NKTR | L1CAM | TSPYL2 | GPC3 | HSPD1 |
| CD68 | SLC25A33 | THBD | PRRC2C | SAMHD1 | HES1 | CADM3 | CCT8 |
| CCDC71L | HAUS2 | S1PR1 | UTRN | KCNMB4 | MAFF | ITM2A | HNRNPM |
| H1F0 | FAM41C | FURIN | C5orf24 | SCCPDH | SERTAD3 | PPIC | RNH1 |
| STEAP1 | C18orf8 | JAG2 | SCAF11 | PCDH9 | H2AFX | SERPINF1 | LDHA |
| SDC4 | DEDD | CD46 | NFIC | METRN | EGR2 | FGFR1 | PSMB5 |
| TNIP1 | BMP6 | PREX1 | ASH1L | CBR1 | UBE2S | OMD | REEP5 |

TABLE 9-continued

| Stroma NMF programs | | | | | | | |
|---|---|---|---|---|---|---|---|
| ZC3H12A | MLF1 | NDRG1 | RBM6 | NTM | ZSWIM4 | VKORC1 | PSMB6 |
| PTGS2 | PCGF5 | LYL1 | MBNL1 | FXYD3 | KLF10 | SEMA3C | COPE |
| TREM1 | ACTR8 | RAPGEF1 | GTF2I | SOX10 | SNHG12 | BIN1 | HNRNPK |
| IL13RA2 | EIF1AD | FLOT1 | CSNK1A1 | SLC22A17 | TCF7 | FIGF | YWHAB |
| NINJ1 | TRAF6 | CARHSP1 | CDC42SE1 | FCGR2B | TNFRSF10D | PHGDH | DAD1 |
| TMEM158 | SPINK4 | PICALM | CAST | IL11RA | ZNF331 | PLD3 | MANE |
| CREG1 | NOC3L | CPNE2 | EIF3A | NCAM1 | MIR22HG | ZNF385A | MDH1 |
| GLIS3 | MAPK6 | NUDT14 | IRF2BP2 | MIA | ZNF274 | MMP23B | PRDX4 |
| CSF3 | SIRT6 | MTRF1L | SETD5 | FSTL3 | RNF139 | CYP4B1 | PGAM1 |
| HMGA1 | ARL5A | PLCB1 | KANSL1 | TIMP4 | LENG9 | PAMR1 | PSMD7 |
| PI15 | CEP44 | CRK | SRSF5 | POLR2F | TTC32 | RSPO3 | ILF2 |
| MMP13 | CAAP1 | TEAD4 | WWTR1 | CADM2 | JMJD6 | GSTM5 | P4HB |
| TMEM132A | PPM1N | AiF1L | | CNP | NFKBIL1 | GSN | PSMB3 |
| ZFAND5 | | NOS3 | | | SRSF2 | C17orf58 | ARF4 |
| SLC39A8 | | SMAD6 | | | ERF | SEMA3E | ARPC2 |
| PLAUR | | ITGA9 | | | ZNF503 | ADAMTSL4 | PSMC3 |
| IL1B | | GRASP | | | ZNF821 | PTGIS | ATP1B3 |
| TNFAIP6 | | CDA | | | CLDN4 | FAM46A | PSMB2 |
| RIPK2 | | SIPA1L2 | | | MBD1 | PIGT | GHITM |
| CHI3L2 | | NR1H2 | | | RPPH1 | PAM | EIF3I |
| PFKFB3 | | ARHGAP4 | | | RNF25 | CREB5 | PA2G4 |
| HSD11B1 | | ORAI1 | | | SLC25A25 | PID1 | |
| ELL2 | | FES | | | KIAA1683 | LTBP4 | |
| SAA1 | | RDX | | | SEMA4A | ADAMTS5 | |
| FAM20C | | RAP1A | | | | TPST1 | |
| TGIF1 | | ZDHHC3 | | | | THBS3 | |
| CDCP1 | | RARG | | | | | |
| ERRFI1 | | ADCY4 | | | | | |
| LIF | | MSX1 | | | | | |
| EREG | | TMEM50B | | | | | |
| TNFRSF11B | | MAX | | | | | |
| MME | | ADARB1 | | | | | |
| POU2F2 | | MAP3K6 | | | | | |
| STEAP2 | | EMCN | | | | | |
| NMB | | GPR4 | | | | | |
| OSMR | | PARVB | | | | | |
| SCG5 | | CDKN2D | | | | | |
| HIF1A | | LUZP1 | | | | | |
| | | MLKL | | | | | |

| outTop-Genes9 | outTop-Genes10 | outTop-Genes11 | outTop-Genes12 | outTop-Genes13 | outTop-Genes14 | outTop-Genes15 | outTop-Genes16 |
|---|---|---|---|---|---|---|---|
| COL4A1 | TAGLN | ISG15 | C10orf10 | CA4 | RGS5 | CCL21 | PLN |
| COL4A2 | ACTA2 | IFI6 | CAV1 | RGCC | NDUFA4L2 | TFF3 | MYH11 |
| HSPG2 | TPM1 | LY6E | ICAM2 | CD36 | LHFP | LYVE1 | DSTN |
| SPARC | TPM2 | BST2 | KCTD12 | PLVAP | PDGFRB | TFPI | TSC22D1 |
| ESM1 | MYL9 | IFI44L | CLEC14A | PRSS23 | HIGD1B | MMRN1 | NET1 |
| CD93 | ACTB | MX1 | LTC4S | F2RL3 | COX4I2 | AKAP12 | SNCG |
| SPRY1 | ACTG2 | IFITM3 | SRGN | FABP5 | NOTCH3 | GNG11 | CRIP1 |
| LAMA4 | MYLK | IFIT3 | PCSK5 | PASK | CALD1 | GYPC | C2orf40 |
| PXDN | TPM4 | IFI35 | CAPZA2 | RBP5 | TPPP3 | FXYD6 | SORBS2 |
| COL15A1 | MYL6 | PSMB9 | TM4SF1 | ID2 | COL18A1 | ARL6IP1 | RCAN2 |
| PDGFB | PDLIM7 | STAT1 | TSPAN2 | SH3BP5 | SEPT4 | PPFIBP1 | SH3BGRL |
| HTRA1 | ACTN1 | PLSCR1 | SEMA3G | NQO1 | KCNJ8 | SDPR | IGFBP5 |
| CDH13 | CSRP1 | UBE2L6 | TMEM100 | TMEM204 | C20orf27 | PPP1R2 | BCAM |
| MCAM | WFDC1 | IFI44 | GAS6 | VAMP5 | PLXDC1 | ECSCR | MIR143HG |
| IVNS1ABP | TGFB1I1 | XAF1 | HLA-C | ITGA6 | ITGA1 | PROX1 | NTRK2 |
| ROBO4 | PPP1R14A | TYMP | EPAS1 | STT3B | NR2F2 | MGST2 | NDUFA4 |
| TP53I11 | ANXA6 | OAS1 | HEY1 | TMEM88 | CHCHD10 | GNAS | CKB |
| RGS3 | PALLD | ODF3B | IGFBP3 | IDO1 | RGS16 | TIMP3 | SOD3 |
| FSCN1 | PDLIM3 | MX2 | GIMAP4 | FRMD8 | LURAP1L | NTS | MTHFD2 |
| TNFRSF4 | NEXN | RSAD2 | GJA5 | EXOC3L2 | MEF2C | KBTBD11 | LBH |
| NOTCH4 | PTRF | IRF7 | PLLP | TEK | CCDC102B | RAB11A | COX7A1 |
| PLXND1 | VCL | OAS3 | SERPINE2 | GMFG | EPS8 | FABP4 | ARPC1A |
| DYSF | RSU1 | EIF2AK2 | JAG1 | CABP1 | ARHGDIB | CYB5R3 | LMOD1 |
| VWA1 | PARVA | OAS2 | PALMD | TM4SF18 | GJC1 | EPHX1 | PPP1R12B |
| EGFL7 | CNN2 | GBP1 | SOX17 | T5PAN12 | FRZB | ARL4A | ANAPC16 |
| CD34 | HOPX | GBP4 | MECOM | CYB5A | CPM | ADD3 | PHLDA2 |
| ITGB1 | C9orf3 | TRIM22 | PTPRB | ATOH8 | EDNRA | LIMS1 | C11orf96 |
| VWF | ALDH1B1 | WARS | H5D17B12 | TBCD | FAM162B | RELN | NRGN |
| ITGA5 | ILK | IFIT2 | ELN | RND1 | H2AFJ | C16orf62 | SYNPO2 |
| APLN | GLIPR2 | CMPK2 | SULF1 | ABCG1 | STEAP4 | SCN3B | KCNA5 |
| CD81 | ACAN | PARP14 | ARL15 | MLEC | PTK2 | EFNA5 | MGST3 |
| CDH5 | FLNA | HLA-B | PKN3 | ME3 | ASAH1 | CTSZ | EFHD1 |
| CCDC85B | TCEAL4 | CHMP5 | OCIAD2 | CLIC2 | EBF1 | SMYD2 | DES |
| PCDH12 | CYFIP2 | EPSTI1 | ANXA3 | ARHGAP18 | ASPN | PLSCR4 | NDUFB7 |
| TNFAIP8L1 | HSD17B6 | SP110 | GFOD1 | BAALC | THY1 | CTSD | DMPK |

TABLE 9-continued

| Stroma NMF programs | | | | | | | |
|---|---|---|---|---|---|---|---|
| NDST1 | WDR1 | TAP1 | MMRN2 | PRKCH | HES4 | NR2F1 | GPRC5C |
| LAMC1 | SOSTDC1 | SHISA5 | HERPUD1 | EGLN3 | GEM | MAF | TMEM38B |
| ANGPTL2 | SMTN | PARP9 | BMX | MCF2L | AXL | TSPAN5 | AKAP1 |
| DOCK6 | TNFRSF12A | IFI16 | APOL3 | PDE1C | SEPT11 | C6orf141 | CCNI |
| TIE1 | SEPT8 | C19orf66 | ASS1 | CIT | OAZ2 | LY96 | RRAD |
| GLT25D1 | CCDC107 | IFIT5 | MAST4 | PRX | IGFBP7 | UGP2 | MFGE8 |
| GJA1 | HHIP | HERC6 | TM6SF1 | CCND3 | FOXS1 | PGM5 | RBPMS2 |
| PGM2L1 | TFF1 | SP100 | ATP2A3 | LNX1 | ARHGEF17 | PNPLA2 | FKBP5 |
| CHST1 | FHL3 | USP18 | CLIC3 | ANKRD65 | COL5A3 | PARD6G | HCFC1R1 |
| MYH9 | GLIPR1 | SAMD9L | GABARAPL1 | KIF19 | ADAMTS4 | BCL7C | HSPB7 |
| PLOD1 | FGF1 | LAP3 | ITPR2 | OSBPL1A | HEYL | SCNN1B | SLC25A4 |
| RASGRP3 | CORO1C | PARP10 | ATP1A1 | PML | GUCY1B3 | F8 | ESD |
| CA2 | ARSJ | SAMD9 | SYNJ2 | KDR | ADAP2 | NFATC1 | PPP1R12A |
| PIM3 | ACTC1 | DTX3L | ZFYVE21 | CARD16 | ABCC9 | PLIN5 | RAMP1 |
| GRPEL2 | STK38L | TAP2 | GAS2L1 | TSPAN14 | MYO1B | DSP | SGCA |
| SPRY4 | DDAH1 | OASL | AZIN1 | JAM3 | TBX2 | KANK3 | WTIP |
| ETS1 | TMSB15A | TRIM69 | MET | HRCT1 | CDH6 | HLA-E | NOL3 |
| GNAI2 | FAM150A | IFIH1 | PLCG2 | PPP2R4 | ENPEP | TBX1 | LDB3 |
| DOCK9 | FAM35A | DDX58 | SSTR1 | SPOCK2 | KRT18 | FCGRT | SLC7A2 |
| KCNE3 | HSPA2 | GBP2 | CAV2 | RIN1 | OLFML2B | HSPB1 | SPEG |
| JUP | MVK | ISG20 | LPCAT2 | FAM177A1 | CAMK2N1 | STON2 | TNS1 |
| CD200 | PDZD11 | PSMB8 | ABI3BP | MFSD6 | UACA | NTAN1 | KCNAB1 |
| AFAP1L1 | RAB23 | LGALS9 | RNF144B | HYAL1 | LPL | LAPTM5 | CNN1 |
| FHOD1 | SRD5A1 | TMEM140 | FAM69B | FMNL2 | GJA4 | GPM6A | ZFHX3 |
| ANKRD28 | AGR2 | PARP12 | FBLN5 | CEACAM1 | SMOC2 | SMAGP | EIF4A2 |
| BCL6B | FMO3 | IRF9 | LMO2 | SLC31A1 | EGFLAM | TC2N | C1QTNF1 |
| ADAMTS7 | SLMAP | DHX58 | VEGFC | HOXB6 | B3GNT2 | HEBP1 | MAP7D3 |
| SEMA6B | MUS81 | PHF11 | GCHFR | APP | LZTS1 | CTSH | MT1A |
| NRP1 | LRP12 | STAT2 | CGNL1 | DGAT1 | KCNE4 | TSHZ2 | AOC3 |
|  | TGFB3 | CHMP1B | CD58 | PRSS3 | CSPG4 | DPEP2 | HSPB6 |
|  | LYPD1 | DDX60 | SEC11C | ARRDC2 | S1PR3 | WFS1 | CAP2 |
|  | FAM127A | IFITM1 | TUSC3 | MATK | IGFBP2 | B3GNT7 | CASQ2 |
|  | RDH5 | PPM1K | NTHL1 | ABI3 | KIAA0040 | PTPRE | NRIP2 |
|  | C3orf70 | RBCK1 | CLDN10 | GRAMD3 | GUCY1A2 | MAN1A1 | NTRK3 |
|  | GDAP2 | APOL1 | FGF2 | PTPRN2 | TRIB2 | BLCAP | ANGPTL1 |
|  | LLGL1 | RTP4 | MANSC1 | CHCHD7 | EHD2 | PDE2A | SNTA1 |
|  | MATN3 | HIST1H2AC | SHE | DNM2 | LRRC32 |  | UBA2 |
|  | EMX2OS | SCARB2 | EPHA4 | HOXB5 | CRISPLD2 |  | TMEM51 |
|  | TRAF5 | NMI | NDRG4 | DRD4 | ID4 |  | TTLL7 |
|  | HNRNPA1L2 | HERC5 | SLC48A1 | MIER2 | SGIP1 |  | CCDC3 |
|  | LYZ | GGPS1 | LRRFIP1 | ZBTB16 | TNS3 |  | PGAM2 |
|  | TSEN15 | CASP7 | LTA4H | HPS3 | ADCY3 |  | ZNF703 |
|  | EARS2 | IL17RC | SLC16A14 | GUCA2B |  |  | CSDC2 |
|  | AGBL5 | PNPT1 | GATA2 | CNFN |  |  | NPY1R |
|  | NMU | AZI2 | KCNN3 | GNGT2 |  |  | SBSPON |
|  | PTGER3 | DCXR | FGF18 | NETO2 |  |  | GRIP2 |
|  | PRR14 | DDX3Y | F11R | OSBPL2 |  |  | SORT1 |
|  | NELL1 | APOL2 | TUBA4A | HAGH |  |  | PDK4 |
|  | SHROOM3 | ZNFX1 | IRF6 | BAIAP2 |  |  | PNKD |
|  | RPE65 | DHRS4 | IFNAR2 | KIFC3 |  |  | ITGA7 |
|  | BOLA2B | OGFR | ADRB2 | JDP2 |  |  | STUB1 |
|  | TBX18 |  | RASL10A | ABCA3 |  |  | SERPINI1 |
|  | TSPYL5 |  | NEBL | SDR16C5 |  |  | SMARCD3 |
|  |  |  | GCH1 | AVPR2 |  |  | SUSD5 |
|  |  |  | CDC42BPA | MSRA |  |  | USP2 |
|  |  |  | LMBRD1 | CDC42EP1 |  |  | CHURC1 |
|  |  |  | TMTC1 | PLCL2 |  |  | LDOC1 |
|  |  |  | LSR | PPFIA3 |  |  | DUSP26 |
|  |  |  | CEP68 | TBC1D8 |  |  | DACT3 |
|  |  |  | C19orf33 | SCN4A |  |  |  |
|  |  |  | ANK1 | INMT |  |  |  |
|  |  |  | NRN1 | GALR1 |  |  |  |
|  |  |  |  | SKAP1 |  |  |  |
|  |  |  |  | TBXA2R |  |  |  |
|  |  |  |  | GUCA2A |  |  |  |

| outTop-Genes17 | outTop-Genes18 | outTop-Genes19 | outTop-Genes20 | outTop-Genes21 | outTop-Genes22 | outTop-Genes23 |
|---|---|---|---|---|---|---|
| PRCP | CD74 | CXCL14 | COL1A1 | LGALS1 | NPC2 | APOE |
| SELE | ENPP2 | F3 | COL1A2 | TMSB4X | CPE | CCL11 |
| FAM167B | HLA-DRB1 | PDGFRA | COL3A1 | TMSB10 | CLU | CCL13 |
| TGM2 | HLA-DRA | PLAT | COL6A3 | PTMA | ITM2B | CTSC |
| PDLIM1 | CD320 | DMKN | SPON2 | SERF2 | LIFR | PTGDS |
| ENTPD1 | HLA-DPB1 | POSTN | LUM | PFN1 | SDCBP | C1S |
| SELP | SPARCL1 | HSD17B2 | CTHRC1 | GAPDH | IL1R1 | CFH |
| DUSP23 | RBP7 | BMP4 | COL12A1 | EEF1A1 | B2M | CCL8 |
| RNASE1 | TXNIP | ENHO | COL5A2 | ACTG1 | CYP1B1 | TCF21 |

TABLE 9-continued

| Stroma NMF programs | | | | | | | |
|---|---|---|---|---|---|---|---|
| SLCO2A1 | HLA-DPA1 | NBL1 | COL5A1 | FKBP1A | HMGN3 | ADAM28 | |
| FXYD5 | HLA-DMA | EDNRB | AEBP1 | UBA52 | CTNNAL1 | A2M | |
| ICAM1 | CLDN5 | TMEM176B | CTSK | S100A11 | MADCAM1 | CCL2 | |
| RAMP3 | FAM107A | FAM150B | BGN | TPT1 | CCL23 | ABCA8 | |
| RAI14 | JAM2 | CXCR4 | PDPN | YBX1 | GLTSCR2 | HAPLN1 | |
| ADAM15 | HLA-DQB1 | RGS10 | INHBA | CFL1 | SNHG7 | EDIL3 | |
| APLNR | INHBB | CEBPD | ANTXR1 | SH3BGRL3 | C7 | STMN2 | |
| CALCRL | TGFBR2 | TRPA1 | VCAN | OST4 | HSD17B11 | SEPP1 | |
| PCDH17 | HLA-F | COL6A2 | MMP11 | CSTB | LEPR | MFAP4 | |
| CXorf36 | MGLL | BMP5 | MMP14 | CHCHD2 | LPCAT4 | TFPI2 | |
| C4orf48 | HLA-DMB | FOXF1 | PCOLCE | PPIA | PERP | RBP1 | |
| CSF2RB | IGFBP4 | AGT | THBS2 | ATP5L | ZNF385D | APOC1 | |
| ELK3 | LCN6 | GADD45G | COL6A1 | H3F3A | TLL1 | CP | |
| ENG | CDC42EP3 | SOX6 | MFAP2 | DYNLL1 | FAM213A | SMPDL3A | |
| CCDC69 | NKX2-3 | VSTM2A | CTSB | H2AFZ | LIMCH1 | PLTP | |
| MEOX1 | NOV | PTCH1 | FKBP10 | NACA | MTUS1 | RND3 | |
| P2RY6 | HLA-DRB5 | APOD | LOXL2 | EEF1B2 | BCAT1 | PTN | |
| SLC29A1 | GPR146 | LGALS3BP | RCN3 | COX7A2 | SRPX | GGT5 | |
| RNF145 | IMP3 | EMID1 | FN1 | POMP | FOXC1 | BASP1 | |
| TMEM2 | SLC14A1 | DDHD1 | RAB31 | FAU | GIMAP7 | ITIH5 | |
| HAPLN3 | GPRC5B | TMEM119 | MXRA8 | HINT1 | TNFSF10 | FBLN1 | |
| CAPNS1 | CNOT6L | LSP1 | HTRA3 | OAZ1 | TPD52L1 | C1R | |
| EPHB4 | BTN3A2 | F2R | PLOD2 | BTF3 | ASRGL1 | CD302 | |
| TAPBP | EHD4 | PDGFD | MXRA5 | SUMO2 | STXBP6 | HAAO | |
| ADAMTS9 | ACVRL1 | SCPEP1 | PDLIM2 | UQCRQ | HHEX | CLEC2B | |
| TRIOBP | ACE | APLP2 | CHPF | CALM1 | SEMA6A | WNT2B | |
| DAAM1 | C1QTNF9 | ST5 | CERCAM | HMGB1 | FAM155A | PTGER4 | |
| SEPN1 | RAPGEF3 | MMP2 | WNT2 | UQCRH | TNFRSF1A | PCDH7 | |
| MED24 | DLL4 | EMILIN1 | ADAMTS2 | NDUFB2 | FAM84B | PROS1 | |
| CFI | CTNNBIP1 | PITX1 | GREM1 | PTMS | TPST2 | SCT | |
| SPNS2 | MKL2 | TMEM176A | ISLR | UBL5 | TSPAN6 | ABCA6 | |
| CPXM2 | SEMA6C | BSG | HDLBP | EIF1 | LMCD1 | TAC3 | |
| ADAMTS6 | CASP10 | PROM1 | DIO2 | HNRNPA1 | CIRBP | RHOBTB3 | |
| STAB1 | NEDD9 | SDC2 | SPATS2L | AP2S1 | SESN3 | NOVA1 | |
| LAMP3 | FZD6 | TSLP | FAP | SEC61B | NTN4 | MAPK10 | |
| UGCG | C19orf76 | CYGB | RABAC1 | ATP5G2 | GIMAP2 | NEGR1 | |
| CD109 | NOSTRIN | COL4A5 | COL11A1 | COX4I1 | POLE4 | FZD1 | |
| GNS | VAMP8 | ECM1 | CMTM3 | EEF1D | OTC | VCAM1 | |
| FAM171A1 | MYLIP | TSPAN33 | CUTA | COX6B1 | PIR | CCL19 | |
| C1orf54 | ETS2 | KREMEN1 | ADAM12 | USMG5 | PLA1A | PAPPA | |
| CTSS | TSPAN13 | PCDH18 | GJB2 | HMGN1 | CTTNBP2 | GPC6 | |
| NHSL2 | TRIM16 | DLL1 | KIAA0930 | SNRPD2 | TIAM1 | RARRES3 | |
| SELL | OFD1 | PROCR | BMP1 | NDUF55 | PHACTR2 | FGFR4 | |
| ECE1 | NCK1 | TSC22D3 | COL10A1 | COX7B | UBXN1 | FAM105A | |
| LIPG | CD79B | S100A13 | TIMP1 | SEC61G | TGFBR3 | MEG3 | |
| MALL | IL3RA | NRG1 | CLEC11A | BRK1 | DIXDC1 | FGFR2 | |
| C4orf32 | ZNF366 | NPY | PODNL1 | TXN | ZFAND1 | EPHA7 | |
| ABLIM1 | KL | FOXO3 | PTK7 | SUB1 | SOX7 | SPON1 | |
| FAM89B | IL27RA | ECHDC2 | TMED3 | ATOX1 | IL33 | C6orf48 | |
| CPD | ASB9 | PCSK6 | CDH11 | PFDN5 | ABCG2 | IGF1 | |
| ADAMTS18 | SYBU | SCUBE2 | EFEMP2 | MZT2B | MYCT1 | ELANE | |
| OLFM1 | BTN3A3 | DEFB1 | TNC | DBI | CLEC7A | UBE2E3 | |
| PKP4 | LRMP | WNT5B | PLAU | SNRPG | SLC40A1 | QSOX1 | |
| RASA4 | SCARB1 | FARP1 | KDELR3 | RHOA | INPP1 | MAMDC2 | |
| CLDN15 | BHLHE40 | DSE | RAB34 | GPX4 | RPGR | HNMT | |
| EPB41L3 | ST6GALNAC1 | GDF15 | SULF2 | FTL | ST13 | NDN | |
| CPLX1 | CIITA | MCTP2 | CKAP4 | COX6C | SNHG8 | SAMD11 | |
| GALNT1 | ARC | ISCU | LOXL1 | SLC25A6 | ST8SIA4 | ABHD14B | |
| SEPT6 | CPNE8 | SEMA4D | CREB3L1 | NOP10 | LRRC1 | LRP1 | |
| BCR | RASIP1 | CH25H | CALU | C19orf53 | | GLUL | |
| VAT1 | OTOA | ALDH1A3 | MAGED1 | SNX3 | | FHL1 | |
| CLSTN3 | WSCD1 | INSC | CST1 | NEDD8 | | PDE3B | |
| LEF1 | TACSTD2 | FOXF2 | LOX | MIF | | IL6ST | |
| ELOVL1 | TBC1D15 | ALDH2 | CPXM1 | C14orf2 | | GPC4 | |
| ELMO1 | ARHGAP25 | PGM1 | FKBP11 | COX8A | | CRYBG3 | |
| ITPR3 | GPIHBP1 | CSF1 | PYCR1 | UQCRB | | C2 | |
| CDKN3 | HOXD1 | LANCL2 | C1QTNF6 | PRDX5 | | SPRY2 | |
| TNFRSF10B | SIGLEC9 | PPP1CC | CRTAP | NPM1 | | PKDCC | |
| MAPK12 | FBXO31 | CLMP | BICC1 | RBM3 | | ST8SIA1 | |
| CNKSR3 | ABO | D10S0S | GPX7 | UQCR11 | | MITF | |
| MAPK11 | TPO | COL4A6 | SPSB1 | C4orf3 | | | |
| BCL3 | IL15 | CHIC2 | SFRP4 | PRELID1 | | | |
| EFHD2 | TUT1 | BMP2 | WNT5A | IL32 | | | |
| EPB41L4A | CD99L2 | RNASET2 | WISP1 | EEF2 | | | |
| GPR137 | WDR81 | GCLC | ARL4C | ANAPC11 | | | |
| SYCE1L | | CIB2 | PRRX1 | | | | |
| NT5E | | PDE4DIP | IRS1 | | | | |
| SLC7A1 | | FHL2 | RARRES1 | | | | |

TABLE 9-continued

| Stroma NMF programs | | |
|---|---|---|
| FNDC4 | HLA-A | SPOCK1 |
| HYAL2 | GLP2R | CRABP2 |
| | | ITGB5 |
| | | JTB |
| | | ADAMTS12 |

TABLE 10

All T cell NMF programs

| outTopGenes1 | outTopGenes2 | outTopGenes3 | outTopGenes4 | outTopGenes5 | outTopGenes6 | outTopGenes7 | outTopGenes8 |
|---|---|---|---|---|---|---|---|
| FOS | CCL4 | S100A4 | JUNB | RGS1 | EEF1A1 | GNLY | LDHA |
| CD69 | CCL3 | S100A6 | ZFP36 | SAMSN1 | EIF3E | GZMB | PKM |
| DUSP1 | CST7 | CD52 | BTG2 | CDKN1B | EEF1B2 | PRF1 | PPIA |
| KLF6 | CMC1 | VIM | DUSP2 | CHIC2 | EEF2 | KLRC1 | TPI1 |
| NFKBIA | GZMK | S100A10 | IER2 | GLI4 | PABPC1 | KLRD1 | ENO1 |
| TNFAIP3 | GZMM | S100A11 | ZNF331 | TBC1D19 | HNRNPA1 | CEBPD | MIF |
| FOSB | KLRF1 | EMP3 | SRSF2 | ZNF200 | GLTSCR2 | AFAP1L2 | CHCHD2 |
| MCL1 | LITAF | SH3BGRL3 | SOCS1 | BRSK1 | NACA | UBE2F | SNRPE |
| MYADM | ITGB2 | IFITM2 | NR4A2 | BBS10 | UBA52 | CD9 | NME1 |
| TSC22D3 | EOMES | LGALS1 | SOCS3 | TMSB4Y | FAU | ITGAX | GAPDH |
| GPR183 | FCGR3A | CALM1 | RGCC | ZNF805 | NBEAL1 | GALNT2 | TXN |
| ATF3 | APOBEC3G | TAGLN2 | IRF1 | ITIH5 | TPT1 | PIK3AP1 | NHP2 |
| EGR1 | CHST12 | PFN1 | YPEL5 | PRSS16 | NPM1 | LILRB1 | SERBP1 |
| TUBA1A | SPON2 | ANXA2 | SLC2A3 | CASKIN2 | BTF3 | METRNL | PSMA7 |
| TAGAP | SH2D1A | PLP2 | EIF4A1 | FRK | TOMM7 | LRRC28 | SEC61B |
| CITED2 | PLEK | CFL1 | FAM177A1 | LAD1 | EEF1D | RRAS2 | RANBP1 |
| NFKBIZ | SAMD3 | AES | KDM6B | SLC1A1 | PFDN5 | PDGFRB | SNRPG |
| ZSWIM4 | KLRG1 | CD99 | CHMP1B | RHAG | LDHB | C9orf139 | ATP5G3 |
| ARL4A | ITM2C | FLT3LG | INTS6 | DZIP1 | COX4I1 | CDA | ATP5G1 |
| IGHG3 | C1orf21 | DSTN | CSRNP1 | HAAO | NAP1L1 | KIR3DX1 | CYCS |
| DUSP6 | XBP1 | TRADD | REL | BATF2 | C6orf48 | FAM49A | SNRPF |
| IFNGR1 | ARPC5L | CLIC1 | IFRD1 | CCDC13 | EIF3L | RALA | YBX1 |
| CD55 | PYHIN1 | ANXA1 | DUSP5 | AOC2 | CCR7 | SPTSSB | CALR |
| IFITM3 | GNG2 | TIMP1 | GPR65 | CLDN1 | SLC25A6 | SETBP1 | APRT |
| BCL2A1 | CCL4L2 | CCDC107 | SERTAD1 | | EIF3H | RNF40 | COX5A |
| ZBTB10 | CCL3L1 | LGALS3 | DNAJB9 | | CCNI | FAM8A1 | GADD45GIP1 |
| LYSMD2 | LPCAT1 | AQP3 | FAM53C | | KLF2 | RAB38 | C1QBP |
| MAP3K13 | TPST2 | TTC39C | SBDS | | SSR2 | ROM1 | SNRPB |
| EFCAB2 | PILRB | TOB1 | METTL12 | | COX7C | HEPH | PARK7 |
| ATXN8OS | TBX21 | ARRB2 | HNRNPA0 | | SELL | PLAU | SLC25A3 |
| RNU12 | FCRL6 | NCF1 | VPS37B | | EIF3F | SYCP3 | RAN |
| NLRP3 | ADRB2 | FLNA | SNHG9 | | EIF3K | KLHL7 | SRM |
| SPINK1 | YPEL1 | CAPN2 | NR4A1 | | CD48 | L3MBTL4 | PPA1 |
| PLAUR | ZEB2 | ITGB1 | CEBPB | | RSL24D1 | SNIP1 | RBM3 |
| ID1 | SLAMF7 | BIN2 | ZC3H12A | | SNHG8 | LCN15 | VDAC1 |
| MTRNR2L1 | PTGDS | S1PR4 | RNF139 | | NOSIP | GOLM1 | NDUFB2 |
| FRY | F2R | CAST | SNHG15 | | UXT | BFSP1 | TIMM13 |
| COQ7 | CLDND1 | AHNAK | HEXIM1 | | FXYD5 | SOX13 | ATP5J |
| KCNN1 | SDCBP | SYTL1 | MAFF | | EIF4B | TEX22 | PSMA2 |
| PLCB1 | IGFBP7 | RGS19 | PNRC1 | | LEF1 | ABHD4 | PGAM1 |
| SPG20 | EGR2 | MYO1F | NFKBID | | ST13 | CREB3L1 | SDF2L1 |
| GPR85 | PTGDR | MYO1G | NFE2L2 | | RSL1D1 | KIF12 | NDUFS5 |
| RPPH1 | BPGM | DPP4 | YME1L1 | | SNRPD2 | STOX2 | PHB |
| CXCL14 | CD300A | CISH | XCL1 | | HINT1 | ABCA3 | UQCRH |
| NT5E | PRSS23 | PRMT2 | DCTN6 | | EIF3D | XKR4 | NDUFAB1 |
| SNORD104 | AKR1C3 | ETHE1 | PFKFB3 | | COMMD6 | CNDP1 | PEBP1 |
| TRIQK | CCL3L3 | RNPEPL1 | EMD | | EIF3G | LBX2 | EIF5A |
| GFPT2 | LYST | TNFSF12 | FAM43A | | CMPK1 | ZNF45 | DCTPP1 |
| MIR3188 | IGFBP2 | ARHGDIA | ATF4 | | LDLRAP1 | ADAMTS14 | COX7B |
| SYNPO2L | CCL4L1 | UBE2Q2 | SNHG12 | | EIF3M | PFKFB4 | PRDX1 |
| ABCG8 | GTF3C1 | GLIPR2 | RBM7 | | TCF7 | ITGA7 | TOMM22 |
| KLF4 | PRR5L | PIM1 | PER1 | | FBL | SCT | ENY2 |
| ANKRD42 | FASLG | MYL6 | JMJD6 | | ZNF90 | PBOV1 | PRELID1 |
| FAM71A | MIB2 | PERP | CDKN1A | | C12orf57 | RBPMS2 | GTF3A |
| ZNF703 | TGFBR3 | TRAPPC6A | BRD2 | | TOMM20 | IL17RC | ERH |
| RNU11 | TBPL1 | MKNK1 | EGR3 | | SERP1 | BCAN | LSM7 |
| ZNF461 | PSTPIP1 | RASSF7 | FADS3 | | ATP5O | WDR93 | TXNDC17 |
| ME1 | S100B | CALHM2 | BHLHE40 | | MAL | SPOCK3 | NDUFB6 |
| RNU4ATAC | SIRT2 | CORO1 | TUBB2A | | EIF2S3 | EFNA5 | SEC61G |
| C12orf61 | LYAR | ATF7IP2 | ZNF250 | | ALKBH7 | AARD | NDUFA6 |
| TPBG | USP28 | TES | OSM | | C1orf162 | MTCP1 | C19orf24 |
| NKX3-1 | RHBDF2 | DYNLT3 | AVPI1 | | UBXN1 | IL20RA | C19orf70 |
| C11orf74 | B4GALT4 | APOL3 | MAP3K11 | | PASK | RSPH9 | CCDC85B |

TABLE 10-continued

| All T cell NMF programs | | | | | | | |
|---|---|---|---|---|---|---|---|
| WDR86 | SLC15A4 | UBXN11 | RNF126 | EPB41L4A-AS1 | ZKSCAN3 | NDUFS6 | |
| NRIP3 | KLHDC4 | ANXA4 | CD83 | ERP29 | GGT5 | NUTF2 | |
| SPEF2 | HBA1 | GOLGA7B | ERF | TMEM123 | FLRT2 | C11orf31 | |
| RAB3B | ARHGAP26 | PXN | SH2D3A | LINC00493 | EMCN | TIMM8B | |
| GPR35 | ASCL2 | MFNG | SPATA2L | SH3YL1 | GPM6A | SNRPD1 | |
| TTLL9 | CTBP2 | LTBP4 | TMEM88 | EIF2A | C6orf52 | FKBP2 | |
| FBXL2 | NFKBIB | CCR2 | PLK2 | ZFAND1 | TBKBP1 | SSBP1 | |
| SPAG4 | GTPBP8 | SH3BP5 | NR1H2 | CCDC109B | RBMS2 | PDCD5 | |
| TTLL7 | FEZ1 | PDLIM2 | NR4A3 | PLAC8 | PALLD | APEX1 | |
| TSPAN6 | MTSS1 | COMTD1 | TRIM39 | OXA1L | IRF6 | C19orf10 | |
| SAMD4A | OSBPL5 | AP1S2 | KIAA1683 | FHIT | RADIL | TRMT112 | |
| C10orf111 | TTC16 | CYB561 | ALG13 | CAMLG | | ROMO1 | |
| SIAH3 | TSPAN32 | | SYAP1 | EEF1G | | PFDN2 | |
| C8orf37 | NXPH4 | | SESN2 | EVI2B | | EIF3I | |
| RASSF8 | ORAI1 | | RFWD2 | CCNG1 | | C17orf89 | |
| WWC2 | CCDC102A | | ZNF566 | ABHD14B | | EEF1E1 | |
| ASIC4 | DKK3 | | BCAS2 | RASGRP2 | | STOML2 | |
| SYT5 | PTRH1 | | SLC2A14 | CSDE1 | | PPIB | |
| CELF4 | GK5 | | CSRNP2 | PABPC4 | | GSTO1 | |
| C10orf91 | ST3GAL4 | | SEZ6 | DPH5 | | FAM96B | |
| UCN3 | PAFAH2 | | TMEM150A | HAX1 | | EIF5B | |
| | ENC1 | | RASD1 | C14orf64 | | | |
| | IGF2R | | ERRFI1 | | | | |
| | ZNF276 | | CSF2 | | | | |
| | SAT2 | | CXCL2 | | | | |
| | LPAR5 | | | | | | |
| | C11orf21 | | | | | | |
| | MIR181A2HG | | | | | | |
| | BCL9L | | | | | | |
| | SLC16A11 | | | | | | |
| | CXCR2 | | | | | | |
| | RASSF4 | | | | | | |
| | PDLIM1 | | | | | | |
| | GAS7 | | | | | | |

| outTopGenes9 | outTopGenes10 | outTopGenes11 | outTopGenes12 | outTopGenes13 | outTopGenes14 | outTopGenes15 | outTopGenes16 |
|---|---|---|---|---|---|---|---|
| FCER1G | ACTB | COTL1 | TXNIP | CCL5 | NEAT1 | CORO1A | RORA |
| CD7 | B2M | ARHGDIB | CXCR4 | FTL | HNRNPH1 | MYL12A | LST1 |
| TYROBP | CD3D | RAC2 | IL7R | ITGA1 | MALAT1 | UBB | NCR3 |
| CD247 | SRGN | ARPC1B | ZFP36L2 | KLRC2 | C1orf56 | MYL12B | TNFSF13B |
| GZMA | CYBA | ARPC2 | BTG1 | HOPX | CDC42SE1 | UBC | TMEM167A |
| GSTP1 | HLA-A | PPP1R18 | PIK3IP1 | C9orf142 | SET | HNRNPK | ZFP36L1 |
| KIR2DL4 | GPSM3 | ARPC2 | HLA-E | FABP1 | TNRC6B | SEPT7 | CTSH |
| TMIGD2 | ACTG1 | C19orf43 | LEPROTL1 | SCML4 | PTPRC | PSME1 | PRR5 |
| CD63 | HLA-B | HIGD2A | CYTIP | CD160 | STK17B | HNRNPA2B1 | CCL20 |
| LAT2 | CD3E | BRK1 | IKZF1 | CD96 | CDC42 | ATP5B | TLE1 |
| TXK | HCST | ISG20 | ODF2L | RARRES3 | MDM4 | TMBIM6 | IL4I1 |
| RHOC | COX6A1 | ISG15 | CIRBP | PTGER2 | DDX17 | ANXA6 | IL23R |
| STARD3NL | LAT | PPP1CA | PPP1R2 | PITPNC1 | PPP1CB | DDX5 | RORC |
| IL2RB | HLA-C | ARPC3 | AIM1 | GGA1 | PNISR | ACTR3 | SMAP1 |
| ARF6 | ATP6V0E1 | FKBP8 | HLA- | MSH3 | ARGLU1 | XRCC2 | B3GALT2 |
| KRT81 | TFF3 | ARPC4 | FYN | ZG16 | RBM39 | PDIA3 | LAIR1 |
| MATK | KRT18 | SEPT9 | GIMAP4 | GUK1 | CTNNB1 | HNRNPM | SPINK2 |
| CTSD | NDUFA13 | CAPZB | GIMAP7 | PDCD4 | N4BP2L2 | ATP5A1 | CA2 |
| CXXC5 | SPCS1 | ARPC5 | CNBP | FXYD3 | RNF213 | PSMA4 | CERK |
| SLC16A3 | DAD1 | GYPC | ITM2B | GABARAPL1 | TRA2A | PSMB1 | GDE1 |
| MPG | RNASET2 | PRR13 | TC2N | CHCHD10 | CAPZA1 | LSP1 | NMRK1 |
| CCND2 | TMCO1 | CNN2 | CD37 | GUCA2A | PRDM1 | PGK1 | TIFA |
| SH2D1B | CHI3L2 | CASP4 | DYNLT1 | PELO | MBNL1 | MORF4L1 | PCDH9 |
| PCID2 | TSPAN8 | CSTB | CD40LG | MT1G | STK4 | GHITM | KIT |
| CLIC3 | TMED10 | RHOA | STT3B | SYTL3 | FUS | SF3B2 | SLC4A10 |
| KRT86 | BSG | TBC1D10C | TNFAIP8 | DZIP3 | PCSK7 | TERF2IP | PLAT |
| SEC11A | ZNF831 | CSK | ERN1 | GUCA2B | CLEC2D | HSPA5 | BLK |
| CD164 | SPINT2 | UBE2L6 | RCSD1 | A1BG | PRRC2C | XRCC5 | COL5A3 |
| S100A13 | OLFM4 | RGS10 | TRIM22 | FAM173A | DDX6 | ICAM3 | TBXAS1 |
| B3GNT7 | EPHB6 | UBE2D2 | TLE4 | LGALS4 | CDC42SE2 | CAP1 | CTDSP2 |
| ZBTB16 | OPRM1 | RBCK1 | SORL1 | ABCB1 | SRSF5 | MDH1 | IL17RE |
| AREG | SLC9A9 | DRAP1 | SYPL1 | CKB | SRSF7 | SNRPB2 | CACNA2D4 |
| SLC25A39 | HECW2 | RHOF | SESN1 | SSBP4 | FNBP1 | IK | IFI44 |
| FGR | SEPN1 | PSMB8 | SPSB3 | PTPN22 | HNRNPU | HNRNPF | TNFSF11 |
| NSMCE1 | PPP1R1B | DYNLRB1 | ITK | ANXA2R | POLR2J3 | RPN2 | MATN2 |
| LCP1 | AGA | TRAPPC1 | LGALS3BP | CAPN12 | ACTR2 | TMEM59 | B4GALT5 |
| FUCA1 | ST8SIA1 | LIMD2 | CCNH | BCAS4 | YWHAZ | COPE | PTPN13 |
| P2RY11 | CXCR5 | RGL4 | SLAMF6 | SPRY1 | APOBEC3C | ECH1 | LIF |
| FES | GPX2 | NOP10 | IL10RA | ADRB1 | MGEA5 | ATP6AP2 | ARNTL |
| HMGN3 | S100A16 | UBE2D3 | TNFSF8 | TMX4 | PNN | LAMP1 | C4orf32 |
| CD151 | S100A14 | POLR3GL | CDC14A | HERPUD2 | RBM6 | VCP | MGAT5 |
| | PVALB | | | | | | |

TABLE 10-continued

All T cell NMF programs

| | | | | | | | |
|---|---|---|---|---|---|---|---|
| NCR1 | CDX2 | ATP6V1F | ANKZF1 | YPEL3 | LUC7L3 | TMBIM4 | PLXNC1 |
| GFOD1 | RAB25 | SSU72 | NCK2 | AUTS2 | ANKRD44 | HSP90B1 | LINC00299 |
| GPR82 | CDK5R1 | PGLS | TMEM71 | C7orf50 | SYNE2 | CCT8 | SLC31A2 |
| TGFB1 | ABHD14A | MIEN1 | FBXO34 | AKAP7 | WSB1 | SPCS2 | MCAM |
| ARHGAP9 | C2orf82 | DBI | RABGAP1L | HAGHL | B4GALT1 | TAP1 | IL22 |
| LYN | PRSS8 | TBCB | SMAP2 | SLA2 | IKZF3 | TRAF3IP3 | ARHGAP10 |
| UBASH3B | KSR2 | RNF7 | NCK1 | METRN | CCNL1 | DHRS7 | HIST1H2AC |
| PLCG2 | 5OD3 | ENSA | TUBA4A | ECI2 | GPBP1 | FERMT3 | SEPP1 |
| APOBR | PRR15 | UFC1 | C19orf66 | DGCR6L | KTN1 | CD53 | HDAC9 |
| SERPINB6 | TSPAN12 | LAMTOR1 | RSBN1 | SLC26A3 | IQGAP1 | SEPT1 | ABCA1 |
| HES4 | GPM6B | FKBP1A | MX2 | STOM | ZC3HAV1 | DNAJC8 | SMOX |
| GNPTAB | KRTCAP3 | COX7A2L | NAAA | CCRL2 | EIF3A | SLC3A2 | DSE |
| PDLIM7 | SOX9 | GMFG | KLF9 | CHPT1 | PRPF38B | PSMB3 | SWT1 |
| SYNGR1 | SMPDL3A | ATPIF1 | CYHR1 | CLDN7 | SCAF11 | CCT7 | MTERFD3 |
| IRF8 | CCL15 | TSC22D4 | LSR | P2RX4 | TSPYL1 | PSMD7 | PPARG |
| ISYNA1 | SLC7A10 | VAMP8 | ARFRP1 | SYTL2 | ARID1B | ITGB7 | AFF3 |
| COL23A1 | RAPGEFL1 | SLC9A3R1 | LPAR6 | PRKACB | ANKRD12 | PSMD4 | PLXND1 |
| TCIRG1 | MGP | NDUFB10 | SRSF8 | GNAS | SF1 | MAGED2 | IL17F |
| RNF187 | C8orf4 | GNAI2 | GIMAP2 | TMEM203 | ARID4B | PSMD13 | NUDT7 |
| CHMP6 | CHGB | VASP | PGRMC2 | UBAC2 | C6orf62 | ATP5C1 | NEO1 |
| RNF130 | TPD52L1 | PTRHD1 | CHD7 | ENDOV | FOXP1 | POLR2G | CD300LF |
| CCDC69 | HULC | PPP1CC | SCRN2 | KRT19 | SMCHD1 | RAB7A | ENPP1 |
| CD81 | LRP4 | SH3BGRL | CEP68 | U2AF1L4 | DOCK8 | PUF60 | LRRN3 |
| EFCAB4A | F8A3 | POLR1D | IPCEF1 | HIC1 | ANKRD11 | SUN2 | RNF144B |
| CD244 | TOX3 | SASH3 | CASP6 | XCL2 | SFPQ | HDAC1 | ZFHX3 |
| ATP8B4 | LMAN2L | DENND2D | LPAR2 | CA1 | TAF1D | EID1 | ESPN |
| WDR83OS | WNK2 | CMTM3 | KDELR1 | GPR18 | EML4 | AIP | NTRK2 |
| SPRY2 | TMEM45B | SHISA5 | CRYZL1 | ZNF32 | WTAP | EWSR1 | LTB4R |
| SKAP2 | STEAP2 | TADA3 | ARHGAP5 | MNAT1 | JAK1 | CCNDBP1 | MAP3K7 |
| CCDC50 | TM4SF1 | SKAP1 | ZNF75A | PLEKHO1 | BCLAF1 | PPP2R1A | CYTH3 |
| FYTTD1 | GDF7 | ARF5 | KLHL36 | CAMK2N1 | ATRX | CPNE1 | PRAM1 |
| CD38 | SLC35G1 | SSNA1 | CASP8 | PARP8 | DDX46 | NDUFS2 | SCN1B |
| | UFSP1 | METTL9 | CTBP1-AS1 | CA4 | | ARHGEF1 | MGAT4A |
| | ALDOB | | SGK3 | SLC25A15 | | ERP44 | CA10 |
| | RAMP2 | | RHOT2 | TPRG1 | | LMAN2 | COLQ |
| | CCND1 | | TRIM4 | AQP8 | | MVP | PLD1 |
| | MEGF11 | | TAPBP | FCGBP | | | B4GALNT1 |
| | SPINK5 | | CABIN1 | ABLIM1 | | | BCAS1 |
| | MYO10 | | | | | | AKT1S1 |
| | NOVA1 | | | | | | TAF6L |
| | ITGB4 | | | | | | SCRN1 |
| | AGPHD1 | | | | | | FSIP1 |
| | UNC13B | | | | | | AHR |
| | TRIM15 | | | | | | |
| | FBLN1 | | | | | | |
| | MMP3 | | | | | | |
| | RASL11A | | | | | | |
| | AQP1 | | | | | | |

| outTopGenes17 | outTopGenes18 | outTopGenes19 | outTopGenes20 | outTopGenes21 | outTopGenes22 | outTopGenes23 |
|---|---|---|---|---|---|---|
| HSPA1A | TMSB4X | STMN1 | CD74 | CXCL13 | TNFRSF4 | ID2 |
| HSPA1B | ATP5E | TUBA1B | HLA-DRA | MT2A | BATF | CKLF |
| DNAJB1 | PTMA | TUBB | HLA-DRB1 | RBPJ | TNFRSF18 | CD2 |
| HSP90AA1 | UQCR11 | HMGB2 | HLA-DPB1 | SLA | BIRC3 | ALOX5AP |
| HSPE1 | SERF2 | H2AFZ | HLA-DPA1 | PDCD1 | SAT1 | CD3G |
| HSPB1 | OST4 | HMGN2 | HLA-DQB1 | FKBP5 | IL2RA | CXCR6 |
| JUN | ATP5L | HIST1H4C | HLA-DQA1 | NR3C1 | SPOCK2 | LAPTM5 |
| HSPA8 | SRP14 | HMGB1 | GZMH | NAP1L4 | TNFRSF1B | ANKRD28 |
| RGS2 | IL32 | CKS1B | HLA-DRB5 | RAB27A | TYMP | ABI3 |
| DNAJA1 | C14orf2 | H2AFV | HLA-DMA | ITM2A | CTLA4 | AMICA1 |
| HSPA6 | H3F3A | TYMS | CD8A | BST2 | CTSC | OSTF1 |
| HSPH1 | UBL5 | UBE2C | CD8B | TGIF1 | ICOS | PTGER4 |
| CACYBP | COX7A2 | DUT | HERPUD1 | MTHFD2 | FOXP3 | GRAP2 |
| RHOB | ATP5I | NUSAP1 | HLA-DMB | PTMS | PIM2 | RAP1B |
| HSP90AB1 | PPDPF | TOP2A | HLA-DQA2 | TOX | TIGIT | FKBP11 |
| HSPD1 | UQCR10 | CKS2 | ZNF683 | CHN1 | LAIR2 | KRTCAP2 |
| EIF4A2 | FTH1 | TUBB4B | VCAM1 | TSHZ2 | CORO1B | SELT |
| DDIT4 | SUB1 | SMC4 | FABP5 | YWHAQ | GBP2 | CRIP1 |
| DNAJB4 | H3F3B | RRM2 | TBCD | NBL1 | PHLDA1 | CAPG |
| ZFAND2A | POLR2L | MKI67 | GLUL | MIR155HG | ARID5B | RNF167 |
| DNAJA4 | SKP1 | DEK | RABAC1 | CLPP | PMAIP1 | IL17A |
| PPP1R15A | TMSB10 | ANP32B | LY6E | ARL3 | SH2D2A | EVL |
| SERPINH1 | COX6B1 | BIRC5 | CXCR3 | CD2BP2 | CARD16 | NDFIP2 |
| NEU1 | SUMO2 | MZT2B | OASL | ZBED2 | IL1R2 | TMEM50A |
| CLK1 | ATP5G2 | UBE2S | JAKMIP1 | HAVCR2 | LTB | GYG1 |
| GADD45B | CALM2 | CDK1 | PLA2G16 | MT1E | TBC1D4 | CD6 |
| DEDD2 | COX6C | ZWINT | CPNE7 | | MAGEH1 | TSEN54 |

TABLE 10-continued

| All T cell NMF programs | | | | | | |
|---|---|---|---|---|---|---|
| ARRDC3 | EIF1 | PCNA | CRTAM | FAM3C | ACP5 | PLEKHF1 |
| CDC42EP3 | NDUFB1 | H2AFX | CPNE2 | DGUOK | GADD45A | TMED2 |
| PLIN2 | USMG5 | CENPF | APOBEC3H | LBH | PBXIP1 | COMMD8 |
| ABHD3 | ANAPC16 | CARHSP1 | C1QB | TMEM173 | CD4 | TMEM50B |
| AHSA1 | ATP6V1G1 | MAD2L1 | GGA2 | DUSP4 | SYNGR2 | SUPT3H |
| IER5 | C19orf53 | PTTG1 | REC8 | SRGAP3 | RTKN2 | GPR34 |
| BAG3 | COX17 | TK1 | MS4A1 | RNF19A | CFLAR | STK17A |
| MYLIP | EDF1 | AURKB | C1QC | GALM | ICA1 | CALCOCO2 |
| FKBP4 | NDUFA11 | KPNA2 | CST3 | IFNG | IL2RG | PGLYRP2 |
| GADD45G | NDUFA3 | SMC2 | APOE | SNAP47 | CD79B | ATP10D |
| DDIT3 | UQCRB | SIVA1 | VPREB3 | PLSCR1 | NAMPT | ELOVL6 |
| ID3 | C4orf3 | CDKN3 | MSC | PDLIM4 | SLAMF1 | IVNS1ABP |
| DOK2 | NDUFA1 | TMPO | CD79A | SNX9 | GLRX | ST3GAL5 |
| DNAJB6 | C4orf48 | NUCKS1 | MAP4K1 | CD226 | MAF | CCR5 |
| TNF | NEDD8 | UBE2T | SGMS1 | IL6ST | CREM | C19orf79 |
| LAX1 | MYEOV2 | TMEM106C | CASP3 | LAG3 | UGP2 | PSENEN |
| TCP1 | C9orf16 | CCNA2 | SPP1 | TRAT1 | NDFIP1 | SURF4 |
| RABGGTB | TSTD1 | ARL6IP1 | MT1F | AHI1 | CUL9 | CNIH4 |
| CHORDC1 | SUMO1 | CENPW | CCR1 | IFI44L | GATA3 | ESYT1 |
| PTGES3 | NDUFA4 | ASF1B | B3GNT2 | PAG1 | ARL6IP5 | IL26 |
| TNFSF14 | SNX3 | CENPM | FXYD2 | GOLIM4 | HTATIP2 | ARHGEF3 |
| ANKRD37 | COX5B | HN1 | HLA-DOA | CBLB | CD28 | TMEM200A |
| SEPHS2 | COX14 | DTYMK | MMP12 | BCL2L11 | TNFRSF9 | CAMK4 |
| NFKBIE | PAIP2 | NUDT1 | APOC1 | MYO7A | ENTPD1 | C10orf128 |
| TSC22D1 | HMGN1 | H2AFY | CD86 | GNG4 | BTG3 | CLSTN3 |
| PLK3 | POLR2K | ANP32E | TIMD4 | NPDC1 | PIM3 | TNFRSF1A |
| TAF7 | ATP5J2 | LSM5 | CIITA | SARDH | FANK1 | POC1B |
| MKNK2 | BLOC1S1 | RHEB | MCOLN2 | MX1 | CMTM6 | QPCT |
| MB21D1 | PHPT1 | ANAPC11 | MARCH1 | CD200 | LAPTM4B | ANKRD35 |
| TSPYL2 | RNF181 | TPX2 | BANK1 | BTLA | LAYN | CLEC2B |
| IRF7 | PIN4 | DNAJC9 | SPI1 | TNS3 | CD59 | CD200R1 |
| GBP3 | MEAF6 | KIF22 | CD68 | TSPO | MAP1LC3A | MMD |
| MAP7D1 | NDUFB7 | SKA2 | SH3BP2 | SLC7A5 | FMNL1 | ELL |
| TMBIM1 | ATP5D | RPA3 | BASP1 | HTRA1 | TNIP1 | ARL2 |
| HSD17B7 | NDUFAF3 | CENPA | LY86 | TSPAN14 | SOX4 | PQLC3 |
| CPA5 | BAX | LMNB1 | TCL1A | KCNK5 | NDUFV2 | VKORC1 |
| HIST2H2AA3 | NDUFA5 | GTSE1 | ASPH | PDE7B | RHBDD2 | YIPF5 |
| C17orf67 | C19orf60 | TUBA1C | RNASE6 | TNFSF4 | CD70 | BCAP29 |
| HIST2H2BE | RBX1 | YWHAH | MYO5B | ELMO1 | OTUD5 | LPCAT4 |
| TMEM140 | GTF2H5 | CCNB2 | ARHGAP24 | CAMK1 | FAS | PDE4D |
| MUM1 | SPINK4 | | TNFRSF13C | PRDX6 | ISCU | MAN1A1 |
| DNAJB2 | DAZAP2 | | FCHSD1 | NUDT16 | CLEC7A | GTDC1 |
| SGK1 | S100A8 | | PARVG | ITGAE | PMVK | SLC10A3 |
| CDKN2AIP | EIF1B | | IL9R | SOD1 | NINJ1 | GFI1 |
| KLF10 | AP3S1 | | BTN3A3 | DGKZ | SDF4 | CLECL1 |
| MID1IP1 | TMEM134 | | SEMA4A | ITPR1 | RHOG | SPNS3 |
| ARL4D | MT1X | | MEF2C | LMO4 | | PCBP4 |
| IER3 | C15orf48 | | SQLE | HECTD2 | | TMEM68 |
| SNORA81 | S100A9 | | HLA-DQB2 | NMB | | TOR1AIP1 |
| PHYH | NDUFC1 | | RNASE1 | SLC4A2 | | PYGO2 |
| ACTRT3 | BRI3 | | PTPRK | CCDC6 | | VPS37A |
| MLKL | S100P | | CD22 | LRMP | | MAN1C1 |
| MICA | LAMTOR3 | | SLC2A6 | SLC27A2 | | RGS18 |
| AZIN1 | MDK | | CD19 | AGFG1 | | GNGT2 |
| BBC3 | GABARAPL2 | | AGR2 | | | OSTM1 |
| MAT2A | ZCCHC10 | | OGG1 | | | ZNF146 |
| SERTAD3 | SLPI | | TNFSF10 | | | TMPRSS3 |
| CCDC117 | AGR3 | | SPIB | | | SLC17A5 |
| FRAT2 | HHLA3 | | ATP1A3 | | | CLEC12A |
| FGFR1OP2 | C2orf76 | | ETS2 | | | PMEPA1 |
| HIST1H3H | FCGR3B | | HVCN1 | | | BOLA2B |
| SIAH2 | KLK1 | | PLA2G2A | | | CD101 |
| POLR2C | FASTKD3 | | ABCA2 | | | PTPN9 |
| IER5L | ASS1 | | CD14 | | | FBXO44 |
| RXRB | ZNF518B | | FGL2 | | | OTUB2 |
| PDRG1 | AQP9 | | BCL11A | | | |
| HIST1H2BD | SAA1 | | ZNF80 | | | |
| PARP10 | CSF3R | | HLA-DOB | | | |
| | REG4 | | VNN2 | | | |
| | CLEC4A | | FCRLA | | | |
| | CMTM2 | | CXCL10 | | | |
| | | | DAB2IP | | | |
| | | | SDCCAG8 | | | |

TABLE 11

| CD4 T cell NMF programs | | | | | | |
|---|---|---|---|---|---|---|
| outTopGenes1 | outTopGenes2 | outTopGenes3 | outTopGenes4 | outTopGenes5 | outTopGenes6 | outTopGenes7 |
| TUBA1B | ACTG1 | TXNIP | RGS1 | CD40LG | FOS | EEF2 |
| TUBB | CORO1A | IL7R | ISG20 | TNFSF13B | CD69 | PABPC1 |
| STMN1 | ARPC2 | ZFP36L2 | HERPUD1 | IFI44 | DUSP1 | NBEAL1 |
| HMGB2 | RAC2 | CXCR4 | SAMSN1 | ABRACL | NFKBIA | NPM1 |
| RAN | ARHGDIB | BTG1 | UGP2 | ERN1 | KLF6 | GLTSCR2 |
| H2AFZ | ARPC1B | GIMAP7 | BTG3 | NMRK1 | TNFAIP3 | HNRNPA1 |
| HIST1H4C | COTL1 | GIMAP4 | GMFG | PEBP1 | TSC22D3 | EIF3E |
| HMGB1 | CFL1 | CNBP | SCAND1 | RBL2 | FOSB | LDHB |
| HMGN2 | LCK | PIK3IP1 | CDKN1B | CTSH | ZFP36 | CCR7 |
| DUT | CAPZB | PPP1R2 | BAX | MGAT4A | ANXA1 | BTF3 |
| PCNA | ARPC3 | CYTIP | CCNG2 | SELT | MYADM | EIF3L |
| RANBP1 | CAP1 | LEPROTL1 | MAST4 | CCL20 | TAGAP | EIF3H |
| PPIA | PPP1R18 | SCML4 | TRIM22 | B3GALT2 | PPP1R15A | C6orf48 |
| HNRNPA2B1 | ACTR3 | PLAC8 | GCHFR | DYNLT3 | ATF3 | EIF3F |
| DEK | PPP1CA | TUBA4A | DYNLT1 | PRR5 | TUBA1A | SELL |
| SLC25A5 | SEPT1 | ARHGAP15 | CASP1 | CACNA2D4 | PTGER4 | NAP1L1 |
| CKS1B | MYL12B | TLE4 | HPGD | IL22 | TOB1 | SSR2 |
| SNRPD1 | TBC1D10C | DDX18 | LINC00239 | CERK | ARL4A | SLC25A6 |
| H2AFV | MYL12A | PTGER2 | SYF2 | REEP3 | ZSWIM4 | FXYD5 |
| TYMS | ARPC5 | TC2N | TANK | C10orf128 | CD55 | CCNI |
| CHCHD2 | PFN1 | LYAR | ELOVL5 | IL17RE | DUSP6 | LEF1 |
| RPA3 | ARPC4 | C11orf58 | CCDC28A | TMEM156 | NHSL2 | EIF3D |
| LDHA | PSME1 | RARRES3 | TIFA | LRRN3 | CITED2 | RSL24D1 |
| YBX1 | GPSM3 | STT3B | TMEM140 | COL5A3 | NFKBIZ | KLF2 |
| SNRPE | TPM4 | RCSD1 | DCK | MYBL1 | IL2 | RSL1D1 |
| CKS2 | UCP2 | XBP1 | CHIC2 | RUNX2 | LIX1L | EIF4B |
| SNRPB | CNN2 | MYC | UBE2B | LZTFL1 | SBF2 | ST13 |
| ANP32B | WDR1 | MED10 | DUSP10 | SLC31A2 | IFI44L | SNHG8 |
| TUBB4B | VASP | ESD | ARID5A | KIT | ATXN8OS | PCBP2 |
| UBE2C | HCLS1 | CCND3 | MAT2B | DSE | MAFF | NOSIP |
| H2AFY | LAT | CAMK4 | ACTA2 | PLXND1 | EGR2 | PFDN5 |
| HNRNPC | RHOA | LPAR6 | PAIP2 | CA2 | AUTS2 | TOMM7 |
| SNRPG | FKBP8 | DHRS3 | OAS1 | PGLYRP2 | C4orf32 | UBXN1 |
| RRM2 | CSK | SRSF8 | NCF4 | LAIR1 | SLC25A43 | CD37 |
| TPI1 | TPM3 | SSB | ADTRP | MCAM | NLRP3 | EIF3M |
| TK1 | LSP1 | C19orf66 | CYTH2 | RNF144B | RNU12 | EIF3G |
| TOP2A | FKBP1A | SYPL1 | RINL | LRRC23 | ZBTB10 | UXT |
| MCM7 | SEPT9 | RBMS1 | EPSTI1 | RGS18 | RIPK2 | LDLRAP1 |
| NUSAP1 | SIT1 | TXK | FAS | ABCA1 | RRAS2 | ZNF90 |
| LSM4 | OSTF1 | LSR | CLDND1 | MATN2 | ID1 | TCF7 |
| PSMA4 | BRK1 | FNTA | FAM45A | TMEM200A | BCL2A1 | CD48 |
| ATP5G3 | RNF167 | RCBTB2 | CCDC90B | NEO1 | ADHFE1 | LITAF |
| SLC25A3 | HIGD2A | ZSCAN18 | ADAM12 | SEPP1 | KCNN1 | EVI2B |
| TUBA1C | RGS10 | VAPA | HOXB2 | SMOX | TRIQK | ALKBH7 |
| KPNA2 | RGL4 | SPOP | NDUFB5 | CTDSP2 | FOXO3 | ERP29 |
| PA2G4 | FAM49B | SPG20 | BCL2L11 | LTK | GPR85 | COX4I1 |
| TMEM106C | TBCB | ASB8 | PPP2R2B | LTB4R | TMCC3 | TOMM20 |
| NUDT1 | RHOH | AKIRIN1 | HS35T3B1 | IL17F | ANKRD42 | FBL |
| BIRC5 | HMOX2 | RSBN1 | UBL7 | NRBP2 | PLCB1 | C1orf162 |
| NME1 | DENND2D | SESN1 | POLR3GL | SIRT5 | DHRS4-AS1 | CCDC109B |
| MKI67 | CALM3 | ARFRP1 | DDB2 | TMEM127 | ZFP62 | CMPK1 |
| PTTG1 | RASAL3 | ANXA2R | ZNF101 | TAF6L | EFCAB2 | POLR1D |
| SERBP1 | PSMB10 | SGK3 | SNRNP35 | EPOR | GPR35 | LINC00493 |
| HN1 | DRAP1 | TRIM4 | UBL3 | GLYCTK | ARHGEF40 | PASK |
| SNRPF | COPE | EAPP | HAGH | DPP4 | TPBG | CCNG1 |
| LSM5 | LPXN | TNFAIP8 | STX5 | NCDN | ZNF703 | IGBP1 |
| NASP | C19orf43 | ST3GAL1 | CORO2A | PROK2 | MPZL2 | GYPC |
| HNRNPR | SASH3 | NKAP | DUSP11 | ZNF510 | ZNF329 | FHIT |
| HNRNPAB | DBNL | SORL1 | HOXB4 | PCDH9 | BCO2 | SH3YL1 |
| HNRNPM | ANXA11 | SSBP2 | HERC6 | ITPRIPL2 | ESPN | EPB41L4A-AS1 |
| DDX39A | SH3KBP1 | GCLM | FOPNL | CYTH3 | CXCL14 | EIF2A |
| PSMA7 | FERMT3 | TMEM71 | WDR53 | METTL21B | ARHGEF37 | MAL |
| DNAJC9 | EVL | GLOD4 | OBFC1 | RAB18 | IRGM | CSDE1 |
| CYCS | C9orf78 | XPA | REXO2 | C2CD4A | ZNF556 | ZFAND1 |
| HNRNPF | ADA | SORBS3 | GLI4 | SLC7A8 | SPON1 | HADHA |
| ZWINT | ARF1 | TAZ | PHLDA3 | WDR13 | NARS2 | C14orf64 |
| SLBP | DEF6 | MID1IP1 | APOC1 | FES | ASAH2B | PABPC4 |
| CCT6A | CMTM3 | CRYZL1 | WIPI2 | MBNL3 | C8orf37 | OXA1L |
| SMC2 | ENSA | RNF125 | C3AR1 | TAF1A | FOXJ1 | CAMLG |
|  | RBCK1 | DEGS1 | MARCH3 | ZSCAN21 | H3F3C | AIF1 |
|  | WAS | FLOT1 | CHST11 | MMP23B | SYT5 | EEF1G |
|  | PRELID1 | MX2 | INPP5K | KIAA1324L | ELOVL4 | ACTN1 |
|  | SLC9A3R1 | AKAP7 | GRPEL2 | SLC26A3 | RAB3B | SERP1 |
|  |  | DNAJC19 | GBP5 | ZNF213 | PLEKHA8 | ATP5O |
|  |  | PITPNC1 | IL7 | LINGO4 | RNU11 | PRMT2 |
|  |  | CCDC59 | FAM19A2 | ZDHHC7 | TMEM231 | SNHG7 |

TABLE 11-continued

CD4 T cell NMF programs

| | | | | | |
|---|---|---|---|---|---|
| CIR1 | CRYL1 | PARP16 | PPP1R14D | PRKCSH |
| EIF4A2 | AIM2 | AQP8 | C10orf111 | TMEM123 |
| | ARNTL | AATK | PAGE5 | LETMD1 |
| | B3GNTL1 | TRPM4 | WWC2 | RASGRP2 |
| | DCP1B | PRDM11 | SNORD104 | DPH5 |
| | KIAA0040 | SLC16A6 | SIGLEC7 | CHMP7 |
| | ACVR1 | PODXL2 | SYNPO2L | RIC3 |
| | SLC35D2 | IMPACT | HRASLS2 | NUCB2 |
| | AZI2 | HSD11B1L | RPPH1 | ABHD14B |
| | MED25 | CCDC106 | SRPX | CHMP3 |
| | JAZF1 | | TTLL9 | SCGB3A1 |
| | TCTA | | AMOT | BEX2 |
| | GANC | | NTN4 | NACA2 |
| | C2orf74 | | SIAH3 | MED28 |
| | | | DKK3 | HSD17B11 |
| | | | ZSWIM5 | NSA2 |
| | | | LMLN | EBPL |
| | | | SNCA | C1orf228 |
| | | | DTX1 | ZNHIT3 |
| | | | SCN1A | ZG16 |
| | | | CSMD2 | LBH |
| | | | IFLTD1 | CHI3L2 |
| | | | FAM188B | FAM175A |
| | | | | APBA2 |

| outTopGenes8 | outTopGenes9 | outTopGenes10 | outTopGenes11 | outTopGenes12 | outTopGenes13 | outTopGenes14 |
|---|---|---|---|---|---|---|
| HSPA1A | HNRNPH1 | TNFRSF4 | ATP5E | CXCL13 | S100A4 | TPT1 |
| HSPA1B | CDC42 | TNFRSF18 | SERF2 | MT2A | S100A6 | EEF1A1 |
| HSP90AA1 | C1orf56 | BATF | SUMO2 | NR3C1 | S100A11 | NACA |
| DNAJB1 | CDC42SE1 | IL2RA | C14orf2 | FKBP5 | VIM | FAU |
| JUN | SET | CD7 | ATP5L | RBPJ | S100A10 | UBA52 |
| HSPE1 | STK17B | TYMP | COMMD6 | CD74 | SH3BGRL3 | EEF1B2 |
| UBC | PPP1CB | TIGIT | HMGN1 | ALOX5AP | TMSB10 | EEF1D |
| HSPA8 | CAPZA1 | TNFRSF1B | PPDPF | NAP1L4 | LGALS1 | ACTB |
| HSPB1 | CD3G | LAIR2 | SRP14 | GAPDH | MYL6 | PTMA |
| HSP90AB1 | MDM4 | CTSC | H3F3A | SLA | IFITM2 | EIF3K |
| UBB | CTNNB1 | SH2D2A | ATP5I | TGIF1 | CD52 | UQCRH |
| DNAJA1 | TNRC6B | FOXP3 | UQCR11 | YWHAQ | TAGLN2 | FXYD3 |
| HSPH1 | CDC42SE2 | IL1R2 | NDUFB1 | MTHFD2 | ANXA2 | MT1G |
| RGS2 | APOBEC3C | ACP5 | UQCRB | PDCD1 | FTH1 | FABP1 |
| HSPA6 | WTAP | TNFRSF9 | UQCR10 | HLA-DPA1 | PLP2 | CKB |
| DDIT4 | TSPYL1 | GBP2 | EIF1 | HLA-DRB1 | EMP3 | CDC42EP5 |
| HSPD1 | TRA2A | IL2RB | H3F3B | ISCU | CRIP1 | CHCHD6 |
| RHOB | C16orf54 | BIRC3 | OAZ1 | CHN1 | APRT | GPR160 |
| CACYBP | EIF5A | ICOS | SUB1 | HLA-DRA | LGALS3 | C10orf99 |
| DNAJB4 | ARF6 | CTLA4 | C19orf53 | SEC11A | TIMP1 | LGALS2 |
| GADD45B | B4GALT1 | SYNGR2 | HINT1 | NMB | NDUFA1 | RAB13 |
| CLK1 | PRDM1 | GADD45A | FTL | RNF19A | CALM1 | PKIB |
| DNAJA4 | CBX6 | PKM | TMSB4X | BTLA | OCIAD2 | CIB2 |
| ZFAND2A | FOXP1 | GLRX | ATP6V1G1 | GNG4 | COX5B | UGT2B17 |
| SERPINH1 | ZC3HAV1 | DUSP4 | COX7A2 | VOPP1 | GTF3A | STAP2 |
| NEU1 | SRSF6 | CCND2 | ATP5G2 | IL6ST | TSPO | PSMA8 |
| TNF | TMED4 | MAGEH1 | ANAPC16 | FAM107B | CLIC1 | RARRES1 |
| DEDD2 | PIP4K2A | PHLDA1 | ATP6V0E1 | HLA-DPB1 | GLIPR2 | GUCA2A |
| AHSA1 | PHKG1 | ENTPD1 | NDUFA4 | ELMO1 | LY6E | GUCA2B |
| MYLIP | EIF2S3 | CUL9 | NDUFA3 | ITM2A | GUK1 | MALL |
| CDC42EP3 | PPP3CA | NINJ1 | C4orf3 | SMAP2 | CD99 | BAIAP2 |
| ABHD3 | ADAM19 | PIM3 | SKP1 | CLPP | NEDD8 | ZDHHC1 |
| NR4A1 | TMEM120B | IFI6 | COX6B1 | AIM1 | NDUFS5 | HOXA10 |
| GADD45G | SUMF2 | LAPTM4B | CIRBP | TOX | CSTB | DCN |
| ID3 | RQCD1 | NAMPT | UBL5 | KIAA0319L | DSTN | ZNF862 |
| IER5 | DDX6 | CD79B | COX8A | METTL8 | MYEOV2 | CHP2 |
| IER3 | CD47 | PMAIP1 | C12orf57 | SRI | TXN | CKMT1B |
| HIST2H2AA3 | R3HDM2 | TNIP1 | COX6C | NUDT16 | MZT2A | ETV2 |
| PLIN2 | SERPINB9 | LAYN | SPCS1 | TSHZ2 | CAPN2 | CCL15 |
| EGR1 | JAK3 | NDFIP1 | NDUFA11 | ITPR1 | PYCARD | SNX7 |
| BAG3 | TLK1 | MAP2K3 | DYNLL1 | ITGAE | MYO1G | SPATA7 |
| TAF7 | SAR1A | CREM | CALM2 | CD200 | C19orf70 | A1CF |
| FKBP4 | CHP1 | RHOG | GPX4 | NPDC1 | ARL6IP4 | REP15 |
| REG4 | MARCH6 | ATOX1 | SNX3 | SNX9 | RABAC1 | SH3RF1 |
| RGS16 | GIGYF1 | PARK7 | TBCA | TMEM173 | SEC61B | DDR2 |
| HIST1H1C | C6orf62 | PRDX5 | OST4 | RILPL2 | NCF1 | COBL |
| FAM46A | CLEC2D | EFHD2 | C9orf16 | PPP1CC | ATP5J2 | THNSL2 |
| LAX1 | APOL2 | SAT1 | RAP1A | CDV3 | VAMP8 | MMP2 |
| ANKRD37 | ADAM17 | GATA3 | BLOC1S1 | AHI1 | ARRB2 | ZNF419 |
| HIST2H2BE | DNAJC3 | PTP4A3 | DAZAP2 | PDE7B | MGST3 | CRB3 |
| RABGGTB | PTP4A2 | HTATIP2 | MINOS1 | WASF2 | FLNA | ALDOB |

TABLE 11-continued

| CD4 T cell NMF programs | | | | | | |
|---|---|---|---|---|---|---|
| CHORDC1 | SEC22B | CXCR3 | SUMO1 | CTSB | TRMT112 | KCTD3 |
| TNFSF14 | RASSF3 | MAP1LC3A | KRT10 | FABP5 | CYSTM1 | TSKS |
| ARRDC3 | IAH1 | IL21R | SEC61G | LRMP | ATP5H | FAAH |
| SPINK4 | THAP5 | ZBTB32 | POLR2K | ZBED2 | AP1S2 | OTOP2 |
| SLC20A1 | ANKRD40 | SLAMF1 | PRR13 | MIR155HG | POLR2L | GPT |
| AGR2 | PPP2R5C | CD177 | C4orf48 | HLA-DQB1 | A1BG | CA7 |
| C17orf67 | TOR1AIP2 | ISG15 | GABARAPL2 | IGFBP4 | STX8 | SLC5A1 |
| MUM1 | SETD5 | FANK1 | NOP10 | CCDC50 | UPP1 | KIF12 |
| MKNK2 | PAN3 | OTUD5 | USMG5 | TRAT1 | KRTCAP2 | |
| TMBIM1 | SERINC5 | TNIP2 | SFT2D1 | CPM | C7orf55 | |
| CPAS | FAM76A | RHBDD2 | GTF2H5 | SMARCA2 | TRAPPC6A | |
| CDKN2AIP | PAFAH1B2 | TBC1D4 | COX7B | SH2D1A | IFITM3 | |
| IRF7 | ZC3H4 | RTKN2 | ATP5D | CCDC167 | KDSR | |
| SEPHS2 | LETM1 | PIM2 | SVIP | DGUOK | UBE2Q2 | |
| HIST3H2A | C2orf68 | ENO1 | SEPW1 | ICA1 | TFF1 | |
| GRPEL1 | SP110 | BCL2L1 | UQCRQ | CDK2AP2 | HEBP2 | |
| DNAJB2 | CSNK1A1 | TRAF1 | POMP | RAB27A | ELK3 | |
| MTO1 | EXOSC6 | SDF4 | ROMO1 | P2RX5 | BLVRB | |
| SERTAD1 | ZNF652 | FAM173A | COX7C | WDR83OS | R3HDM4 | |
| FRAT2 | BROX | SEC11C | RWDD1 | CCDC6 | CYB5R3 | |
| WBP2 | SRSF3 | BST2 | MEAF6 | SFXN1 | UBXN11 | |
| EPS8 | RBM6 | CCDC12 | C7orf73 | LMO4 | RASSF7 | |
| NANS | TRIM59 | SOD1 | NDUFS7 | SARDH | PQLC3 | |
| MB21D1 | ADNP | | SRSF9 | PSMB9 | ANXA4 | |
| OR11G2 | GAN | | EIF1B | GLUL | APOBEC3H | |
| HSPA2 | THUMPD1 | | LSM6 | CREG1 | ZNF480 | |
| SUCLG2 | RSRC1 | | POLR2J | TARSL2 | MINK1 | |
| DDIT3 | TLE3 | | PNRC2 | SORD | HCFC1R1 | |
| | ZFX | | SS18L2 | | COMTD1 | |
| | TP53 | | C19orf79 | | LINC00324 | |
| | AMFR | | POLR2I | | TMEM8A | |
| | LSM12 | | PAPOLA | | NDUFB2 | |
| | | | CMTM7 | | TMEM65 | |
| | | | TMEM14B | | CLU | |
| | | | TMEM230 | | EEPD1 | |
| | | | CDC26 | | LTC4S | |
| | | | MTIF3 | | SELPLG | |
| | | | CAMTA1 | | SLC25A24 | |
| | | | SNRPD2 | | LTBP4 | |
| | | | UBE2D3 | | COX14 | |
| | | | ZNHIT1 | | CCR2 | |
| | | | MOB1A | | PLOD3 | |
| | | | | | ACYP2 | |
| | | | | | GDPD5 | |
| | | | | | CLYBL | |
| | | | | | PLCB3 | |
| | | | | | ULK4 | |
| | | | | | PLEKHG3 | |
| | | | | | FGFBP3 | |

| outTopGenes15 | outTopGenes16 | outTopGenes17 | outTopGenes18 | outTopGenes19 |
|---|---|---|---|---|
| NEAT1 | JUNB | CD3D | CCL5 | LTB |
| MALAT1 | BTG2 | B2M | GZMA | IL32 |
| N4BP2L2 | DUSP2 | HLA-C | CCL4 | LIMD2 |
| PNISR | 50053 | HLA-A | ID2 | AES |
| PTPRC | ZNF331 | HLA-B | GZMB | TRAF3IP3 |
| DDX17 | RGCC | CD2 | HCST | BIN2 |
| RNF213 | SLC2A3 | CYBA | CKLF | IL27RA |
| VMP1 | NR4A2 | ITM2B | GNLY | ITGB1 |
| STK4 | PNRC1 | CD3E | CD8A | HMHA1 |
| SRSF7 | YPEL5 | HLA-E | HOPX | SUN2 |
| ANKRD12 | IER2 | TMBIM6 | TMIGD2 | HNRNPK |
| POLR2J3 | SOCS1 | NDUFA13 | ANKRD28 | PIM1 |
| RBM39 | IRF1 | TMEM59 | CD63 | ICAM2 |
| MBNL1 | HNRNPA0 | SPOCK2 | PRF1 | S1PR4 |
| AAK1 | SDCBP | PPIB | CLEC2B | IL10RA |
| CD44 | CHMP1B | GPR183 | CEBPD | CAST |
| FUS | EIF4A1 | DAD1 | KLRD1 | GRK6 |
| FNBP1 | DNAJB9 | CD164 | NCR3 | IK |
| ACAP1 | KDM6B | LAPTM5 | CXCR6 | NECAP2 |
| LUC7L3 | IFRD1 | BSG | AMICA1 | SYTL1 |
| PRRC2C | SBDS | SSR4 | C9orf142 | TTC19 |
| DDX5 | FAM53C | TMCO1 | CCL3 | FLT3LG |
| SON | RNF139 | SPCS2 | FKBP11 | TGFB1 |
| SYNE2 | FAM177A1 | SRGN | ITGA1 | SH3BP5 |
| PCSK7 | METTL12 | HLA-F | CD96 | CRBN |
| YWHAZ | AMD1 | CD247 | GZMH | UBQLN2 |

TABLE 11-continued

| CD4 T cell NMF programs | | | | |
|---|---|---|---|---|
| MGEA5 | CSRNP1 | IL2RG | CHST12 | TRAM1 |
| MCL1 | BCAS2 | PBXIP1 | RAP1B | STMN3 |
| SMCHD1 | SIAH2 | COX6A1 | ITM2C | TRADD |
| PRPF38B | YME1L1 | CUTA | SPRY1 | SPSB3 |
| MYH9 | SRSF2 | SEP15 | IFNG | TMEM63A |
| RORA | SNHG15 | CD53 | RUNX3 | CCM2 |
| EML4 | SNHG9 | LMAN2 | LAG3 | ADD3 |
| IQGAP1 | SNHG12 | ARL6IP5 | CAPG | FLI1 |
| SF1 | MARCKSL1 | ARL6IP1 | CD8B | ORAI1 |
| GCC2 | INTS6 | PDIA3 | STOM | TNFSF10 |
| IFI16 | HEXIM1 | CALR | GYG1 | ITGB2 |
| WIPF1 | EMD | BCAP31 | PTMS | MORF4L1 |
| ACTR2 | NFKBID | RNASET2 | GPR65 | TNFRSF25 |
| CELF2 | ODC1 | ATP6AP2 | CLIC3 | RASA3 |
| DOCK8 | STAT3 | DPP7 | CCDC85B | CBX7 |
| NKTR | WDR74 | ICAM3 | KLRC1 | CORO7 |
| ATRX | DCTN6 | TMED10 | CCDC107 | M6PR |
| IKZF1 | MAT2A | OCIAD1 | CTSD | GALT |
| SCAF11 | RBM7 | TECR | SEPT7 | ALDH9A1 |
| AKAP13 | ALG13 | LAMP1 | MSN | ZRSR2 |
| AKAP9 | PHF1 | LAPTM4A | NBL1 | SMAGP |
| BCL11B | DNAJB6 | PSAP | XCL2 | SAMD3 |
| MAF | PLK3 | TMEM50A | IL17A | OPTN |
| JUND | TBCC | PPT1 | SUPT3H | TCEA1 |
| PNN | SH2D3A | TMBIM4 | IL26 | CCNDBP1 |
| ADAR | COQ7 | HSPA5 | PERP | FLOT2 |
| AKNA | ISG20L2 | CD6 | GPR34 | TRPV2 |
| | AREG | RPN2 | XCL1 | PCIF1 |
| | SLC2A14 | REEP5 | CMC1 | AP1G2 |
| | AVPI1 | TXNDC12 | ITGB7 | HSF1 |
| | CMTM8 | KRT18 | FAM3C | ABTB1 |
| | ERF | TFF3 | PTPN6 | CDKN2D |
| | SPATA2L | MTDH | FASLG | RNPEPL1 |
| | MTFP1 | SLC3A2 | CPNE7 | FBXO18 |
| | FADS3 | ERP44 | DUSP5 | ARHGEF2 |
| | KIAA1683 | PCMT1 | SRGAP3 | ACTR10 |
| | MAP3K11 | SEC62 | GFI1 | RNF166 |
| | TUBB2A | PDIA6 | TSEN54 | CXXC1 |
| | ZNF394 | KRT8 | PRDX6 | FBXO3 |
| | HIST4H4 | DDOST | F2R | SURF1 |
| | NXF1 | TAP1 | FKBP2 | FGFR1OP2 |
| | OSM | MESDC2 | APOBEC3G | CBLL1 |
| | SESN2 | P4HB | GZMM | SOCS2 |
| | ZBTB4 | CTSA | PDE4D | LMF2 |
| | ZNF844 | | SPN | ULK3 |
| | TRIM39 | | MATK | KRI1 |
| | PRR7 | | PPP1R14B | RHOT2 |
| | PARD6A | | ELOVL6 | B3GAT2 |
| | ZNF250 | | LST1 | TSPAN32 |
| | HIVEP2 | | CCR5 | MED15 |
| | NAF1 | | SYTL2 | AKAP8L |
| | ZNF846 | | | PRR14 |
| | ZNF10 | | | SLC38A10 |
| | ZNF165 | | | STX4 |
| | TRAF4 | | | STUB1 |
| | SEZ6 | | | CRIP2 |
| | ZHX2 | | | PI4KB |
| | | | | WHAMM |
| | | | | ARHGAP4 |
| | | | | RAB37 |
| | | | | TSNAX |
| | | | | SULF2 |

TABLE 12

| CD8 T cell NMF programs | | | | | | |
|---|---|---|---|---|---|---|
| outTopGenes1 | outTopGenes2 | outTopGenes3 | outTopGenes4 | outTopGenes5 | outTopGenes6 | outTopGenes7 |
| GNLY | COTL1 | HNRNPH1 | HSPA1A | NEAT1 | GZMA | HLA-DRA |
| KLRC2 | ARHGDIB | APOBEC3C | HSPA1B | PTPRC | CD7 | CD74 |
| GZMB | ACTG1 | CDC42 | DNAJB1 | PNISR | CD3D | HLA-DRB1 |
| PRF1 | RAC2 | C1orf56 | HSP90AA1 | RNF213 | ALOX5AP | HLA-DPA1 |
| KLRC1 | ARPC2 | CDC42SE1 | HSPB1 | DDX17 | ACTB | HLA-DPB1 |
| KLRD1 | CFL1 | CAPZA1 | HSPE1 | RBM39 | CCL5 | HLA-DQA1 |

TABLE 12-continued

| CD8 T cell NMF programs | | | | | | | |
|---|---|---|---|---|---|---|---|
| CD63 | ISG20 | SET | HSPA8 | SAT1 | ANKRD28 | HLA-DQB1 |
| KIR2DL4 | LY6E | PRDM1 | RGS2 | SRSF7 | ITGAE | HLA-DMA |
| CEBPD | PPP1R18 | CD3G | HSPA6 | ETS1 | CAPG | HLA-DRB5 |
| HAVCR2 | PPP1CA | STK17B | JUN | MBNL1 | CKLF | HLA-DMB |
| ACP5 | ARPC1B | PPP1CB | DNAJA1 | IKZF3 | OSTF1 | GLUL |
| CTSA | UBE2L6 | CTNNB1 | CACYBP | FNBP1 | ZNF683 | VCAM1 |
| GALNT2 | ARPC5 | MDM4 | HSPH1 | RUNX3 | DAPK2 | ANXA5 |
| AFAP1L2 | CNN2 | TRA2A | RHOB | WIPF1 | C9orf142 | MAP4K1 |
| ECI2 | SUB1 | EIF5A | EIF4A2 | FUS | STOM | HLA-DQA2 |
| PTMS | GPSM3 | C16orf54 | UBC | MGEA5 | XIST | CD79A |
| CSF1 | CAPZB | B4GALT1 | HSP90AB1 | N4BP2L2 | GPR82 | C1QC |
| ITGB1 | BIN1 | WTAP | GADD45B | CCNL1 | TMEM123 | TBCD |
| NDFIP2 | CLIC1 | PTMA | HSPD1 | STK4 | CLNK | AIF1 |
| HPGD | HIGD2A | CDC42SE2 | SERPINH1 | IQGAP1 | UBAC2 | MSC |
| IL2RB | GYPC | SERPINB9 | ZFAND2A | PRRC2C | BSG | FCER1G |
| DBN1 | ISG15 | TSPYL1 | ID3 | ELF1 | CCDC69 | FXYD2 |
| LRRC28 | ARPC3 | CALR | DNAJA4 | CNOT6L | SURF4 | HLA-DOA |
| ATP8B4 | LSP1 | SAR1A | DNAJB4 | PRPF38B | NSMCE1 | SH3BP2 |
| PCID2 | VIM | CBX6 | PLIN2 | ZEB2 | ECH1 | REC8 |
| HAPLN3 | LGALS1 | PIP4K2A | PPP1R2 | JAK1 | GPA33 | VOPP1 |
| LAT2 | ZYX | PPP3CA | PMAIP1 | RBM25 | MZB1 | APOE |
| SLA2 | UBE2D3 | TMEM120B | CDC42EP3 | ARID4B | NARF | C1QB |
| FURIN | TPM3 | PHKG1 | NEU1 | AKAP13 | ARSG | HEXA |
| PIK3AP1 | CAP1 | TNRC6B | ABHD3 | SMCHD1 | P2RY11 | CTSH |
| LILRB1 | MYL6 | GOLIM4 | CLK1 | ARGLU1 | GSG2 | BASP1 |
| CXXC5 | PFN1 | ADAM19 | BAG3 | JUND | PTDSS1 | NPC2 |
| DUSP10 | AES | RQCD1 | SERTAD1 | KTN1 | CD244 | CD68 |
| PDGFRB | FKBP1A | APOL2 | AHSA1 | FYN | TMEM242 | HLA-DQB2 |
| NCR1 | RAP1B | GIGYF1 | IER5 | NCOR1 | C17orf62 | AKIRIN2 |
| ISCA1 | RHOA | SRSF6 | DEDD2 | STAT3 | PLEKHF1 | HVCN1 |
| PELI1 | TSPO | TMED4 | GADD45G | TNFAIP3 | TM65F1 | SPI1 |
| SLC25A15 | ARHGDIA | SUMF2 | TCP1 | EIF3A | SRGAP3 | CD86 |
| HDDC3 | PSMB8 | EIF2S3 | TMBIM1 | SRSF5 | OSTM1 | LYL1 |
| FAM49A | GNB2 | CHP1 | DEF6 | CD84 | ATP10D | APH1B |
| RASD1 | WDR1 | R3HDM2 | CCT3 | CBLB | TM7SF2 | APOC1 |
| CASP10 | UBE2L3 | IAH1 | CPA5 | ATRX | CD101 | LY86 |
| HSCB | TPM4 | SRSF3 | GADD45A | SCAF11 | FUCA1 | CIITA |
| BCL3 | TRAPPC1 | ARRDC3 | DDIT3 | HNRNPU | TMEM200A | HMGCL |
| KIR3DX1 | COX7A2L | TRIM59 | FKBP4 | WNK1 | CLSTN3 | SLC2A6 |
| CHMP6 | CMTM3 | LETM1 | PRNP | SYNE2 | ALDOC | PI4KB |
| FES | TAGLN2 | DNAJC3 | GEM | VMP1 | WIPI1 | MARCH1 |
| PRKAR1B | LCP1 | CSNK1A1 | STIP1 | ANKRD12 | RGS18 | VPREB3 |
| ACP2 | RGL4 | ARPC4 | NFKBIE | SLC38A1 | QPCT | DRG2 |
| POC1B | BRK1 | JAK3 | SEPHS2 | TCF25 | SLC27A1 | RNASE6 |
| ECE1 | LAMTOR1 | ADAM17 | MB21D1 | NKTR | JAG2 | ARMC6 |
| HEPH | GLRX | C6orf62 | TNFSF14 | ADAR | SPRY1 | RASSF4 |
| NR5A2 | HMGA1 | MTA2 | MID1IP1 | RNF19A | ARID3B | HCCS |
| PIK3R6 | PPP1CC | ANKRD40 | RABGGTB | MYH9 | B3GAT3 | FCHSD1 |
| C2orf49 | MT1E | SEC22B | SGK1 | LUC7L3 | FAM105A | TCL1A |
| GORASP1 | H1FX | RHOF | HSD17B7 | | ABCG1 | TFEB |
| SFTPB | LGALS3 | MARCH6 | PTGES3 | | HES4 | MMP9 |
| FUT7 | LPXN | SENP5 | GBP3 | | EML3 | GPATCH1 |
| FAM213B | UFC1 | ADNP | SIAH2 | | CHST10 | SPIB |
| MPI | ARRB2 | C2orf68 | MUM1 | | CLEC12A | EMC2 |
| FBXO22 | VASP | THAP5 | RGS16 | | CORO2A | BANK1 |
| PPM1F | VAMP8 | RBM6 | FGFR1OP2 | | SLC35C2 | CXCL10 |
| SEN | RGS19 | ZC3H4 | SP100 | | SLC39A6 | MEF2C |
| MFSD7 | EFHD2 | SYNC | MAP7D1 | | GREB1 | CASP3 |
| KLHL2 | SEPT9 | SETD5 | TECR | | ARRB1 | LHPP |
| ZNF880 | SH3BP1 | PRKD3 | LAX1 | | BRSK1 | CD19 |
| SPINT1 | GNAI2 | ZC3HAV1 | UPP1 | | WDR25 | MS4A1 |
| BTBD16 | MAP2K2 | TOR1AIP2 | IRF7 | | WDR5B | BLK |
| TMEM74B | SASH3 | PAN3 | ANKRD37 | | ATP2C2 | C9orf139 |
| C17orf100 | CD99 | FAM76A | EHD1 | | EGLN3 | DAB2IP |
| RNF40 | TADA3 | CD47 | TSPYL2 | | TTC12 | SCIMP |
| C11orf21 | CASP4 | TOB1 | PELO | | GALNT7 | CCDC141 |
| PDIA5 | ATP5G2 | NUDT19 | BBC3 | | LRRC1 | SPATA20 |
| STK32C | | BROX | TSC22D1 | | ZNF468 | CD40 |
| BIVM | | RASSF3 | UGP2 | | ZFHX3 | TNFRSF13B |
| RAB38 | | EAF1 | CHORDC1 | | SLC44A3 | NIT1 |
| PAOX | | DNAJC7 | RHBDD2 | | OLFM2 | SARS2 |
| F8 | | AP1G1 | MED15 | | RNF222 | RASGEF1A |
| DPY19L1 | | ZFX | TMEM140 | | MYOM1 | CD22 |
| BNC2 | | STRN3 | HERC5 | | COPZ2 | ARHGAP24 |
| DPP4 | | RASGEF1B | TRIB1 | | ILDR2 | DNASE1L3 |
| ITGA7 | | YWHAE | TBX21 | | LZTR1 | UAP1L1 |
| ABCA3 | | SLC12A2 | C17orf67 | | ZNF777 | BCL11A |
| | | DCUN1D1 | HBP1 | | BCL9 | SWAP70 |

TABLE 12-continued

| CD8 T cell NMF programs | |
|---|---|
| XYLT2 | DNAJB2 |
| IRF2BPL | KLF10 |
| NDUFV3 | N4BP2L1 |
| RIT1 | TXNDC12 |
| TP53 | VTRNA1-3 |
| BCL10 | PPID |
| TLE3 | ACTRT3 |
| TTC39C | AZIN1 |
| GAN | PGM2L1 |
| PAFAH1B2 | PDRG1 |
| EYA3 | |
| RSRC1 | |
| AMFR | |
| ZNF121 | |
| RBBP5 | |
| DOCK5 | |

| outTopGenes8 | outTopGenes9 | outTopGenes10 | outTopGenes11 | outTopGenes12 | outTopGenes13 | outTopGenes14 |
|---|---|---|---|---|---|---|
| MYL12A | TPI1 | HOPX | CCL3 | CD8A | GZMK | FOS |
| MYL12B | PKM | ID2 | CCL4 | CD8B | CST7 | JUNB |
| EMP3 | ENO1 | S100A4 | IFNG | CD2 | CMC1 | CD69 |
| HNRNPK | LDHA | IFITM2 | CCL3L1 | IFITM1 | DUSP2 | BTG2 |
| IL32 | RANBP1 | CD52 | MIR155HG | NBEAL1 | CYBA | KLF6 |
| CALM1 | CHCHD2 | CEBPB | CRTAM | CRIP1 | HLA-A | FOSB |
| TMBIM6 | YBX1 | RHOC | CCL4L2 | CHST12 | SRGN | IER2 |
| PSMA4 | SNRPB | FTH1 | EGR2 | APOBEC3G | GIMAP4 | ANXA1 |
| ANXA6 | PARK7 | ARF6 | SDCBP | HNRNPA1 | B2M | NFKBIA |
| SEPT7 | PPIA | FXYD5 | RILPL2 | CXCR6 | MALAT1 | ZFP36 |
| CORO1A | SNRPE | MIF | PTPN7 | CD3E | HCST | DUSP1 |
| PSME1 | COX5A | C11orf31 | PHLDA1 | SIT1 | HLA-B | MCL1 |
| SNRPB2 | SNRPG | LTB | CCL4L1 | PSMB10 | SH2D1A | MYADM |
| PSME2 | NME1 | TSTD1 | SEMA7A | KRTCAP2 | GZMH | NR4A2 |
| SKP1 | PGAM1 | CSTB | CCL3L3 | LCK | KLRG1 | EGR1 |
| TMEM59 | ATP5G1 | ABRACL | NFKBID | LIMD2 | GIMAP7 | SRSF2 |
| ARL6IP5 | ATP5G3 | UBE2F | NR4A3 | ARF5 | CLDND1 | TAGAP |
| STK17A | SNRPF | GUK1 | DUSP5 | DRAP1 | CD44 | TSC22D3 |
| PSMB3 | TXN | CDK2AP2 | EGR3 | CNBP | TRAT1 | XCL2 |
| ATP5B | GSTP1 | TMEM230 | NAB2 | HBB | EOMES | ZNF331 |
| TMBIM4 | SDF2L1 | C19orf60 | S100A14 | CTLA4 | ITM2C | SOCS3 |
| HNRNPA2B1 | LDHB | SH2D2A | BTBD10 | CARD16 | LYAR | FAM53C |
| ANXA2 | SERBP1 | WDR83OS | XBP1 | C19orf43 | LITAF | RGCC |
| HSP90B1 | NHP2 | ATP6V0E1 | POLB | CD37 | SAMD3 | EIF4A1 |
| XRCC6 | NDUFA4 | PTPN6 | APOBEC3F | CTSC | CUTA | YPEL5 |
| UBB | EDF1 | C12orf57 | BCL2L13 | MRFAP1 | ITGB2 | NFKBIZ |
| PGK1 | CYCS | NBL1 | DRAM1 | RASAL3 | F2R | YME1L1 |
| MORF4L1 | ATP5J | SNX3 | ZNF195 | C19orf66 | TC2N | SNHG8 |
| ITM2B | VDAC1 | CMPK1 | ZBTB45 | M6PR | PLEK | IFRD1 |
| SEPT1 | MCM5 | RAP1A | DDA1 | DAD1 | LYST | KLF2 |
| ATP5F1 | SLC25A3 | CCDC107 | EDARADD | SQSTM1 | SSR4 | SLC2A3 |
| PDIA3 | SEC61B | NOP10 | CXCL2 | TBC1D10C | SLAMF7 | TNF |
| HNRNPM | C1QBP | ANAPC16 | ADO | RHOH | SIGIRR | ATF3 |
| PSMA7 | PSMA2 | OAZ1 | SLC16A11 | ABI3 | DENND2D | GPR65 |
| PSMB9 | SRM | DSTN | FBXL19 | EIF1AY | TNFAIP8 | CHMP1B |
| DHRS7 | NPM1 | C4orf48 | ZC3H12C | TAP1 | C1orf21 | CSRNP1 |
| PSMB1 | PHB | NUDT14 | ALG13 | OASL | TIMD4 | INTS6 |
| MGST3 | GADD45GIP1 | NHSL2 | MAP3K7 | SUMO2 | GIMAP2 | TUBA1A |
| HSPA5 | NDUFS6 | HMGN3 | ZNF740 | LAT | CHI3L2 | HEXIM1 |
| MDH1 | NDUFS8 | RAC1 | ZNF184 | ARF1 | GTPBP8 | TCF7 |
| REEP5 | NDUFA6 | CORO1B | CCDC9 | TNIP3 | ZNF831 | ATP1A1 |
| GHITM | SOD1 | FAM173A | RAMP1 | TRAF3IP3 | DKK3 | KDM6B |
| SPCS2 | PPA1 | EPS8L2 | ZNF79 | DYNLRB1 | LPCAT1 | DNAJB9 |
| CD53 | SNRPD1 | AMZ2 | SH2B3 | CD247 | RAB9A | XCL1 |
| IK | GAPDH | LMO4 | TMEM117 | GBP5 | GRK6 | LMNA |
| RBM8A | ERH | TIMP1 | DNAAF1 | SSU72 | MIB2 | PITPNC1 |
| ITGB7 | NASP | C9orf78 | GSTO2 | TMCO1 | STX11 | ZSWIM4 |
| FERMT3 | DCTPP1 | STARD3NL | FAM149B1 | PSTPIP1 | EPHA1 | NR4A1 |
| IL2RG | ROMO1 | FAM45A | RELL1 | LAG3 | PILRB | PPP1R15A |
| VCP | GPX4 | RNF11 | MAGIX | UCP2 | IGFBP2 | MAFF |
| ATP6AP2 | PRDX5 | NAA38 | FIG4 | BAX | GPM6B | SNHG9 |
| CCT7 | SEC61G | JTB | POMZP3 | RNF5 | ARPC5L | METTL12 |
| EZR | LSM7 | TNFSF12 | HS3ST1 | TMEM9B | FGR | PTGER2 |
| COPE | | APRT | ZNF614 | APH1A | ICAM2 | DUSP6 |
| ACTR3 | | A1BG | PRODH | SH3GLB1 | LEPROTL1 | FAM177A1 |
| POLR2G | | SUMO1 | IL21 | TSEN54 | ATHL1 | BEX2 |
| SF3B2 | | NCF4 | ZP3 | COPS6 | GPX7 | SBDS |
| LAPTM4A | | RCN2 | GRIN2B | PRKD2 | ITGA5 | SNHG15 |
| TMEM50A | | SNRPN | TNNI2 | ICOS | ZFYVE21 | METTL15 |

TABLE 12-continued

| CD8 T cell NMF programs | | | | | |
|---|---|---|---|---|---|
| MAGED2 | NCF1 | TMTC2 | FASLG | LINC00239 | MX2 |
| TERF2IP | FYTTD1 | ASB7 | TMEM179B | KLF3 | PLK3 |
| | TMED2 | ZKSCAN3 | C8orf59 | FCGR3A | LSR |
| | LSM10 | MTMR12 | ORMDL3 | GPKOW | PER1 |
| | RASSF5 | FERMT1 | CD48 | PTRH1 | KCNQ10T1 |
| | FAM3C | KLC3 | ELOF1 | TTC39B | ZNF566 |
| | PGLYRP2 | ZNF546 | SLC9A3R1 | PHF1 | MMGT1 |
| | C10orf128 | ATAT1 | WAS | PACSIN1 | MARCH9 |
| | SELT | C9orf163 | ASB2 | NAA50 | SLC25A4 |
| | CLECL1 | PPT2 | ASCC2 | CD300A | ACAT1 |
| | TPST2 | C10orf91 | ASF1A | BPGM | IER3 |
| | SCPEP1 | FOXC1 | PRKCH | CNPY3 | IGFBP3 |
| | ESYT1 | NIPAL4 | MUC2 | RASA3 | ABHD5 |
| | CD9 | JAG1 | IL12RB1 | TTC16 | ZSCAN18 |
| | TPD52 | MED26 | METTL23 | ORAI1 | MTIF2 |
| | CAPN12 | CARD10 | SCAMP2 | FAM102A | VCL |
| | SBF2 | TPSD1 | IEI35 | | PLA2G12A |
| | KRT10 | DGKI | LRP10 | | TTPAL |
| | FBXL15 | BRPF1 | PSENEN | | GPR35 |
| | PTP4A1 | MAOB | CD70 | | ZBTB10 |
| | STUB1 | ZNF341 | | | CLU |
| | ABHD14A | ZNF251 | | | |
| | HIC1 | RABEP2 | | | |
| | ARL2 | CCDC122 | | | |
| | TMEM134 | THSD4 | | | |
| | KRT81 | NTSR1 | | | |
| | UBASH3B | | | | |
| | COX20 | | | | |
| | POLR2J | | | | |
| | PDE4A | | | | |
| | MAPKAPK3 | | | | |
| | SPNS3 | | | | |
| | ATF1 | | | | |
| | DPF3 | | | | |
| | DDAH2 | | | | |
| | RAB5A | | | | |

| outTopGenes15 | outTopGenes16 | outTopGenes17 | outTopGenes18 | outTopGenes19 | outTopGenes20 | outTopGenes21 |
|---|---|---|---|---|---|---|
| TXNIP | FKBP11 | TUBA1B | CXCL13 | TMSB10 | RGS1 | EEF1A1 |
| ZFP36L2 | AMICA1 | STMN1 | RBPJ | ATP5E | PNRC1 | TPT1 |
| PIK3IP1 | GMFG | TUBB | TNFRSF18 | MT2A | H3F3B | EEF1D |
| EVL | ATP5D | HMGB2 | PDCD1 | S100A6 | HERPUD1 | UBA52 |
| HLA-E | PTGER4 | H2AFZ | SAMSN1 | OST4 | SCAND1 | FAU |
| IL7R | RORA | HMGN2 | DUSP4 | UQCR11 | VAMP2 | EEF1B2 |
| BTG1 | H3F3A | HIST1H4C | GALM | COX7A2 | SRP14 | NACA |
| LAPTM5 | ENTPD1 | HMGB1 | SLA | SERF2 | GABARAPL2 | GLTSCR2 |
| CYTIP | C9orf16 | UBE2C | TMEM173 | UBL5 | TBCC | TOMM7 |
| CXCR4 | TMIGD2 | CKS1B | ITM2A | ATP5L | POLR2K | PFDN5 |
| HLA-C | GGA1 | H2AFV | TIGIT | C14orf2 | EVI2B | EEF2 |
| CD96 | IL17A | NUSAP1 | BATF | USMG5 | MAT2B | FTL |
| SYTL3 | CD160 | TOP2A | CTSD | UQCR10 | POLR3GL | EIF3E |
| SPON2 | VPS28 | TYMS | CCL20 | TMSB4X | CCDC28A | SLC25A6 |
| AIM1 | IVNS1ABP | TUBB4B | BST2 | COX6B1 | CAPZA2 | UQCRB |
| POLR2J3 | LAYN | CKS2 | IFI6 | POLR2L | CHIC2 | BTF3 |
| SCML4 | OXNAD1 | BIRC5 | TSHZ2 | NDUFA3 | EIF1B | EIF1 |
| IKZF1 | RGS10 | RRM2 | CD2BP2 | MYEOV2 | CITED2 | COX4I1 |
| TAPBP | MSH3 | CDK1 | LAIR2 | C19orf79 | CLEC2B | PABPC1 |
| HLA-F | CLIC3 | MKI67 | ZBED2 | ATP5I | REG4 | C6orf48 |
| ATF6B | ABCB1 | UBE2S | TOX | MT1X | MPLKIP | EIF3L |
| SMAP2 | TMEM14C | SMC4 | SNX9 | ATP5J2 | CCDC90B | NAP1L1 |
| IL10RA | TMEM167A | H2AFX | ARL3 | COX6C | EAPP | EIF3F |
| KRT8 | ARNTL | PTTG1 | NAP1L4 | COX17 | RBM7 | UXT |
| DYNLT1 | SSBP4 | ARL6IP1 | S100A11 | COX7C | RSL24D1 | HINT1 |
| HNRNPL | TMEM160 | ANP32B | CLPP | NDUFB1 | FIS1 | COMMD6 |
| PDCD4 | CARS | ZWINT | CD164 | PPDPF | LCMT1 | ERP29 |
| GZMM | TNFRSF25 | AURKB | NPDC1 | NEDD8 | HENMT1 | SSR2 |
| ARHGEF1 | LRRN3 | MZT2B | TNFRSF4 | BLOC1S1 | DUSP11 | EIF3G |
| FKBP5 | APBB1IP | MAD2L1 | TYMP | C4orf3 | RNF139 | EIF3K |
| S100A10 | MAST4 | CENPF | IFI44L | NDUFA1 | ZNF567 | EIF4B |
| ERN1 | IL26 | CCNA2 | MX1 | SUPT3H | GRAMD1A | CAMLG |
| CCND3 | PVT1 | CDKN3 | CD82 | SNRPD2 | IP6K1 | EIF3H |
| CD6 | CASS4 | KPNA2 | SNAP47 | UQCRQ | AKAP7 | ERGIC3 |
| EXOC7 | CAMK4 | NUCKS1 | PAIP2 | NDUFB7 | ZNF350 | TOMM20 |
| PHF20 | RAB37 | UBE2T | TANK | NDUFS5 | SYAP1 | ST13 |
| APBA2 | SMAP1 | KIF22 | ICA1 | SH3BGRL3 | HSF1 | ALKBH7 |
| GPATCH8 | KRCC1 | SMC2 | TGIF1 | NDUFC1 | CGRRF1 | TRAPPC6A |
| SEPT6 | DZIP3 | CENPW | OAS1 | CCDC57 | C7orf55 | BCL2A1 |

TABLE 12-continued

| CD8 T cell NMF programs | | | | | | |
|---|---|---|---|---|---|---|
| KLF13 | SERTAD2 | TMPO | SLC3A2 | VAMP5 | COMMD10 | ZFAND1 |
| SLC25A45 | GPR34 | HN1 | GSPT1 | NDUFA13 | NMRK1 | OXA1L |
| DPP7 | SPOCK2 | RHEB | NINJ2 | PIN4 | ZNF830 | PLAC8 |
| PRMT2 | GABARAPL1 | COX8A | DGUOK | C14orf64 | HIBCH | DNAJC4 |
| STMN3 | HECW2 | TPX2 | PRKAG2 | GNGT2 | HINT3 | DAP3 |
| UBL3 | SWT1 | LSM5 | TSPAN13 | CPNE7 | TMCC1 | NME4 |
| MAPK1 | OBFC1 | DTYMK | CTSB | S100A8 | NEIL2 | DALRD3 |
| PARP8 | BCAS4 | HMGN1 | TNS3 | ASS1 | C6orf1 | RAB4A |
| RINL | UEVLD | CDC20 | CD4 | IFITM3 | COQ6 | C11orf1 |
| PDCD7 | GPR55 | SKA2 | CD226 | C22orf39 | HACL1 | EIF2D |
| CABIN1 | RPP25L | CENPA | CD200 | BOLA2B | CRADD | FLOT1 |
| ZNF276 | ZG16 | CARHSP1 | METTL8 | TSPAN32 | MED21 | PABPC4 |
| TTC19 | LGALS4 | CALM2 | YPEL2 | CPNE2 | POLR3C | RASGRP2 |
| CDV3 | PLAGL1 | ASF1B | IGFLR1 | MAL2 | PORCN | TNFRSF13C |
| TLE4 | KIF5C | DEK | MTHFD2 | FLYWCH2 | SCRN2 | CKB |
| GPR155 | ZCCHC7 | GTSE1 | MTUS1 | DCLRE1A | NDUFAF5 | EPB41L4A-AS1 |
| NMT2 | FSD1 | CCNB2 | HECTD2 | MDK | EPS8L1 | PASK |
| PTP4A2 | RBMX2 | SPC25 | IL4R | PRMT7 | GRAP | SORBS3 |
| ZNF302 | ZNF414 | ANP32E | TIAM1 | CAPN10 | PYGB | ANAPC10 |
| LPAR2 | NCR3 | MXD3 | SLC16A3 | TMEM238 | ENOX2 | KPNA5 |
| NCK2 | B3GALT2 | CALM3 | SLC4A2 | ZFPM1 | NECAB3 | CCDC59 |
| AUTS2 | COX11 | SAC3D1 | SARDH | SAA1 | BMPR2 | ZNF814 |
| GALT | SLAMF8 | KIF20B | TSPAN5 | CYB5D2 | DCTN4 | SLC35B3 |
| SLAMF6 | B4GALT5 | KIFC1 | CSGALNACT1 | MAPKBP1 | ZNF75D | GUCA2A |
| KIAA0513 | ASPSCR1 | CDCA5 | PDLIM4 | RLN1 | MED22 | VAMP3 |
| GRAP2 | FGL2 | C12orf75 | SEC11A | GML | PACRGL | DPH5 |
| RSBN1 | ARL15 | MZT1 | LINC00158 | DCAF17 | ANKS1A | SH3YL1 |
| KRT18 | SPIN1 | YWHAH | SEMA4A | PIK3R3 | ZNF461 | PARP11 |
| POLM | MICAL2 | CENPM | STAMBP | SULT1A3 | ZNF510 | PRKCSH |
| YPEL3 | EFCAB4B | ANAPC11 | | GANC | | AGPAT1 |
| | CCDC94 | CDCA4 | | KCNRG | | IL2 |
| | SOBP | | | POU5F2 | | SKAP2 |
| | EID2B | | | BAIAP2L1 | | TMEM116 |
| | ZNF827 | | | CDC42EP1 | | S100B |
| | FABP1 | | | TJP1 | | C16orf74 |
| | SLC35A2 | | | ADAMTS13 | | MPP5 |
| | EXD3 | | | CNIH2 | | SCARB2 |
| | UBL7 | | | ZNF28 | | ATG4C |
| | TBC1D19 | | | PTAFR | | GUCA2B |
| | TAB1 | | | | | IL13RA1 |
| | CHST2 | | | | | TEX2 |
| | MPND | | | | | GNG7 |
| | MGAT4A | | | | | TUBB4A |
| | PPP1R1B | | | | | TJP3 |
| | PRDM5 | | | | | MKKS |
| | PIK3C2B | | | | | PBX1 |
| | INTS12 | | | | | NT5DC3 |
| | CERK | | | | | ADH1C |
| | RORC | | | | | IMMP2L |
| | MLF1 | | | | | |
| | ST14 | | | | | |

TABLE 13

| Innate T cell NMF programs | | | | | | |
|---|---|---|---|---|---|---|
| outTopGenes1 | outTopGenes2 | outTopGenes3 | outTopGenes4 | outTopGenes5 | outTopGenes6 | outTopGenes7 |
| FOS | GZMA | CST7 | HSPA1A | GNLY | CCL4 | MALAT1 |
| JUNB | ACP5 | GZMH | DNAJB1 | LGALS3 | CCL3 | NEAT1 |
| NFKBIA | ALOX5AP | PRF1 | HSP90AA1 | TFF3 | SDCBP | HNRNPH1 |
| DUSP1 | HES4 | FCGR3A | HSPA1B | SETBP1 | CCL3L1 | STK17B |
| CD69 | LMBR1 | SPON2 | JUN | QPCT | SLA | PTPRC |
| BTG2 | P2RY11 | PLAC8 | HSPE1 | SNX18 | NFKBID | SET |
| ZFP36 | NFIL3 | ITGB2 | HSPA8 | NR5A2 | CCL4L2 | FUS |
| IER2 | CHERP | KLF2 | RGS2 | HAVCR2 | EGR2 | C1orf56 |
| TNFAIP3 | AMZ1 | GZMB | HSPA6 | ENTPD6 | ARHGEF3 | ARGLU1 |
| MCL1 | HS3ST3B1 | EFHD2 | KLF6 | SLAMF8 | CCL4L1 | CTNNB1 |
| ZNF331 | GIMAP8 | CYBA | HSPB1 | ECE1 | POLR2K | CDC42SE1 |
| EGR1 | TMEM205 | GZMM | DNAJA1 | MEGF8 | PIK3AP1 | TNRC6B |
| FOSB | BAIAP2 | RAP1B | HSPH1 | DSE | CCL3L3 | RBM39 |
| NFKBIZ | FBXO2 | ARL4C | RHOB | SLC9A1 | EHD4 | N4BP2L2 |
| DUSP2 | FAM45A | CCND3 | HSP90AB1 | TIMD4 | NR4A3 | DDX17 |
| BIRC3 | GSTM4 | BIN2 | UBC | NUPR1 | AUTS2 | PPP1CB |
| GPR65 | ZNF143 | AES | SAT1 | EPHB4 | CD72 | PNISR |

TABLE 13-continued

| Innate T cell NMF programs | | | | | | |
|---|---|---|---|---|---|---|
| YPEL5 | ARHGAP21 | PTGDS | ANXA1 | TMEM63B | STX11 | MDM4 |
| RGCC | PLEKHG2 | IGFBP7 | IFNG | TTC31 | GOLT1B | TRA2A |
| KDM6B | CDYL2 | XBP1 | CACYBP | CCL2 | EGR3 | SRSF5 |
| MYADM | FGFRL1 | EMP3 | GADD45B | NACC2 | DNPEP | PIP4K2A |
| PHLDA1 | ZNF79 | HLA-C | HSPD1 | KCNN4 | RUNX1 | JAK1 |
| INTS6 | FAM35A | HLA-E | CLK1 | CCL18 | SNAP47 | APOBEC3C |
| NR4A1 | PHLDA2 | TMSB10 | DNAJB4 | ZFYVE19 | KLF9 | PRRC2C |
| CSRNP1 | KIF3B | LITAF | ZFAND2A | TACSTD2 | HYOU1 | CLEC2D |
| SOCS3 | SEPN1 | UCP2 | CITED2 | TMC4 | RAB35 | SRSF7 |
| DUSP10 | CNKSR2 | PLEK | DNAJA4 | TM4SF1 | STAMBP | ANKRD12 |
| NFE2L2 | ZNF251 | MYO1F | NEU1 | CA11 | SPRYD3 | MBNL1 |
| ZC3H12A | ASB1 | AKR1C3 | ARRDC3 | PLAUR | ZFPL1 | CAPZA1 |
| FAM53C | CALU | C1orf21 | MYLIP | TUBB6 | DNTTIP2 | DDX6 |
| ZSWIM4 | RNF24 | FLNA | ATF3 | RBPMS | GKAP1 | HNRNPU |
| LMNA | ZNF468 | FAM49B | AHSA1 | ZNF552 | STARD4 | LUC7L3 |
| DUSP5 | SLC35E4 | ICAM2 | SERPINH1 | FABP6 | EGLN1 | SCAF11 |
| IRF1 | | PRSS23 | PMAIP1 | TDRD7 | RILPL2 | SON |
| IER3 | | GNG2 | DEDD2 | SNX25 | SCIMP | PPP3CA |
| NFKB2 | | TPST2 | IEI6 | CLRN3 | FNDC3B | NR4A2 |
| IFRD1 | | LIMD2 | SERTAD1 | SPATA17 | AGTPBP1 | PNN |
| CHMP1B | | CD47 | GIMAP2 | FAM129B | MAPRE3 | ACTR2 |
| RBM23 | | SYTL1 | TNFSF14 | NDOR1 | HYLS1 | POLR2J3 |
| METTL12 | | TTC38 | PPP1R15A | ROM1 | STX1A | STAT3 |
| PIM3 | | TBX21 | ANKRD37 | TIGD4 | NXPH4 | NKTR |
| EIF4A1 | | TCF25 | FAM46A | MUC17 | AP1S3 | ZFP36L1 |
| CD83 | | HLA-B | DDIT3 | PROM1 | ACER3 | GCC2 |
| IRS2 | | GIMAP4 | DOK2 | | TRIM23 | PRPF38B |
| YME1L1 | | SH3BP5 | BAG3 | | FBXL2 | PCSK7 |
| MAP3K11 | | ZEB2 | TAGAP | | DAGLB | G3BP2 |
| GPM6B | | ADRB2 | CDC42EP3 | | C21orf33 | YWHAZ |
| ZBTB10 | | LAIR2 | GPR18 | | KIAA1522 | SMCHD1 |
| MEPCE | | SORL1 | DNAJB6 | | NCF2 | CREM |
| ADPGK | | GLRX | DYNLL1 | | PLD2 | SAMSN1 |
| OSM | | S100B | FKBP4 | | MSR1 | REL |
| FAM43A | | RASGRP2 | TSC22D1 | | DPY19L4 | SYTL3 |
| TMEM88 | | SELPLG | CHORDC1 | | KIAA0391 | GPBP1 |
| BCL3 | | NCR3 | VMP1 | | POU6F1 | WSB1 |
| COQ7 | | PXN | GADD45G | | VLDLR | BCLAF1 |
| TGIF2 | | KLRG1 | ABHD3 | | ZNF219 | DDX3X |
| RBKS | | DSTN | GBP3 | | P4HA3 | PIK3R1 |
| FRY | | FCRL6 | PLIN2 | | CYP51A1 | EIF3A |
| SPINK1 | | SIGIRR | MX1 | | PPP1R12C | |
| DCTN6 | | CD300A | HIST2H2AA3 | | ZNF808 | |
| P2RX5 | | LPCAT1 | PLK3 | | TSPYL5 | |
| SLC5A6 | | ATM | LMO4 | | SPATA2 | |
| ZNF250 | | ORAI1 | LAX1 | | ATXN7L3 | |
| OAT | | F2R | NFKBIE | | PALB2 | |
| CHRNE | | ASCL2 | GADD45A | | ZNF239 | |
| KCNN1 | | UBE2F | FASLG | | | |
| ZFAND5 | | S1PR4 | TCP1 | | | |
| CXCL2 | | PRKCB | IER5 | | | |
| C10orf91 | | PYHIN1 | MB21D1 | | | |
| HDAC8 | | HDDC2 | FNIP1 | | | |
| C12orf61 | | CEP78 | SLC5A3 | | | |
| MIR3188 | | BPGM | MARCKSL1 | | | |
| KLHL26 | | HIPK2 | PLSCR1 | | | |
| PIEZO1 | | CHST2 | PPP1R2 | | | |
| SIAE | | KLF3 | MKNK2 | | | |
| KANSL3 | | HBA1 | OASL | | | |
| CC2D2A | | TGFBR3 | EIF2AK2 | | | |
| PIK3C3 | | CCDC107 | | | | |
| PPIC | | MTSS1 | | | | |
| SPOP | | RASA3 | | | | |
| C1QTNF3 | | FMNL1 | | | | |
| MMP14 | | CD99 | | | | |
| TMLHE | | ADD3 | | | | |
| TTLL9 | | | | | | |
| ZNF579 | | | | | | |
| C17orf107 | | | | | | |
| PODXL2 | | | | | | |
| CXCL16 | | | | | | |

TABLE 13-continued

| Innate T cell NMF programs |
|---|
| SNORA70 |
| MTRR |
| TYMP |
| ZFYVE1 |
| GLTSCR1 |
| EGR4 |
| TMC5 |
| CYGB |

| outTopGenes8 | outTopGenes9 | outTopGenes10 | outTopGenes11 | outTopGenes12 | outTopGenes13 | outTopGenes14 |
|---|---|---|---|---|---|---|
| CD3D | TPI1 | CORO1A | TMSB4X | FCER1G | ETS1 | LGALS1 |
| CD3G | GAPDH | MYL12B | CCL5 | TNFRSF18 | CUTA | PFN1 |
| CD8A | LDHA | PSME1 | B2M | CD247 | MPLKIP | ACTB |
| HCST | RANBP1 | UBB | PTMA | TYROBP | CD38 | ACTG1 |
| CD3E | CHCHD2 | ARPC3 | IL32 | CKLF | TCEAL8 | ARPC2 |
| TIGIT | SNRPB | ATP5B | H3F3A | KRT81 | GDE1 | CFL1 |
| FABP1 | NME1 | ITM2B | FTL | KIR2DL4 | HENMT1 | ARPC5 |
| CD8B | ATP5G1 | ATP5A1 | HOPX | CTSD | WBP11 | ARF6 |
| C12orf57 | UQCRQ | HLA-A | EEF1D | S100A13 | MAP3K1 | RHOA |
| CD96 | PARK7 | CD53 | SRP14 | CD7 | MAPRE2 | ACTR3 |
| AMICA1 | PGAM1 | TMBIM6 | SERF2 | KRT86 | LCMT1 | ARHGDIB |
| ATP6V0E1 | PPIA | PDIA3 | SCML4 | CAPG | CTDSP2 | ARPC4 |
| ID2 | ENO1 | PGK1 | RARRES3 | MPG | TATDN1 | MYL12A |
| RGS10 | SNRPE | CAPZB | ISG20 | IL2RB | ABHD13 | SUMO2 |
| TRAT1 | NHP2 | HNRNPK | CLIC3 | CD63 | IST1 | RBM3 |
| LAG3 | CYCS | PSMB1 | TPT1 | TMIGD2 | UNK | ABRACL |
| PTGER2 | COX5A | CLIC1 | TMEM14C | ENTPD1 | ABTB1 | SNX3 |
| LGALS4 | ATP5G3 | CAP1 | CDV3 | PCID2 | CRLF3 | TPM4 |
| FAM3C | SOD1 | ITGB7 | MAPK1 | LAT2 | KPNA6 | SUMO1 |
| PELO | SNRPG | XRCC6 | SKP1 | NDFIP2 | LZTFL1 | VAMP8 |
| TRAM1 | COX7B | GHITM | SNTB2 | LSP1 | CUEDC2 | S100A11 |
| TMBIM4 | TXN | GIMAP7 | ATXN1 | SLC16A3 | ORMDL3 | PPP1R18 |
| TMEM9B | EIF5A | HNRNPM | NAP1L4 | CD81 | MXD4 | PRR13 |
| PERP | NDUFB2 | ANXA6 | PHTF1 | WDR83OS | FRG1 | ATP5E |
| LAYN | SRM | COPE | FIS1 | STARD3NL | HIBADH | SCP2 |
| TNIP3 | VDAC1 | ITGAE | IPCEF1 | CXXC5 | DUSP28 | PPP1CA |
| ASB2 | ATP5J | ANXA2 | GSTP1 | SEC11A | ZNF691 | C14orf166 |
| RHOH | NDUFS5 | HCLS1 | YPEL2 | ID3 | CCNB1IP1 | TRAPPC1 |
| FXYD3 | SNRPF | STK17A | TMEM141 | COL23A1 | PAAF1 | RAP1A |
| NBL1 | SERBP1 | ITM2A | CPD | ZBTB16 | TRAPPC6A | COX20 |
| CORO1B | GPX4 | SEPT7 | SERTAD2 | CSF1 | RPRD1B | COX7A2L |
| U2AF1L4 | C19orf53 | PTPN6 | KRCC1 | NSMCE1 | SUPT7L | NEDD8 |
| TMEM50B | DCTPP1 | PSMA5 | TP53INP1 | SH2D1B | TSSC4 | GABARAPL2 |
| HAX1 | ERH | VCP | MALT1 | C17orf62 | ALG13 | RAC1 |
| PITPNC1 | YBX1 | ECH1 | HMOX1 | FUCA1 | MCEE | YWHAE |
| GUCA2A | RBX1 | PSMD8 | IL6ST | PRELID1 | ZNF623 | SRP9 |
| ARL2 | CALR | ICAM3 | TGFBR2 | CD164 | HIBCH | PPP1CC |
| DAD1 | ROMO1 | YWHAB | TMEM80 | TGFB1 | UBOX5 | CNN2 |
| CA10 | SUB1 | PSMB8 | RCSD1 | CD151 | DCUN1D4 | TMED2 |
| GGA1 | TIMM13 | UQCRC2 | HEBP2 | SH3BP1 | PMS1 | HMGN1 |
| ABI3 | PSMA2 | SF3B2 | FCRL3 | GPR82 | YBEY | COMMD8 |
| CCRL2 | NDUFB11 | PSMA4 | OPRM1 | SURF4 | ZBTB7B | TADA3 |
| CKB | NDUFA4 | ARF1 | NBN | FGR | ADHFE1 | ARHGDIA |
| C15orf48 | SDF2L1 | ATP5F1 | RAD9A | POLR2L | ARL8B | SEC61G |
| TBC1D10C | NDUFS6 | MDH1 | DTNB | PDLIM7 | DCAF17 | POMP |
| GRK6 | APRT | GSDMD | CASP8 | GPR34 | C16orf87 | HIGD1A |
| ZG16 | PKM | CDC37 | TMCO6 | CYTH4 | ENG | LLPH |
| HIC1 | PSMA7 | PSMD4 | MAP2K6 | EPS8L2 | HIST1H4H | COX17 |
| PQLC3 | FABP5 | CCT8 | C15orf40 | EFCAB4A | ZFP90 | CAPZA2 |
| CAMK4 | COX6A1 | MAGED2 | EBPL | CHMP6 | SYNJ1 | RHOF |
| RCN2 | PHPT1 | HNRNPC | TSPAN8 | CMTM6 | UHRF1BP1 | C9orf78 |
| OLFM2 | NDUFB6 | EIF3I | C12orf76 | NCR2 | LTA | SFT2D1 |
| C10orf128 | PA2G4 | PSAP | RNU12 | TIMP1 | OSBPL9 | FAM104A |
| FBXL15 | SF3B5 | DHRS7 | TRIM33 | AFAP1L2 | UBXN6 | LSM6 |
| TPD52 | MINOS1 | TERF2IP | ABCD2 | SLC9A3R1 | FAM174A | ZYX |
| CISH | PPA1 | ANXA11 | AP3S1 | GPR68 | CXorf23 | ZNHIT1 |
| P2RX4 | C1QBP | XRCC5 | OSGIN2 | OTUD5 | TCP11L2 | SRP19 |
| NENF | NDUFAB1 | RPN2 | FLAD1 | NUDT14 | KIT | TRIAP1 |
| CARS | NDUFA6 | SP100 | EBLN2 | ETFB | NAGLU | ZFAND6 |
| NPM2 | SEC61B | PPP2R1A | SSR3 | PTP4A1 | KIF9 | SS18L2 |
| CLECL1 | CDK4 | SLC25A3 | MAP4 | TOX | POC1B | PTRHD1 |
| CA2 | HNRNPA3 | PSMB3 | METTL7A | SPRY1 | DIS3L | SH3GLB1 |
| LRRN3 | USMG5 | GBP2 | FLVCR1-AS1 | CLNK | DMXL1 | TMEM167A |
| FAM134B | GTF3A | PSMD13 | LIAS | SUPT3H | SLC35D1 | TMEM50A |
| LSR | NDUFB1 | TWF2 | CCDC146 | CTSA | DEAF1 | DDAH2 |
| MORF4L1 | TIMM8B | | RNF170 | BAX | ERP27 | C11orf73 |
| VKORC1 | NDUFA13 | | RNF38 | DPF3 | ZNF646 | PCNP |

TABLE 13-continued

Innate T cell NMF programs

| | | | | | |
|---|---|---|---|---|---|
| SLC26A3 | EIF5B | C9orf85 | BCAS4 | C2orf42 | BUD31 |
| A1BG | NAA10 | SLC30A6 | AP1S1 | | KXD1 |
| IFNAR2 | SRSF2 | C16orf86 | SERPINE2 | | GLTP |
| TMEM123 | TOMM22 | TSC1 | PLCG2 | | EIF1B |
| SEP15 | | ZMYM1 | MAST4 | | CHCHD5 |
| LPAR2 | | CHIC1 | KCTD5 | | TAF12 |
| CLDN7 | | GTF2A1 | STUB1 | | MED28 |
| GRAP2 | | MFSD7 | | | MARCH2 |
| H2AFY2 | | WDR5B | | | TBPL1 |
| OSTM1 | | INTS3 | | | GIPC1 |
| UBASH3A | | S1PR3 | | | TBCB |
| AKTIP | | FAM175B | | | MCRS1 |
| PGLYRP2 | | NEURL4 | | | THOC7 |
| NME7 | | GALNT2 | | | CORO1C |
| GPR137B | | C19orf33 | | | MTIF3 |
| PLAGL1 | | KCNK5 | | | UBE2D1 |
| AGPAT2 | | ACBD4 | | | |
| FAM105A | | HKR1 | | | |
| AGFG2 | | CYB5D2 | | | |
| ADSS | | CTBP1-AS1 | | | |
| MXRA7 | | VSTM2L | | | |
| ASF1A | | DGCR8 | | | |
| RIN3 | | AGRN | | | |
| SLC9A3R2 | | SETD1B | | | |
| CA1 | | SUPV3L1 | | | |
| CD101 | | PPP2R2D | | | |
| | | FAM160B1 | | | |
| | | ALDOB | | | |
| | | ATP11C | | | |
| | | KRTCAP3 | | | |
| | | WDR44 | | | |

| outTopGenes15 | outTopGenes16 | outTopGenes17 | outTopGenes18 | outTopGenes19 | outTopGenes20 |
|---|---|---|---|---|---|
| RGS1 | S100A4 | PPDPF | KLRC1 | EEF2 | STMN1 |
| CXCR4 | CD52 | COTL1 | XCL2 | GLTSCR2 | TUBA1B |
| ZFP36L2 | S100A6 | NBEAL1 | XCL1 | NACA | HMGB2 |
| BTG1 | CD74 | MIF | KLRD1 | EEF1A1 | TUBB |
| TSC22D3 | SH3BGRL3 | CD160 | CMC1 | EEF1B2 | H2AFZ |
| LEPROTL1 | CD2 | RAC2 | IFITM2 | HNRNPA1 | HIST1H4C |
| TXNIP | S100A10 | ISG15 | SRGN | BTF3 | HMGN2 |
| CYTIP | UQCR11 | RHOC | CD44 | PABPC1 | HMGB1 |
| H1FX | MYL6 | IFITM1 | CEBPD | EIF3E | H2AFV |
| IL7R | ATP5L | OAZ1 | GZMK | PFDN5 | CKS1B |
| PIK3IP1 | UBL5 | DRAP1 | IFITM3 | SLC25A6 | UBE2C |
| KLRC2 | OST4 | BRK1 | ITM2C | COX7C | TYMS |
| ODF2L | COMMD6 | PCBP2 | TXK | TOMM7 | SMC4 |
| ANKRD28 | TSPO | PRDX5 | GPR183 | FAU | NUSAP1 |
| GABARAPL1 | LTB | SSBP4 | EIF3G | UQCRB | MKI67 |
| EIF4A2 | HLA-DPB1 | ENSA | MATK | UBA52 | TOP2A |
| PNRC1 | NDUFA1 | C11orf31 | LY6E | COX4I1 | TUBB4B |
| PPP2R5C | HLA-DRB1 | GUK1 | SELL | EIF3F | CKS2 |
| PAIP2 | ZNF683 | C4orf3 | DDIT4 | NPM1 | ANP32B |
| SCAND1 | COX7A2 | GYPC | FXYD5 | EIF3L | BIRC5 |
| VAMP2 | ATP5I | CCDC69 | GLIPR2 | EIF3H | UBE2S |
| C11orf58 | HLA-DPA1 | JTB | CLDND1 | CCNI | CALM2 |
| PTGER4 | MYEOV2 | NDUFA3 | SH2D1A | CD48 | RRM2 |
| AIM1 | RBPJ | ARPC1B | IGFBP2 | C6orf48 | H2AFX |
| OXNAD1 | CRIP1 | FYN | IKZF1 | NAP1L1 | CENPF |
| DYNLT1 | PSMB9 | SSU72 | CFLAR | SNRPD2 | NUCKS1 |
| HERPUD1 | C19orf79 | DBI | SOCS1 | TOMM20 | CALM3 |
| TGIF1 | BLOC1S1 | FKBP8 | SSR4 | C19orf43 | DEK |
| CEBPB | C4orf48 | ARL6IP4 | LYST | FBL | ZWINT |
| EVL | MGST3 | CCDC85B | EOMES | EIF3D | ARL6IP1 |
| UBE2D3 | C12orf75 | PGLS | CIRBP | YPEL3 | CARHSP1 |
| UGP2 | C19orf70 | C9orf16 | AREG | EIF4B | CDK1 |
| ELF1 | NDUFB7 | C7orf73 | SPTSSB | UBXN1 | MAD2L1 |
| CLEC2B | RABAC1 | SEPT9 | STT3B | RSL24D1 | AURKB |
| IL10RA | DAZAP2 | MRFAP1 | TAGLN2 | ATP5G2 | KPNA2 |
| HNRNPL | VAMP5 | TPM3 | BCO2 | CD37 | MZT2B |
| SELT | C19orf60 | RBCK1 | GPATCH8 | SSR2 | HN1 |
| CCNH | SPOCK2 | TAPBP | NCAM1 | UXT | CDKN3 |
| COQ10B | OCIAD2 | ARF5 | MCTP2 | HSD17B11 | SMC2 |
| GFI1 | HLA-DRA | CAPNS1 | APOBEC3G | HIGD2A | TMPO |
| PDE4D | PIN4 | GFOD1 | FAM177A1 | RSL1D1 | PTTG1 |
| TLE4 | FTH1 | RGL4 | TCF7 | ALKBH7 | RHEB |
| ERV3-1 | SIT1 | ANAPC16 | SPINK2 | OXA1L | YWHAH |
| CHIC2 | HLA-DQB1 | NCF1 | CRTAM | IGBP1 | DUT |

TABLE 13-continued

| Innate T cell NMF programs | | | | | |
|---|---|---|---|---|---|
| SLA2 | NDUFB10 | SHISA5 | RABGAP1L | ABHD14B | CENPM |
| PHF1 | TSPAN14 | UBE2L6 | RUNX2 | EVI2B | ASF1B |
| PPM1K | NAA38 | DENND2D | SATB1 | NSA2 | CCNA2 |
| MEAF6 | CD6 | RNF7 | CD55 | LINC00493 | TMEM106C |
| TM2D3 | S100A9 | UBE2D2 | TNFRSF4 | CAMLG | SKA2 |
| SRSF8 | NDUFC1 | METTL9 | CLPP | ATP6V1G1 | DTYMK |
| KRT19 | ISCU | FAM118A | SMAP2 | ERGIC3 | CENPA |
| CHPT1 | HLA-DQA1 | VPS37B | BEX2 | CMPK1 | GTSE1 |
| ERN1 | S100A8 | C8orf59 | SOX4 | MAF1 | RAD21 |
| AKAP7 | CAPN2 | VASP | PLP2 | QARS | CENPW |
| AKIRIN2 | GLUL | SNRPN | ARID5A | POLR1D | TPX2 |
| DYNLT3 | BCL11B | GPSM3 | PRPF6 | ST13 | KIF22 |
| NHLRC3 | FLT3LG | CMTM3 | TMED10 | BRI3 | ANP32E |
| KLRC4 | TRMT112 | GNAS | FLOT1 | RBM7 | TK1 |
| PDE3B | G0S2 | MIEN1 | BHLHE40 | MFNG | UBE2T |
| GPR155 | TNFRSF25 | LAMTOR1 | THEM4 | EIF3K | LMNB1 |
| RNF11 | MT1X | PDCD2 | TNFSF10 | DEXI | TUBA1C |
| CRYZL1 | GMFG | CDK2AP2 | SESN1 | SH3YL1 | SAC3D1 |
| EIF4E | MAD1L1 | PPCS | GAS7 | ISCA1 | KIF20B |
| LYRM5 | JAKMIP1 | TMEM230 | PSTPIP1 | ESD | |
| MED6 | HINT1 | LCP1 | IL1B | EIF2A | |
| GGPS1 | CD5 | UBAC2 | ITGAX | PQBP1 | |
| RNF113A | STMN3 | POLR3GL | LDLRAP1 | PRKCSH | |
| DUSP16 | COMT | CSTB | PARP8 | TBCA | |
| ANKRD49 | LAT | CDC26 | CCR7 | LETMD1 | |
| MTRNR2L1 | CD4 | PPP1R11 | IGFBP4 | EEF1G | |
| UBL3 | TNFSF13B | DCXR | SNHG8 | DBP | |
| SIAH2 | DPM3 | UBASH3B | HIF1A | ZNF581 | |
| BLMH | PAG1 | CNBP | FKBP5 | MOB2 | |
| NMRK1 | CTLA4 | TAF10 | TC2N | FAM32A | |
| SLAMF6 | SURF1 | PLA2G16 | TRABD | USE1 | |
| MPZL3 | BBIP1 | PRR7 | IRF2BPL | TEN1 | |
| UBQLN2 | SLAMF1 | EIF1AY | CHST12 | TMEM204 | |
| RSBN1 | SYF2 | ZNF428 | WIPF3 | DNAJC4 | |
| | LST1 | C1orf43 | CXCR3 | MOSPD3 | |
| | DPH3 | KRT10 | GSN | BET1L | |
| | PPP2R2B | GNGT2 | SPRY2 | AMZ2 | |
| | MT1E | POLR2J | BEX4 | HGSNAT | |
| | VCAM1 | LCP2 | VAV3 | SLC27A5 | |
| | ARHGAP4 | TMEM14B | NCK2 | LY9 | |
| | CD82 | C6orf1 | IFI44L | VPREB3 | |
| | CTSH | C9orf142 | ZNF22 | C7orf55 | |
| | CCL20 | MYH9 | BBC3 | EPS15L1 | |
| | SLC25A24 | FBXW5 | UNC93B1 | CHMP3 | |
| | OGDH | KRTCAP2 | | ARID5B | |
| | MICAL2 | PDE4A | | SLC25A45 | |
| | | LSM2 | | TRIM4 | |
| | | C19orf66 | | FRA10AC1 | |
| | | | | PFDN4 | |
| | | | | TOM1 | |
| | | | | RAB5B | |
| | | | | SLC2A11 | |
| | | | | XPNPEP3 | |
| | | | | ZXDC | |
| | | | | S100A14 | |
| | | | | TRAF7 | |

TABLE 14

| Malignant epithelial NMF programs | | | | | |
|---|---|---|---|---|---|
| 1_Goblet | 2_Fos, Jun, stress response | 3_Mito, Redox, OxPhos (C15orf48) | 4_RNA processing, quality (MALAT1) | | 5_Metallothioneins |
| FCN3 | TNFRSF9 | GJA4 | MXRA8 | | KAZN |
| OAZ3 | AMPD1 | IGKV3D_15 | FCGR2B | | YTHDF2 |
| SCAMP3 | ANKRD35 | NOSTRIN | RGS18 | | TIE1 |
| SELL | KCNN3 | KLHDC8B | LMOD1 | | GJA5 |
| CR1 | RIT1 | KCNAB1 | LAX1 | | RGS18 |
| GCSAML | CD1E | NSG1 | ICOS | | CDK18 |
| C2orf40 | LMOD1 | JAKMIP1 | CLEC3B | | ANTXR1 |
| KCNE4 | SNX17 | PDGFRA | KCNAB1 | | STK39 |
| FAM212A | CDK15 | PPA2 | HTRA3 | | RBMS3 |
| KCNAB1 | GPBAR1 | PALLD | ADH1B | | RP11_884K10_5 |

TABLE 14-continued

| Malignant epithelial NMF programs | | | | |
|---|---|---|---|---|
| ENAM | CNTN4 | ZFYVE16 | PDGFC | HHIP |
| EGFLAM | FGD5 | TWIST1 | PRR16 | VEGFC |
| ZNF366 | BFSP2 | SH2D3C | FLT4 | SDHA |
| FAM174A | MAPK10 | MS4A2 | XXbac_BPG13B8_10 | EDIL3 |
| PRR16 | ADH1B | CRTAM | BACH2 | PCDH12 |
| WNT2 | HAND2 | KCNA5 | THSD7A | FGD2 |
| RP11_383H13_1 | VEGFC | VWF | NUGGC | PEX6 |
| BNC2 | BASP1 | CLEC1A | BNC2 | MOXD1 |
| ENHO | ADAMTS12 | NUAK1 | SFMBT2 | PILRA |
| OGN | PRR16 | MFAP4 | CXCL12 | SFRP1 |
| AIF1L | SLC39A7 | SP2 | LDB3 | STMN2 |
| PIP4K2A | PLN | SGCA | MPEG1 | GPIHBP1 |
| MFSD13A | VSTM2A | PRAM1 | FXYD6 | PKN3 |
| FIBIN | TFEC | SLC25A42 | WNT5B | RP11_354E11_2 |
| NTM | MSR1 | FKBP1A | CLEC12A | FRA10AC1 |
| MFAP5 | SOX17 | RAC2 | CLEC1A | TMEM126A |
| ABCC9 | OGN | | DCN | RP11_118B22_2 |
| SDS | LCN6 | | PCDH9 | KLRC1 |
| CMA1 | RIC3 | | TBX2 | DDX55 |
| ASB2 | CXCR5 | | LILRA6 | MLYCD |
| AL928768_3 | RP11_744N12_2 | | LILRB2 | RAPGEFL1 |
| KLF13 | NTM | | KIR2DL4 | ABCA8 |
| RP11_358M11_2 | JAM3 | | SIRPG | ABCA6 |
| ISLR | KCNA5 | | RP3_477O4_14 | CNDP2 |
| TMEM204 | CLEC1A | | JAM2 | CD209 |
| CTD_3203P2_2 | RERG | | | LILRB5 |
| FOXF1 | RERGL | | | WISP2 |
| CD226 | PYM1 | | | SOX18 |
| FCER2 | GPR18 | | | |
| AC011526_1 | CMA1 | | | |
| ACSS2 | HDC | | | |
| ATP5L2 | HACD3 | | | |
| | ISLR | | | |
| | RP11_805I24_2 | | | |
| | MYO1C | | | |
| | AOC3 | | | |
| | MEOX1 | | | |
| | GJC1 | | | |
| | ABCA8 | | | |
| | CCDC94 | | | |
| | RETN | | | |
| | CNN1 | | | |
| | SYDE1 | | | |
| | CCDC9 | | | |
| | SIGLEC1 | | | |

| 6_ER | 7_Mitochondrion, OxPhos | 8_Keratinocyte | 9_Hypoxia | 10_House keeping |
|---|---|---|---|---|
| SAMD11 | CHI3L2 | FHL3 | MXRA8 | PODN |
| CHI3L2 | FCRL1 | LY9 | AKR1A1 | S1PR1 |
| DDR2 | PRRX1 | CDK18 | PLPP3 | CHI3L2 |
| CR1 | RBBP5 | OPN3 | LRRC8C | TMIGD3 |
| GPBAR1 | IL10 | AC011753_3 | GCSAML | FCRL2 |
| GPD1L | CR1 | AC079767_4 | SLC8A1 | MNDA |
| DZIP3 | NKTR | TXK | COL5A2 | SLAMF1 |
| RP11_65F13_2 | FAM212A | ZNF746 | CLEC3B | FCGR2A |
| TAP2 | SFMBT1 | DOCK5 | CD96 | XCL2 |
| HEY2 | GYG1 | SOX17 | LIFR | CR1 |
| TRG_AS1 | NRROS | CBWD5 | CAMK4 | AC093818_1 |
| VSTM2A | ABCE1 | OMD | SPOCK1 | CALCRL |
| NUGGC | LHFPL2 | LCN6 | CSF1R | CYTL1 |
| FBXO18 | FLT4 | VCL | FLT4 | RHOH |
| LDB3 | CDYL | TSPAN14 | TREM2 | ENAM |
| RP11_322M19_1 | EPB41L2 | PAMR1 | COL12A1 | EMCN |
| ACTA2 | MLLT4 | CD6 | INHBA | GUCY1B3 |
| CPXM2 | HERPUD2 | CLMP | WNT2 | ADAMTS12 |
| PKP3 | ELMO1 | RP11_744N12_2 | CERCAM | PCDH12 |
| LYVE1 | SMARCD3 | LMBR1L | AP2A2 | HRH2 |
| PICALM | LDB3 | C12orf43 | CRYAB | DOK3 |
| KLRD1 | CD248 | ZNF219 | KCNA5 | PLN |
| RP11_834C11_4 | UBASH3B | LTBP2 | MAX | TCF21 |
| CCDC41 | AEBP2 | DNAJC17 | CCDC88C | THSD7A |
| CYFIP1 | GPR18 | CCL14 | TLCD1 | VSTM2A |
| LOXL1 | CMA1 | COPZ2 | CCL18 | TFPI2 |
| GALK1 | MAX | SYNGR2 | 4-Sep | SFRP1 |
| MEX3C | OAZ2 | TUBB6 | CD300A | SOX17 |
| ADNP2 | HS3ST3B1 | ROCK1 | CCDC102B | BAALC |

TABLE 14-continued

| Malignant epithelial NMF programs | | | | |
|---|---|---|---|---|
| CNN2 | MRC2 | CCDC9 | RETN | SH2D3C |
| RP11_886P16_3 | PRAM1 | SIGLEC1 | PGLYRP2 | CH25H |
| CTC_425F1_4 | MAP4K1 | | FPR3 | MFAP5 |
| PODNL1 | HRC | | SIRPG | CLEC2B |
| LILRB3 | TRPM2 | | THBD | KRT1 |
| LILRB5 | CCDC117 | | C21orf91 | ISLR |
| IFNAR2 | | | | CCL11 |
| BRWD1 | | | | CCL8 |
| AP001055_6 | | | | PLXDC1 |
| ATRX | | | | CCDC102B |
| | | | | F2RL3 |
| | | | | LILRA5 |
| | | | | COX4I2 |
| | | | | RP3_477O4_14 |

| 11_Mature enterocytes (FABP1) | 12_House keeping (HSPB1) | 13_OxPhos, Proteasome | 14_Enterocyte | 15_ISG, mucin |
|---|---|---|---|---|
| TIE1 | CD52 | GPX7 | HSPB7 | THEMIS2 |
| RP5_887A10_1 | MIER1 | PODN | BSDC1 | PEF1 |
| CHI3L2 | WLS | LIX1L | PODN | S100PBP |
| PYHIN1 | FASLG | GCSAML | PLPP3 | CSF3R |
| DDR2 | RGS18 | ANKZF1 | TMIGD3 | S1PR1 |
| SELE | RP11_343J24_1 | EFCC1 | CD48 | FCGR1B |
| AC104699_1 | EMILIN1 | NSG1 | C1orf186 | ANKRD35 |
| EHBP1 | CNRIP1 | CYTL1 | TRAF3IP3 | FCRL3 |
| COL5A2 | CD8A | C1QTNF7 | CLEC3B | SLAMF7 |
| KLF7 | CYTL1 | PACRGL | RP11_861A13_4 | DNM3OS |
| PECR | LDB2 | RP11_290F5_1 | RNF145 | KMO |
| DUSP28 | RP11_792D21_2 | C7 | FLT4 | MAL |
| FBLN2 | CDH6 | KIAA0141 | BMP6 | RP11_347P5_1 |
| CMTM8 | LY86 | CAP2 | DXO | CLEC3B |
| ADAMTS12 | PDE1C | RP3_523C21_1 | BMP5 | KLHDC8B |
| MOCS2 | SERPINE1 | RHBDD2 | RP11_383H13_1 | TMEM156 |
| CAMK4 | RP11_325F22_4 | SGCE | GPIHBP1 | CD180 |
| FOXF2 | GIMAP7 | TRIM4 | HACD4 | PCDH12 |
| CDYL | GIMAP4 | MTPN | MAMDC2 | LZTS1 |
| PI16 | GIMAP1 | FGD3 | TNC | RP11_536O18_2 |
| GIMAP8 | SNAI2 | LCN6 | PLAC9 | RP11_251M1_1 |
| GIMAP7 | MSC | OSBPL5 | LDB3 | IL2RA |
| DOK2 | FABP4 | ZNF143 | MRGPRF | CH25H |
| MAMDC2 | C9orf72 | LYVE1 | LAYN | CPXM2 |
| CENPP | NRP1 | RPS6KB2 | CLEC4A | MRVI1 |
| RP11_251M1_1 | BRMS1 | P2RY6 | RERGL | PDE2A |
| CH25H | ME3 | RERG | SERPINA9 | CXCR5 |
| MS4A1 | CLEC4E | KANSL2 | PLD4 | KCNA5 |
| NAALADL1 | KRT86 | IGHV3_11 | CTD_3203P2_3 | CLEC7A |
| CTSW | TESPA1 | APBA2 | DPEP2 | OLR1 |
| KCNA5 | TMEM119 | RTF1 | VMO1 | RP11_834C11_4 |
| R3HDM2 | GPR18 | DBP | HS3ST3B1 | TESPA1 |
| LTBP2 | CCDC102A | LILRB5 | AC104024_1 | MSRB3 |
| APBA2 | ADGRG1 | HSPA12B | CCL14 | SDS |
| DHX38 | KLHDC4 | FOXS1 | GZMM | C1QTNF9 |
| EVI2A | SPATA2L | BRWD1 | RETN | PSMA3 |
| MEOX1 | PLXDC1 | AP001055_6 | CD22 | RP11_164H13_1 |
| SEPT4 | CD226 | IGLV5_45 | HSD17B14 | RGMA |
| OTOP2 | F2RL3 | MPST | LILRA5 | RP11_345J4_5 |
| ATP5D | RP3_477O4_14 | | RP3_477O4_14 | MEOX1 |
| FCER2 | ATP5O | | ZNF831 | PPM1D |
| SYDE1 | CBX6 | | BTG3 | CD300LF |
| WISP2 | | | | RETN |
| IGLC6 | | | | CD209 |
| | | | | AC006129_2 |
| | | | | GPR4 |

| 16_TA/stem cell | 17_Myc targets | 18_KRT18 and Ig | 19_Cystatin C, MHCI | 20_Protein synthesis, house keeping |
|---|---|---|---|---|
| RUNX3 | ADORA3 | C1orf228 | FCN3 | RP5_887A10_1 |
| VCAM1 | CTA_134P22_2 | CTSK | FCGR1B | FCRL2 |
| TNFAIP8L2 | FCER1A | ANGPTL1 | CADM3 | FCRL1 |
| CD1C | C1orf186 | CR1 | ADAMTS4 | CTA_134P22_2 |
| CADM3 | IL10 | RP11_17H4_2 | C1orf186 | SELP |
| SLAMF6 | ACTG2 | CYP1B1 | HLX | C1orf186 |
| CR1 | AC093818_1 | CTLA4 | CNRIP1 | KCNE4 |
| RHOU | CDK15 | AC079767_4 | ZNF385D | ZNF385D |

TABLE 14-continued

| Malignant epithelial NMF programs | | | | |
|---|---|---|---|---|
| SEPT10 | GMPPA | FAM212A | P2RY14 | CCR5 |
| ZEB2 | EFHD1 | STAB1 | ADH1B | CD96 |
| CNTN4 | ZNF385D | P2RY13 | SFRP2 | MRAS |
| SEMA3G | FAM107A | KDR | TLL1 | ENAM |
| COL8A1 | VEGFC | TLL1 | VEGFC | ADH1B |
| RP11_792D21_2 | ZNF366 | GAPT | ADAMTS12 | DHX29 |
| SYNPO2 | ITK | TSLP | PRR16 | SPOCK1 |
| PCDH18 | FOXF2 | MOXD1 | HRH2 | XXbac_BPG13B8_10 |
| GUCY1B3 | TMEM170B | LAT2 | FLT4 | PI16 |
| VEGFC | BMP5 | PIK3CG | BMP5 | RSPO3 |
| BASP1 | TFEC | LZTS1 | COL12A1 | TWIST1 |
| EGFLAM | RP11_383H13_1 | ADGRA2 | RSPO3 | VSTM2A |
| RFESD | FABP4 | FABP4 | FNDC1 | HGF |
| PRR16 | GPR20 | PFKFB3 | VSTM2A | ZNF394 |
| SPOCK1 | OGN | AFAP1L2 | SFRP1 | WNT2 |
| FOXF2 | OMD | PAMR1 | ANGPT1 | RP11_622O11_2 |
| XXbac_BPG13B8_10 | CH25H | FOLR2 | GPIHBP1 | OGN |
| TWIST1 | NKX2_3 | CD3G | APLNR | RGS3 |
| TRBC2 | CTD_2003C8_1 | MFAP5 | MS4A2 | COL5A1 |
| ADAMDEC1 | CHST1 | LRRK2 | CD248 | CHST1 |
| TEK | FOLR2 | RP11_693J15_5 | LPAR5 | FEZ1 |
| C9orf72 | THY1 | PCDH9 | C1S | RP11_744N12_2 |
| RP11_251M1_1 | CLEC1A | CILP | CMA1 | NTM |
| SNCG | RP11_693J15_5 | MEOX1 | FLRT2 | PLEKHG6 |
| SLC18A2 | CMA1 | TMEM101 | SERPINA9 | RP11_834C11_4 |
| RIC3 | AL928768_3 | PPM1D | IGHV5_51 | RHOJ |
| MRVI1 | IGHV3_9 | PGLYRP2 | CDYL2 | C14orf132 |
| C11orf31 | ISLR | PPP1R14A | MIS12 | IGHV1_2 |
| CRTAM | C16orf52 | AC011526_1 | MEOX1 | IGHV3_11 |
| NRGN | CD19 | LILRB5 | ADCYAP1 | TNFRSF17 |
| CLEC1A | CDH13 | IGLC6 | PTPRM | CD209 |
| KRT1 | P2RX1 | EMID1 | CHEK2 | ZNF296 |
| SELPLG | CD300E | | | HSPA12B |
| RNASE2 | GAA | | | |
| IGHV5_51 | LDLRAD4 | | | |
| CILP | DACT3 | | | |
| RASAL3 | TMX4 | | | |
| PGLYRP2 | LINC00528 | | | |

| 21_MHCII, ISG | 22_Mitochondrion, Redox | 23_prolif | 24_Reg family | N1_cl4EpiMat_AQP8 |
|---|---|---|---|---|
| CHI3L2 | FCN3 | SAMD11 | NECAP2 | VAMP3 |
| TMIGD3 | GPX7 | ADORA3 | CSF3R | RBP7 |
| FCRL1 | PODN | ITGA10 | ATG4C | GJA4 |
| SLAMF6 | GJA5 | FCER1A | ANKRD35 | PODN |
| ANGPTL1 | MNDA | FCRLA | RCSD1 | RP11_284N8_3 |
| MIXL1 | LY9 | AC017048_3 | PIGF | CHI3L2 |
| GCSAML | LMOD1 | CDK15 | DYSF | ADORA3 |
| AC012368_2 | CHI3L1 | C1QTNF7 | SDPR | FCGR1B |
| MAL | IL10 | TLR10 | FBLN2 | GJA5 |
| P2RY13 | ERLEC1 | IRF2 | FILIP1L | PEAR1 |
| NRROS | IL1RL1 | ESM1 | TXK | CADM3 |
| CYTL1 | AC093818_1 | KCNMB1 | HPGDS | DNM3OS |
| MMRN1 | CDK15 | FOXF2 | TLL1 | PTPN7 |
| RP11_290F5_1 | FBLN2 | BMP6 | EGFLAM | CHI3L1 |
| ESM1 | CCR5 | SAMD3 | EDIL3 | C1orf186 |
| PRR16 | RP11_792D21_2 | VSTM2A | ECSCR | FAM89A |
| ECSCR | HAND2 | GIMAP8 | FNDC1 | NID1 |
| PCDH12 | ADRB2 | SCARA5 | GIMAP7 | ZNF692 |
| KCNMB1 | NDST1 | FABP4 | LZTS1 | FAM150B |
| ADGRF5 | FLT4 | GPIHBP1 | SOX17 | REG1B |
| PIK3CG | HLA_DQB2 | LCN6 | FABP4 | IGKV2_30 |
| LZTS1 | ENPP4 | UEVLD | TEK | IL1RL1 |
| ANGPT1 | ADGRF5 | CLEC1A | EGFL7 | INHBB |
| RP11_622O11_2 | RP3_325F22_5 | HVCN1 | LCN6 | RAPGEF4 |
| OMD | ADAMDEC1 | TMEM233 | NKX2_3 | COL3A1 |
| DIP2C | ANGPT1 | CMA1 | DKK3 | FBLN2 |
| CHST1 | LAMC3 | GNG2 | CHST1 | FGD5 |
| RP11_744N12_2 | ZEB1 | AL928768_3 | NTM | NR1D2 |
| C12orf65 | PLAC9 | ITGA11 | VWF | CXCR6 |
| PCDH17 | VPS11 | SPN | KLRG1 | KLHDC8B |
| GPR18 | MCAM | LIMD2 | TMEM119 | DNASE1L3 |
| CLEC14A | TMTC1 | ADCYAP1 | SLITRK6 | ABI3BP |
| VASH1 | PCDH9 | ARHGAP28 | RNASE2 | TM4SF18 |
| FBLN5 | APBA2 | GZMM | ITGA11 | RPL22L1 |
| TCL1A | CCL11 | CD22 | TMEM204 | KLHL6 |
| PLD4 | PLXDC1 | LILRA2 | CCL13 | CYTL1 |

TABLE 14-continued

| Malignant epithelial NMF programs | | | | |
|---|---|---|---|---|
| RP11_327J17_3 | ARHGAP28 | LILRB1 | CCL23 | JAKMIP1 |
| CD19 | CNN2 | REM1 | MEOX1 | C1QTNF7 |
| CD209 | RFX1 | SGK2 | RP11_332H18_4 | CXCL13 |
| AC011526_1 | RP3_477O4_14 | CSF2RB | ABCA6 | MMRN1 |
| COX4I2 | WISP2 | | APOBEC3H | SYNPO2 |
| FOXS1 | GGT5 | | | PCDH18 |
| NAGA | | | | EDNRA |
| | | | | GUCY1B3 |
| | | | | PDLIM3 |
| | | | | ESM1 |
| | | | | RP11_65F13_2 |
| | | | | NR2F1 |
| | | | | CAMK4 |
| | | | | PRR16 |
| | | | | CSF1R |
| | | | | FOXF2 |
| | | | | XXbac_BPG13B8_10 |
| | | | | LST1 |
| | | | | HLA_DQA2 |
| | | | | BMP5 |
| | | | | FBXL4 |
| | | | | HEY2 |
| | | | | SAMD3 |
| | | | | SYNE1 |
| | | | | FSCN1 |
| | | | | CREB5 |
| | | | | VSTM2A |
| | | | | ELN |
| | | | | COL1A2 |
| | | | | SGCE |
| | | | | SERPINE1 |
| | | | | CPED1 |
| | | | | GIMAP7 |
| | | | | GIMAP6 |
| | | | | LZTS1 |
| | | | | ADGRA2 |
| | | | | PLAT |
| | | | | RP11_383H13_1 |
| | | | | BAALC |
| | | | | ANGPT1 |
| | | | | PGM5 |
| | | | | SVEP1 |
| | | | | AIF1L |
| | | | | APBB1IP |
| | | | | NRP1 |
| | | | | LDB3 |
| | | | | ITPRIP |
| | | | | SLC18A2 |
| | | | | FIBIN |
| | | | | PAMR1 |
| | | | | SPI1 |
| | | | | CATSPER1 |
| | | | | MRGPRF |
| | | | | RP11_744N12_2 |
| | | | | JAM3 |
| | | | | KCNA5 |
| | | | | VWF |
| | | | | CD4 |
| | | | | MFAP5 |
| | | | | KLRG1 |
| | | | | CLEC1A |
| | | | | BCAT1 |
| | | | | TESPA1 |
| | | | | XPOT |
| | | | | ALDH1L2 |
| | | | | CMKLR1 |
| | | | | CIT |
| | | | | ORAI1 |
| | | | | C1QTNF9 |
| | | | | FLT1 |
| | | | | PCDH17 |
| | | | | FAM155A |
| | | | | RAB2B |
| | | | | SAV1 |
| | | | | FERMT2 |
| | | | | LTBP2 |
| | | | | IRF2BPL |
| | | | | FBLN5 |

TABLE 14-continued

| Malignant epithelial NMF programs | | | | | |
|---|---|---|---|---|---|
| | | | | | IGHV5_51 |
| | | | | | APBA2 |
| | | | | | LOXL1 |
| | | | | | POLR3K |
| | | | | | HAGHL |
| | | | | | ITGAM |
| | | | | | SNX20 |
| | | | | | ADGRG5 |
| | | | | | CMTM3 |
| | | | | | RP11_805I24_2 |
| | | | | | CCL8 |
| | | | | | MMP28 |
| | | | | | CCL3L1 |
| | | | | | COPZ2 |
| | | | | | SGCA |
| | | | | | TBX2 |
| | | | | | RP11_838N2_4 |
| | | | | | SLC14A1 |
| | | | | | DSEL |
| | | | | | FSTL3 |
| | | | | | TNFSF14 |
| | | | | | CD209 |
| | | | | | KANK3 |
| | | | | | SYDE1 |
| | | | | | ZNF626 |
| | | | | | TSHZ3 |
| | | | | | HSPB6 |
| | | | | | EXOC3L2 |
| | | | | | FPR1 |
| | | | | | FOXS1 |
| | | | | | SPAG4 |
| | | | | | STMN3 |
| | | | | | AP001055_6 |
| | | | | | CYTH4 |
| | | | | | APOBEC3H |
| N2_OxPhos | N3_cl5d8Goblet_ZG16 | N4_cl1Best4cl7C124 | N5_FosJun | | N6_Enterocyte CKB CA1 SLC26A2 |
| RBP7 | MXRA8 | SAMD11 | HEYL | | TMEM52 |
| PDPN | MAD2L2 | NEGR1 | RP5_887A10_1 | | TNFRSF9 |
| GJA4 | HSPB7 | GBP5 | RNF115 | | FGR |
| CD1E | RUNX3 | RPAP2 | GJA5 | | GJA4 |
| AIM2 | LCK | CHI3L2 | TNFAIP8L2 | | FAM159A |
| CADM3 | PLPP3 | AMPD1 | AIM2 | | GJA5 |
| SLAMF8 | LEPR | ECM1 | FCER1A | | CADM3 |
| SELE | GBP5 | TNFAIP8L2 | XCL1 | | KIAA0040 |
| IPO9 | PALMD | SHE | SELP | | CHI3L1 |
| MIXL1 | ADAMTSL4 | NES | DNM3OS | | AC104699_1 |
| PQLC3 | PRUNE | CRABP2 | LMOD1 | | EVA1A |
| QPCT | FCGR3A | OLFML2B | FAM89A | | GNLY |
| CALCRL | XCL1 | XCL2 | PLEKHH2 | | MAL |
| WDR75 | SELP | XCL1 | INHBB | | ZEB2 |
| CD28 | PRRX1 | KLHL20 | LIMS2 | | CD28 |
| CCR1 | PRELP | CFH | CHN1 | | FN1 |
| DNASE1L3 | HLX | SNRPE | HECW2 | | AC116035_1 |
| VGLL3 | LDAH | IL10 | EFHD1 | | CACNA2D3 |
| CRYBG3 | AC104699_1 | NID1 | ACKR3 | | VGLL3 |
| BTLA | CYP1B1 | SLC3A1 | CRBN | | CRYBG3 |
| MRAS | RNU2_63P | AC012368_2 | FBLN2 | | NSG1 |
| PCOLCE2 | IGKV1_16 | CD8A | QARS | | PDE5A |
| TM4SF18 | C2orf40 | TNFAIP6 | FAM212A | | ZNF330 |
| P2RY14 | KYNU | SCN7A | CACNA2D3 | | TDO2 |
| MME | TNFAIP6 | CHN1 | EFCC1 | | MRPL36 |
| SERPINI1 | UBR3 | FAM171B | MRAS | | C7 |
| KLHL6 | CDK15 | CALCRL | P2RY13 | | ESM1 |
| UTP3 | CD28 | HECW2 | HTRA3 | | CAMK4 |
| TDO2 | CLEC3B | PPIL3 | C1QTNF7 | | HRH2 |
| EGFLAM | CCR1 | CDK15 | MMRN1 | | GFPT2 |
| RP11_65F13_2 | KLHDC8B | EFHD1 | GUCY1B3 | | FOXF2 |
| CTC_276P9_1 | VGLL3 | AC116035_1 | VEGFC | | HLA_DQB2 |
| SPOCK1 | FILIP1L | ITGA9 | ESM1 | | BMP5 |
| GFRA3 | FSTL1 | CLEC3B | PRR16 | | MOXD1 |
| PCDH12 | BFSP2 | CCR5 | LINC00340 | | CREB5 |
| ADRB2 | CP | BTLA | SAYSD1 | | TRIL |
| XXbac_BPG13B8_10 | P2RY14 | GATA2 | HEY2 | | NOS3 |
| NOTCH4 | CYTL1 | UBA5 | THBS2 | | MSC |

TABLE 14-continued

| Malignant epithelial NMF programs | | | | |
|---|---|---|---|---|
| HLA_DQB2 | TMEM156 | WWTR1 | LZTS1 | ANGPT1 |
| SYNGAP1 | PDGFRA | TACC3 | MSC | GPR20 |
| TREM1 | ENAM | CYTL1 | ANGPT1 | RP11_536O18_2 |
| RCAN2 | CXCL13 | WFS1 | GPR20 | S1PR3 |
| GJA1 | SYNPO2 | GRSF1 | COL15A1 | OMD |
| ARHGAP18 | TLR2 | MMRN1 | FAM69B | FAM69B |
| STX11 | GUCY1A3 | EMCN | RP11_124N14_4 | RP1_186E20_2 |
| MYCT1 | PDGFC | GUCY1B3 | ZNF32 | NRP1 |
| INHBA | NAF1 | 1-Mar | PRF1 | CXCL12 |
| RP11_11N9_4 | SLC1A3 | TLL1 | FIBIN | C10orf128 |
| PLAT | MAN2A1 | RP11_701P16_5 | PAMR1 | HHEX |
| DNAJC5B | FBN2 | CDH6 | LDLRAD3 | POLL |
| OMD | ADAM19 | LIFR | MPEG1 | ITPRIP |
| LHX6 | ADAMTS2 | ANXA2R | GAL | TSPAN4 |
| OLFML2A | NRN1 | PELO | NRIP2 | APLNR |
| COL5A1 | BMP6 | KIF2A | C3AR1 | EFEMP2 |
| IL2RA | HULC | F2R | KLRG1 | CATSPER1 |
| GATA3 | NOTCH4 | VCAN | CLEC12A | NRIP2 |
| RP11_354E11_2 | HLA_DQA1 | CTC_276P9_1 | TMTC1 | KCNA5 |
| CH25H | FAM26F | ITK | PCED1B | RP11_291B21_2 |
| LPXN | HEY2 | NRN1 | CCT2 | BIN2 |
| MS4A6A | RSPO3 | RIPOR2 | FGD6 | RP11_834C11_4 |
| CST6 | MOXD1 | RCAN2 | GLT8D2 | NUAK1 |
| CATSPER1 | FNDC1 | RAB23 | ALKBH2 | CMKLR1 |
| KLC2 | THBS2 | VNN2 | RILPL2 | TMEM233 |
| DDX10 | TWIST1 | TCF21 | RASA3 | C1QTNF9 |
| CADM1 | IL6 | TWIST1 | TRDC | PCDH17 |
| UBASH3B | CREB5 | TWISTNB | HAUS4 | PCDH9 |
| FEZ1 | CPVL | TRG_AS1 | DCAF11 | GZMB |
| JAM3 | PSPH | SEMA3E | FUT8 | FBLN5 |
| ENO2 | ERV3_1 | NOS3 | RP11_327J17_3 | KIAA1370 |
| ABCC9 | PTN | MSR1 | DPEP2 | RASL12 |
| KANSL2 | MSR1 | LZTS1 | TMEM100 | CSPG4 |
| CSRNP2 | ADAM28 | SCARA5 | RP11_332H18_4 | SALL1 |
| ITGA5 | CLU | ADGRA2 | SS18 | CDYL2 |
| SDS | SFRP1 | SOX17 | SLC14A1 | FOXF1 |
| DCLK1 | SULF1 | SULF1 | DYM | NXN |
| HAUS4 | RP11_383H13_1 | ENPP2 | FSTL3 | VMO1 |
| ADPGK | MSC | GPIHBP1 | C3 | TMEM97 |
| IL16 | BAALC | TEK | CEACAM4 | RAB34 |
| CD19 | PVT1 | NR4A3 | FPR3 | AOC3 |
| SALL1 | PGM5 | SVEP1 | LILRA6 | CYGB |
| RP11_805I24_2 | CENPP | PAPPA | KIR2DL4 | CD70 |
| FENDRR | OLFML2A | ANGPTL2 | ISOC2 | C3 |
| NXN | ANGPTL2 | SH2D3C | ADAMTS5 | WDR83 |
| HS3ST3B1 | AIF1L | ITIH5 | AL844908_5 | LILRA6 |
| AOC3 | LCN6 | ITGA8 | GGT5 | LILRB5 |
| CD300E | ANAPC2 | SNCG | | COL6A1 |
| CBX4 | GATA3 | SORBS1 | | DERL3 |
| RETN | GALNT18 | NKX2_3 | | MEI1 |
| SYDE1 | MS4A4A | LSP1 | | A4GALT |
| RASIP1 | LRRN4CL | PAMR1 | | |
| FPR1 | DPF2 | PTGDR2 | | |
| LAIR2 | FIBP | LAYN | | |
| TNNT1 | PCF11 | CD3G | | |
| THBD | LAYN | CRTAM | | |
| CD93 | C11orf1 | RP11_744N12_2 | | |
| REM1 | FEZ1 | JAM3 | | |
| LINC01272 | IFFO1 | NRIP2 | | |
| KIAA1671 | RP11_118B22_2 | RP11_118B22_2 | | |
| OSM | RERGL | VDR | | |
| CYTH4 | TMTC1 | RP1_288H2_5 | | |
| GRAP2 | KRT1 | CSRP2 | | |
| | POSTN | GLT8D2 | | |
| | RCBTB2 | ALDH1L2 | | |
| | SETDB2 | WDR66 | | |
| | THSD1 | MEDAG | | |
| | FERMT2 | LPAR6 | | |
| | VRK1 | PCDH17 | | |
| | PLD4 | EDNRB | | |
| | FBN1 | PLD4 | | |
| | AQP9 | DUOXA2 | | |
| | SNAPC5 | FBN1 | | |
| | TM6SF1 | HDC | | |
| | HAPLN3 | LARP6 | | |
| | SALL1 | BCL2A1 | | |
| | DPEP2 | MFGE8 | | |
| | FENDRR | ALDH1A3 | | |

TABLE 14-continued

| Malignant epithelial NMF programs | | |
|---|---|---|
| | TNFSF12 | MRPS34 |
| | RAB34 | GPRC5B |
| | AOC3 | BBS2 |
| | GJC1 | KIFC3 |
| | SGCA | FOXF1 |
| | LIMD2 | CLEC10A |
| | GADD45B | AOC3 |
| | DNMT1 | HIGD1B |
| | SYDE1 | SLC14A1 |
| | LRRC25 | GNA15 |
| | TSHZ3 | S1PR4 |
| | LRP3 | TMIGD2 |
| | CD22 | CD70 |
| | HNRNPL | TNFSF14 |
| | AC011526__1 | CD209 |
| | CEACAM4 | PRAM1 |
| | TNNT1 | LRRC25 |
| | CD93 | TSHZ3 |
| | ADAMTS5 | AC011526__1 |
| | LINC00528 | CEACAM4 |
| | IGLV4__69 | EXOC3L2 |
| | MEI1 | GPR4 |
| | CTA__29F11__1 | IL411 |
| | | FPR3 |
| | | LILRA6 |
| | | LILRB5 |
| | | SIRPG |
| | | BMP7 |
| | | MIR99AHG |
| | | COL18A1 |
| | | CHEK2 |
| | | EMID1 |
| | | APOL3 |
| | | FAM118A |

| N7__Enterocyte genes | N8__S100 patient specific clusters | N9__unclear high in lowQC | N10__Metallothioneins | N11__ISG15 |
|---|---|---|---|---|
| CEACAM SLCs | | TNFRSF4 | CAMTA1 | FGR |
| FHL3 | ANKRD65 | RBP7 | FHL3 | HEYL |
| LRRC8C | PDPN | GBP5 | TMEM69 | SGIP1 |
| FCGR1B | ALPL | ARHGAP29 | CTBS | ADORA3 |
| SHE | LMO4 | ADORA3 | TMIGD3 | TSPAN2 |
| AIM2 | ARHGAP29 | ADAMTSL4 | AMPD1 | SEMA6C |
| SLAMF1 | ADORA3 | OAZ3 | ANKRD35 | OLFML2B |
| CD247 | FCGR1B | IL10 | SLAMF8 | RGS18 |
| CHI3L1 | GJA5 | AC104699__1 | FCER1G | CD34 |
| MIXL1 | ADAMTSL4 | RASGRP3 | ANGPTL1 | EPHX1 |
| COMMD1 | SLAMF9 | KYNU | FAM129A | MIXL1 |
| KYNU | DPT | TNFAIP6 | CHI3L1 | FAM89A |
| GALNT15 | SELP | WNT10A | CAPN2 | TRIB2 |
| CMTM7 | PRELP | SP140 | GALNT2 | AC012368__2 |
| NT5DC2 | CR1 | RFTN1 | KCNS3 | REG1B |
| DNASE1L3 | MIXL1 | AC116035__1 | EMILIN1 | SCN7A |
| RP11__861A13__4 | AC012368__2 | PPM1M | PAIP2B | ITGA9 |
| GTPBP8 | AC133644__2 | P2RY13 | DARS | LSAMP |
| BOC | FAP | C1QTNF7 | GALNT3 | RFC4 |
| MME | ITGA4 | TNFAIP8 | ZNF385D | TACC3 |
| NSG1 | CD28 | FBN2 | CACNA2D3 | CYTL1 |
| JAKMIP1 | CTLA4 | BMP6 | PLSCR4 | PDGFRA |
| EDNRA | FN1 | TREM2 | P2RY14 | SYNPO2 |
| TLR2 | GPC1 | TUBE1 | CYTL1 | PCDH18 |
| RP11__701P16__5 | RBMS3 | MYCT1 | JAKMIP1 | TMEM154 |
| SLC1A3 | AC116035__1 | CREB5 | C1QTNF7 | ZNF366 |
| OSMR | CCR1 | IGFBP3 | ENAM | NR2F1 |
| RP11__65F13__2 | FAM212A | ZNF394 | TLR2 | PITX1 |
| NR2F1 | PPM1M | NSMAF | FST | GFRA3 |
| PAM | CACNA2D3 | SIT1 | SLC25A46 | AFAP1L1 |
| LOX | CHST2 | AUH | AFAP1L1 | SH3PXD2B |
| ITK | HTRA3 | EGFL7 | MIR143HG | TFAP2A |
| XXbac__BPG13B8__10 | SHISA3 | GATA3 | F13A1 | NCR3 |
| IPCEF1 | TNIP3 | TCTN3 | XXbac__BPG13B8__10 | PLA2G7 |
| QKI | PCDH18 | MFSD13A | SESN1 | ADGRF5 |
| TRGC1 | ARHGAP10 | PAMR1 | HGF | SESN1 |
| MYO1G | TDO2 | NNMT | GIMAP8 | RP3__523C21__1 |
| HGF | ADAMTS12 | RP11__744N12__2 | LOXL2 | VNN2 |
| CUL1 | LCP2 | CLEC4E | RBPMS | FNDC1 |
| LZTS1 | HRH2 | RERG | WISP1 | IL6 |

TABLE 14-continued

| Malignant epithelial NMF programs | | | | |
|---|---|---|---|---|
| RP11_51J9_5 | GFPT2 | MGST1 | GPR20 | SERPINE1 |
| MSC | XXbac_BPG13B8_10 | RERGL | TEK | RP11_11N9_4 |
| NSMCE2 | NOTCH4 | PLEKHA5 | CBWD6 | SOX17 |
| SVEP1 | HLA_DQA1 | KRT1 | INSC | DNAJC5B |
| ANGPTL2 | TREM1 | ITGA7 | TSKU | STMN2 |
| RP11_492E3_2 | NDUFAF4 | KLHL28 | NRIP2 | BAALC |
| IL2RA | RP3_523C21_1 | SERPINA9 | SRSF9 | COL14A1 |
| CREM | CREB5 | NEIL1 | RNASEH2B | RP11_536O18_2 |
| C10orf128 | SGCE | MYH11 | TDRD3 | OMD |
| FAM13C | GIMAP6 | ITGAX | SERPINA9 | C9orf3 |
| EIF5AL1 | NOS3 | DPEP2 | APBA2 | AAED1 |
| TSPAN4 | RBPMS | TNFRSF13B | HDC | FCN1 |
| SLC43A3 | SUSD3 | CCL8 | CSPG4 | FAM69B |
| DDB1 | PDCL | RP11_332H18_4 | FLYWCH2 | FBXO18 |
| CST6 | FAM69B | PITPNC1 | SALL1 | FAM13C |
| MRGPRF | LCN6 | ADCYAP1 | CDH11 | ACTA2 |
| INTS4 | PRF1 | CCDC178 | NFAT5 | ADAM8 |
| PDGFD | PLAC9 | CD226 | FAM92B | LDLRAD3 |
| FXYD6 | HHEX | CD70 | UBE2G1 | APLNR |
| CLMP | CALHM2 | HOMER3 | CLEC10A | CD248 |
| JAM3 | PAMR1 | LILRA6 | CCL14 | CTD_3074O7_5 |
| NRIP2 | LRRN4CL | LILRB2 | AOC3 | GAL |
| KLRG1 | FRMD8 | LAIR1 | SGCA | FOLR2 |
| CLEC12A | TBC1D10C | THBD | ABHD17A | CXCR5 |
| CLEC1A | NRIP2 | FOXS1 | C19orf59 | CLMP |
| KANSL2 | C1S | MIR99AHG | SNAPC2 | RP11_877E17_2 |
| IGFBP6 | A2M | MAP3K7CL | CNN1 | RP1_288H2_5 |
| TESPA1 | CLEC12A | IGLV1_40 | BISPR | NTN4 |
| IFNG | IFNG | TIMP3 | GRWD1 | C1QTNF9 |
| HVCN1 | TMEM119 | | PPP2R1A | USPL1 |
| RNASE2 | TMEM233 | | LILRB4 | POSTN |
| GZMH | RP11_164H13_1 | | REM1 | RNASEH2B |
| ASB2 | RGMA | | PTGIS | FAM155A |
| CRIP2 | NXN | | CLDN5 | FRMD6 |
| IGHD | CYB5D2 | | | VASH1 |
| MAP1A | ACAP1 | | | MEG8 |
| HDC | CCL3L1 | | | ZNF106 |
| HAGHL | CTD_3193K9_4 | | | IMP3 |
| SREBF1 | CD70 | | | CSPG4 |
| CCL11 | SYDE1 | | | HAGHL |
| CCL3L1 | HOMER3 | | | METTL22 |
| KRT24 | HAMP | | | RP11_455F5_5 |
| FKBP10 | LMTK3 | | | ITGAX |
| COLEC12 | LILRA5 | | | DNAAF1 |
| GNG7 | LAIR1 | | | SCIMP |
| DENND1C | LILRB1 | | | MED31 |
| COX7A1 | SIGLEC1 | | | CCL2 |
| MAP4K1 | C20orf27 | | | CCL3L1 |
| CEACAM4 | COX4I2 | | | KRT24 |
| GPR4 | OSER1 | | | CYGB |
| FLT3LG | PTGIS | | | ARHGAP28 |
| LILRA6 | MIR155HG | | | CCDC178 |
| LILRB5 | CTA_243E7_1 | | | PRAM1 |
| LILRB2 | EMID1 | | | CNN1 |
| LAIR1 | PARVG | | | RINL |
| CTB_61M7_2 | LMF2 | | | EXOC3L2 |
| A1BG | | | | PLEKHA4 |
| FOXS1 | | | | LILRB5 |
| IGLC6 | | | | HSPA12B |
| MMP11 | | | | COX4I2 |
| PARVG | | | | PTGIS |
| | | | | RP13_152O15_2 |
| | | | | TRPM2 |
| | | | | LINC00528 |
| | | | | IGLV1_47 |
| | | | | IGLL5 |
| | | | | RHBDD3 |
| | | | | APOBEC3H |

| N12_MALAT1 | N13_ATPoxphos | N14_TAprolif | N15_Entero | N16_cl6 |
|---|---|---|---|---|
| AGTRAP | SGIP1 | TNFRSF4 | PDPN | GJA4 |
| PDPN | VCAM1 | MXRA8 | EVA1B | SGIP1 |
| DDOST | FCGR1B | ANKRD65 | PDE4B | AMPD1 |
| ALPL | GJA5 | HSPB7 | AMPD1 | TNFAIP8L2 |
| CSF3R | ADAMTSL4 | C1QB | FCGR1B | SELE |
| ANKRD35 | NPR1 | PODN | S100A12 | DNM3OS |
| CD160 | SLC27A3 | LRRC8C | SLAMF8 | CD34 |

TABLE 14-continued

| Malignant epithelial NMF programs | | | | |
|---|---|---|---|---|
| TRAF3IP3 | OLFML2B | PALMD | ST3GAL5 | AGT |
| KHK | SELE | GSTM5 | MARCO | RP11_343J24_1 |
| AC012368_2 | PRRX1 | TMIGD3 | LIMS2 | PLEKHH2 |
| C2orf40 | SNAP47 | FCGR1B | TNFAIP6 | CCDC88A |
| RP11_803D5_4 | IL1RL1 | FCRL3 | TNS1 | AC012368_2 |
| AC020571_3 | INHBB | PYHIN1 | SP140 | CNRIP1 |
| ACKR3 | FAM171B | AIM2 | PLCD1 | DYSF |
| GCSAM | CAMK1 | XCL1 | CXCR6 | REG1B |
| MRAS | UBE2E2 | SELP | P2RY13 | CCDC93 |
| CYTL1 | CSTA | PRRX1 | TNK2 | HECW2 |
| SCD5 | EFCC1 | ANGPTL1 | CPLX1 | CDK15 |
| HAND2 | CPA3 | C1orf186 | NSG1 | SP140 |
| CDH6 | MSX1 | CR1 | CYTL1 | ACKR3 |
| RNF180 | HTRA3 | AC104699_1 | TMEM156 | COL6A3 |
| RFESD | SHISA3 | EVA1A | SHISA3 | FGD5 |
| PRR16 | PCDH18 | AC093818_1 | BANK1 | GATA2 |
| GFPT2 | ADAMTS12 | AC020571_3 | LEF1 | ZMAT3 |
| FOXF2 | FLT4 | CTLA4 | TLR2 | GUCY1B3 |
| THEMIS | SLC22A23 | GALNT15 | AFAP1L1 | RP11_701P16_5 |
| GPR146 | TMEM170B | AC116035_1 | HAVCR2 | ADAMTS12 |
| RAMP3 | TREM2 | CSRNP1 | HRH2 | SLC1A3 |
| NOS3 | CD109 | FAM212A | FOXF2 | MAP1B |
| FGFR1 | FILIP1 | VGLL3 | BAG2 | JMY |
| WISP1 | RRAGD | MRAS | AKAP12 | RP11_213H15_3 |
| GPIHBP1 | NUS1 | CHST2 | TRIL | FBN2 |
| PAPPA | RSPO3 | TM4SF18 | TRGC1 | CXCL14 |
| LHX6 | TFPI2 | C3orf70 | INHBA | PCDH12 |
| TNNI2 | RBPMS | NRROS | RP11_792A8_4 | HRH2 |
| MRVI1 | MSC | RP11_539L10_3 | LOXL2 | GFPT2 |
| PAMR1 | SBSPON | C1QTNF7 | RP11_536O18_2 | PXDC1 |
| MPEG1 | MAMDC2 | ENAM | BNC2 | F13A1 |
| TMEM119 | OMD | LEF1 | GNA14 | NCR3 |
| C1QTNF9 | ANGPTL2 | GUCY1A3 | SVEP1 | C2 |
| APBA2 | ST6GALNAC4 | HAND2 | INSC | TREM2 |
| CDH5 | COL5A1 | PDLIM3 | PAMR1 | TREM1 |
| FOXF1 | FAM69B | CDH6 | CHST1 | PLA2G7 |
| IKZF3 | RP1_186E20_2 | ADAMTS12 | MS4A4A | FAM26F |
| HIGD1B | KIAA1462 | FST | CLEC4E | PERP |
| ABCA8 | APLNR | NR2F1 | ZNF385A | FSCN1 |
| NFATC1 | MS4A2 | LOX | IGF1 | TWIST1 |
| RETN | MRGPRF | FBN2 | HSPB8 | TFPI2 |
| C19orf59 | RP11_744N12_2 | AFAP1L1 | DCLK1 | COL1A2 |
| PGLYRP2 | CLEC4E | GFPT2 | RHOJ | POLR2J3 |
| REM1 | SPRYD3 | FOXF2 | ASB2 | BLK |
| COX4I2 | RP11_834C11_4 | BMP6 | PLD4 | MSC |
| GGT5 | IFNG | FAM8A1 | APBA2 | MTERF3 |
| | GLT8D2 | TREM2 | FBN1 | TMEM71 |
| | POSTN | COL12A1 | AQP9 | TEK |
| | PCDH17 | LAMA4 | ALDH1A3 | COL15A1 |
| | GPRC5B | FNDC1 | GPRC5B | FCN1 |
| | CCL2 | TWIST1 | AC002331_1 | CLIC3 |
| | RETN | CREB5 | FOXF1 | CASC10 |
| | PLEKHF1 | TRGC1 | CCL3 | KIAA1462 |
| | TSHZ3 | INHBA | KRT24 | EGR2 |
| | LILRA6 | FGL2 | RP11_332H18_4 | PRF1 |
| | TNNT1 | SMARCD3 | ARHGAP28 | ZMIZ1 |
| | SIGLEC1 | MSR1 | NFATC1 | LDB3 |
| | HSPA12B | LZTS1 | TBXA2R | HTRA1 |
| | PLCB1 | RP11_11N9_4 | RETN | RIC3 |
| | COX4I2 | IDO1 | TGFBR3L | MRVI1 |
| | ADAMTS5 | MSC | KANK3 | PAMR1 |
| | MAP3K7CL | SBSPON | PGLYRP2 | CHST1 |
| | TCN2 | WISP1 | AXL | SPI1 |
| | | CNTNAP3B | GPR4 | MS4A7 |
| | | NR4A3 | LILRB2 | LRRN4CL |
| | | LHX6 | TNNT1 | CTSF |
| | | IL2RA | CST7 | TBC1D10C |
| | | GATA3 | COL18A1 | FOLR2 |
| | | PLAC9 | GGT5 | NTF3 |
| | | LDB3 | HSCB | SLC2A3 |
| | | MMP7 | EMID1 | OLR1 |
| | | MMP1 | | RP11_81H14_2 |
| | | THY1 | | CMKLR1 |
| | | FEZ1 | | TMEM119 |
| | | JAM3 | | POSTN |
| | | CLEC4E | | TNFSF13B |
| | | OLR1 | | TRAC |
| | | ABCC9 | | CSPG4 |

TABLE 14-continued

| Malignant epithelial NMF programs | | | |
|---|---|---|---|
| | TMTC1 | CTD_3203P2_3 | |
| | RAPGEF3 | ITGAM | |
| | KRT86 | ITGAX | |
| | RP11_834C11_4 | MMP2 | |
| | MMP19 | KIFC3 | |
| | SDS | CDH5 | |
| | POSTN | DNAAF1 | |
| | PCDH9 | CENPV | |
| | PRKCH | MFAP4 | |
| | RHOJ | CCL11 | |
| | LTBP2 | HIGD1B | |
| | VASH1 | CYGB | |
| | AHNAK2 | SLC14A1 | |
| | ITGA11 | NFATC1 | |
| | RGMA | REEP6 | |
| | GPRC5B | KANK3 | |
| | IGSF6 | KANK2 | |
| | ITGAX | BISPR | |
| | KIFC3 | LRRC25 | |
| | CDH5 | LILRB2 | |
| | C16orf74 | LILRA5 | |
| | FOXF1 | LILRA2 | |
| | RFLNB | THBD | |
| | PMP22 | REM1 | |
| | CCL8 | IGLV3_10 | |
| | MEOX1 | OSM | |
| | GJC1 | CTA_384D8_34 | |
| | SGCA | | |
| | CD300E | | |
| | ZNF521 | | |
| | CCDC178 | | |
| | TNFSF14 | | |
| | C3 | | |
| | ICAM4 | | |
| | CNN1 | | |
| | COX7A1 | | |
| | EXOC3L2 | | |
| | IL4I1 | | |
| | FPR2 | | |
| | LILRA5 | | |
| | SIGLEC1 | | |
| | FOXS1 | | |
| | ERG | | |
| | OSM | | |

| | N17_cl11Tuft | N18_cl10C124 | N19_TA elongation factors |
|---|---|---|---|
| | RBP7 | MIB2 | HSPB7 |
| | HSPB7 | PDPN | GSTM5 |
| | PODN | FCN3 | ANKRD35 |
| | S1PR1 | PODN | GJA5 |
| | GSTM5 | NEGR1 | ECM1 |
| | ANKRD35 | S1PR1 | ADAMTSL4 |
| | C1orf54 | ANKRD35 | S100A3 |
| | SLAMF8 | NES | TPM3 |
| | LY9 | CRABP2 | SELP |
| | PRRX1 | CADM3 | DNM3OS |
| | LAMC1 | SLAMF8 | CFH |
| | LAX1 | SLAMF1 | MAPKAPK2 |
| | AGT | DDR2 | MIXL1 |
| | FAM150B | SOAT1 | FAM150B |
| | TRIB2 | PRELP | AC133644_2 |
| | AC104699_1 | GCSAML | IGKV1D_8 |
| | AC012368_2 | FAM150B | C2orf40 |
| | ACTG2 | AC012368_2 | KYNU |
| | EVA1A | ANTXR1 | RAPGEF4 |
| | CHN1 | TNFAIP6 | CDK15 |
| | HECW2 | FAM171B | FZD7 |
| | AC020571_3 | GPBAR1 | WNT10A |
| | WNT10A | WNT10A | COL8A1 |
| | SP140 | DNPEP | PLA1A |
| | FBLN2 | RFTN1 | GATA2 |
| | CD86 | TMEM158 | MYL5 |
| | GATA2 | CCR5 | CYTL1 |
| | C1QTNF7 | SEMA3G | SHISA3 |
| | LDB2 | COL8A1 | SNCA |
| | PAPD7 | CCDC80 | HHIP |

TABLE 14-continued

| Malignant epithelial NMF programs | | |
|---|---|---|
| EGFLAM | BOC | GUCY1B3 |
| PRR16 | LSAMP | RP11_290F5_1 |
| F13A1 | TLR10 | RP11_701P16_5 |
| MOCS1 | ENAM | EGFLAM |
| RSPO3 | SCD5 | ESM1 |
| THEMIS | PCDH18 | VCAN |
| IFNGR1 | GUCY1B3 | ST8SIA4 |
| THBS2 | HMGB2 | PRR16 |
| CREB5 | ZNF366 | SPOCK1 |
| TFEC | CAMK4 | PCDH12 |
| MSR1 | DXO | ADAMTS2 |
| LZTS1 | FGD2 | FOXQ1 |
| SCARA5 | TWIST1 | XXbac_BPG32J3_19 |
| RP11_11N9_4 | GPNMB | TREM2 |
| SNAI2 | MYO1G | COL12A1 |
| SULF1 | RAMP3 | VNN2 |
| GPR20 | TMEM60 | FNDC1 |
| PGM5 | MAK16 | CPVL |
| CERCAM | IDO1 | VSTM2A |
| SFMBT2 | PLAT | CD36 |
| ITGA8 | LY96 | HGF |
| FAM13C | S1PR3 | TFPI2 |
| INSC | MSANTD3 | SCARA5 |
| MMP12 | MAPKAP1 | NUGGC |
| LAYN | SH2D3C | RP11_11N9_4 |
| IL10RA | CERCAM | IDO1 |
| CLMP | RP11_492E3_2 | BAALC |
| NRIP2 | RP1_186E20_2 | ANGPT1 |
| CD4 | APBB1IP | GPR20 |
| CLEC4E | PAMR1 | TEK |
| KLRC1 | MMP1 | S1PR3 |
| RERG | SORL1 | OMD |
| KCNJ8 | CRTAM | LHX6 |
| RP11_877E17_2 | JAM3 | ANGPTL2 |
| CMKLR1 | P3H3 | PKN3 |
| TMEM233 | RP11_118B22_2 | RP1_186E20_2 |
| BMP4 | KCNJ8 | KIAA1462 |
| SAMD4A | IGFBP6 | C10orf10 |
| SERPINA9 | IGF1 | LDB3 |
| NDN | NUAK1 | SLC18A2 |
| RASL12 | TMEM233 | OR51E1 |
| ISLR | DCLK1 | SMPD1 |
| TMEM204 | FRMD6 | PAMR1 |
| AC002331_1 | PGF | CHST1 |
| FOXF1 | FLRT2 | APLNR |
| AC104024_1 | CILP | EFEMP2 |
| RAB34 | RPL4 | BRMS1 |
| CCL18 | LOXL1 | CRYAB |
| ARL4D | SYNM | C1S |
| MXRA7 | SPN | CLEC12A |
| SLC14A1 | ITGAX | BCAT1 |
| CD226 | SNX20 | TMTC1 |
| PALM | CCDC144A | USP15 |
| C19orf59 | TLCD1 | IFNG |
| ICAM1 | CCL13 | GLT8D2 |
| ICAM4 | IKZF3 | TMEM233 |
| AXL | SEPT4 | PCDH17 |
| AC011526_1 | CD300A | GPR18 |
| CEACAM4 | ZNF521 | FAM155A |
| GPR4 | ICAM4 | TNFSF13B |
| LMTK3 | RFX1 | DACT1 |
| ZNF600 | LRRC25 | RHOJ |
| LILRB5 | CEACAM4 | IGHV1_24 |
| LILRB2 | IL4I1 | IGHV3_49 |
| CTB_61M7_2 | SIRPG | CSPG4 |
| MCM8 | CD93 | ALDH1A3 |
| REM1 | OSM | CDH11 |
| MIR99AHG | GRAP2 | CMTM3 |
| SELO | CTA_384D8_34 | FOXC2 |
| | | NXN |
| | | ASPA |
| | | HS3ST3B1 |
| | | CCL3L1 |
| | | KRT24 |
| | | AOC3 |
| | | MEOX1 |
| | | RP11_332H18_4 |
| | | MRC2 |

TABLE 14-continued

Malignant epithelial NMF programs

|  |
| --- |
| ARHGAP28 |
| FSTL3 |
| RETN |
| S1PR2 |
| ICAM4 |
| LRP3 |
| B9D2 |
| CEACAM4 |
| GPR4 |
| SIGLEC10 |
| LILRB5 |
| LAIR2 |
| CTB_61M7_2 |
| SIGLEC1 |
| COX4I2 |
| PTGIS |
| ADAMTS5 |
| S100B |
| DERL3 |
| GGT5 |
| MAPK12 |
| ODF3B |

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. An engineered T cell comprising:
a CXCL13 gene program comprising expression of CXCL13 and RBPJ, wherein the engineered T cell is modified to express a chimeric antigen receptor (CAR) or a tumor specific T cell receptor (TCR).

2. The engineered T cell of claim 1, wherein the CXCL13 gene program further comprises expression of one or more genes selected from the group consisting of MT2A, SLA, PDCD1, FKBP5, NR3C1, NAP1L4, RAB27A, ITM2A, BST2, TGIF1, MTHFD2, PTMS, TOX, CHN1, TSHZ2, YWHAQ, NBL1, MIR155HG, CLPP, LY6E, ARL3, CD2BP2, ZBED2, HAVCR2, MT1E, FAM3C, DGUOK, LBH, TMEM173, DUSP4, SRGAP3, RNF19A, GALM, IFNG, SNAP47, PLSCR1, PDLIM4, SNX9, CD226, IL6ST, LAG3, TRAT1, AHI1, IFI44L, PAG1, GOLIM4, CBLB, BCL2L11, MYO7A, GNG4, NPDC1, SARDH, MX1, CD200, BTLA, TNS3, TSPO, SLC7A5, HTRA1, TSPAN14, KCNK5, PDE7B, TNFSF4, ELMO1, CAMK1, PRDX6, NUDT16, ITGAE, SOD1, DGKZ, ITPR1, LMO4, HECTD2, NMB, SLC4A2, CCDC6, LRMP, SLC27A2 and AGFG1.

3. A population of T cells comprising one or more engineered T cells according to claim 1.

4. The engineered T cell of claim 1, wherein the engineered T cell is isolated from a subject suffering from colorectal cancer (CRC) prior to modifying the engineered T cell to express a CAR or TCR.

5. A method of treating colorectal cancer in a subject in need thereof comprising:
administering a population of T cells comprising one or more engineered T cells according to claim 1 to the subject.

6. The engineered T cell of claim 1, wherein the engineered T cell is CD8+.

7. The population of T cells of claim 3, wherein the population of T cells is expanded ex vivo.

8. The population of T cells of claim 3, wherein the one or more engineered T cells are CD8+.

9. The method of claim 5, wherein the population of T cells is expanded ex vivo prior to administration.

10. The method of claim 5, wherein the population of engineered T cells are a population of CD8+ T cells.

11. The method of claim 5, further comprising administering an immunotherapy to the subject.

12. The method of claim 11, wherein the immunotherapy comprises a checkpoint blockade (CPB) therapy, an IDO1 inhibitor, or both.

13. The method of claim 12, wherein the CPB therapy comprises an anti-PD-1 therapy, an anti-CTLA4 therapy, an anti-PD-L1 therapy, an anti-TIM3 therapy, an anti-TIGIT therapy, an anti-LAG3 therapy, or any combination thereof.

14. The method of claim 5, wherein the population of T cells are isolated from a subject suffering from colorectal cancer (CRC) prior to modifying the population of T cells to express a CAR or TCR.

15. The method of claim 14, wherein the population of T cells are autologous.

16. The method of claim 14, wherein the population of T cells are allogeneic.

* * * * *

SEQUENCE LISTING

```
<160> NUMBER OF SEQ ID NOS: 21

<210> SEQ ID NO 1
<211> LENGTH: 288
<212> TYPE: PRT
<213> ORGANISM: Artificial Sequence
<220> FEATURE:
<223> OTHER INFORMATION: Synthetic

<400> SEQUENCE: 1

Met Asp Pro Ile Arg Ser Arg Thr Pro Ser Pro Ala Arg Glu Leu Leu
1               5                   10                  15

Ser Gly Pro Gln Pro Asp Gly Val Gln Pro Thr Ala Asp Arg Gly Val
            20                  25                  30

Ser Pro Pro Ala Gly Gly Pro Leu Asp Gly Leu Pro Ala Arg Arg Thr
        35                  40                  45

Met Ser Arg Thr Arg Leu Pro Ser Pro Ala Pro Ser Pro Ala Phe
    50                  55                  60

Ser Ala Asp Ser Phe Ser Asp Leu Leu Arg Gln Phe Asp Pro Ser Leu
65                  70                  75                  80

Phe Asn Thr Ser Leu Phe Asp Ser Leu Pro Pro Phe Gly Ala His His
                85                  90                  95

Thr Glu Ala Ala Thr Gly Glu Trp Asp Glu Val Gln Ser Gly Leu Arg
            100                 105                 110

Ala Ala Asp Ala Pro Pro Pro Thr Met Arg Val Ala Val Thr Ala Ala
        115                 120                 125

Arg Pro Pro Arg Ala Lys Pro Ala Pro Arg Arg Arg Ala Ala Gln Pro
    130                 135                 140
```

```
Ser Asp Ala Ser Pro Ala Ala Gln Val Asp Leu Arg Thr Leu Gly Tyr
145                 150                 155                 160

Ser Gln Gln Gln Glu Lys Ile Lys Pro Lys Val Arg Ser Thr Val
            165                 170                 175

Ala Gln His His Glu Ala Leu Val Gly His Gly Phe Thr His Ala His
            180                 185                 190

Ile Val Ala Leu Ser Gln His Pro Ala Ala Leu Gly Thr Val Ala Val
            195                 200                 205

Lys Tyr Gln Asp Met Ile Ala Ala Leu Pro Glu Ala Thr His Glu Ala
            210                 215                 220

Ile Val Gly Val Gly Lys Gln Trp Ser Gly Ala Arg Ala Leu Glu Ala
225                 230                 235                 240

Leu Leu Thr Val Ala Gly Glu Leu Arg Gly Pro Pro Leu Gln Leu Asp
            245                 250                 255

Thr Gly Gln Leu Leu Lys Ile Ala Lys Arg Gly Gly Val Thr Ala Val
            260                 265                 270

Glu Ala Val His Ala Trp Arg Asn Ala Leu Thr Gly Ala Pro Leu Asn
            275                 280                 285

<210> SEQ ID NO 2
<211> LENGTH: 183
<212> TYPE: PRT
<213> ORGANISM: Artificial Sequence
<220> FEATURE:
<223> OTHER INFORMATION: Synthetic

<400> SEQUENCE: 2

Arg Pro Ala Leu Glu Ser Ile Val Ala Gln Leu Ser Arg Pro Asp Pro
1               5                   10                  15

Ala Leu Ala Ala Leu Thr Asn Asp His Leu Val Ala Leu Ala Cys Leu
            20                  25                  30

Gly Gly Arg Pro Ala Leu Asp Ala Val Lys Lys Gly Leu Pro His Ala
        35                  40                  45

Pro Ala Leu Ile Lys Arg Thr Asn Arg Arg Ile Pro Glu Arg Thr Ser
50                  55                  60

His Arg Val Ala Asp His Ala Gln Val Val Arg Val Leu Gly Phe Phe
65                  70                  75                  80

Gln Cys His Ser His Pro Ala Gln Ala Phe Asp Asp Ala Met Thr Gln
                85                  90                  95

Phe Gly Met Ser Arg His Gly Leu Leu Gln Leu Phe Arg Arg Val Gly
            100                 105                 110

Val Thr Glu Leu Glu Ala Arg Ser Gly Thr Leu Pro Pro Ala Ser Gln
        115                 120                 125

Arg Trp Asp Arg Ile Leu Gln Ala Ser Gly Met Lys Arg Ala Lys Pro
    130                 135                 140

Ser Pro Thr Ser Thr Gln Thr Pro Asp Gln Ala Ser Leu His Ala Phe
145                 150                 155                 160

Ala Asp Ser Leu Glu Arg Asp Leu Asp Ala Pro Ser Pro Met His Glu
                165                 170                 175

Gly Asp Gln Thr Arg Ala Ser
            180

<210> SEQ ID NO 3
<211> LENGTH: 7
<212> TYPE: PRT
<213> ORGANISM: Simian virus 40
```

<400> SEQUENCE: 3

Pro Lys Lys Lys Arg Lys Val
1               5

<210> SEQ ID NO 4
<211> LENGTH: 10
<212> TYPE: PRT
<213> ORGANISM: Simian virus 40

<400> SEQUENCE: 4

Pro Lys Lys Lys Arg Lys Val Glu Ala Ser
1               5                   10

<210> SEQ ID NO 5
<211> LENGTH: 16
<212> TYPE: PRT
<213> ORGANISM: Xenopus tropicalis

<400> SEQUENCE: 5

Lys Arg Pro Ala Ala Thr Lys Lys Ala Gly Gln Ala Lys Lys Lys Lys
1               5                   10                  15

<210> SEQ ID NO 6
<211> LENGTH: 9
<212> TYPE: PRT
<213> ORGANISM: Homo sapiens

<400> SEQUENCE: 6

Pro Ala Ala Lys Arg Val Lys Leu Asp
1               5

<210> SEQ ID NO 7
<211> LENGTH: 11
<212> TYPE: PRT
<213> ORGANISM: Homo sapiens

<400> SEQUENCE: 7

Arg Gln Arg Arg Asn Glu Leu Lys Arg Ser Pro
1               5                   10

<210> SEQ ID NO 8
<211> LENGTH: 38
<212> TYPE: PRT
<213> ORGANISM: Homo sapiens

<400> SEQUENCE: 8

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
        35

<210> SEQ ID NO 9
<211> LENGTH: 42
<212> TYPE: PRT
<213> ORGANISM: Homo sapiens

<400> SEQUENCE: 9

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys

```
              20                  25                  30

Asp Glu Gln Ile Leu Lys Arg Arg Asn Val
        35                  40

<210> SEQ ID NO 10
<211> LENGTH: 8
<212> TYPE: PRT
<213> ORGANISM: Homo sapiens

<400> SEQUENCE: 10

Val Ser Arg Lys Arg Pro Arg Pro
1               5

<210> SEQ ID NO 11
<211> LENGTH: 8
<212> TYPE: PRT
<213> ORGANISM: Homo sapiens

<400> SEQUENCE: 11

Pro Pro Lys Lys Ala Arg Glu Asp
1               5

<210> SEQ ID NO 12
<211> LENGTH: 8
<212> TYPE: PRT
<213> ORGANISM: Homo sapiens

<400> SEQUENCE: 12

Pro Gln Pro Lys Lys Lys Pro Leu
1               5

<210> SEQ ID NO 13
<211> LENGTH: 12
<212> TYPE: PRT
<213> ORGANISM: Mus sp.

<400> SEQUENCE: 13

Ser Ala Leu Ile Lys Lys Lys Lys Lys Met Ala Pro
1               5                  10

<210> SEQ ID NO 14
<211> LENGTH: 5
<212> TYPE: PRT
<213> ORGANISM: Influenza virus

<400> SEQUENCE: 14

Asp Arg Leu Arg Arg
1               5

<210> SEQ ID NO 15
<211> LENGTH: 7
<212> TYPE: PRT
<213> ORGANISM: Influenza virus

<400> SEQUENCE: 15

Pro Lys Gln Lys Lys Arg Lys
1               5

<210> SEQ ID NO 16
<211> LENGTH: 10
<212> TYPE: PRT
<213> ORGANISM: Hepatitis D virus

<400> SEQUENCE: 16
```

Arg Lys Leu Lys Lys Ile Lys Lys Leu
1               5                   10

<210> SEQ ID NO 17
<211> LENGTH: 10
<212> TYPE: PRT
<213> ORGANISM: Mus sp.

<400> SEQUENCE: 17

Arg Glu Lys Lys Lys Phe Leu Lys Arg Arg
1               5                   10

<210> SEQ ID NO 18
<211> LENGTH: 20
<212> TYPE: PRT
<213> ORGANISM: Homo sapiens

<400> SEQUENCE: 18

Lys Arg Lys Gly Asp Glu Val Asp Gly Val Asp Glu Val Ala Lys Lys
1               5                   10                  15

Lys Ser Lys Lys
            20

<210> SEQ ID NO 19
<211> LENGTH: 17
<212> TYPE: PRT
<213> ORGANISM: Homo sapiens

<400> SEQUENCE: 19

Arg Lys Cys Leu Gln Ala Gly Met Asn Leu Glu Ala Arg Lys Thr Lys
1               5                   10                  15

Lys

<210> SEQ ID NO 20
<211> LENGTH: 107
<212> TYPE: PRT
<213> ORGANISM: Homo sapiens

<400> SEQUENCE: 20

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
            35                  40                  45

Val Leu Ala Cys Tyr Ser Leu Leu Val Thr Val Ala Phe Ile Ile Phe
        50                  55                  60

Trp Val Arg Ser Lys Arg Ser Arg Leu Leu His Ser Asp Tyr Met Asn
65                  70                  75                  80

Met Thr Pro Arg Arg Pro Gly Pro Thr Arg Lys His Tyr Gln Pro Tyr
                85                  90                  95

Ala Pro Pro Arg Asp Phe Ala Ala Tyr Arg Ser
            100                 105

```
<210> SEQ ID NO 21
<211> LENGTH: 9
<212> TYPE: PRT
<213> ORGANISM: Homo sapiens

<400> SEQUENCE: 21

Ile Glu Val Met Tyr Pro Pro Pro Tyr
1               5
```